(12) United States Patent
Malley et al.

(10) Patent No.: US 11,701,416 B2
(45) Date of Patent: Jul. 18, 2023

(54) MULTIVALENT PNEUMOCOCCAL VACCINES

(71) Applicant: Affinivax, Inc., Cambridge, MA (US)

(72) Inventors: Richard Malley, Beverly, MA (US); Yingjie Lu, West Roxbury, MA (US); Fan Zhang, West Roxbury, MA (US); Teresa J. Broering, Brookline, MA (US); Shite Sebastian, Shrewsbury, MA (US); Velupillai Puvanesarajah, Chapel Hill, NC (US); George R. Siber, New York, NY (US)

(73) Assignee: Affinivax, Inc., Cambridge, MA (US)

( * ) Notice: Subject to any disclaimer, the term of this patent is extended or adjusted under 35 U.S.C. 154(b) by 0 days.

(21) Appl. No.: 17/237,168

(22) Filed: Apr. 22, 2021

(65) Prior Publication Data

US 2021/0346487 A1 Nov. 11, 2021

Related U.S. Application Data

(62) Division of application No. 16/569,579, filed on Sep. 12, 2019, now Pat. No. 11,013,793.

(60) Provisional application No. 62/730,471, filed on Sep. 12, 2018.

(51) Int. Cl.
*A61K 39/09* (2006.01)
*A61K 39/00* (2006.01)

(52) U.S. Cl.
CPC .. *A61K 39/092* (2013.01); *A61K 2039/55505* (2013.01); *A61K 2039/62* (2013.01); *A61K 2039/70* (2013.01)

(58) Field of Classification Search
None
See application file for complete search history.

(56) References Cited

U.S. PATENT DOCUMENTS

| | | |
|---|---|---|
| 6,287,568 B1 | 9/2001 | Wang et al. |
| 7,217,791 B2 | 5/2007 | Chen et al. |
| 7,585,669 B2 | 9/2009 | Chen et al. |
| 9,499,593 B2 | 11/2016 | Malley et al. |
| 10,017,548 B2 | 7/2018 | Malley et al. |
| 11,013,793 B2 | 5/2021 | Malley et al. |
| 2002/0032323 A1 | 3/2002 | Kunsch et al. |
| 2005/0002948 A1 | 1/2005 | Ryall |
| 2005/0226899 A1 | 10/2005 | Castiglioni et al. |
| 2006/0251675 A1 | 11/2006 | Hagen |
| 2007/0082005 A1 | 4/2007 | Doucette-Stamm et al. |
| 2007/0128183 A1 | 6/2007 | Meinke et al. |
| 2007/0184443 A1 | 8/2007 | Covacci |
| 2008/0032340 A1 | 2/2008 | Ghosh et al. |
| 2008/0112964 A1 | 5/2008 | Kirkham et al. |
| 2008/0160045 A1 | 7/2008 | Contorni et al. |
| 2009/0054251 A1 | 2/2009 | O'Connor et al. |
| 2009/0068288 A1 | 3/2009 | Kruger |
| 2009/0148894 A1 | 6/2009 | Broedel et al. |
| 2009/0148897 A1 | 6/2009 | Dai |
| 2009/0285846 A1 | 11/2009 | Tweten |
| 2010/0003266 A1 | 1/2010 | Simon |
| 2010/0020945 A1 | 1/2010 | Li et al. |
| 2010/0022401 A1 | 1/2010 | Nordlund et al. |
| 2010/0166802 A1 | 7/2010 | Caplan et al. |
| 2010/0209450 A1 | 8/2010 | Diemans et al. |
| 2010/0330112 A1 | 12/2010 | Long et al. |
| 2011/0020386 A1 | 1/2011 | Gierahn et al. |
| 2011/0065660 A1 | 3/2011 | Daron et al. |
| 2011/0159040 A1 | 6/2011 | Malley et al. |
| 2011/0293664 A1 | 12/2011 | Cohane et al. |
| 2012/0135025 A1 | 5/2012 | Flechtner et al. |
| 2012/0189649 A1 | 7/2012 | Gierahn et al. |
| 2012/0251577 A1 | 10/2012 | Malley et al. |
| 2013/0115230 A1 | 5/2013 | Simon |
| 2013/0121958 A1 | 5/2013 | Leclerc et al. |
| 2014/0154286 A1 | 6/2014 | Malley et al. |
| 2014/0154287 A1 | 6/2014 | Malley et al. |
| 2015/0374811 A1 | 12/2015 | Malley et al. |
| 2016/0090404 A1 | 3/2016 | Malley et al. |
| 2017/0021006 A1 | 1/2017 | Watson et al. |
| 2019/0119335 A1 | 4/2019 | Malley et al. |
| 2020/0087361 A1 | 3/2020 | Malley et al. |
| 2020/0222522 A1 | 7/2020 | Malley et al. |
| 2020/0407404 A1 | 12/2020 | Malley et al. |

FOREIGN PATENT DOCUMENTS

| | | |
|---|---|---|
| EP | 0497524 A2 | 8/1992 |
| EP | 1838345 A2 | 10/2007 |
| JP | H11-502820 A | 3/1999 |
| JP | 2001-505415 A | 4/2001 |
| JP | 2002-504096 A | 2/2002 |
| JP | 2002-521058 A | 7/2002 |
| JP | 2007-504237 A | 3/2007 |
| JP | 2008-509682 A | 4/2008 |
| JP | 2010-517532 A | 5/2010 |
| JP | 2014-514363 A | 6/2014 |

(Continued)

OTHER PUBLICATIONS

Chichili, G.R. et al., Phase 1/2 study of a novel 24-valent pneumococcal vaccine in healthy adults aged 18 to 64 years and in older adults aged 65 to 85 years, Vaccine, 40(31):4190-4198, (2022).

(Continued)

*Primary Examiner* — Brian Gangle
(74) *Attorney, Agent, or Firm* — Choate, Hall & Stewart LLP; Rolando Medina; Janet M. Tse

(57) ABSTRACT

Technologies for the prevention and/or treatment of pneumococcal infections.

38 Claims, 35 Drawing Sheets
Specification includes a Sequence Listing.

(56) References Cited

FOREIGN PATENT DOCUMENTS

| | | |
|---|---|---|
| JP | 2014-517835 A | 7/2014 |
| KR | 20080090411 A | 10/2008 |
| RU | 2164943 C2 | 4/2001 |
| RU | 2006117425 A | 12/2007 |
| RU | 2378008 C2 | 1/2010 |
| RU | 2407749 C2 | 12/2010 |
| WO | WO-90/11087 A1 | 10/1990 |
| WO | WO-1995/021195 A1 | 8/1995 |
| WO | WO-1996/029094 A1 | 9/1996 |
| WO | WO-1998/18930 A2 | 5/1998 |
| WO | WO-98/47530 A2 | 10/1998 |
| WO | WO-99/03884 A2 | 1/1999 |
| WO | WO-00/06737 A2 | 2/2000 |
| WO | WO-2000/06738 A2 | 2/2000 |
| WO | WO-01/40472 A2 | 6/2001 |
| WO | WO-02/077021 A2 | 10/2002 |
| WO | WO-2003/044185 A2 | 5/2003 |
| WO | WO-2003/094960 A2 | 11/2003 |
| WO | WO-2004/092209 A2 | 10/2004 |
| WO | WO-2005/037190 A2 | 4/2005 |
| WO | WO-2005/039501 A2 | 5/2005 |
| WO | WO-2006/017929 A1 | 2/2006 |
| WO | WO-2006/067632 A2 | 6/2006 |
| WO | WO-2006/084467 A1 | 8/2006 |
| WO | WO-2007/026249 A2 | 3/2007 |
| WO | WO-2007/067681 A2 | 6/2007 |
| WO | WO-2007/081583 A2 | 7/2007 |
| WO | WO-2007/150020 A1 | 12/2007 |
| WO | WO-2008/094986 A2 | 8/2008 |
| WO | WO-2008/119358 A2 | 10/2008 |
| WO | WO-2008/152448 A2 | 12/2008 |
| WO | WO-2009/016515 A2 | 2/2009 |
| WO | WO-2009/021548 A1 | 2/2009 |
| WO | WO-2009/029831 A1 | 3/2009 |
| WO | WO-2009/143413 A1 | 11/2009 |
| WO | WO-2010/053559 A1 | 5/2010 |
| WO | WO-2010/071986 A1 | 7/2010 |
| WO | WO-2010/081875 A1 | 7/2010 |
| WO | WO-2011/008548 A1 | 1/2011 |
| WO | WO-2011/137354 A2 | 11/2011 |
| WO | WO-2012/155007 A1 | 11/2012 |
| WO | WO-2012/155053 A1 | 11/2012 |
| WO | WO-2014/018904 A1 | 1/2014 |
| WO | WO-2014/124228 A1 | 8/2014 |
| WO | WO-2017/013548 A1 | 1/2017 |
| WO | WO-2018/183475 A1 | 10/2018 |
| WO | WO-2020/056127 A1 | 3/2020 |
| WO | WO-2020/056202 A1 | 3/2020 |

OTHER PUBLICATIONS

International Search Report for PCT/US2018/024810 (A Multiple Antigen Presenting System (MAPS)-Based *Staphylococcus aureus* Vaccine, Immunogenic Composition, and Uses Thereof, filed Mar. 28, 2018), issued by ISA/US, 6 pages (dated Aug. 31, 2018).
Written Opinion for PCT/US2018/024810 (A Multiple Antigen Presenting System (MAPS)-Based *Staphylococcus aureus* Vaccine, Immunogenic Composition, and Uses Thereof, filed Mar. 28, 2018), issued by ISA/US, 9 pages (dated Aug. 31, 2018).
Zhang, F. et al., Protection against *Staphylococcus aureus* Colonization and Infection by B- and T-Cell-Mediated Mechanisms, mBio, 9(5):e01949-18 (2018).
"Centers for Disease Control and Prevention." "Preventing pneumococcal disease among infants and young children." "Morbidity and Mortality Weekly Report. 49: 1-55 (2000)".
Ahmad, A. et al., Sequential release of antigens from chloroform-treated *Staphylococcus epidermidis*: application towards a possible vaccine, J. Appl. Bacteriol., 69(5):676-685 (1990).
Anttila, M. et al., Avidity of IgG for *Streptococcus pneumoniae* type 6B and 23F polysaccharides in infants primed with pneumococcal conjugates and boosted with polysaccharide or conjugate vaccines, J. Infect. Dis., 177(6):1614-1621 (1998).
Avci, F.Y. et al., A mechanism for glycoconjugate vaccine activation of the adaptive immune system and its implications or vaccine design, Nat. Med., 17(12): 1602-1609 (2011).
Basset, A. et al., Antibody-independent, CD4+ T-Cell-Dependent protection against pneumococcal colonization elicited by intranasal immunization with purified pneumococcal proteins, Infection and Immunity, 75(11):5460-5464 (2007).
Beghetto, E. et al., Discovery of novel *Streptococcus pneumoniae* antigens by screening a whole-genome lambda-display library, FEMS Microbial Lett., 262(1):14-21 (2006).
Berry, M. A. et al., Effect of Defined Point Mutations in Pneumolysin Gene on the Virulence of *Streptococcus pneumonia*, Infection and Immunity, 63(5):1969-1974 (1995).
Boslego et al., "Gonorrhea Vaccines" Vaccine and Immunotherapy Ch. 17 211 (1991).
Bowie, J. U. et al., Deciphering the message in protein sequences: tolerance to amino acid substitutions, Science, 257(4948):1306-1310 (1990).
Caierao, J. et al., Characteristics of serogroup 20 S.pneumoniae isolates from Brazil, BMC Infectious Diseases, 16:418 (2016).
Centers for Disease Control and Prevention. "Prevention of pneumococcal disease among infants and children—use of 13-valent pneumococcal conjugate vaccine and 23-valent pneumococcal polysaccharide vaccine." Morbidity and Mortality Weekly Report. 59: 1-24 (2010).
Colino, J. et al., Non-covalent association of protein and capsular polysaccharide on bacteria-sized latex beads as a model for polysaccharide-specific humoral immunity to intact Gram-positive extracellular bacteria, J. Immunol., 191(6): 3254-3263 (2013).
Colino, J. et al, Parameters Underlying Distinct T Cell-Dependent Polysaccharide-Specific IgG Responses to an Intact Gram-Positive Bacterium versus a Soluble Conjugate Vaccine, The Journal of Immunology, 1552-1559 (2009).
Cortajarena, A.L. et al., A receptor-binding region in *Escherichia coli* alpha-haemolysin, J. Biol. Chem., 278(21):19159-63 (2003).
Dagan, R. et al., Glycoconjugate vaccines and immune interference: A review, Vaccine, 28(34): 5513-5523 (2010).
Daniels, C. C. et al., The Proline-Rich Region of Pneumococcal Surface Proteins A and C Contains Surface-Accessible Epitopes Common to All Pneumococci and Elicits Antibody-Mediated Protection against Sepsis, Infection and Immunity, 78(5):2163-2172 (2010).
Database, UniProt KB/TrEMBL, B3Q265_RHIE6, retrieved Jan. 3, 2021.
Database, UniProt KB/TrEMBL, F2AA21_RHIET, retrieved Jan. 4, 2021.
Database, UniProt KB/TrEMBL, Q8KKW2_RHIEC, retrieved Jan. 4, 2021.
Douce, G. et al., Genetically detoxified mutants of heat-labile toxin from *Escherichia coli* are able to act as oral adjuvants, Infect Immun., 67(9):4400-4406 (1999).
Douce, G. et al., Mutants of *Escherichia coli* heat-labile toxin lacking ADP-ribosyltransferase activity act as non-toxic, mucosal adjuvants, PNAS 92:1644-1648 (1995).
Elgert, K. D., Immunology Understanding the Immune System, John Wiley & Sons, Inc. Hoboken, New Jersey, p. 111 (2009).
Ellis, New Technologies for making vaccines, Vaccine Ch. 29, 568-574 (1988).
Evans, J. T. et al., Enhancement of antigen-specific immunity via the TLR4 ligands MPL adjuvant and Ribi.529, Expert Rev Vaccines, 2(2):219-229 (2003).
Fauvart, M. et al., Genome Sequence of Rhizobium etli CNPAF512, a Nitrogen-Fixing Symbiont Isolated from Bean Root Nodules in Brazil, Journal of Bacteriology, 193(12): 3158-3159 (2011).
Ferreira, D. M. et al., DNA vaccines based on genetically detoxified derivatives of pneumolysin fail to protect mice against challenge with *Streptococcus pneumonia*, FEMS Immunology Med. Microbial 46: 291-297 (2006).
Gaj, T. et al., The AviD-tag, a NeutrAvidin/avidin specific peptide affinity tag for the immobilization and purification of recombinant proteins, Protein Expr. Purif., 56(1):54-61 (2007).

(56) References Cited

OTHER PUBLICATIONS

Giuliani, M. M. et al., Mucosal adjuvanticity and immunogenicity of LTR72, a novel mutant of *Escherichia coli* heat-labile enterotoxin with partial knockout of ADP-ribosyltransferase activity, J. Exp. Med., 187(7):1123-1132 (1998).

González, V. et al., The mosaic structure of the symbiotic plasmid of Rhizobium etli CFN42 and its relation to other symbiotic genome compartments, Genome Biol., 4(6): R36 (2003).

Greenspan, N. S. and Cera, E. D., Defining epitopes: It's not easy as it seems, Nature Biotechnology, 17:936-937 (1999).

Gruber, M.F. et al., Licensing of pneumococcal conjugate vaccines for children and adults: Regulatory perspective from the European Medicines Agency and the U.S. Food and Drug Administration, Pneumococcal Vaccines: The Impact of Conjugate Vaccine, 183-96 (2008).

Grun, C. H. et al., One-step biotinylation procedure for carbohydrates to study carbohydrate-protein interactions, Anal. Biochem., 354(1):54-63 (2006).

Helppolainen, S. H. et al., Bradavidin II from Bradyrhizobium japonicum: a new avidin-like biotin-binding protein, Biochim. Biophys. Acta., 1784(7-8):1002-10 (2008).

Helppolainen, S.H. et al., Rhizavidin from Rhizobium etli: the first natural dimer in the avidin protein family, Biochem J., 405(3): 397-405 (2007).

Hermanson, G. T., Bioconjugate Techniques, Elsevier Science, ProQuest Ebook Central, http://ebookcentral.proquest.com/lib.uspto-ebooks/detail.action?docID=307203, created from uspto-ebooks on Sep. 6, 2017, 570-592 (1996).

Holliger, P. et al., "Diabodies": small bivalent and bi specific antibody fragments, Proc. Natl. Acad, Sci, USA, 90:6444-6448 (1993).

Hsu, T-L. et al., Profiling Carbohydrate-Receptor Interaction with Recombinant Innate Immunity Receptor-Fc Fusion Proteins, J. Biol. Chem., 284(50): 34479-34489 (2009).

Huang, H. et al., Robust stimulation of humoral and cellular immune responses following vaccination with antigen-loaded beta-glucan particles, MBio, 1(3):e00164-10 (2010).

Hytonen, V.P. et al., Efficient production of active chicken avidin using a bacterial signal peptide in *Escherichia coli*, Biochem J., 384(Pt 2): 385-90 (2004).

Insel, R. et al., Response to oligosaccharide-protein conjugate vaccine against Hemophilus influenzae b in two patients with IgG2 deficiency unresponsive to capsular polysaccharide vaccine, N. Engl J. Med., 315:8, p. 499-503 (1986).

International Search Report for PCT/US19/50800, 4 pages (dated Dec. 31, 2019).

International Search Report for PCT/US2012/037412 (Multiple Antigen Presenting Immunogenic Composition, and Methods and Uses Thereof, filed May 11, 2012), issued by ISA/FIPS, 3 pages (dated Aug. 23, 2012).

International Search Report for PCT/US2012/037541 (Modified Biotin-Binding Protein, Fusion Proteins Thereof and Applications, filed May 11, 2012), issued by ISA/FIPS, 4 pages (dated Aug. 30, 2012).

International Search Report for PCT/US2014/015254 (Protein Antigens That Provide Protection Against Pneumococcal Colonization and/or Disease, filed Feb. 7, 2014), issued by ISA/US, 4 pages (dated May 5, 2014).

International Search Report for PCT2019050907, 5 pages (dated Feb. 2, 2020).

Ishizaka, S.T. and Hawkins, L.D., E6020: a synthetic Toll-like receptor 4 agonist as a vaccine adjuvant, Expert Rev. Vaccines, 6(5):773-784 (2007).

Izard, J. W. and Kendall, D. A., Signal peptides: exquisitely designed transport promoters, Mol. Microbiol. 13(5):765-73 (1994).

Jin, Z. et al., Conjugates of group A and W135 capsular polysaccharides of neisseria meningitidis bound to recombinant *Staphylococcus aureus* enterotoxin C1: preparation, physicochemical characterization, and immunological properties in mice, Infect Immun, 73(12)7887-7893 (2005).

Kehoe, M. et al., Cloning, Expression, and Mapping of the *Staphylococcus aureus* a-Hemolysin Determinant in *Escherichia coli* K-12, 41(3):1105-1111 (1985).

Kim, K. H. et al., Efficiency of a Pneumococcal Opsonophagocytic Killing Assay Improved by Multiplexing and by Coloring Colonies, Clin. Diagn. Lab. Immunol., 10(4):616-621 (2003).

Kojima, K. et al., Quantitation of IgG subclass antibodies to pneumococcal capsular polysaccharides by ELISA, using Pneumovax-specific antibodies as a reference, Tohoku J. Exp. Med., 161(3):209-215 (1990).

Koskela, M. and Leinonen, M., Comparison of ELISA and RIA for measurement of pneumococcal antibodies before and after vaccination with 14-valent pneumococcal capsular polysaccharide vaccine, J. Clin. Pathol., 34(1):93-98 (1981).

Laine, C. et al., Age-specific immunoglobulin G (IgG) and IgA to pneumococcal protein antigens in a population in coastal Kenya, Infection and Immunity, 72(6):3331-3335 (2004).

Lees, A. et al., Enhanced immunogenicity of protein-dextran conjugates: I. Rapid stimulation of enhanced antibody responses to poorly immunogenic molecules, Vaccine, 12(13): 1160-1166 (1994).

Ling, E. et al., Glycolytic enzymes associated with the cell surface of *Streptococcus pneumoniae* are antigenic in humans and elicit protective immune responses in the mouse, Clin. Exp. Immunol., 138:290-298 (2004).

Lu, Y. J. et al., A Bivalent Vaccine to Protect against *Streptococcus pneumoniae* and *Salmonella typhi*, Vaccine, 30(23):3405-3412 (2012).

Lu, Y. J. et al., Protection against Pneumococcal Colonization and Fatal Pneumonia by a Trivalent Conjugate of a Fusion Protein with the Cell Wall Polysaccharide, Infection and Immunity, 77(5):2076-2083 (2009).

Lu, Y. J. et al., Interleukin-17A Mediates Acquired Immunity to Pneumococcal Colonization, PLoS Pathogens, 4(9):1-11 (2008).

Malley, R. et al., Antibody and cell-mediated immunity to *Streptococcus pneumoniae*: implications for vaccine development, Journal of Molecular Medicine, 88(2):135-142 (2010).

Malley, R. et al., CD4+T Cells Mediate Antibody-Independent Acquired Immunity to Pneumococcal Colonization, PNAS, 102(13):4848-4853 (2005).

Malley, R. et al., Intranasal Immunization with Killed Unencapsulated Whole Cells Prevents Colonization and Invasive Disease by Capsulated Pneumococci, Infection and Immunity, 69(8):4870-4873 (2001).

Malley, R. et al., Multiserotype Protection of Mice Against Pneumococcal Colonization of the Nasopharynx and Middle 3 Ear by Killed Nonencapsulated Cells Given Intranasally with a Nontoxic Adjuvant, Infection and Immunity, 72 (7):4290-4292 (2004).

Martinez, J. E. et al., A flow cytometric opsonophagocytic assay for measurement of functional antibodies elicited after vaccination with the 23-valent pneumococcal polysaccharide vaccine, Clin. Diagn. Lab Immunol., 6(4):581-586 (1999).

Moffitt, K. L. et al., Identification of Protective Pneumococcal Th 17 Antigens from the Soluble Fraction of a Killed Whole Cell Vaccine, PLoS One 7(8):e43445 (2012).

Moffitt, K. L. et al., TH17-Based vaccine design for prevention of *Streptococcus pneumoniae* colonization, Cell Host and Microbe, 9:158-165 (2011).

Munro, C. S. et al., Assessment of biological activity of immunoglobulin preparations by using opsonized micro-organisms to stimulate neutrophil chemiluminescence, Clin. Exp. Immunol., 61(1):183-188 (1985).

Nordlund, H. R. et al., Tetravalent single-chain avidin: from subunits to protein domains via circularly permuted avidins, Biochem. J., 392(Pt 3): 485-491 (2005).

Nuorti, J. P. and Whitney, C. G., Prevention of pneumococcal disease among infants and children—use of 13-valent pneumococcal conjugate vaccine and 23-valent pneumococcal polysaccharide vaccine, Morbidity and Mortality Weekly Report, 59:1-24 (2010).

Ojo-Amaize, E. A. et al., A rapid and sensitive chemiluminescence assay for evaluation of functional opsonic activity of Haemophilus influenzae type b-specific antibodies, Clin. Diagn. Lab. Immunol., 2(3):286-290 (1995).

(56) References Cited

OTHER PUBLICATIONS

O'Reilly, M. et al., Inactivation of the alpha-haemolysin gene of *Staphylococcus aureus* 8325-4 by site-directed mutagenesis and studies on the expression of its haemolysins, Microbial Pathogenesis, 1:125-138 (1986).
Paton, P C. et al., Purification and immunogenicity of genetically obtained pneumolysin toxoids and their conjugation to *Streptococcus pneumoniae* type 19F polysaccharide, Infect. Lmmun., 59(7):2297-2304 (1991).
PNEUMOVAX® 23 (prescribing information). Whitehouse Station, NJ: Merck & Co.; May 2015.
Poljak, R. J., Production and structure of diabodies, Structure. 2(12):1121-1123 (1994).
Pollabauer, E. M. et al., The influence of carrier protein on the immunogenicity of simultaneously administered conjugate vaccines in infants, Vaccine, 27(11): 1674-1679 (2009).
Portnoi, M. et al., The vaccine potential of *Streptococcus pneumoniae* surface lectin- and non-lectin proteins, Vaccine, 24:1868-1873 (2006).
PREVNAR 13® (prescribing information). New York, NY: Pfizer; Aug. 2017.
Richter, S. S. et al., Changes in pneumococcal serotypes and antimicrobial resistance after introduction of the 13 valent conjugate vaccine in the United States, Antimicrob Agents Chemother., 58:6484-6489 (2014).
Romero-Steiner, S. et al., Avidity determinations for Haemophilus influenzae Type b anti-polyribosylribitol phosphate antibodies, Clin. Diagn. Lab. Immunol., 12(9):1029-1035 (2005).
Romero-Steiner, S. et al., Standardization of an opsonophagocytic assay for the measurement of functional antibody activity against *Streptococcus pneumoniae* using differentiated HL-60 cells, Clin. Diagn. Lab. Immunol., 4(4):415-422 (1997).
Rosenberg, I.M., Protein Analysis and Purification, Springer Science + Business Media New York, 153-182 (1996).
Saeland, E. et al., Pneumococcal pneumonia and bacteremia model in mice for the analysis of protective antibodies, Microb. Pathog., 29(2):81-91 (2000).
Sanabria-Valentin, Dissertation, Department of Basic Medical Sciences, NYU, p. 8-9 describing the general structure of LPS (2008).
Sano, T. et al, Methods in Enzymology, Elsevier, 326: 305-307 (2000).
Saunders, F. K. et al., Pneumolysin, the thiol-activated toxin of *Streptococcus pneumoniae*, does not require a thiol group for in vitro activity, Infect. Immun. 57(8):2547-2552 (1989).
Scott, D. et al., Immunogenicity of biotinylated hapten-avidin complexes, Mol. Immunol., 21(11):1055-1060 (1984).
Sen, G. et al., In vivo humoral immune responses to isolated Pneumococcal polysaccharides are dependent on the presence of associated TLR ligands, The Journal of Immunology, 175(5):3084-3091 (2005).
Singh, M. and Indresh S., Advances in vaccine adjuvants for infectious diseases, Current HIV research 1(3):309-320 (2003).
Skolnick, J. and Fetrow, J. S., From genes to protein structure and function: novel applications of computational approaches in the genomic era, Trends in Biotechnology, 18: 34-39 (2000).
Stack, A. M. et al., Minimum protective serum concentrations of pneumococcal anti-capsular antibodies in infant rats, J. Infect. Dis., 177(4):986-990 (1998).
Takakura, Y. et al., Tamavidin, a versatile affinity tag for protein purification and immobilization, J. Biotechnol., 145(4): 317-322 (2010).
Thermo Scientific Avidin-Biotin Technical Handbook, 2009, p. 16-17. Found on the Internet on May 5, 2016 at: https://www.thermofisher.com/content/dam/LifeTech/Images/integration/1601675_AvBi_HB_INTL.pdf.
Trzcinski, K. et al., Antibodies to Conserved Pneumococcal Antigens Correlate with, but Are Not Required for, 5 Protection Against Pneumococcal Colonization Induced by Prior Exposure in a Mouse Model, Infection and Immunity, 73(10):7043-7046 (2005).
Vickerman, M. M. et al., Genome-wide transcriptional changes in *Streptococcus gordonii* in response to competence signaling peptide, Journal of Bacteriology, 189(21):7799-7807 (2007).
Wardenburg, J. and Schneewind, O., Vaccine protection against *Staphylococcus aureus* pneumonia, J. Exp. Med., 205(2): 287-94 (2008).
Williams et al., Innate Imprinting by the Modified Heat-Labile Toxin of *Escherichia coli* (LTK63) Provides Generic Protection against Lung Infectious Disease, The Journal of Immunology, 173: 7435-7443 (2004).
Wizeman et al., Use of a while Genome Approach to Identify Vaccine Molecules Affording Protection against *Streptococcus pneumoniae* Infection, Infection and Immunity, 69(3):1593-1598 (2001).
Written Opinion for PCT/US19/50800, 8 pages (dated Dec. 31, 2019).
Written Opinion for PCT/US2012/037412 (Multiple Antigen Presenting Immunogenic Composition, and Methods and Uses Thereof, filed May 11, 2012), issued by ISA/FIPS, 4 pages (dated Aug. 23, 2012).
Written Opinion for PCT/US2012/037541 (Modified Biotin-Binding Protein, Fusion Proteins Thereof and Applications, filed May 11, 2012), issued by ISA/FIPS, 3 pages (dated Aug. 30, 2012).
Written Opinion for PCT/US2014/015254 (Protein Antigens That Provide Protection Against Pneumococcal Colonization and/or Disease, filed Feb. 7, 2014), issued by ISA/US, 5 pages (dated May 5, 2014).
Written Opinion for PCT2019050907, 6 pages (dated Feb. 2, 2020).
Wu, W. et al., Th17-stimulating protein vaccines confer protection against Pseudomonas aeruginosa pneumonia, Am. J. Respir. Grit. Care Med., 186(5):420-427 (2012).
Zhang, F. et al., Design and evaluation of multiple antigen presenting system (MAPS)-based pneumococcal vaccine to prevent invasive disease and carriage, poster presented at the 10th International Symposium on Pneumococci and Pneumococcal Diseases (ISPPD-10), Glasgow, Scotland, Jun. 26-30, 2016.
Zhang, F. et al., Multiple antigen-presenting system (MAPS) to induce comprehensive B- and T-cell immunity, Proc. Natl. Acad. Sci., 110(33):13564-13569 (2013).

| TYPE | STRUCTURE | ADDITIONAL INFORMATION |
|---|---|---|
| 4 | [→3D-ManpNAc1→3L-FucpNAc1→3D-GalpNAc1→4D-Galp1→]n, 3↑Pyr↓2 | MW: 847.283<br>Monosaccharides: 1 D-Gal, 1 D-GalNac, 1 D-ManNac, 1 L-FucNac<br>Structure: Linear<br>Net Charge: −1<br>Pyruvate: 1 |
| 5 | [→4D-Galp1→4L-FucpNAc1→3D-Sugp1→]n, L-PnepNAc1→2D-GlcpA1↓3 | MW: 919.305<br>Monosaccharides: 1 D-Glc, 1 L-FucNac, 1 D-GlcA, 1 D-Sug, 1 L-PneNAc<br>D-Sug: 2-acetamido-2,6,-dideoxy-D-xylohexos-4-ulose (pneumosamine)<br>L-PneNac: 2-acetamido-2,6,-dideoxy-L-talose<br>Structure: Branched<br>Net Charge: −1 |
| 6A | [→2D-Galp1→3D-Glcp1→3L-Rhap1→4D-Ribitol5→PO4→]n | MW: 706.170<br>Monosaccharides: 1 D-Glc, 1 D-Gal, 1 L-Rha, 1 Ribitol<br>Structure: Linear<br>Net Charge: −1<br>Phosphorous: 1 in polysaccharide backbone |

FIG. 3 Continued

| TYPE | STRUCTURE | ADDITIONAL INFORMATION |
|---|---|---|
| 6B | 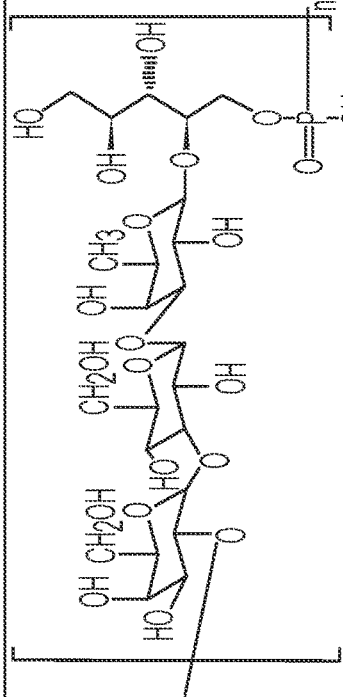 | MW: 706.170<br><br>Monosaccharides: 1 D-Glc, 1 D-Gal, 1 L-Rha, 1 Ribitol<br>Structure: Linear<br>Net Charge: -1<br>Phosphorous: 1 in polysaccharide backbone |
| 7F | 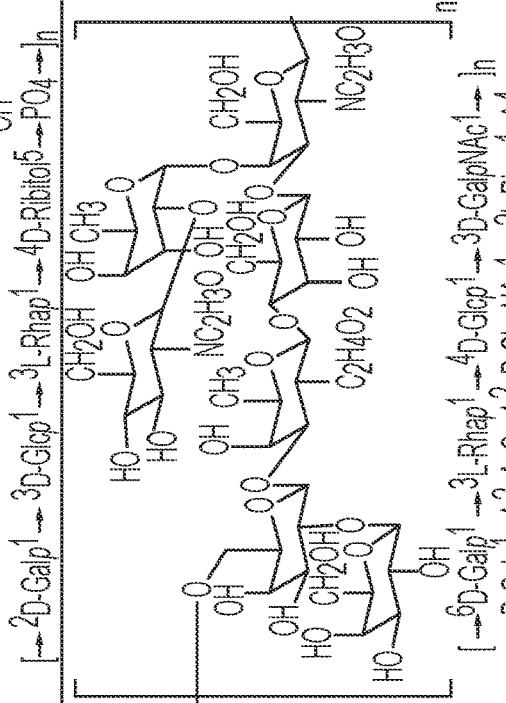 | MW: 1,226.444<br><br>Monosaccharides: 1 D-Glc, 2 D-Gal, 2 L-Rha, 1 D-GlcNac, 1 D-GalNac<br>Structure: Branched<br>Net Charge: 0<br>O-Acetate: 1 |
| 8 | 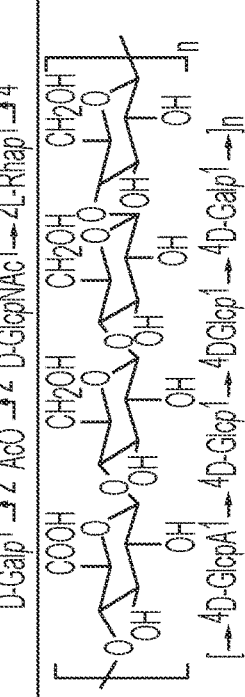 | MW: 684.528<br><br>Monosaccharides: 2 D-Glc, 1 D-Gal, 1 D-GlcA<br>Structure: Linear<br>Net Charge: -1 |

FIG. 3
Continued

| TYPE | STRUCTURE | ADDITIONAL INFORMATION |
|---|---|---|
| 9N | [→4D-GlcpA1→3D-Galp1→3D-ManpNAc1→4D-Glcp1→4D-GlcpNAc1→]n | MW: 928.772<br>Monosaccharides: 1 D-Glc, 1 D-Gal, 1D-GlcNac, 1 D-ManNac, 1 D-GlcA<br>Structure: Linear<br>Net Charge: −1 |
| 9V | [→4D-GlcpA1→3D-Galp1→3D-ManpNAc1→4D-Glcp1→4D-Glcp1→]n | MW: 971.794<br>Monosaccharides: 2 D-Glc, 1 D-Gal, 1 D-ManNac, 1 D-GlcA<br>Structure: Linear<br>Net Charge: −1<br>O-Acetate: 2 |
| 10A | [→5D-Galf1→3D-Galp1→4D-GalpNAc1→3D-Galp1→2D-Ribitol5→PO4→]n<br>D-Glcp1→6<br>D-Galf1→3 | MW: 1,249.989<br>Monosaccharides: 5 D-Gal, 1 D-GalNac, 1 Ribitol<br>Structure: Branched<br>Net Charge: −1<br>Phosphorous: 1 in polysaccharide backbone |

FIG. 3
Continued

| TYPE | STRUCTURE | ADDITIONAL INFORMATION |
|---|---|---|
| 11A | 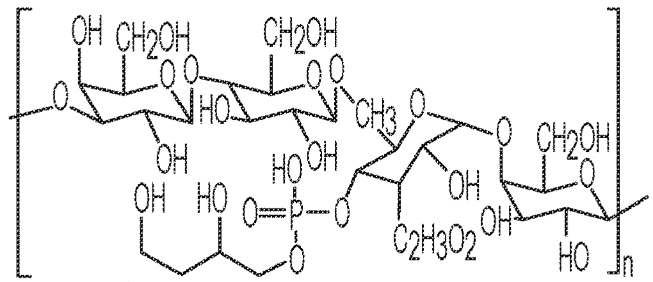 | MW: 933.900<br><br>Monosaccharides: 2 D-Glc, 2 D-Gal, 1 Glycerol<br>Structure: Linear<br>Net Charge: -1<br>Phosphorous: 1 in polysaccharide sidechaine<br>O-Acetate: 1 |
| 12F | 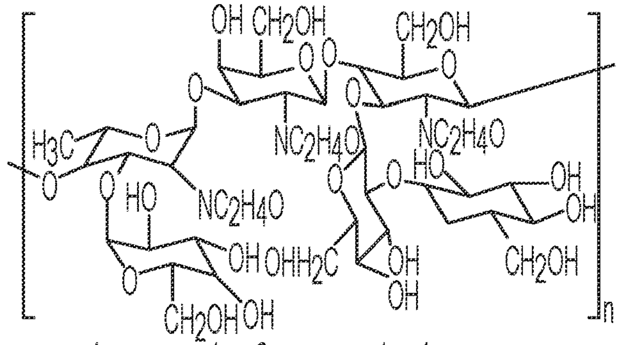 | Monosaccharides: 2 D-Glc, 1 D-Gal, 1 D-GalNac, 1 L-FucNac, 1D-ManNacA<br>Structure: Branched<br>Net Charge: -1<br><br>MW: 1,116.02 |
| 14 | 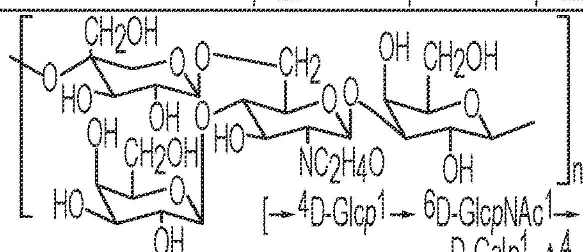 | Monosaccharides: 1 D-Glc, 2 D-Gal, 1 D-GlcNac<br>Structure: Branched<br>Net Charge: 0<br><br>MW: 689.238 |

| TYPE | STRUCTURE | ADDITIONAL INFORMATION |
|---|---|---|
| 15B | 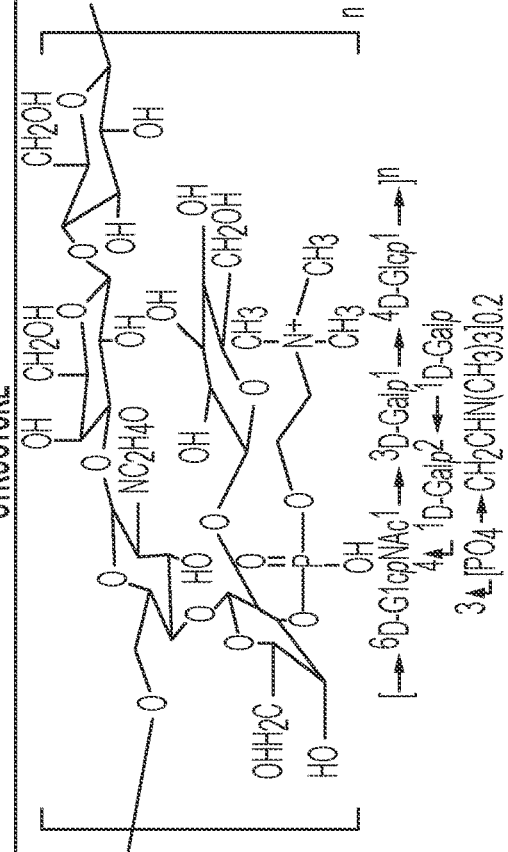 | MW: 1,011,420<br><br>Monosaccharides: 1 D-Glc, 3 D-Gal, 1 D-GlcNac<br>Structure: Branched<br>Net Charge: -1<br>Phosphorous: 1 in polysaccharide sidechain<br>O-Acetate: 1<br>Pyruvate: 1<br>Note: Published stucture indicates 0.2 mol of phosphocholine per mol of repeat unit. Nuclear magnetic resonance analysis at Merck suggests that phosphocholine is not present. |
| 17F | 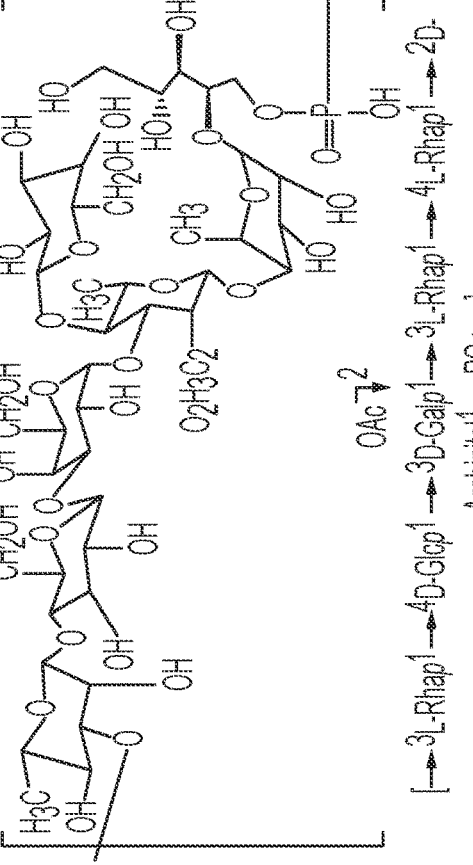 | MW: 1,202,920<br><br>Monosaccharides: 1 D-Glc, 2 D-Gal, 3 L-Rha, 1 Arabinitol<br>Structure: Branched<br>Net Charge: -1<br>Phosphorous: 1 in polysaccharide backbone<br>O-Acetate: 1<br>Pyruvate: |

FIG. 3 cont'd

| TYPE | STRUCTURE | ADDITIONAL INFORMATION |
|---|---|---|
| 18C | [→4D-Glcp1→4D-Galp1→3L-Rhap1→]$_n$<br>D-Glcp1→2<br>Glycerol1→PO$_4$→3 | MW: 1,012.265<br><br>Monosaccharides: 3 D-Glc, 1 D-Gal, 1 L-Rha, 1 Glycerol<br>Structure: Branched<br>Net Charge: -1<br>Phosphorous: 1 in polysaccharide sidechain<br>O-Acetate: 1 |
| 19A | [→4D-ManpNAc1→4D-Glcp1→3L-Rhap1→PO$_4$→]$_n$ | MW: 613.138<br><br>Monosaccharides: 1 D-Glc, 1 L-Rha, 1 D-ManNac<br>Structure: Linear<br>Net Charge: -1<br>Phosphorous: 1 in polysaccharide backbone |
| 19F | [→4D-ManpNAc1→4D-Glcp1→2L-Rhap1→PO$_4$→]$_n$ | MW: 613.138<br><br>Monosaccharides: 1 D-Glc, 1 L-Rha, 1 D-ManNac<br>Structure: Linear<br>Net Charge: -1<br>Phosphorous: 1 in polysaccharide backbone |

FIG. 3 cont'd

| TYPE | STRUCTURE | ADDITIONAL INFORMATION |
|---|---|---|
| 18C | [→6D-Glcp1→6D-Glcp1→3D-Galf1→3D-Glcp1→3D-GlcpNAc1→PO₄→]n<br>D-Galf1↓4 | MW: 1,391,498<br>Monosaccharides: 3 D-Glc, 2 D-Gal, 1 D-GlcNac<br>Structure: Branched<br>Net Charge: -1<br>Phosphorous: 1 in polysaccharide backbone<br>O-Acetate: 1 |
| 22F | [→4D-GlcpA1→4L-Rhap1→4D-Glcp1→3D-Galf1→2L-Rhap1→]n<br>D-Glcp1↓3<br>OAc↓2 | MW: 1,010,447<br>Monosaccharides: 2 D-Glc, 1 D-Gal, 2 L-Rha, 1 D-GlcA<br>Structure: Branched<br>Net Charge: -1<br>O-Acetate: 1 |

FIG. 3 cont'd

| TYPE | STRUCTURE | ADDITIONAL INFORMATION |
|---|---|---|
| 23F | [→4D-Glcp1→4D-Galp1→4L-Rhap1→]<br>L-Rhap1↑2  3<br>Glycerol2→PO4 | MW: 792.207<br><br>Monosaccharides: 1 D-Glc, 1 D-Gal, 2 L-Rha, 1 Glycerol<br>Structure: Branched<br>Net Charge: -1<br>Phosphorous: 1 in polysaccharide sidechain |
| 33F | [→3D-Galp1→3D-Galf1→3D-Galf1→3D-Glcp1→5D-Galf1→]n<br>D-Galp1↑2  2<br>OAc | MW: 993.862<br><br>Monosaccharides: 1 D-Glc, 5 D-Gal<br>Structure: Branched<br>Net Charge: 0<br>O-Acetate: 1 |

SEQUENCE LISTING

<160> NUMBER OF SEQ ID NOS: 14

<210> SEQ ID NO 1
<211> LENGTH: 179

```
<212> TYPE: PRT
<213> ORGANISM: Unknown
<220> FEATURE:
<223> OTHER INFORMATION: Description of Unknown:
      Rhizavidin protein sequence

<400> SEQUENCE: 1

Met Ile Ile Thr Ser Leu Tyr Ala Thr Phe Gly Thr Ile Ala Asp Gly
1               5                   10                  15

Arg Arg Thr Ser Gly Gly Lys Thr Met Ile Arg Thr Asn Ala Val Ala
                20                  25                  30

Ala Leu Val Phe Ala Val Ala Thr Ser Ala Leu Ala Phe Asp Ala Ser
            35                  40                  45

Asn Phe Lys Asp Phe Ser Ser Ile Ala Ser Ala Ser Ser Ser Trp Gln
    50                  55                  60

Asn Gln Ser Gly Ser Thr Met Ile Ile Gln Val Asp Ser Phe Gly Asn
65                  70                  75                  80

Val Ser Gly Gln Tyr Val Asn Arg Ala Gln Gly Thr Gly Cys Gln Asn
                85                  90                  95

Ser Pro Tyr Pro Leu Thr Gly Arg Val Asn Gly Thr Phe Ile Ala Phe
            100                 105                 110

Ser Val Gly Trp Asn Ser Thr Glu Asn Cys Asn Ser Ala Thr Gly
    115                 120                 125

Trp Thr Gly Tyr Ala Gln Val Asn Gly Asn Asn Thr Glu Ile Val Thr
130                 135                 140

Ser Trp Asn Leu Ala Tyr Glu Gly Gly Ser Gly Pro Ala Ile Glu Gln
145                 150                 155                 160

Gly Gln Asp Thr Phe Gln Tyr Val Pro Thr Thr Glu Asn Lys Ser Leu
                165                 170                 175

Leu Lys Asp

<210> SEQ ID NO 2
<211> LENGTH: 135
<212> TYPE: PRT
<213> ORGANISM: Unknown
<220> FEATURE:
<223> OTHER INFORMATION: Description of Unknown:
      Rhizavidin protein sequence

<400> SEQUENCE: 2

Phe Asp Ala Ser Asn Phe Lys Asp Phe Ser Ser Ile Ala Ser Ala Ser
1               5                   10                  15

Ser Ser Trp Gln Asn Gln Ser Gly Ser Thr Met Ile Ile Gln Val Asp
                20                  25                  30

Ser Phe Gly Asn Val Ser Gly Gln Tyr Val Asn Arg Ala Gln Gly Thr
            35                  40                  45

Gly Cys Gln Asn Ser Pro Tyr Pro Leu Thr Gly Arg Val Asn Gly Thr
    50                  55                  60

Phe Ile Ala Phe Ser Val Gly Trp Asn Ser Thr Glu Asn Cys Asn
65                  70                  75                  80

Ser Ala Thr Gly Trp Thr Gly Tyr Ala Gln Val Asn Gly Asn Asn Thr
                85                  90                  95

Glu Ile Val Thr Ser Trp Asn Leu Ala Tyr Glu Gly Gly Ser Gly Pro
            100                 105                 110

Ala Ile Glu Gln Gly Gln Asp Thr Phe Gln Tyr Val Pro Thr Thr Glu
    115                 120                 125

Asn Lys Ser Leu Leu Lys Asp
```

```
            130                 135

<210> SEQ ID NO 3
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Gly Gly Gly Ser Ser Ser
1               5

<210> SEQ ID NO 4
<211> LENGTH: 367
<212> TYPE: PRT
<213> ORGANISM: Streptococcus pneumoniae

<400> SEQUENCE: 4

Phe Arg Gln Pro Ser Gln Thr Ala Leu Lys Asp Glu Pro Thr His Leu
1               5                   10                  15

Val Val Ala Lys Glu Gly Ser Val Ala Ser Ser Val Leu Leu Ser Gly
            20                  25                  30

Thr Val Thr Ala Lys Asn Glu Gln Tyr Val Tyr Phe Asp Ala Ser Lys
        35                  40                  45

Gly Asp Leu Asp Glu Ile Leu Val Ser Val Gly Asp Lys Val Ser Glu
    50                  55                  60

Gly Gln Ala Leu Val Lys Tyr Ser Ser Ser Glu Ala Gln Ala Ala Tyr
65                  70                  75                  80

Asp Ser Ala Ser Arg Ala Val Ala Arg Ala Asp Arg His Ile Asn Glu
                85                  90                  95

Leu Asn Gln Ala Arg Asn Glu Ala Ala Ser Ala Pro Ala Pro Gln Leu
            100                 105                 110

Pro Ala Pro Val Gly Gly Glu Asp Ala Thr Val Gln Ser Pro Thr Pro
        115                 120                 125

Val Ala Gly Asn Ser Val Ala Ser Ile Asp Ala Gln Leu Gly Asp Ala
    130                 135                 140

Arg Asp Ala Arg Ala Asp Ala Ala Ala Gln Leu Ser Lys Ala Gln Ser
145                 150                 155                 160

Gln Leu Asp Ala Thr Thr Val Leu Ser Thr Leu Glu Gly Thr Val Val
                165                 170                 175

Glu Val Asn Ser Asn Val Ser Lys Ser Pro Thr Gly Ala Ser Gln Val
            180                 185                 190

Met Val His Ile Val Ser Asn Glu Asn Leu Gln Val Lys Gly Glu Leu
        195                 200                 205

Ser Glu Tyr Asn Leu Ala Asn Leu Ser Val Gly Gln Glu Val Ser Phe
    210                 215                 220

Thr Ser Lys Val Tyr Pro Asp Lys Lys Trp Thr Gly Lys Leu Ser Tyr
225                 230                 235                 240

Ile Ser Asp Tyr Pro Lys Asn Asn Gly Glu Ala Ala Ser Pro Ala Ala
                245                 250                 255

Gly Asn Asn Thr Gly Ser Lys Tyr Pro Tyr Thr Ile Asp Val Thr Gly
            260                 265                 270

Glu Val Gly Asp Leu Lys Gln Gly Phe Ser Val Asn Ile Glu Val Lys
        275                 280                 285

Ser Lys Thr Lys Ala Ile Leu Val Pro Val Ser Ser Leu Val Met Asp
```

```
                290                 295                 300
Asp Ser Lys Asn Tyr Val Trp Ile Val Asp Glu Gln Gln Lys Ala Lys
305                 310                 315                 320

Lys Val Glu Val Ser Leu Gly Asn Ala Asp Ala Glu Asn Gln Glu Ile
            325                 330                 335

Thr Ser Gly Leu Thr Asn Gly Ala Lys Val Ile Ser Asn Pro Thr Ser
            340                 345                 350

Ser Leu Glu Glu Gly Lys Glu Val Lys Ala Asp Glu Ala Thr Asn
            355                 360                 365

<210> SEQ ID NO 5
<211> LENGTH: 252
<212> TYPE: PRT
<213> ORGANISM: Streptococcus pneumoniae

<400> SEQUENCE: 5

Thr Ser Gly Asp Asn Trp Ser Lys Tyr Gln Ser Asn Lys Ser Ile Thr
1               5                   10                  15

Ile Gly Phe Asp Ser Thr Phe Val Pro Met Gly Phe Ala Gln Lys Asp
            20                  25                  30

Gly Ser Tyr Ala Gly Phe Asp Ile Asp Leu Ala Thr Ala Val Phe Glu
        35                  40                  45

Lys Tyr Gly Ile Thr Val Asn Trp Gln Pro Ile Asp Trp Asp Leu Lys
50                  55                  60

Glu Ala Glu Leu Thr Lys Gly Thr Ile Asp Leu Ile Trp Asn Gly Tyr
65                  70                  75                  80

Ser Ala Thr Asp Glu Arg Arg Glu Lys Val Ala Phe Ser Asn Ser Tyr
                85                  90                  95

Met Lys Asn Glu Gln Val Leu Val Thr Lys Lys Ser Ser Gly Ile Thr
            100                 105                 110

Thr Ala Lys Asp Met Thr Gly Lys Thr Leu Gly Ala Gln Ala Gly Ser
        115                 120                 125

Ser Gly Tyr Ala Asp Phe Glu Ala Asn Pro Glu Ile Leu Lys Asn Ile
130                 135                 140

Val Ala Asn Lys Glu Ala Asn Gln Tyr Gln Thr Phe Asn Glu Ala Leu
145                 150                 155                 160

Ile Asp Leu Lys Asn Asp Arg Ile Asp Gly Leu Leu Ile Asp Arg Val
                165                 170                 175

Tyr Ala Asn Tyr Tyr Leu Glu Ala Glu Gly Val Leu Asn Asp Tyr Asn
            180                 185                 190

Val Phe Thr Val Gly Leu Glu Thr Glu Ala Phe Ala Val Gly Ala Arg
        195                 200                 205

Lys Glu Asp Thr Asn Leu Val Lys Lys Ile Asn Glu Ala Phe Ser Ser
210                 215                 220

Leu Tyr Lys Asp Gly Lys Phe Gln Glu Ile Ser Gln Lys Trp Phe Gly
225                 230                 235                 240

Glu Asp Val Ala Thr Lys Glu Val Lys Glu Gly Gln
                245                 250

<210> SEQ ID NO 6
<211> LENGTH: 765
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 6

```
Met Phe Asp Ala Ser Asn Phe Lys Asp Phe Ser Ser Ile Ala Ser Ala
1               5                   10                  15

Ser Ser Ser Trp Gln Asn Gln Ser Gly Ser Thr Met Ile Ile Gln Val
            20                  25                  30

Asp Ser Phe Gly Asn Val Ser Gly Gln Tyr Val Asn Arg Ala Gln Gly
        35                  40                  45

Thr Gly Cys Gln Asn Ser Pro Tyr Pro Leu Thr Gly Arg Val Asn Gly
    50                  55                  60

Thr Phe Ile Ala Phe Ser Val Gly Trp Asn Asn Ser Thr Glu Asn Cys
65                  70                  75                  80

Asn Ser Ala Thr Gly Trp Thr Gly Tyr Ala Gln Val Asn Gly Asn Asn
                85                  90                  95

Thr Glu Ile Val Thr Ser Trp Asn Leu Ala Tyr Glu Gly Gly Ser Gly
                100                 105                 110

Pro Ala Ile Glu Gln Gly Gln Asp Thr Phe Gln Tyr Val Pro Thr Thr
            115                 120                 125

Glu Asn Lys Ser Leu Leu Lys Asp Gly Gly Gly Ser Ser Ser Thr
    130                 135                 140

Ser Gly Asp Asn Trp Ser Lys Tyr Gln Ser Asn Lys Ser Ile Thr Ile
145                 150                 155                 160

Gly Phe Asp Ser Thr Phe Val Pro Met Gly Phe Ala Gln Lys Asp Gly
                165                 170                 175

Ser Tyr Ala Gly Phe Asp Ile Asp Leu Ala Thr Ala Val Phe Glu Lys
            180                 185                 190

Tyr Gly Ile Thr Val Asn Trp Gln Pro Ile Asp Trp Asp Leu Lys Glu
        195                 200                 205

Ala Glu Leu Thr Lys Gly Thr Ile Asp Leu Ile Trp Asn Gly Tyr Ser
    210                 215                 220

Ala Thr Asp Glu Arg Arg Glu Lys Val Ala Phe Ser Asn Ser Tyr Met
225                 230                 235                 240

Lys Asn Glu Gln Val Leu Val Thr Lys Lys Ser Ser Gly Ile Thr Thr
                245                 250                 255

Ala Lys Asp Met Thr Gly Lys Thr Leu Gly Ala Gln Ala Gly Ser Ser
                260                 265                 270

Gly Tyr Ala Asp Phe Glu Ala Asn Pro Glu Ile Leu Lys Asn Ile Val
            275                 280                 285

Ala Asn Lys Glu Ala Asn Gln Tyr Gln Thr Phe Asn Glu Ala Leu Ile
        290                 295                 300

Asp Leu Lys Asn Asp Arg Ile Asp Gly Leu Leu Ile Asp Arg Val Tyr
305                 310                 315                 320

Ala Asn Tyr Tyr Leu Glu Ala Glu Gly Val Leu Asn Asp Tyr Asn Val
                325                 330                 335

Phe Thr Val Gly Leu Glu Thr Glu Ala Phe Ala Val Gly Ala Arg Lys
                340                 345                 350

Glu Asp Thr Asn Leu Val Lys Lys Ile Asn Glu Ala Phe Ser Ser Leu
            355                 360                 365

Tyr Lys Asp Gly Lys Phe Gln Val Ile Ser Gln Lys Trp Phe Gly Glu
        370                 375                 380

Asp Val Ala Thr Lys Glu Val Lys Gly Gln Ala Ala Ala Phe Arg
385                 390                 395                 400

Gln Pro Ser Gln Thr Ala Leu Lys Asp Glu Pro Thr His Leu Val Val
                405                 410                 415
```

Ala Lys Glu Gly Ser Val Ala Ser Ser Val Leu Leu Ser Gly Thr Val
            420                 425                 430

Thr Ala Lys Asn Glu Gln Tyr Val Tyr Phe Asp Ala Ser Lys Gly Asp
        435                 440                 445

Leu Asp Glu Ile Leu Val Ser Val Gly Asp Lys Val Ser Glu Gly Gln
    450                 455                 460

Ala Leu Val Lys Tyr Ser Ser Glu Ala Gln Ala Tyr Asp Ser
465                 470                 475                 480

Ala Ser Arg Ala Val Ala Arg Ala Asp Arg His Ile Asn Glu Leu Asn
                485                 490                 495

Gln Ala Arg Asn Glu Ala Ala Ser Ala Pro Ala Pro Gln Leu Pro Ala
            500                 505                 510

Pro Val Gly Gly Glu Asp Ala Thr Val Gln Ser Pro Thr Pro Val Ala
        515                 520                 525

Gly Asn Ser Val Ala Ser Ile Asp Ala Gln Leu Gly Asp Ala Arg Asp
    530                 535                 540

Ala Arg Ala Asp Ala Ala Ala Gln Leu Ser Lys Ala Gln Ser Gln Leu
545                 550                 555                 560

Asp Ala Thr Thr Val Leu Ser Thr Leu Glu Gly Thr Val Val Glu Val
                565                 570                 575

Asn Ser Asn Val Ser Lys Ser Pro Thr Gly Ala Ser Gln Val Met Val
            580                 585                 590

His Ile Val Ser Asn Glu Asn Leu Gln Val Lys Gly Glu Leu Ser Glu
        595                 600                 605

Tyr Asn Leu Ala Asn Leu Ser Val Gly Gln Glu Val Ser Phe Thr Ser
    610                 615                 620

Lys Val Tyr Pro Asp Lys Lys Trp Thr Gly Lys Leu Ser Tyr Ile Ser
625                 630                 635                 640

Asp Tyr Pro Lys Asn Asn Gly Glu Ala Ala Ser Pro Ala Ala Gly Asn
                645                 650                 655

Asn Thr Gly Ser Lys Tyr Pro Tyr Thr Ile Asp Val Thr Gly Glu Val
            660                 665                 670

Gly Asp Leu Lys Gln Gly Phe Ser Val Asn Ile Glu Val Lys Ser Lys
        675                 680                 685

Thr Lys Ala Ile Leu Val Pro Val Ser Ser Leu Val Met Asp Asp Ser
    690                 695                 700

Lys Asn Tyr Val Trp Ile Val Asp Glu Gln Gln Lys Ala Lys Lys Val
705                 710                 715                 720

Glu Val Ser Leu Gly Asn Ala Asp Ala Glu Asn Gln Glu Ile Thr Ser
                725                 730                 735

Gly Leu Thr Asn Gly Ala Lys Val Ile Ser Asn Pro Thr Ser Ser Leu
            740                 745                 750

Glu Glu Gly Lys Glu Val Lys Ala Asp Glu Ala Thr Asn
        755                 760                 765

<210> SEQ ID NO 7
<211> LENGTH: 1101
<212> TYPE: DNA
<213> ORGANISM: Streptococcus pneumoniae

<400> SEQUENCE: 7
tttagacaac cttctcagac tgctctaaaa gatgagccta ctcatcttgt tgttgccaag    60
gaaggaagcg tggcctcctc tgtttttattg tcagggacag taacagcaaa aaatgaacaa   120

```
tatgtttatt ttgatgctag taagggtgat ttagatgaaa tccttgtttc tgtgggcgat        180
aaggtcagcg aagggcaggc tttagtcaag tacagtagtt cagaagcgca ggcggcctat        240
gattcagcta gtcgagcagt agctagggca gatcgtcata tcaatgaact caatcaagca        300
cgaaatgaag ccgcttcagc tccggctcca cagttaccag cgccagtagg aggagaagat        360
gcaacggtgc aaagcccaac tccagtggct ggaaattctg ttgcttctat tgacgctcaa        420
ttgggtgatg cccgtgatgc gcgtgcagat gctgcggcgc aattaagcaa ggctcaaagt        480
caattggatg caacaactgt tctcagtacc ctagagggaa ctgtggtcga agtcaatagc        540
aatgtttcta atctccaac aggggcgagt caagttatgg ttcatattgt cagcaatgaa        600
aatttacaag tcaagggaga attgtctgag tacaatctag ccaacctttc tgtaggtcaa        660
gaagtaagct ttacttctaa agtgtatcct gataaaaaat ggactgggaa attaagctat        720
atttctgact atcctaaaaa caatggtgaa gcagctagtc cagcagccgg aataatacag        780
ggttctaaat acccttatac tattgatgtg acaggcgagg ttggtgattt gaaacaaggt        840
ttttctgtca acattgaggt taaaagcaaa actaaggcta ttcttgttcc tgttagcagt        900
ctagtaatgg atgatagtaa aaattatgtc tggattgtgg atgaacaaca aaaggctaaa        960
aaagttgagg tttcattggg aaatgctgac gcagaaaatc aagaaatcac ttctggttta       1020
acgaacggtg ctaaggtcat cagtaatcca acatcttcct tggaagaagg aaaagaggtg       1080
aaggctgatg aagcaactaa t                                                 1101

<210> SEQ ID NO 8
<211> LENGTH: 756
<212> TYPE: DNA
<213> ORGANISM: Streptococcus pneumoniae

<400> SEQUENCE: 8
actagtggag ataattggtc aaagtaccag tctaacaagt ctattactat tggatttgat         60 agtactttg ttccaatggg atttgctcag aaagatggtt cttatgcagg atttgatatt        120
gatttagcta cagctgtttt tgaaaaatac ggaatcacgg taaattggca accgattgat        180
tgggatttga agaagctga attgacaaaa ggaacgattg atctgatttg gaatggctat        240
tccgctacag acgaacgccg tgaaaaggtg gctttcagta actcatatat gaagaatgag        300
caggtattgg ttacgaagaa atcatctggt atcacgactg caaaggatat gactggaaag        360
acattaggag ctcaagctgg ttcatctggt tatgcggact ttgaagcaaa tccagaaatt        420
ttgaagaata ttgtcgctaa taggaagcg aatcaatacc aaacctttaa tgaagccttg        480
attgatttga aaaacgatcg aattgatggt ctattgattg accgtgtcta tgcaaactat        540
tatttagaag cagaaggtgt tttaaacgat tataatgtct ttacagttgg actagaaaca        600
gaagcttttg cggttggagc ccgtaaggaa gatacaaact tggttaagaa gataaatgaa        660
gcttttctta gtctttacaa ggacggcaag ttccaagaaa tcagccaaaa atggtttgga        720
gaagatgtag caaccaaaga agtaaaagaa ggacag                                  756

<210> SEQ ID NO 9
<211> LENGTH: 2295
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
```

-continued

```
atgttcgacg catccaactt taaagacttt agcagcatcg cgtccgcaag ctctagctgg      60
cagaatcaat ctggtagcac catgattatc caagtggaca gctttggtaa cgtcagcggt     120
caatatgtta atcgtgcaca gggtacgggt tgtcagaatt ctccgtaccc gctgaccggt     180
cgtgttaacg gcacgttcat cgctttcagc gtcggttgga acaattctac tgaaaattgc     240
aacagcgcga ccggttggac gggctatgca caagtgaatg gcaataacac cgaaatcgtc     300
acgtcctgga atctggcgta tgagggtggc agcggtccgg ctattgaaca gggccaggat     360
accttccaat acgtccctac gaccgagaat aagtcccttc tgaaagacgg cggtggcggt     420
tcgagctcga ccagcggcga caattggtcc aaataccaga gcaacaagag catcacgatc     480
ggcttcgaca gcacttttgt gccgatgggt ttcgcgcaaa agacggtag ctacgcgggt      540
ttcgatattg acctggcgac cgctgtcttt gagaaatacg gcattacggt taattggcag     600
ccgattgatt gggacctgaa agaggccgaa ctcaccaaag gcaccatcga cctgatctgg     660
aatggttact ccgcaaccga tgagcgtcgc gaaaaagttg ccttcagcaa cagctatatg     720
aagaatgaac aagtgttggt aaccaagaaa tctagcggca ttacgaccgc gaaagacatg     780
accggtaaga cgctgggtgc gcaggccggt agctctggct atgcggattt cgaggcgaat     840
cctgagattc tgaaaaacat cgttgcgaat aaagaggcga accagtacca gacctttaac     900
gaagcactga tcgacctgaa aaacgatcgc attgacggtc tgctgatcga tcgtgtgtac     960
gcgaactatt atctggaagc cgagggcgtt ctgaacgatt ataatgtttt taccgtgggt    1020
ctggagactg aggcattcgc ggttggtgcg cgcaaggaag ataccaacct ggttaaaaag    1080
attaatgagg catttagctc actgtacaag gacggcaagt ccaagaaat tagccagaag     1140
tggttcggtg aagatgttgc gacgaaagag gttaaagagg ccaagcggc cgcatttcgc     1200
caaccgagcc agactgcgtt gaaagatgag ccgacccatc tggttgttgc gaaagagggc    1260
agcgtggcat cgagcgtgct gctgagcggt acggttactg ccaaaaacga acaatacgtg    1320
tacttcgatg ctagcaaggg tgatctggat gaaattctgg tgagcgtggg tgacaaagtt    1380
agcgaaggcc aggcactggt gaagtattca tcctccgagg cacaggcagc gtacgacagc    1440
gcaagccgcg cagtggcgcg tgccgaccgt cacattaacg aattgaacca agcgcgtaac    1500
gaggccgcaa gcgcgccagc accgcagctg ccggctccgg tgggtggcga agatgcgacg    1560
gtgcagagcc cgaccccggt tgcgggtaat tcggtcgcca gcatcgatgc gcagctgggt    1620
gacgcgcgtg atgcccgtgc ggatgcggct gctcaactga gcaaggctca gagccaactg    1680
gacgcgacga cggtgctgag caccttggag ggtaccgttg tcgaagtcaa cagcaatgtg    1740
agcaagagcc caacgggtgc gagccaggtt atggtccaca ttgtgagcaa tgaaaactta    1800
caggtcaagg gtgagctgag cgagtataac ctggcgaatc tgagcgttgg tcaagaggtc    1860
agctttacca gcaaggtcta cccggataag aaatggaccg gcaagttgag ctacatcagc    1920
gactacccga agaacaatgg cgaggcagcc tccccggcag ccggcaacaa taccggctct    1980
aagtatccgt acaccatcga cgtaaccggt gaggtcggcg acctgaaaca gggttttagc    2040
gtgaatatcg aagtgaagtc caagaccaag gcaattttgg ttccggttag ctccctggtg    2100
atggacgata gcaagaatta tgtgtggatt gtcgacgagc aacagaaagc gaaaaaagtt    2160
gaagtgagcc tgggcaatgc tgatgccgag aaccaagaaa tcacgtctgg tctgaccaac    2220
ggtgcgaaag ttattagcaa cccgaccagc agcctggaag agggtaaaga ggtcaaagcc    2280
gacgaagcta cgaac                                                     2295
```

```
<210> SEQ ID NO 10
<211> LENGTH: 399
<212> TYPE: PRT
<213> ORGANISM: Streptococcus pneumoniae

<400> SEQUENCE: 10

Met Lys Lys Lys Asn Gly Lys Ala Lys Lys Trp Gln Leu Tyr Ala Ala
1               5                   10                  15

Ile Gly Ala Ala Ser Val Val Leu Gly Ala Gly Ile Leu Leu
            20                  25                  30

Phe Arg Gln Pro Ser Gln Thr Ala Leu Lys Asp Glu Pro Thr His Leu
        35                  40                  45

Val Val Ala Lys Glu Gly Ser Val Ala Ser Ser Val Leu Leu Ser Gly
    50                  55                  60

Thr Val Thr Ala Lys Asn Glu Gln Tyr Val Tyr Phe Asp Ala Ser Lys
65                  70                  75                  80

Gly Asp Leu Asp Glu Ile Leu Val Ser Val Gly Asp Lys Val Ser Glu
                85                  90                  95

Gly Gln Ala Leu Val Lys Tyr Ser Ser Ser Glu Ala Gln Ala Ala Tyr
            100                 105                 110

Asp Ser Ala Ser Arg Ala Val Ala Arg Ala Asp Arg His Ile Asn Glu
        115                 120                 125

Leu Asn Gln Ala Arg Asn Glu Ala Ala Ser Ala Pro Ala Pro Gln Leu
    130                 135                 140

Pro Ala Pro Val Gly Gly Glu Asp Ala Thr Val Gln Ser Pro Thr Pro
145                 150                 155                 160

Val Ala Gly Asn Ser Val Ala Ser Ile Asp Ala Gln Leu Gly Asp Ala
                165                 170                 175

Arg Asp Ala Arg Ala Asp Ala Ala Gln Leu Ser Lys Ala Gln Ser
            180                 185                 190

Gln Leu Asp Ala Thr Thr Val Leu Ser Thr Leu Glu Gly Thr Val Val
        195                 200                 205

Glu Val Asn Ser Asn Val Ser Lys Ser Pro Thr Gly Ala Ser Gln Val
    210                 215                 220

Met Val His Ile Val Ser Asn Glu Asn Leu Gln Val Lys Gly Glu Leu
225                 230                 235                 240

Ser Glu Tyr Asn Leu Ala Asn Leu Ser Val Gly Gln Glu Val Ser Phe
                245                 250                 255

Thr Ser Lys Val Tyr Pro Asp Lys Lys Trp Thr Gly Lys Leu Ser Tyr
            260                 265                 270

Ile Ser Asp Tyr Pro Lys Asn Asn Gly Glu Ala Ala Ser Pro Ala Ala
        275                 280                 285

Gly Asn Asn Thr Gly Ser Lys Tyr Pro Tyr Thr Ile Asp Val Thr Gly
    290                 295                 300

Glu Val Gly Asp Leu Lys Gln Gly Phe Ser Val Asn Ile Glu Val Lys
305                 310                 315                 320

Ser Lys Thr Lys Ala Ile Leu Val Pro Val Ser Ser Leu Val Met Asp
                325                 330                 335

Asp Ser Lys Asn Tyr Val Trp Ile Val Asp Glu Gln Gln Lys Ala Lys
            340                 345                 350

Lys Val Glu Val Ser Leu Gly Asn Ala Asp Ala Glu Asn Gln Glu Ile
        355                 360                 365

Thr Ser Gly Leu Thr Asn Gly Ala Lys Val Ile Ser Asn Pro Thr Ser
    370                 375                 380
```

Ser Leu Glu Glu Gly Lys Glu Val Lys Ala Asp Glu Ala Thr Asn
385                 390                 395

<210> SEQ ID NO 11
<211> LENGTH: 1197
<212> TYPE: DNA
<213> ORGANISM: Streptococcus pneumoniae

<400> SEQUENCE: 11

| | | | | | |
|---|---|---|---|---|---|
| atgaagaaaa | agaatggtaa | agctaaaaag | tggcaactgt | atgcagcaat | cggtgctgcg | 60 |
| agtgtagttg | tattgggtgc | tgggggatt | ttactctttta | gacaaccttc | tcagactgct | 120 |
| ctaaagatg | agcctactca | tcttgttgtt | gccaaggaag | gaagcgtggc | ctcctctgtt | 180 |
| ttattgtcag | ggacagtaac | agcaaaaaat | gaacaatatg | tttattttga | tgctagtaag | 240 |
| ggtgatttag | atgaaatcct | tgtttctgtg | ggcgataagg | tcagcgaagg | gcaggcttta | 300 |
| gtcaagtaca | gtagttcaga | agcgcaggcg | gcctatgatt | cagctagtcg | agcagtagct | 360 |
| agggcagatc | gtcatatcaa | tgaactcaat | caagcacgaa | atgaagccgc | ttcagctccg | 420 |
| gctccacagt | taccagcgcc | agtaggagga | gaagatgcaa | cggtgcaaag | cccaactcca | 480 |
| gtggctggaa | attctgttgc | ttctattgac | gctcaattgg | gtgatgcccg | tgatgcgcgt | 540 |
| gcagatgctg | cggcgcaatt | aagcaaggct | caaagtcaat | ggatgcaac | aactgttctc | 600 |
| agtaccctag | agggaactgt | ggtcgaagtc | aatagcaatg | tttctaaatc | tccaacaggg | 660 |
| gcgagtcaag | ttatggttca | tattgtcagc | aatgaaaatt | tacaagtcaa | gggagaattg | 720 |
| tctgagtaca | atctagccaa | cctttctgta | ggtcaagaag | taagctttac | ttctaaagtg | 780 |
| tatcctgata | aaaatggac | tgggaaatta | agctatattt | ctgactatcc | taaaaacaat | 840 |
| ggtgaagcag | ctagtccagc | agccgggaat | aatacaggtt | ctaaataccc | ttatactatt | 900 |
| gatgtgacag | gcgaggttgg | tgatttgaaa | caaggttttt | ctgtcaacat | tgaggttaaa | 960 |
| agcaaaacta | aggctattct | tgttcctgtt | agcagtctag | taatggatga | tagtaaaaat | 1020 |
| tatgtctgga | ttgtggatga | acaacaaaag | gctaaaaaag | ttgaggtttc | attgggaaat | 1080 |
| gctgacgcag | aaaatcaaga | aatcacttct | ggtttaacga | acggtgctaa | ggtcatcagt | 1140 |
| aatccaacat | cttccttgga | agaaggaaaa | gaggtgaagg | ctgatgaagc | aactaat | 1197 |

<210> SEQ ID NO 12
<211> LENGTH: 278
<212> TYPE: PRT
<213> ORGANISM: Streptococcus pneumoniae

<400> SEQUENCE: 12

Met Lys Lys Trp Met Leu Val Leu Val Ser Leu Met Thr Ala Leu Phe
1               5                   10                  15

Leu Val Ala Cys Gly Lys Asn Ser Ser Glu Thr Ser Gly Asp Asn Trp
                20                  25                  30

Ser Lys Tyr Gln Ser Asn Lys Ser Ile Thr Ile Gly Phe Asp Ser Thr
            35                  40                  45

Phe Val Pro Met Gly Phe Ala Gln Lys Asp Gly Ser Tyr Ala Gly Phe
        50                  55                  60

Asp Ile Asp Leu Ala Thr Ala Val Phe Glu Lys Tyr Gly Ile Thr Val
65                  70                  75                  80

Asn Trp Gln Pro Ile Asp Trp Asp Leu Lys Glu Ala Glu Leu Thr Lys
                85                  90                  95

Gly Thr Ile Asp Leu Ile Trp Asn Gly Tyr Ser Ala Thr Asp Glu Arg
            100                 105                 110

Arg Glu Lys Val Ala Phe Ser Asn Ser Tyr Met Lys Asn Glu Gln Val
            115                 120                 125
Leu Val Thr Lys Lys Ser Ser Gly Ile Thr Thr Ala Lys Asp Met Thr
        130                 135                 140
Gly Lys Thr Leu Gly Ala Gln Ala Gly Ser Ser Gly Tyr Ala Asp Phe
145                 150                 155                 160
Glu Ala Asn Pro Glu Ile Leu Lys Asn Ile Val Ala Asn Lys Glu Ala
                165                 170                 175
Asn Gln Tyr Gln Thr Phe Asn Glu Ala Leu Ile Asp Leu Lys Asn Asp
            180                 185                 190
Arg Ile Asp Gly Leu Leu Ile Asp Arg Val Tyr Ala Asn Tyr Tyr Leu
        195                 200                 205
Glu Ala Glu Gly Val Leu Asn Asp Tyr Asn Val Phe Thr Val Gly Leu
210                 215                 220
Glu Thr Glu Ala Phe Ala Val Gly Ala Arg Lys Glu Asp Thr Asn Leu
225                 230                 235                 240
Val Lys Lys Ile Asn Glu Ala Phe Ser Ser Leu Tyr Lys Asp Gly Lys
                245                 250                 255
Phe Gln Glu Ile Ser Gln Lys Trp Phe Gly Asp Val Ala Thr Lys
            260                 265                 270
Glu Val Lys Glu Gly Gln
        275

<210> SEQ ID NO 13
<211> LENGTH: 834
<212> TYPE: DNA
<213> ORGANISM: Streptococcus pneumoniae

<400> SEQUENCE: 13
atgaaaaaat ggatgcttgt attagtcagt ctgatgactg ctttgttctt agtagcttgt      60
gggaaaaatt ctagcgaaac tagtggagat aattggtcaa agtaccagtc taacaagtct     120
attactattg gatttgatag tacttttgtt ccaatgggat ttgctcagaa agatggttct     180
tatgcaggat ttgatattga tttagctaca gctgtttttg aaaatacgg aatcacggta      240 aattggcaac cgattgattg ggatttgaaa gaagctgaat tgacaaaagg aacgattgat     300
ctgatttgga tggctattc cgctacagac gaacgccgtg aaaaggtggc tttcagtaac     360
tcatatatga agaatgagca ggtattggtt acgaagaaat catctggtat cacgactgca     420
aaggatatga ctggaaagac attaggagct caagctggtt catctggtta tgcggacttt     480
gaagcaaatc cagaaatttt gaagaatatt gtcgctaata aggaagcgaa tcaataccaa     540
acctttaatg aagccttgat tgatttgaaa aacgatcgaa ttgatggtct attgattgac     600
cgtgtctatg caaactatta tttagaagca gaaggtgttt taaacgatta taatgtcttt     660
acagttggac tagaaacaga agcttttgcg gttggagccc gtaaggaaga tacaaacttg     720
gttaagaaga taatgaagc ttttctagt ctttacaagg acggcaagtt ccaagaaatc     780
agccaaaaat ggtttggaga agatgtagca accaagaag taaagaagg acag             834

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 14

Gly Gly Gly Gly
1
```

MULTIVALENT PNEUMOCOCCAL VACCINES

CROSS-REFERENCE TO RELATED APPLICATIONS

This application is a divisional of U.S. application Ser. No. 16/569,579, filed Sep. 12, 2019, which claims the benefit of U.S. Provisional Application No. 62/730,471 filed Sep. 12, 2018, the contents of all of which are hereby incorporated herein in their entirety.

SEQUENCE LISTING

The instant application contains a Sequence Listing which has been submitted electronically in ASCII format and is hereby incorporated by reference in its entirety. Said ASCII copy, created on Jun. 29, 2021, is named 2011588-0142_SL.txt and is 30,276 bytes in size.

BACKGROUND

*Streptococcus pneumoniae* remains a leading cause of serious illness, including bacteremia, sepsis, meningitis and pneumonia, among children and adults worldwide. Morbidity and mortality among infants, young children, the elderly and subjects who have certain underlying medical conditions is high.

*S. pneumoniae* is a Gram-positive encapsulated coccus that colonizes the nasopharynx in about 5-10% of healthy adults and 20-40% of healthy children. Normal colonization becomes infectious when *S. pneumoniae* is carried into the Eustachian tubes, nasal sinuses, lungs, bloodstream, meninges, joint spaces, bones and peritoneal cavity. *S. pneumoniae* infection is the most frequent cause of bacteremia, pneumonia, meningitis, sinusitis and acute otitis media [CDC, 2010].

Pneumococcal disease can be invasive or non-invasive. The most common form of non-invasive disease, non-bacteremic pneumococcal pneumonia, remains one of the most frequent causes for pneumonia hospitalizations. Invasive pneumococcal disease (IPD) is defined as *S. pneumoniae* isolated from a normally sterile site (e.g., cerebrospinal fluid, blood, joint fluid, pleural fluid or peritoneal fluid). The highest incidence of IPD is found at the extremes of age—in elderly adults and in young children younger than 2 years of age. In the U.S., prior to advent of the first pneumococcal vaccine, *S. pneumoniae* caused approximately 17,000 cases of invasive disease each year among children younger than 5 years of age, including 700 cases of meningitis and 200 deaths [CDC, 2000]. The highest morbidity and mortality rates have been reported in developing countries, but the disease burden is also considerable in industrialized countries.

*S. pneumoniae* has several virulence factors that enable the organism to evade the immune system. Examples include a polysaccharide capsule that prevents phagocytosis by host immune cells, proteases that inhibit complement-mediated opsonization, and proteins that cause lysis of host cells. In the polysaccharide capsule, the presence of complex polysaccharides forms the basis for dividing pneumococci into different serotypes. To date, close to 100 serotypes of *S. pneumoniae* have been identified.

Two vaccines for *S. pneumoniae* are currently available in the U.S.; PCV13 and PPSV23. PCV13 cannot confer protection against most of the known serotypes of *S. pneumoniae*. While PPSV23 includes polysaccharide components of more serotypes of *S. pneumoniae* than PCV13, it induces an immune response that is neither long-lasting nor anamnestic upon subsequent challenge. PPSV23 protects adults and the elderly against invasive pneumococcal disease; however, no consistent effect has been observed in the prevention of pneumonia [Gruber et al, 2008].

Thus, there is a medical need for a vaccine that provides T-cell dependent immunity against a broad range of serotypes of *S. pneumoniae*.

SUMMARY

The present disclosure addresses the lack of suitable technologies for the prevention and/or treatment of pneumococcal infection. Among other things, the present disclosure addresses challenges in providing vaccines with sufficient immunogenicity to protect against invasive pneumococcal disease and pneumonia, by inducing a T- and B-cell response providing immunity against a broad range of *S. pneumoniae* serotypes including those serotypes not included in the vaccine.

Among other things, the present disclosure provides compositions and methods for prevention and/or treatment of pneumococcal infections in patient populations in need thereof.

In some embodiments, a vaccine comprises an immunogenic complex, wherein the immunogenic complex comprises: (a) a biotinylated polysaccharide antigen; and (b) a fusion protein comprising: (i) a biotin-binding moiety; and (ii) at least one polypeptide antigen; wherein the biotinylated polysaccharide antigen is non-covalently associated with the biotin-binding moiety of the fusion protein to form an immunogenic complex.

In some embodiments, the at least one polypeptide antigen comprises: an SP1500 polypeptide or antigenic fragment thereof; or an SP0785 polypeptide or antigenic fragment thereof. In some embodiments, the at least one polypeptide antigen comprises: (a) a first polypeptide antigen comprising an SP1500 polypeptide or antigenic fragment thereof; and (b) a second polypeptide antigen comprising an SP0785 polypeptide or antigenic fragment thereof.

In some embodiments, the biotinylated polysaccharide antigen comprises a polysaccharide of *Streptococcus pneumoniae*. In some embodiments, the biotinylated polysaccharide antigen comprises a polysaccharide of *Streptococcus pneumoniae* having a serotype selected from one or more of 1, 2, 3, 4, 5, 6A, 6B, 6C, 6D, 6E, 6F, 6G, 6H, 7A, 7B, 7C, 7F, 8, 9A, 9L, 9N, 9V, 10A, 10B, 10C, 10F, 11A, 11B, 11C, 11D, 11E, 11F, 12A, 12B, 12F, 13, 14, 15A, 15B, 15C, 15F, 16A, 16F, 17A, 17F, 18A, 18B, 18C, 18F, 19A, 19B, 19C, 19F, 20A, 20B, 21, 22A, 22F, 23A, 23B, 23F, 24A, 24B, 24F, 25A, 25F, 27, 28A, 28F, 29, 31, 32A, 32F, 33A, 33B, 33C, 33D, 33E, 33F, 34, 35A, 35B, 35C, 35F, 36, 37, 38, 39, 40, 41A, 41F, 42, 43, 44, 45, 46, 47A, 47F, and 48.

In some embodiments, the biotinylated polysaccharide antigen comprises a polysaccharide of *Streptococcus pneumoniae* having a serotype selected from one or more of 1, 2, 3, 4, 5, 6A, 6B, 7F, 8, 9N, 9V, 10A, 11A, 12F, 14, 15B, 17F, 18C, 19A, 19F, 20B, 22F, 23F, and 33F.

In some embodiments, the biotinylated polysaccharide antigen comprises a polysaccharide of *Streptococcus pneumoniae* having a serotype selected from one or more of 1, 3, 4, 5, 6A, 6B, 7F, 9V, 14, 18C, 19A, 19F, 22F, 23F, and 33F.

In some embodiments, the biotinylated polysaccharide antigen comprises a polysaccharide of *Streptococcus pneu-*

*moniae* having a serotype selected from one or more of 2, 8, 9N, 10A, 11A, 12F, 15B, 17F, and 20B.

In some embodiments, a vaccine comprises a plurality of immunogenic complexes comprising: (a) a plurality of biotinylated polysaccharide antigens, wherein the plurality comprises polysaccharide antigens of one or more of *Streptococcus pneumoniae* serotypes 1, 2, 3, 4, 5, 6A, 6B, 6C, 6D, 6E, 6F, 6G, 6H, 7A, 7B, 7C, 7F, 8, 9A, 9L, 9N, 9V, 10A, 10B, 10C, 10F, 11A, 11B, 11C, 11D, 11E, 11F, 12A, 12B, 12F, 13, 14, 15A, 15B, 15C, 15F, 16A, 16F, 17A, 17F, 18A, 18B, 18C, 18F, 19A, 19B, 19C, 19F, 20A, 20B, 21, 22A, 22F, 23A, 23B, 23F, 24A, 24B, 24F, 25A, 25F, 27, 28A, 28F, 29, 31, 32A, 32F, 33A, 33B, 33C, 33D, 33E, 33F, 34, 35A, 35B, 35C, 35F, 36, 37, 38, 39, 40, 41A, 41F, 42, 43, 44, 45, 46, 47A, 47F, and 48; and (b) a plurality of fusion proteins, each fusion protein comprising (i) a biotin-binding moiety; (ii) a first polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:5 or an antigenic fragment thereof; and (iii) a second polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:4 or an antigenic fragment thereof; wherein each of the first plurality of biotinylated polysaccharide antigens is non-covalently associated with the biotin-binding moiety of one or more of the plurality of fusion proteins to form an immunogenic complex.

In some embodiments, a vaccine comprises a plurality of immunogenic complexes comprising: (a) a plurality of biotinylated polysaccharide antigens, wherein the plurality comprises polysaccharide antigens of one or more of *Streptococcus pneumoniae* serotypes 1, 2, 3, 4, 5, 6A, 6B, 7F, 8, 9N, 9V, 10A, 11A, 12F, 14, 15B, 17F, 18C, 19A, 19F, 20B, 22F, 23F, and 33F; and (b) a plurality of fusion proteins, each fusion protein comprising (i) a biotin-binding moiety; (ii) a first polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:5 or an antigenic fragment thereof; and (iii) a second polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:4 or an antigenic fragment thereof; wherein each of the first plurality of biotinylated polysaccharide antigens is non-covalently associated with the biotin-binding moiety of one or more of the plurality of fusion proteins to form an immunogenic complex.

In some embodiments, a vaccine comprises a plurality of immunogenic complexes comprising: (a) a plurality of biotinylated polysaccharide antigens, wherein the plurality comprises polysaccharide antigens of each of *Streptococcus pneumoniae* serotypes 1, 2, 3, 4, 5, 6A, 6B, 7F, 8, 9N, 9V, 10A, 11A, 12F, 14, 15B, 17F, 18C, 19A, 19F, 20B, 22F, 23F, and 33F; and (b) a plurality of fusion proteins, each fusion protein comprising (i) a biotin-binding moiety; (ii) a first polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:5 or an antigenic fragment thereof; and (iii) a second polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:4 or an antigenic fragment thereof; wherein each of the first plurality of biotinylated polysaccharide antigens is non-covalently associated with the biotin-binding moiety of one or more of the plurality of fusion proteins to form an immunogenic complex.

In some embodiments, a vaccine comprises a plurality of immunogenic complexes comprising: (a) a plurality of biotinylated polysaccharide antigens, wherein the plurality comprises polysaccharide antigens of one or more of *Streptococcus pneumoniae* serotypes 1, 3, 4, 5, 6A, 6B, 7F, 9V, 14, 18C, 19A, 19F, 22F, 23F, and 33F; and (b) a plurality of fusion proteins, each fusion protein comprising (i) a biotin-binding moiety; (ii) a first polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:5 or an antigenic fragment thereof; and (iii) a second polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:4 or an antigenic fragment thereof; wherein each of the first plurality of biotinylated polysaccharide antigens is non-covalently associated with the biotin-binding moiety of one or more of the plurality of fusion proteins to form an immunogenic complex.

In some embodiments, a vaccine comprises a plurality of immunogenic complexes comprising: (a) a plurality of biotinylated polysaccharide antigens, wherein the plurality comprises polysaccharide antigens of each of *Streptococcus pneumoniae* serotypes 1, 3, 4, 5, 6A, 6B, 7F, 9V, 14, 18C, 19A, 19F, 22F, 23F, and 33F; and (b) a plurality of fusion proteins, each fusion protein comprising (i) a biotin-binding moiety; (ii) a first polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:5 or an antigenic fragment thereof; and (iii) a second polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:4 or an antigenic fragment thereof; wherein each of the first plurality of biotinylated polysaccharide antigens is non-covalently associated with the biotin-binding moiety of one or more of the plurality of fusion proteins to form an immunogenic complex.

In some embodiments, a vaccine comprises a plurality of immunogenic complexes comprising: (a) a plurality of biotinylated polysaccharide antigens, wherein the plurality comprises polysaccharide antigens of one or more of *Streptococcus pneumoniae* serotypes 2, 8, 9N, 10A, 11A, 12F, 15B, 17F, and 20B; and (b) a plurality of fusion proteins, each fusion protein comprising (i) a biotin-binding moiety; (ii) a first polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:5 or an antigenic fragment thereof; and (iii) a second polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:4 or an antigenic fragment thereof; wherein each of the first plurality of biotinylated polysaccharide antigens is non-covalently associated with the biotin-binding moiety of one or more of the plurality of fusion proteins to form an immunogenic complex.

In some embodiments, a vaccine comprises a plurality of immunogenic complexes comprising: (a) a plurality of biotinylated polysaccharide antigens, wherein the plurality comprises polysaccharide antigens of each of *Streptococcus pneumoniae* serotypes 2, 8, 9N, 10A, 11A, 12F, 15B, 17F, and 20B; and (b) a plurality of fusion proteins, each fusion protein comprising (i) a biotin-binding moiety; (ii) a first polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:5 or an antigenic fragment thereof; and (iii) a second polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:4 or an antigenic fragment thereof; wherein each of the first plurality of biotinylated polysaccharide antigens is non-covalently associated with the biotin-binding moiety of one or more of the plurality of fusion proteins to form an immunogenic complex.

In some embodiments, a vaccine comprises a biotin-binding moiety, wherein the biotin-binding moiety is a polypeptide that has or comprises an amino acid sequence at least 90%, at least 91%, at least 92%, at least 93%, at least 94%, at least 95%, at least 96%, at least 97%, at least 98%, at least 99%, or at least 99.5% identical to SEQ ID NO:1 or a biotin-binding fragment thereof; or a polypeptide that has or comprises an amino acid sequence at least 90%, at least 91%, at least 92%, at least 93%, at least 94%, at least 95%, at least 96%, at least 97%, at least 98%, at least 99%, or at least 99.5% identical to SEQ ID NO:2 or a biotin-binding fragment thereof. In some embodiments, a vaccine comprises a fusion protein that is or comprises an amino acid sequence at least 90%, at least 91%, at least 92%, at least 93%, at least 94%, at least 95%, at least 96%, at least 97%, at least 98%, at least 99%, or at least 99.5% identical to SEQ ID NO:6. In some embodiments, a vaccine comprises the fusion protein CP1.

In some embodiments, a vaccine comprises a plurality of immunogenic complexes comprising one or more species of immunogenic complexes, wherein a species refers to complexes comprising a polysaccharide antigen of a single *Streptococcus pneumoniae* serotype. In some embodiments, a vaccine comprises a plurality of immunogenic complexes comprising two or more species of immunogenic complexes, wherein a species refers to complexes comprising a polysaccharide antigen of a single *Streptococcus pneumoniae* serotype. In some embodiments, a vaccine comprises a plurality of immunogenic complexes comprising nine or more species of immunogenic complexes, wherein a species refers to complexes comprising a polysaccharide antigen of a single *Streptococcus pneumoniae* serotype.

In some embodiments, a vaccine comprises a plurality of immunogenic complexes comprising fifteen or more species of immunogenic complexes, wherein a species refers to complexes comprising a polysaccharide antigen of a single *Streptococcus pneumoniae* serotype.

In some embodiments, a vaccine comprises a plurality of immunogenic complexes comprising twenty-four or more species of immunogenic complexes, wherein a species refers to complexes comprising a polysaccharide antigen of a single *Streptococcus pneumoniae* serotype.

In some embodiments, a vaccine comprises a plurality of immunogenic complexes comprising: a first species of immunogenic complex comprising a biotinylated polysaccharide antigen of *Streptococcus pneumoniae* serotype 1 non-covalently complexed with a fusion protein; a second species of immunogenic complex comprising a biotinylated polysaccharide antigen of *Streptococcus pneumoniae* serotype 2 non-covalently complexed with a fusion protein; a third species of immunogenic complex comprising a biotinylated polysaccharide antigen of *Streptococcus pneumoniae* serotype 3 non-covalently complexed with a fusion protein; a fourth species of immunogenic complex comprising a biotinylated polysaccharide antigen of *Streptococcus pneumoniae* serotype 4 non-covalently complexed with a fusion protein; a fifth species of immunogenic complex comprising a biotinylated polysaccharide antigen of *Streptococcus pneumoniae* serotype 5 non-covalently complexed with a fusion protein; a sixth species of immunogenic complex comprising a biotinylated polysaccharide antigen of *Streptococcus pneumoniae* serotype 6A non-covalently complexed with a fusion protein; a seventh species of immunogenic complex comprising a biotinylated polysaccharide antigen of *Streptococcus pneumoniae* serotype 6B non-covalently complexed with a fusion protein; an eighth species of immunogenic complex comprising a biotinylated polysaccharide antigen of *Streptococcus pneumoniae* serotype 7F non-covalently complexed with a fusion protein; a ninth species of immunogenic complex comprising a biotinylated polysaccharide antigen of *Streptococcus pneumoniae* serotype 8 non-covalently complexed with a fusion protein; a tenth species of immunogenic complex comprising a biotinylated polysaccharide antigen of *Streptococcus pneumoniae* serotype 9N non-covalently complexed with a fusion protein; an eleventh species of immunogenic complex comprising a biotinylated polysaccharide antigen of *Streptococcus pneumoniae* serotype 9V non-covalently complexed with a fusion protein; a twelfth species of immunogenic complex comprising a biotinylated polysaccharide antigen of *Streptococcus pneumoniae* serotype 10A non-covalently complexed with a fusion protein; a thirteenth species of immunogenic complex comprising a biotinylated polysaccharide antigen of *Streptococcus pneumoniae* serotype 11A non-covalently complexed with a fusion protein; a fourteenth species of immunogenic complex comprising a biotinylated polysaccharide antigen of *Streptococcus pneumoniae* serotype 12F non-covalently complexed with a fusion protein; a fifteenth species of immunogenic complex comprising a biotinylated polysaccharide antigen of *Streptococcus pneumoniae* serotype 14 non-covalently complexed with a fusion protein; a sixteenth species of immunogenic complex comprising a biotinylated polysaccharide antigen of *Streptococcus pneumoniae* serotype 15B non-covalently complexed with a fusion protein; a seventeenth species of immunogenic complex comprising a biotinylated polysaccharide antigen of *Streptococcus pneumoniae* serotype 17F non-covalently complexed with a fusion protein; an eighteenth species of immunogenic complex comprising a biotinylated polysaccharide antigen of *Streptococcus pneumoniae* serotype 18C non-covalently complexed with a fusion protein; a nineteenth species of immunogenic complex comprising a biotinylated polysaccharide antigen of *Streptococcus pneumoniae* serotype 19A non-covalently complexed with a fusion protein; a twentieth species of immunogenic complex comprising a biotinylated polysaccharide antigen of *Streptococcus pneumoniae* serotype 19F non-covalently complexed with a fusion protein; a twenty-first species of immunogenic complex comprising a biotinylated polysaccharide antigen of *Streptococcus pneumoniae* serotype 20B non-covalently complexed with a fusion protein; a twenty-second species of immunogenic complex comprising a biotinylated polysaccharide antigen of *Streptococcus pneumoniae* serotype 22F non-covalently complexed with a fusion protein; a twenty-third species of immunogenic complex comprising a biotinylated polysaccharide antigen of *Streptococcus pneumoniae* serotype 23F non-covalently complexed with a fusion protein; a twenty-fourth species of immunogenic complex comprising a biotinylated polysaccharide antigen of *Streptococcus pneumoniae* serotype 33F non-covalently complexed with a fusion protein; wherein each fusion protein comprises (a) a biotin-binding moiety; (b) a first polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:5 or an antigenic fragment thereof; and (c) a second polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:4 or an antigenic fragment thereof; and wherein each of the first through twenty-fourth biotinylated polysaccharide antigens is non-covalently associated with the biotin-binding moiety of at least one fusion protein to form immunogenic complexes.

In some embodiments, a vaccine comprises a plurality of immunogenic complexes comprising: a first species of immunogenic complex comprising a biotinylated polysaccharide antigen of *Streptococcus pneumoniae* serotype 1 non-covalently complexed with a fusion protein; a second species of immunogenic complex comprising a biotinylated polysaccharide antigen of *Streptococcus pneumoniae* serotype 3 non-covalently complexed with a fusion protein; a third species of immunogenic complex comprising a biotinylated polysaccharide antigen of *Streptococcus pneumoniae* serotype 4 non-covalently complexed with a fusion protein; a fourth species of immunogenic complex comprising a biotinylated polysaccharide antigen of *Streptococcus pneumoniae* serotype 5 non-covalently complexed with a fusion protein; a fifth species of immunogenic complex comprising a biotinylated polysaccharide antigen of *Streptococcus pneumoniae* serotype 6A non-covalently complexed with a fusion protein; a sixth species of immunogenic complex comprising a biotinylated polysaccharide antigen of *Streptococcus pneumoniae* serotype 6B non-covalently complexed with a fusion protein; a seventh species of immunogenic complex comprising a biotinylated polysaccharide antigen of *Streptococcus pneumoniae* serotype 7F non-covalently complexed with a fusion protein; an eighth species of immunogenic complex comprising a biotinylated polysaccharide antigen of *Streptococcus pneumoniae* serotype 9V non-covalently complexed with a fusion protein; a ninth species of immunogenic complex comprising a biotinylated polysaccharide antigen of *Streptococcus pneumoniae* serotype 14 non-covalently complexed with a fusion protein; a tenth species of immunogenic complex comprising a biotinylated polysaccharide antigen of *Streptococcus pneumoniae* serotype 18C non-covalently complexed with a fusion protein; an eleventh species of immunogenic complex comprising a biotinylated polysaccharide antigen of *Streptococcus pneumoniae* serotype 19A non-covalently complexed with a fusion protein; a twelfth species of immunogenic complex comprising a biotinylated polysaccharide antigen of *Streptococcus pneumoniae* serotype 19F non-covalently complexed with a fusion protein; a thirteenth species of immunogenic complex comprising a biotinylated polysaccharide antigen of *Streptococcus pneumoniae* serotype 22F non-covalently complexed with a fusion protein; a fourteenth species of immunogenic complex comprising a biotinylated polysaccharide antigen of *Streptococcus pneumoniae* serotype 23F non-covalently complexed with a fusion protein; a fifteenth species of immunogenic complex comprising a biotinylated polysaccharide antigen of *Streptococcus pneumoniae* serotype 33F non-covalently complexed with a fusion protein; wherein each fusion protein comprises (a) a biotin-binding moiety; (b) a first polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:5 or an antigenic fragment thereof; and (c) a second polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:4 or an antigenic fragment thereof; and wherein each of the first through fifteenth biotinylated polysaccharide antigens is non-covalently associated with the biotin-binding moiety of at least one fusion protein to form immunogenic complexes.

In some embodiments, a vaccine comprises a plurality of immunogenic complexes comprising: a first species of immunogenic complex comprising a biotinylated polysaccharide antigen of *Streptococcus pneumoniae* serotype 2 non-covalently complexed with a fusion protein; a second species of immunogenic complex comprising a biotinylated polysaccharide antigen of *Streptococcus pneumoniae* serotype 8 non-covalently complexed with a fusion protein; a third species of immunogenic complex comprising a biotinylated polysaccharide antigen of *Streptococcus pneumoniae* serotype 9N non-covalently complexed with a fusion protein; a fourth species of immunogenic complex comprising a biotinylated polysaccharide antigen of *Streptococcus pneumoniae* serotype 10A non-covalently complexed with a fusion protein; a fifth species of immunogenic complex comprising a biotinylated polysaccharide antigen of *Streptococcus pneumoniae* serotype 11A non-covalently complexed with a fusion protein; a sixth species of immunogenic complex comprising a biotinylated polysaccharide antigen of *Streptococcus pneumoniae* serotype 12F non-covalently complexed with a biotin-binding fusion protein; a seventh species of immunogenic complex comprising a biotinylated polysaccharide antigen of *Streptococcus pneumoniae* serotype 15B non-covalently complexed with a fusion protein; an eighth species of immunogenic complex comprising a biotinylated polysaccharide antigen of *Streptococcus pneumoniae* serotype 17F non-covalently complexed with a fusion protein; and a ninth species of immunogenic complex comprising a biotinylated polysaccharide antigen of *Streptococcus pneumoniae* serotype 20B non-covalently complexed with a fusion protein; wherein each fusion protein comprises (a) a biotin-binding moiety; (b) a first polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:5 or an antigenic fragment thereof; and (c) a second polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:4 or an antigenic fragment thereof; and wherein each of the first through ninth biotinylated polysaccharide antigens is non-covalently associated with the biotin-binding moiety of at least one fusion protein to form immunogenic complexes.

In some embodiments, a vaccine comprises a plurality of immunogenic complexes comprising two or more species of immunogenic complexes, wherein each species of immunogenic complexes contributes a stoichiometrically equal ratio, by weight, of the polysaccharide antigen.

In some embodiments, a vaccine comprises a plurality of immunogenic complexes comprising two or more species of immunogenic complexes, wherein at least one species of immunogenic complex contributes a stoichiometrically different ratio, by weight, of the polysaccharide antigen.

In some embodiments, a vaccine comprises a plurality of immunogenic complexes comprising two or more species of immunogenic complexes, wherein different species of immunogenic complexes contribute a stoichiometrically different ratio, by weight, of the polysaccharide antigen.

In some embodiments, a vaccine comprises a fusion protein comprising a biotin-binding moiety, wherein the biotin-binding moiety is a polypeptide comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:1 or a biotin-binding fragment thereof; or a polypeptide comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:2 or a biotin-binding fragment thereof.

In some embodiments, an immunogenic complex comprises a fusion protein comprising a biotin-binding moiety, wherein the biotin-binding moiety is a polypeptide comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:1 or a biotin-binding fragment thereof; or a polypeptide comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:2 or a biotin-binding fragment thereof.

In some embodiments, an immunogenic complex comprises a biotinylated polysaccharide antigen of *Streptococcus pneumoniae* non-covalently associated with a fusion protein, wherein the fusion protein comprises a biotin-binding moiety and at least one polypeptide antigen.

In some embodiments, an immunogenic complex comprises a biotinylated polysaccharide antigen, wherein the biotinylated polysaccharide antigen comprises a polysaccharide of *Streptococcus pneumoniae* having a serotype selected from one or more of 1, 2, 3, 4, 5, 6A, 6B, 6C, 6D, 6E, 6F, 6G, 6H, 7A, 7B, 7C, 7F, 8, 9A, 9L, 9N, 9V, 10A, 10B, 10C, 10F, 11A, 11B, 11C, 11D, 11E, 11F, 12A, 12B, 12F, 13, 14, 15A, 15B, 15C, 15F, 16A, 16F, 17A, 17F, 18A, 18B, 18C, 18F, 19A, 19B, 19C, 19F, 20A, 20B, 21, 22A, 22F, 23A, 23B, 23F, 24A, 24B, 24F, 25A, 25F, 27, 28A, 28F, 29, 31, 32A, 32F, 33A, 33B, 33C, 33D, 33E, 33F, 34, 35A, 35B, 35C, 35F, 36, 37, 38, 39, 40, 41A, 41F, 42, 43, 44, 45, 46, 47A, 47F, and 48.

In some embodiments, an immunogenic complex comprises a biotinylated polysaccharide antigen, wherein the biotinylated polysaccharide antigen comprises a polysaccharide of *Streptococcus pneumoniae* having a serotype selected from one or more of 1, 2, 3, 4, 5, 6A, 6B, 7F, 8, 9N, 9V, 10A, 11A, 12F, 14, 15B, 17F, 18C, 19A, 19F, 20B, 22F, 23F, and 33F.

In some embodiments, an immunogenic complex comprises a biotinylated polysaccharide antigen, wherein the biotinylated polysaccharide antigen comprises a polysaccharide of *Streptococcus pneumoniae* having a serotype selected from one or more of 1, 3, 4, 5, 6A, 6B, 7F, 9V, 14, 18C, 19A, 19F, 22F, 23F, and 33F.

In some embodiments, an immunogenic complex comprises a biotinylated polysaccharide antigen, wherein the biotinylated polysaccharide antigen comprises a polysaccharide of *Streptococcus pneumoniae* having a serotype selected from one or more of 2, 8, 9N, 10A, 11A, 12F, 15B, 17F, and 20B.

In some embodiments, an immunogenic complex comprises at least one peptide antigen, wherein the at least one polypeptide antigen comprises an SP1500 polypeptide or antigenic fragment thereof; an SP0785 polypeptide or antigenic fragment thereof; or a combination thereof.

In some embodiments, an immunogenic complex comprises at least one peptide antigen, wherein the at least one polypeptide antigen comprises: (a) a first polypeptide antigen comprising an SP1500 polypeptide or antigenic fragment thereof; and (b) a second polypeptide antigen comprising an SP0785 polypeptide or antigenic fragment thereof.

In some embodiments, an immunogenic complex comprises at least one peptide antigen, wherein the at least one polypeptide antigen comprises: (a) a first polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:5 or an antigenic fragment thereof; and (b) a second polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:4 or an antigenic fragment thereof.

In some embodiments, an immunogenic complex comprises a biotinylated polysaccharide antigen of *Streptococcus pneumoniae* serotype 1 non-covalently associated with a fusion protein, wherein the fusion protein comprises (a) a biotin-binding moiety; (b) a first polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:5 or an antigenic fragment thereof; and (c) a second polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:4 or an antigenic fragment thereof.

In some embodiments, an immunogenic complex comprises a biotinylated polysaccharide antigen of *Streptococcus pneumoniae* serotype 2 non-covalently associated with a fusion protein, wherein the fusion protein comprises (a) a biotin-binding moiety; (b) a first polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:5 or an antigenic fragment thereof; and (c) a second polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:4 or an antigenic fragment thereof.

In some embodiments, an immunogenic complex comprises a biotinylated polysaccharide antigen of *Streptococ-

*cus pneumoniae* serotype 3 non-covalently associated with a fusion protein, wherein the fusion protein comprises (a) a biotin-binding moiety; (b) a first polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:5 or an antigenic fragment thereof; and (c) a second polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:4 or an antigenic fragment thereof.

In some embodiments, an immunogenic complex comprises a biotinylated polysaccharide antigen of *Streptococcus pneumoniae* serotype 4 non-covalently associated with a fusion protein, wherein the fusion protein comprises (a) a biotin-binding moiety; (b) a first polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:5 or an antigenic fragment thereof; and (c) a second polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:4 or an antigenic fragment thereof.

In some embodiments, an immunogenic complex comprises a biotinylated polysaccharide antigen of *Streptococcus pneumoniae* serotype 5 non-covalently associated with a fusion protein, wherein the fusion protein comprises (a) a biotin-binding moiety; (b) a first polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:5 or an antigenic fragment thereof; and (c) a second polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:4 or an antigenic fragment thereof.

In some embodiments, an immunogenic complex comprises a biotinylated polysaccharide antigen of *Streptococcus pneumoniae* serotype 6A non-covalently associated with a fusion protein, wherein the fusion protein comprises (a) a biotin-binding moiety; (b) a first polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:5 or an antigenic fragment thereof; and (c) a second polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:4 or an antigenic fragment thereof.

In some embodiments, an immunogenic complex comprises a biotinylated polysaccharide antigen of *Streptococcus pneumoniae* serotype 6B non-covalently associated with a fusion protein, wherein the fusion protein comprises (a) a biotin-binding moiety; (b) a first polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:5 or an antigenic fragment thereof; and (c) a second polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:4 or an antigenic fragment thereof.

In some embodiments, an immunogenic complex comprises a biotinylated polysaccharide antigen of *Streptococcus pneumoniae* serotype 7F non-covalently associated with a fusion protein, wherein the fusion protein comprises (a) a biotin-binding moiety; (b) a first polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:5 or an antigenic fragment thereof; and (c) a second polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:4 or an antigenic fragment thereof.

In some embodiments, an immunogenic complex comprises a biotinylated polysaccharide antigen of *Streptococcus pneumoniae* serotype 8 non-covalently associated with a fusion protein, wherein the fusion protein comprises (a) a biotin-binding moiety; (b) a first polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:5 or an antigenic fragment thereof; and (c) a second polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:4 or an antigenic fragment thereof.

In some embodiments, an immunogenic complex comprises a biotinylated polysaccharide antigen of *Streptococcus pneumoniae* serotype 9N non-covalently associated with a fusion protein, wherein the fusion protein comprises (a) a biotin-binding moiety; (b) a first polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:5 or an antigenic fragment thereof; and (c) a second polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:4 or an antigenic fragment thereof.

In some embodiments, an immunogenic complex comprises a biotinylated polysaccharide antigen of *Streptococcus pneumoniae* serotype 9V non-covalently associated with a fusion protein, wherein the fusion protein comprises (a) a biotin-binding moiety; (b) a first polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:5 or an antigenic fragment thereof; and (c) a second polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:4 or an antigenic fragment thereof.

In some embodiments, an immunogenic complex comprises a biotinylated polysaccharide antigen of *Streptococcus pneumoniae* serotype 10A non-covalently associated with a fusion protein, wherein the fusion protein comprises (a) a biotin-binding moiety; (b) a first polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:5 or an antigenic fragment thereof; and (c) a second polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:4 or an antigenic fragment thereof.

In some embodiments, an immunogenic complex comprises a biotinylated polysaccharide antigen of *Streptococcus pneumoniae* serotype 11A non-covalently associated with a fusion protein, wherein the fusion protein comprises (a) a biotin-binding moiety; (b) a first polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:5 or an antigenic fragment thereof; and (c) a second polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:4 or an antigenic fragment thereof.

In some embodiments, an immunogenic complex comprises a biotinylated polysaccharide antigen of *Streptococcus pneumoniae* serotype 12F non-covalently associated with a fusion protein, wherein the fusion protein comprises (a) a biotin-binding moiety; (b) a first polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:5 or an antigenic fragment thereof; and (c) a second polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:4 or an antigenic fragment thereof.

In some embodiments, an immunogenic complex comprises a biotinylated polysaccharide antigen of *Streptococcus pneumoniae* serotype 14 non-covalently associated with a fusion protein, wherein the fusion protein comprises (a) a biotin-binding moiety; (b) a first polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:5 or an antigenic fragment thereof; and (c) a second polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:4 or an antigenic fragment thereof.

In some embodiments, an immunogenic complex comprises a biotinylated polysaccharide antigen of *Streptococcus pneumoniae* serotype 15B non-covalently associated with a fusion protein, wherein the fusion protein comprises (a) a biotin-binding moiety; (b) a first polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:5 or an antigenic fragment thereof; and (c) a second polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:4 or an antigenic fragment thereof.

In some embodiments, an immunogenic complex comprises a biotinylated polysaccharide antigen of *Streptococcus pneumoniae* serotype 17F non-covalently associated with a fusion protein, wherein the fusion protein comprises (a) a biotin-binding moiety; (b) a first polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:5 or an antigenic fragment thereof; and (c) a second polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:4 or an antigenic fragment thereof.

In some embodiments, an immunogenic complex comprises a biotinylated polysaccharide antigen of *Streptococcus pneumoniae* serotype 18C non-covalently associated with a fusion protein, wherein the fusion protein comprises (a) a biotin-binding moiety; (b) a first polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:5 or an antigenic fragment thereof; and (c) a second polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:4 or an antigenic fragment thereof.

In some embodiments, an immunogenic complex comprises a biotinylated polysaccharide antigen of *Streptococcus pneumoniae* serotype 19A non-covalently associated with a fusion protein, wherein the fusion protein comprises (a) a biotin-binding moiety; (b) a first polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:5 or an antigenic fragment thereof; and (c) a second polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:4 or an antigenic fragment thereof.

In some embodiments, an immunogenic complex comprises a biotinylated polysaccharide antigen of *Streptococcus pneumoniae* serotype 19F non-covalently associated with a fusion protein, wherein the fusion protein comprises (a) a biotin-binding moiety; (b) a first polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:5 or an antigenic fragment thereof; and (c) a second polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:4 or an antigenic fragment thereof.

In some embodiments, an immunogenic complex comprises a biotinylated polysaccharide antigen of *Streptococcus pneumoniae* serotype 20B non-covalently associated with a fusion protein, wherein the fusion protein comprises (a) a biotin-binding moiety; (b) a first polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:5 or an antigenic fragment thereof; and (c) a second polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:4 or an antigenic fragment thereof.

In some embodiments, an immunogenic complex comprises a biotinylated polysaccharide antigen of *Streptococcus pneumoniae* serotype 22F non-covalently associated with a fusion protein, wherein the fusion protein comprises (a) a biotin-binding moiety; (b) a first polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:5 or an antigenic fragment thereof; and (c) a second polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:4 or an antigenic fragment thereof.

In some embodiments, an immunogenic complex comprises a biotinylated polysaccharide antigen of *Streptococcus pneumoniae* serotype 23F non-covalently associated with a fusion protein, wherein the fusion protein comprises (a) a biotin-binding moiety; (b) a first polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:5 or an antigenic fragment thereof; and (c) a second polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:4 or an antigenic fragment thereof.

In some embodiments, an immunogenic complex comprises a biotinylated polysaccharide antigen of *Streptococcus pneumoniae* serotype 33F non-covalently associated with a fusion protein, wherein the fusion protein comprises (a) a biotin-binding moiety; (b) a first polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:5 or an antigenic fragment thereof and (c) a second polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:4 or an antigenic fragment thereof.

In some embodiments, an immunogenic complex comprises a biotin-binding moiety, wherein the biotin-binding moiety is a polypeptide comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:1 or a biotin-binding fragment thereof or a polypeptide comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:2 or a biotin-binding fragment thereof.

In some embodiments, an immunogenic complex comprises a fusion protein and a polysaccharide antigen, wherein the ratio of fusion protein to polysaccharide antigen in the complex is about 1:1, about 2:1, about 3:1, about 4:1, about 5:1, about 6:1, about 7:1, about 8:1, about 9:1, or about 10:1 by weight. In some embodiments, a vaccine comprises one or more immunogenic complexes disclosed herein.

In some embodiments, a pharmaceutical composition comprises a vaccine or vaccine composition disclosed herein, and a pharmaceutically acceptable carrier. In some embodiments, a pharmaceutical composition comprises an immunogenic complex disclosed herein, and a pharmaceutically acceptable carrier. In some embodiments, a pharmaceutical composition disclosed herein comprises one or more adjuvants. In some embodiments, the one or more adjuvants is or comprises a co-stimulation factor.

In some embodiments, the one or more adjuvants are selected from the group consisting of aluminum phosphate, aluminum hydroxide, and phosphated aluminum hydroxide. In some embodiments, wherein the one or more adjuvants is or comprises aluminum phosphate. In some embodiments, a pharmaceutical composition disclosed herein is formulated for injection.

In some embodiments, upon administration to a subject, a pharmaceutical composition disclosed herein induces an immune response. In some embodiments, the immune response comprises an innate immune response. In some embodiments, the immune response comprises an antibody or B cell response. In some embodiments, the immune response comprises a CD4+ T cell response (e.g., $T_H1$, $T_H2$, or $T_H17$ response), a CD8+ T cell response, a CD4+ and CD8+ T cell response, or a CD4−/CD8− T cell response. In some embodiments, the immune response comprises (i) an antibody or B cell response, and (ii) a T cell response. In some embodiments, the immune response comprises (i) an antibody or B cell response, (ii) a T cell response, and (iii) an innate immune response. In some embodiments, the immune response is to at least one polysaccharide antigen or at least one polypeptide antigen of a fusion protein. In some embodiments, the immune response comprises (i) an antibody or B cell response to at least one polysaccharide antigen, and (ii) a CD4+ T cell response (e.g., $T_H1$, $T_H2$, or $T_H17$ response), a CD8+ T cell response, a CD4+ and CD8+ T cell response, or a CD4−/CD8− T cell response to at least one polypeptide of a fusion protein. In some embodiments, the immune response comprises (i) an antibody or B cell response to at least one polysaccharide antigen, and (ii) an antibody or B cell response to at least one polypeptide of a fusion protein. In some embodiments, the immune response comprises (i) an antibody or B cell response to at least one polysaccharide antigen, and (ii) an antibody or B cell response, and a CD4+ T cell response, including a $T_H1$, $T_H2$, or $T_H17$ response, a CD8+ T cell response, a CD4+ and CD8+ T cell response, or a CD4−/CD8− T cell response, to at least one polypeptide of a fusion protein.

In some embodiments, upon administration to a subject, a pharmaceutical composition disclosed herein induces an opsonic/bactericidal response against one or more serotypes of *Streptococcus pneumoniae*. In some embodiments, such an opsonic/bactericidal response may be directed against one or more (e.g., 1, 2, 3, 4, 5, 6, 7, 8, 9, 10 or more) serotypes of *Streptococcus pneumoniae*, wherein a pharmaceutical composition described herein includes polysaccharide(s) present in at least one or more (e.g., 1, 2, 3, 4, 5, 6, 7, 8, 9, 10 or more) of such serotype(s). In some embodiments, such an opsonic/bactericidal response may be directed against one or more (e.g., 1, 2, 3, 4, 5, 6, 7, 8, 9, 10 or more) serotypes of *Streptococcus pneumoniae*, wherein a pharmaceutical composition described herein does not include polysaccharide(s) present in at least one or more (e.g., 1, 2, 3, 4, 5, 6, 7, 8, 9, 10 or more) of such serotype(s).

In some embodiments, such an opsonic/bactericidal response may be directed against two or more (e.g., 2, 3, 4, 5, 6, 7, 8, 9, 10 or more) serotypes of *Streptococcus pneumoniae*, wherein a pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s). In some embodiments, an opsonic/bactericidal response can include production of antibodies that opsonize one or more serotypes of *Streptococcus pneumoniae*, which leads to killing of such serotype(s) by one or more immune pathways. In some embodiments, such an opsonic/bactericidal response can be determined by an opsonophagocytic assay (OPA) or a concentrated opsonophagocytic assay (COPA) known in the art and/or as described herein. In some embodiments, upon administration to a subject, a pharmaceutical composition disclosed herein inhibits transmission of one or more serotypes of *Streptococcus pneumoniae* from the subject to another subject. In some embodiments, such inhibition of transmission may be directed against one or more (e.g., 1, 2, 3, 4, 5, 6, 7, 8, 9, 10 or more) serotypes of *Streptococcus pneumoniae*, wherein a pharmaceutical composition described herein includes polysaccharide(s) present in at least one or more (e.g., 1, 2, 3, 4, 5, 6, 7, 8, 9, 10 or more) of such serotype(s). In some embodiments, such inhibition of transmission may be directed against one or more (e.g., 1, 2, 3, 4, 5, 6, 7, 8, 9, 10 or more) serotypes of *Streptococcus pneumoniae*, wherein a pharmaceutical composition described herein does not include polysaccharide(s) present in at least one or more (e.g., 1, 2, 3, 4, 5, 6, 7, 8, 9, 10 or more) of such serotype(s). In some embodiments, such inhibition of transmission may be directed against two or more (e.g., 2, 3, 4, 5, 6, 7, 8, 9, 10 or more) serotypes of *Streptococcus pneumoniae*, wherein a pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s).

In some embodiments, upon administration to a subject, a pharmaceutical composition disclosed herein inhibits or reduces the rate of occurrence of Invasive Pneumococcal Disease (IPD) associated with or induced by one or more serotypes of *Streptococcus pneumoniae*. In some embodiments, such inhibition of IPD or reduction in the rate of occurrence of IPD may be directed against one or more (e.g., 1, 2, 3, 4, 5, 6, 7, 8, 9, 10 or more) serotypes of *Streptococcus pneumoniae*, wherein a pharmaceutical composition described herein includes polysaccharide(s) present in at least one or more (e.g., 1, 2, 3, 4, 5, 6, 7, 8, 9, 10 or more) of such serotype(s). In some embodiments, such inhibition of IPD or reduction in the rate of occurrence of IPD may be directed against one or more (e.g., 1, 2, 3, 4, 5, 6, 7, 8, 9, 10 or more) serotypes of *Streptococcus pneumoniae*, wherein a pharmaceutical composition described herein does not include polysaccharide(s) present in at least one or more (e.g., 1, 2, 3, 4, 5, 6, 7, 8, 9, 10 or more) of such serotype(s). In some embodiments, such inhibition of IPD or reduction in the rate of occurrence of IPD may be directed against two or more (e.g., 2, 3, 4, 5, 6, 7, 8, 9, 10 or more) serotypes of *Streptococcus pneumoniae*, wherein a pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s). In some embodiments, upon administration to a subject, a pharmaceutical composition disclosed herein reduces the severity of Invasive Pneumococcal Disease (IPD) associated with or induced by one or more serotypes of *Streptococcus pneumoniae*. In some embodiments, such reduction in the severity of IPD may be directed against one or more (e.g., 1, 2, 3, 4, 5, 6, 7, 8, 9, 10 or more) serotypes of *Streptococcus pneumoniae*, wherein a pharmaceutical composition described herein includes polysaccharide(s) present in at least one or more (e.g., 1, 2, 3, 4, 5, 6, 7, 8, 9, 10 or more) of such serotype(s). In some embodiments, such reduction in the severity of IPD may be directed against one or more (e.g., 1, 2, 3, 4, 5, 6, 7, 8, 9, 10 or more) serotypes of *Streptococcus pneumoniae*, wherein a pharmaceutical composition described herein does not include polysaccharide(s) present in at least one or more (e.g., 1, 2, 3, 4, 5, 6, 7, 8, 9, 10 or more) of such serotype(s). In some embodiments, such reduction in the severity of IPD may be directed against two or more (e.g., 2, 3, 4, 5, 6, 7, 8, 9, 10 or more) serotypes of *Streptococcus pneumoniae*, wherein a pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s).

In some embodiments, upon administration to a subject, a pharmaceutical composition disclosed herein inhibits or reduces the rate of occurrence of bacteremia, sepsis, and/or meningitis associated with or induced by one or more serotypes of *Streptococcus pneumoniae*. In some embodiments, such inhibition, or reduction in the rate of occurrence, of bacteremia, sepsis, and/or meningitis may be directed against one or more (e.g., 1, 2, 3, 4, 5, 6, 7, 8, 9, 10 or more) serotypes of *Streptococcus pneumoniae*, wherein a pharmaceutical composition described herein includes polysaccharide(s) present in at least one or more (e.g., 1, 2, 3, 4, 5, 6, 7, 8, 9, 10 or more) of such serotype(s). In some embodiments, such inhibition, or reduction in the rate of occurrence, of bacteremia, sepsis, and/or meningitis may be directed against one or more (e.g., 1, 2, 3, 4, 5, 6, 7, 8, 9, 10 or more) serotypes of *Streptococcus pneumoniae*, wherein a pharmaceutical composition described herein does not include polysaccharide(s) present in at least one or more (e.g., 1, 2, 3, 4, 5, 6, 7, 8, 9, 10 or more) of such serotype(s). In some embodiments, such inhibition, or reduction in the rate of occurrence, of bacteremia, sepsis, and/or meningitis may be directed against two or more (e.g., 2, 3, 4, 5, 6, 7, 8, 9, 10 or more) serotypes of *Streptococcus pneumoniae*, wherein a pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s). In some embodiments, upon administration to a subject, a pharmaceutical composition disclosed herein reduces the severity of bacteremia, sepsis, and/or meningitis associated with or induced by one or more serotypes of *Streptococcus pneumoniae*. In some embodiments, such reduction in the severity of bacteremia, sepsis, and/or meningitis may be directed against one or more (e.g., 1, 2, 3, 4, 5, 6, 7, 8, 9, 10 or more) serotypes of *Streptococcus pneumoniae*, wherein a pharmaceutical composition described herein includes polysaccharide(s) present in at least one or more (e.g., 1, 2, 3, 4, 5, 6, 7, 8, 9, 10 or more) of such serotype(s). In some embodiments, such reduction in the severity of bacteremia, sepsis, and/or meningitis may be directed against one or more (e.g., 1, 2, 3, 4, 5, 6, 7, 8, 9, 10 or more) serotypes of *Streptococcus pneumoniae*, wherein a pharmaceutical composition described herein does not include polysaccharide(s) present in at least one or more (e.g., 1, 2, 3, 4, 5, 6, 7, 8, 9, 10 or more) of such serotype(s). In some embodiments, such reduction in the severity of bacteremia, sepsis, and/or meningitis may be directed against two or more (e.g., 2, 3, 4, 5, 6, 7, 8, 9, 10 or more) serotypes of *Streptococcus pneumoniae*, wherein a pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s).

In some embodiments, upon administration to a subject, a pharmaceutical composition disclosed herein inhibits or reduces the rate of occurrence of organ damage associated with or induced by one or more serotypes of *Streptococcus pneumoniae*. In some embodiments, such inhibition, or reduction in the rate of occurrence, of organ damage may be directed against one or more (e.g., 1, 2, 3, 4, 5, 6, 7, 8, 9, 10 or more) serotypes of *Streptococcus pneumoniae*, wherein a pharmaceutical composition described herein includes polysaccharide(s) present in at least one or more (e.g., 1, 2, 3, 4, 5, 6, 7, 8, 9, 10 or more) of such serotype(s). In some embodiments, such inhibition, or reduction in the rate of occurrence, of organ damage may be directed against one or more (e.g., 1, 2, 3, 4, 5, 6, 7, 8, 9, 10 or more) serotypes of *Streptococcus pneumoniae*, wherein a pharmaceutical composition described herein does not include polysaccharide(s) present in at least one or more (e.g., 1, 2, 3, 4, 5, 6, 7, 8, 9, 10 or more) of such serotype(s). In some embodiments, such inhibition, or reduction in the rate of occurrence, of organ damage may be directed against two or more (e.g., 2, 3, 4, 5, 6, 7, 8, 9, 10 or more) serotypes of *Streptococcus pneumoniae*, wherein a pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s). In some embodiments, upon administration to a subject, a pharmaceutical composition disclosed herein reduces, the severity of organ damage associated with or induced by one or more serotypes of *Streptococcus pneumoniae*. In some embodiments, such reduction in the severity of organ damage may be directed against one or more (e.g., 1, 2, 3, 4, 5, 6, 7, 8, 9, 10 or more) serotypes of *Streptococcus pneumoniae*, wherein a pharmaceutical composition described herein includes polysaccharide(s) present in at least one or more (e.g., 1, 2, 3, 4, 5, 6, 7, 8, 9, 10 or more) of such serotype(s). In some embodiments, such reduction in the severity of organ damage may be directed against one or more (e.g., 1, 2, 3, 4, 5, 6, 7, 8, 9, 10 or more) serotypes of *Streptococcus pneumoniae*, wherein a pharmaceutical composition described herein does not include polysaccharide(s) present in at least one or more (e.g., 1, 2, 3, 4, 5, 6, 7, 8, 9, 10 or more) of such serotype(s). In some embodiments, such reduction in the severity of organ damage may be directed against two or more (e.g., 2, 3, 4, 5, 6, 7, 8, 9, 10 or more) serotypes of *Streptococcus pneumoniae*, wherein a pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s).

In some embodiments, upon administration to a subject, a pharmaceutical composition disclosed herein inhibits or reduces the rate of occurrence of pneumonia associated with or induced by one or more serotypes of *Streptococcus pneumoniae*. In some embodiments, such inhibition, or reduction in the rate of occurrence, of pneumonia may be directed against one or more (e.g., 1, 2, 3, 4, 5, 6, 7, 8, 9, 10 or more) serotypes of *Streptococcus pneumoniae*, wherein a pharmaceutical composition described herein includes polysaccharide(s) present in at least one or more (e.g., 1, 2, 3, 4, 5, 6, 7, 8, 9, 10 or more) of such serotype(s). In some embodiments, such inhibition, or reduction in the rate of occurrence, of pneumonia may be directed against one or more (e.g., 1, 2, 3, 4, 5, 6, 7, 8, 9, 10 or more) serotypes of *Streptococcus pneumoniae*, wherein a pharmaceutical composition described herein does not include polysaccharide(s) present in at least one or more (e.g., 1, 2, 3, 4, 5, 6, 7, 8, 9, 10 or more) of such serotype(s). In some embodiments, such inhibition, or reduction in the rate of occurrence, of pneumonia may be directed against two or more (e.g., 2, 3, 4, 5, 6, 7, 8, 9, 10 or more) serotypes of *Streptococcus pneumoniae*, wherein a pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s). In some embodiments, upon administration to a subject, a pharmaceutical composition disclosed herein reduces the severity of pneumonia associated with or induced by one or more serotypes of *Streptococcus pneumoniae*. In some embodiments, such reduction in the severity of pneumonia may be directed against one or more (e.g., 1, 2, 3, 4, 5, 6, 7, 8, 9, 10 or more) serotypes of *Streptococcus pneumoniae*, wherein a pharmaceutical composition described herein includes polysaccharide(s) present in at least one or more (e.g., 1, 2, 3, 4, 5, 6, 7, 8, 9, 10 or more) of such serotype(s). In some embodiments, such reduction in the severity of pneumonia may be directed against one or more (e.g., 1, 2, 3, 4, 5, 6, 7, 8, 9, 10 or more) serotypes of *Streptococcus pneumoniae*, wherein a pharmaceutical composition described herein does not include polysaccharide(s) present in at least one or more (e.g., 1, 2, 3, 4, 5, 6, 7, 8, 9, 10 or more) of such serotype(s). In some embodiments, such reduction in the severity of pneumonia may be directed against two or more (e.g., 2, 3, 4, 5, 6, 7, 8, 9, 10 or more) serotypes of *Streptococcus pneumoniae*, wherein a pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s).

In some embodiments, upon administration to a subject, a pharmaceutical composition disclosed herein inhibits or reduces the rate of occurrence of otitis media associated with or induced by one or more serotypes of *Streptococcus pneumoniae*. In some embodiments, such inhibition, or reduction in the rate of occurrence, of otitis media may be directed against one or more (e.g., 1, 2, 3, 4, 5, 6, 7, 8, 9, 10 or more) serotypes of *Streptococcus pneumoniae*, wherein a pharmaceutical composition described herein includes polysaccharide(s) present in at least one or more (e.g., 1, 2, 3, 4, 5, 6, 7, 8, 9, 10 or more) of such serotype(s). In some embodiments, such inhibition, or reduction in the rate of occurrence, of otitis media may be directed against one or more (e.g., 1, 2, 3, 4, 5, 6, 7, 8, 9, 10 or more) serotypes of *Streptococcus pneumoniae*, wherein a pharmaceutical composition described herein does not include polysaccharide(s) present in at least one or more (e.g., 1, 2, 3, 4, 5, 6, 7, 8, 9, 10 or more) of such serotype(s). In some embodiments, such inhibition, or reduction in the rate of occurrence, of otitis media may be directed against two or more (e.g., 2, 3, 4, 5, 6, 7, 8, 9, 10 or more) serotypes of *Streptococcus pneumoniae*, wherein a pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s). In some embodiments, upon administration to a subject, a pharmaceutical composition disclosed herein reduces the severity of otitis media associated with or induced by one or more serotypes of *Streptococcus pneumoniae*. In some embodiments, such reduction in the severity of otitis media may be directed against one or more (e.g., 1, 2, 3, 4, 5, 6, 7, 8, 9, 10 or more) serotypes of *Streptococcus pneumoniae*, wherein a pharmaceutical composition described herein includes polysaccharide(s) present in at least one or more (e.g., 1, 2, 3, 4, 5, 6, 7, 8, 9, 10 or more) of such serotype(s). In some embodiments, such reduction in the severity of otitis media may be directed against one or more (e.g., 1, 2, 3, 4, 5, 6, 7, 8, 9, 10 or more) serotypes of *Streptococcus pneumoniae*, wherein a pharmaceutical composition described herein does not include polysaccharide(s) present in at least one or more (e.g., 1, 2, 3, 4, 5, 6, 7, 8, 9, 10 or more) of such serotype(s). In some embodiments, such reduction in the severity of otitis media may be directed against two or more (e.g., 2, 3, 4, 5, 6, 7, 8, 9, 10 or more) serotypes of *Streptococcus pneumoniae*, wherein a pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s).

In some embodiments, upon administration to a subject, a pharmaceutical composition disclosed herein inhibits or reduces the rate of occurrence of sinusitis associated with or induced by one or more serotypes of *Streptococcus pneumoniae*. In some embodiments, such inhibition, or reduction in the rate of occurrence, of sinusitis may be directed against one or more (e.g., 1, 2, 3, 4, 5, 6, 7, 8, 9, 10 or more) serotypes of *Streptococcus pneumoniae*, wherein a pharmaceutical composition described herein includes polysaccharide(s) present in at least one or more (e.g., 1, 2, 3, 4, 5, 6, 7, 8, 9, 10 or more) of such serotype(s). In some embodiments, such inhibition, or reduction in the rate of occurrence, of sinusitis may be directed against one or more (e.g., 1, 2, 3, 4, 5, 6, 7, 8, 9, 10 or more) serotypes of *Streptococcus pneumoniae*, wherein a pharmaceutical composition described herein does not include polysaccharide(s) present in at least one or more (e.g., 1, 2, 3, 4, 5, 6, 7, 8, 9, 10 or more) of such serotype(s). In some embodiments, such inhibition, or reduction in the rate of occurrence, of sinusitis may be directed against two or more (e.g., 2, 3, 4, 5, 6, 7, 8, 9, 10 or more) serotypes of *Streptococcus pneumoniae*, wherein a pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s). In some embodiments, upon administration to a subject, a pharmaceutical composition disclosed herein reduces the severity of sinusitis associated with or induced by one or more serotypes of *Streptococcus pneumoniae*. In some embodiments, such reduction in the severity of sinusitis may be directed against one or more (e.g., 1, 2, 3, 4, 5, 6, 7, 8, 9, 10 or more) serotypes of *Streptococcus pneumoniae*, wherein a pharmaceutical composition described herein includes polysaccharide(s) present in at least one or more (e.g., 1, 2, 3, 4, 5, 6, 7, 8, 9, 10 or more) of such serotype(s). In some embodiments, such reduction in the severity of sinusitis may be directed against one or more (e.g., 1, 2, 3, 4, 5, 6, 7, 8, 9, 10 or more) serotypes of *Streptococcus pneumoniae*, wherein a pharmaceutical composition described herein does not include polysaccharide(s) present in at least one or more (e.g., 1, 2, 3, 4, 5, 6, 7, 8, 9, 10 or more) of such serotype(s). In some embodiments, such reduction in the severity of sinusitis may be directed against two or more (e.g., 2, 3, 4, 5, 6, 7, 8, 9, 10 or more) serotypes of *Streptococcus pneumoniae*, wherein a pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s).

In some embodiments, upon administration to a subject, a pharmaceutical composition disclosed herein inhibits colonization of mucosal surface(s) by one or more serotypes of *Streptococcus pneumoniae*. In some embodiments, such inhibition of colonization of mucosal surface(s) may be directed against one or more (e.g., 1, 2, 3, 4, 5, 6, 7, 8, 9, 10 or more) serotypes of *Streptococcus pneumoniae*, wherein a pharmaceutical composition described herein includes polysaccharide(s) present in at least one or more (e.g., 1, 2, 3, 4, 5, 6, 7, 8, 9, 10 or more) of such serotype(s). In some embodiments, such inhibition of colonization of mucosal surface(s) may be directed against one or more (e.g., 1, 2, 3, 4, 5, 6, 7, 8, 9, 10 or more) serotypes of *Streptococcus pneumoniae*, wherein a pharmaceutical composition described herein does not include polysaccharide(s) present in at least one or more (e.g., 1, 2, 3, 4, 5, 6, 7, 8, 9, 10 or more) of such serotype(s). In some embodiments, such inhibition of colonization of mucosal surface(s) may be directed against two or more (e.g., 2, 3, 4, 5, 6, 7, 8, 9, 10 or more) serotypes of *Streptococcus pneumoniae*, wherein a pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s). In some embodiments, upon administration to a subject, a pharmaceutical composition disclosed herein inhibits colonization of the nasopharynx by one or more serotypes of *Streptococcus pneumoniae*. In some embodiments, such inhibition of colonization of nasopharynx may be directed against one or more (e.g., 1, 2, 3, 4, 5, 6, 7, 8, 9, 10 or more) serotypes of *Streptococcus pneumoniae*, wherein a pharmaceutical composition described herein includes polysaccharide(s) present in at least one or more (e.g., 1, 2, 3, 4, 5, 6, 7, 8, 9, 10 or more) of such serotype(s). In some embodiments, such inhibition of colonization of nasopharynx may be directed against one or more (e.g., 1, 2, 3, 4, 5, 6, 7, 8, 9, 10 or more) serotypes of *Streptococcus pneumoniae*, wherein a pharmaceutical composition described herein does not include polysaccharide(s) present in at least one or more (e.g., 1, 2, 3, 4, 5, 6, 7, 8, 9, 10 or more) of such serotype(s). In some embodiments, such inhibition of colonization of nasopharynx may be directed against two or more (e.g., 2, 3, 4, 5, 6, 7, 8, 9, 10 or more) serotypes of *Streptococcus pneumoniae*, wherein a pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s).

Some embodiments provide a method of making a vaccine, the method comprising non-covalently complexing a plurality of biotinylated polysaccharide antigens with a plurality of a fusion protein comprising at least one polypeptide antigen selected from: an SP1500 polypeptide or antigenic fragment thereof; an SP0785 polypeptide or antigenic fragment thereof or a combination thereof. In some embodiments, the plurality of biotinylated polysaccharide antigens comprises a polysaccharide of *Streptococcus pneumoniae* having a serotype selected from one or more of 1, 2, 3, 4, 5, 6A, 6B, 6C, 6D, 6E, 6F, 6G, 6H, 7A, 7B, 7C, 7F, 8, 9A, 9L, 9N, 9V, 10A, 10B, 10C, 10F, 11A, 11B, 11C, 11D, 11E, 11F, 12A, 12B, 12F, 13, 14, 15A, 15B, 15C, 15F, 16A, 16F, 17A, 17F, 18A, 18B, 18C, 18F, 19A, 19B, 19C, 19F, 20A, 20B, 21, 22A, 22F, 23A, 23B, 23F, 24A, 24B, 24F, 25A, 25F, 27, 28A, 28F, 29, 31, 32A, 32F, 33A, 33B, 33C, 33D, 33E, 33F, 34, 35A, 35B, 35C, 35F, 36, 37, 38, 39, 40, 41A, 41F, 42, 43, 44, 45, 46, 47A, 47F, and 48. In some embodiments, the plurality of biotinylated polysaccharide antigens comprises a polysaccharide of *Streptococcus pneumoniae* having a serotype selected from one or more of 1, 2, 3, 4, 5, 6A, 6B, 7F, 8, 9N, 9V, 10A, 11A, 12F, 14, 15B, 17F, 18C, 19A, 19F, 20B, 22F, 23F, and 33F. In some embodiments, the plurality of biotinylated polysaccharide antigens comprises a polysaccharide of *Streptococcus pneumoniae* having a serotype selected from each of 1, 2, 3, 4, 5, 6A, 6B, 7F, 8, 9N, 9V, 10A, 11A, 12F, 14, 15B, 17F, 18C, 19A, 19F, 20B, 22F, 23F, and 33F. In some embodiments, the plurality of biotinylated polysaccharide antigens comprises a polysaccharide of *Streptococcus pneumoniae* having a serotype selected from one or more of 1, 3, 4, 5, 6A, 6B, 7F, 9V, 14, 18C, 19A, 19F, 22F, 23F, and 33F. In some embodiments, the plurality of biotinylated polysaccharide antigens comprises a polysaccharide of *Streptococcus pneumoniae* having a serotype selected from each of 1, 3, 4, 5, 6A, 6B, 7F, 9V, 14, 18C, 19A, 19F, 22F, 23F, and 33F. In some embodiments, the plurality of biotinylated polysaccharide antigens comprises a polysaccharide of *Streptococcus pneumoniae* having a serotype selected from one or more of 2, 8, 9N, 10A, 11A, 12F, 15B, 17F, and 20B. In some embodiments, the plurality of biotinylated polysaccharide antigens comprises a polysaccharide of *Streptococcus pneumoniae* having a serotype selected from each of 2, 8, 9N, 10A, 11A, 12F, 15B, 17F, and 20B.

Some embodiments provide for a method of immunizing a subject against *Streptococcus pneumoniae* infection and/or colonization, the method comprising administering to the subject an immunologically effective amount of a vaccine disclosed herein. In some embodiments, a method of immunizing a subject against *Streptococcus pneumoniae* infection and/or colonization, comprises administering to a subject an immunologically effective amount of an immunogenic complex disclosed herein. In some embodiments, a method of immunizing a subject against *Streptococcus pneumoniae* infection and/or colonization, comprises administering to a subject an immunologically effective amount of a pharmaceutical composition disclosed herein.

In some embodiments, administration of the vaccine, immunogenic complex, or pharmaceutical composition induces an immune response. In some embodiments, the immune response comprises an innate immune response. In some embodiments, the immune response comprises an antibody or B cell response. In some embodiments, the immune response comprises a CD4+ T cell response (e.g., $T_H1$, $T_H2$, or $T_H17$ response), a CD8+ T cell response, a CD4+ and CD8+ T cell response, or a CD4−/CD8− T cell response. In some embodiments, the immune response comprises (i) an antibody or B cell response and (ii) a T cell response. In some embodiments, the immune response comprises (i) an antibody or B cell response, (ii) a T cell response, and (iii) an innate immune response. In some embodiments, the immune response is to at least one polysaccharide antigen or at least one polypeptide of a fusion protein. In some embodiments, the immune response comprises (i) an antibody or B cell response to at least one polysaccharide antigen, and (ii) a CD4+ T cell response (e.g., $T_H1$, $T_H2$, or $T_H17$ response), a CD8+ T cell response, a CD4+ and CD8+ T cell response, or a CD4−/CD8− T cell response to at least one polypeptide of a fusion protein. In some embodiments, the immune response comprises (i) an antibody or B cell response to at least one polysaccharide antigen, and (ii) an antibody or B cell response to at least one polypeptide of a fusion protein. In some embodiments, the immune response comprises (i) an antibody or B cell response to at least one polysaccharide antigen, and (ii) an antibody or B cell response, and a CD4+ T cell response, including $T_H1$, $T_H2$, or $T_H17$ response, or a CD8+ T cell response, a CD4+ and CD8+ T cell response, or a CD4−/CD8− T cell response, to at least one polypeptide of a fusion protein.

In some embodiments, administration of a vaccine, immunogenic complex, or pharmaceutical composition (e.g., ones described and/or utilized herein) induces an opsonic/bactericidal response against one or more serotypes of *Streptococcus pneumoniae*. In some embodiments, such an opsonic/bactericidal response may be directed against one or more (e.g., 1, 2, 3, 4, 5, 6, 7, 8, 9, 10 or more) serotypes of *Streptococcus pneumoniae*, wherein a vaccine, immunogenic complex, or pharmaceutical composition described herein includes polysaccharide(s) present in at least one or more (e.g., 1, 2, 3, 4, 5, 6, 7, 8, 9, 10 or more) of such serotype(s). In some embodiments, such an opsonic/bactericidal response may be directed against one or more (e.g., 1, 2, 3, 4, 5, 6, 7, 8, 9, 10 or more) serotypes of *Streptococcus pneumoniae*, wherein a vaccine, immunogenic complex, or pharmaceutical composition described herein does not include polysaccharide(s) present in at least one or more (e.g., 1, 2, 3, 4, 5, 6, 7, 8, 9, 10 or more) of such serotype(s). In some embodiments, such an opsonic/bactericidal response may be directed against two or more (e.g., 2, 3, 4, 5, 6, 7, 8, 9, 10 or more) serotypes of *Streptococcus pneumoniae*, wherein a vaccine, immunogenic complex, or pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s). In some embodiments, administration of a vaccine, immunogenic complex, or pharmaceutical composition (e.g., ones as described and/or utilized herein) inhibits transmission of one or more serotypes of *Streptococcus pneumoniae* from the subject to another subject. In some embodiments, such inhibition of transmission may be directed against one or more (e.g., 1, 2, 3, 4, 5, 6, 7, 8, 9, 10 or more) serotypes of *Streptococcus pneumoniae*, wherein a vaccine, immunogenic complex, or pharmaceutical composition described herein includes polysaccharide(s) present in at least one or more (e.g., 1, 2, 3, 4, 5, 6, 7, 8, 9, 10 or more) of such serotype(s). In some embodiments, such inhibition of transmission may be directed against one or more (e.g., 1, 2, 3, 4, 5, 6, 7, 8, 9, 10 or more) serotypes of *Streptococcus pneumoniae*, wherein a vaccine, immunogenic complex, or pharmaceutical composition described herein does not include polysaccharide(s) present in at least one or more (e.g., 1, 2, 3, 4, 5, 6, 7, 8, 9, 10 or more) of such serotype(s). In some embodiments, such inhibition of transmission may be directed against two or more (e.g., 2, 3, 4, 5, 6, 7, 8, 9, 10 or more) serotypes of *Streptococcus pneumoniae*, wherein a vaccine, immunogenic complex, or pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s).

In some embodiments, administration of a vaccine, immunogenic complex, or pharmaceutical composition (e.g., ones described and/or utilized herein) inhibits or reduces the rate of occurrence of Invasive Pneumococcal Disease (IPD) associated with or induced by one or more serotypes of *Streptococcus pneumoniae*. In some embodiments, such inhibition, or reduction in the rate of occurrence, of IPD may be directed against one or more (e.g., 1, 2, 3, 4, 5, 6, 7, 8, 9, 10 or more) serotypes of *Streptococcus pneumoniae*, wherein a vaccine, immunogenic complex, or pharmaceutical composition described herein includes polysaccharide(s) present in at least one or more (e.g., 1, 2, 3, 4, 5, 6, 7, 8, 9, 10 or more) of such serotype(s). In some embodiments, such inhibition, or reduction in the rate of occurrence, of IPD may be directed against one or more (e.g., 1, 2, 3, 4, 5, 6, 7, 8, 9, 10 or more) serotypes of *Streptococcus pneumoniae*, wherein a vaccine, immunogenic complex, or pharmaceutical composition described herein does not include polysaccharide(s) present in at least one or more (e.g., 1, 2, 3, 4, 5, 6, 7, 8, 9, 10 or more) of such serotype(s). In some embodiments, such inhibition, or reduction in the rate of occurrence, of IPD may be directed against two or more (e.g., 2, 3, 4, 5, 6, 7, 8, 9, 10 or more) serotypes of *Streptococcus pneumoniae*, wherein a vaccine, immunogenic complex, or pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s). In some embodiments, administration of a vaccine, immunogenic complex, or pharmaceutical composition (e.g., ones described and/or utilized herein) reduces the severity of Invasive Pneumococcal Disease (IPD) associated with or induced by one or more serotypes of *Streptococcus pneumoniae*. In some embodiments, such reduction in the severity of IPD may be directed against one or more (e.g., 1, 2, 3, 4, 5, 6, 7, 8, 9, 10 or more) serotypes of *Streptococcus pneumoniae*, wherein a vaccine, immunogenic complex, or pharmaceutical composition described herein includes polysaccharide(s) present in at least one or more (e.g., 1, 2, 3, 4, 5, 6, 7, 8, 9, 10 or more) of such serotype(s). In some embodiments, such reduction in the severity of IPD may be directed against one or more (e.g., 1, 2, 3, 4, 5, 6, 7, 8, 9, 10 or more) serotypes of *Streptococcus pneumoniae*, wherein a vaccine, immunogenic complex, or pharmaceutical composition described herein does not include polysaccharide(s) present in at least one or more (e.g., 1, 2, 3, 4, 5, 6, 7, 8, 9, 10 or more) of such serotype(s). In some embodiments, such reduction in the severity of IPD may be directed against two or more (e.g., 2, 3, 4, 5, 6, 7, 8, 9, 10 or more) serotypes of *Streptococcus pneumoniae*, wherein a vaccine, immunogenic complex, or pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s).

In some embodiments, administration of a vaccine, immunogenic complex, or pharmaceutical composition (e.g., ones described and/or utilized herein) inhibits or reduces the rate of occurrence of bacteremia, sepsis, and/or meningitis associated with or induced by one or more serotypes of *Streptococcus pneumoniae*. In some embodiments, such inhibition, or reduction in rate of occurrence, of bacteremia, sepsis, and/or meningitis may be directed against one or more (e.g., 1, 2, 3, 4, 5, 6, 7, 8, 9, 10 or more) serotypes of *Streptococcus pneumoniae*, wherein a vaccine, immunogenic complex, or pharmaceutical composition described herein includes polysaccharide(s) present in at least one or more (e.g., 1, 2, 3, 4, 5, 6, 7, 8, 9, 10 or more) of such serotype(s). In some embodiments, such inhibition, or reduction in rate of occurrence, of bacteremia, sepsis, and/or meningitis may be directed against one or more (e.g., 1, 2, 3, 4, 5, 6, 7, 8, 9, 10 or more) serotypes of *Streptococcus pneumoniae*, wherein a vaccine, immunogenic complex, or pharmaceutical composition described herein does not include polysaccharide(s) present in at least one or more (e.g., 1, 2, 3, 4, 5, 6, 7, 8, 9, 10 or more) of such serotype(s). In some embodiments, such inhibition, or reduction in rate of occurrence, of bacteremia, sepsis, and/or meningitis may be directed against two or more (e.g., 2, 3, 4, 5, 6, 7, 8, 9, 10 or more) serotypes of *Streptococcus pneumoniae*, wherein a vaccine, immunogenic complex, or pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s). In some embodiments, administration of a vaccine, immunogenic complex, or pharmaceutical composition (e.g., ones described and/or utilized herein) reduces the severity of bacteremia, sepsis, and/or meningitis associated with or induced by one or more serotypes of *Streptococcus pneumoniae*. In some embodiments, such reduction in the severity of bacteremia, sepsis, and/or meningitis may be directed against one or more (e.g., 1, 2, 3, 4, 5, 6, 7, 8, 9, 10 or more) serotypes of *Streptococcus pneumoniae*, wherein a vaccine, immunogenic complex, or pharmaceutical composition described herein includes polysaccharide(s) present in at least one or more (e.g., 1, 2, 3, 4, 5, 6, 7, 8, 9, 10 or more) of such serotype(s). In some embodiments, such reduction in the severity of bacteremia, sepsis, and/or meningitis may be directed against one or more (e.g., 1, 2, 3, 4, 5, 6, 7, 8, 9, 10 or more) serotypes of *Streptococcus pneumoniae*, wherein a vaccine, immunogenic complex, or pharmaceutical composition described herein does not include polysaccharide(s) present in at least one or more (e.g., 1, 2, 3, 4, 5, 6, 7, 8, 9, 10 or more) of such serotype(s). In some embodiments, such reduction in the severity of bacteremia, sepsis, and/or meningitis may be directed against two or more (e.g., 2, 3, 4, 5, 6, 7, 8, 9, 10 or more) serotypes of *Streptococcus pneumoniae*, wherein a vaccine, immunogenic complex, or pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s).

In some embodiments, administration of a vaccine, immunogenic complex, or pharmaceutical composition (e.g., ones described and/or utilized herein) inhibits or reduces the rate of occurrence of organ damage associated with or induced by one or more serotypes of *Streptococcus pneumoniae*. In some embodiments, such inhibition, or reduction in the rate of occurrence, of organ damage may be directed against one or more (e.g., 1, 2, 3, 4, 5, 6, 7, 8, 9, 10 or more) serotypes of *Streptococcus pneumoniae*, wherein a vaccine, immunogenic complex, or pharmaceutical composition described herein includes polysaccharide(s) present in at least one or more (e.g., 1, 2, 3, 4, 5, 6, 7, 8, 9, 10 or more) of such serotype(s). In some embodiments, such inhibition, or reduction in the rate of occurrence, of organ damage may be directed against one or more (e.g., 1, 2, 3, 4, 5, 6, 7, 8, 9, 10 or more) serotypes of *Streptococcus pneumoniae*, wherein a vaccine, immunogenic complex, or pharmaceutical composition described herein does not include polysaccharide(s) present in at least one or more (e.g., 1, 2, 3, 4, 5, 6, 7, 8, 9, 10 or more) of such serotype(s). In some embodiments, such inhibition, or reduction in the rate of occurrence, of organ damage may be directed against two or more (e.g., 2, 3, 4, 5, 6, 7, 8, 9, 10 or more) serotypes of *Streptococcus pneumoniae*, wherein a vaccine, immunogenic complex, or pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s). In some embodiments, administration of a vaccine, immunogenic complex, or pharmaceutical composition (e.g., ones described and/or utilized herein) reduces the severity of organ damage associated with or induced by one or more serotypes of *Streptococcus pneumoniae*. In some embodiments, such reduction in the severity of organ damage may be directed against one or more (e.g., 1, 2, 3, 4, 5, 6, 7, 8, 9, 10 or more) serotypes of *Streptococcus pneumoniae*, wherein a vaccine, immunogenic complex, or pharmaceutical composition described herein includes polysaccharide(s) present in at least one or more (e.g., 1, 2, 3, 4, 5, 6, 7, 8, 9, 10 or more) of such serotype(s). In some embodiments, such reduction in the severity of organ damage may be directed against one or more (e.g., 1, 2, 3, 4, 5, 6, 7, 8, 9, 10 or more) serotypes of *Streptococcus pneumoniae*, wherein a vaccine, immunogenic complex, or pharmaceutical composition described herein does not include polysaccharide(s) present in at least one or more (e.g., 1, 2, 3, 4, 5, 6, 7, 8, 9, 10 or more) of such serotype(s). In some embodiments, such reduction in the severity of organ damage may be directed against two or more (e.g., 2, 3, 4, 5, 6, 7, 8, 9, 10 or more) serotypes of *Streptococcus pneumoniae*, wherein a vaccine, immunogenic complex, or pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s).

In some embodiments, administration of a vaccine, immunogenic complex, or pharmaceutical composition (e.g., ones described and/or utilized herein) inhibits or reduces the rate of occurrence of pneumonia associated with or induced by one or more serotypes of *Streptococcus pneumoniae*. In some embodiments, such inhibition, or reduction in the rate of occurrence, of pneumonia may be directed against one or more (e.g., 1, 2, 3, 4, 5, 6, 7, 8, 9, 10 or more) serotypes of *Streptococcus pneumoniae*, wherein a vaccine, immunogenic complex, or pharmaceutical composition described herein includes polysaccharide(s) present in at least one or more (e.g., 1, 2, 3, 4, 5, 6, 7, 8, 9, 10 or more) of such serotype(s). In some embodiments, such inhibition, or reduction in the rate of occurrence, of pneumonia may be directed against one or more (e.g., 1, 2, 3, 4, 5, 6, 7, 8, 9, 10 or more) serotypes of *Streptococcus pneumoniae*, wherein a vaccine, immunogenic complex, or pharmaceutical composition described herein does not include polysaccharide(s) present in at least one or more (e.g., 1, 2, 3, 4, 5, 6, 7, 8, 9, 10 or more) of such serotype(s). In some embodiments, such inhibition, or reduction in the rate of occurrence, of pneumonia may be directed against two or more (e.g., 2, 3, 4, 5, 6, 7, 8, 9, 10 or more) serotypes of *Streptococcus pneumoniae*, wherein a vaccine, immunogenic complex, or pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s). In some embodiments, administration of a vaccine, immunogenic complex, or pharmaceutical composition (e.g., ones described and/or utilized herein) reduces the severity of pneumonia associated with or induced by one or more serotypes of *Streptococcus pneumoniae*. In some embodiments, such reduction in the severity of pneumonia may be directed against one or more (e.g., 1, 2, 3, 4, 5, 6, 7, 8, 9, 10 or more) serotypes of *Streptococcus pneumoniae*, wherein a vaccine, immunogenic complex, or pharmaceutical composition described herein includes polysaccharide(s) present in at least one or more (e.g., 1, 2, 3, 4, 5, 6, 7, 8, 9, 10 or more) of such serotype(s). In some embodiments, such reduction in the severity of pneumonia may be directed against one or more (e.g., 1, 2, 3, 4, 5, 6, 7, 8, 9, 10 or more) serotypes of *Streptococcus pneumoniae*, wherein a vaccine, immunogenic complex, or pharmaceutical composition described herein does not include polysaccharide(s) present in at least one or more (e.g., 1, 2, 3, 4, 5, 6, 7, 8, 9, 10 or more) of such serotype(s). In some embodiments, such reduction in the severity of pneumonia may be directed against two or more (e.g., 2, 3, 4, 5, 6, 7, 8, 9, 10 or more) serotypes of *Streptococcus pneumoniae*, wherein a vaccine, immunogenic complex, or pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s).

In some embodiments, administration of a vaccine, immunogenic complex, or pharmaceutical composition (e.g., ones described and/or utilized herein) inhibits or reduces the rate of occurrence of otitis media associated with or induced by one or more serotypes of *Streptococcus pneumoniae*. In some embodiments, such inhibition, or reduction in the rate of occurrence, of otitis media may be directed against one or more (e.g., 1, 2, 3, 4, 5, 6, 7, 8, 9, 10 or more) serotypes of *Streptococcus pneumoniae*, wherein a vaccine, immunogenic complex, or pharmaceutical composition described herein includes polysaccharide(s) present in at least one or more (e.g., 1, 2, 3, 4, 5, 6, 7, 8, 9, 10 or more) of such serotype(s). In some embodiments, such inhibition, or reduction in the rate of occurrence, of otitis media may be directed against one or more (e.g., 1, 2, 3, 4, 5, 6, 7, 8, 9, 10 or more) serotypes of *Streptococcus pneumoniae*, wherein a vaccine, immunogenic complex, or pharmaceutical composition described herein does not include polysaccharide(s) present in at least one or more (e.g., 1, 2, 3, 4, 5, 6, 7, 8, 9, 10 or more) of such serotype(s). In some embodiments, such inhibition, or reduction in the rate of occurrence, of otitis media may be directed against two or more (e.g., 2, 3, 4, 5, 6, 7, 8, 9, 10 or more) serotypes of *Streptococcus pneumoniae*, wherein a vaccine, immunogenic complex, or pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s). In some embodiments, administration of a vaccine, immunogenic complex, or pharmaceutical composition (e.g., ones described and/or utilized herein) reduces the severity of otitis media associated with or induced by one or more serotypes of *Streptococcus pneumoniae*. In some embodiments, such reduction in the severity of otitis media may be directed against one or more (e.g., 1, 2, 3, 4, 5, 6, 7, 8, 9, 10 or more) serotypes of *Streptococcus pneumoniae*, wherein a vaccine, immunogenic complex, or pharmaceutical composition described herein includes polysaccharide(s) present in at least one or more (e.g., 1, 2, 3, 4, 5, 6, 7, 8, 9, 10 or more) of such serotype(s). In some embodiments, such reduction in the severity of otitis media may be directed against one or more (e.g., 1, 2, 3, 4, 5, 6, 7, 8, 9, 10 or more) serotypes of *Streptococcus pneumoniae*, wherein a vaccine, immunogenic complex, or pharmaceutical composition described herein does not include polysaccharide(s) present in at least one or more (e.g., 1, 2, 3, 4, 5, 6, 7, 8, 9, 10 or more) of such serotype(s). In some embodiments, such reduction in the severity of otitis media may be directed against two or more (e.g., 2, 3, 4, 5, 6, 7, 8, 9, 10 or more) serotypes of *Streptococcus pneumoniae*, wherein a vaccine, immunogenic complex, or pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s).

In some embodiments, administration of a vaccine, immunogenic complex, or pharmaceutical composition (e.g., ones described and/or utilized herein) inhibits or reduces the rate of occurrence of sinusitis associated with or induced by one or more serotypes of *Streptococcus pneumoniae*. In some embodiments, such inhibition, or reduction in the rate of occurrence, of sinusitis may be directed against one or more (e.g., 1, 2, 3, 4, 5, 6, 7, 8, 9, 10 or more) serotypes of *Streptococcus pneumoniae*, wherein a vaccine, immunogenic complex, or pharmaceutical composition described herein includes polysaccharide(s) present in at least one or more (e.g., 1, 2, 3, 4, 5, 6, 7, 8, 9, 10 or more) of such serotype(s). In some embodiments, such inhibition, or reduction in the rate of occurrence, of sinusitis be directed against one or more (e.g., 1, 2, 3, 4, 5, 6, 7, 8, 9, 10 or more) serotypes of *Streptococcus pneumoniae*, wherein a vaccine, immunogenic complex, or pharmaceutical composition described herein does not include polysaccharide(s) present in at least one or more (e.g., 1, 2, 3, 4, 5, 6, 7, 8, 9, 10 or more) of such serotype(s). In some embodiments, such inhibition, or reduction in the rate of occurrence, of sinusitis may be directed against two or more (e.g., 2, 3, 4, 5, 6, 7, 8, 9, 10 or more) serotypes of *Streptococcus pneumoniae*, wherein a vaccine, immunogenic complex, or pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s). In some embodiments, administration of a vaccine, immunogenic complex, or pharmaceutical composition (e.g., ones described and/or utilized herein) reduces the severity of sinusitis associated with or induced by one or more serotypes of *Streptococcus pneumoniae*. In some embodiments, such reduction in the severity of sinusitis may be directed against one or more (e.g., 1, 2, 3, 4, 5, 6, 7, 8, 9, 10 or more) serotypes of *Streptococcus pneumoniae*, wherein a vaccine, immunogenic complex, or pharmaceutical composition described herein includes polysaccharide(s) present in at least one or more (e.g., 1, 2, 3, 4, 5, 6, 7, 8, 9, 10 or more) of such serotype(s). In some embodiments, such reduction in the severity of sinusitis may be directed against one or more (e.g., 1, 2, 3, 4, 5, 6, 7, 8, 9, 10 or more) serotypes of *Streptococcus pneumoniae*, wherein a vaccine, immunogenic complex, or pharmaceutical composition described herein does not include polysaccharide(s) present in at least one or more (e.g., 1, 2, 3, 4, 5, 6, 7, 8, 9, 10 or more) of such serotype(s). In some embodiments, such reduction in the severity of sinusitis may be directed against two or more (e.g., 2, 3, 4, 5, 6, 7, 8, 9, 10 or more) serotypes of *Streptococcus pneumoniae*, wherein a vaccine, immunogenic complex, or pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s).

In some embodiments, administration of a vaccine, immunogenic complex, or pharmaceutical composition (e.g., ones described and/or utilized herein) inhibits colonization of mucosal surface(s) by one or more serotypes of *Streptococcus pneumoniae*. In some embodiments, such inhibition of colonization of mucosal surface(s) may be directed against one or more (e.g., 1, 2, 3, 4, 5, 6, 7, 8, 9, 10 or more) serotypes of *Streptococcus pneumoniae*, wherein a vaccine, immunogenic complex, or pharmaceutical composition described herein includes polysaccharide(s) present in at least one or more (e.g., 1, 2, 3, 4, 5, 6, 7, 8, 9, 10 or more) of such serotype(s). In some embodiments, such inhibition of colonization of mucosal surface(s) may be directed against one or more (e.g., 1, 2, 3, 4, 5, 6, 7, 8, 9, 10 or more) serotypes of *Streptococcus pneumoniae*, wherein a vaccine, immunogenic complex, or pharmaceutical composition described herein does not include polysaccharide(s) present in at least one or more (e.g., 1, 2, 3, 4, 5, 6, 7, 8, 9, 10 or more) of such serotype(s). In some embodiments, such inhibition of colonization of mucosal surface(s) may be directed against two or more (e.g., 2, 3, 4, 5, 6, 7, 8, 9, 10 or more) serotypes of *Streptococcus pneumoniae*, wherein a vaccine, immunogenic complex, or pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s). In some embodiments, administration of a vaccine, immunogenic complex, or pharmaceutical composition (e.g., ones described and/or utilized herein) inhibits colonization of nasopharynx by one or more serotypes of *Streptococcus pneumoniae*. In some embodiments, such inhibition of colonization of nasopharynx may be directed against one or more (e.g., 1, 2, 3, 4, 5, 6, 7, 8, 9, 10 or more) serotypes of *Streptococcus pneumoniae*, wherein a vaccine, immunogenic complex, or pharmaceutical composition described herein includes polysaccharide(s) present in at least one or more (e.g., 1, 2, 3, 4, 5, 6, 7, 8, 9, 10 or more) of such serotype(s). In some embodiments, such inhibition of colonization of nasopharynx may be directed against one or more (e.g., 1, 2, 3, 4, 5, 6, 7, 8, 9, 10 or more) serotypes of

*Streptococcus pneumoniae*, wherein a vaccine, immunogenic complex, or pharmaceutical composition described herein does not include polysaccharide(s) present in at least one or more (e.g., 1, 2, 3, 4, 5, 6, 7, 8, 9, 10 or more) of such serotype(s). In some embodiments, such inhibition of colonization of nasopharynx may be directed against two or more (e.g., 2, 3, 4, 5, 6, 7, 8, 9, 10 or more) serotypes of *Streptococcus pneumoniae*, wherein a vaccine, immunogenic complex, or pharmaceutical composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s).

In some embodiments of the methods disclosed herein, the *Streptococcus pneumoniae* has a serotype selected from one or more of 1, 2, 3, 4, 5, 6A, 6B, 6C, 6D, 6E, 6F, 6G, 6H, 7A, 7B, 7C, 7F, 8, 9A, 9L, 9N, 9V, 10A, 10B, 10C, 10F, 11A, 11B, 11C, 11D, 11E, 11F, 12A, 12B, 12F, 13, 14, 15A, 15B, 15C, 15F, 16A, 16F, 17A, 17F, 18A, 18B, 18C, 18F, 19A, 19B, 19C, 19F, 20A, 20B, 21, 22A, 22F, 23A, 23B, 23F, 24A, 24B, 24F, 25A, 25F, 27, 28A, 28F, 29, 31, 32A, 32F, 33A, 33B, 33C, 33D, 33E, 33F, 34, 35A, 35B, 35C, 35F, 36, 37, 38, 39, 40, 41A, 41F, 42, 43, 44, 45, 46, 47A, 47F, and 48. In some embodiments, the *Streptococcus pneumoniae* has a serotype selected from one or more of 1, 2, 3, 4, 5, 6A, 6B, 7F, 8, 9N, 9V, 10A, 11A, 12F, 14, 15B, 17F, 18C, 19A, 19F, 20B, 22F, 23F, and 33F. In some embodiments, the *Streptococcus pneumoniae* has a serotype selected from one or more of 1, 3, 4, 5, 6A, 6B, 7F, 9V, 14, 18C, 19A, 19F, 22F, 23F, and 33F. In some embodiments, the *Streptococcus pneumoniae* has a serotype selected from one or more of 2, 8, 9N, 10A, 11A, 12F, 15B, 17F, and 20B.

In some embodiments, the subject is immunized against *Streptococcus pneumoniae* infection and/or colonization with one dose of a vaccine. In some embodiments, the subject is immunized against *Streptococcus pneumoniae* infection and/or colonization with two doses of a vaccine. In some embodiments, the subject is immunized against *Streptococcus pneumoniae* infection and/or colonization with three doses of a vaccine.

BRIEF DESCRIPTION OF THE DRAWINGS

The present teachings described herein will be more fully understood from the following description of various illustrative embodiments, when read together with the accompanying drawings. It should be understood that the drawings described below are for illustration purposes only and are not intended to limit the scope of the present teachings in any way.

and two weeks following second immunization (P2). Results are expressed as percent survival, i.e., the percent reduction in S. pneumoniae colony forming units (CFU) following incubation with immune (P2) sera, relative to incubation with matched pre-immune (P0) sera. Each vertical bar of the graphs represents the percent survival of S. pneumoniae serotype 16F observed with MAPS24 immune sera (Panel A) or Prevnar 13 immune sera (Panel B) at the indicated dilution (bottom of each graph). Error bars show the ±95% confidence interval. Abbreviations: Prevnar: 13-valent Prevnar 13 vaccine; MAPS24: 24-valent MAPS24 vaccine; *p<0.05 and **p<0.01 for Wilcoxon matched pairs test; ns: not statistically significant.

Figure 24:
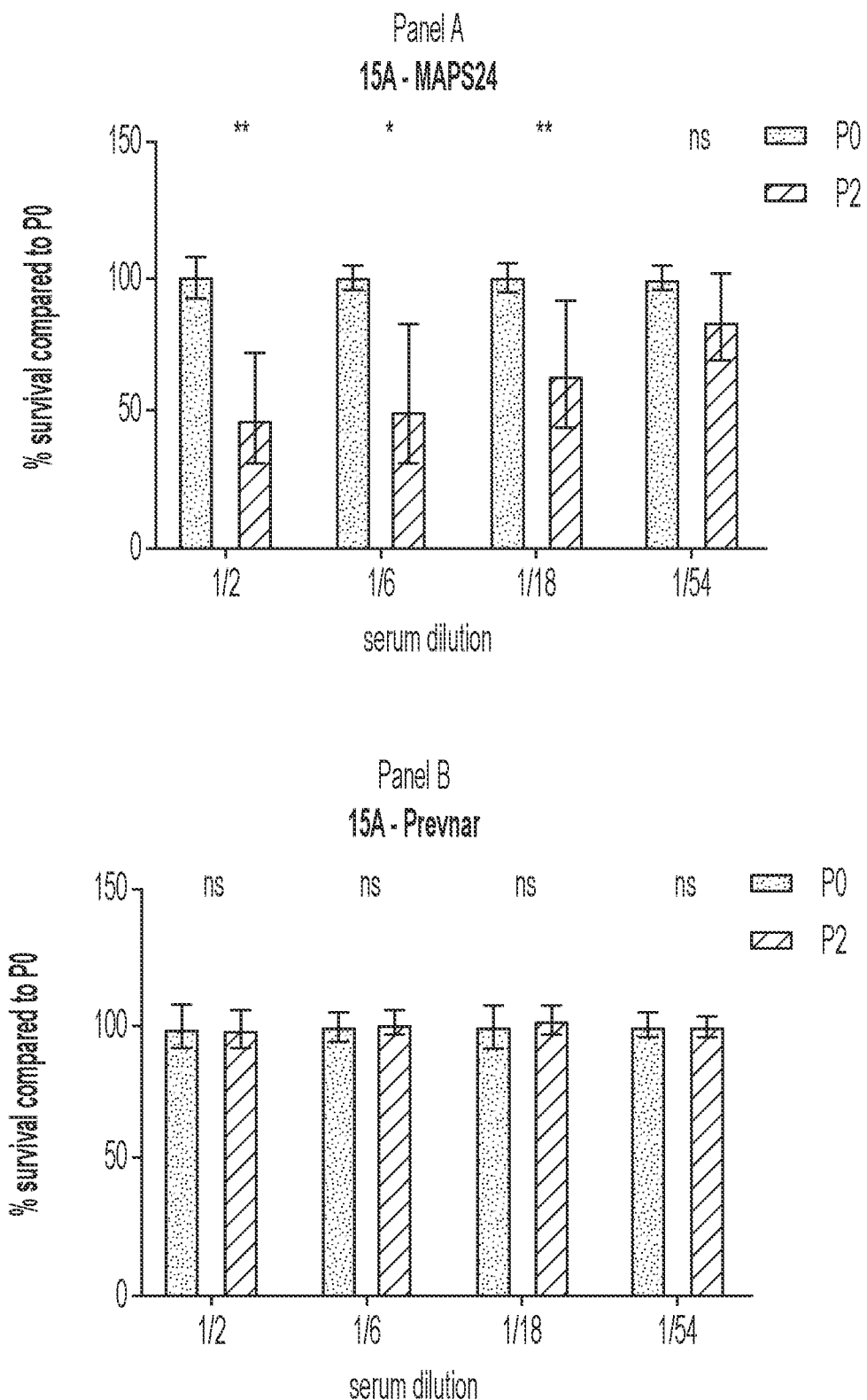

FIG. 24 illustrates the presence of functional antibodies against a representative non-vaccine serotype of S. pneumoniae (e.g., serotype 15A) in MAPS24 immune sera, compared to Prevnar 13 immune sera, using an opsonophagocytic killing assay. S. pneumoniae serotype 15A, polysaccharide(s) of which is/are not included in MAPS24 vaccine or Prevnar 13, was incubated in a modified concentrated opsonophagocytic assay (COPA) with heat-inactivated sera from rabbits immunized with an exemplary formulation of the 24-valent MAPS24 vaccine or with Prevnar 13. The presence of functional antibodies was shown by killing of incubated S. pneumoniae. Sera were collected prior to immunization (P0) and two weeks following second immunization (P2). Results are expressed as percent survival, i.e., the percent reduction in S. pneumoniae colony forming units (CFU) following incubation with immune (P2) sera, relative to incubation with matched pre-immune (P0) sera. Each vertical bar of the graphs represents the percent survival of S. pneumoniae serotype 15A observed with MAPS24 immune sera (Panel A) or Prevnar 13 immune sera (Panel B) at the indicated dilution (bottom of each graph). Error bars show the ±95% confidence interval. Abbreviations: Prevnar: 13-valent Prevnar 13 vaccine; MAPS24: 24-valent MAPS24 vaccine; *p<0.05 and **p<0.01 for Wilcoxon matched pairs test; ns: not statistically significant.

Figure 25:
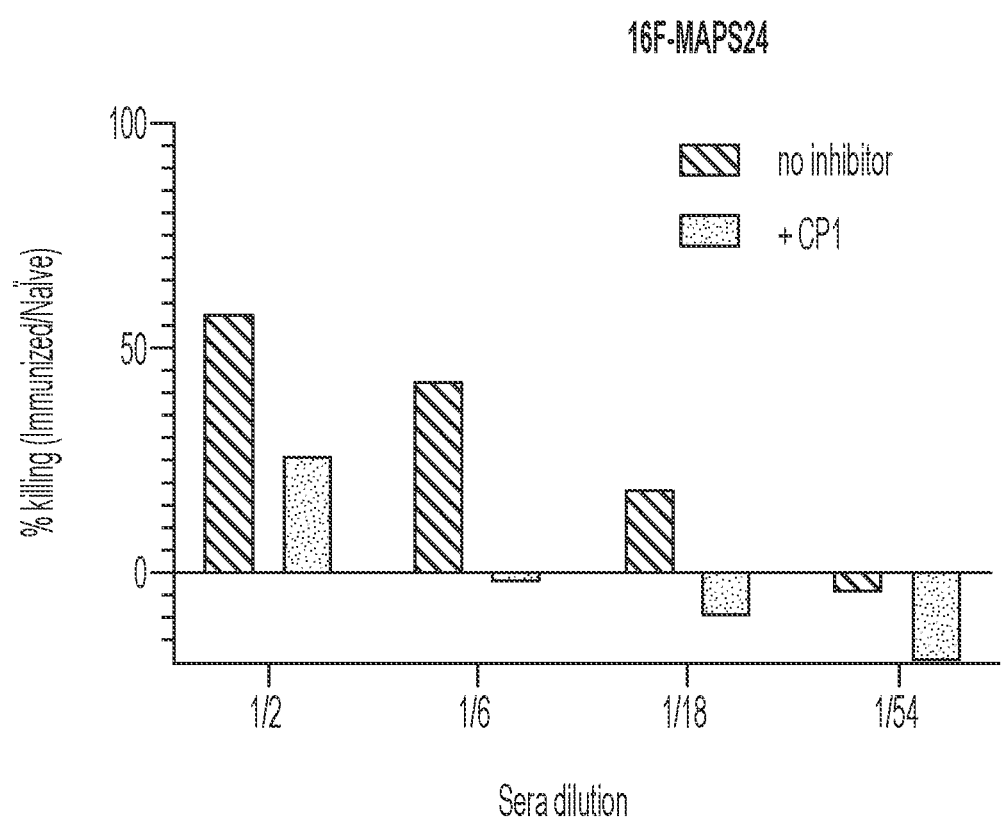

FIG. 25 illustrates specificity of functional antibodies against a representative non-vaccine serotype of S. pneumoniae (e.g., serotype 16F), polysaccharide(s) of which is/are not included in MAPS24 vaccine. The specificity of functional antibodies was assayed using an inhibition variant of the modified concentrated opsonophagocytic assay (iCOPA), in which immune sera are pre-incubated with a specific inhibitory reagent (e.g., purified fusion protein CP1) that inhibits or competes with binding of functional antibodies to a target antigen. Pre-incubated sera are then incubated with S. pneumoniae to determine whether killing by functional antibodies is inhibited. Rabbits were immunized with an exemplary formulation of the 24-valent MAPS24 vaccine. Sera were collected prior to immunization (P0) and two weeks following second immunization (P2). Results are expressed as percent killing activity, i.e., the percent reduction in S. pneumoniae colony forming units (CFU) following incubation with immune (P2) sera, relative to incubation with matched pre-immune (P0) sera. Each vertical bar on the graph represents the percent killing activity against S. pneumoniae serotype 16F observed with MAPS24 immune sera, pre-incubated as indicated with purified fusion protein CP1 (+CP1) or no inhibitor, at the indicated dilution (bottom of graph).

Figure 26:
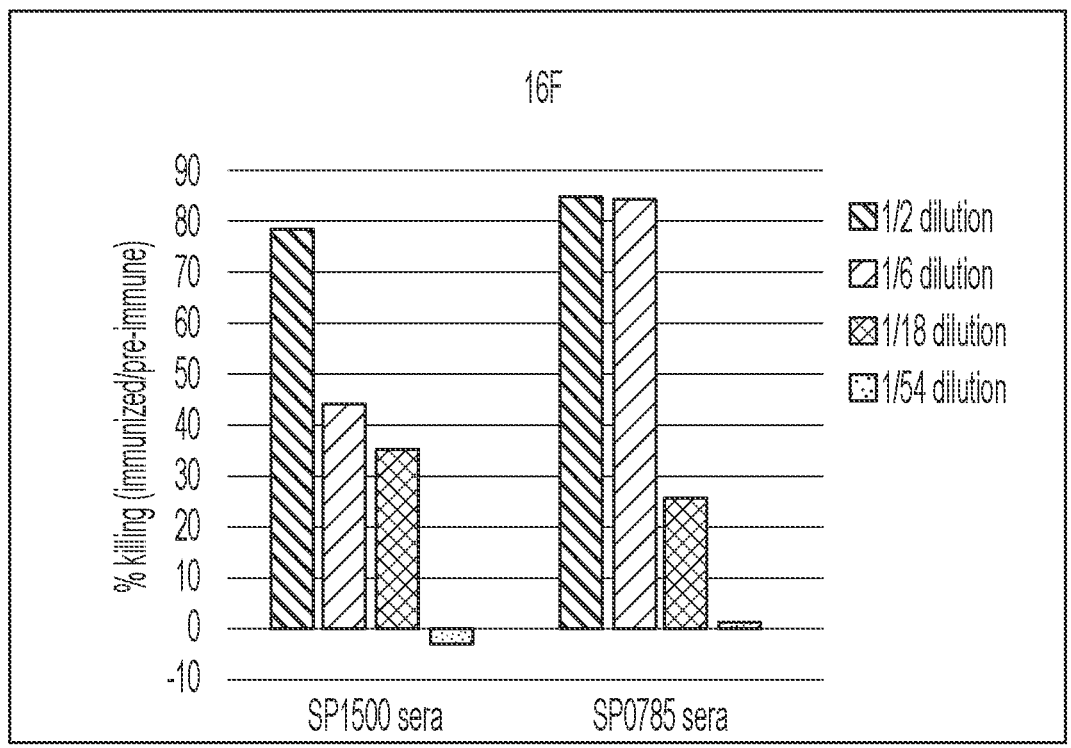

FIG. 26 illustrates the presence of functional antibodies against a representative non-vaccine serotype of S. pneumoniae (e.g., serotype 16F) in SP1500 and SP0785 immune sera, using an opsonophagocytic killing assay. S. pneumoniae serotype 16F, polysaccharide(s) of which is/are not included in MAPS24 vaccine or Prevnar 13, was incubated in a modified concentrated opsonophagocytic assay (COPA) with heat-inactivated sera from rabbits immunized with SP1500 or SP0785 proteins. The presence of functional antibodies was shown by killing of incubated S. pneumoniae. Sera were collected prior to immunization (P0) and two weeks following third immunization (P3). Results are expressed as percent killing activity, i.e., the percent reduction in S. pneumoniae colony forming units (CFU) following incubation with immune (P3) sera, relative to incubation with matched pre-immune (P0) sera. Each vertical bar of the graph represents the percent killing activity against S. pneumoniae serotype 16F observed with the indicated SP1500 or SP0785 immune sera at the indicated dilution.

DEFINITIONS

In this application, unless otherwise clear from context, (i) the term "a" may be understood to mean "at least one"; (ii) the term "or" may be understood to mean "and/or"; (iii) the terms "comprising" and "including" may be understood to encompass itemized components or steps whether presented by themselves or together with one or more additional components or steps; and (iv) the terms "about" and "approximately" may be understood to permit standard variation as would be understood by those of ordinary skill in the art; and (v) where ranges are provided, endpoints are included.

About: The term "about", when used herein in reference to a value, refers to a value that is similar, in context to the referenced value. In general, those skilled in the art, familiar with the context, will appreciate the relevant degree of variance encompassed by "about" in that context. For example, in some embodiments, the term "about" may encompass a range of values that within 25%, 20%, 19%, 18%, 17%, 16%, 15%, 14%, 13%, 12%, 11%, 10%, 9%, 8%, 7%, 6%, 5%, 4%, 3%, 2%, 1%, or less of the referred value.

Administration: As used herein, the term "administration" typically refers to the administration of a composition to a subject or system to achieve delivery of an agent that is, or is included in, the composition. Those of ordinary skill in the art will be aware of a variety of routes that may, in appropriate circumstances, be utilized for administration to a subject, for example a human. For example, in some embodiments, administration may be ocular, oral, parenteral, topical, etc. In some particular embodiments, administration may be bronchial (e.g., by bronchial instillation), buccal, dermal (which may be or comprise, for example, one or more of topical to the dermis, intradermal, interdermal, transdermal, etc.), enteral, intra-arterial, intradermal, intragastrical, intramedullary, intramuscular, intranasal, intraperitoneal, intrathecal, intravenous, intraventricular, within a specific organ (e.g., intrahepatic), mucosal, nasal, oral, rectal, subcutaneous, sublingual, topical, tracheal (e.g., by intratracheal instillation), vaginal, vitreal, etc. In some embodiments, administration may involve only a single dose. In some embodiments, administration may involve application of a fixed number of doses. In some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected period of time.

Agent: In general, the term "agent", as used herein, may be used to refer to a compound or entity of any chemical class including, for example, a polypeptide, nucleic acid, saccharide, lipid, small molecule, metal, or combination or complex thereof. In appropriate circumstances, as will be clear from context to those skilled in the art, the term may be utilized to refer to an entity that is or comprises a cell or organism, or a fraction, extract, or component thereof. Alternatively or additionally, as context will make clear, the term may be used to refer to a natural product in that it is found in and/or is obtained from nature. In some instances, again as will be clear from context, the term may be used to refer to one or more entities that is man-made in that it is designed, engineered, and/or produced through action of the hand of man and/or is not found in nature. In some embodiments, an agent may be utilized in isolated or pure form; in some embodiments, an agent may be utilized in crude form. In some embodiments, potential agents may be provided as collections or libraries, for example that may be screened to identify or characterize active agents within them. In some cases, the term "agent" may refer to a compound or entity that is or comprises a polymer; in some cases, the term may refer to a compound or entity that comprises one or more polymeric moieties. In some embodiments, the term "agent" may refer to a compound or entity that is not a polymer and/or is substantially free of any polymer and/or of one or more particular polymeric moieties. In some embodiments, the term may refer to a compound or entity that lacks or is substantially free of any polymeric moiety.

Amino acid: In its broadest sense, the term "amino acid", as used herein, refers to any compound and/or substance that can be incorporated into a polypeptide chain, e.g., through formation of one or more peptide bonds. In some embodiments, an amino acid has the general structure $H_2N-C(H)(R)-COOH$. In some embodiments, an amino acid is a naturally-occurring amino acid. In some embodiments, an amino acid is a non-natural amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Non-standard amino acid" refers to any amino acid, other than the standard amino acids, regardless of whether it is prepared synthetically or obtained from a natural source. In some embodiments, an amino acid, including a carboxy- and/or amino-terminal amino acid in a polypeptide, can contain a structural modification as compared with the general structure above. For example, in some embodiments, an amino acid may be modified by methylation, amidation, acetylation, pegylation, glycosylation, phosphorylation, and/or substitution (e.g., of the amino group, the carboxylic acid group, one or more protons, and/or the hydroxyl group) as compared with the general structure. In some embodiments, such modification may, for example, alter the circulating half-life of a polypeptide containing the modified amino acid as compared with one containing an otherwise identical unmodified amino acid. In some embodiments, such modification does not significantly alter a relevant activity of a polypeptide containing the modified amino acid, as compared with one containing an otherwise identical unmodified amino acid. As will be clear from context, in some embodiments, the term "amino acid" may be used to refer to a free amino acid; in some embodiments it may be used to refer to an amino acid residue of a polypeptide.

Antibody: As used herein, the term "antibody" refers to a polypeptide that includes canonical immunoglobulin sequence elements sufficient to confer specific binding to a particular target antigen. As is known in the art, intact antibodies as produced in nature are approximately 150 kDa tetrameric agents comprised of two identical heavy chain polypeptides (about 50 kDa each) and two identical light chain polypeptides (about 25 kDa each) that associate with each other into what is commonly referred to as a "Y-shaped" structure. Each heavy chain is comprised of at least four domains (each about 110 amino acids long)—an amino-terminal variable (VH) domain (located at the tips of the Y structure), followed by three constant domains: CH1, CH2, and the carboxy-terminal CH3 (located at the base of the Y's stem). A short region, known as the "switch", connects the heavy chain variable and constant regions. The "hinge" connects CH2 and CH3 domains to the rest of the antibody. Two disulfide bonds in this hinge region connect the two heavy chain polypeptides to one another in an intact antibody. Each light chain is comprised of two domains—an amino-terminal variable (VL) domain, followed by a carboxy-terminal constant (CL) domain, separated from one another by another "switch". Intact antibody tetramers are comprised of two heavy chain-light chain dimers in which the heavy and light chains are linked to one another by a single disulfide bond; two other disulfide bonds connect the heavy chain hinge regions to one another, so that the dimers are connected to one another and the tetramer is formed. Naturally-produced antibodies are also glycosylated, typically on the CH2 domain. Each domain in a natural antibody has a structure characterized by an "immunoglobulin fold" formed from two beta sheets (e.g., 3-, 4-, or 5-stranded sheets) packed against each other in a compressed antiparallel beta barrel. Each variable domain contains three hypervariable loops known as "complement determining regions" (CDR1, CDR2, and CDR3) and four somewhat invariant "framework" regions (FR1, FR2, FR3, and FR4). When natural antibodies fold, the FR regions form the beta sheets that provide the structural framework for the domains, and the CDR loop regions from both the heavy and light chains are brought together in three-dimensional space so that they create a single hypervariable antigen binding site located at the tip of the Y structure. The Fc region of naturally-occurring antibodies binds to elements of the complement system, and also to receptors on effector cells, including for example effector cells that mediate cytotoxicity. As is known in the art, affinity and/or other binding attributes of Fc regions for Fc receptors can be modulated through glycosylation or other modification. In some embodiments, antibodies produced and/or utilized in accordance with the present invention include glycosylated Fc domains, including Fc domains with modified or engineered such glycosylation. For purposes of the present invention, in certain embodiments, any polypeptide or complex of polypeptides that includes sufficient immunoglobulin domain sequences as found in natural antibodies can be referred to and/or used as an "antibody", whether such polypeptide is naturally produced (e.g., generated by an organism reacting to an antigen), or produced by recombinant engineering, chemical synthesis, or other artificial system or methodology. In some embodiments, an antibody is polyclonal; in some embodiments, an antibody is monoclonal. In some embodiments, an antibody has constant region sequences that are characteristic of mouse, rabbit, primate, or human antibodies. In some embodiments, antibody sequence elements are humanized, primatized, chimeric, etc., as is known in the art. Moreover, the term "antibody" as used herein, can refer in appropriate embodiments (unless otherwise stated or clear from context) to any of the art-known or developed constructs or formats for utilizing antibody structural and functional features in alternative presentation. For example, embodiments, an antibody utilized in accordance with the present invention is in a format selected from, but not limited to, intact IgA, IgG, IgE or IgM antibodies; bi- or multi-specific antibodies (e.g., Zybodies®, etc.); antibody fragments such as Fab fragments, Fab' fragments, F(ab')2 fragments, Fd' fragments, Fd fragments, and isolated CDRs or sets thereof; single chain Fvs; polypeptide-Fc fusions; single domain antibodies (e.g., shark single domain antibodies such as IgNAR or fragments thereof); cameloid antibodies; masked antibodies (e.g.) Probodies®; Small Modular ImmunoPharmaceuticals ("SMIPs™"); single chain or Tandem diabodies)(TandAb®); VHHs; Anticalins®; Nanobodies® minibodies; BiTE® s; ankyrin repeat proteins or DARPINs®; Avimers®; DARTs; TCR-like antibodies; Adnectins®; Affilins®; Trans-Bodies®; Affibodies®; TrimerX®; MicroProteins; Fynomers®, Centyrins®; and KALBITOR®s. In some embodiments, an antibody may lack a covalent modification (e.g., attachment of a glycan) that it would have if produced naturally. In some embodiments, an antibody may contain a covalent modification (e.g., attachment of a glycan, a payload [e.g., a detectable moiety, a therapeutic moiety, a catalytic moiety, etc.], or other pendant group [e.g., poly-ethylene glycol, etc.]).

Antigen: The term "antigen", as used herein, refers to (i) an agent that induces an immune response; and/or (ii) an agent that binds to a T cell receptor (e.g., when presented by an MEW molecule) or to an antibody. In some embodiments, an antigen induces a humoral response (e.g., including production of antigen-specific antibodies); in some embodiments, an antigen induces a cellular response (e.g., involving T cells whose receptors specifically interact with the antigen). In some embodiments, an antigen induces a humoral response and a cellular response. In some embodiments, an antigen binds to an antibody and may or may not induce a particular physiological response in an organism. In general, an antigen may be or include any chemical entity such as, for example, a small molecule, a nucleic acid, a polypeptide, a carbohydrate, a lipid, a polymer (in some embodiments other than a biologic polymer (e.g., other than a nucleic acid or amino acid polymer)), etc. In some embodiments, an antigen is or comprises a polypeptide. In some embodiments, an antigen is or comprises a polysaccharide. Those of ordinary skill in the art will appreciate that, in general, an antigen may be provided in isolated or pure form, or alternatively may be provided in crude form (e.g., together with other materials, for example in an extract such as a cellular extract or other relatively crude preparation of an antigen-containing source). In some embodiments, antigens utilized in accordance with the present invention are provided in a crude form. In some embodiments, an antigen is a recombinant antigen. In some embodiments, an antigen is a polypeptide or a polysaccharide that, upon administration to a subject, induces a specific and/or clinically relevant immune response to such polypeptide or polysaccharide. In some embodiments, an antigen is selected to induce a specific and/or clinically relevant immune response to such polypeptide or polysaccharide.

Associated with: Two entities are "associated" with one another, as that term is used herein, if the presence, level and/or form of one is correlated with that of the other. In some embodiments, two or more entities are physically "associated" with one another if they interact, directly or indirectly, so that they are and/or remain in physical proximity with one another. In some embodiments, two or more entities that are physically associated with one another are covalently linked to one another. In some embodiments, two or more entities that are physically associated with one another are not covalently linked to one another but are non-covalently associated, for example by means of affinity interactions, electrostatic interactions, hydrogen bonds, van der Waals interaction, hydrophobic interactions, magnetism, and combinations thereof.

Binding: It will be understood that the term "binding", as used herein, typically refers to a non-covalent association between or among two or more entities. "Direct" binding involves physical contact between entities or moieties; indirect binding involves physical interaction by way of physical contact with one or more intermediate entities. Binding between two or more entities can typically be assessed in any of a variety of contexts—including where interacting entities or moieties are studied in isolation or in the context of more complex systems (e.g., while covalently or otherwise associated with a carrier entity and/or in a biological system or cell).

Carrier protein: As used herein, the term "carrier protein" refers to a protein or peptide that is coupled, or complexed, or otherwise associated with a hapten (e.g., a small peptide or lipid) or less immunogenic antigen (e.g., a polysaccharide) and that induces or improves an immune response to such a coupled, or complexed, or otherwise associated hapten (e.g., a small peptide or lipid) or less immunogenic antigen (e.g., a polysaccharide). In some embodiments, such an immune response is or comprises a response to a hapten or less immunogenic antigen that is coupled, or complexed, or otherwise associated with such a carrier protein. In some embodiments, such an immune response is or comprises a response to both a carrier protein and a hapten or less immunogenic antigen that is coupled, or complexed, or otherwise associated with such a carrier protein. In some embodiments, no significant immune response to a carrier protein itself occurs. In some embodiments, immune response to a carrier protein may be detected; in some embodiments, immune response to such a carrier protein is strong. In some embodiments, a carrier protein is coupled, or complexed, or otherwise associated with one or more other molecules.

Colonization: As used herein, the term "colonization" generally refers to the ability of a microbe to grow at a target site or surface. For example, the terms "colonization" refers to the ability of a microbe (e.g., a bacterium) to grow at an anatomical site (e.g., a mucosal membrane, gastrointestinal tract, injury site, organ, etc.) of a host.

Combination therapy: As used herein, the term "combination therapy" refers to those situations in which a subject is exposed to two or more therapeutic regimens (e.g., two or more therapeutic agents). In some embodiments, the two or more regimens may be administered simultaneously; in some embodiments, such regimens may be administered sequentially (e.g., all "doses" of a first regimen are administered prior to administration of any doses of a second regimen); in some embodiments, such agents are administered in overlapping dosing regimens. In some embodiments, "administration" of combination therapy may involve administration of one or more agent(s) or modality(ies) to a subject receiving the other agent(s) or modality(ies) in the combination. For clarity, combination therapy does not require that individual agents be administered together in a single composition (or even necessarily at the same time), although in some embodiments, two or more agents, or active moieties thereof, may be administered together in a combination composition, or even in a combination compound (e.g., as part of a single chemical complex or covalent entity).

Derivative: As used herein, the term "derivative", or grammatical equivalents thereof, refers to a structural analogue of a reference substance. That is, a "derivative" is a substance that shows significant structural similarity with the reference substance, for example sharing a core or consensus structure, but also differs in certain discrete ways. Such a substance would be said to be "derived from" said reference substance. In some embodiments, a derivative is a substance that can be generated from the reference substance by chemical manipulation. In some embodiments, a derivative is a substance that can be generated through performance of a synthetic process substantially similar to (e.g., sharing a plurality of steps with) one that generates the reference substance.

Domain: The term "domain" as used herein refers to a section or portion of an entity. In some embodiments, a "domain" is associated with a particular structural and/or functional feature of the entity so that, when the domain is physically separated from the rest of its parent entity, it substantially or entirely retains the particular structural and/or functional feature. Alternatively or additionally, a domain may be or include a portion of an entity that, when separated from that (parent) entity and linked with a different (recipient) entity, substantially retains and/or imparts on the recipient entity one or more structural and/or functional features that characterized it in the parent entity. In some embodiments, a domain is a section or portion of a molecule (e.g., a small molecule, carbohydrate, lipid, nucleic acid, or polypeptide). In some embodiments, a domain is a section of a polypeptide; in some such embodiments, a domain is characterized by a particular structural element (e.g., a particular amino acid sequence or sequence motif, $\alpha$-helix character, $\beta$-sheet character, coiled-coil character, random coil character, etc.), and/or by a particular functional feature (e.g., binding activity, enzymatic activity, folding activity, signaling activity, etc.).

Dosage form or unit dosage form: Those skilled in the art will appreciate that the term "dosage form" may be used to refer to a physically discrete unit of an active agent (e.g., a therapeutic or diagnostic agent) for administration to a subject. Typically, each such unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). Those of ordinary skill in the art appreciate that the total amount of a therapeutic composition or agent administered to a particular subject is determined by one or more attending physicians and may involve administration of multiple dosage forms.

Dosing regimen: Those skilled in the art will appreciate that the term "dosing regimen" may be used to refer to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which is separated in time from other doses. In some embodiments, individual doses are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount. In some embodiments, a dosing regimen is correlated with a desired or beneficial outcome when administered across a relevant population (i.e., is a therapeutic dosing regimen).

Fragment: A "fragment" of a material or entity as described herein has a structure that includes a discrete portion of the whole, but lacks one or more moieties found in the whole. In some embodiments, a fragment consists of such a discrete portion. In some embodiments, a fragment includes a discrete portion of the whole which discrete portion shares one or more functional characteristics found in the whole. In some embodiments, a fragment consists of such a discrete portion. In some embodiments, a fragment consists of or comprises a characteristic structural element or moiety found in the whole. In some embodiments, a fragment of a polymer, e.g., a polypeptide or a polysaccharide, comprises or consists of at least 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 275, 300, 325, 350, 375, 400, 425, 450, 475, 500 or more monomeric units (e.g., residues) as found in the whole polymer. In some embodiments, a polymer fragment comprises or consists of at least about 5%, 10%, 15%, 20%, 25%, 30%, 25%, 40%, 45%, 50%, 55%, 60%, 65%, 70%, 75%, 80%, 85%, 90%, 95%, 96%, 97%, 98%, 99% or more of the monomeric units (e.g., residues) found in the whole polymer. The whole material or entity may in some embodiments be referred to as the "parent" of the whole.

Homology: As used herein, the term "homology" refers to the overall relatedness between polymeric molecules, e.g., between nucleic acid molecules (e.g., DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, 96%, 97%, 98%, or 99% identical. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, 96%, 97%, 98%, or 99% similar (e.g., containing residues with related chemical properties at corresponding positions). For example, as is well known by those of ordinary skill in the art, certain amino acids are typically classified as similar to one another as "hydrophobic" or "hydrophilic" amino acids, and/or as having "polar" or "non-polar" side chains. Substitution of one amino acid for another of the same type may often be considered a "homologous" substitution.

Identity: As used herein, the term "identity" refers to the overall relatedness between polymeric molecules, e.g., between nucleic acid molecules (e.g., DNA molecules and/or RNA molecules) and/or between polypeptide molecules. In some embodiments, polymeric molecules are considered to be "substantially identical" to one another if their sequences are at least 25%, 30%, 35%, 40%, 45%, 50%, 55%, 60%, 65%, 70%, 75%, 80%, 85%, 90%, 95%, 96%, 97%, 98%, or 99% identical. Calculation of the percent identity of two nucleic acid or polypeptide sequences, for example, can be performed by aligning the two sequences for optimal comparison purposes (e.g., gaps can be introduced in one or both of a first and a second sequence for optimal alignment and non-identical sequences can be disregarded for comparison purposes). In certain embodiments, the length of a sequence aligned for comparison purposes is at least 30%, at least 40%, at least 50%, at least 60%, at least 70%, at least 75%, at least 80%, at least 85%, at least 90%, at least 95%, at least 96%, at least 97%, at least 98%, at least 99%, or substantially 100% of the length of a reference sequence. The nucleotides at corresponding positions are then compared. When a position in the first sequence is occupied by the same residue (e.g., nucleotide or amino acid) as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using the algorithm of Meyers and Miller, 1989, which has been incorporated into the ALIGN program (version 2.0). In some exemplary embodiments, nucleic acid sequence comparisons made with the ALIGN program use a PAM120 weight residue table, a gap length penalty of 12 and a gap penalty of 4. The percent identity between two nucleotide sequences can, alternatively, be determined using the GAP program in the GCG software package using an NWSgapdna.CMP matrix.

Improve, increase, inhibit or reduce: As used herein, the terms "improve", "increase", "inhibit", "reduce", or grammatical equivalents thereof, indicate values that are relative to a baseline or other reference measurement. In some embodiments, an appropriate reference measurement may be or comprise a measurement in a particular system (e.g., in a single subject) under otherwise comparable conditions absent presence of (e.g., prior to and/or after) a particular agent or treatment, or in presence of an appropriate comparable reference agent. In some embodiments, an appropriate reference measurement may be or comprise a measurement in comparable system known or expected to respond in a particular way, in presence of the relevant agent or treatment.

Immunologically effective amount or immunologically effective dose: As used herein, "immunologically effective amount" or "immunologically effective dose" refers to an amount of an antigenic or immunogenic substance, e.g., an antigen, immunogen, immunogenic complex, immunogenic composition, vaccine, or pharmaceutical composition, which when administered to a subject, either in a single dose or as part of a series of doses, that is sufficient to enhance a subject's own immune response against a subsequent exposure to a pathogen. In some embodiments, the pathogen is S. pneumoniae. In some embodiments, the immune response is against one or more different serotypes of S. pneumoniae. In some embodiments, the immune response is against two or more different serotypes of S. pneumoniae. In some embodiments, the immune response is against nine or more different serotypes of S. pneumoniae. In some embodiments, the immune response is against thirteen or more different serotypes of S. pneumoniae. In some embodiments, the immune response is against fifteen or more different serotypes of S. pneumoniae. In some embodiments, the immune response is against twenty-three or more different serotypes of S. pneumoniae. In some embodiments, the immune response is against twenty-four or more different serotypes of S. pneumoniae. An immunologically effective amount may vary based on the subject to be treated, the species of the subject, the degree of immune response desired to induce, etc. In some embodiments, an immunologically effective amount is sufficient for treatment or protection of a subject having or at risk of having disease. In some embodiments, an immunologically effective amount refers to a non-toxic but sufficient amount that can be an amount to treat, attenuate, or prevent infection and/or disease (e.g., bacterial infection, pneumococcal infection, bacterial colonization, pneumococcal colonization, complications associated with bacterial infection, complications associated with pneumococcal infection, etc.) in any subject. In some embodiments, an immunologically effective amount is sufficient to induce an immunoprotective response upon administration to a subject.

Immunoprotective response or protective response: As used herein, "immunoprotective response" or "protective response" refers to an immune response that mediates antigen or immunogen-induced immunological memory. In some embodiments, an immunoprotective response is induced by the administration of a substance, e.g., an antigen, immunogen, immunogenic complex, immunogenic composition, vaccine, or pharmaceutical composition to a subject. In some embodiments, immunoprotection involves one or more of active immune surveillance, a more rapid and effective response upon immune activation as compared to a response observed in a naïve subject, efficient clearance of the activating agent or pathogen, followed by rapid resolution of inflammation. In some embodiments, an immunoprotective response is an adaptive immune response. In some embodiments, an immunoprotective response is sufficient to protect an immunized subject from productive infection by a particular pathogen or pathogens to which a vaccine is directed (e.g., S. pneumoniae infection).

Immunization: As used herein, "immunization", or grammatical equivalents thereof, refers to a process of inducing an immune response to an infectious organism or agent in a subject ("active immunization"), or alternatively, providing immune system components against an infectious organism or agent to a subject ("passive immunization"). In some embodiments, immunization involves the administration of one or more antigens, immunogens, immunogenic complexes, vaccines, immune molecules such as antibodies, immune sera, immune cells such as T cells or B cells, or pharmaceutical compositions to a subject. In some embodiments, immunization is performed by administering an immunologically effective amount of a substance, e.g., an antigen, immunogen, immunogenic complex, immunogenic composition, vaccine, immune molecule such as an antibody, immune serum, immune cell such as a T cell or B cell, or pharmaceutical composition to a subject. In some embodiments, immunization results in an immunoprotective response in the subject. In some embodiments, active immunization is performed by administering to a subject an antigenic or immunogenic substance, e.g., an antigen, immunogen, immunogenic complex, vaccine, or pharmaceutical composition. In some embodiments, passive immunization is performed by administering to a subject an immune system component, e.g., an immune molecule such as an antibody, immune serum, or immune cell such as a T cell or B cell.

Isolated: As used herein, the term "isolated", or grammatical equivalents thereof, refers to a substance and/or entity that has been (1) separated from at least some of the components with which it was associated when initially produced (whether in nature and/or in an experimental setting), and/or (2) designed, produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. In some embodiments, as will be understood by those skilled in the art, a substance may still be considered "isolated" or even "pure", after having been combined with certain other components such as, for example, one or more carriers or excipients (e.g., buffer, solvent, water, etc.); in such embodiments, percent isolation or purity of the substance is calculated without including such carriers or excipients. To give but one example, in some embodiments, a biological polymer such as a polypeptide or polysaccharide that occurs in nature is considered to be "isolated" when, a) by virtue of its origin or source of derivation is not associated with some or all of the components that accompany it in its native state in nature; b) it is substantially free of other polypeptides or nucleic acids of the same species from the species that produces it in nature; c) is expressed by or is otherwise in association with components from a cell or other expression system that is not of the species that produces it in nature. Thus, for instance, in some embodiments, a polypeptide or polysaccharide that is chemically synthesized or is synthesized in a cellular system different from that which produces it in nature is considered to be an "isolated" polypeptide or polysaccharide. Alternatively or additionally, in some embodiments, a polypeptide or polysaccharide that has been subjected to one or more purification techniques may be considered to be an "isolated" polypeptide or polysaccharide to the extent that it has been separated from other components a) with which it is associated in nature; and/or b) with which it was associated when initially produced.

Linker: As used herein, the term "linker" is used to refer to an entity that connects two or more elements to form a multi-element agent. For example, those of ordinary skill in the art appreciate that a polypeptide whose structure includes two or more functional or organizational domains often includes a stretch of amino acids between such domains that links them to one another. In some embodiments, a polypeptide comprising a linker element has an overall structure of the general form S1-L-S2, wherein S1 and S2 may be the same or different and represent two domains associated with one another by the linker (L). In some embodiments, a polypeptide linker is at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100 or more amino acids in length. In some embodiments, a linker is characterized in that it tends not to adopt a rigid three-dimensional structure, but rather provides flexibility to the polypeptide. A variety of different linker elements that can appropriately be used when engineering polypeptides (e.g., fusion polypeptides) are known in the art (Holliger et al, 1993; Poljak, 1994).

Non-inferior: As used herein, the term "non-inferior" in the context of evaluating a test pharmaceutical composition refers to a test pharmaceutical composition that is (e.g., in terms of immunogenicity and/or functional antibody titer generated by the test composition) at least as effective as a reference composition. In some embodiments, non-inferiority is demonstrated when the lower bound of the 95% confidence interval (CI) for the geometric mean titer (GMT) ratio of a test pharmaceutical composition over a reference composition is at least greater than or equal to 0.4 or above, including, e.g., at least 0.5, at least 0.6, at least 0.7, at least 0.8, at least 0.9, at least 0.95, at least 0.98, at least 1.0, or higher. For example, in some embodiments, an immunogenic composition or vaccine described herein is non-inferior to a reference vaccine (e.g., PCV13 or PPSV23) when the lower bound of the 95% confidence interval (CI) for the geometric mean titer (GMT) ratio of the immunogenic composition or vaccine over the reference vaccine is at least greater than or equal to 0.4 or above, including, e.g., at least 0.5, at least 0.6, at least 0.7, at least 0.8, at least 0.9, at least 0.95, at least 0.98, at least 1.0, or higher. In some embodiments, an immunogenic composition or vaccine described herein is non-inferior to a reference vaccine (e.g., PCV13 or PPSV23) when the lower bound of the 95% confidence interval (CI) for the geometric mean titer (GMT) ratio of the immunogenic composition or vaccine over the reference vaccine is at least greater than or equal to 0.95 or above, including, e.g., at least 0.96, at least 0.97, at least 0.98, at least 0.99, at least 1.0, at least 1.1, at least 1.3, at least 1.5, or higher. In some embodiments, an immunogenic composition or vaccine described herein is non-inferior to a reference vaccine (e.g., PCV13 or PPSV23) when the seroconversion rates, or percentages of vaccine recipients with immune responses, are above a pre-defined threshold, e.g., the lower bound of the 95% confidence interval for the difference between the percentage of subjects who seroconvert, following immunization with an immunogenic composition or vaccine described herein or immunization with the reference vaccine (e.g., PCV13 or PPSV23), is greater than −0.10.

Pharmaceutical composition: As used herein, the term "pharmaceutical composition" refers to a composition in which an active agent is formulated together with one or more pharmaceutically acceptable carriers. In some embodiments, the active agent is present in unit dose amount appropriate for administration in a therapeutic regimen that shows a statistically significant probability of achieving a predetermined therapeutic effect when administered to a relevant population. In some embodiments, a pharmaceutical composition may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

Pharmaceutically acceptable: As used herein, the term "pharmaceutically acceptable" applied to the carrier, diluent, or excipient used to formulate a composition as disclosed herein means that the carrier, diluent, or excipient must be compatible with the other ingredients of the composition and not deleterious to the recipient thereof.

Polysaccharide: The term "polysaccharide" as used herein refers to a polymeric carbohydrate molecule composed of long chains of monosaccharide units bound together by glycosidic, phosphodiester, or other linkages and on hydrolysis give the constituent monosaccharides or oligosaccharides. Polysaccharides range in structure from linear to highly branched. Examples include storage polysaccharides such as starch and glycogen, structural polysaccharides such as cellulose and chitin and microbial polysaccharides, and antigenic polysaccharides found in microorganisms including, but not limited to, capsular polysaccharides (CPS), 0 polysaccharides (OPS), core 0 polysaccharides (COPS), and lipopolysaccharides (LP S).

Polypeptide: The term "polypeptide", as used herein, generally has its art-recognized meaning of a polymer of at least three amino acids, e.g, linked to each other by peptide bonds. Those of ordinary skill in the art will appreciate that the term "polypeptide" is intended to be sufficiently general as to encompass not only polypeptides having a complete sequence recited herein, but also to encompass polypeptides that represent functional fragments (i.e., fragments retaining at least one activity) of such complete polypeptides. Moreover, those of ordinary skill in the art understand that protein sequences generally tolerate some substitution without destroying activity. Thus, any polypeptide that retains activity and shares at least about 30-40% overall sequence identity, often greater than about 50%, 60%, 70%, or 80%, and further usually including at least one region of much higher identity, often greater than 90% or even 95%, 96%, 97%, 98%, or 99% in one or more highly conserved regions, usually encompassing at least 3-4 and often up to 20 or more amino acids, with another polypeptide of the same class, is encompassed within the relevant term "polypeptide" as used herein. Polypeptides may contain L-amino acids, D-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof.

Prevention: The term "prevent" or "prevention", as used herein in connection with a disease, disorder, and/or medical condition, refers to reducing the risk of developing the disease, disorder and/or condition, and/or a delay of onset, and/or reduction in frequency and/or severity of one or more characteristics or symptoms of a particular disease, disorder or condition. In some embodiments, prevention is assessed on a population basis such that an agent is considered to "prevent" a particular disease, disorder or condition if a statistically significant decrease in the development, frequency, and/or intensity of one or more symptoms of the disease, disorder or condition is observed in a population susceptible to the disease, disorder, or condition. In some embodiments, prevention may be considered complete when onset of a disease, disorder or condition has been delayed for a pre-defined period of time.

Protein: As used herein, the term "protein" encompasses a polypeptide. Proteins may include moieties other than amino acids (e.g., may be glycoproteins, proteoglycans, etc.) and/or may be otherwise processed or modified. Those of ordinary skill in the art will appreciate that a "protein" can be a complete polypeptide chain as produced by a cell (with or without a signal sequence), or can be a characteristic portion thereof. Those of ordinary skill will appreciate that a protein can sometimes include more than one polypeptide chain, for example linked by one or more disulfide bonds or associated by other means. Polypeptides may contain 1-amino acids, d-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids. In some embodiments, proteins are antibodies, antibody fragments, biologically active portions thereof, and/or characteristic portions thereof.

Recombinant: As used herein, the term "recombinant" is intended to refer to polypeptides that are designed, engineered, prepared, expressed, created, manufactured, and/or isolated by recombinant means, such as polypeptides expressed using a recombinant expression vector transfected into a host cell; polypeptides isolated from a recombinant, combinatorial human polypeptide library; polypeptides isolated from an animal (e.g., a mouse, rabbit, sheep, fish, etc.) that is transgenic for or otherwise has been manipulated to express a gene or genes, or gene components that encode and/or direct expression of the polypeptide or one or more component(s), portion(s), element(s), or domain(s) thereof; and/or polypeptides prepared, expressed, created or isolated by any other means that involves splicing or ligating selected nucleic acid sequence elements to one another, chemically synthesizing selected sequence elements, and/or otherwise generating a nucleic acid that encodes and/or directs expression of the polypeptide or one or more component(s), portion(s), element(s), or domain(s) thereof. In some embodiments, one or more of such selected sequence elements is found in nature. In some embodiments, one or more of such selected sequence elements is designed in silico. In some embodiments, one or more such selected sequence elements results from mutagenesis (e.g., in vivo or in vitro) of a known sequence element, e.g., from a natural or synthetic source such as, for example, in the germline of a source organism of interest (e.g., of a human, a mouse, etc.).

Reference: As used herein, the term "reference" describes a standard or control relative to which a comparison is performed. For example, in some embodiments, an agent, animal, subject, population, sample, sequence or value of interest is compared with a reference or control agent, animal, subject, population, sample, sequence or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control.

Response: As used herein, a "response" to treatment may refer to any beneficial alteration in a subject's condition that occurs as a result of or correlates with treatment. Such alteration may include stabilization of the condition (e.g., prevention of deterioration that would have taken place in the absence of the treatment), amelioration of symptoms of the condition, and/or improvement in the prospects for cure of the condition, etc. It may refer to a subject's response or to a tumor's response. Subject or tumor response may be measured according to a wide variety of criteria, including clinical criteria and objective criteria. Techniques for assessing response include, but are not limited to, clinical examination, positron emission tomography, chest X-ray CT scan, MRI, ultrasound, endoscopy, laparoscopy, presence or level of biomarkers in a sample obtained from a subject, cytology, and/or histology. The exact response criteria can be selected in any appropriate manner, provided that when comparing groups of subjects and/or tumors, the groups to be compared are assessed based on the same or comparable criteria for determining response rate. One of ordinary skill in the art will be able to select appropriate criteria.

Risk: As will be understood from context, "risk" of a disease, disorder, and/or condition refers to a likelihood that a particular subject will develop the disease, disorder, and/or condition. In some embodiments, risk is expressed as a percentage. In some embodiments, risk is from 0, 1, 2, 3, 4, 5, 6, 7, 8, 9, 10, 20, 30, 40, 50, 60, 70, 80, 90 up to 100%. In some embodiments risk is expressed as a risk relative to a risk associated with a reference sample or group of reference samples. In some embodiments, a reference sample or group of reference samples have a known risk of a disease, disorder, condition and/or event. In some embodiments a reference sample or group of reference samples are from subjects comparable to a particular subject. In some embodiments, relative risk is 0, 1, 2, 3, 4, 5, 6, 7, 8, 9, 10, or more.

Serotype: As used herein, the term "serotype", also referred to as a serovar, refers to a distinct variation within a species of bacteria or virus or among immune cells of different subjects. These microorganisms, viruses, or cells are classified together based on their cell surface antigens, allowing the epidemiologic classification of organisms to the sub-species level. A group of serovars with common antigens may be referred to as a serogroup or sometimes serocomplex.

Subject: As used herein, the term "subject" refers an organism, typically a mammal (e.g., a human, in some embodiments including prenatal human forms). In some embodiments, a subject is suffering from a relevant disease, disorder or condition. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. In some embodiments, a subject is a patient. In some embodiments, a subject is an subject to whom diagnosis and/or therapy is and/or has been administered.

Superior: As used herein, the term "superior" in the context of evaluating a test pharmaceutical composition refers to a test pharmaceutical composition that performs (e.g., in terms of immunogenicity and/or functional antibody titer generated by the test composition) better than a reference composition. In some embodiments, superiority is demonstrated when the upper bound of the 95% confidence interval (CI) for the geometric mean titer (GMT) ratio of a test pharmaceutical composition over a reference composition is at least 1.3 or above, including, e.g., at least 1.4, at least 1.5, at least 2, at least 2.5, at least 3, at least 4, or higher. For example, in some embodiments, an immunogenic composition or vaccine described herein is superior to a reference vaccine (e.g., PCV13 or PPSV23) when the upper bound of the 95% confidence interval (CI) for the geometric mean titer (GMT) ratio of the immunogenic composition or vaccine over the reference vaccine is at least 1.3 or above, including, e.g., at least 1.4, at least 1.5, at least 2, at least 2.5, at least 3, at least 4, or higher. In some embodiments, an immunogenic composition or vaccine described herein is superior to a reference vaccine (e.g., PCV13 or PPSV23) when the two-sided 95% confidence interval (CI) for the geometric mean titer (GMT) ratio of the immunogenic composition or vaccine over the reference vaccine excludes zero.

Susceptible to: A subject who is "susceptible to" a disease, disorder, or condition is at risk for developing the disease, disorder, or condition. In some embodiments, a subject who is susceptible to a disease, disorder, or condition does not display any symptoms of the disease, disorder, or condition. In some embodiments, a subject who is susceptible to a disease, disorder, or condition has not been diagnosed with the disease, disorder, and/or condition. In some embodiments, a subject who is susceptible to a disease, disorder, or condition is a subject who has been exposed to conditions associated with development of the disease, disorder, or condition. In some embodiments, a risk of developing a disease, disorder, and/or condition is a population-based risk (e.g., family members of subjects suffering from the disease, disorder, or condition).

Symptoms are reduced: As used herein, "symptoms are reduced" when one or more symptoms of a particular disease, disorder or condition is reduced in magnitude (e.g., intensity, severity, etc.) and/or frequency, e.g., to a statistically and/or clinically significant or relevant level. For purposes of clarity, a delay in the onset of a particular symptom is considered one form of reducing the frequency of that symptom.

Treatment: As used herein, the term "treatment" (also "treat" or "treating") refers to any administration of a therapy that partially or completely alleviates, ameliorates, relieves, inhibits, delays onset of, reduces severity of, and/or reduces incidence of one or more symptoms, features, and/or causes of a particular disease, disorder, and/or condition. In some embodiments, such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

Vaccination: As used herein, the term "vaccination" refers to the administration of a composition intended to generate an immune response, for example to a disease-causing agent. For the purposes of the present invention, vaccination can be administered before, during, and/or after exposure to a disease-causing agent, and in certain embodiments, before, during, and/or shortly after exposure to the agent. In some embodiments, vaccination includes multiple administrations, appropriately spaced in time, of a vaccinating composition. In some embodiments, vaccination initiates immunization.

DETAILED DESCRIPTION

The present disclosure relates, generally, to compositions, systems, and methods that include novel complexed proteins and polysaccharides, e.g., vaccines of complexed proteins and polysaccharides. Such complexes can be used, e.g., to induce and/or increase an immunoprotective response in subjects at risk of or suffering from pneumococcal infection.

Previous attempts at preparing a vaccine to protect against pneumococcal infection have had limited efficacy.

Wyeth's first polyvalent polysaccharide conjugate vaccine, Prevnar 7 (PCV7), was licensed in 2000 in the United States and Europe. GlaxoSmithKline's 10-valent polysaccharide conjugate vaccine Synflorix (PCV10) was licensed in Europe, but not the United States, in 2009. Synflorix was not licensed in the United States because clinical trials did not demonstrate non-inferiority in infants compared to Prevnar 7; also, despite coverage of three additional serotypes compared to Prevnar 7, Synflorix did not formally have coverage of the clinically important S. pneumoniae serotype 19A. Also, Synflorix had originally been designed as an 11-valent polysaccharide conjugate vaccine (PCV11), but one S. pneumoniae serotype (serotype 3) was removed when clinical trials suggested no efficacy against this serotype, despite immunogenicity.

Merck's polyvalent polysaccharide conjugate vaccine PCV-15, is still in clinical trials. PCV15 has undergone clinical evaluation in adults, where it appears to be non-inferior to Prevnar 13 in adults. PCV15 also appeared to be non-inferior in toddlers, but then failed to meet non-inferiority in infants, so was returned to formulation. The newly-formulated PCV15 is now being evaluated in adults and infants.

A first protein vaccine based on PspA was evaluated by Sanofi Pasteur. An early clinical trial (published in 2000, PMID: 10699322) was a Phase 1 trial with 5-125 µg recombinant PspA (rPspA), which was associated with a clear rise in antibody levels, antibodies that were reactive with heterologous rPspA molecules, and increased binding of post-immune sera to 37 pneumococcal strains expressing a variety of PspA clades and capsular serotypes. Some concerns were raised over a region of PspA that has homology with cardiac myosin, and the program was terminated by Sanofi Pasteur.

Another protein vaccine based on a combination of the three proteins, PhtD, pneumolysoid, and PcpA, was evaluated by Sanofi Pasteur from 2011 to 2014. The vaccine passed Phase 1 in adults and was then tested in toddlers (12-13 mo) and infants (6 weeks). A study in Bangladesh showed immunogenicity; however, no evidence of impact on S. pneumoniae carriage was reported (presented at ISPPD 2014; the study was not powered to detect a small difference in prevalence of carriage). The program was terminated by Sanofi Pasteur.

A protein vaccine based on the combination of PhtD and pneumolysoid was evaluated by GlaxoSmithKline from 2012 to 2016. The vaccine was deemed safe and immunogenic in all ages (adults, toddlers, infants). However, in two further infant trials conducted in The Gambia and the Navajo Nation in the United States, there was no evidence of clinical efficacy (no impact on S. pneumoniae carriage in The Gambia, or on otitis media in the Navajo Nation). The program was terminated by GlaxoSmithKline.

A protein vaccine GEN-004, based on a combination of three proteins, SP0148, SP1912 and SP2108 adjuvanted with aluminum hydroxide, was developed and evaluated by Genocea Biosciences. GEN-004 was shown to be safe and immunogenic in adults in Phase 1. However, a Phase 2 trial of intentional pneumococcal challenge, conducted in the UK, showed no significant effect on S. pneumoniae carriage. The GEN-004 development program was suspended in 2015.

A live attenuated, engineered Salmonella vaccine was developed at Arizona State University. Mutant Salmonella typhi strains engineered to express PspA were evaluated in a Phase 1 clinical trial in adults (PMID: 23916987) from 2009 to 2011. Three different strains were evaluated. No significant adverse events were reported, but one patient had a positive blood culture for Salmonella typhi. No subjects shed vaccine in stool. There were no differences in pre- or post-vaccination ELISA or ELISPOT results between groups. The vaccine was deemed safe but non-immunogenic, therefore not efficacious, and development was stopped.

There are two S. pneumoniae vaccines currently available in the U.S. Wyeth-Pfizer's second polyvalent polysaccharide conjugate vaccine, Prevnar 13 (PCV13), was licensed in 2010 in the U.S. and Europe. PCV13 has been approved for the prevention of IPD caused by the 13 serotypes contained in the vaccine in children and for the prevention of pneumonia and IPD in adults. In this vaccine, covalent conjugation of saccharides from 13 pneumococcal serotypes to a diphtheria toxoid mutant (CRM197) protein creates saccharide-protein conjugates, which are capable of inducing a T cell-dependent immune response against one or more of the 13 pneumococcal serotypes represented by the saccharides. [PREVNAR 13 prescribing information, 2017].

PCV13 did not formally meet non-inferiority criteria compared to PCV7 and was not immunogenic against several serotypes. However, the inclusion of S. pneumoniae serotype 19A assisted with licensure of PCV13, since serotype 19A had emerged between 2000-2010 as a major cause of morbidity and mortality and was associated with antibiotic resistance. While infections with S. pneumoniae of multidrug-resistant serotypes contained in PCV13 appeared to decrease after approval of this vaccine, an increase of infections with multidrug-resistant serotypes 35B, 23A, 23B and 15B, which are just a few of the close to 100 known serotypes of S. pneumoniae not included in PCV13, was noted. Also, PCV13 was reported to have marginal activity against serotype 3, as its prevalence persists in the population [Richter et al, 2014].

The second vaccine, PPSV23, is a 23-valent polysaccharide vaccine developed by Merck, and is indicated for the prevention of pneumococcal disease in adults greater than 50 years of age, or in persons greater than 2 years of age at increased risk of pneumococcal disease. It is composed of purified capsular polysaccharides from 23 pneumococcal serotypes. While this vaccine has the potential to protect against more serotypes when compared to PCV13, it does not provide protection against the emerging serotypes 35B, 23A and 23B. In addition, PPSV23 elicits a T cell-independent polysaccharide immune response that stimulates mature B-lymphocytes, but not T-lymphocytes. Thus, this vaccine induces an immune response that is neither long-lasting nor anamnestic upon subsequent challenge. PPSV23 is not effective against colonization. In addition, polysaccharide-type vaccines are not used in infants and children less than 2 years of age, because these children respond poorly to T cell-independent antigens [PNEUMOVAX 23 prescribing information, 2017; CDC, 2010]. Data suggest that PPSV23 may protect adults and the elderly against IPD; however, no consistent effect has been observed in the prevention of pneumonia [Gruber et al, 2008].

The presently disclosed novel complexed proteins and polysaccharides, e.g., vaccines of complexed proteins and polysaccharides, and combinations thereof represent a substantial advance over the previous attempts at S. pneumoniae vaccine development and over the currently available options for immunizing patients against pneumococcal infection. Such novel complexes and vaccines can be used, e.g., to induce and/or increase an immunoprotective response in subjects, such as those at risk of or suffering from pneumococcal infection.

Immunogenic Complexes

The present disclosure encompasses immunogenic complexes that include one or more polysaccharides and/or polypeptides of *S. pneumoniae*.

In some embodiments, immunogenic complexes are, or are based on, Multiple Antigen Presenting System (MAPS) complexes. Aspects of the MAPS platform have been previously described in WO2012/155007, the contents of which are herein incorporated by reference in their entirety, and are shown schematically in FIG. 1. See also Zhang et al, 2013.

As described herein, immunogenic complexes of the disclosure include one or more antigenic polypeptides non-covalently complexed with one or more antigenic polysaccharides. In some embodiments, one or more antigenic polypeptides are complexed via affinity interaction with one or more antigenic polysaccharides. In some embodiments, immunogenic complexes of the disclosure include one or more antigenic polypeptides non-covalently complexed with one or more antigenic polysaccharides using one or more affinity molecule/complementary affinity molecule pairs. In some embodiments, an immunogenic complex includes (i) a first affinity molecule described herein conjugated to one or more antigenic polysaccharides, and (ii) a fusion protein that is or comprises a complementary affinity molecule described herein and a polypeptide. In some embodiments, an immunogenic complex includes (i) a plurality of a first affinity molecule described herein conjugated to one or more antigenic polysaccharides, and (ii) a fusion protein that is or comprises a complementary affinity molecule described herein and a polypeptide. Upon association of the first affinity molecule and the complementary affinity molecule, the one or more antigenic polypeptides are non-covalently complexed to the one or more antigenic polysaccharides.

In some embodiments, one or more antigenic polypeptides are complexed via affinity interaction with one antigenic polysaccharide. In some embodiments, immunogenic complexes of the disclosure include one or more antigenic polypeptides non-covalently complexed with one antigenic polysaccharide using one affinity molecule/complementary affinity molecule pair. In some embodiments, immunogenic complexes of the disclosure include one or more antigenic polypeptides non-covalently complexed with one antigenic polysaccharide using one or more affinity molecule/complementary affinity molecule pairs. In some embodiments, each of the affinity molecule/complementary affinity molecule pairs is the same, e.g., biotin/biotin-binding moiety pairs. In some embodiments, an immunogenic complex includes (i) a first affinity molecule described herein conjugated to one antigenic polysaccharide, and (ii) a fusion protein that is or comprises a complementary affinity molecule described herein and a polypeptide. In some embodiments, an immunogenic complex includes (i) a plurality of a first affinity molecule described herein conjugated to one antigenic polysaccharide, and (ii) a fusion protein that is or comprises a complementary affinity molecule described herein and a polypeptide. Upon association of the first affinity molecule and the complementary affinity molecule, the one or more antigenic polypeptides are non-covalently complexed to the one antigenic polysaccharide.

In some embodiments, the affinity molecule/complementary affinity molecule pair is selected from one or more of biotin/biotin-binding moiety, antibody/antigen, enzyme/substrate, receptor/ligand, metal/metal-binding protein, carbohydrate/carbohydrate binding protein, lipid/lipid-binding protein, and His tag/His tag-binding molecule.

In some embodiments, the first affinity molecule is biotin (or a derivative or fragment thereof), and the complementary affinity molecule is a moiety, e.g., a biotin-binding protein, or a biotin-binding domain or biotin-binding fragment thereof. In some embodiments, the biotin-binding moiety is rhizavidin, avidin, streptavidin, bradavidin, tamavidin, lentiavidin, zebavidin, NeutrAvidin, CaptAvidin™, or a biotin-binding domain or biotin-binding fragment thereof, or a combination thereof. In some embodiments, the biotin-binding moiety is rhizavidin, or a biotin-binding domain or biotin-binding fragment thereof. In some embodiments, the biotin-binding moiety is or comprises a polypeptide of SEQ ID NO:1, or a biotin-binding domain or biotin-binding fragment thereof. In some embodiments, the biotin-binding moiety is or comprises a polypeptide of SEQ ID NO:2, or a biotin-binding domain or biotin-binding fragment thereof.

In some embodiments, the one or more antigenic polysaccharides are, or are derived from Gram-negative bacteria and/or Gram-positive bacteria. In some embodiments, one or more bacterial antigenic polysaccharides are, or are derived from *S. pneumoniae*. In some embodiments, one or more antigenic polysaccharides are, or are derived from one or more pathogens. In some embodiments, one or more antigenic polysaccharides are, or are derived from 1, 2, 3, 4, 5, 6, 7, 8, 9, 10, 11, 12, 13, 14, 15, 16, 17, 18, 19, 20, 21, 22, 23, 24, or 25 serotypes or strains of a pathogen. In some embodiments, one or more antigenic polysaccharides are, or are derived from more than 25 serotypes or strains of a pathogen, e.g., 26, 27, 28, 29, 30, 35, 40, 45, or 50 serotypes or strains. In some embodiments, one or more antigenic polysaccharides are, or are derived from more than 60, 70, 80, 90, or 100 serotypes or strains of a pathogen.

In some embodiments, the one or more antigenic polysaccharides comprise one or more affinity molecules conjugated to the antigenic polysaccharides. In some embodiments, the one or more affinity molecules comprise biotin or biotin derivatives.

In some embodiments, the antigenic polysaccharides comprise a plurality of affinity molecules conjugated to the antigenic polysaccharides. In some embodiments, the affinity molecules comprise biotin or biotin derivatives.

In some embodiments, one or more antigenic polypeptides are covalently linked (e.g., fused) to a complementary affinity molecule described herein. In some embodiments a fusion protein comprises one or more antigenic polypeptides and a complementary affinity molecule disclosed herein. In some embodiments, the complementary affinity molecule is or comprises a biotin-binding moiety. In some embodiments, the biotin-binding moiety comprises rhizavidin or a biotin-binding portion thereof.

In some embodiments, antigenic polysaccharides and/or antigenic polypeptides that may be included in immunogenic complexes are recombinantly or synthetically produced. In some embodiments, antigenic polysaccharides and/or antigenic polypeptides that may be included in immunogenic complexes are isolated and/or derived from natural sources. In some embodiments antigenic polysaccharides and/or antigenic polypeptides that may be included in immunogenic complexes are isolated from bacterial cells. Exemplary polysaccharides and/or polypeptides are described below.

Antigenic Polypeptides

In some embodiments, an immunogenic complex described herein comprises one or more polypeptide antigens. In some embodiments, a polypeptide antigen is a bacterial polypeptide, a fungal polypeptide, and/or a viral polypeptide. In some embodiments, a polypeptide antigen is a polypeptide of, or derived from S. pneumoniae. In some embodiments, the one or more polypeptide antigen is a polypeptide of, or derived from, a pathogen other than S. pneumoniae. In some embodiments, the one or more polypeptide antigens comprise (i) a polypeptide of, or derived from S. pneumoniae, and (ii) a polypeptide of, or derived from, a pathogen other than S. pneumoniae. In some embodiments, an immunogenic complex includes one or more of the following S. pneumoniae antigenic polypeptides, or portions thereof.

SP0785 Polypeptides

SP0785 is a conserved hypothetical S. pneumoniae protein described in WO 2014/124228. In some embodiments, an SP0785 polypeptide is an efflux transporter protein conserved across S. pneumoniae strains. In some embodiments, an SP0785 polypeptide is or comprises a full-length SP0785 polypeptide. For example, in some embodiments, a full-length SP0785 polypeptide has 399 amino acids (38 kDa) and is represented by the amino acid sequence as set forth in SEQ ID NO: 10. Amino acids 1-32 of SEQ ID NO:10 are predicted to be a signal sequence and transmembrane domain of an SP0785 polypeptide (amino acids 1-32 of the full-length protein). In some embodiments, an SP0785 polypeptide includes a portion of an SP0785 polypeptide (e.g., a portion of the SP0785 polypeptide of SEQ ID NO:10, which portion includes at least 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 150, 200, 250, 300, 350, or more contiguous amino acids of SEQ ID NO:10). In some embodiments, a portion of an SP0785 polypeptide corresponds to a protein having amino acids 33-399 of the amino acid sequence set forth in SEQ ID NO: 10. In some embodiments, an SP0785 polypeptide contains one or more amino acid alterations (e.g., deletion, substitution, and/or insertion) from a naturally-occurring wild-type SP0785 polypeptide sequence. For example, an SP0785 polypeptide may contain an amino acid sequence that is at least 60% or more (e.g., at least 65%, 70%, 75%, 80%, 85%, 90%, 95%, or 98%) identical to SEQ ID NO:10 or a portion thereof (e.g., at least 7, 8, 9, 10, 11, 12, 13, 14, 15, 16, 17, 18, 19, 20, 25, 30, 35, 45, 50, 60, 65, 70, 75, 80, 85, 90, 95, 100, 150, 200, 250, 300, 350, or more consecutive amino acids of the sequence shown in SEQ ID NO:10). Alternatively, an SP0785 polypeptide may contain a portion (e.g., at least 7, 8, 9, 10, 11, 12, 13, 14, 15, 16, 17, 18, 19, 20, 25, 30, 35, 45, 50, 60, 65, 70, 75, 80, 85, 90, 95, 100, 150, 200, 250, 300, 350, or 400 consecutive amino acids) of a sequence that is at least 60% or more (e.g., at least 65%, 70%, 75%, 80%, 85%, 90%, 95%, or 98%) identical to SEQ ID NO:10. A nucleotide sequence encoding an SP0785 polypeptide is provided herein as SEQ ID NO:11.

SP1500 Polypeptides

SP1500 is a S. pneumoniae protein described in WO 2014/124228. In some embodiments, an SP1500 polypeptide is an Amino Acid ABC Transporter, amino acid-binding polypeptide conserved across S. pneumoniae strains. In some embodiments, an SP1500 polypeptide is or comprises a full-length SP1500 polypeptide. For example, in some embodiments, a full-length SP1500 polypeptide has 278 amino acids (28 kDa) and is represented by the amino acid sequence as set forth in SEQ ID NO: 12. Amino acids 1-26 of SEQ ID NO:12 are predicted to be a signal sequence of an SP1500 polypeptide (amino acids 1-26 of the full-length protein). In some embodiments, an SP1500 polypeptide includes a portion of an SP1500 polypeptide (e.g., a portion of the SP1500 polypeptide of SEQ ID NO:12, which portion includes at least 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 150, 200, 250, or more contiguous amino acids of SEQ ID NO:12). In some embodiments, a portion of an SP1500 polypeptide corresponds to a protein having amino acids 27-278 of the amino acid sequence set forth in SEQ ID NO: 12. In some embodiments, an SP1500 polypeptide contains one or more amino acid alterations (e.g., deletion, substitution, and/or insertion) from a naturally-occurring wild-type SP1500 polypeptide sequence. For example, an SP1500 polypeptide may contain an amino acid sequence that is at least 60% or more (e.g., at least 65%, 70%, 75%, 80%, 85%, 90%, 95%, or 98%) identical to SEQ ID NO:12 or a portion thereof (e.g., at least 7, 8, 9, 10, 11, 12, 13, 14, 15, 16, 17, 18, 19, 20, 25, 30, 35, 45, 50, 60, 65, 70, 75, 80, 85, 90, 95, 100, 150, 200, 250, or more consecutive amino acids of the sequence shown in SEQ ID NO:12). Alternatively, an SP1500 polypeptide may contain a portion (e.g., at least 7, 8, 9, 10, 11, 12, 13, 14, 15, 16, 17, 18, 19, 20, 25, 30, 35, 45, 50, 60, 65, 70, 75, 80, 85, 90, 95, 100, 150, 200, 250, or more consecutive amino acids) of a sequence that is at least 60% or more (e.g., at least 65%, 70%, 75%, 80%, 85%, 90%, 95%, or 98%) identical to SEQ ID NO:12. A nucleotide sequence encoding an SP1500 polypeptide is provided herein as SEQ ID NO:13.

In some embodiments, nucleic acid sequences encoding an SP0785 polypeptide (SEQ ID NO:10), an SP1500 polypeptide (SEQ ID NO:12), and a CP1 polypeptide (SEQ ID NO:6) are provided as SEQ ID NOS: 11, 13, and 9, respectively. Due to degeneracy in the genetic code, those of ordinary skill in the art would understand that other DNA sequences (including codon-optimized sequences) could encode these polypeptides, as well as the others disclosed herein.

Fusion Proteins that Include Antigenic Polypeptides

Antigenic polypeptides described herein can be part of a fusion protein. For example, in some embodiments, an immunogenic complex described herein comprises a fusion protein that is or comprises a complementary affinity molecule and one or more antigenic polypeptides described herein. In some embodiments, a fusion protein of the immunogenic complex has carrier properties. In some embodiments, a fusion protein of the immunogenic complex has antigenic properties. In some embodiments, a fusion protein of the immunogenic complex has carrier properties and antigenic properties.

In some embodiments, the fusion protein of the immunogenic complex comprises one or more linkers and/or tags, e.g., a histidine tag. In some embodiments, the linker comprises a polypeptide comprising an amino acid sequence of SEQ ID NO:3 (GGGGSSS). In some embodiments, the linker comprises a polypeptide comprising an amino acid sequence having at least 80%, 85%, 90%, 95%, 96%, 97%, 98%, or 99% identity to the sequence of SEQ ID NO:3. In some embodiments, the linker comprises the amino acid sequence AAA. In some embodiments, the fusion protein of the immunogenic complex comprises a first linker comprising a polypeptide comprising the amino acid sequence of SEQ ID NO:3 (GGGGSSS), and a second linker comprising the amino acid sequence AAA. In some embodiments, such a linker may be synthesized, or derived from amino acid residues from a restriction site (e.g., a Not I restriction site).

Complementary Affinity Molecules

In some embodiments, a complementary affinity molecule comprises a biotin-binding moiety. In some embodiments, a fusion protein of the immunogenic complex comprises a biotin-binding moiety, and one or more polypeptide antigens. In some embodiments, a fusion protein comprises a biotin-binding moiety and two or more polypeptide antigens. As used herein, a "biotin-binding moiety" refers to a biotin-binding protein, a biotin-binding fragment thereof, or a biotin-binding domain thereof.

In some embodiments, MAPS complexes disclosed herein utilize the high affinity (dissociation constant [KD]≈$10^{15}$M) non-covalent binding between biotin and rhizavidin, a biotin-binding protein that has no significant predicted homology with human proteins. Rhizavidin, a naturally occurring dimeric protein in the avidin protein family, was first discovered in *Rhizobium etli*, a symbiotic bacterium of the common bean. Rhizavidin has only a 22% amino acid identity with chicken avidin, a protein commonly found in eggs, but with high conservation of amino acid residues involved in biotin binding. No cross-reactivity to rhizavidin is observed in human serum samples obtained from subjects exposed to avidin [Helppolainen et al, 2007], suggesting that rhizavidin antibodies may not cross-react with chicken avidin. Biotin conjugates have been used in several clinical applications without any reported adverse events [Buller et al, 2014; Paty et al, 2010; Lazzeri et al, 2004].

In some embodiments, the biotin-binding moiety of the fusion protein comprises rhizavidin or a biotin-binding domain or biotin-binding fragment thereof, as further described in WO 2012/155053 the contents of which are herein incorporated by reference in their entirety. In some embodiments, a biotin-binding moiety is or comprises a polypeptide having at least 80%, 85%, 90%, 95%, 96%, 97%, 98%, or 99% identity to rhizavidin, or a biotin-binding domain or biotin-binding fragment thereof. In some embodiments, the biotin-binding moiety comprises a polypeptide of SEQ ID NO:1 or a biotin-binding domain or biotin-binding fragment thereof. In some embodiments, the biotin-binding moiety is or comprises a polypeptide having at least 80%, 85%, 90%, 95%, 96%, 97%, 98%, or 99% identity to the sequence of SEQ ID NO:1, or biotin-binding domain or biotin-binding fragment thereof. In some embodiments, the biotin-binding moiety comprises a polypeptide of SEQ ID NO:2 or a biotin-binding domain or biotin-binding fragment thereof. In some embodiments, the biotin-binding moiety is or comprises a polypeptide having at least 80%, 85%, 90%, 95%, 96%, 97%, 98%, or 99% identity to the sequence of SEQ ID NO:2, or biotin-binding domain or biotin-binding fragment thereof.

In some embodiments, the fusion protein is or comprises a complementary affinity molecule described herein (e.g., a biotin-binding moiety described herein), and one or more polypeptides of or derived from *S. pneumoniae*. In some embodiments, the fusion protein of the immunogenic complex is CP1, further described in U.S. Provisional Application No. 62/730,199, entitled "Pneumococcal Fusion Protein Vaccines" and filed Sep. 12, 2018 ("'199 application") as well as in a PCT Application entitled "Pneumococcal Fusion Protein Vaccines" and filed Sep. 12, 2019, which claims priority to the '199 application, the contents of each of which are incorporated herein by reference in their entirety. In some embodiments, the fusion protein comprises a complementary affinity molecule described herein (e.g., a biotin-binding moiety described herein) and a polypeptide comprising an amino acid sequence having at least 80%, 85%, 90%, 95%, 96%, 97%, 98%, 99%, or 100% identity to the sequence of SEQ ID NO:4 (amino acids 33-399 of *S. pneumoniae* SP0785) or an antigenic fragment thereof and a polypeptide comprising an amino acid sequence having at least 80%, 85%, 90%, 95%, 96%, 97%, 98%, 99%, or 100% identity to the sequence of SEQ ID NO:5 (amino acids 27-278 of *S. pneumoniae* SP1500) or an antigenic fragment thereof. In some embodiments, the fusion protein comprises a polypeptide comprising an amino acid sequence having at least 80%, 85%, 90%, 95%, 96%, 97%, 98%, 99%, or 100% identity to the sequence of SEQ ID NO: 6. In some embodiments, the fusion protein is or comprises a complementary affinity molecule described herein (e.g., a biotin-binding moiety described herein), a polypeptide having at least 80%, 85%, 90%, 95%, 96%, 97%, 98%, or 99% identity to SP0785 or an antigenic fragment thereof, and a polypeptide having at least 80%, 85%, 90%, 95%, 96%, 97%, 98%, or 99% identity to SP1500 or an antigenic fragment thereof.

In some embodiments, the fusion protein of the immunogenic complex comprises a complementary affinity molecule described herein (e.g., a biotin-binding moiety described herein) and a polypeptide comprising an amino acid sequence having at least 80%, 85%, 90%, 95%, 96%, 97%, 98%, 99%, or 100% identity to the sequence of SEQ ID NO:4 (amino acids 33-399 of *S. pneumoniae* SP0785) or an antigenic fragment thereof. In some embodiments, a fusion protein comprises a complementary affinity molecule described herein (e.g., a biotin-binding moiety described herein) and a polypeptide comprising an amino acid sequence having at least 80%, 85%, 90%, 95%, 96%, 97%, 98%, 99%, or 100% identity to the sequence of SEQ ID NO:5 (amino acids 27-278 of *S. pneumoniae* SP1500) or an antigenic fragment thereof.

In some embodiments, the fusion protein of the immunogenic complex comprises a biotin-binding moiety that is or comprises a polypeptide having at least 80%, 85%, 90%, 95%, 96%, 97%, 98%, or 99% identity to the sequence of SEQ ID NO:1 (rhizavidin), or biotin-binding fragment thereof. In some embodiments, the fusion protein comprises a biotin-binding moiety that is or comprises a polypeptide having at least 80%, 85%, 90%, 95%, 96%, 97%, 98%, or 99% identity to the sequence of SEQ ID NO:2 (amino acids 45-179 of rhizavidin), or biotin-binding fragment thereof. In some embodiments, the fusion protein comprises a polypeptide comprising an amino acid sequence having at least 80%, 85%, 90%, 95%, 96%, 97%, 98%, 99%, or 100% identity to the sequence of SEQ ID NO:4 (amino acids 33-399 of *S. pneumoniae* SP0785) or an antigenic fragment thereof. In some embodiments, the fusion protein comprises a polypeptide comprising an amino acid sequence having at least 80%, 85%, 90%, 95%, 96%, 97%, 98%, 99%, or 100% identity to the sequence of SEQ ID NO:5 (amino acids 27-278 of *S. pneumoniae* SP1500) or an antigenic fragment thereof.

In some embodiments, the fusion protein of the immunogenic complex comprises each of: (a) a biotin-binding moiety that is or comprises a polypeptide having at least 80%, 85%, 90%, 95%, 96%, 97%, 98%, or 99% identity to the sequence of SEQ ID NO:1 (rhizavidin), or biotin-binding fragment thereof; (b) a polypeptide comprising an amino acid sequence having at least 80%, 85%, 90%, 95%, 96%, 97%, 98%, 99%, or 100% identity to the sequence of SEQ ID NO:4 (amino acids 33-399 of *S. pneumoniae* SP0785) or an antigenic fragment thereof; and (c) a polypeptide comprising an amino acid sequence having at least 80%, 85%, 90%, 95%, 96%, 97%, 98%, 99%, or 100% identity to the sequence of SEQ ID NO:5 (amino acids 27-278 of *S. pneumoniae* SP1500) or an antigenic fragment thereof. In some embodiments, the fusion protein further comprises one or more linkers.

In some embodiments, the fusion protein of the immunogenic complex comprises each of: (a) a biotin-binding moiety that is or comprises a polypeptide having at least 80%, 85%, 90%, 95%, 96%, 97%, 98%, or 99% identity to the sequence of SEQ ID NO:2 (amino acids 45-179 of rhizavidin), or biotin-binding fragment thereof; (b) a polypeptide comprising an amino acid sequence having at least 80%, 85%, 90%, 95%, 96%, 97%, 98%, 99%, or 100% identity to the sequence of SEQ ID NO:4 (amino acids 33-399 of S. pneumoniae SP0785) or an antigenic fragment thereof; and (c) a polypeptide comprising an amino acid sequence having at least 80%, 85%, 90%, 95%, 96%, 97%, 98%, 99%, or 100% identity to the sequence of SEQ ID NO:5 (amino acids 27-278 of S. pneumoniae SP1500) or an antigenic fragment thereof. In some embodiments, the fusion protein further comprises one or more linkers.

In some embodiments, the fusion protein of the immunogenic complex is or comprises a CP1 fusion protein. In some embodiments, a CP1 fusion protein comprises (a) a biotin-binding moiety that is or comprises a polypeptide having at least 80%, 85%, 90%, 95%, 96%, 97%, 98%, or 99% identity to the sequence of SEQ ID NO:1 (rhizavidin) or to the sequence of SEQ ID NO:2 (amino acids 45-179 of rhizavidin), or biotin-binding fragment thereof (b) a first polypeptide linker comprising the amino acid sequence of SEQ ID NO:3 (GGGGSSS); (c) an SP0785 polypeptide described herein; (d) a second polypeptide linker comprising the amino acid sequence AAA; and (e) an SP1500 polypeptide described herein. In some embodiments, such a CP1 fusion protein may further comprise a detection or purification tag, e.g., a His tag. In some such embodiments, a CP1 fusion protein comprises an SP1500 polypeptide between a biotin-binding moiety and an SP0785 polypeptide. In some embodiments, a CP1 fusion protein may comprise an SP0785 polypeptide between a biotin-binding moiety and a SP1500 polypeptide. In some embodiments, an SP0785 polypeptide included in a fusion protein of an immunogenic complex is or comprises an amino acid sequence having at least 80%, 85%, 90%, 95%, 96%, 97%, 98%, 99%, or 100% identity to the sequence of SEQ ID NO:4 (amino acids 33-399 of S. pneumoniae SP0785) or an antigenic fragment thereof. In some embodiments, an SP1500 polypeptide included in a fusion protein of an immunogenic complex is or comprises an amino acid sequence having at least 80%, 85%, 90%, 95%, 96%, 97%, 98%, 99%, or 100% identity to the sequence of SEQ ID NO:5 (amino acids 27-278 of S. pneumoniae SP1500) or an antigenic fragment thereof. In some embodiments, the fusion protein comprises an amino acid sequence having at least 80%, 85%, 90%, 95%, 96%, 97%, 98%, 99%, or 100% identity to the sequence SEQ ID NO:6. In some embodiments, the fusion protein comprises the amino acid sequence SEQ ID NO:6. In some embodiments, the fusion protein consists of the amino acid sequence SEQ ID NO:6.

Antigenic Polysaccharides

In some embodiments, an immunogenic complex described herein includes one or more S. pneumoniae polysaccharides. In some embodiments, an immunogenic complex described herein includes one S. pneumoniae polysaccharide. Capsular polysaccharides are used to distinguish serotypes of S. pneumoniae. There are at least 97 distinct serotypes of S. pneumoniae polysaccharides, each having a different chemical structure. Serotype designations as used herein are designations according to Danish nomenclature [Kauffmann et al, 1960; Geno et al, 2015]. (N.B. Serotype 20 in U.S. nomenclature is referred to as serotype 20A in Danish nomenclature.)

In some embodiments, an immunogenic complex includes one or more S. pneumoniae capsular polysaccharides from, or derived from, one or more S. pneumoniae serotypes selected from 1, 2, 3, 4, 5, 6A, 6B, 6C, 6D, 6E, 6F, 6G, 6H, 7A, 7B, 7C, 7F, 8, 9A, 9L, 9N, 9V, 10A, 10B, 10C, 10F, 11A, 11B, 11C, 11D, 11E, 11F, 12A, 12B, 12F, 13, 14, 15A, 15B, 15C, 15F, 16A, 16F, 17A, 17F, 18A, 18B, 18C, 18F, 19A, 19B, 19C, 19F, 20A, 20B, 21, 22A, 22F, 23A, 23B, 23F, 24A, 24B, 24F, 25A, 25F, 27, 28A, 28F, 29, 31, 32A, 32F, 33A, 33B, 33C, 33D, 33E, 33F, 34, 35A, 35B, 35C, 35F, 36, 37, 38, 39, 40, 41A, 41F, 42, 43, 44, 45, 46, 47A, 47F, and 48.

In some embodiments, an immunogenic complex includes one or more S. pneumoniae capsular polysaccharides from, or derived from, one or more S. pneumoniae serotypes selected from 1, 2, 3, 4, 5, 6A, 6B, 7F, 8, 9N, 9V, 10A, 11A, 12F, 14, 15B, 17F, 18C, 19A, 19F, 20B, 22F, 23F, and 33F. In some embodiments, an immunogenic complex includes one or more S. pneumoniae capsular polysaccharides from, or derived from, one or more S. pneumoniae serotypes selected from 1, 3, 4, 5, 6A, 6B, 7F, 9V, 14, 18C, 19A, 19F, 22F, 23F, and 33F. In some embodiments, an immunogenic complex includes one or more S. pneumoniae capsular polysaccharides from, or derived from, one or more S. pneumoniae serotypes selected from 2, 8, 9N, 10A, 11A, 12F, 15B, 17F, and 20B.

In some embodiments, an immunogenic complex includes one S. pneumoniae capsular polysaccharide from, or derived from, one S. pneumoniae serotype. In some embodiments, an immunogenic complex includes one S. pneumoniae capsular polysaccharide from, or derived from, one S. pneumoniae serotype selected from 1, 2, 3, 4, 5, 6A, 6B, 6C, 6D, 6E, 6F, 6G, 6H, 7A, 7B, 7C, 7F, 8, 9A, 9L, 9N, 9V, 10A, 10B, 10C, 10F, 11A, 11B, 11C, 11D, 11E, 11F, 12A, 12B, 12F, 13, 14, 15A, 15B, 15C, 15F, 16A, 16F, 17A, 17F, 18A, 18B, 18C, 18F, 19A, 19B, 19C, 19F, 20A, 20B, 21, 22A, 22F, 23A, 23B, 23F, 24A, 24B, 24F, 25A, 25F, 27, 28A, 28F, 29, 31, 32A, 32F, 33A, 33B, 33C, 33D, 33E, 33F, 34, 35A, 35B, 35C, 35F, 36, 37, 38, 39, 40, 41A, 41F, 42, 43, 44, 45, 46, 47A, 47F, and 48. In some embodiments, an immunogenic complex includes one S. pneumoniae capsular polysaccharide from, or derived from, one S. pneumoniae serotype selected from 1, 2, 3, 4, 5, 6A, 6B, 7F, 8, 9N, 9V, 10A, 11A, 12F, 14, 15B, 17F, 18C, 19A, 19F, 20B, 22F, 23F, and 33F. In some embodiments, an immunogenic complex includes one S. pneumoniae capsular polysaccharide from, or derived from, one S. pneumoniae serotype selected from 1, 3, 4, 5, 6A, 6B, 7F, 9V, 14, 18C, 19A, 19F, 22F, 23F, and 33F. In some embodiments, an immunogenic complex includes one S. pneumoniae capsular polysaccharide from, or derived from, one S. pneumoniae serotype selected from 2, 8, 9N, 10A, 11A, 12F, 15B, 17F, and 20B.

Methods of Isolating and Purifying Polysaccharides

In some embodiments, the disclosure provides methods of purifying one or more polysaccharides described herein from one or more cellular components of bacteria. In some embodiments, methods comprise purifying capsular polysaccharides from one or more cellular components of bacteria.

In some embodiments, the bacteria are Gram-negative. In some embodiments, the bacteria are Gram-positive. In some embodiments, the bacteria are S. pneumoniae.

In some embodiments, the cellular components include protein. In some embodiments, the cellular proteins include nucleic acid. In some embodiments, the cellular components include lipids. In some embodiments, the cellular components include polysaccharides. In some embodiments, the cellular components are part of a lysate.

In some embodiments, the polysaccharide purification processes incorporate a series of ethanol precipitations, washes of crude polysaccharide preparations with ethanol, diethyl ether, and/or acetone, and drying under vacuum to furnish purified products. In some embodiments, a phenol extraction step is incorporated for polysaccharide purifications. In some embodiments the purification process employs a CTAB (cetyltrimethyl ammonium bromide) precipitation step in addition to using ethanol and phenol precipitation steps.

Figure 3:
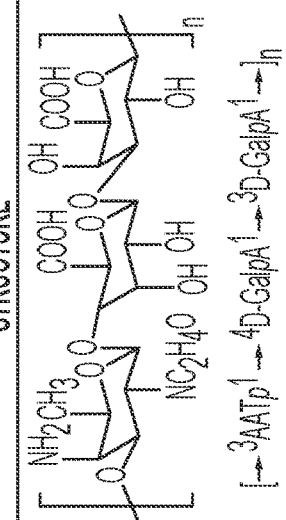
FIG. 3 is a table showing exemplary structures of *S. pneumoniae* antigenic polysaccharides of serotypes 1, 2, 3, 4, 5, 6A, 6B, 7F, 8, 9N, 9V, 10A, 11A, 12F, 14, 15B, 17F, 18C, 19A, 19F, 20B, 22F, 23F, and 33F.

FIG. 3 depicts exemplary structures and chemical information for S. pneumoniae capsular polysaccharides included in immunogenic complexes of the invention. All structures are from European Pharmacopoeia 9.0.

Methods of Biotinylating Polysaccharides

In some embodiments, the disclosure provides methods of biotinylating one or more polysaccharides described herein. In some embodiments, the method comprises reacting purified polysaccharides with 1-cyano-4-dimethylaminopyridinium tetrafluoroborate (CDAP) for activation of hydroxyl groups in the polysaccharides followed by the addition of amine PEG biotin under conditions that result in covalent linkage of biotin to the polysaccharides. In some embodiments, the desired level of biotinylation is achieved by varying the ratio of CDAP to polysaccharide. In some embodiments, the biotinylated polysaccharides are purified by filtration to remove process residuals such as unreacted biotin, dimethylaminopyridine, acetonitrile, cyanide and unreacted glycine. In some embodiments, the level of polysaccharide biotinylation described herein is optimized to reduce the amount of accessible biotin following MAPS complexation.

Manufacture of Immunogenic Complexes

The present disclosure includes methods for manufacturing immunogenic complexes described herein. In some embodiments, a method of manufacturing immunogenic complexes comprises complexing at least one biotinylated polysaccharide with at least one biotin-binding fusion protein. In some embodiments, the fusion protein comprises an amino acid sequence having at least 80%, 85%, 90%, 95%, 96%, 97%, 98%, 99%, or 100% identity to SEQ ID NO:6.

In some embodiments, the average (e.g., the mean) protein (e.g., antigenic protein) to polysaccharide ratio of a plurality of immunogenic complexes is approximately 1:1, 1.5:1, 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1, or 10:1 (weight/weight [w/w]). In some embodiments, the average protein to polysaccharide ratio of a plurality of immunogenic complexes is approximately 1:1 (w/w). In some embodiments, the average protein to polysaccharide ratio of a plurality of immunogenic complexes is approximately 2:1 (w/w). In some embodiments, the average protein to polysaccharide ratio of a plurality of immunogenic complexes is approximately 3:1 (w/w). In some embodiments, the average protein to polysaccharide ratio of a plurality of immunogenic complexes is approximately 4:1 (w/w). In some embodiments, the average protein to polysaccharide ratio of a plurality of immunogenic complexes is approximately 5:1 (w/w). In some embodiments, the average protein to polysaccharide ratio of a plurality of immunogenic complexes is approximately 6:1 (w/w). In some embodiments, the average protein to polysaccharide ratio of a plurality of immunogenic complexes is approximately 7:1 (w/w). In some embodiments, the average protein to polysaccharide ratio of a plurality of immunogenic complexes is approximately 8:1 (w/w). In some embodiments, the average protein to polysaccharide ratio of a plurality of immunogenic complexes is approximately 9:1 (w/w). In some embodiments, the average protein to polysaccharide ratio of a plurality of immunogenic complexes is approximately 10:1 (w/w). In some embodiments, the average protein:PS ratios are chosen to enhance the polysaccharide immunogenicity potential (carrier function) and/or to elicit protection against, or to inhibit, pneumococcal colonization by any pneumococcus (independent of polysaccharide serotype) through a protein-specific immune response. Immunogenic compositions and vaccines of the invention may comprise mixtures of immunogenic complexes with different average protein to polysaccharide ratios.

In some embodiments, a vaccine or immunogenic composition comprises a plurality of immunogenic complexes comprising a CP1 protein and a capsular polysaccharide, from or derived from S. pneumoniae serotype 1. In some embodiments, the average ratio of CP1 protein to capsular polysaccharide from or derived from S. pneumoniae serotype 1 in the plurality of immunogenic complexes is approximately 1:1, 1.5:1, 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1, or 10:1 (weight/weight [w/w]). In some embodiments, the average ratio of CP1 protein to capsular polysaccharide from or derived from S. pneumoniae serotype 1 in the plurality of immunogenic complexes is approximately 1:1 (w/w). In some embodiments, the average ratio of CP1 protein to capsular polysaccharide from or derived from S. pneumoniae serotype 1 in the plurality of immunogenic complexes is approximately 2:1 (w/w). In some embodiments, the average ratio of CP1 protein to capsular polysaccharide from or derived from S. pneumoniae serotype 1 in the plurality of immunogenic complexes is approximately 3:1 (w/w). In some embodiments, the average ratio of CP1 protein to capsular polysaccharide from or derived from S. pneumoniae serotype 1 in the plurality of immunogenic complexes is approximately 4:1 (w/w). In some embodiments, the average ratio of CP1 protein to capsular polysaccharide from or derived from S. pneumoniae serotype 1 in the plurality of immunogenic complexes is approximately 5:1 (w/w). In some embodiments, the average ratio of CP1 protein to capsular polysaccharide from or derived from S. pneumoniae serotype 1 in the plurality of immunogenic complexes is approximately 6:1 (w/w). In some embodiments, the average ratio of CP1 protein to capsular polysaccharide from or derived from S. pneumoniae serotype 1 in the plurality of immunogenic complexes is approximately 7:1 (w/w). In some embodiments, the average ratio of CP1 protein to capsular polysaccharide from or derived from S. pneumoniae serotype 1 in the plurality of immunogenic complexes is approximately 8:1 (w/w). In some embodiments, the average ratio of CP1 protein to capsular polysaccharide from or derived from S. pneumoniae serotype 1 in the plurality of immunogenic complexes is approximately 9:1 (w/w). In some embodiments, the average ratio of CP1 protein to capsular polysaccharide from or derived from S. pneumoniae serotype 1 in the plurality of immunogenic complexes is approximately 10:1 (w/w). In some embodiments, the average ratio of CP1 protein to capsular polysaccharide from or derived from S. pneumoniae serotype 1 in the plurality of immunogenic complexes is chosen to enhance the polysaccharide immunogenicity potential (carrier function) and/or to elicit protection against, or to inhibit, pneumococcal colonization by any pneumococcus (independent of polysaccharide serotype) through a protein-specific immune response. Immunogenic compositions and vaccines of the invention may comprise mixtures of immunogenic complexes with different average protein to polysaccharide ratios.

In some embodiments, a vaccine or immunogenic composition comprises a plurality of immunogenic complexes comprising a CP1 protein and a capsular polysaccharide, from or derived from *S. pneumoniae* serotype 2. In some embodiments, the average ratio of CP1 protein to capsular polysaccharide from or derived from *S. pneumoniae* serotype 2 in the plurality of immunogenic complexes is approximately 1:1, 1.5:1, 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1, or 10:1 (weight/weight [w/w]). In some embodiments, the average ratio of CP1 protein to capsular polysaccharide from or derived from *S. pneumoniae* serotype 2 in the plurality of immunogenic complexes is approximately 1:1 (w/w). In some embodiments, the average ratio of CP1 protein to capsular polysaccharide from or derived from *S. pneumoniae* serotype 2 in the plurality of immunogenic complexes is approximately 2:1 (w/w). In some embodiments, the average ratio of CP1 protein to capsular polysaccharide from or derived from *S. pneumoniae* serotype 2 in the plurality of immunogenic complexes is approximately 3:1 (w/w). In some embodiments, the average ratio of CP1 protein to capsular polysaccharide from or derived from *S. pneumoniae* serotype 2 in the plurality of immunogenic complexes is approximately 4:1 (w/w). In some embodiments, the average ratio of CP1 protein to capsular polysaccharide from or derived from *S. pneumoniae* serotype 2 in the plurality of immunogenic complexes is approximately 5:1 (w/w). In some embodiments, the average ratio of CP1 protein to capsular polysaccharide from or derived from *S. pneumoniae* serotype 2 in the plurality of immunogenic complexes is approximately 6:1 (w/w). In some embodiments, the average ratio of CP1 protein to capsular polysaccharide from or derived from *S. pneumoniae* serotype 2 in the plurality of immunogenic complexes is approximately 7:1 (w/w). In some embodiments, the average ratio of CP1 protein to capsular polysaccharide from or derived from *S. pneumoniae* serotype 2 in the plurality of immunogenic complexes is approximately 8:1 (w/w). In some embodiments, the average ratio of CP1 protein to capsular polysaccharide from or derived from *S. pneumoniae* serotype 2 in the plurality of immunogenic complexes is approximately 9:1 (w/w). In some embodiments, the average ratio of CP1 protein to capsular polysaccharide from or derived from *S. pneumoniae* serotype 2 in the plurality of immunogenic complexes is approximately 10:1 (w/w). In some embodiments, the average ratio of CP1 protein to capsular polysaccharide from or derived from *S. pneumoniae* serotype 2 in the plurality of immunogenic complexes is chosen to enhance the polysaccharide immunogenicity potential (carrier function) and/or to elicit protection against, or to inhibit, pneumococcal colonization by any pneumococcus (independent of polysaccharide serotype) through a protein-specific immune response. Immunogenic compositions and vaccines of the invention may comprise mixtures of immunogenic complexes with different average protein to polysaccharide ratios.

In some embodiments, a vaccine or immunogenic composition comprises a plurality of immunogenic complexes comprising a CP1 protein and a capsular polysaccharide, from or derived from *S. pneumoniae* serotype 3. In some embodiments, the average ratio of CP1 protein to capsular polysaccharide from or derived from *S. pneumoniae* serotype 3 in the plurality of immunogenic complexes is approximately 1:1, 1.5:1, 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1, or 10:1 (weight/weight [w/w]). In some embodiments, the average ratio of CP1 protein to capsular polysaccharide from or derived from *S. pneumoniae* serotype 3 in the plurality of immunogenic complexes is approximately 1:1 (w/w). In some embodiments, the average ratio of CP1 protein to capsular polysaccharide from or derived from *S. pneumoniae* serotype 3 in the plurality of immunogenic complexes is approximately 2:1 (w/w). In some embodiments, the average ratio of CP1 protein to capsular polysaccharide from or derived from *S. pneumoniae* serotype 3 in the plurality of immunogenic complexes is approximately 3:1 (w/w). In some embodiments, the average ratio of CP1 protein to capsular polysaccharide from or derived from *S. pneumoniae* serotype 3 in the plurality of immunogenic complexes is approximately 4:1 (w/w). In some embodiments, the average ratio of CP1 protein to capsular polysaccharide from or derived from *S. pneumoniae* serotype 3 in the plurality of immunogenic complexes is approximately 5:1 (w/w). In some embodiments, the average ratio of CP1 protein to capsular polysaccharide from or derived from *S. pneumoniae* serotype 3 in the plurality of immunogenic complexes is approximately 6:1 (w/w). In some embodiments, the average ratio of CP1 protein to capsular polysaccharide from or derived from *S. pneumoniae* serotype 3 in the plurality of immunogenic complexes is approximately 7:1 (w/w). In some embodiments, the average ratio of CP1 protein to capsular polysaccharide from or derived from *S. pneumoniae* serotype 3 in the plurality of immunogenic complexes is approximately 8:1 (w/w). In some embodiments, the average ratio of CP1 protein to capsular polysaccharide from or derived from *S. pneumoniae* serotype 3 in the plurality of immunogenic complexes is approximately 9:1 (w/w). In some embodiments, the average ratio of CP1 protein to capsular polysaccharide from or derived from *S. pneumoniae* serotype 3 in the plurality of immunogenic complexes is approximately 10:1 (w/w). In some embodiments, the average ratio of CP1 protein to capsular polysaccharide from or derived from *S. pneumoniae* serotype 3 in the plurality of immunogenic complexes is chosen to enhance the polysaccharide immunogenicity potential (carrier function) and/or to elicit protection against, or to inhibit, pneumococcal colonization by any pneumococcus (independent of polysaccharide serotype) through a protein-specific immune response. Immunogenic compositions and vaccines of the invention may comprise mixtures of immunogenic complexes with different average protein to polysaccharide ratios.

In some embodiments, a vaccine or immunogenic composition comprises a plurality of immunogenic complexes comprising a CP1 protein and a capsular polysaccharide, from or derived from *S. pneumoniae* serotype 4. In some embodiments, the average ratio of CP1 protein to capsular polysaccharide from or derived from *S. pneumoniae* serotype 4 in the plurality of immunogenic complexes is approximately 1:1, 1.5:1, 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1, or 10:1 (weight/weight [w/w]). In some embodiments, the average ratio of CP1 protein to capsular polysaccharide from or derived from *S. pneumoniae* serotype 4 in the plurality of immunogenic complexes is approximately 1:1 (w/w). In some embodiments, the average ratio of CP1 protein to capsular polysaccharide from or derived from *S. pneumoniae* serotype 4 in the plurality of immunogenic complexes is approximately 2:1 (w/w). In some embodiments, the average ratio of CP1 protein to capsular polysaccharide from or derived from *S. pneumoniae* serotype 4 in the plurality of immunogenic complexes is approximately 3:1 (w/w). In some embodiments, the average ratio of CP1 protein to capsular polysaccharide from or derived from *S. pneumo-

*niae* serotype 4 in the plurality of immunogenic complexes is approximately 4:1 (w/w). In some embodiments, the average ratio of CP1 protein to capsular polysaccharide from or derived from *S. pneumoniae* serotype 4 in the plurality of immunogenic complexes is approximately 5:1 (w/w). In some embodiments, the average ratio of CP1 protein to capsular polysaccharide from or derived from *S. pneumoniae* serotype 4 in the plurality of immunogenic complexes is approximately 6:1 (w/w). In some embodiments, the average ratio of CP1 protein to capsular polysaccharide from or derived from *S. pneumoniae* serotype 4 in the plurality of immunogenic complexes is approximately 7:1 (w/w). In some embodiments, the average ratio of CP1 protein to capsular polysaccharide from or derived from *S. pneumoniae* serotype 4 in the plurality of immunogenic complexes is approximately 8:1 (w/w). In some embodiments, the average ratio of CP1 protein to capsular polysaccharide from or derived from *S. pneumoniae* serotype 4 in the plurality of immunogenic complexes is approximately 9:1 (w/w). In some embodiments, the average ratio of CP1 protein to capsular polysaccharide from or derived from *S. pneumoniae* serotype 4 in the plurality of immunogenic complexes is approximately 10:1 (w/w). In some embodiments, the average ratio of CP1 protein to capsular polysaccharide from or derived from *S. pneumoniae* serotype 4 in the plurality of immunogenic complexes is chosen to enhance the polysaccharide immunogenicity potential (carrier function) and/or to elicit protection against, or to inhibit, pneumococcal colonization by any pneumococcus (independent of polysaccharide serotype) through a protein-specific immune response. Immunogenic compositions and vaccines of the invention may comprise mixtures of immunogenic complexes with different average protein to polysaccharide ratios.

In some embodiments, a vaccine or immunogenic composition comprises a plurality of immunogenic complexes comprising a CP1 protein and a capsular polysaccharide, from or derived from *S. pneumoniae* serotype 5. In some embodiments, the average ratio of CP1 protein to capsular polysaccharide from or derived from *S. pneumoniae* serotype 5 in the plurality of immunogenic complexes is approximately 1:1, 1.5:1, 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1, or 10:1 (weight/weight [w/w]). In some embodiments, the average ratio of CP1 protein to capsular polysaccharide from or derived from *S. pneumoniae* serotype 5 in the plurality of immunogenic complexes is approximately 1:1 (w/w). In some embodiments, the average ratio of CP1 protein to capsular polysaccharide from or derived from *S. pneumoniae* serotype 5 in the plurality of immunogenic complexes is approximately 2:1 (w/w). In some embodiments, the average ratio of CP1 protein to capsular polysaccharide from or derived from *S. pneumoniae* serotype 5 in the plurality of immunogenic complexes is approximately 3:1 (w/w). In some embodiments, the average ratio of CP1 protein to capsular polysaccharide from or derived from *S. pneumoniae* serotype 5 in the plurality of immunogenic complexes is approximately 4:1 (w/w). In some embodiments, the average ratio of CP1 protein to capsular polysaccharide from or derived from *S. pneumoniae* serotype 5 in the plurality of immunogenic complexes is approximately 5:1 (w/w). In some embodiments, the average ratio of CP1 protein to capsular polysaccharide from or derived from *S. pneumoniae* serotype 5 in the plurality of immunogenic complexes is approximately 6:1 (w/w). In some embodiments, the average ratio of CP1 protein to capsular polysaccharide from or derived from *S. pneumoniae* serotype 5 in the plurality of immunogenic complexes is approximately 7:1 (w/w). In some embodiments, the average ratio of CP1 protein to capsular polysaccharide from or derived from *S. pneumoniae* serotype 5 in the plurality of immunogenic complexes is approximately 8:1 (w/w). In some embodiments, the average ratio of CP1 protein to capsular polysaccharide from or derived from *S. pneumoniae* serotype 5 in the plurality of immunogenic complexes is approximately 9:1 (w/w). In some embodiments, the average ratio of CP1 protein to capsular polysaccharide from or derived from *S. pneumoniae* serotype 5 in the plurality of immunogenic complexes is approximately 10:1 (w/w). In some embodiments, the average ratio of CP1 protein to capsular polysaccharide from or derived from *S. pneumoniae* serotype 5 in the plurality of immunogenic complexes is chosen to enhance the polysaccharide immunogenicity potential (carrier function) and/or to elicit protection against, or to inhibit, pneumococcal colonization by any pneumococcus (independent of polysaccharide serotype) through a protein-specific immune response. Immunogenic compositions and vaccines of the invention may comprise mixtures of immunogenic complexes with different average protein to polysaccharide ratios.

In some embodiments, a vaccine or immunogenic composition comprises a plurality of immunogenic complexes comprising a CP1 protein and a capsular polysaccharide, from or derived from *S. pneumoniae* serotype 6A. In some embodiments, the average ratio of CP1 protein to capsular polysaccharide from or derived from *S. pneumoniae* serotype 6A in the plurality of immunogenic complexes is approximately 1:1, 1.5:1, 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1, or 10:1 (weight/weight [w/w]). In some embodiments, the average ratio of CP1 protein to capsular polysaccharide from or derived from *S. pneumoniae* serotype 6A in the plurality of immunogenic complexes is approximately 1:1 (w/w). In some embodiments, the average ratio of CP1 protein to capsular polysaccharide from or derived from *S. pneumoniae* serotype 6A in the plurality of immunogenic complexes is approximately 2:1 (w/w). In some embodiments, the average ratio of CP1 protein to capsular polysaccharide from or derived from *S. pneumoniae* serotype 6A in the plurality of immunogenic complexes is approximately 3:1 (w/w). In some embodiments, the average ratio of CP1 protein to capsular polysaccharide from or derived from *S. pneumoniae* serotype 6A in the plurality of immunogenic complexes is approximately 4:1 (w/w). In some embodiments, the average ratio of CP1 protein to capsular polysaccharide from or derived from *S. pneumoniae* serotype 6A in the plurality of immunogenic complexes is approximately 5:1 (w/w). In some embodiments, the average ratio of CP1 protein to capsular polysaccharide from or derived from *S. pneumoniae* serotype 6A in the plurality of immunogenic complexes is approximately 6:1 (w/w). In some embodiments, the average ratio of CP1 protein to capsular polysaccharide from or derived from *S. pneumoniae* serotype 6A in the plurality of immunogenic complexes is approximately 7:1 (w/w). In some embodiments, the average ratio of CP1 protein to capsular polysaccharide from or derived from *S. pneumoniae* serotype 6A in the plurality of immunogenic complexes is approximately 8:1 (w/w). In some embodiments, the average ratio of CP1 protein to capsular polysaccharide from or derived from *S. pneumoniae* serotype 6A in the plurality of immunogenic complexes is approximately 9:1 (w/w). In some embodiments, the average ratio of CP1 protein to capsular polysaccharide from or derived from *S. pneumoniae* serotype 6A in the plurality of immunogenic complexes is approximately 10:1 (w/w). In some embodiments, the average ratio of CP1 protein to capsular polysaccharide from or derived from S. pneumoniae serotype 6A in the plurality of immunogenic complexes is chosen to enhance the polysaccharide immunogenicity potential (carrier function) and/or to elicit protection against, or to inhibit, pneumococcal colonization by any pneumococcus (independent of polysaccharide serotype) through a protein-specific immune response. Immunogenic compositions and vaccines of the invention may comprise mixtures of immunogenic complexes with different average protein to polysaccharide ratios.

In some embodiments, a vaccine or immunogenic composition comprises a plurality of immunogenic complexes comprising a CP1 protein and a capsular polysaccharide, from or derived from S. pneumoniae serotype 6B. In some embodiments, the average ratio of CP1 protein to capsular polysaccharide from or derived from S. pneumoniae serotype 6B in the plurality of immunogenic complexes is approximately 1:1, 1.5:1, 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1, or 10:1 (weight/weight [w/w]). In some embodiments, the average ratio of CP1 protein to capsular polysaccharide from or derived from S. pneumoniae serotype 6B in the plurality of immunogenic complexes is approximately 1:1 (w/w). In some embodiments, the average ratio of CP1 protein to capsular polysaccharide from or derived from S. pneumoniae serotype 6B in the plurality of immunogenic complexes is approximately 2:1 (w/w). In some embodiments, the average ratio of CP1 protein to capsular polysaccharide from or derived from S. pneumoniae serotype 6B in the plurality of immunogenic complexes is approximately 3:1 (w/w). In some embodiments, the average ratio of CP1 protein to capsular polysaccharide from or derived from S. pneumoniae serotype 6B in the plurality of immunogenic complexes is approximately 4:1 (w/w). In some embodiments, the average ratio of CP1 protein to capsular polysaccharide from or derived from S. pneumoniae serotype 6B in the plurality of immunogenic complexes is approximately 5:1 (w/w). In some embodiments, the average ratio of CP1 protein to capsular polysaccharide from or derived from S. pneumoniae serotype 6B in the plurality of immunogenic complexes is approximately 6:1 (w/w). In some embodiments, the average ratio of CP1 protein to capsular polysaccharide from or derived from S. pneumoniae serotype 6B in the plurality of immunogenic complexes is approximately 7:1 (w/w). In some embodiments, the average ratio of CP1 protein to capsular polysaccharide from or derived from S. pneumoniae serotype 6B in the plurality of immunogenic complexes is approximately 8:1 (w/w). In some embodiments, the average ratio of CP1 protein to capsular polysaccharide from or derived from S. pneumoniae serotype 6B in the plurality of immunogenic complexes is approximately 9:1 (w/w). In some embodiments, the average ratio of CP1 protein to capsular polysaccharide from or derived from S. pneumoniae serotype 6B in the plurality of immunogenic complexes is approximately 10:1 (w/w). In some embodiments, the average ratio of CP1 protein to capsular polysaccharide from or derived from S. pneumoniae serotype 6B in the plurality of immunogenic complexes is chosen to enhance the polysaccharide immunogenicity potential (carrier function) and/or to elicit protection against, or to inhibit, pneumococcal colonization by any pneumococcus (independent of polysaccharide serotype) through a protein-specific immune response. Immunogenic compositions and vaccines of the invention may comprise mixtures of immunogenic complexes with different average protein to polysaccharide ratios.

In some embodiments, a vaccine or immunogenic composition comprises a plurality of immunogenic complexes comprising a CP1 protein and a capsular polysaccharide, from or derived from S. pneumoniae serotype 7F. In some embodiments, the average ratio of CP1 protein to capsular polysaccharide from or derived from S. pneumoniae serotype 7F in the plurality of immunogenic complexes is approximately 1:1, 1.5:1, 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1, or 10:1 (weight/weight [w/w]). In some embodiments, the average ratio of CP1 protein to capsular polysaccharide from or derived from S. pneumoniae serotype 7F in the plurality of immunogenic complexes is approximately 1:1 (w/w). In some embodiments, the average ratio of CP1 protein to capsular polysaccharide from or derived from S. pneumoniae serotype 7F in the plurality of immunogenic complexes is approximately 2:1 (w/w). In some embodiments, the average ratio of CP1 protein to capsular polysaccharide from or derived from S. pneumoniae serotype 7F in the plurality of immunogenic complexes is approximately 3:1 (w/w). In some embodiments, the average ratio of CP1 protein to capsular polysaccharide from or derived from S. pneumoniae serotype 7F in the plurality of immunogenic complexes is approximately 4:1 (w/w). In some embodiments, the average ratio of CP1 protein to capsular polysaccharide from or derived from S. pneumoniae serotype 7F in the plurality of immunogenic complexes is approximately 5:1 (w/w). In some embodiments, the average ratio of CP1 protein to capsular polysaccharide from or derived from S. pneumoniae serotype 7F in the plurality of immunogenic complexes is approximately 6:1 (w/w). In some embodiments, the average ratio of CP1 protein to capsular polysaccharide from or derived from S. pneumoniae serotype 7F in the plurality of immunogenic complexes is approximately 7:1 (w/w). In some embodiments, the average ratio of CP1 protein to capsular polysaccharide from or derived from S. pneumoniae serotype 7F in the plurality of immunogenic complexes is approximately 8:1 (w/w). In some embodiments, the average ratio of CP1 protein to capsular polysaccharide from or derived from S. pneumoniae serotype 7F in the plurality of immunogenic complexes is approximately 9:1 (w/w). In some embodiments, the average ratio of CP1 protein to capsular polysaccharide from or derived from S. pneumoniae serotype 7F in the plurality of immunogenic complexes is approximately 10:1 (w/w). In some embodiments, the average ratio of CP1 protein to capsular polysaccharide from or derived from S. pneumoniae serotype 7F in the plurality of immunogenic complexes is chosen to enhance the polysaccharide immunogenicity potential (carrier function) and/or to elicit protection against, or to inhibit, pneumococcal colonization by any pneumococcus (independent of polysaccharide serotype) through a protein-specific immune response. Immunogenic compositions and vaccines of the invention may comprise mixtures of immunogenic complexes with different average protein to polysaccharide ratios.

In some embodiments, a vaccine or immunogenic composition comprises a plurality of immunogenic complexes comprising a CP1 protein and a capsular polysaccharide, from or derived from S. pneumoniae serotype 8. In some embodiments, the average ratio of CP1 protein to capsular polysaccharide from or derived from S. pneumoniae serotype 8 in the plurality of immunogenic complexes is approximately 1:1, 1.5:1, 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1, or 10:1 (weight/weight [w/w]). In some embodiments, the average ratio of CP1 protein to capsular polysaccharide from or derived from *S. pneumoniae* serotype 8 in the plurality of immunogenic complexes is approximately 1:1 (w/w). In some embodiments, the average ratio of CP1 protein to capsular polysaccharide from or derived from *S. pneumoniae* serotype 8 in the plurality of immunogenic complexes is approximately 2:1 (w/w). In some embodiments, the average ratio of CP1 protein to capsular polysaccharide from or derived from *S. pneumoniae* serotype 8 in the plurality of immunogenic complexes is approximately 3:1 (w/w). In some embodiments, the average ratio of CP1 protein to capsular polysaccharide from or derived from *S. pneumoniae* serotype 8 in the plurality of immunogenic complexes is approximately 4:1 (w/w). In some embodiments, the average ratio of CP1 protein to capsular polysaccharide from or derived from *S. pneumoniae* serotype 8 in the plurality of immunogenic complexes is approximately 5:1 (w/w). In some embodiments, the average ratio of CP1 protein to capsular polysaccharide from or derived from *S. pneumoniae* serotype 8 in the plurality of immunogenic complexes is approximately 6:1 (w/w). In some embodiments, the average ratio of CP1 protein to capsular polysaccharide from or derived from *S. pneumoniae* serotype 8 in the plurality of immunogenic complexes is approximately 7:1 (w/w). In some embodiments, the average ratio of CP1 protein to capsular polysaccharide from or derived from *S. pneumoniae* serotype 8 in the plurality of immunogenic complexes is approximately 8:1 (w/w). In some embodiments, the average ratio of CP1 protein to capsular polysaccharide from or derived from *S. pneumoniae* serotype 8 in the plurality of immunogenic complexes is approximately 9:1 (w/w). In some embodiments, the average ratio of CP1 protein to capsular polysaccharide from or derived from *S. pneumoniae* serotype 8 in the plurality of immunogenic complexes is approximately 10:1 (w/w). In some embodiments, the average ratio of CP1 protein to capsular polysaccharide from or derived from *S. pneumoniae* serotype 8 in the plurality of immunogenic complexes is chosen to enhance the polysaccharide immunogenicity potential (carrier function) and/or to elicit protection against, or to inhibit, pneumococcal colonization by any pneumococcus (independent of polysaccharide serotype) through a protein-specific immune response. Immunogenic compositions and vaccines of the invention may comprise mixtures of immunogenic complexes with different average protein to polysaccharide ratios.

In some embodiments, a vaccine or immunogenic composition comprises a plurality of immunogenic complexes comprising a CP1 protein and a capsular polysaccharide, from or derived from *S. pneumoniae* serotype 9N. In some embodiments, the average ratio of CP1 protein to capsular polysaccharide from or derived from *S. pneumoniae* serotype 9N in the plurality of immunogenic complexes is approximately 1:1, 1.5:1, 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1, or 10:1 (weight/weight [w/w]). In some embodiments, the average ratio of CP1 protein to capsular polysaccharide from or derived from *S. pneumoniae* serotype 9N in the plurality of immunogenic complexes is approximately 1:1 (w/w). In some embodiments, the average ratio of CP1 protein to capsular polysaccharide from or derived from *S. pneumoniae* serotype 9N in the plurality of immunogenic complexes is approximately 2:1 (w/w). In some embodiments, the average ratio of CP1 protein to capsular polysaccharide from or derived from *S. pneumoniae* serotype 9N in the plurality of immunogenic complexes is approximately 3:1 (w/w). In some embodiments, the average ratio of CP1 protein to capsular polysaccharide from or derived from *S. pneumoniae* serotype 9N in the plurality of immunogenic complexes is approximately 4:1 (w/w). In some embodiments, the average ratio of CP1 protein to capsular polysaccharide from or derived from *S. pneumoniae* serotype 9N in the plurality of immunogenic complexes is approximately 5:1 (w/w). In some embodiments, the average ratio of CP1 protein to capsular polysaccharide from or derived from *S. pneumoniae* serotype 9N in the plurality of immunogenic complexes is approximately 6:1 (w/w). In some embodiments, the average ratio of CP1 protein to capsular polysaccharide from or derived from *S. pneumoniae* serotype 9N in the plurality of immunogenic complexes is approximately 7:1 (w/w). In some embodiments, the average ratio of CP1 protein to capsular polysaccharide from or derived from *S. pneumoniae* serotype 9N in the plurality of immunogenic complexes is approximately 8:1 (w/w). In some embodiments, the average ratio of CP1 protein to capsular polysaccharide from or derived from *S. pneumoniae* serotype 9N in the plurality of immunogenic complexes is approximately 9:1 (w/w). In some embodiments, the average ratio of CP1 protein to capsular polysaccharide from or derived from *S. pneumoniae* serotype 9N in the plurality of immunogenic complexes is approximately 10:1 (w/w). In some embodiments, the average ratio of CP1 protein to capsular polysaccharide from or derived from *S. pneumoniae* serotype 9N in the plurality of immunogenic complexes is chosen to enhance the polysaccharide immunogenicity potential (carrier function) and/or to elicit protection against, or to inhibit, pneumococcal colonization by any pneumococcus (independent of polysaccharide serotype) through a protein-specific immune response. Immunogenic compositions and vaccines of the invention may comprise mixtures of immunogenic complexes with different average protein to polysaccharide ratios.

In some embodiments, a vaccine or immunogenic composition comprises a plurality of immunogenic complexes comprising a CP1 protein and a capsular polysaccharide, from or derived from *S. pneumoniae* serotype 9V. In some embodiments, the average ratio of CP1 protein to capsular polysaccharide from or derived from *S. pneumoniae* serotype 9V in the plurality of immunogenic complexes is approximately 1:1, 1.5:1, 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1, or 10:1 (weight/weight [w/w]). In some embodiments, the average ratio of CP1 protein to capsular polysaccharide from or derived from *S. pneumoniae* serotype 9V in the plurality of immunogenic complexes is approximately 1:1 (w/w). In some embodiments, the average ratio of CP1 protein to capsular polysaccharide from or derived from *S. pneumoniae* serotype 9V in the plurality of immunogenic complexes is approximately 2:1 (w/w). In some embodiments, the average ratio of CP1 protein to capsular polysaccharide from or derived from *S. pneumoniae* serotype 9V in the plurality of immunogenic complexes is approximately 3:1 (w/w). In some embodiments, the average ratio of CP1 protein to capsular polysaccharide from or derived from *S. pneumoniae* serotype 9V in the plurality of immunogenic complexes is approximately 4:1 (w/w). In some embodiments, the average ratio of CP1 protein to capsular polysaccharide from or derived from *S. pneumoniae* serotype 9V in the plurality of immunogenic complexes is approximately 5:1 (w/w). In some embodiments, the average ratio of CP1 protein to capsular polysaccharide from or derived from *S. pneumoniae* serotype 9V in the plurality of immunogenic complexes is approximately 6:1 (w/w). In some embodiments, the average ratio of CP1 protein to capsular polysaccharide from or derived from *S. pneumoniae* serotype 9V in the plurality of immunogenic complexes is approximately 7:1 (w/w). In some embodiments, the average ratio of CP1 protein to capsular polysaccharide from or derived from *S. pneumoniae* serotype 9V in the plurality of immunogenic complexes is approximately 8:1 (w/w). In some embodiments, the average ratio of CP1 protein to capsular polysaccharide from or derived from *S. pneumoniae* serotype 9V in the plurality of immunogenic complexes is approximately 9:1 (w/w). In some embodiments, the average ratio of CP1 protein to capsular polysaccharide from or derived from *S. pneumoniae* serotype 9V in the plurality of immunogenic complexes is approximately 10:1 (w/w). In some embodiments, the average ratio of CP1 protein to capsular polysaccharide from or derived from *S. pneumoniae* serotype 9V in the plurality of immunogenic complexes is chosen to enhance the polysaccharide immunogenicity potential (carrier function) and/or to elicit protection against, or to inhibit, pneumococcal colonization by any pneumococcus (independent of polysaccharide serotype) through a protein-specific immune response. Immunogenic compositions and vaccines of the invention may comprise mixtures of immunogenic complexes with different average protein to polysaccharide ratios.

In some embodiments, a vaccine or immunogenic composition comprises a plurality of immunogenic complexes comprising a CP1 protein and a capsular polysaccharide, from or derived from *S. pneumoniae* serotype 10A. In some embodiments, the average ratio of CP1 protein to capsular polysaccharide from or derived from *S. pneumoniae* serotype 10A in the plurality of immunogenic complexes is approximately 1:1, 1.5:1, 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1, or 10:1 (weight/weight [w/w]). In some embodiments, the average ratio of CP1 protein to capsular polysaccharide from or derived from *S. pneumoniae* serotype 10A in the plurality of immunogenic complexes is approximately 1:1 (w/w). In some embodiments, the average ratio of CP1 protein to capsular polysaccharide from or derived from *S. pneumoniae* serotype 10A in the plurality of immunogenic complexes is approximately 2:1 (w/w). In some embodiments, the average ratio of CP1 protein to capsular polysaccharide from or derived from *S. pneumoniae* serotype 10A in the plurality of immunogenic complexes is approximately 3:1 (w/w). In some embodiments, the average ratio of CP1 protein to capsular polysaccharide from or derived from *S. pneumoniae* serotype 10A in the plurality of immunogenic complexes is approximately 4:1 (w/w). In some embodiments, the average ratio of CP1 protein to capsular polysaccharide from or derived from *S. pneumoniae* serotype 10A in the plurality of immunogenic complexes is approximately 5:1 (w/w). In some embodiments, the average ratio of CP1 protein to capsular polysaccharide from or derived from *S. pneumoniae* serotype 10A in the plurality of immunogenic complexes is approximately 6:1 (w/w). In some embodiments, the average ratio of CP1 protein to capsular polysaccharide from or derived from *S. pneumoniae* serotype 10A in the plurality of immunogenic complexes is approximately 7:1 (w/w). In some embodiments, the average ratio of CP1 protein to capsular polysaccharide from or derived from *S. pneumoniae* serotype 10A in the plurality of immunogenic complexes is approximately 8:1 (w/w). In some embodiments, the average ratio of CP1 protein to capsular polysaccharide from or derived from *S. pneumoniae* serotype 10A in the plurality of immunogenic complexes is approximately 9:1 (w/w). In some embodiments, the average ratio of CP1 protein to capsular polysaccharide from or derived from *S. pneumoniae* serotype 10A in the plurality of immunogenic complexes is approximately 10:1 (w/w). In some embodiments, the average ratio of CP1 protein to capsular polysaccharide from or derived from *S. pneumoniae* serotype 10A in the plurality of immunogenic complexes is chosen to enhance the polysaccharide immunogenicity potential (carrier function) and/or to elicit protection against, or to inhibit, pneumococcal colonization by any pneumococcus (independent of polysaccharide serotype) through a protein-specific immune response. Immunogenic compositions and vaccines of the invention may comprise mixtures of immunogenic complexes with different average protein to polysaccharide ratios.

In some embodiments, a vaccine or immunogenic composition comprises a plurality of immunogenic complexes comprising a CP1 protein and a capsular polysaccharide, from or derived from *S. pneumoniae* serotype 11A. In some embodiments, the average ratio of CP1 protein to capsular polysaccharide from or derived from *S. pneumoniae* serotype 11A in the plurality of immunogenic complexes is approximately 1:1, 1.5:1, 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1, or 10:1 (weight/weight [w/w]). In some embodiments, the average ratio of CP1 protein to capsular polysaccharide from or derived from *S. pneumoniae* serotype 11A in the plurality of immunogenic complexes is approximately 1:1 (w/w). In some embodiments, the average ratio of CP1 protein to capsular polysaccharide from or derived from *S. pneumoniae* serotype 11A in the plurality of immunogenic complexes is approximately 2:1 (w/w). In some embodiments, the average ratio of CP1 protein to capsular polysaccharide from or derived from *S. pneumoniae* serotype 11A in the plurality of immunogenic complexes is approximately 3:1 (w/w). In some embodiments, the average ratio of CP1 protein to capsular polysaccharide from or derived from *S. pneumoniae* serotype 11A in the plurality of immunogenic complexes is approximately 4:1 (w/w). In some embodiments, the average ratio of CP1 protein to capsular polysaccharide from or derived from *S. pneumoniae* serotype 11A in the plurality of immunogenic complexes is approximately 5:1 (w/w). In some embodiments, the average ratio of CP1 protein to capsular polysaccharide from or derived from *S. pneumoniae* serotype 11A in the plurality of immunogenic complexes is approximately 6:1 (w/w). In some embodiments, the average ratio of CP1 protein to capsular polysaccharide from or derived from *S. pneumoniae* serotype 11A in the plurality of immunogenic complexes is approximately 7:1 (w/w). In some embodiments, the average ratio of CP1 protein to capsular polysaccharide from or derived from *S. pneumoniae* serotype 11A in the plurality of immunogenic complexes is approximately 8:1 (w/w). In some embodiments, the average ratio of CP1 protein to capsular polysaccharide from or derived from *S. pneumoniae* serotype 11A in the plurality of immunogenic complexes is approximately 9:1 (w/w). In some embodiments, the average ratio of CP1 protein to capsular polysaccharide from or derived from *S. pneumoniae* serotype 11A in the plurality of immunogenic complexes is approximately 10:1 (w/w). In some embodiments, the average ratio of CP1 protein to capsular polysaccharide from or derived from *S. pneumoniae* serotype 11A in the plurality of immunogenic complexes is chosen to enhance the polysaccharide immunogenicity potential (carrier function) and/or to elicit protection against, or to inhibit, pneumococcal colonization by any pneumococcus (independent of polysaccharide serotype) through a protein-specific immune response. Immunogenic compositions and vaccines of the invention may comprise mixtures of immunogenic complexes with different average protein to polysaccharide ratios.

In some embodiments, a vaccine or immunogenic composition comprises a plurality of immunogenic complexes comprising a CP1 protein and a capsular polysaccharide, from or derived from *S. pneumoniae* serotype 12F. In some embodiments, the average ratio of CP1 protein to capsular polysaccharide from or derived from *S. pneumoniae* serotype 12F in the plurality of immunogenic complexes is approximately 1:1, 1.5:1, 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1, or 10:1 (weight/weight [w/w]). In some embodiments, the average ratio of CP1 protein to capsular polysaccharide from or derived from *S. pneumoniae* serotype 12F in the plurality of immunogenic complexes is approximately 1:1 (w/w). In some embodiments, the average ratio of CP1 protein to capsular polysaccharide from or derived from *S. pneumoniae* serotype 12F in the plurality of immunogenic complexes is approximately 2:1 (w/w). In some embodiments, the average ratio of CP1 protein to capsular polysaccharide from or derived from *S. pneumoniae* serotype 12F in the plurality of immunogenic complexes is approximately 3:1 (w/w). In some embodiments, the average ratio of CP1 protein to capsular polysaccharide from or derived from *S. pneumoniae* serotype 12F in the plurality of immunogenic complexes is approximately 4:1 (w/w). In some embodiments, the average ratio of CP1 protein to capsular polysaccharide from or derived from *S. pneumoniae* serotype 12F in the plurality of immunogenic complexes is approximately 5:1 (w/w). In some embodiments, the average ratio of CP1 protein to capsular polysaccharide from or derived from *S. pneumoniae* serotype 12F in the plurality of immunogenic complexes is approximately 6:1 (w/w). In some embodiments, the average ratio of CP1 protein to capsular polysaccharide from or derived from *S. pneumoniae* serotype 12F in the plurality of immunogenic complexes is approximately 7:1 (w/w). In some embodiments, the average ratio of CP1 protein to capsular polysaccharide from or derived from *S. pneumoniae* serotype 12F in the plurality of immunogenic complexes is approximately 8:1 (w/w). In some embodiments, the average ratio of CP1 protein to capsular polysaccharide from or derived from *S. pneumoniae* serotype 12F in the plurality of immunogenic complexes is approximately 9:1 (w/w). In some embodiments, the average ratio of CP1 protein to capsular polysaccharide from or derived from *S. pneumoniae* serotype 12F in the plurality of immunogenic complexes is approximately 10:1 (w/w). In some embodiments, the average ratio of CP1 protein to capsular polysaccharide from or derived from *S. pneumoniae* serotype 12F in the plurality of immunogenic complexes is chosen to enhance the polysaccharide immunogenicity potential (carrier function) and/or to elicit protection against, or to inhibit, pneumococcal colonization by any pneumococcus (independent of polysaccharide serotype) through a protein-specific immune response. Immunogenic compositions and vaccines of the invention may comprise mixtures of immunogenic complexes with different average protein to polysaccharide ratios.

In some embodiments, a vaccine or immunogenic composition comprises a plurality of immunogenic complexes comprising a CP1 protein and a capsular polysaccharide, from or derived from *S. pneumoniae* serotype 14. In some embodiments, the average ratio of CP1 protein to capsular polysaccharide from or derived from *S. pneumoniae* serotype 14 in the plurality of immunogenic complexes is approximately 1:1, 1.5:1, 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1, or 10:1 (weight/weight [w/w]). In some embodiments, the average ratio of CP1 protein to capsular polysaccharide from or derived from *S. pneumoniae* serotype 14 in the plurality of immunogenic complexes is approximately 1:1 (w/w). In some embodiments, the average ratio of CP1 protein to capsular polysaccharide from or derived from *S. pneumoniae* serotype 14 in the plurality of immunogenic complexes is approximately 2:1 (w/w). In some embodiments, the average ratio of CP1 protein to capsular polysaccharide from or derived from *S. pneumoniae* serotype 14 in the plurality of immunogenic complexes is approximately 3:1 (w/w). In some embodiments, the average ratio of CP1 protein to capsular polysaccharide from or derived from *S. pneumoniae* serotype 14 in the plurality of immunogenic complexes is approximately 4:1 (w/w). In some embodiments, the average ratio of CP1 protein to capsular polysaccharide from or derived from *S. pneumoniae* serotype 14 in the plurality of immunogenic complexes is approximately 5:1 (w/w). In some embodiments, the average ratio of CP1 protein to capsular polysaccharide from or derived from *S. pneumoniae* serotype 14 in the plurality of immunogenic complexes is approximately 6:1 (w/w). In some embodiments, the average ratio of CP1 protein to capsular polysaccharide from or derived from *S. pneumoniae* serotype 14 in the plurality of immunogenic complexes is approximately 7:1 (w/w). In some embodiments, the average ratio of CP1 protein to capsular polysaccharide from or derived from *S. pneumoniae* serotype 14 in the plurality of immunogenic complexes is approximately 8:1 (w/w). In some embodiments, the average ratio of CP1 protein to capsular polysaccharide from or derived from *S. pneumoniae* serotype 14 in the plurality of immunogenic complexes is approximately 9:1 (w/w). In some embodiments, the average ratio of CP1 protein to capsular polysaccharide from or derived from *S. pneumoniae* serotype 14 in the plurality of immunogenic complexes is approximately 10:1 (w/w). In some embodiments, the average ratio of CP1 protein to capsular polysaccharide from or derived from *S. pneumoniae* serotype 14 in the plurality of immunogenic complexes is chosen to enhance the polysaccharide immunogenicity potential (carrier function) and/or to elicit protection against, or to inhibit, pneumococcal colonization by any pneumococcus (independent of polysaccharide serotype) through a protein-specific immune response. Immunogenic compositions and vaccines of the invention may comprise mixtures of immunogenic complexes with different average protein to polysaccharide ratios.

In some embodiments, a vaccine or immunogenic composition comprises a plurality of immunogenic complexes comprising a CP1 protein and a capsular polysaccharide, from or derived from *S. pneumoniae* serotype 15B. In some embodiments, the average ratio of CP1 protein to capsular polysaccharide from or derived from *S. pneumoniae* serotype 15B in the plurality of immunogenic complexes is approximately 1:1, 1.5:1, 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1, or 10:1 (weight/weight [w/w]). In some embodiments, the average ratio of CP1 protein to capsular polysaccharide from or derived from *S. pneumoniae* serotype 15B in the plurality of immunogenic complexes is approximately 1:1 (w/w). In some embodiments, the average ratio of CP1 protein to capsular polysaccharide from or derived from *S. pneumoniae* serotype 15B in the plurality of immunogenic complexes is approximately 2:1 (w/w). In some embodiments, the average ratio of CP1 protein to capsular polysaccharide from or derived from *S. pneumoniae* serotype 15B in the plurality of immunogenic complexes is approximately 3:1 (w/w). In some embodiments, the average ratio of CP1 protein to capsular polysaccharide from or derived from *S. pneumoniae* serotype 15B in the plurality of immunogenic complexes is approximately 4:1 (w/w). In some embodiments, the average ratio of CP1 protein to capsular polysaccharide from or derived from *S. pneumoniae* serotype 15B in the plurality of immunogenic complexes is approximately 5:1 (w/w). In some embodiments, the average ratio of CP1 protein to capsular polysaccharide from or derived from *S. pneumoniae* serotype 15B in the plurality of immunogenic complexes is approximately 6:1 (w/w). In some embodiments, the average ratio of CP1 protein to capsular polysaccharide from or derived from *S. pneumoniae* serotype 15B in the plurality of immunogenic complexes is approximately 7:1 (w/w). In some embodiments, the average ratio of CP1 protein to capsular polysaccharide from or derived from *S. pneumoniae* serotype 15B in the plurality of immunogenic complexes is approximately 8:1 (w/w). In some embodiments, the average ratio of CP1 protein to capsular polysaccharide from or derived from *S. pneumoniae* serotype 15B in the plurality of immunogenic complexes is approximately 9:1 (w/w). In some embodiments, the average ratio of CP1 protein to capsular polysaccharide from or derived from *S. pneumoniae* serotype 15B in the plurality of immunogenic complexes is approximately 10:1 (w/w). In some embodiments, the average ratio of CP1 protein to capsular polysaccharide from or derived from *S. pneumoniae* serotype 15B in the plurality of immunogenic complexes is chosen to enhance the polysaccharide immunogenicity potential (carrier function) and/or to elicit protection against, or to inhibit, pneumococcal colonization by any pneumococcus (independent of polysaccharide serotype) through a protein-specific immune response. Immunogenic compositions and vaccines of the invention may comprise mixtures of immunogenic complexes with different average protein to polysaccharide ratios.

In some embodiments, a vaccine or immunogenic composition comprises a plurality of immunogenic complexes comprising a CP1 protein and a capsular polysaccharide, from or derived from *S. pneumoniae* serotype 17F. In some embodiments, the average ratio of CP1 protein to capsular polysaccharide from or derived from *S. pneumoniae* serotype 17F in the plurality of immunogenic complexes is approximately 1:1, 1.5:1, 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1, or 10:1 (weight/weight [w/w]). In some embodiments, the average ratio of CP1 protein to capsular polysaccharide from or derived from *S. pneumoniae* serotype 17F in the plurality of immunogenic complexes is approximately 1:1 (w/w). In some embodiments, the average ratio of CP1 protein to capsular polysaccharide from or derived from *S. pneumoniae* serotype 17F in the plurality of immunogenic complexes is approximately 2:1 (w/w). In some embodiments, the average ratio of CP1 protein to capsular polysaccharide from or derived from *S. pneumoniae* serotype 17F in the plurality of immunogenic complexes is approximately 3:1 (w/w). In some embodiments, the average ratio of CP1 protein to capsular polysaccharide from or derived from *S. pneumoniae* serotype 17F in the plurality of immunogenic complexes is approximately 4:1 (w/w). In some embodiments, the average ratio of CP1 protein to capsular polysaccharide from or derived from *S. pneumoniae* serotype 17F in the plurality of immunogenic complexes is approximately 5:1 (w/w). In some embodiments, the average ratio of CP1 protein to capsular polysaccharide from or derived from *S. pneumoniae* serotype 17F in the plurality of immunogenic complexes is approximately 6:1 (w/w). In some embodiments, the average ratio of CP1 protein to capsular polysaccharide from or derived from *S. pneumoniae* serotype 17F in the plurality of immunogenic complexes is approximately 7:1 (w/w). In some embodiments, the average ratio of CP1 protein to capsular polysaccharide from or derived from *S. pneumoniae* serotype 17F in the plurality of immunogenic complexes is approximately 8:1 (w/w). In some embodiments, the average ratio of CP1 protein to capsular polysaccharide from or derived from *S. pneumoniae* serotype 17F in the plurality of immunogenic complexes is approximately 9:1 (w/w). In some embodiments, the average ratio of CP1 protein to capsular polysaccharide from or derived from *S. pneumoniae* serotype 17F in the plurality of immunogenic complexes is approximately 10:1 (w/w). In some embodiments, the average ratio of CP1 protein to capsular polysaccharide from or derived from *S. pneumoniae* serotype 17F in the plurality of immunogenic complexes is chosen to enhance the polysaccharide immunogenicity potential (carrier function) and/or to elicit protection against, or to inhibit, pneumococcal colonization by any pneumococcus (independent of polysaccharide serotype) through a protein-specific immune response. Immunogenic compositions and vaccines of the invention may comprise mixtures of immunogenic complexes with different average protein to polysaccharide ratios.

In some embodiments, a vaccine or immunogenic composition comprises a plurality of immunogenic complexes comprising a CP1 protein and a capsular polysaccharide, from or derived from *S. pneumoniae* serotype 18C. In some embodiments, the average ratio of CP1 protein to capsular polysaccharide from or derived from *S. pneumoniae* serotype 18C in the plurality of immunogenic complexes is approximately 1:1, 1.5:1, 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1, or 10:1 (weight/weight [w/w]). In some embodiments, the average ratio of CP1 protein to capsular polysaccharide from or derived from *S. pneumoniae* serotype 18C in the plurality of immunogenic complexes is approximately 1:1 (w/w). In some embodiments, the average ratio of CP1 protein to capsular polysaccharide from or derived from *S. pneumoniae* serotype 18C in the plurality of immunogenic complexes is approximately 2:1 (w/w). In some embodiments, the average ratio of CP1 protein to capsular polysaccharide from or derived from *S. pneumoniae* serotype 18C in the plurality of immunogenic complexes is approximately 3:1 (w/w). In some embodiments, the average ratio of CP1 protein to capsular polysaccharide from or derived from *S. pneumoniae* serotype 18C in the plurality of immunogenic complexes is approximately 4:1 (w/w). In some embodiments, the average ratio of CP1 protein to capsular polysaccharide from or derived from *S. pneumoniae* serotype 18C in the plurality of immunogenic complexes is approximately 5:1 (w/w). In some embodiments, the average ratio of CP1 protein to capsular polysaccharide from or derived from *S. pneumoniae* serotype 18C in the plurality of immunogenic complexes is approximately 6:1 (w/w). In some embodiments, the average ratio of CP1 protein to capsular polysaccharide from or derived from *S. pneumoniae* serotype 18C in the plurality of immunogenic complexes is approximately 7:1 (w/w). In some embodiments, the average ratio of CP1 protein to capsular polysaccharide from or derived from *S. pneumoniae* serotype 18C in the plurality of immunogenic complexes is approximately 8:1 (w/w). In some embodiments, the average ratio of CP1 protein to capsular polysaccharide from or derived from *S. pneumo-* niae serotype 18C in the plurality of immunogenic complexes is approximately 9:1 (w/w). In some embodiments, the average ratio of CP1 protein to capsular polysaccharide from or derived from S. pneumoniae serotype 18C in the plurality of immunogenic complexes is approximately 10:1 (w/w). In some embodiments, the average ratio of CP1 protein to capsular polysaccharide from or derived from S. pneumoniae serotype 18C in the plurality of immunogenic complexes is chosen to enhance the polysaccharide immunogenicity potential (carrier function) and/or to elicit protection against, or to inhibit, pneumococcal colonization by any pneumococcus (independent of polysaccharide serotype) through a protein-specific immune response. Immunogenic compositions and vaccines of the invention may comprise mixtures of immunogenic complexes with different average protein to polysaccharide ratios.

In some embodiments, a vaccine or immunogenic composition comprises a plurality of immunogenic complexes comprising a CP1 protein and a capsular polysaccharide, from or derived from S. pneumoniae serotype 19A. In some embodiments, the average ratio of CP1 protein to capsular polysaccharide from or derived from S. pneumoniae serotype 19A in the plurality of immunogenic complexes is approximately 1:1, 1.5:1, 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1, or 10:1 (weight/weight [w/w]). In some embodiments, the average ratio of CP1 protein to capsular polysaccharide from or derived from S. pneumoniae serotype 19A in the plurality of immunogenic complexes is approximately 1:1 (w/w). In some embodiments, the average ratio of CP1 protein to capsular polysaccharide from or derived from S. pneumoniae serotype 19A in the plurality of immunogenic complexes is approximately 2:1 (w/w). In some embodiments, the average ratio of CP1 protein to capsular polysaccharide from or derived from S. pneumoniae serotype 19A in the plurality of immunogenic complexes is approximately 3:1 (w/w). In some embodiments, the average ratio of CP1 protein to capsular polysaccharide from or derived from S. pneumoniae serotype 19A in the plurality of immunogenic complexes is approximately 4:1 (w/w). In some embodiments, the average ratio of CP1 protein to capsular polysaccharide from or derived from S. pneumoniae serotype 19A in the plurality of immunogenic complexes is approximately 5:1 (w/w). In some embodiments, the average ratio of CP1 protein to capsular polysaccharide from or derived from S. pneumoniae serotype 19A in the plurality of immunogenic complexes is approximately 6:1 (w/w). In some embodiments, the average ratio of CP1 protein to capsular polysaccharide from or derived from S. pneumoniae serotype 19A in the plurality of immunogenic complexes is approximately 7:1 (w/w). In some embodiments, the average ratio of CP1 protein to capsular polysaccharide from or derived from S. pneumoniae serotype 19A in the plurality of immunogenic complexes is approximately 8:1 (w/w). In some embodiments, the average ratio of CP1 protein to capsular polysaccharide from or derived from S. pneumoniae serotype 19A in the plurality of immunogenic complexes is approximately 9:1 (w/w). In some embodiments, the average ratio of CP1 protein to capsular polysaccharide from or derived from S. pneumoniae serotype 19A in the plurality of immunogenic complexes is approximately 10:1 (w/w). In some embodiments, the average ratio of CP1 protein to capsular polysaccharide from or derived from S. pneumoniae serotype 19A in the plurality of immunogenic complexes is chosen to enhance the polysaccharide immunogenicity potential (carrier function) and/or to elicit protection against, or to inhibit, pneumococcal colonization by any pneumococcus (independent of polysaccharide serotype) through a protein-specific immune response. Immunogenic compositions and vaccines of the invention may comprise mixtures of immunogenic complexes with different average protein to polysaccharide ratios.

In some embodiments, a vaccine or immunogenic composition comprises a plurality of immunogenic complexes comprising a CP1 protein and a capsular polysaccharide, from or derived from S. pneumoniae serotype 19F. In some embodiments, the average ratio of CP1 protein to capsular polysaccharide from or derived from S. pneumoniae serotype 19F in the plurality of immunogenic complexes is approximately 1:1, 1.5:1, 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1, or 10:1 (weight/weight [w/w]). In some embodiments, the average ratio of CP1 protein to capsular polysaccharide from or derived from S. pneumoniae serotype 19F in the plurality of immunogenic complexes is approximately 1:1 (w/w). In some embodiments, the average ratio of CP1 protein to capsular polysaccharide from or derived from S. pneumoniae serotype 19F in the plurality of immunogenic complexes is approximately 2:1 (w/w). In some embodiments, the average ratio of CP1 protein to capsular polysaccharide from or derived from S. pneumoniae serotype 19F in the plurality of immunogenic complexes is approximately 3:1 (w/w). In some embodiments, the average ratio of CP1 protein to capsular polysaccharide from or derived from S. pneumoniae serotype 19F in the plurality of immunogenic complexes is approximately 4:1 (w/w). In some embodiments, the average ratio of CP1 protein to capsular polysaccharide from or derived from S. pneumoniae serotype 19F in the plurality of immunogenic complexes is approximately 5:1 (w/w). In some embodiments, the average ratio of CP1 protein to capsular polysaccharide from or derived from S. pneumoniae serotype 19F in the plurality of immunogenic complexes is approximately 6:1 (w/w). In some embodiments, the average ratio of CP1 protein to capsular polysaccharide from or derived from S. pneumoniae serotype 19F in the plurality of immunogenic complexes is approximately 7:1 (w/w). In some embodiments, the average ratio of CP1 protein to capsular polysaccharide from or derived from S. pneumoniae serotype 19F in the plurality of immunogenic complexes is approximately 8:1 (w/w). In some embodiments, the average ratio of CP1 protein to capsular polysaccharide from or derived from S. pneumoniae serotype 19F in the plurality of immunogenic complexes is approximately 9:1 (w/w). In some embodiments, the average ratio of CP1 protein to capsular polysaccharide from or derived from S. pneumoniae serotype 19F in the plurality of immunogenic complexes is approximately 10:1 (w/w). In some embodiments, the average ratio of CP1 protein to capsular polysaccharide from or derived from S. pneumoniae serotype 19F in the plurality of immunogenic complexes is chosen to enhance the polysaccharide immunogenicity potential (carrier function) and/or to elicit protection against, or to inhibit, pneumococcal colonization by any pneumococcus (independent of polysaccharide serotype) through a protein-specific immune response. Immunogenic compositions and vaccines of the invention may comprise mixtures of immunogenic complexes with different average protein to polysaccharide ratios.

In some embodiments, a vaccine or immunogenic composition comprises a plurality of immunogenic complexes comprising a CP1 protein and a capsular polysaccharide, from or derived from S. pneumoniae serotype 20B. In some embodiments, the average ratio of CP1 protein to capsular polysaccharide from or derived from S. pneumoniae serotype 20B in the plurality of immunogenic complexes is approximately 1:1, 1.5:1, 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1, or 10:1 (weight/weight [w/w]). In some embodiments, the average ratio of CP1 protein to capsular polysaccharide from or derived from *S. pneumoniae* serotype 20B in the plurality of immunogenic complexes is approximately 1:1 (w/w). In some embodiments, the average ratio of CP1 protein to capsular polysaccharide from or derived from *S. pneumoniae* serotype 20B in the plurality of immunogenic complexes is approximately 2:1 (w/w). In some embodiments, the average ratio of CP1 protein to capsular polysaccharide from or derived from *S. pneumoniae* serotype 20B in the plurality of immunogenic complexes is approximately 3:1 (w/w). In some embodiments, the average ratio of CP1 protein to capsular polysaccharide from or derived from *S. pneumoniae* serotype 20B in the plurality of immunogenic complexes is approximately 4:1 (w/w). In some embodiments, the average ratio of CP1 protein to capsular polysaccharide from or derived from *S. pneumoniae* serotype 20B in the plurality of immunogenic complexes is approximately 5:1 (w/w). In some embodiments, the average ratio of CP1 protein to capsular polysaccharide from or derived from *S. pneumoniae* serotype 20B in the plurality of immunogenic complexes is approximately 6:1 (w/w). In some embodiments, the average ratio of CP1 protein to capsular polysaccharide from or derived from *S. pneumoniae* serotype 20B in the plurality of immunogenic complexes is approximately 7:1 (w/w). In some embodiments, the average ratio of CP1 protein to capsular polysaccharide from or derived from *S. pneumoniae* serotype 20B in the plurality of immunogenic complexes is approximately 8:1 (w/w). In some embodiments, the average ratio of CP1 protein to capsular polysaccharide from or derived from *S. pneumoniae* serotype 20B in the plurality of immunogenic complexes is approximately 9:1 (w/w). In some embodiments, the average ratio of CP1 protein to capsular polysaccharide from or derived from *S. pneumoniae* serotype 20B in the plurality of immunogenic complexes is approximately 10:1 (w/w). In some embodiments, the average ratio of CP1 protein to capsular polysaccharide from or derived from *S. pneumoniae* serotype 20B in the plurality of immunogenic complexes is chosen to enhance the polysaccharide immunogenicity potential (carrier function) and/or to elicit protection against, or to inhibit, pneumococcal colonization by any pneumococcus (independent of polysaccharide serotype) through a protein-specific immune response. Immunogenic compositions and vaccines of the invention may comprise mixtures of immunogenic complexes with different average protein to polysaccharide ratios.

In some embodiments, a vaccine or immunogenic composition comprises a plurality of immunogenic complexes comprising a CP1 protein and a capsular polysaccharide, from or derived from *S. pneumoniae* serotype 22F. In some embodiments, the average ratio of CP1 protein to capsular polysaccharide from or derived from *S. pneumoniae* serotype 22F in the plurality of immunogenic complexes is approximately 1:1, 1.5:1, 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1, or 10:1 (weight/weight [w/w]). In some embodiments, the average ratio of CP1 protein to capsular polysaccharide from or derived from *S. pneumoniae* serotype 22F in the plurality of immunogenic complexes is approximately 1:1 (w/w). In some embodiments, the average ratio of CP1 protein to capsular polysaccharide from or derived from *S. pneumoniae* serotype 22F in the plurality of immunogenic complexes is approximately 2:1 (w/w). In some embodiments, the average ratio of CP1 protein to capsular polysaccharide from or derived from *S. pneumoniae* serotype 22F in the plurality of immunogenic complexes is approximately 3:1 (w/w). In some embodiments, the average ratio of CP1 protein to capsular polysaccharide from or derived from *S. pneumoniae* serotype 22F in the plurality of immunogenic complexes is approximately 4:1 (w/w). In some embodiments, the average ratio of CP1 protein to capsular polysaccharide from or derived from *S. pneumoniae* serotype 22F in the plurality of immunogenic complexes is approximately 5:1 (w/w). In some embodiments, the average ratio of CP1 protein to capsular polysaccharide from or derived from *S. pneumoniae* serotype 22F in the plurality of immunogenic complexes is approximately 6:1 (w/w). In some embodiments, the average ratio of CP1 protein to capsular polysaccharide from or derived from *S. pneumoniae* serotype 22F in the plurality of immunogenic complexes is approximately 7:1 (w/w). In some embodiments, the average ratio of CP1 protein to capsular polysaccharide from or derived from *S. pneumoniae* serotype 22F in the plurality of immunogenic complexes is approximately 8:1 (w/w). In some embodiments, the average ratio of CP1 protein to capsular polysaccharide from or derived from *S. pneumoniae* serotype 22F in the plurality of immunogenic complexes is approximately 9:1 (w/w). In some embodiments, the average ratio of CP1 protein to capsular polysaccharide from or derived from *S. pneumoniae* serotype 22F in the plurality of immunogenic complexes is approximately 10:1 (w/w). In some embodiments, the average ratio of CP1 protein to capsular polysaccharide from or derived from *S. pneumoniae* serotype 22F in the plurality of immunogenic complexes is chosen to enhance the polysaccharide immunogenicity potential (carrier function) and/or to elicit protection against, or to inhibit, pneumococcal colonization by any pneumococcus (independent of polysaccharide serotype) through a protein-specific immune response. Immunogenic compositions and vaccines of the invention may comprise mixtures of immunogenic complexes with different average protein to polysaccharide ratios.

In some embodiments, a vaccine or immunogenic composition comprises a plurality of immunogenic complexes comprising a CP1 protein and a capsular polysaccharide, from or derived from *S. pneumoniae* serotype 23F. In some embodiments, the average ratio of CP1 protein to capsular polysaccharide from or derived from *S. pneumoniae* serotype 23F in the plurality of immunogenic complexes is approximately 1:1, 1.5:1, 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1, or 10:1 (weight/weight [w/w]). In some embodiments, the average ratio of CP1 protein to capsular polysaccharide from or derived from *S. pneumoniae* serotype 23F in the plurality of immunogenic complexes is approximately 1:1 (w/w). In some embodiments, the average ratio of CP1 protein to capsular polysaccharide from or derived from *S. pneumoniae* serotype 23F in the plurality of immunogenic complexes is approximately 2:1 (w/w). In some embodiments, the average ratio of CP1 protein to capsular polysaccharide from or derived from *S. pneumoniae* serotype 23F in the plurality of immunogenic complexes is approximately 3:1 (w/w). In some embodiments, the average ratio of CP1 protein to capsular polysaccharide from or derived from *S. pneumoniae* serotype 23F in the plurality of immunogenic complexes is approximately 4:1 (w/w). In some embodiments, the average ratio of CP1 protein to capsular polysaccharide from or derived from *S. pneumoniae* serotype 23F in the plurality of immunogenic complexes is approximately 5:1 (w/w). In some embodiments, the average ratio of CP1 protein to capsular polysaccharide from or derived from *S. pneumoniae* serotype 23F in the plurality of immunogenic complexes is approximately 6:1 (w/w). In some embodiments, the average ratio of CP1 protein to capsular polysaccharide from or derived from *S. pneumoniae* serotype 23F in the plurality of immunogenic complexes is approximately 7:1 (w/w). In some embodiments, the average ratio of CP1 protein to capsular polysaccharide from or derived from *S. pneumoniae* serotype 23F in the plurality of immunogenic complexes is approximately 8:1 (w/w). In some embodiments, the average ratio of CP1 protein to capsular polysaccharide from or derived from *S. pneumoniae* serotype 23F in the plurality of immunogenic complexes is approximately 9:1 (w/w). In some embodiments, the average ratio of CP1 protein to capsular polysaccharide from or derived from *S. pneumoniae* serotype 23F in the plurality of immunogenic complexes is approximately 10:1 (w/w). In some embodiments, the average ratio of CP1 protein to capsular polysaccharide from or derived from *S. pneumoniae* serotype 23F in the plurality of immunogenic complexes is chosen to enhance the polysaccharide immunogenicity potential (carrier function) and/or to elicit protection against, or to inhibit, pneumococcal colonization by any pneumococcus (independent of polysaccharide serotype) through a protein-specific immune response. Immunogenic compositions and vaccines of the invention may comprise mixtures of immunogenic complexes with different average protein to polysaccharide ratios.

In some embodiments, a vaccine or immunogenic composition comprises a plurality of immunogenic complexes comprising a CP1 protein and a capsular polysaccharide, from or derived from *S. pneumoniae* serotype 33F. In some embodiments, the average ratio of CP1 protein to capsular polysaccharide from or derived from *S. pneumoniae* serotype 33F in the plurality of immunogenic complexes is approximately 1:1, 1.5:1, 2:1, 2.5:1, 3:1, 3.5:1, 4:1, 4.5:1, 5:1, 5.5:1, 6:1, 6.5:1, 7:1, 7.5:1, 8:1, 8.5:1, 9:1, 9.5:1, or 10:1 (weight/weight [w/w]). In some embodiments, the average ratio of CP1 protein to capsular polysaccharide from or derived from *S. pneumoniae* serotype 33F in the plurality of immunogenic complexes is approximately 1:1 (w/w). In some embodiments, the average ratio of CP1 protein to capsular polysaccharide from or derived from *S. pneumoniae* serotype 33F in the plurality of immunogenic complexes is approximately 2:1 (w/w). In some embodiments, the average ratio of CP1 protein to capsular polysaccharide from or derived from *S. pneumoniae* serotype 33F in the plurality of immunogenic complexes is approximately 3:1 (w/w). In some embodiments, the average ratio of CP1 protein to capsular polysaccharide from or derived from *S. pneumoniae* serotype 33F in the plurality of immunogenic complexes is approximately 4:1 (w/w). In some embodiments, the average ratio of CP1 protein to capsular polysaccharide from or derived from *S. pneumoniae* serotype 33F in the plurality of immunogenic complexes is approximately 5:1 (w/w). In some embodiments, the average ratio of CP1 protein to capsular polysaccharide from or derived from *S. pneumoniae* serotype 33F in the plurality of immunogenic complexes is approximately 6:1 (w/w). In some embodiments, the average ratio of CP1 protein to capsular polysaccharide from or derived from *S. pneumoniae* serotype 33F in the plurality of immunogenic complexes is approximately 7:1 (w/w). In some embodiments, the average ratio of CP1 protein to capsular polysaccharide from or derived from *S. pneumoniae* serotype 33F in the plurality of immunogenic complexes is approximately 8:1 (w/w). In some embodiments, the average ratio of CP1 protein to capsular polysaccharide from or derived from *S. pneumoniae* serotype 33F in the plurality of immunogenic complexes is approximately 9:1 (w/w). In some embodiments, the average ratio of CP1 protein to capsular polysaccharide from or derived from *S. pneumoniae* serotype 33F in the plurality of immunogenic complexes is approximately 10:1 (w/w). In some embodiments, the average ratio of CP1 protein to capsular polysaccharide from or derived from *S. pneumoniae* serotype 33F in the plurality of immunogenic complexes is chosen to enhance the polysaccharide immunogenicity potential (carrier function) and/or to elicit protection against, or to inhibit, pneumococcal colonization by any pneumococcus (independent of polysaccharide serotype) through a protein-specific immune response. Immunogenic compositions and vaccines of the invention may comprise mixtures of immunogenic complexes with different average protein to polysaccharide ratios.

In some embodiments, a vaccine or immunogenic composition comprises:
(1) a plurality of immunogenic complexes comprising a CP1 protein and a capsular polysaccharide, from or derived from *S. pneumoniae* serotype 1, wherein the average ratio of CP1 protein to capsular polysaccharide from or derived from *S. pneumoniae* serotype 1 in the plurality of immunogenic complexes is between about 2.5:1 and about 3.5:1 (w/w);
(2) a plurality of immunogenic complexes comprising a CP1 protein and a capsular polysaccharide, from or derived from *S. pneumoniae* serotype 2, wherein the average ratio of CP1 protein to capsular polysaccharide from or derived from *S. pneumoniae* serotype 2 in the plurality of immunogenic complexes is between about 2.5:1 and about 3.5:1 (w/w);
(3) a plurality of immunogenic complexes comprising a CP1 protein and a capsular polysaccharide, from or derived from *S. pneumoniae* serotype 3, wherein the average ratio of CP1 protein to capsular polysaccharide from or derived from *S. pneumoniae* serotype 3 in the plurality of immunogenic complexes is between about 2.5:1 and about 3.5:1 (w/w);
(4) a plurality of immunogenic complexes comprising a CP1 protein and a capsular polysaccharide, from or derived from *S. pneumoniae* serotype 4, wherein the average ratio of CP1 protein to capsular polysaccharide from or derived from *S. pneumoniae* serotype 4 in the plurality of immunogenic complexes is between about 2.5:1 and about 3.5:1 (w/w);
(5) a plurality of immunogenic complexes comprising a CP1 protein and a capsular polysaccharide, from or derived from *S. pneumoniae* serotype 5, wherein the average ratio of CP1 protein to capsular polysaccharide from or derived from *S. pneumoniae* serotype 5 in the plurality of immunogenic complexes is between about 2.5:1 and about 3.5:1 (w/w);
(6) a plurality of immunogenic complexes comprising a CP1 protein and a capsular polysaccharide, from or derived from *S. pneumoniae* serotype 6A, wherein the average ratio of CP1 protein to capsular polysaccharide from or derived from *S. pneumoniae* serotype 6A in the plurality of immunogenic complexes is between about 2.5:1 and about 3.5:1 (w/w);
(7) a plurality of immunogenic complexes comprising a CP1 protein and a capsular polysaccharide, from or derived from *S. pneumoniae* serotype 6B, wherein the average ratio of CP1 protein to capsular polysaccharide from or derived from *S. pneumoniae* serotype 6B in the plurality of immunogenic complexes is between about 2.5:1 and about 3.5:1 (w/w);
(8) a plurality of immunogenic complexes comprising a CP1 protein and a capsular polysaccharide, from or derived from *S. pneumoniae* serotype 7F, wherein the average ratio of CP1 protein to capsular polysaccharide from or derived from *S. pneumoniae* serotype 7F in the plurality of immunogenic complexes is between about 2.5:1 and about 3.5:1 (w/w);
(9) a plurality of immunogenic complexes comprising a CP1 protein and a capsular polysaccharide, from or derived from *S. pneumoniae* serotype 8, wherein the average ratio of CP1 protein to capsular polysaccharide from or derived from *S. pneumoniae* serotype 8 in the plurality of immunogenic complexes is between about 2.5:1 and about 3.5:1 (w/w);
(10) a plurality of immunogenic complexes comprising a CP1 protein and a capsular polysaccharide, from or derived from *S. pneumoniae* serotype 9N, wherein the average ratio of CP1 protein to capsular polysaccharide from or derived from *S. pneumoniae* serotype 9N in the plurality of immunogenic complexes is between about 2.5:1 and about 3.5:1 (w/w);
(11) a plurality of immunogenic complexes comprising a CP1 protein and a capsular polysaccharide, from or derived from *S. pneumoniae* serotype 9V, wherein the average ratio of CP1 protein to capsular polysaccharide from or derived from *S. pneumoniae* serotype 9V in the plurality of immunogenic complexes is between about 2.5:1 and about 3.5:1 (w/w);
(12) a plurality of immunogenic complexes comprising a CP1 protein and a capsular polysaccharide, from or derived from *S. pneumoniae* serotype 10A, wherein the average ratio of CP1 protein to capsular polysaccharide from or derived from *S. pneumoniae* serotype 10A in the plurality of immunogenic complexes is between about 2.5:1 and about 3.5:1 (w/w);
(13) a plurality of immunogenic complexes comprising a CP1 protein and a capsular polysaccharide, from or derived from *S. pneumoniae* serotype 11A, wherein the average ratio of CP1 protein to capsular polysaccharide from or derived from *S. pneumoniae* serotype 11A in the plurality of immunogenic complexes is between about 2.5:1 and about 3.5:1 (w/w);
(14) a plurality of immunogenic complexes comprising a CP1 protein and a capsular polysaccharide, from or derived from *S. pneumoniae* serotype 12F, wherein the average ratio of CP1 protein to capsular polysaccharide from or derived from *S. pneumoniae* serotype 12F in the plurality of immunogenic complexes is between about 2.5:1 and about 3.5:1 (w/w);
(15) a plurality of immunogenic complexes comprising a CP1 protein and a capsular polysaccharide, from or derived from *S. pneumoniae* serotype 14, wherein the average ratio of CP1 protein to capsular polysaccharide from or derived from *S. pneumoniae* serotype 14 in the plurality of immunogenic complexes is between about 2.5:1 and about 3.5:1 (w/w);
(16) a plurality of immunogenic complexes comprising a CP1 protein and a capsular polysaccharide, from or derived from *S. pneumoniae* serotype 15B, wherein the average ratio of CP1 protein to capsular polysaccharide from or derived from *S. pneumoniae* serotype 15B in the plurality of immunogenic complexes is between about 2.5:1 and about 3.5:1 (w/w);
(17) a plurality of immunogenic complexes comprising a CP1 protein and a capsular polysaccharide, from or derived from *S. pneumoniae* serotype 17F, wherein the average ratio of CP1 protein to capsular polysaccharide from or derived from *S. pneumoniae* serotype 17F in the plurality of immunogenic complexes is between about 2.5:1 and about 3.5:1 (w/w);
(18) a plurality of immunogenic complexes comprising a CP1 protein and a capsular polysaccharide, from or derived from *S. pneumoniae* serotype 18C, wherein the average ratio of CP1 protein to capsular polysaccharide from or derived from *S. pneumoniae* serotype 18C in the plurality of immunogenic complexes is between about 2.5:1 and about 3.5:1 (w/w);
(19) a plurality of immunogenic complexes comprising a CP1 protein and a capsular polysaccharide, from or derived from *S. pneumoniae* serotype 19A, wherein the average ratio of CP1 protein to capsular polysaccharide from or derived from *S. pneumoniae* serotype 19A in the plurality of immunogenic complexes is between about 5.5:1 and about 6.5:1 (w/w);
(20) a plurality of immunogenic complexes comprising a CP1 protein and a capsular polysaccharide, from or derived from *S. pneumoniae* serotype 19F, wherein the average ratio of CP1 protein to capsular polysaccharide from or derived from *S. pneumoniae* serotype 19F in the plurality of immunogenic complexes is between about 2.5:1 and about 3.5:1 (w/w);
(21) a plurality of immunogenic complexes comprising a CP1 protein and a capsular polysaccharide, from or derived from *S. pneumoniae* serotype 20B, wherein the average ratio of CP1 protein to capsular polysaccharide from or derived from *S. pneumoniae* serotype 20B in the plurality of immunogenic complexes is between about 2.5:1 and about 3.5:1 (w/w);
(22) a plurality of immunogenic complexes comprising a CP1 protein and a capsular polysaccharide, from or derived from *S. pneumoniae* serotype 22F, wherein the average ratio of CP1 protein to capsular polysaccharide from or derived from *S. pneumoniae* serotype 22F in the plurality of immunogenic complexes is between about 2.5:1 and about 3.5:1 (w/w);
(23) a plurality of immunogenic complexes comprising a CP1 protein and a capsular polysaccharide, from or derived from *S. pneumoniae* serotype 23F, wherein the average ratio of CP1 protein to capsular polysaccharide from or derived from *S. pneumoniae* serotype 23F in the plurality of immunogenic complexes is between about 2.5:1 and about 3.5:1 (w/w); and
(24) a plurality of immunogenic complexes comprising a CP1 protein and a capsular polysaccharide, from or derived from *S. pneumoniae* serotype 33F, wherein the average ratio of CP1 protein to capsular polysaccharide from or derived from *S. pneumoniae* serotype 33F in the plurality of immunogenic complexes is between about 2.5:1 and about 3.5:1 (w/w).

In some embodiments, a vaccine or immunogenic composition comprises:
(1) a plurality of immunogenic complexes comprising a CP1 protein and a capsular polysaccharide, from or derived from *S. pneumoniae* serotype 1, wherein the average ratio of CP1 protein to capsular polysaccharide from or derived from *S. pneumoniae* serotype 1 in the plurality of immunogenic complexes is between about 2.5:1 and about 3.5:1 (w/w);
(2) a plurality of immunogenic complexes comprising a CP1 protein and a capsular polysaccharide, from or derived from *S. pneumoniae* serotype 3, wherein the average ratio of CP1 protein to capsular polysaccharide from or derived from *S. pneumoniae* serotype 3 in the plurality of immunogenic complexes is between about 2.5:1 and about 3.5:1 (w/w);

(3) a plurality of immunogenic complexes comprising a CP1 protein and a capsular polysaccharide, from or derived from *S. pneumoniae* serotype 4, wherein the average ratio of CP1 protein to capsular polysaccharide from or derived from *S. pneumoniae* serotype 4 in the plurality of immunogenic complexes is between about 2.5:1 and about 3.5:1 (w/w);

(4) a plurality of immunogenic complexes comprising a CP1 protein and a capsular polysaccharide, from or derived from *S. pneumoniae* serotype 5, wherein the average ratio of CP1 protein to capsular polysaccharide from or derived from *S. pneumoniae* serotype 5 in the plurality of immunogenic complexes is between about 2.5:1 and about 3.5:1 (w/w);

(5) a plurality of immunogenic complexes comprising a CP1 protein and a capsular polysaccharide, from or derived from *S. pneumoniae* serotype 6A, wherein the average ratio of CP1 protein to capsular polysaccharide from or derived from *S. pneumoniae* serotype 6A in the plurality of immunogenic complexes is between about 2.5:1 and about 3.5:1 (w/w);

(6) a plurality of immunogenic complexes comprising a CP1 protein and a capsular polysaccharide, from or derived from *S. pneumoniae* serotype 6B, wherein the average ratio of CP1 protein to capsular polysaccharide from or derived from *S. pneumoniae* serotype 6B in the plurality of immunogenic complexes is between about 2.5:1 and about 3.5:1 (w/w);

(7) a plurality of immunogenic complexes comprising a CP1 protein and a capsular polysaccharide, from or derived from *S. pneumoniae* serotype 7F, wherein the average ratio of CP1 protein to capsular polysaccharide from or derived from *S. pneumoniae* serotype 7F in the plurality of immunogenic complexes is between about 2.5:1 and about 3.5:1 (w/w);

(8) a plurality of immunogenic complexes comprising a CP1 protein and a capsular polysaccharide, from or derived from *S. pneumoniae* serotype 9V, wherein the average ratio of CP1 protein to capsular polysaccharide from or derived from *S. pneumoniae* serotype 9V in the plurality of immunogenic complexes is between about 2.5:1 and about 3.5:1 (w/w);

(9) a plurality of immunogenic complexes comprising a CP1 protein and a capsular polysaccharide, from or derived from *S. pneumoniae* serotype 14, wherein the average ratio of CP1 protein to capsular polysaccharide from or derived from *S. pneumoniae* serotype 14 in the plurality of immunogenic complexes is between about 2.5:1 and about 3.5:1 (w/w);

(10) a plurality of immunogenic complexes comprising a CP1 protein and a capsular polysaccharide, from or derived from *S. pneumoniae* serotype 18C, wherein the average ratio of CP1 protein to capsular polysaccharide from or derived from *S. pneumoniae* serotype 18C in the plurality of immunogenic complexes is between about 2.5:1 and about 3.5:1 (w/w);

(11) a plurality of immunogenic complexes comprising a CP1 protein and a capsular polysaccharide, from or derived from *S. pneumoniae* serotype 19A, wherein the average ratio of CP1 protein to capsular polysaccharide from or derived from *S. pneumoniae* serotype 19A in the plurality of immunogenic complexes is between about 5.5:1 and about 6.5:1 (w/w);

(12) a plurality of immunogenic complexes comprising a CP1 protein and a capsular polysaccharide, from or derived from *S. pneumoniae* serotype 19F, wherein the average ratio of CP1 protein to capsular polysaccharide from or derived from *S. pneumoniae* serotype 19F in the plurality of immunogenic complexes is between about 2.5:1 and about 3.5:1 (w/w);

(13) a plurality of immunogenic complexes comprising a CP1 protein and a capsular polysaccharide, from or derived from *S. pneumoniae* serotype 22F, wherein the average ratio of CP1 protein to capsular polysaccharide from or derived from *S. pneumoniae* serotype 22F in the plurality of immunogenic complexes is between about 2.5:1 and about 3.5:1 (w/w);

(14) a plurality of immunogenic complexes comprising a CP1 protein and a capsular polysaccharide, from or derived from *S. pneumoniae* serotype 23F, wherein the average ratio of CP1 protein to capsular polysaccharide from or derived from *S. pneumoniae* serotype 23F in the plurality of immunogenic complexes is between about 2.5:1 and about 3.5:1 (w/w); and

(15) a plurality of immunogenic complexes comprising a CP1 protein and a capsular polysaccharide, from or derived from *S. pneumoniae* serotype 33F, wherein the average ratio of CP1 protein to capsular polysaccharide from or derived from *S. pneumoniae* serotype 33F in the plurality of immunogenic complexes is between about 2.5:1 and about 3.5:1 (w/w).

In some embodiments, a vaccine or immunogenic composition comprises:

(1) a plurality of immunogenic complexes comprising a CP1 protein and a capsular polysaccharide, from or derived from *S. pneumoniae* serotype 2, wherein the average ratio of CP1 protein to capsular polysaccharide from or derived from *S. pneumoniae* serotype 2 in the plurality of immunogenic complexes is between about 2.5:1 and about 3.5:1 (w/w);

(2) a plurality of immunogenic complexes comprising a CP1 protein and a capsular polysaccharide, from or derived from *S. pneumoniae* serotype 8, wherein the average ratio of CP1 protein to capsular polysaccharide from or derived from *S. pneumoniae* serotype 8 in the plurality of immunogenic complexes is between about 2.5:1 and about 3.5:1 (w/w);

(3) a plurality of immunogenic complexes comprising a CP1 protein and a capsular polysaccharide, from or derived from *S. pneumoniae* serotype 9N, wherein the average ratio of CP1 protein to capsular polysaccharide from or derived from *S. pneumoniae* serotype 9N in the plurality of immunogenic complexes is between about 2.5:1 and about 3.5:1 (w/w);

(4) a plurality of immunogenic complexes comprising a CP1 protein and a capsular polysaccharide, from or derived from *S. pneumoniae* serotype 10A, wherein the average ratio of CP1 protein to capsular polysaccharide from or derived from *S. pneumoniae* serotype 10A in the plurality of immunogenic complexes is between about 2.5:1 and about 3.5:1 (w/w);

(5) a plurality of immunogenic complexes comprising a CP1 protein and a capsular polysaccharide, from or derived from *S. pneumoniae* serotype 11A, wherein the average ratio of CP1 protein to capsular polysaccharide from or derived from *S. pneumoniae* serotype 11A in the plurality of immunogenic complexes is between about 2.5:1 and about 3.5:1 (w/w);

(6) a plurality of immunogenic complexes comprising a CP1 protein and a capsular polysaccharide, from or derived from *S. pneumoniae* serotype 12F, wherein the average ratio of CP1 protein to capsular polysaccharide from or derived from *S. pneumoniae* serotype 12F in the plurality of immunogenic complexes is between about 2.5:1 and about 3.5:1 (w/w);

(7) a plurality of immunogenic complexes comprising a CP1 protein and a capsular polysaccharide, from or derived from *S. pneumoniae* serotype 15B, wherein the average ratio of CP1 protein to capsular polysaccharide from or derived from *S. pneumoniae* serotype 15B in the plurality of immunogenic complexes is between about 2.5:1 and about 3.5:1 (w/w);

(8) a plurality of immunogenic complexes comprising a CP1 protein and a capsular polysaccharide, from or derived from *S. pneumoniae* serotype 17F, wherein the average ratio of CP1 protein to capsular polysaccharide from or derived from *S. pneumoniae* serotype 17F in the plurality of immunogenic complexes is between about 2.5:1 and about 3.5:1 (w/w); and (9) a plurality of immunogenic complexes comprising a CP1 protein and a capsular polysaccharide, from or derived from *S. pneumoniae* serotype 20B, wherein the average ratio of CP1 protein to capsular polysaccharide from or derived from *S. pneumoniae* serotype 20B in the plurality of immunogenic complexes is between about 2.5:1 and about 3.5:1 (w/w).

In some embodiments, a vaccine or immunogenic composition comprises:

(1) a plurality of immunogenic complexes comprising a CP1 protein and a capsular polysaccharide, from or derived from *S. pneumoniae* serotype 1, wherein the average ratio of CP1 protein to capsular polysaccharide from or derived from *S. pneumoniae* serotype 1 in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(2) a plurality of immunogenic complexes comprising a CP1 protein and a capsular polysaccharide, from or derived from *S. pneumoniae* serotype 2, wherein the average ratio of CP1 protein to capsular polysaccharide from or derived from *S. pneumoniae* serotype 2 in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(3) a plurality of immunogenic complexes comprising a CP1 protein and a capsular polysaccharide, from or derived from *S. pneumoniae* serotype 3, wherein the average ratio of CP1 protein to capsular polysaccharide from or derived from *S. pneumoniae* serotype 3 in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(4) a plurality of immunogenic complexes comprising a CP1 protein and a capsular polysaccharide, from or derived from *S. pneumoniae* serotype 4, wherein the average ratio of CP1 protein to capsular polysaccharide from or derived from *S. pneumoniae* serotype 4 in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(5) a plurality of immunogenic complexes comprising a CP1 protein and a capsular polysaccharide, from or derived from *S. pneumoniae* serotype 5, wherein the average ratio of CP1 protein to capsular polysaccharide from or derived from *S. pneumoniae* serotype 5 in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(6) a plurality of immunogenic complexes comprising a CP1 protein and a capsular polysaccharide, from or derived from *S. pneumoniae* serotype 6A, wherein the average ratio of CP1 protein to capsular polysaccharide from or derived from *S. pneumoniae* serotype 6A in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(7) a plurality of immunogenic complexes comprising a CP1 protein and a capsular polysaccharide, from or derived from *S. pneumoniae* serotype 6B, wherein the average ratio of CP1 protein to capsular polysaccharide from or derived from *S. pneumoniae* serotype 6B in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(8) a plurality of immunogenic complexes comprising a CP1 protein and a capsular polysaccharide, from or derived from *S. pneumoniae* serotype 7F, wherein the average ratio of CP1 protein to capsular polysaccharide from or derived from *S. pneumoniae* serotype 7F in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(9) a plurality of immunogenic complexes comprising a CP1 protein and a capsular polysaccharide, from or derived from *S. pneumoniae* serotype 8, wherein the average ratio of CP1 protein to capsular polysaccharide from or derived from *S. pneumoniae* serotype 8 in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(10) a plurality of immunogenic complexes comprising a CP1 protein and a capsular polysaccharide, from or derived from *S. pneumoniae* serotype 9N, wherein the average ratio of CP1 protein to capsular polysaccharide from or derived from *S. pneumoniae* serotype 9N in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(11) a plurality of immunogenic complexes comprising a CP1 protein and a capsular polysaccharide, from or derived from *S. pneumoniae* serotype 9V, wherein the average ratio of CP1 protein to capsular polysaccharide from or derived from *S. pneumoniae* serotype 9V in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(12) a plurality of immunogenic complexes comprising a CP1 protein and a capsular polysaccharide, from or derived from *S. pneumoniae* serotype 10A, wherein the average ratio of CP1 protein to capsular polysaccharide from or derived from *S. pneumoniae* serotype 10A in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(13) a plurality of immunogenic complexes comprising a CP1 protein and a capsular polysaccharide, from or derived from *S. pneumoniae* serotype 11A, wherein the average ratio of CP1 protein to capsular polysaccharide from or derived from *S. pneumoniae* serotype 11A in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(14) a plurality of immunogenic complexes comprising a CP1 protein and a capsular polysaccharide, from or derived from *S. pneumoniae* serotype 12F, wherein the average ratio of CP1 protein to capsular polysaccharide from or derived from *S. pneumoniae* serotype 12F in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(15) a plurality of immunogenic complexes comprising a CP1 protein and a capsular polysaccharide, from or derived from *S. pneumoniae* serotype 14, wherein the average ratio of CP1 protein to capsular polysaccharide from or derived from *S. pneumoniae* serotype 14 in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(16) a plurality of immunogenic complexes comprising a CP1 protein and a capsular polysaccharide, from or derived from *S. pneumoniae* serotype 15B, wherein the average ratio of CP1 protein to capsular polysaccharide from or derived from *S. pneumoniae* serotype 15B in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(17) a plurality of immunogenic complexes comprising a CP1 protein and a capsular polysaccharide, from or derived from *S. pneumoniae* serotype 17F, wherein the average ratio of CP1 protein to capsular polysaccharide from or derived from *S. pneumoniae* serotype 17F in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(18) a plurality of immunogenic complexes comprising a CP1 protein and a capsular polysaccharide, from or derived from *S. pneumoniae* serotype 18C, wherein the average ratio of CP1 protein to capsular polysaccharide from or derived from *S. pneumoniae* serotype 18C in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(19) a plurality of immunogenic complexes comprising a CP1 protein and a capsular polysaccharide, from or derived from *S. pneumoniae* serotype 19A, wherein the average ratio of CP1 protein to capsular polysaccharide from or derived from *S. pneumoniae* serotype 19A in the plurality of immunogenic complexes is approximately 5.5:1, 5.6:1, 5.7:1, 5.8:1, 5.9:1, 6:1, 6.1:1, 6.2:1, 6.3:1, 6.4:1, or 6.5:1 (w/w);

(20) a plurality of immunogenic complexes comprising a CP1 protein and a capsular polysaccharide, from or derived from *S. pneumoniae* serotype 19F, wherein the average ratio of CP1 protein to capsular polysaccharide from or derived from *S. pneumoniae* serotype 19F in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(21) a plurality of immunogenic complexes comprising a CP1 protein and a capsular polysaccharide, from or derived from *S. pneumoniae* serotype 20B, wherein the average ratio of CP1 protein to capsular polysaccharide from or derived from *S. pneumoniae* serotype 20B in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(22) a plurality of immunogenic complexes comprising a CP1 protein and a capsular polysaccharide, from or derived from *S. pneumoniae* serotype 22F, wherein the average ratio of CP1 protein to capsular polysaccharide from or derived from *S. pneumoniae* serotype 22F in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(23) a plurality of immunogenic complexes comprising a CP1 protein and a capsular polysaccharide, from or derived from *S. pneumoniae* serotype 23F, wherein the average ratio of CP1 protein to capsular polysaccharide from or derived from *S. pneumoniae* serotype 23F in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w); and

(24) a plurality of immunogenic complexes comprising a CP1 protein and a capsular polysaccharide, from or derived from *S. pneumoniae* serotype 33F, wherein the average ratio of CP1 protein to capsular polysaccharide from or derived from *S. pneumoniae* serotype 33F in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w).

In some embodiments, a vaccine or immunogenic composition comprises:

(1) a plurality of immunogenic complexes comprising a CP1 protein and a capsular polysaccharide, from or derived from *S. pneumoniae* serotype 1, wherein the average ratio of CP1 protein to capsular polysaccharide from or derived from *S. pneumoniae* serotype 1 in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(2) a plurality of immunogenic complexes comprising a CP1 protein and a capsular polysaccharide, from or derived from *S. pneumoniae* serotype 3, wherein the average ratio of CP1 protein to capsular polysaccharide from or derived from *S. pneumoniae* serotype 3 in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(3) a plurality of immunogenic complexes comprising a CP1 protein and a capsular polysaccharide, from or derived from *S. pneumoniae* serotype 4, wherein the average ratio of CP1 protein to capsular polysaccharide from or derived from *S. pneumoniae* serotype 4 in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(4) a plurality of immunogenic complexes comprising a CP1 protein and a capsular polysaccharide, from or derived from *S. pneumoniae* serotype 5, wherein the average ratio of CP1 protein to capsular polysaccharide from or derived from *S. pneumoniae* serotype 5 in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(5) a plurality of immunogenic complexes comprising a CP1 protein and a capsular polysaccharide, from or derived from *S. pneumoniae* serotype 6A, wherein the average ratio of CP1 protein to capsular polysaccharide from or derived from *S. pneumoniae* serotype 6A in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(6) a plurality of immunogenic complexes comprising a CP1 protein and a capsular polysaccharide, from or derived from *S. pneumoniae* serotype 6B, wherein the average ratio of CP1 protein to capsular polysaccharide from or derived from *S. pneumoniae* serotype 6B in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(7) a plurality of immunogenic complexes comprising a CP1 protein and a capsular polysaccharide, from or derived from *S. pneumoniae* serotype 7F, wherein the average ratio of CP1 protein to capsular polysaccharide from or derived from *S. pneumoniae* serotype 7F in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(8) a plurality of immunogenic complexes comprising a CP1 protein and a capsular polysaccharide, from or derived from *S. pneumoniae* serotype 9V, wherein the average ratio of CP1 protein to capsular polysaccharide from or derived from *S. pneumoniae* serotype 9V in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(9) a plurality of immunogenic complexes comprising a CP1 protein and a capsular polysaccharide, from or derived from *S. pneumoniae* serotype 14, wherein the average ratio of CP1 protein to capsular polysaccharide from or derived from *S. pneumoniae* serotype 14 in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(10) a plurality of immunogenic complexes comprising a CP1 protein and a capsular polysaccharide, from or derived from *S. pneumoniae* serotype 18C, wherein the average ratio of CP1 protein to capsular polysaccharide from or derived from *S. pneumoniae* serotype 18C in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(11) a plurality of immunogenic complexes comprising a CP1 protein and a capsular polysaccharide, from or derived from *S. pneumoniae* serotype 19A, wherein the average ratio of CP1 protein to capsular polysaccharide from or derived from *S. pneumoniae* serotype 19A in the plurality of immunogenic complexes is approximately 5.5:1, 5.6:1, 5.7:1, 5.8:1, 5.9:1, 6:1, 6.1:1, 6.2:1, 6.3:1, 6.4:1, or 6.5:1 (w/w);

(12) a plurality of immunogenic complexes comprising a CP1 protein and a capsular polysaccharide, from or derived from *S. pneumoniae* serotype 19F, wherein the average ratio of CP1 protein to capsular polysaccharide from or derived from *S. pneumoniae* serotype 19F in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(13) a plurality of immunogenic complexes comprising a CP1 protein and a capsular polysaccharide, from or derived from *S. pneumoniae* serotype 22F, wherein the average ratio of CP1 protein to capsular polysaccharide from or derived from *S. pneumoniae* serotype 22F in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(14) a plurality of immunogenic complexes comprising a CP1 protein and a capsular polysaccharide, from or derived from *S. pneumoniae* serotype 23F, wherein the average ratio of CP1 protein to capsular polysaccharide from or derived from *S. pneumoniae* serotype 23F in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w); and

(15) a plurality of immunogenic complexes comprising a CP1 protein and a capsular polysaccharide, from or derived from *S. pneumoniae* serotype 33F, wherein the average ratio of CP1 protein to capsular polysaccharide from or derived from *S. pneumoniae* serotype 33F in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w).

In some embodiments, a vaccine or immunogenic composition comprises:

(1) a plurality of immunogenic complexes comprising a CP1 protein and a capsular polysaccharide, from or derived from *S. pneumoniae* serotype 2, wherein the average ratio of CP1 protein to capsular polysaccharide from or derived from *S. pneumoniae* serotype 2 in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(2) a plurality of immunogenic complexes comprising a CP1 protein and a capsular polysaccharide, from or derived from *S. pneumoniae* serotype 8, wherein the average ratio of CP1 protein to capsular polysaccharide from or derived from *S. pneumoniae* serotype 8 in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(3) a plurality of immunogenic complexes comprising a CP1 protein and a capsular polysaccharide, from or derived from *S. pneumoniae* serotype 9N, wherein the average ratio of CP1 protein to capsular polysaccharide from or derived from *S. pneumoniae* serotype 9N in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(4) a plurality of immunogenic complexes comprising a CP1 protein and a capsular polysaccharide, from or derived from *S. pneumoniae* serotype 10A, wherein the average ratio of CP1 protein to capsular polysaccharide from or derived from *S. pneumoniae* serotype 10A in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(5) a plurality of immunogenic complexes comprising a CP1 protein and a capsular polysaccharide, from or derived from *S. pneumoniae* serotype 11A, wherein the average ratio of CP1 protein to capsular polysaccharide from or derived from *S. pneumoniae* serotype 11A in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(6) a plurality of immunogenic complexes comprising a CP1 protein and a capsular polysaccharide, from or derived from *S. pneumoniae* serotype 12F, wherein the average ratio of CP1 protein to capsular polysaccharide from or derived from *S. pneumoniae* serotype 12F in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);

(7) a plurality of immunogenic complexes comprising a CP1 protein and a capsular polysaccharide, from or derived from *S. pneumoniae* serotype 15B, wherein the average ratio of CP1 protein to capsular polysaccharide from or derived from *S. pneumoniae* serotype 15B in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w);
(8) a plurality of immunogenic complexes comprising a CP1 protein and a capsular polysaccharide, from or derived from *S. pneumoniae* serotype 17F, wherein the average ratio of CP1 protein to capsular polysaccharide from or derived from *S. pneumoniae* serotype 17F in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w); and
(9) a plurality of immunogenic complexes comprising a CP1 protein and a capsular polysaccharide, from or derived from *S. pneumoniae* serotype 20B, wherein the average ratio of CP1 protein to capsular polysaccharide from or derived from *S. pneumoniae* serotype 20B in the plurality of immunogenic complexes is approximately 2.5:1, 2.6:1, 2.7:1, 2.8:1, 2.9:1, 3:1, 3.1:1, 3.2:1, 3.3:1, 3.4:1, or 3.5:1 (w/w).

In some embodiments, a vaccine or immunogenic composition comprises:
(1) a plurality of immunogenic complexes comprising a CP1 protein and a capsular polysaccharide, from or derived from *S. pneumoniae* serotype 1, wherein the average ratio of CP1 protein to capsular polysaccharide from or derived from *S. pneumoniae* serotype 1 in the plurality of immunogenic complexes is between about 2.9:1 and about 3.1:1 (w/w);
(2) a plurality of immunogenic complexes comprising a CP1 protein and a capsular polysaccharide, from or derived from *S. pneumoniae* serotype 2, wherein the average ratio of CP1 protein to capsular polysaccharide from or derived from *S. pneumoniae* serotype 2 in the plurality of immunogenic complexes is between about 2.9:1 and about 3.1:1 (w/w);
(3) a plurality of immunogenic complexes comprising a CP1 protein and a capsular polysaccharide, from or derived from *S. pneumoniae* serotype 3, wherein the average ratio of CP1 protein to capsular polysaccharide from or derived from *S. pneumoniae* serotype 3 in the plurality of immunogenic complexes is between about 2.9:1 and about 3.1:1 (w/w);
(4) a plurality of immunogenic complexes comprising a CP1 protein and a capsular polysaccharide, from or derived from *S. pneumoniae* serotype 4, wherein the average ratio of CP1 protein to capsular polysaccharide from or derived from *S. pneumoniae* serotype 4 in the plurality of immunogenic complexes is between about 2.9:1 and about 3.1:1 (w/w);
(5) a plurality of immunogenic complexes comprising a CP1 protein and a capsular polysaccharide, from or derived from *S. pneumoniae* serotype 5, wherein the average ratio of CP1 protein to capsular polysaccharide from or derived from *S. pneumoniae* serotype 5 in the plurality of immunogenic complexes is between about 2.9:1 and about 3.1:1 (w/w);
(6) a plurality of immunogenic complexes comprising a CP1 protein and a capsular polysaccharide, from or derived from *S. pneumoniae* serotype 6A, wherein the average ratio of CP1 protein to capsular polysaccharide from or derived from *S. pneumoniae* serotype 6A in the plurality of immunogenic complexes is between about 2.9:1 and about 3.1:1 (w/w);
(7) a plurality of immunogenic complexes comprising a CP1 protein and a capsular polysaccharide, from or derived from *S. pneumoniae* serotype 6B, wherein the average ratio of CP1 protein to capsular polysaccharide from or derived from *S. pneumoniae* serotype 6B in the plurality of immunogenic complexes is between about 2.9:1 and about 3.1:1 (w/w);
(8) a plurality of immunogenic complexes comprising a CP1 protein and a capsular polysaccharide, from or derived from *S. pneumoniae* serotype 7F, wherein the average ratio of CP1 protein to capsular polysaccharide from or derived from *S. pneumoniae* serotype 7F in the plurality of immunogenic complexes is between about 2.9:1 and about 3.1:1 (w/w);
(9) a plurality of immunogenic complexes comprising a CP1 protein and a capsular polysaccharide, from or derived from *S. pneumoniae* serotype 8, wherein the average ratio of CP1 protein to capsular polysaccharide from or derived from *S. pneumoniae* serotype 8 in the plurality of immunogenic complexes is between about 2.9:1 and about 3.1:1 (w/w);
(10) a plurality of immunogenic complexes comprising a CP1 protein and a capsular polysaccharide, from or derived from *S. pneumoniae* serotype 9N, wherein the average ratio of CP1 protein to capsular polysaccharide from or derived from *S. pneumoniae* serotype 9N in the plurality of immunogenic complexes is between about 2.9:1 and about 3.1:1 (w/w);
(11) a plurality of immunogenic complexes comprising a CP1 protein and a capsular polysaccharide, from or derived from *S. pneumoniae* serotype 9V, wherein the average ratio of CP1 protein to capsular polysaccharide from or derived from *S. pneumoniae* serotype 9V in the plurality of immunogenic complexes is between about 2.9:1 and about 3.1:1 (w/w);
(12) a plurality of immunogenic complexes comprising a CP1 protein and a capsular polysaccharide, from or derived from *S. pneumoniae* serotype 10A, wherein the average ratio of CP1 protein to capsular polysaccharide from or derived from *S. pneumoniae* serotype 10A in the plurality of immunogenic complexes is between about 2.9:1 and about 3.1:1 (w/w);
(13) a plurality of immunogenic complexes comprising a CP1 protein and a capsular polysaccharide, from or derived from *S. pneumoniae* serotype 11A, wherein the average ratio of CP1 protein to capsular polysaccharide from or derived from *S. pneumoniae* serotype 11A in the plurality of immunogenic complexes is between about 2.9:1 and about 3.1:1 (w/w);
(14) a plurality of immunogenic complexes comprising a CP1 protein and a capsular polysaccharide, from or derived from *S. pneumoniae* serotype 12F, wherein the average ratio of CP1 protein to capsular polysaccharide from or derived from *S. pneumoniae* serotype 12F in the plurality of immunogenic complexes is between about 2.9:1 and about 3.1:1 (w/w);
(15) a plurality of immunogenic complexes comprising a CP1 protein and a capsular polysaccharide, from or derived from *S. pneumoniae* serotype 14, wherein the average ratio of CP1 protein to capsular polysaccharide from or derived from *S. pneumoniae* serotype 14 in the plurality of immunogenic complexes is between about 2.9:1 and about 3.1:1 (w/w);
(16) a plurality of immunogenic complexes comprising a CP1 protein and a capsular polysaccharide, from or derived from *S. pneumoniae* serotype 15B, wherein the average ratio of CP1 protein to capsular polysaccharide from or derived from *S. pneumoniae* serotype 15B in the plurality of immunogenic complexes is between about 2.9:1 and about 3.1:1 (w/w);
(17) a plurality of immunogenic complexes comprising a CP1 protein and a capsular polysaccharide, from or derived from *S. pneumoniae* serotype 17F, wherein the average ratio of CP1 protein to capsular polysaccharide from or derived from *S. pneumoniae* serotype 17F in the plurality of immunogenic complexes is between about 2.9:1 and about 3.1:1 (w/w);

(18) a plurality of immunogenic complexes comprising a CP1 protein and a capsular polysaccharide, from or derived from *S. pneumoniae* serotype 18C, wherein the average ratio of CP1 protein to capsular polysaccharide from or derived from *S. pneumoniae* serotype 18C in the plurality of immunogenic complexes is between about 2.9:1 and about 3.1:1 (w/w);

(19) a plurality of immunogenic complexes comprising a CP1 protein and a capsular polysaccharide, from or derived from *S. pneumoniae* serotype 19A, wherein the average ratio of CP1 protein to capsular polysaccharide from or derived from *S. pneumoniae* serotype 19A in the plurality of immunogenic complexes is between about 5.9:1 and about 6.1:1 (w/w);

(20) a plurality of immunogenic complexes comprising a CP1 protein and a capsular polysaccharide, from or derived from *S. pneumoniae* serotype 19F, wherein the average ratio of CP1 protein to capsular polysaccharide from or derived from *S. pneumoniae* serotype 19F in the plurality of immunogenic complexes is between about 2.9:1 and about 3.1:1 (w/w);

(21) a plurality of immunogenic complexes comprising a CP1 protein and a capsular polysaccharide, from or derived from *S. pneumoniae* serotype 20B, wherein the average ratio of CP1 protein to capsular polysaccharide from or derived from *S. pneumoniae* serotype 20B in the plurality of immunogenic complexes is between about 2.9:1 and about 3.1:1 (w/w);

(22) a plurality of immunogenic complexes comprising a CP1 protein and a capsular polysaccharide, from or derived from *S. pneumoniae* serotype 22F, wherein the average ratio of CP1 protein to capsular polysaccharide from or derived from *S. pneumoniae* serotype 22F in the plurality of immunogenic complexes is between about 2.9:1 and about 3.1:1 (w/w);

(23) a plurality of immunogenic complexes comprising a CP1 protein and a capsular polysaccharide, from or derived from *S. pneumoniae* serotype 23F, wherein the average ratio of CP1 protein to capsular polysaccharide from or derived from *S. pneumoniae* serotype 23F in the plurality of immunogenic complexes is between about 2.9:1 and about 3.1:1 (w/w); and

(24) a plurality of immunogenic complexes comprising a CP1 protein and a capsular polysaccharide, from or derived from *S. pneumoniae* serotype 33F, wherein the average ratio of CP1 protein to capsular polysaccharide from or derived from *S. pneumoniae* serotype 33F in the plurality of immunogenic complexes is between about 2.9:1 and about 3.1:1 (w/w).

In some embodiments, a vaccine or immunogenic composition comprises:

(1) a plurality of immunogenic complexes comprising a CP1 protein and a capsular polysaccharide, from or derived from *S. pneumoniae* serotype 1, wherein the average ratio of CP1 protein to capsular polysaccharide from or derived from *S. pneumoniae* serotype 1 in the plurality of immunogenic complexes is between about 2.9:1 and about 3.1:1 (w/w);

(2) a plurality of immunogenic complexes comprising a CP1 protein and a capsular polysaccharide, from or derived from *S. pneumoniae* serotype 3, wherein the average ratio of CP1 protein to capsular polysaccharide from or derived from *S. pneumoniae* serotype 3 in the plurality of immunogenic complexes is between about 2.9:1 and about 3.1:1 (w/w);

(3) a plurality of immunogenic complexes comprising a CP1 protein and a capsular polysaccharide, from or derived from *S. pneumoniae* serotype 4, wherein the average ratio of CP1 protein to capsular polysaccharide from or derived from *S. pneumoniae* serotype 4 in the plurality of immunogenic complexes is between about 2.9:1 and about 3.1:1 (w/w);

(4) a plurality of immunogenic complexes comprising a CP1 protein and a capsular polysaccharide, from or derived from *S. pneumoniae* serotype 5, wherein the average ratio of CP1 protein to capsular polysaccharide from or derived from *S. pneumoniae* serotype 5 in the plurality of immunogenic complexes is between about 2.9:1 and about 3.1:1 (w/w);

(5) a plurality of immunogenic complexes comprising a CP1 protein and a capsular polysaccharide, from or derived from *S. pneumoniae* serotype 6A, wherein the average ratio of CP1 protein to capsular polysaccharide from or derived from *S. pneumoniae* serotype 6A in the plurality of immunogenic complexes is between about 2.9:1 and about 3.1:1 (w/w);

(6) a plurality of immunogenic complexes comprising a CP1 protein and a capsular polysaccharide, from or derived from *S. pneumoniae* serotype 6B, wherein the average ratio of CP1 protein to capsular polysaccharide from or derived from *S. pneumoniae* serotype 6B in the plurality of immunogenic complexes is between about 2.9:1 and about 3.1:1 (w/w);

(7) a plurality of immunogenic complexes comprising a CP1 protein and a capsular polysaccharide, from or derived from *S. pneumoniae* serotype 7F, wherein the average ratio of CP1 protein to capsular polysaccharide from or derived from *S. pneumoniae* serotype 7F in the plurality of immunogenic complexes is between about 2.9:1 and about 3.1:1 (w/w);

(8) a plurality of immunogenic complexes comprising a CP1 protein and a capsular polysaccharide, from or derived from *S. pneumoniae* serotype 9V, wherein the average ratio of CP1 protein to capsular polysaccharide from or derived from *S. pneumoniae* serotype 9V in the plurality of immunogenic complexes is between about 2.9:1 and about 3.1:1 (w/w);

(9) a plurality of immunogenic complexes comprising a CP1 protein and a capsular polysaccharide, from or derived from *S. pneumoniae* serotype 14, wherein the average ratio of CP1 protein to capsular polysaccharide from or derived from *S. pneumoniae* serotype 14 in the plurality of immunogenic complexes is between about 2.9:1 and about 3.1:1 (w/w);

(10) a plurality of immunogenic complexes comprising a CP1 protein and a capsular polysaccharide, from or derived from *S. pneumoniae* serotype 18C, wherein the average ratio of CP1 protein to capsular polysaccharide from or derived from *S. pneumoniae* serotype 18C in the plurality of immunogenic complexes is between about 2.9:1 and about 3.1:1 (w/w);

(11) a plurality of immunogenic complexes comprising a CP1 protein and a capsular polysaccharide, from or derived from *S. pneumoniae* serotype 19A, wherein the average ratio of CP1 protein to capsular polysaccharide from or derived from *S. pneumoniae* serotype 19A in the plurality of immunogenic complexes is between about 5.9:1 and about 6.1:1 (w/w);

(12) a plurality of immunogenic complexes comprising a CP1 protein and a capsular polysaccharide, from or derived from *S. pneumoniae* serotype 19F, wherein the average ratio of CP1 protein to capsular polysaccharide from or derived from *S. pneumoniae* serotype 19F in the plurality of immunogenic complexes is between about 2.9:1 and about 3.1:1 (w/w);

(13) a plurality of immunogenic complexes comprising a CP1 protein and a capsular polysaccharide, from or derived from *S. pneumoniae* serotype 22F, wherein the average ratio of CP1 protein to capsular polysaccharide from or derived from *S. pneumoniae* serotype 22F in the plurality of immunogenic complexes is between about 2.9:1 and about 3.1:1 (w/w);

(14) a plurality of immunogenic complexes comprising a CP1 protein and a capsular polysaccharide, from or derived from *S. pneumoniae* serotype 23F, wherein the average ratio of CP1 protein to capsular polysaccharide from or derived from *S. pneumoniae* serotype 23F in the plurality of immunogenic complexes is between about 2.9:1 and about 3.1:1 (w/w); and

(15) a plurality of immunogenic complexes comprising a CP1 protein and a capsular polysaccharide, from or derived from *S. pneumoniae* serotype 33F, wherein the average ratio of CP1 protein to capsular polysaccharide from or derived from *S. pneumoniae* serotype 33F in the plurality of immunogenic complexes is between about 2.9:1 and about 3.1:1 (w/w).

In some embodiments, a vaccine or immunogenic composition comprises:

(1) a plurality of immunogenic complexes comprising a CP1 protein and a capsular polysaccharide, from or derived from *S. pneumoniae* serotype 2, wherein the average ratio of CP1 protein to capsular polysaccharide from or derived from *S. pneumoniae* serotype 2 in the plurality of immunogenic complexes is between about 2.9:1 and about 3.1:1 (w/w);

(2) a plurality of immunogenic complexes comprising a CP1 protein and a capsular polysaccharide, from or derived from *S. pneumoniae* serotype 8, wherein the average ratio of CP1 protein to capsular polysaccharide from or derived from *S. pneumoniae* serotype 8 in the plurality of immunogenic complexes is between about 2.9:1 and about 3.1:1 (w/w);

(3) a plurality of immunogenic complexes comprising a CP1 protein and a capsular polysaccharide, from or derived from *S. pneumoniae* serotype 9N, wherein the average ratio of CP1 protein to capsular polysaccharide from or derived from *S. pneumoniae* serotype 9N in the plurality of immunogenic complexes is between about 2.9:1 and about 3.1:1 (w/w);

(4) a plurality of immunogenic complexes comprising a CP1 protein and a capsular polysaccharide, from or derived from *S. pneumoniae* serotype 10A, wherein the average ratio of CP1 protein to capsular polysaccharide from or derived from *S. pneumoniae* serotype 10A in the plurality of immunogenic complexes is between about 2.9:1 and about 3.1:1 (w/w);

(5) a plurality of immunogenic complexes comprising a CP1 protein and a capsular polysaccharide, from or derived from *S. pneumoniae* serotype 11A, wherein the average ratio of CP1 protein to capsular polysaccharide from or derived from *S. pneumoniae* serotype 11A in the plurality of immunogenic complexes is between about 2.9:1 and about 3.1:1 (w/w);

(6) a plurality of immunogenic complexes comprising a CP1 protein and a capsular polysaccharide, from or derived from *S. pneumoniae* serotype 12F, wherein the average ratio of CP1 protein to capsular polysaccharide from or derived from *S. pneumoniae* serotype 12F in the plurality of immunogenic complexes is between about 2.9:1 and about 3.1:1 (w/w);

(7) a plurality of immunogenic complexes comprising a CP1 protein and a capsular polysaccharide, from or derived from *S. pneumoniae* serotype 15B, wherein the average ratio of CP1 protein to capsular polysaccharide from or derived from *S. pneumoniae* serotype 15B in the plurality of immunogenic complexes is between about 2.9:1 and about 3.1:1 (w/w);

(8) a plurality of immunogenic complexes comprising a CP1 protein and a capsular polysaccharide, from or derived from *S. pneumoniae* serotype 17F, wherein the average ratio of CP1 protein to capsular polysaccharide from or derived from *S. pneumoniae* serotype 17F in the plurality of immunogenic complexes is between about 2.9:1 and about 3.1:1 (w/w); and (9) a plurality of immunogenic complexes comprising a CP1 protein and a capsular polysaccharide, from or derived from *S. pneumoniae* serotype 20B, wherein the average ratio of CP1 protein to capsular polysaccharide from or derived from *S. pneumoniae* serotype 20B in the plurality of immunogenic complexes is between about 2.9:1 and about 3.1:1 (w/w).

In some embodiments, a vaccine or immunogenic composition comprises:

(1) a plurality of immunogenic complexes comprising a CP1 protein and a capsular polysaccharide, from or derived from *S. pneumoniae* serotype 1, wherein the average ratio of CP1 protein to capsular polysaccharide from or derived from *S. pneumoniae* serotype 1 in the plurality of immunogenic complexes is about 3:1;

(2) a plurality of immunogenic complexes comprising a CP1 protein and a capsular polysaccharide, from or derived from *S. pneumoniae* serotype 2, wherein the average ratio of CP1 protein to capsular polysaccharide from or derived from *S. pneumoniae* serotype 2 in the plurality of immunogenic complexes is about 3:1;

(3) a plurality of immunogenic complexes comprising a CP1 protein and a capsular polysaccharide, from or derived from *S. pneumoniae* serotype 3, wherein the average ratio of CP1 protein to capsular polysaccharide from or derived from *S. pneumoniae* serotype 3 in the plurality of immunogenic complexes is about 3:1;

(4) a plurality of immunogenic complexes comprising a CP1 protein and a capsular polysaccharide, from or derived from *S. pneumoniae* serotype 4, wherein the average ratio of CP1 protein to capsular polysaccharide from or derived from *S. pneumoniae* serotype 4 in the plurality of immunogenic complexes is about 3:1;

(5) a plurality of immunogenic complexes comprising a CP1 protein and a capsular polysaccharide, from or derived from *S. pneumoniae* serotype 5, wherein the average ratio of CP1 protein to capsular polysaccharide from or derived from *S. pneumoniae* serotype 5 in the plurality of immunogenic complexes is about 3:1;

(6) a plurality of immunogenic complexes comprising a CP1 protein and a capsular polysaccharide, from or derived from *S. pneumoniae* serotype 6A, wherein the average ratio of CP1 protein to capsular polysaccharide from or derived from *S. pneumoniae* serotype 6A in the plurality of immunogenic complexes is about 3:1;

(7) a plurality of immunogenic complexes comprising a CP1 protein and a capsular polysaccharide, from or derived from *S. pneumoniae* serotype 6B, wherein the average ratio of CP1 protein to capsular polysaccharide from or derived from *S. pneumoniae* serotype 6B in the plurality of immunogenic complexes is about 3:1;
(8) a plurality of immunogenic complexes comprising a CP1 protein and a capsular polysaccharide, from or derived from *S. pneumoniae* serotype 7F, wherein the average ratio of CP1 protein to capsular polysaccharide from or derived from *S. pneumoniae* serotype 7F in the plurality of immunogenic complexes is about 3:1;
(9) a plurality of immunogenic complexes comprising a CP1 protein and a capsular polysaccharide, from or derived from *S. pneumoniae* serotype 8, wherein the average ratio of CP1 protein to capsular polysaccharide from or derived from *S. pneumoniae* serotype 8 in the plurality of immunogenic complexes is about 3:1;
(10) a plurality of immunogenic complexes comprising a CP1 protein and a capsular polysaccharide, from or derived from *S. pneumoniae* serotype 9N, wherein the average ratio of CP1 protein to capsular polysaccharide from or derived from *S. pneumoniae* serotype 9N in the plurality of immunogenic complexes is about 3:1;
(11) a plurality of immunogenic complexes comprising a CP1 protein and a capsular polysaccharide, from or derived from *S. pneumoniae* serotype 9V, wherein the average ratio of CP1 protein to capsular polysaccharide from or derived from *S. pneumoniae* serotype 9V in the plurality of immunogenic complexes is about 3:1;
(12) a plurality of immunogenic complexes comprising a CP1 protein and a capsular polysaccharide, from or derived from *S. pneumoniae* serotype 10A, wherein the average ratio of CP1 protein to capsular polysaccharide from or derived from *S. pneumoniae* serotype 10A in the plurality of immunogenic complexes is about 3:1;
(13) a plurality of immunogenic complexes comprising a CP1 protein and a capsular polysaccharide, from or derived from *S. pneumoniae* serotype 11A, wherein the average ratio of CP1 protein to capsular polysaccharide from or derived from *S. pneumoniae* serotype 11A in the plurality of immunogenic complexes is about 3:1;
(14) a plurality of immunogenic complexes comprising a CP1 protein and a capsular polysaccharide, from or derived from *S. pneumoniae* serotype 12F, wherein the average ratio of CP1 protein to capsular polysaccharide from or derived from *S. pneumoniae* serotype 12F in the plurality of immunogenic complexes is about 3:1;
(15) a plurality of immunogenic complexes comprising a CP1 protein and a capsular polysaccharide, from or derived from *S. pneumoniae* serotype 14, wherein the average ratio of CP1 protein to capsular polysaccharide from or derived from *S. pneumoniae* serotype 14 in the plurality of immunogenic complexes is about 3:1;
(16) a plurality of immunogenic complexes comprising a CP1 protein and a capsular polysaccharide, from or derived from *S. pneumoniae* serotype 15B, wherein the average ratio of CP1 protein to capsular polysaccharide from or derived from *S. pneumoniae* serotype 15B in the plurality of immunogenic complexes is about 3:1;
(17) a plurality of immunogenic complexes comprising a CP1 protein and a capsular polysaccharide, from or derived from *S. pneumoniae* serotype 17F, wherein the average ratio of CP1 protein to capsular polysaccharide from or derived from *S. pneumoniae* serotype 17F in the plurality of immunogenic complexes is about 3:1;
(18) a plurality of immunogenic complexes comprising a CP1 protein and a capsular polysaccharide, from or derived from *S. pneumoniae* serotype 18C, wherein the average ratio of CP1 protein to capsular polysaccharide from or derived from *S. pneumoniae* serotype 18C in the plurality of immunogenic complexes is about 3:1;
(19) a plurality of immunogenic complexes comprising a CP1 protein and a capsular polysaccharide, from or derived from *S. pneumoniae* serotype 19A, wherein the average ratio of CP1 protein to capsular polysaccharide from or derived from *S. pneumoniae* serotype 19A in the plurality of immunogenic complexes is about 6:1 (w/w);
(20) a plurality of immunogenic complexes comprising a CP1 protein and a capsular polysaccharide, from or derived from *S. pneumoniae* serotype 19F, wherein the average ratio of CP1 protein to capsular polysaccharide from or derived from *S. pneumoniae* serotype 19F in the plurality of immunogenic complexes is about 3:1;
(21) a plurality of immunogenic complexes comprising a CP1 protein and a capsular polysaccharide, from or derived from *S. pneumoniae* serotype 20B, wherein the average ratio of CP1 protein to capsular polysaccharide from or derived from *S. pneumoniae* serotype 20B in the plurality of immunogenic complexes is about 3:1;
(22) a plurality of immunogenic complexes comprising a CP1 protein and a capsular polysaccharide, from or derived from *S. pneumoniae* serotype 22F, wherein the average ratio of CP1 protein to capsular polysaccharide from or derived from *S. pneumoniae* serotype 22F in the plurality of immunogenic complexes is about 3:1;
(23) a plurality of immunogenic complexes comprising a CP1 protein and a capsular polysaccharide, from or derived from *S. pneumoniae* serotype 23F, wherein the average ratio of CP1 protein to capsular polysaccharide from or derived from *S. pneumoniae* serotype 23F in the plurality of immunogenic complexes is about 3:1; and
(24) a plurality of immunogenic complexes comprising a CP1 protein and a capsular polysaccharide, from or derived from *S. pneumoniae* serotype 33F, wherein the average ratio of CP1 protein to capsular polysaccharide from or derived from *S. pneumoniae* serotype 33F in the plurality of immunogenic complexes is about 3:1.

In some embodiments, a vaccine or immunogenic composition comprises:
(1) a plurality of immunogenic complexes comprising a CP1 protein and a capsular polysaccharide, from or derived from *S. pneumoniae* serotype 1, wherein the average ratio of CP1 protein to capsular polysaccharide from or derived from *S. pneumoniae* serotype 1 in the plurality of immunogenic complexes is about 3:1;
(2) a plurality of immunogenic complexes comprising a CP1 protein and a capsular polysaccharide, from or derived from *S. pneumoniae* serotype 3, wherein the average ratio of CP1 protein to capsular polysaccharide from or derived from *S. pneumoniae* serotype 3 in the plurality of immunogenic complexes is about 3:1;
(3) a plurality of immunogenic complexes comprising a CP1 protein and a capsular polysaccharide, from or derived from *S. pneumoniae* serotype 4, wherein the average ratio of CP1 protein to capsular polysaccharide from or derived from *S. pneumoniae* serotype 4 in the plurality of immunogenic complexes is about 3:1;
(4) a plurality of immunogenic complexes comprising a CP1 protein and a capsular polysaccharide, from or derived from *S. pneumoniae* serotype 5, wherein the average ratio of CP1 protein to capsular polysaccharide from or derived from *S. pneumoniae* serotype 5 in the plurality of immunogenic complexes is about 3:1;

(5) a plurality of immunogenic complexes comprising a CP1 protein and a capsular polysaccharide, from or derived from S. pneumoniae serotype 6A, wherein the average ratio of CP1 protein to capsular polysaccharide from or derived from S. pneumoniae serotype 6A in the plurality of immunogenic complexes is about 3:1;

(6) a plurality of immunogenic complexes comprising a CP1 protein and a capsular polysaccharide, from or derived from S. pneumoniae serotype 6B, wherein the average ratio of CP1 protein to capsular polysaccharide from or derived from S. pneumoniae serotype 6B in the plurality of immunogenic complexes is about 3:1;

(7) a plurality of immunogenic complexes comprising a CP1 protein and a capsular polysaccharide, from or derived from S. pneumoniae serotype 7F, wherein the average ratio of CP1 protein to capsular polysaccharide from or derived from S. pneumoniae serotype 7F in the plurality of immunogenic complexes is about 3:1;

(8) a plurality of immunogenic complexes comprising a CP1 protein and a capsular polysaccharide, from or derived from S. pneumoniae serotype 9V, wherein the average ratio of CP1 protein to capsular polysaccharide from or derived from S. pneumoniae serotype 9V in the plurality of immunogenic complexes is about 3:1;

(9) a plurality of immunogenic complexes comprising a CP1 protein and a capsular polysaccharide, from or derived from S. pneumoniae serotype 14, wherein the average ratio of CP1 protein to capsular polysaccharide from or derived from S. pneumoniae serotype 14 in the plurality of immunogenic complexes is about 3:1;

(10) a plurality of immunogenic complexes comprising a CP1 protein and a capsular polysaccharide, from or derived from S. pneumoniae serotype 18C, wherein the average ratio of CP1 protein to capsular polysaccharide from or derived from S. pneumoniae serotype 18C in the plurality of immunogenic complexes is about 3:1;

(11) a plurality of immunogenic complexes comprising a CP1 protein and a capsular polysaccharide, from or derived from S. pneumoniae serotype 19A, wherein the average ratio of CP1 protein to capsular polysaccharide from or derived from S. pneumoniae serotype 19A in the plurality of immunogenic complexes is about 6:1 (w/w);

(12) a plurality of immunogenic complexes comprising a CP1 protein and a capsular polysaccharide, from or derived from S. pneumoniae serotype 19F, wherein the average ratio of CP1 protein to capsular polysaccharide from or derived from S. pneumoniae serotype 19F in the plurality of immunogenic complexes is about 3:1;

(13) a plurality of immunogenic complexes comprising a CP1 protein and a capsular polysaccharide, from or derived from S. pneumoniae serotype 22F, wherein the average ratio of CP1 protein to capsular polysaccharide from or derived from S. pneumoniae serotype 22F in the plurality of immunogenic complexes is about 3:1;

(14) a plurality of immunogenic complexes comprising a CP1 protein and a capsular polysaccharide, from or derived from S. pneumoniae serotype 23F, wherein the average ratio of CP1 protein to capsular polysaccharide from or derived from S. pneumoniae serotype 23F in the plurality of immunogenic complexes is about 3:1; and

(15) a plurality of immunogenic complexes comprising a CP1 protein and a capsular polysaccharide, from or derived from S. pneumoniae serotype 33F, wherein the average ratio of CP1 protein to capsular polysaccharide from or derived from S. pneumoniae serotype 33F in the plurality of immunogenic complexes is about 3:1.

In some embodiments, a vaccine or immunogenic composition comprises:

(1) a plurality of immunogenic complexes comprising a CP1 protein and a capsular polysaccharide, from or derived from S. pneumoniae serotype 2, wherein the average ratio of CP1 protein to capsular polysaccharide from or derived from S. pneumoniae serotype 2 in the plurality of immunogenic complexes is about 3:1;

(2) a plurality of immunogenic complexes comprising a CP1 protein and a capsular polysaccharide, from or derived from S. pneumoniae serotype 8, wherein the average ratio of CP1 protein to capsular polysaccharide from or derived from S. pneumoniae serotype 8 in the plurality of immunogenic complexes is about 3:1;

(3) a plurality of immunogenic complexes comprising a CP1 protein and a capsular polysaccharide, from or derived from S. pneumoniae serotype 9N, wherein the average ratio of CP1 protein to capsular polysaccharide from or derived from S. pneumoniae serotype 9N in the plurality of immunogenic complexes is about 3:1;

(4) a plurality of immunogenic complexes comprising a CP1 protein and a capsular polysaccharide, from or derived from S. pneumoniae serotype 10A, wherein the average ratio of CP1 protein to capsular polysaccharide from or derived from S. pneumoniae serotype 10A in the plurality of immunogenic complexes is about 3:1;

(5) a plurality of immunogenic complexes comprising a CP1 protein and a capsular polysaccharide, from or derived from S. pneumoniae serotype 11A, wherein the average ratio of CP1 protein to capsular polysaccharide from or derived from S. pneumoniae serotype 11A in the plurality of immunogenic complexes is about 3:1;

(6) a plurality of immunogenic complexes comprising a CP1 protein and a capsular polysaccharide, from or derived from S. pneumoniae serotype 12F, wherein the average ratio of CP1 protein to capsular polysaccharide from or derived from S. pneumoniae serotype 12F in the plurality of immunogenic complexes is about 3:1;

(7) a plurality of immunogenic complexes comprising a CP1 protein and a capsular polysaccharide, from or derived from S. pneumoniae serotype 15B, wherein the average ratio of CP1 protein to capsular polysaccharide from or derived from S. pneumoniae serotype 15B in the plurality of immunogenic complexes is about 3:1;

(8) a plurality of immunogenic complexes comprising a CP1 protein and a capsular polysaccharide, from or derived from S. pneumoniae serotype 17F, wherein the average ratio of CP1 protein to capsular polysaccharide from or derived from S. pneumoniae serotype 17F in the plurality of immunogenic complexes is about 3:1; and (9) a plurality of immunogenic complexes comprising a CP1 protein and a capsular polysaccharide, from or derived from S. pneumoniae serotype 20B, wherein the average ratio of CP1 protein to capsular polysaccharide from or derived from S. pneumoniae serotype 20B in the plurality of immunogenic complexes is about 3:1.

Immunogenic and Vaccine Compositions

Another aspect of the disclosure provides compositions that include one or more immunogenic complexes described herein. For example, an immunogenic composition, e.g., vaccine composition, can include one or more immunogenic complexes described herein. In some embodiments, such compositions can include a plurality of one type of immunogenic complex described herein. For example, a composition can include a population of one type of immunogenic complex, where all of the immunogenic complexes include the same antigenic polypeptide and the same antigenic polysaccharide. Additionally or alternatively, such compositions can include a plurality of more than one type of immunogenic complex described herein. For example, a composition can include populations of different types of immunogenic complexes. In some embodiments, a composition can include a population of a first type of immunogenic complex and a population of a second type of immunogenic complex, where the first type and the second type of the immunogenic complex have different antigenic polypeptides and/or different antigenic polysaccharides. In some embodiments, a composition can include a population of a first type of immunogenic complex and a population of a second type of immunogenic complex, where the first type and the second type of the immunogenic complex include the same antigenic polypeptide and different antigenic polysaccharides (e.g., polysaccharides of different serotypes). In some embodiments, immunogenic complexes described herein are formulated into a pharmaceutical composition. In some embodiments a pharmaceutical composition may be a vaccine. In some embodiments a pharmaceutical composition comprises a pharmaceutically acceptable carrier. In some embodiments a pharmaceutical composition comprises an adjuvant.

In some embodiments, an immunogenic composition comprises one or more (e.g., 1, 2, 3, 4, 5, 6, 7, 8, 9, 10, 15, 20, 25, 30, 40, 50, or more) species of immunogenic complexes selected from:

(1) an immunogenic complex comprising a biotinylated *S. pneumoniae* serotype 1 capsular polysaccharide, and one or more CP1 fusion proteins non-covalently complexed to the biotinylated polysaccharide;

(2) an immunogenic complex comprising a biotinylated *S. pneumoniae* serotype 2 capsular polysaccharide, and one or more CP1 fusion proteins non-covalently complexed to the biotinylated polysaccharide;

(3) an immunogenic complex comprising a biotinylated *S. pneumoniae* serotype 3 capsular polysaccharide, and one or more CP1 fusion proteins non-covalently complexed to the biotinylated polysaccharide;

(4) an immunogenic complex comprising a biotinylated *S. pneumoniae* serotype 4 capsular polysaccharide, and one or more CP1 fusion proteins non-covalently complexed to the biotinylated polysaccharide;

(5) an immunogenic complex comprising a biotinylated *S. pneumoniae* serotype 5 capsular polysaccharide, and one or more CP1 fusion proteins non-covalently complexed to the biotinylated polysaccharide;

(6) an immunogenic complex comprising a biotinylated *S. pneumoniae* serotype 6A capsular polysaccharide, and one or more CP1 fusion proteins non-covalently complexed to the biotinylated polysaccharide;

(7) an immunogenic complex comprising a biotinylated *S. pneumoniae* serotype 6B capsular polysaccharide, and one or more CP1 fusion proteins non-covalently complexed to the biotinylated polysaccharide;

(8) an immunogenic complex comprising a biotinylated *S. pneumoniae* serotype 6C capsular polysaccharide, and one or more CP1 fusion proteins non-covalently complexed to the biotinylated polysaccharide;

(9) an immunogenic complex comprising a biotinylated *S. pneumoniae* serotype 6D capsular polysaccharide, and one or more CP1 fusion proteins non-covalently complexed to the biotinylated polysaccharide;

(10) an immunogenic complex comprising a biotinylated *S. pneumoniae* serotype 6E capsular polysaccharide, and one or more CP1 fusion proteins non-covalently complexed to the biotinylated polysaccharide;

(11) an immunogenic complex comprising a biotinylated *S. pneumoniae* serotype 6F capsular polysaccharide, and one or more CP1 fusion proteins non-covalently complexed to the biotinylated polysaccharide;

(12) an immunogenic complex comprising a biotinylated *S. pneumoniae* serotype 6G capsular polysaccharide, and one or more CP1 fusion proteins non-covalently complexed to the biotinylated polysaccharide;

(13) an immunogenic complex comprising a biotinylated *S. pneumoniae* serotype 6H capsular polysaccharide, and one or more CP1 fusion proteins non-covalently complexed to the biotinylated polysaccharide;

(14) an immunogenic complex comprising a biotinylated *S. pneumoniae* serotype 7A capsular polysaccharide, and one or more CP1 fusion proteins non-covalently complexed to the biotinylated polysaccharide;

(15) an immunogenic complex comprising a biotinylated *S. pneumoniae* serotype 7B capsular polysaccharide, and one or more CP1 fusion proteins non-covalently complexed to the biotinylated polysaccharide;

(16) an immunogenic complex comprising a biotinylated *S. pneumoniae* serotype 7C capsular polysaccharide, and one or more CP1 fusion proteins non-covalently complexed to the biotinylated polysaccharide;

(17) an immunogenic complex comprising a biotinylated *S. pneumoniae* serotype 7F capsular polysaccharide, and one or more CP1 fusion proteins non-covalently complexed to the biotinylated polysaccharide;

(18) an immunogenic complex comprising a biotinylated *S. pneumoniae* serotype 8 capsular polysaccharide, and one or more CP1 fusion proteins non-covalently complexed to the biotinylated polysaccharide;

(19) an immunogenic complex comprising a biotinylated *S. pneumoniae* serotype 9A capsular polysaccharide, and one or more CP1 fusion proteins non-covalently complexed to the biotinylated polysaccharide;

(20) an immunogenic complex comprising a biotinylated *S. pneumoniae* serotype 9L capsular polysaccharide, and one or more CP1 fusion proteins non-covalently complexed to the biotinylated polysaccharide;

(21) an immunogenic complex comprising a biotinylated *S. pneumoniae* serotype 9N capsular polysaccharide, and one or more CP1 fusion proteins non-covalently complexed to the biotinylated polysaccharide;

(22) an immunogenic complex comprising a biotinylated *S. pneumoniae* serotype 9V capsular polysaccharide, and one or more CP1 fusion proteins non-covalently complexed to the biotinylated polysaccharide;

(23) an immunogenic complex comprising a biotinylated *S. pneumoniae* serotype 10A capsular polysaccharide, and one or more CP1 fusion proteins non-covalently complexed to the biotinylated polysaccharide;

(24) an immunogenic complex comprising a biotinylated *S. pneumoniae* serotype 10B capsular polysaccharide, and one or more CP1 fusion proteins non-covalently complexed to the biotinylated polysaccharide;

(25) an immunogenic complex comprising a biotinylated *S. pneumoniae* serotype 10C capsular polysaccharide, and one or more CP1 fusion proteins non-covalently complexed to the biotinylated polysaccharide;

(26) an immunogenic complex comprising a biotinylated *S. pneumoniae* serotype 10F capsular polysaccharide, and one or more CP1 fusion proteins non-covalently complexed to the biotinylated polysaccharide;
(27) an immunogenic complex comprising a biotinylated *S. pneumoniae* serotype 11A capsular polysaccharide, and one or more CP1 fusion proteins non-covalently complexed to the biotinylated polysaccharide;
(28) an immunogenic complex comprising a biotinylated *S. pneumoniae* serotype 11B capsular polysaccharide, and one or more CP1 fusion proteins non-covalently complexed to the biotinylated polysaccharide;
(29) an immunogenic complex comprising a biotinylated *S. pneumoniae* serotype 11C capsular polysaccharide, and one or more CP1 fusion proteins non-covalently complexed to the biotinylated polysaccharide;
(30) an immunogenic complex comprising a biotinylated *S. pneumoniae* serotype 11D capsular polysaccharide, and one or more CP1 fusion proteins non-covalently complexed to the biotinylated polysaccharide;

(31) an immunogenic complex comprising a biotinylated *S. pneumoniae* serotype 11E capsular polysaccharide, and one or more CP1 fusion proteins non-covalently complexed to the biotinylated polysaccharide;

(32) an immunogenic complex comprising a biotinylated *S. pneumoniae* serotype 11F capsular polysaccharide, and one or more CP1 fusion proteins non-covalently complexed to the biotinylated polysaccharide;

(33) an immunogenic complex comprising a biotinylated *S. pneumoniae* serotype 12A capsular polysaccharide, and one or more CP1 fusion proteins non-covalently complexed to the biotinylated polysaccharide;

(34) an immunogenic complex comprising a biotinylated *S. pneumoniae* serotype 12B capsular polysaccharide, and one or more CP1 fusion proteins non-covalently complexed to the biotinylated polysaccharide;

(35) an immunogenic complex comprising a biotinylated *S. pneumoniae* serotype 12F capsular polysaccharide, and one or more CP1 fusion proteins non-covalently complexed to the biotinylated polysaccharide;

(36) an immunogenic complex comprising a biotinylated *S. pneumoniae* serotype 13 capsular polysaccharide, and one or more CP1 fusion proteins non-covalently complexed to the biotinylated polysaccharide;

(37) an immunogenic complex comprising a biotinylated *S. pneumoniae* serotype 14 capsular polysaccharide, and one or more CP1 fusion proteins non-covalently complexed to the biotinylated polysaccharide;

(38) an immunogenic complex comprising a biotinylated *S. pneumoniae* serotype 15A capsular polysaccharide, and one or more CP1 fusion proteins non-covalently complexed to the biotinylated polysaccharide;

(39) an immunogenic complex comprising a biotinylated *S. pneumoniae* serotype 15B capsular polysaccharide, and one or more CP1 fusion proteins non-covalently complexed to the biotinylated polysaccharide;

(40) an immunogenic complex comprising a biotinylated *S. pneumoniae* serotype 15C capsular polysaccharide, and one or more CP1 fusion proteins non-covalently complexed to the biotinylated polysaccharide;

(41) an immunogenic complex comprising a biotinylated *S. pneumoniae* serotype 15F capsular polysaccharide, and one or more CP1 fusion proteins non-covalently complexed to the biotinylated polysaccharide;

(42) an immunogenic complex comprising a biotinylated *S. pneumoniae* serotype 16A capsular polysaccharide, and one or more CP1 fusion proteins non-covalently complexed to the biotinylated polysaccharide;

(43) an immunogenic complex comprising a biotinylated *S. pneumoniae* serotype 16F capsular polysaccharide, and one or more CP1 fusion proteins non-covalently complexed to the biotinylated polysaccharide;

(44) an immunogenic complex comprising a biotinylated *S. pneumoniae* serotype 17A capsular polysaccharide, and one or more CP1 fusion proteins non-covalently complexed to the biotinylated polysaccharide;

(45) an immunogenic complex comprising a biotinylated *S. pneumoniae* serotype 17F capsular polysaccharide, and one or more CP1 fusion proteins non-covalently complexed to the biotinylated polysaccharide;

(46) an immunogenic complex comprising a biotinylated *S. pneumoniae* serotype 18A capsular polysaccharide, and one or more CP1 fusion proteins non-covalently complexed to the biotinylated polysaccharide;

(47) an immunogenic complex comprising a biotinylated *S. pneumoniae* serotype 18B capsular polysaccharide, and one or more CP1 fusion proteins non-covalently complexed to the biotinylated polysaccharide;

(48) an immunogenic complex comprising a biotinylated *S. pneumoniae* serotype 18C capsular polysaccharide, and one or more CP1 fusion proteins non-covalently complexed to the biotinylated polysaccharide;

(49) an immunogenic complex comprising a biotinylated *S. pneumoniae* serotype 18F capsular polysaccharide, and one or more CP1 fusion proteins non-covalently complexed to the biotinylated polysaccharide;

(50) an immunogenic complex comprising a biotinylated *S. pneumoniae* serotype 19A capsular polysaccharide, and one or more CP1 fusion proteins non-covalently complexed to the biotinylated polysaccharide;

(51) an immunogenic complex comprising a biotinylated *S. pneumoniae* serotype 19B capsular polysaccharide, and one or more CP1 fusion proteins non-covalently complexed to the biotinylated polysaccharide;

(52) an immunogenic complex comprising a biotinylated *S. pneumoniae* serotype 19C capsular polysaccharide, and one or more CP1 fusion proteins non-covalently complexed to the biotinylated polysaccharide;

(53) an immunogenic complex comprising a biotinylated *S. pneumoniae* serotype 19F capsular polysaccharide, and one or more CP1 fusion proteins non-covalently complexed to the biotinylated polysaccharide;

(54) an immunogenic complex comprising a biotinylated *S. pneumoniae* serotype 20A capsular polysaccharide, and one or more CP1 fusion proteins non-covalently complexed to the biotinylated polysaccharide;

(55) an immunogenic complex comprising a biotinylated *S. pneumoniae* serotype 20B capsular polysaccharide, and one or more CP1 fusion proteins non-covalently complexed to the biotinylated polysaccharide;

(56) an immunogenic complex comprising a biotinylated *S. pneumoniae* serotype 21 capsular polysaccharide, and one or more CP1 fusion proteins non-covalently complexed to the biotinylated polysaccharide;

(57) an immunogenic complex comprising a biotinylated *S. pneumoniae* serotype 22A capsular polysaccharide, and one or more CP1 fusion proteins non-covalently complexed to the biotinylated polysaccharide;

(58) an immunogenic complex comprising a biotinylated *S. pneumoniae* serotype 22F capsular polysaccharide, and one or more CP1 fusion proteins non-covalently complexed to the biotinylated polysaccharide;

(59) an immunogenic complex comprising a biotinylated *S. pneumoniae* serotype 23A capsular polysaccharide, and one or more CP1 fusion proteins non-covalently complexed to the biotinylated polysaccharide;

(60) an immunogenic complex comprising a biotinylated *S. pneumoniae* serotype 23B capsular polysaccharide, and one or more CP1 fusion proteins non-covalently complexed to the biotinylated polysaccharide;

(61) an immunogenic complex comprising a biotinylated *S. pneumoniae* serotype 23F capsular polysaccharide, and one or more CP1 fusion proteins non-covalently complexed to the biotinylated polysaccharide;

(62) an immunogenic complex comprising a biotinylated *S. pneumoniae* serotype 24A capsular polysaccharide, and one or more CP1 fusion proteins non-covalently complexed to the biotinylated polysaccharide;

(63) an immunogenic complex comprising a biotinylated *S. pneumoniae* serotype 24B capsular polysaccharide, and one or more CP1 fusion proteins non-covalently complexed to the biotinylated polysaccharide;

(64) an immunogenic complex comprising a biotinylated *S. pneumoniae* serotype 24F capsular polysaccharide, and one or more CP1 fusion proteins non-covalently complexed to the biotinylated polysaccharide;

(65) an immunogenic complex comprising a biotinylated *S. pneumoniae* serotype 25A capsular polysaccharide, and one or more CP1 fusion proteins non-covalently complexed to the biotinylated polysaccharide;

(66) an immunogenic complex comprising a biotinylated *S. pneumoniae* serotype 25F capsular polysaccharide, and one or more CP1 fusion proteins non-covalently complexed to the biotinylated polysaccharide;

(67) an immunogenic complex comprising a biotinylated *S. pneumoniae* serotype 27 capsular polysaccharide, and one or more CP1 fusion proteins non-covalently complexed to the biotinylated polysaccharide;

(68) an immunogenic complex comprising a biotinylated *S. pneumoniae* serotype 28A capsular polysaccharide, and one or more CP1 fusion proteins non-covalently complexed to the biotinylated polysaccharide;

(69) an immunogenic complex comprising a biotinylated *S. pneumoniae* serotype 28F capsular polysaccharide, and one or more CP1 fusion proteins non-covalently complexed to the biotinylated polysaccharide;

(70) an immunogenic complex comprising a biotinylated *S. pneumoniae* serotype 29 capsular polysaccharide, and one or more CP1 fusion proteins non-covalently complexed to the biotinylated polysaccharide;

(71) an immunogenic complex comprising a biotinylated *S. pneumoniae* serotype 31 capsular polysaccharide, and one or more CP1 fusion proteins non-covalently complexed to the biotinylated polysaccharide;

(72) an immunogenic complex comprising a biotinylated *S. pneumoniae* serotype 32A capsular polysaccharide, and one or more CP1 fusion proteins non-covalently complexed to the biotinylated polysaccharide;

(73) an immunogenic complex comprising a biotinylated *S. pneumoniae* serotype 32F capsular polysaccharide, and one or more CP1 fusion proteins non-covalently complexed to the biotinylated polysaccharide;

(74) an immunogenic complex comprising a biotinylated *S. pneumoniae* serotype 33A capsular polysaccharide, and one or more CP1 fusion proteins non-covalently complexed to the biotinylated polysaccharide;

(75) an immunogenic complex comprising a biotinylated *S. pneumoniae* serotype 33B capsular polysaccharide, and one or more CP1 fusion proteins non-covalently complexed to the biotinylated polysaccharide;

(76) an immunogenic complex comprising a biotinylated *S. pneumoniae* serotype 33C capsular polysaccharide, and one or more CP1 fusion proteins non-covalently complexed to the biotinylated polysaccharide;

(77) an immunogenic complex comprising a biotinylated *S. pneumoniae* serotype 33D capsular polysaccharide, and one or more CP1 fusion proteins non-covalently complexed to the biotinylated polysaccharide;

(78) an immunogenic complex comprising a biotinylated *S. pneumoniae* serotype 33E capsular polysaccharide, and one or more CP1 fusion proteins non-covalently complexed to the biotinylated polysaccharide;

(79) an immunogenic complex comprising a biotinylated *S. pneumoniae* serotype 33F capsular polysaccharide, and one or more CP1 fusion proteins non-covalently complexed to the biotinylated polysaccharide;

(80) an immunogenic complex comprising a biotinylated *S. pneumoniae* serotype 34 capsular polysaccharide, and one or more CP1 fusion proteins non-covalently complexed to the biotinylated polysaccharide;

(81) an immunogenic complex comprising a biotinylated *S. pneumoniae* serotype 35A capsular polysaccharide, and one or more CP1 fusion proteins non-covalently complexed to the biotinylated polysaccharide;

(82) an immunogenic complex comprising a biotinylated *S. pneumoniae* serotype 35B capsular polysaccharide, and one or more CP1 fusion proteins non-covalently complexed to the biotinylated polysaccharide;

(83) an immunogenic complex comprising a biotinylated *S. pneumoniae* serotype 35C capsular polysaccharide, and one or more CP1 fusion proteins non-covalently complexed to the biotinylated polysaccharide;

(84) an immunogenic complex comprising a biotinylated *S. pneumoniae* serotype 35F capsular polysaccharide, and one or more CP1 fusion proteins non-covalently complexed to the biotinylated polysaccharide;

(85) an immunogenic complex comprising a biotinylated *S. pneumoniae* serotype 36 capsular polysaccharide, and one or more CP1 fusion proteins non-covalently complexed to the biotinylated polysaccharide;

(86) an immunogenic complex comprising a biotinylated *S. pneumoniae* serotype 37 capsular polysaccharide, and one or more CP1 fusion proteins non-covalently complexed to the biotinylated polysaccharide;

(87) an immunogenic complex comprising a biotinylated *S. pneumoniae* serotype 38 capsular polysaccharide, and one or more CP1 fusion proteins non-covalently complexed to the biotinylated polysaccharide;

(88) an immunogenic complex comprising a biotinylated *S. pneumoniae* serotype 39 capsular polysaccharide, and one or more CP1 fusion proteins non-covalently complexed to the biotinylated polysaccharide;

(89) an immunogenic complex comprising a biotinylated *S. pneumoniae* serotype 40 capsular polysaccharide, and one or more CP1 fusion proteins non-covalently complexed to the biotinylated polysaccharide;

(90) an immunogenic complex comprising a biotinylated *S. pneumoniae* serotype 41A capsular polysaccharide, and one or more CP1 fusion proteins non-covalently complexed to the biotinylated polysaccharide;

(91) an immunogenic complex comprising a biotinylated *S. pneumoniae* serotype 41F capsular polysaccharide, and one or more CP1 fusion proteins non-covalently complexed to the biotinylated polysaccharide;

(92) an immunogenic complex comprising a biotinylated *S. pneumoniae* serotype 42 capsular polysaccharide, and one or more CP1 fusion proteins non-covalently complexed to the biotinylated polysaccharide;
(93) an immunogenic complex comprising a biotinylated S. pneumoniae serotype 43 capsular polysaccharide, and one or more CP1 fusion proteins non-covalently complexed to the biotinylated polysaccharide;
(94) an immunogenic complex comprising a biotinylated S. pneumoniae serotype 44 capsular polysaccharide, and one or more CP1 fusion proteins non-covalently complexed to the biotinylated polysaccharide;
(95) an immunogenic complex comprising a biotinylated S. pneumoniae serotype 45 capsular polysaccharide, and one or more CP1 fusion proteins non-covalently complexed to the biotinylated polysaccharide;
(96) an immunogenic complex comprising a biotinylated *S. pneumoniae* serotype 46 capsular polysaccharide, and one or more CP1 fusion proteins non-covalently complexed to the biotinylated polysaccharide;

(97) an immunogenic complex comprising a biotinylated *S. pneumoniae* serotype 47A capsular polysaccharide, and one or more CP1 fusion proteins non-covalently complexed to the biotinylated polysaccharide;

(98) an immunogenic complex comprising a biotinylated *S. pneumoniae* serotype 47F capsular polysaccharide, and one or more CP1 fusion proteins non-covalently complexed to the biotinylated polysaccharide; and

(99) an immunogenic complex comprising a biotinylated *S. pneumoniae* serotype 48 capsular polysaccharide, and one or more CP1 fusion proteins non-covalently complexed to the biotinylated polysaccharide.

In some embodiments, an immunogenic composition comprises one or more (e.g., 1, 2, 3, 4, 5, 6, 7, 8, 9, 10, 15, 20, 21, 22, 23, or 24) species of immunogenic complexes selected from:

(1) an immunogenic complex comprising a biotinylated *S. pneumoniae* serotype 1 capsular polysaccharide, and one or more CP1 fusion proteins non-covalently complexed to the biotinylated polysaccharide;

(2) an immunogenic complex comprising a biotinylated *S. pneumoniae* serotype 2 capsular polysaccharide, and one or more CP1 fusion proteins non-covalently complexed to the biotinylated polysaccharide;

(3) an immunogenic complex comprising a biotinylated *S. pneumoniae* serotype 3 capsular polysaccharide, and one or more CP1 fusion proteins non-covalently complexed to the biotinylated polysaccharide;

(4) an immunogenic complex comprising a biotinylated *S. pneumoniae* serotype 4 capsular polysaccharide, and one or more CP1 fusion proteins non-covalently complexed to the biotinylated polysaccharide;

(5) an immunogenic complex comprising a biotinylated *S. pneumoniae* serotype 5 capsular polysaccharide, and one or more CP1 fusion proteins non-covalently complexed to the biotinylated polysaccharide;

(6) an immunogenic complex comprising a biotinylated *S. pneumoniae* serotype 6A capsular polysaccharide, and one or more CP1 fusion proteins non-covalently complexed to the biotinylated polysaccharide;

(7) an immunogenic complex comprising a biotinylated *S. pneumoniae* serotype 6B capsular polysaccharide, and one or more CP1 fusion proteins non-covalently complexed to the biotinylated polysaccharide;

(8) an immunogenic complex comprising a biotinylated *S. pneumoniae* serotype 7F capsular polysaccharide, and one or more CP1 fusion proteins non-covalently complexed to the biotinylated polysaccharide;

(9) an immunogenic complex comprising a biotinylated *S. pneumoniae* serotype 8 capsular polysaccharide, and one or more CP1 fusion proteins non-covalently complexed to the biotinylated polysaccharide;

(10) an immunogenic complex comprising a biotinylated *S. pneumoniae* serotype 9N capsular polysaccharide, and one or more CP1 fusion proteins non-covalently complexed to the biotinylated polysaccharide;

(11) an immunogenic complex comprising a biotinylated *S. pneumoniae* serotype 9V capsular polysaccharide, and one or more CP1 fusion proteins non-covalently complexed to the biotinylated polysaccharide;

(12) an immunogenic complex comprising a biotinylated *S. pneumoniae* serotype 10A capsular polysaccharide, and one or more CP1 fusion proteins non-covalently complexed to the biotinylated polysaccharide;

(13) an immunogenic complex comprising a biotinylated *S. pneumoniae* serotype 11A capsular polysaccharide, and one or more CP1 fusion proteins non-covalently complexed to the biotinylated polysaccharide;

(14) an immunogenic complex comprising a biotinylated *S. pneumoniae* serotype 12F capsular polysaccharide, and one or more CP1 fusion proteins non-covalently complexed to the biotinylated polysaccharide;

(15) an immunogenic complex comprising a biotinylated *S. pneumoniae* serotype 14 capsular polysaccharide, and one or more CP1 fusion proteins non-covalently complexed to the biotinylated polysaccharide;

(16) an immunogenic complex comprising a biotinylated *S. pneumoniae* serotype 15B capsular polysaccharide, and one or more CP1 fusion proteins non-covalently complexed to the biotinylated polysaccharide;

(17) an immunogenic complex comprising a biotinylated *S. pneumoniae* serotype 17F capsular polysaccharide, and one or more CP1 fusion proteins non-covalently complexed to the biotinylated polysaccharide;

(18) an immunogenic complex comprising a biotinylated *S. pneumoniae* serotype 18C capsular polysaccharide, and one or more CP1 fusion proteins non-covalently complexed to the biotinylated polysaccharide;

(19) an immunogenic complex comprising a biotinylated *S. pneumoniae* serotype 19A capsular polysaccharide, and one or more CP1 fusion proteins non-covalently complexed to the biotinylated polysaccharide;

(20) an immunogenic complex comprising a biotinylated *S. pneumoniae* serotype 19F capsular polysaccharide, and one or more CP1 fusion proteins non-covalently complexed to the biotinylated polysaccharide;

(21) an immunogenic complex comprising a biotinylated *S. pneumoniae* serotype 20B capsular polysaccharide, and one or more CP1 fusion proteins non-covalently complexed to the biotinylated polysaccharide;

(22) an immunogenic complex comprising a biotinylated *S. pneumoniae* serotype 22F capsular polysaccharide, and one or more CP1 fusion proteins non-covalently complexed to the biotinylated polysaccharide;

(23) an immunogenic complex comprising a biotinylated *S. pneumoniae* serotype 23F capsular polysaccharide, and one or more CP1 fusion proteins non-covalently complexed to the biotinylated polysaccharide; and

(24) an immunogenic complex comprising a biotinylated *S. pneumoniae* serotype 33F capsular polysaccharide, and one or more CP1 fusion proteins non-covalently complexed to the biotinylated polysaccharide.

In some embodiments, a vaccine composition comprises one or more (e.g., 1, 2, 3, 4, 5, 6, 7, 8, 9, 10, 11, 12, 13, 14, or 15) species of immunogenic complexes selected from:

(1) an immunogenic complex comprising a biotinylated *S. pneumoniae* serotype 1 capsular polysaccharide, and one or more CP1 fusion proteins non-covalently complexed to the biotinylated polysaccharide;
(2) an immunogenic complex comprising a biotinylated *S. pneumoniae* serotype 3 capsular polysaccharide, and one or more CP1 fusion proteins non-covalently complexed to the biotinylated polysaccharide;
(3) an immunogenic complex comprising a biotinylated *S. pneumoniae* serotype 4 capsular polysaccharide, and one or more CP1 fusion proteins non-covalently complexed to the biotinylated polysaccharide;

(4) an immunogenic complex comprising a biotinylated *S. pneumoniae* serotype 5 capsular polysaccharide, and one or more CP1 fusion proteins non-covalently complexed to the biotinylated polysaccharide;

(5) an immunogenic complex comprising a biotinylated *S. pneumoniae* serotype 6A capsular polysaccharide, and one or more CP1 fusion proteins non-covalently complexed to the biotinylated polysaccharide;

(6) an immunogenic complex comprising a biotinylated *S. pneumoniae* serotype 6B capsular polysaccharide, and one or more CP1 fusion proteins non-covalently complexed to the biotinylated polysaccharide;

(7) an immunogenic complex comprising a biotinylated *S. pneumoniae* serotype 7F capsular polysaccharide, and one or more CP1 fusion proteins non-covalently complexed to the biotinylated polysaccharide;

(8) an immunogenic complex comprising a biotinylated *S. pneumoniae* serotype 9V capsular polysaccharide, and one or more CP1 fusion proteins non-covalently complexed to the biotinylated polysaccharide;

(9) an immunogenic complex comprising a biotinylated *S. pneumoniae* serotype 14 capsular polysaccharide, and one or more CP1 fusion proteins non-covalently complexed to the biotinylated polysaccharide;

(10) an immunogenic complex comprising a biotinylated *S. pneumoniae* serotype 18C capsular polysaccharide, and one or more CP1 fusion proteins non-covalently complexed to the biotinylated polysaccharide;

(11) an immunogenic complex comprising a biotinylated *S. pneumoniae* serotype 19A capsular polysaccharide, and one or more CP1 fusion proteins non-covalently complexed to the biotinylated polysaccharide;

(12) an immunogenic complex comprising a biotinylated *S. pneumoniae* serotype 19F capsular polysaccharide, and one or more CP1 fusion proteins non-covalently complexed to the biotinylated polysaccharide;

(13) an immunogenic complex comprising a biotinylated *S. pneumoniae* serotype 22F capsular polysaccharide, and one or more CP1 fusion proteins non-covalently complexed to the biotinylated polysaccharide;

(14) an immunogenic complex comprising a biotinylated *S. pneumoniae* serotype 23F capsular polysaccharide, and one or more CP1 fusion proteins non-covalently complexed to the biotinylated polysaccharide; and

(15) an immunogenic complex comprising a biotinylated *S. pneumoniae* serotype 33F capsular polysaccharide, and one or more CP1 fusion proteins non-covalently complexed to the biotinylated polysaccharide.

In some embodiments, a vaccine composition comprises one or more (e.g., 1, 2, 3, 4, 5, 6, 7, 8, or 9) species of immunogenic complexes selected from:

(1) an immunogenic complex comprising a biotinylated *S. pneumoniae* serotype 2 capsular polysaccharide, and one or more CP1 fusion proteins non-covalently complexed to the biotinylated polysaccharide;

(2) an immunogenic complex comprising a biotinylated *S. pneumoniae* serotype 8 capsular polysaccharide, and one or more CP1 fusion proteins non-covalently complexed to the biotinylated polysaccharide;

(3) an immunogenic complex comprising a biotinylated *S. pneumoniae* serotype 9N capsular polysaccharide, and one or more CP1 fusion proteins non-covalently complexed to the biotinylated polysaccharide;

(4) an immunogenic complex comprising a biotinylated *S. pneumoniae* serotype 10A capsular polysaccharide, and one or more CP1 fusion proteins non-covalently complexed to the biotinylated polysaccharide;

(5) an immunogenic complex comprising a biotinylated *S. pneumoniae* serotype 11A capsular polysaccharide, and one or more CP1 fusion proteins non-covalently complexed to the biotinylated polysaccharide;

(6) an immunogenic complex comprising a biotinylated *S. pneumoniae* serotype 12F capsular polysaccharide, and one or more CP1 fusion proteins non-covalently complexed to the biotinylated polysaccharide;

(7) an immunogenic complex comprising a biotinylated *S. pneumoniae* serotype 15B capsular polysaccharide, and one or more CP1 fusion proteins non-covalently complexed to the biotinylated polysaccharide;

(8) an immunogenic complex comprising a biotinylated *S. pneumoniae* serotype 17F capsular polysaccharide, and one or more CP1 fusion proteins non-covalently complexed to the biotinylated polysaccharide; and (9) an immunogenic complex comprising a biotinylated *S. pneumoniae* serotype 20B capsular polysaccharide, and one or more CP1 fusion proteins non-covalently complexed to the Biotinylated Polysaccharide.

Vaccine Compositions

In some embodiments, a vaccine composition is a polyvalent or multivalent vaccine. In some embodiments, the valency of a vaccine composition refers to the number of species of immunogenic complexes present in the vaccine composition. The valency of a vaccine described herein is not limiting with respect to the total antigens present in said pharmaceutical composition, immunogenic complex, or vaccine, or to the number of pathogen strains for which administration of said pharmaceutical composition, immunogenic complex, immunogenic composition, or vaccine composition may induce an immune-protective response. In a non-limiting example, a 24-valent vaccine composition may comprise more than 24 antigenic components (e.g., peptide and/or polysaccharide components) and may induce an immunoprotective response against more than 24 pathogens, or pathogenic serotypes or strains.

In some embodiments, a vaccine composition comprises between 1-50 species of immunogenic complexes. In some embodiments, a vaccine composition comprises between 1-40 species of immunogenic complexes. In some embodiments, a vaccine composition comprises between 1-35 species of immunogenic complexes. In some embodiments, a vaccine composition comprises between 1-30 species of immunogenic complexes. In some embodiments, a vaccine composition comprises between 1-30 species of immunogenic complexes. In some embodiments, a vaccine composition comprises between 1-24 species of immunogenic complexes. In some embodiments, a vaccine composition comprises between 1-15 species of immunogenic complexes. In some embodiments, a vaccine composition comprises between 1-9 species of immunogenic complexes. In some embodiments, a vaccine composition comprises between 1-5 species of immunogenic complexes. In some embodiments, a vaccine is a polyvalent vaccine.

In some embodiments, a vaccine composition comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 species of immunogenic complexes. In some embodiments, a vaccine composition comprises 1 type of immunogenic complex. In some embodiments, a vaccine composition comprises 2 species of immunogenic complexes. In some embodiments, a vaccine composition comprises 4 species of immunogenic complexes. In some embodiments, a vaccine composition comprises 6 species of immunogenic complexes. In some embodiments, a vaccine composition comprises 7 species of immunogenic complexes. In some embodiments, a vaccine composition comprises 8 species of immunogenic complexes. In some embodiments, a vaccine composition comprises 9 species of immunogenic complexes. In some embodiments, a vaccine composition comprises 10 species of immunogenic complexes. In some embodiments, a vaccine composition comprises 11 species of immunogenic complexes. In some embodiments, a vaccine composition comprises 12 species of immunogenic complexes. In some embodiments, a vaccine composition comprises 13 species of immunogenic complexes. In some embodiments, a vaccine composition comprises 14 species of immunogenic complexes. In some embodiments, a vaccine composition comprises 15 species of immunogenic complexes. In some embodiments, a vaccine composition comprises 16 species of immunogenic complexes. In some embodiments, a vaccine composition comprises 17 species of immunogenic complexes. In some embodiments, a vaccine composition comprises 18 species of immunogenic complexes. In some embodiments, a vaccine composition comprises 19 species of immunogenic complexes. In some embodiments, a vaccine composition comprises 20 species of immunogenic complexes. In some embodiments, a vaccine composition comprises 21 species of immunogenic complexes. In some embodiments, a vaccine composition comprises 22 species of immunogenic complexes. In some embodiments, a vaccine composition comprises 23 species of immunogenic complexes. In some embodiments, a vaccine composition comprises 24 species of immunogenic complexes. In some embodiments, a vaccine composition comprises 25 species of immunogenic complexes. In some embodiments, a vaccine composition comprises 26 species of immunogenic complexes. In some embodiments, a vaccine composition comprises 27 species of immunogenic complexes. In some embodiments, a vaccine composition comprises 28 species of immunogenic complexes. In some embodiments, a vaccine composition comprises 29 species of immunogenic complexes. In some embodiments, a vaccine composition comprises 30 species of immunogenic complexes. In some embodiments, a vaccine composition comprises 35 species of immunogenic complexes. In some embodiments, a vaccine composition comprises 40 species of immunogenic complexes. In some embodiments, a vaccine composition comprises 45 species of immunogenic complexes. In some embodiments, a vaccine composition comprises 50 species of immunogenic complexes.

In some embodiments, a vaccine composition comprises two or more species of immunogenic complexes (e.g., in immunogenic compositions) in amounts such that the weight of polysaccharides in the vaccine composition from each immunogenic complex is about the same, e.g., present in a w/w ratio of about 1:1. In some embodiments, the weight of polysaccharides in the vaccine contributed by each immunogenic complex is about 0.20 µg. In some embodiments, the weight of polysaccharides in the vaccine contributed by each immunogenic complex is about 0.25 µg. In some embodiments, the weight of polysaccharides in the vaccine contributed by each immunogenic complex is about 0.5 µg. In some embodiments, the weight of polysaccharides in the vaccine contributed by each immunogenic complex is about 1 µg. In some embodiments, the weight of polysaccharides in the vaccine contributed by each immunogenic complex is about 1.5 µg. In some embodiments, the weight of polysaccharides in the vaccine contributed by each immunogenic complex is about 2 µg. In some embodiments, the weight of polysaccharides in the vaccine contributed by each immunogenic complex is about 2.5 µg. In some embodiments, the weight of polysaccharides in the vaccine contributed by each immunogenic complex is about 3 µg. In some embodiments, the weight of polysaccharides in the vaccine contributed by each immunogenic complex is about 3.5 µg. In some embodiments, the weight of polysaccharides in the vaccine contributed by each immunogenic complex is about 4 µg. In some embodiments, the weight of polysaccharides in the vaccine contributed by each immunogenic complex is about 4.5 µg. In some embodiments, the weight of polysaccharides in the vaccine contributed by each immunogenic complex is about 5 µg. In some embodiments, the weight of polysaccharides in the vaccine contributed by each immunogenic complex is about 5.5 µg. In some embodiments, the weight of polysaccharides in the vaccine contributed by each immunogenic complex is about 6 µg. In some embodiments, the weight of polysaccharides in the vaccine contributed by each immunogenic complex is about 7 µg. In some embodiments, the weight of polysaccharides in the vaccine contributed by each immunogenic complex is about 8 µg. In some embodiments, the weight of polysaccharides in the vaccine contributed by each immunogenic complex is about 9 µg. In some embodiments, the weight of polysaccharides in the vaccine contributed by each immunogenic complex is about 10 µg. In some embodiments, the weight of polysaccharides in the vaccine contributed by each immunogenic complex is about 11 µg. In some embodiments, the weight of polysaccharides in the vaccine contributed by each immunogenic complex is about 12 µg. In some embodiments, the weight of polysaccharides in the vaccine contributed by each immunogenic complex is more than 12 µg, e.g., 13 µg, 14 µg, 15 µg, 16 µg, 17 µg, 18 µg, 19 µg, 20 µg, 21 µg, 22 µg, 23 µg, 24 µg, 25 µg, or more.

In some embodiments, a vaccine composition comprises two or more species of immunogenic complexes (e.g., in immunogenic compositions) in amounts such that the weight of polysaccharides in the vaccine composition contributed by each immunogenic complex is different, e.g., present in a w/w ratio that is not about 1:1. In some embodiments, a vaccine composition comprises two or more species of immunogenic complexes (e.g., in immunogenic compositions) in amounts such that the weight of polysaccharide in the vaccine composition contributed by a first immunogenic complex and a second immunogenic complex is 1:2. In some embodiments, a vaccine composition comprises two or more species of immunogenic complexes (e.g., in immunogenic compositions) in amounts such that the weight of polysaccharide in the vaccine composition contributed by a first immunogenic complex and a second immunogenic complex is 1:3. In some embodiments, a vaccine composition comprises two or more species of immunogenic complexes (e.g., in immunogenic compositions) in amounts such that the weight of polysaccharide in the vaccine composition contributed by a first immunogenic complex and a second immunogenic complex is 1:4. In some embodiments, a vaccine composition comprises two or more species of immunogenic complexes (e.g., in immunogenic compositions) in amounts such that the weight of polysaccharide in the vaccine composition contributed by a first immunogenic complex and a second immunogenic complex is 1:5. In some embodiments, a vaccine composition comprises two or more species of immunogenic complexes (e.g., in immunogenic compositions) in amounts such that the weight of polysaccharide in the vaccine composition contributed by a first immunogenic complex and a second immunogenic complex is 1:6. In some embodiments, a vaccine composition comprises two or more species of immunogenic complexes (e.g., in immunogenic compositions) in amounts such that the weight of polysaccharide in the vaccine composition contributed by a first immunogenic complex and a second immunogenic complex is 1:7. In some embodiments, a vaccine composition comprises two or more species of immunogenic complexes (e.g., in immunogenic compositions) in amounts such that the weight of polysaccharide in the vaccine composition contributed by a first immunogenic complex and a second immunogenic complex is 1:8. In some embodiments, a vaccine composition comprises two or more species of immunogenic complexes (e.g., in immunogenic compositions) in amounts such that the weight of polysaccharide in the vaccine composition contributed by a first immunogenic complex and a second immunogenic complex is 1:9. In some embodiments, a vaccine composition comprises two or more species of immunogenic complexes (e.g., in immunogenic compositions) in amounts such that the weight of polysaccharide in the vaccine composition contributed by a first immunogenic complex and a second immunogenic complex is 1:10. In some embodiments, the vaccine composition comprises a mixture of immunogenic complexes, such that the weight of polysaccharide in a vaccine contributed by an immunogenic complex ranges from about 0.20 µg to about 6 µg. In some embodiments, the vaccine composition comprises a mixture of immunogenic complexes, such that the weight of polysaccharide in a vaccine contributed by an immunogenic complex ranges from about 0.20 µg to about 12 µg. In some embodiments, the vaccine composition comprises a mixture of immunogenic complexes, such that the weight of polysaccharides in the vaccine contributed by each immunogenic complex ranges from about 0.20 µg to about 20 µg. In some embodiments, the vaccine composition comprises a mixture of immunogenic complexes, such that the weight of polysaccharides in the vaccine contributed by each immunogenic complex ranges from about 0.20 µg to about 40 µg.

In some embodiments, a vaccine composition comprises two or more species of immunogenic complexes (e.g., in immunogenic compositions) in amounts such that the combined weight of polysaccharides and polypeptides in the vaccine composition contributed by each immunogenic complex (e.g., in an immunogenic composition) is about the same, e.g., present in a w/w protein:PS ratio of about 1:1. In some embodiments, a vaccine composition comprises two or more species of immunogenic complexes (e.g., in immunogenic compositions) in amounts such that the combined weight of polysaccharides and polypeptides in the vaccine composition contributed by each immunogenic complex (e.g., in an immunogenic composition) is present in a w/w protein:PS ratio of about 2:1. In some embodiments, a vaccine composition comprises two or more species of immunogenic complexes (e.g., in immunogenic compositions) in amounts such that the combined weight of polysaccharides and polypeptides in the vaccine composition contributed by each immunogenic complex (e.g., in an immunogenic composition) is present in a w/w protein:PS ratio of about 3:1. In some embodiments, a vaccine composition comprises two or more species of immunogenic complexes (e.g., in immunogenic compositions) in amounts such that the combined weight of polysaccharides and polypeptides in the vaccine composition contributed by each immunogenic complex (e.g., in an immunogenic composition) is present in a w/w protein:PS ratio of about 4:1. In some embodiments, a vaccine composition comprises two or more species of immunogenic complexes (e.g., in immunogenic compositions) in amounts such that the combined weight of polysaccharides and polypeptides in the vaccine composition contributed by each immunogenic complex (e.g., in an immunogenic composition) is present in a w/w protein:PS ratio of about 5:1. In some embodiments, a vaccine composition comprises two or more species of immunogenic complexes (e.g., in immunogenic compositions) in amounts such that the combined weight of polysaccharides and polypeptides in the vaccine composition contributed by each immunogenic complex (e.g., in an immunogenic composition) is present in a w/w protein:PS ratio of about 6:1. In some embodiments, a vaccine composition comprises two or more species of immunogenic complexes (e.g., in immunogenic compositions) in amounts such that the combined weight of polysaccharides and polypeptides in the vaccine composition contributed by each immunogenic complex (e.g., in an immunogenic composition) is present in a w/w protein:PS ratio of about 7:1. In some embodiments, a vaccine composition comprises two or more species of immunogenic complexes (e.g., in immunogenic compositions) in amounts such that the combined weight of polysaccharides and polypeptides in the vaccine composition contributed by each immunogenic complex (e.g., in an immunogenic composition) is present in a w/w protein:PS ratio of about 8:1. In some embodiments, a vaccine composition comprises two or more species of immunogenic complexes (e.g., in immunogenic compositions) in amounts such that the combined weight of polysaccharides and polypeptides in the vaccine composition contributed by each immunogenic complex (e.g., in an immunogenic composition) is present in a w/w protein:PS ratio of about 9:1. In some embodiments, a vaccine composition comprises two or more species of immunogenic complexes (e.g., in immunogenic compositions) in amounts such that the combined weight of polysaccharides and polypeptides in the vaccine composition contributed by each immunogenic complex (e.g., in an immunogenic composition) is present in a w/w protein:PS ratio of about 10:1.

In some embodiments, the combined weight of polysaccharides and polypeptides in the vaccine contributed by each immunogenic complex is about 0.20 µg. In some embodiments, the combined weight of polysaccharides and polypeptides in the vaccine contributed by each immunogenic complex is about 0.40 µg. In some embodiments, the combined weight of polysaccharides and polypeptides in the vaccine contributed by each immunogenic complex is about 1 µg. In some embodiments, the combined weight of polysaccharides and polypeptides in the vaccine contributed by each immunogenic complex is about 2 µg. In some embodiments, the combined weight of polysaccharides and polypeptides in the vaccine contributed by each immunogenic composition is about 3 µg. In some embodiments, the combined weight of polysaccharides and polypeptides in the vaccine contributed by each immunogenic composition is about 4 µg. In some embodiments, the combined weight of polysaccharides and polypeptides in the vaccine contributed by each immunogenic composition is about 5 µg. In some embodiments, the combined weight of polysaccharides and polypeptides in the vaccine contributed by each immunogenic composition is about 6 µg. In some embodiments, the combined weight of polysaccharides and polypeptides in the vaccine contributed by each immunogenic composition is about 7 µg. In some embodiments, the combined weight of polysaccharides and polypeptides in the vaccine contributed by each immunogenic composition is about 8 µg. In some embodiments, the combined weight of polysaccharides and polypeptides in the vaccine contributed by each immunogenic composition is about 9 µg. In some embodiments, the combined weight of polysaccharides and polypeptides in the vaccine contributed by each immunogenic composition is about 10 µg. In some embodiments, the combined weight of polysaccharides and polypeptides in the vaccine contributed by each immunogenic composition is about 11 µg. In some embodiments, the combined weight of polysaccharides and polypeptides in the vaccine contributed by each immunogenic composition is about 12 µg. In some embodiments, the combined weight of polysaccharides and polypeptides in the vaccine contributed by each immunogenic composition is about 14 µg. In some embodiments, the combined weight of polysaccharides and polypeptides in the vaccine contributed by each immunogenic composition is about 16 µg. In some embodiments, the combined weight of polysaccharides and polypeptides in the vaccine contributed by each immunogenic composition is about 18 µg. In some embodiments, the combined weight of polysaccharides and polypeptides in the vaccine contributed by each immunogenic composition is about 20 µg. In some embodiments, the combined weight of polysaccharides and polypeptides in the vaccine contributed by each immunogenic composition is about 21 µg. In some embodiments, the combined weight of polysaccharides and polypeptides in the vaccine contributed by each immunogenic composition is about 22 µg. In some embodiments, the combined weight of polysaccharides and polypeptides in the vaccine contributed by each immunogenic composition is about 23 µg. In some embodiments, the combined weight of polysaccharides and polypeptides in the vaccine contributed by each immunogenic composition is about 24 µg. In some embodiments, the combined weight of polysaccharides and polypeptides in the vaccine contributed by each immunogenic composition is about 25 µg. In some embodiments, the combined weight of polysaccharides and polypeptides in the vaccine contributed by each immunogenic composition is about 30 µg. In some embodiments, the combined weight of polysaccharides and polypeptides in the vaccine contributed by each immunogenic composition is about 40 µg. In some embodiments, the combined weight of polysaccharides and polypeptides in the vaccine contributed by each immunogenic composition is about 50 µg. In some embodiments, the combined weight of polysaccharides and polypeptides in the vaccine contributed by each immunogenic composition is about 60 µg. In some embodiments, the combined weight of polysaccharides and polypeptides in the vaccine contributed by each immunogenic composition is about 70 µg. In some embodiments, the combined weight of polysaccharides and polypeptides in the vaccine contributed by each immunogenic composition is about 80 µg. In some embodiments, the combined weight of polysaccharides and polypeptides in the vaccine contributed by each immunogenic composition is about 90 µg. In some embodiments, the combined weight of polysaccharides and polypeptides in the vaccine contributed by each immunogenic composition is about 100 µg. In some embodiments, the combined weight of polysaccharides and polypeptides in the vaccine contributed by each immunogenic composition is about 110 µg.

In some embodiments, a vaccine composition comprises two or more species of immunogenic complexes (e.g., in immunogenic compositions) in amounts such that the combined weight of polysaccharides and polypeptides in the vaccine composition contributed by each immunogenic complex is different, e.g., present in a w/w protein:PS ratio that is not about 1:1, e.g., a protein:PS ratio that is 2:1, 3:1, 4:1, 5:1. 6:1, 7:1, 8:1, 9:1, or 10:1. In some embodiments, the vaccine composition comprises a mixture of immunogenic complexes, such that the combined weight of polysaccharides and polypeptides in the vaccine contributed by each immunogenic complex ranges from about 0.4 µg to about 110 µg.

In some embodiments, a vaccine composition comprises one or more (e.g., 1, 2, 3, 4, 5, 6, 7, 8, 9, 10, 15, 20, 25, 30, 40, 50, or more) species of immunogenic complexes selected from:

(1) an immunogenic complex comprising a biotinylated *S. pneumoniae* serotype 1 capsular polysaccharide, and one or more CP1 fusion proteins non-covalently complexed to the biotinylated polysaccharide;

(2) an immunogenic complex comprising a biotinylated *S. pneumoniae* serotype 2 capsular polysaccharide, and one or more CP1 fusion proteins non-covalently complexed to the biotinylated polysaccharide;

(3) an immunogenic complex comprising a biotinylated *S. pneumoniae* serotype 3 capsular polysaccharide, and one or more CP1 fusion proteins non-covalently complexed to the biotinylated polysaccharide;

(4) an immunogenic complex comprising a biotinylated *S. pneumoniae* serotype 4 capsular polysaccharide, and one or more CP1 fusion proteins non-covalently complexed to the biotinylated polysaccharide;

(5) an immunogenic complex comprising a biotinylated *S. pneumoniae* serotype 5 capsular polysaccharide, and one or more CP1 fusion proteins non-covalently complexed to the biotinylated polysaccharide;

(6) an immunogenic complex comprising a biotinylated *S. pneumoniae* serotype 6A capsular polysaccharide, and one or more CP1 fusion proteins non-covalently complexed to the biotinylated polysaccharide;

(7) an immunogenic complex comprising a biotinylated *S. pneumoniae* serotype 6B capsular polysaccharide, and one or more CP1 fusion proteins non-covalently complexed to the biotinylated polysaccharide;

(8) an immunogenic complex comprising a biotinylated *S. pneumoniae* serotype 6C capsular polysaccharide, and one or more CP1 fusion proteins non-covalently complexed to the biotinylated polysaccharide;

(9) an immunogenic complex comprising a biotinylated *S. pneumoniae* serotype 6D capsular polysaccharide, and one or more CP1 fusion proteins non-covalently complexed to the biotinylated polysaccharide;

(10) an immunogenic complex comprising a biotinylated *S. pneumoniae* serotype 6E capsular polysaccharide, and one or more CP1 fusion proteins non-covalently complexed to the biotinylated polysaccharide;

(11) an immunogenic complex comprising a biotinylated *S. pneumoniae* serotype 6F capsular polysaccharide, and one or more CP1 fusion proteins non-covalently complexed to the biotinylated polysaccharide;

(12) an immunogenic complex comprising a biotinylated *S. pneumoniae* serotype 6G capsular polysaccharide, and one or more CP1 fusion proteins non-covalently complexed to the biotinylated polysaccharide;

(13) an immunogenic complex comprising a biotinylated *S. pneumoniae* serotype 6H capsular polysaccharide, and one or more CP1 fusion proteins non-covalently complexed to the biotinylated polysaccharide;

(14) an immunogenic complex comprising a biotinylated *S. pneumoniae* serotype 7A capsular polysaccharide, and one or more CP1 fusion proteins non-covalently complexed to the biotinylated polysaccharide;

(15) an immunogenic complex comprising a biotinylated *S. pneumoniae* serotype 7B capsular polysaccharide, and one or more CP1 fusion proteins non-covalently complexed to the biotinylated polysaccharide;

(16) an immunogenic complex comprising a biotinylated *S. pneumoniae* serotype 7C capsular polysaccharide, and one or more CP1 fusion proteins non-covalently complexed to the biotinylated polysaccharide;

(17) an immunogenic complex comprising a biotinylated *S. pneumoniae* serotype 7F capsular polysaccharide, and one or more CP1 fusion proteins non-covalently complexed to the biotinylated polysaccharide;

(18) an immunogenic complex comprising a biotinylated *S. pneumoniae* serotype 8 capsular polysaccharide, and one or more CP1 fusion proteins non-covalently complexed to the biotinylated polysaccharide;

(19) an immunogenic complex comprising a biotinylated *S. pneumoniae* serotype 9A capsular polysaccharide, and one or more CP1 fusion proteins non-covalently complexed to the biotinylated polysaccharide;

(20) an immunogenic complex comprising a biotinylated *S. pneumoniae* serotype 9L capsular polysaccharide, and one or more CP1 fusion proteins non-covalently complexed to the biotinylated polysaccharide;

(21) an immunogenic complex comprising a biotinylated *S. pneumoniae* serotype 9N capsular polysaccharide, and one or more CP1 fusion proteins non-covalently complexed to the biotinylated polysaccharide;

(22) an immunogenic complex comprising a biotinylated *S. pneumoniae* serotype 9V capsular polysaccharide, and one or more CP1 fusion proteins non-covalently complexed to the biotinylated polysaccharide;

(23) an immunogenic complex comprising a biotinylated *S. pneumoniae* serotype 10A capsular polysaccharide, and one or more CP1 fusion proteins non-covalently complexed to the biotinylated polysaccharide;

(24) an immunogenic complex comprising a biotinylated *S. pneumoniae* serotype 10B capsular polysaccharide, and one or more CP1 fusion proteins non-covalently complexed to the biotinylated polysaccharide;

(25) an immunogenic complex comprising a biotinylated *S. pneumoniae* serotype 10C capsular polysaccharide, and one or more CP1 fusion proteins non-covalently complexed to the biotinylated polysaccharide;

(26) an immunogenic complex comprising a biotinylated *S. pneumoniae* serotype 10F capsular polysaccharide, and one or more CP1 fusion proteins non-covalently complexed to the biotinylated polysaccharide;

(27) an immunogenic complex comprising a biotinylated *S. pneumoniae* serotype 11A capsular polysaccharide, and one or more CP1 fusion proteins non-covalently complexed to the biotinylated polysaccharide;

(28) an immunogenic complex comprising a biotinylated *S. pneumoniae* serotype 11B capsular polysaccharide, and one or more CP1 fusion proteins non-covalently complexed to the biotinylated polysaccharide;

(29) an immunogenic complex comprising a biotinylated *S. pneumoniae* serotype 11C capsular polysaccharide, and one or more CP1 fusion proteins non-covalently complexed to the biotinylated polysaccharide;

(30) an immunogenic complex comprising a biotinylated *S. pneumoniae* serotype 11D capsular polysaccharide, and one or more CP1 fusion proteins non-covalently complexed to the biotinylated polysaccharide;

(31) an immunogenic complex comprising a biotinylated *S. pneumoniae* serotype 11E capsular polysaccharide, and one or more CP1 fusion proteins non-covalently complexed to the biotinylated polysaccharide;

(32) an immunogenic complex comprising a biotinylated *S. pneumoniae* serotype 11F capsular polysaccharide, and one or more CP1 fusion proteins non-covalently complexed to the biotinylated polysaccharide;

(33) an immunogenic complex comprising a biotinylated *S. pneumoniae* serotype 12A capsular polysaccharide, and one or more CP1 fusion proteins non-covalently complexed to the biotinylated polysaccharide;

(34) an immunogenic complex comprising a biotinylated *S. pneumoniae* serotype 12B capsular polysaccharide, and one or more CP1 fusion proteins non-covalently complexed to the biotinylated polysaccharide;

(35) an immunogenic complex comprising a biotinylated *S. pneumoniae* serotype 12F capsular polysaccharide, and one or more CP1 fusion proteins non-covalently complexed to the biotinylated polysaccharide;

(36) an immunogenic complex comprising a biotinylated *S. pneumoniae* serotype 13 capsular polysaccharide, and one or more CP1 fusion proteins non-covalently complexed to the biotinylated polysaccharide;

(37) an immunogenic complex comprising a biotinylated *S. pneumoniae* serotype 14 capsular polysaccharide, and one or more CP1 fusion proteins non-covalently complexed to the biotinylated polysaccharide;

(38) an immunogenic complex comprising a biotinylated *S. pneumoniae* serotype 15A capsular polysaccharide, and one or more CP1 fusion proteins non-covalently complexed to the biotinylated polysaccharide;

(39) an immunogenic complex comprising a biotinylated *S. pneumoniae* serotype 15B capsular polysaccharide, and one or more CP1 fusion proteins non-covalently complexed to the biotinylated polysaccharide;

(40) an immunogenic complex comprising a biotinylated *S. pneumoniae* serotype 15C capsular polysaccharide, and one or more CP1 fusion proteins non-covalently complexed to the biotinylated polysaccharide;

(41) an immunogenic complex comprising a biotinylated *S. pneumoniae* serotype 15F capsular polysaccharide, and one or more CP1 fusion proteins non-covalently complexed to the biotinylated polysaccharide;

(42) an immunogenic complex comprising a biotinylated *S. pneumoniae* serotype 16A capsular polysaccharide, and one or more CP1 fusion proteins non-covalently complexed to the biotinylated polysaccharide;

(43) an immunogenic complex comprising a biotinylated *S. pneumoniae* serotype 16F capsular polysaccharide, and one or more CP1 fusion proteins non-covalently complexed to the biotinylated polysaccharide;

(44) an immunogenic complex comprising a biotinylated *S. pneumoniae* serotype 17A capsular polysaccharide, and one or more CP1 fusion proteins non-covalently complexed to the biotinylated polysaccharide;

(45) an immunogenic complex comprising a biotinylated *S. pneumoniae* serotype 17F capsular polysaccharide, and one or more CP1 fusion proteins non-covalently complexed to the biotinylated polysaccharide;

(46) an immunogenic complex comprising a biotinylated *S. pneumoniae* serotype 18A capsular polysaccharide, and one or more CP1 fusion proteins non-covalently complexed to the biotinylated polysaccharide;
(47) an immunogenic complex comprising a biotinylated *S. pneumoniae* serotype 18B capsular polysaccharide, and one or more CP1 fusion proteins non-covalently complexed to the biotinylated polysaccharide;

(48) an immunogenic complex comprising a biotinylated *S. pneumoniae* serotype 18C capsular polysaccharide, and one or more CP1 fusion proteins non-covalently complexed to the biotinylated polysaccharide;

(49) an immunogenic complex comprising a biotinylated *S. pneumoniae* serotype 18F capsular polysaccharide, and one or more CP1 fusion proteins non-covalently complexed to the biotinylated polysaccharide;

(50) an immunogenic complex comprising a biotinylated *S. pneumoniae* serotype 19A capsular polysaccharide, and one or more CP1 fusion proteins non-covalently complexed to the biotinylated polysaccharide;

(51) an immunogenic complex comprising a biotinylated *S. pneumoniae* serotype 19B capsular polysaccharide, and one or more CP1 fusion proteins non-covalently complexed to the biotinylated polysaccharide;

(52) an immunogenic complex comprising a biotinylated *S. pneumoniae* serotype 19C capsular polysaccharide, and one or more CP1 fusion proteins non-covalently complexed to the biotinylated polysaccharide;

(53) an immunogenic complex comprising a biotinylated *S. pneumoniae* serotype 19F capsular polysaccharide, and one or more CP1 fusion proteins non-covalently complexed to the biotinylated polysaccharide;

(54) an immunogenic complex comprising a biotinylated *S. pneumoniae* serotype 20A capsular polysaccharide, and one or more CP1 fusion proteins non-covalently complexed to the biotinylated polysaccharide;

(55) an immunogenic complex comprising a biotinylated *S. pneumoniae* serotype 20B capsular polysaccharide, and one or more CP1 fusion proteins non-covalently complexed to the biotinylated polysaccharide;

(56) an immunogenic complex comprising a biotinylated *S. pneumoniae* serotype 21 capsular polysaccharide, and one or more CP1 fusion proteins non-covalently complexed to the biotinylated polysaccharide;

(57) an immunogenic complex comprising a biotinylated *S. pneumoniae* serotype 22A capsular polysaccharide, and one or more CP1 fusion proteins non-covalently complexed to the biotinylated polysaccharide;

(58) an immunogenic complex comprising a biotinylated *S. pneumoniae* serotype 22F capsular polysaccharide, and one or more CP1 fusion proteins non-covalently complexed to the biotinylated polysaccharide;

(59) an immunogenic complex comprising a biotinylated *S. pneumoniae* serotype 23A capsular polysaccharide, and one or more CP1 fusion proteins non-covalently complexed to the biotinylated polysaccharide;

(60) an immunogenic complex comprising a biotinylated *S. pneumoniae* serotype 23B capsular polysaccharide, and one or more CP1 fusion proteins non-covalently complexed to the biotinylated polysaccharide;

(61) an immunogenic complex comprising a biotinylated *S. pneumoniae* serotype 23F capsular polysaccharide, and one or more CP1 fusion proteins non-covalently complexed to the biotinylated polysaccharide;

(62) an immunogenic complex comprising a biotinylated *S. pneumoniae* serotype 24A capsular polysaccharide, and one or more CP1 fusion proteins non-covalently complexed to the biotinylated polysaccharide;

(63) an immunogenic complex comprising a biotinylated *S. pneumoniae* serotype 24B capsular polysaccharide, and one or more CP1 fusion proteins non-covalently complexed to the biotinylated polysaccharide;

(64) an immunogenic complex comprising a biotinylated *S. pneumoniae* serotype 24F capsular polysaccharide, and one or more CP1 fusion proteins non-covalently complexed to the biotinylated polysaccharide;

(65) an immunogenic complex comprising a biotinylated *S. pneumoniae* serotype 25A capsular polysaccharide, and one or more CP1 fusion proteins non-covalently complexed to the biotinylated polysaccharide;

(66) an immunogenic complex comprising a biotinylated *S. pneumoniae* serotype 25F capsular polysaccharide, and one or more CP1 fusion proteins non-covalently complexed to the biotinylated polysaccharide;

(67) an immunogenic complex comprising a biotinylated *S. pneumoniae* serotype 27 capsular polysaccharide, and one or more CP1 fusion proteins non-covalently complexed to the biotinylated polysaccharide;

(68) an immunogenic complex comprising a biotinylated *S. pneumoniae* serotype 28A capsular polysaccharide, and one or more CP1 fusion proteins non-covalently complexed to the biotinylated polysaccharide;

(69) an immunogenic complex comprising a biotinylated *S. pneumoniae* serotype 28F capsular polysaccharide, and one or more CP1 fusion proteins non-covalently complexed to the biotinylated polysaccharide;

(70) an immunogenic complex comprising a biotinylated *S. pneumoniae* serotype 29 capsular polysaccharide, and one or more CP1 fusion proteins non-covalently complexed to the biotinylated polysaccharide;

(71) an immunogenic complex comprising a biotinylated *S. pneumoniae* serotype 31 capsular polysaccharide, and one or more CP1 fusion proteins non-covalently complexed to the biotinylated polysaccharide;

(72) an immunogenic complex comprising a biotinylated *S. pneumoniae* serotype 32A capsular polysaccharide, and one or more CP1 fusion proteins non-covalently complexed to the biotinylated polysaccharide;

(73) an immunogenic complex comprising a biotinylated *S. pneumoniae* serotype 32F capsular polysaccharide, and one or more CP1 fusion proteins non-covalently complexed to the biotinylated polysaccharide;

(74) an immunogenic complex comprising a biotinylated *S. pneumoniae* serotype 33A capsular polysaccharide, and one or more CP1 fusion proteins non-covalently complexed to the biotinylated polysaccharide;

(75) an immunogenic complex comprising a biotinylated *S. pneumoniae* serotype 33B capsular polysaccharide, and one or more CP1 fusion proteins non-covalently complexed to the biotinylated polysaccharide;

(76) an immunogenic complex comprising a biotinylated *S. pneumoniae* serotype 33C capsular polysaccharide, and one or more CP1 fusion proteins non-covalently complexed to the biotinylated polysaccharide;

(77) an immunogenic complex comprising a biotinylated *S. pneumoniae* serotype 33D capsular polysaccharide, and one or more CP1 fusion proteins non-covalently complexed to the biotinylated polysaccharide;

(78) an immunogenic complex comprising a biotinylated *S. pneumoniae* serotype 33E capsular polysaccharide, and one or more CP1 fusion proteins non-covalently complexed to the biotinylated polysaccharide;

(79) an immunogenic complex comprising a biotinylated *S. pneumoniae* serotype 33F capsular polysaccharide, and one or more CP1 fusion proteins non-covalently complexed to the biotinylated polysaccharide;
(80) an immunogenic complex comprising a biotinylated S. pneumoniae serotype 34 capsular polysaccharide, and one or more CP1 fusion proteins non-covalently complexed to the biotinylated polysaccharide;
(81) an immunogenic complex comprising a biotinylated S. pneumoniae serotype 35A capsular polysaccharide, and one or more CP1 fusion proteins non-covalently complexed to the biotinylated polysaccharide;
(82) an immunogenic complex comprising a biotinylated S. pneumoniae serotype 35B capsular polysaccharide, and one or more CP1 fusion proteins non-covalently complexed to the biotinylated polysaccharide;
(83) an immunogenic complex comprising a biotinylated S. pneumoniae serotype 35C capsular polysaccharide, and one or more CP1 fusion proteins non-covalently complexed to the biotinylated polysaccharide;
(84) an immunogenic complex comprising a biotinylated S. pneumoniae serotype 35F capsular polysaccharide, and one or more CP1 fusion proteins non-covalently complexed to the biotinylated polysaccharide;
(85) an immunogenic complex comprising a biotinylated S. pneumoniae serotype 36 capsular polysaccharide, and one or more CP1 fusion proteins non-covalently complexed to the biotinylated polysaccharide;
(86) an immunogenic complex comprising a biotinylated S. pneumoniae serotype 37 capsular polysaccharide, and one or more CP1 fusion proteins non-covalently complexed to the biotinylated polysaccharide;
(87) an immunogenic complex comprising a biotinylated S. pneumoniae serotype 38 capsular polysaccharide, and one or more CP1 fusion proteins non-covalently complexed to the biotinylated polysaccharide;
(88) an immunogenic complex comprising a biotinylated S. pneumoniae serotype 39 capsular polysaccharide, and one or more CP1 fusion proteins non-covalently complexed to the biotinylated polysaccharide;
(89) an immunogenic complex comprising a biotinylated S. pneumoniae serotype 40 capsular polysaccharide, and one or more CP1 fusion proteins non-covalently complexed to the biotinylated polysaccharide;
(90) an immunogenic complex comprising a biotinylated S. pneumoniae serotype 41A capsular polysaccharide, and one or more CP1 fusion proteins non-covalently complexed to the biotinylated polysaccharide;
(91) an immunogenic complex comprising a biotinylated S. pneumoniae serotype 41F capsular polysaccharide, and one or more CP1 fusion proteins non-covalently complexed to the biotinylated polysaccharide;
(92) an immunogenic complex comprising a biotinylated S. pneumoniae serotype 42 capsular polysaccharide, and one or more CP1 fusion proteins non-covalently complexed to the biotinylated polysaccharide;
(93) an immunogenic complex comprising a biotinylated S. pneumoniae serotype 43 capsular polysaccharide, and one or more CP1 fusion proteins non-covalently complexed to the biotinylated polysaccharide;
(94) an immunogenic complex comprising a biotinylated S. pneumoniae serotype 44 capsular polysaccharide, and one or more CP1 fusion proteins non-covalently complexed to the biotinylated polysaccharide;
(95) an immunogenic complex comprising a biotinylated S. pneumoniae serotype 45 capsular polysaccharide, and one or more CP1 fusion proteins non-covalently complexed to the biotinylated polysaccharide;
(96) an immunogenic complex comprising a biotinylated S. pneumoniae serotype 46 capsular polysaccharide, and one or more CP1 fusion proteins non-covalently complexed to the biotinylated polysaccharide;
(97) an immunogenic complex comprising a biotinylated S. pneumoniae serotype 47A capsular polysaccharide, and one or more CP1 fusion proteins non-covalently complexed to the biotinylated polysaccharide;
(98) an immunogenic complex comprising a biotinylated S. pneumoniae serotype 47F capsular polysaccharide, and one or more CP1 fusion proteins non-covalently complexed to the biotinylated polysaccharide; and
(99) an immunogenic complex comprising a biotinylated S. pneumoniae serotype 48 capsular polysaccharide, and one or more CP1 fusion proteins non-covalently complexed to the biotinylated polysaccharide.

In some embodiments, a vaccine composition comprises two or more (e.g., 2, 3, 4, 5, 6, 7, 8, 9, 10, 15, 20, 21, 22, 23, or 24) species of immunogenic complexes selected from:
(1) an immunogenic complex comprising a biotinylated S. pneumoniae serotype 1 capsular polysaccharide, and one or more CP1 fusion proteins non-covalently complexed to the biotinylated polysaccharide;
(2) an immunogenic complex comprising a biotinylated S. pneumoniae serotype 2 capsular polysaccharide, and one or more CP1 fusion proteins non-covalently complexed to the biotinylated polysaccharide;
(3) an immunogenic complex comprising a biotinylated S. pneumoniae serotype 3 capsular polysaccharide, and one or more CP1 fusion proteins non-covalently complexed to the biotinylated polysaccharide;
(4) an immunogenic complex comprising a biotinylated S. pneumoniae serotype 4 capsular polysaccharide, and one or more CP1 fusion proteins non-covalently complexed to the biotinylated polysaccharide;
(5) an immunogenic complex comprising a biotinylated S. pneumoniae serotype 5 capsular polysaccharide, and one or more CP1 fusion proteins non-covalently complexed to the biotinylated polysaccharide;
(6) an immunogenic complex comprising a biotinylated S. pneumoniae serotype 6A capsular polysaccharide, and one or more CP1 fusion proteins non-covalently complexed to the biotinylated polysaccharide;
(7) an immunogenic complex comprising a biotinylated S. pneumoniae serotype 6B capsular polysaccharide, and one or more CP1 fusion proteins non-covalently complexed to the biotinylated polysaccharide;
(8) an immunogenic complex comprising a biotinylated S. pneumoniae serotype 7F capsular polysaccharide, and one or more CP1 fusion proteins non-covalently complexed to the biotinylated polysaccharide;
(9) an immunogenic complex comprising a biotinylated S. pneumoniae serotype 8 capsular polysaccharide, and one or more CP1 fusion proteins non-covalently complexed to the biotinylated polysaccharide;
(10) an immunogenic complex comprising a biotinylated S. pneumoniae serotype 9N capsular polysaccharide, and one or more CP1 fusion proteins non-covalently complexed to the biotinylated polysaccharide;
(11) an immunogenic complex comprising a biotinylated S. pneumoniae serotype 9V capsular polysaccharide, and one or more CP1 fusion proteins non-covalently complexed to the biotinylated polysaccharide;
(12) an immunogenic complex comprising a biotinylated S. pneumoniae serotype 10A capsular polysaccharide, and one or more CP1 fusion proteins non-covalently complexed to the biotinylated polysaccharide;

(13) an immunogenic complex comprising a biotinylated *S. pneumoniae* serotype 11A capsular polysaccharide, and one or more CP1 fusion proteins non-covalently complexed to the biotinylated polysaccharide;
(14) an immunogenic complex comprising a biotinylated *S. pneumoniae* serotype 12F capsular polysaccharide, and one or more CP1 fusion proteins non-covalently complexed to the biotinylated polysaccharide;
(15) an immunogenic complex comprising a biotinylated *S. pneumoniae* serotype 14 capsular polysaccharide, and one or more CP1 fusion proteins non-covalently complexed to the biotinylated polysaccharide;
(16) an immunogenic complex comprising a biotinylated *S. pneumoniae* serotype 15B capsular polysaccharide, and one or more CP1 fusion proteins non-covalently complexed to the biotinylated polysaccharide;
(17) an immunogenic complex comprising a biotinylated *S. pneumoniae* serotype 17F capsular polysaccharide, and one or more CP1 fusion proteins non-covalently complexed to the biotinylated polysaccharide;
(18) an immunogenic complex comprising a biotinylated *S. pneumoniae* serotype 18C capsular polysaccharide, and one or more CP1 fusion proteins non-covalently complexed to the biotinylated polysaccharide;
(19) an immunogenic complex comprising a biotinylated *S. pneumoniae* serotype 19A capsular polysaccharide, and one or more CP1 fusion proteins non-covalently complexed to the biotinylated polysaccharide;
(20) an immunogenic complex comprising a biotinylated *S. pneumoniae* serotype 19F capsular polysaccharide, and one or more CP1 fusion proteins non-covalently complexed to the biotinylated polysaccharide;
(21) an immunogenic complex comprising a biotinylated *S. pneumoniae* serotype 20B capsular polysaccharide, and one or more CP1 fusion proteins non-covalently complexed to the biotinylated polysaccharide;
(22) an immunogenic complex comprising a biotinylated *S. pneumoniae* serotype 22F capsular polysaccharide, and one or more CP1 fusion proteins non-covalently complexed to the biotinylated polysaccharide;
(23) an immunogenic complex comprising a biotinylated *S. pneumoniae* serotype 23F capsular polysaccharide, and one or more CP1 fusion proteins non-covalently complexed to the biotinylated polysaccharide; and
(24) an immunogenic complex comprising a biotinylated *S. pneumoniae* serotype 33F capsular polysaccharide, and one or more CP1 fusion proteins non-covalently complexed to the biotinylated polysaccharide.

In some embodiments, a vaccine composition comprises two or more (e.g., 2, 3, 4, 5, 6, 7, 8, 9, 10, 11, 12, 13, 14, or 15) species of immunogenic complexes selected from:
(1) an immunogenic complex comprising a biotinylated *S. pneumoniae* serotype 1 capsular polysaccharide, and one or more CP1 fusion proteins non-covalently complexed to the biotinylated polysaccharide;
(2) an immunogenic complex comprising a biotinylated *S. pneumoniae* serotype 3 capsular polysaccharide, and one or more CP1 fusion proteins non-covalently complexed to the biotinylated polysaccharide;
(3) an immunogenic complex comprising a biotinylated *S. pneumoniae* serotype 4 capsular polysaccharide, and one or more CP1 fusion proteins non-covalently complexed to the biotinylated polysaccharide;
(4) an immunogenic complex comprising a biotinylated *S. pneumoniae* serotype 5 capsular polysaccharide, and one or more CP1 fusion proteins non-covalently complexed to the biotinylated polysaccharide;
(5) an immunogenic complex comprising a biotinylated *S. pneumoniae* serotype 6A capsular polysaccharide, and one or more CP1 fusion proteins non-covalently complexed to the biotinylated polysaccharide;
(6) an immunogenic complex comprising a biotinylated *S. pneumoniae* serotype 6B capsular polysaccharide, and one or more CP1 fusion proteins non-covalently complexed to the biotinylated polysaccharide;
(7) an immunogenic complex comprising a biotinylated *S. pneumoniae* serotype 7F capsular polysaccharide, and one or more CP1 fusion proteins non-covalently complexed to the biotinylated polysaccharide;
(8) an immunogenic complex comprising a biotinylated *S. pneumoniae* serotype 9V capsular polysaccharide, and one or more CP1 fusion proteins non-covalently complexed to the biotinylated polysaccharide;
(9) an immunogenic complex comprising a biotinylated *S. pneumoniae* serotype 14 capsular polysaccharide, and one or more CP1 fusion proteins non-covalently complexed to the biotinylated polysaccharide;
(10) an immunogenic complex comprising a biotinylated *S. pneumoniae* serotype 18C capsular polysaccharide, and one or more CP1 fusion proteins non-covalently complexed to the biotinylated polysaccharide;
(11) an immunogenic complex comprising a biotinylated *S. pneumoniae* serotype 19A capsular polysaccharide, and one or more CP1 fusion proteins non-covalently complexed to the biotinylated polysaccharide;
(12) an immunogenic complex comprising a biotinylated *S. pneumoniae* serotype 19F capsular polysaccharide, and one or more CP1 fusion proteins non-covalently complexed to the biotinylated polysaccharide;
(13) an immunogenic complex comprising a biotinylated *S. pneumoniae* serotype 22F capsular polysaccharide, and one or more CP1 fusion proteins non-covalently complexed to the biotinylated polysaccharide;
(14) an immunogenic complex comprising a biotinylated *S. pneumoniae* serotype 23F capsular polysaccharide, and one or more CP1 fusion proteins non-covalently complexed to the biotinylated polysaccharide; and
(15) an immunogenic complex comprising a biotinylated *S. pneumoniae* serotype 33F capsular polysaccharide, and one or more CP1 fusion proteins non-covalently complexed to the biotinylated polysaccharide.

In some embodiments, a vaccine composition comprises two or more (e.g., 2, 3, 4, 5, 6, 7, 8, or 9) species of immunogenic complexes selected from:
(1) an immunogenic complex comprising a biotinylated *S. pneumoniae* serotype 2 capsular polysaccharide, and one or more CP1 fusion proteins non-covalently complexed to the biotinylated polysaccharide;
(2) an immunogenic complex comprising a biotinylated *S. pneumoniae* serotype 8 capsular polysaccharide, and one or more CP1 fusion proteins non-covalently complexed to the biotinylated polysaccharide;
(3) an immunogenic complex comprising a biotinylated *S. pneumoniae* serotype 9N capsular polysaccharide, and one or more CP1 fusion proteins non-covalently complexed to the biotinylated polysaccharide;
(4) an immunogenic complex comprising a biotinylated *S. pneumoniae* serotype 10A capsular polysaccharide, and one or more CP1 fusion proteins non-covalently complexed to the biotinylated polysaccharide;
(5) an immunogenic complex comprising a biotinylated *S. pneumoniae* serotype 11A capsular polysaccharide, and one or more CP1 fusion proteins non-covalently complexed to the biotinylated polysaccharide;

(6) an immunogenic complex comprising a biotinylated *S. pneumoniae* serotype 12F capsular polysaccharide, and one or more CP1 fusion proteins non-covalently complexed to the biotinylated polysaccharide;
(7) an immunogenic complex comprising a biotinylated *S. pneumoniae* serotype 15B capsular polysaccharide, and one or more CP1 fusion proteins non-covalently complexed to the biotinylated polysaccharide;
(8) an immunogenic complex comprising a biotinylated *S. pneumoniae* serotype 17F capsular polysaccharide, and one or more CP1 fusion proteins non-covalently complexed to the biotinylated polysaccharide; and
(9) an immunogenic complex comprising a biotinylated *S. pneumoniae* serotype 20B capsular polysaccharide, and one or more CP1 fusion proteins non-covalently complexed to the biotinylated polysaccharide.

In some embodiments, a vaccine composition comprises:
(1) a first immunogenic complex comprising a biotinylated *S. pneumoniae* serotype 1 capsular polysaccharide, and one or more CP1 fusion proteins non-covalently complexed to the biotinylated polysaccharide;
(2) a second immunogenic complex comprising a biotinylated *S. pneumoniae* serotype 2 capsular polysaccharide, and one or more CP1 fusion proteins non-covalently complexed to the biotinylated polysaccharide;
(3) a third immunogenic complex comprising a biotinylated *S. pneumoniae* serotype 3 capsular polysaccharide, and one or more CP1 fusion proteins non-covalently complexed to the biotinylated polysaccharide;
(4) a fourth immunogenic complex comprising a biotinylated *S. pneumoniae* serotype 4 capsular polysaccharide, and one or more CP1 fusion proteins non-covalently complexed to the biotinylated polysaccharide;
(5) a fifth immunogenic complex comprising a biotinylated *S. pneumoniae* serotype 5 capsular polysaccharide, and one or more CP1 fusion proteins non-covalently complexed to the biotinylated polysaccharide;
(6) a sixth immunogenic complex comprising a biotinylated *S. pneumoniae* serotype 6A capsular polysaccharide, and one or more CP1 fusion proteins non-covalently complexed to the biotinylated polysaccharide;
(7) a seventh immunogenic complex comprising a biotinylated *S. pneumoniae* serotype 6B capsular polysaccharide, and one or more CP1 fusion proteins non-covalently complexed to the biotinylated polysaccharide;
(8) an eighth immunogenic complex comprising a biotinylated *S. pneumoniae* serotype 7F capsular polysaccharide, and one or more CP1 fusion proteins non-covalently complexed to the biotinylated polysaccharide;
(9) a ninth immunogenic complex comprising a biotinylated *S. pneumoniae* serotype 8 capsular polysaccharide, and one or more CP1 fusion proteins non-covalently complexed to the biotinylated polysaccharide;
(10) a tenth immunogenic complex comprising a biotinylated *S. pneumoniae* serotype 9N capsular polysaccharide, and one or more CP1 fusion proteins non-covalently complexed to the biotinylated polysaccharide;
(11) an eleventh immunogenic complex comprising a biotinylated *S. pneumoniae* serotype 9V capsular polysaccharide, and one or more CP1 fusion proteins non-covalently complexed to the biotinylated polysaccharide;
(12) a twelfth immunogenic complex comprising a biotinylated *S. pneumoniae* serotype 10A capsular polysaccharide, and one or more CP1 fusion proteins non-covalently complexed to the biotinylated polysaccharide;
(13) a thirteenth immunogenic complex comprising a biotinylated *S. pneumoniae* serotype 11A capsular polysaccharide, and one or more CP1 fusion proteins non-covalently complexed to the biotinylated polysaccharide;
(14) a fourteenth immunogenic complex comprising a biotinylated *S. pneumoniae* serotype 12F capsular polysaccharide, and one or more CP1 fusion proteins non-covalently complexed to the biotinylated polysaccharide;
(15) a fifteenth immunogenic complex comprising a biotinylated *S. pneumoniae* serotype 14 capsular polysaccharide, and one or more CP1 fusion proteins non-covalently complexed to the biotinylated polysaccharide;
(16) a sixteenth immunogenic complex comprising a biotinylated *S. pneumoniae* serotype 15B capsular polysaccharide, and one or more CP1 fusion proteins non-covalently complexed to the biotinylated polysaccharide;
(17) a seventeenth immunogenic complex comprising a biotinylated *S. pneumoniae* serotype 17F capsular polysaccharide, and one or more CP1 fusion proteins non-covalently complexed to the biotinylated polysaccharide;
(18) an eighteenth immunogenic complex comprising a biotinylated *S. pneumoniae* serotype 18C capsular polysaccharide, and one or more CP1 fusion proteins non-covalently complexed to the biotinylated polysaccharide;
(19) a nineteenth immunogenic complex comprising a biotinylated *S. pneumoniae* serotype 19A capsular polysaccharide, and one or more CP1 fusion proteins non-covalently complexed to the biotinylated polysaccharide;
(20) a twentieth immunogenic complex comprising a biotinylated *S. pneumoniae* serotype 19F capsular polysaccharide, and one or more CP1 fusion proteins non-covalently complexed to the biotinylated polysaccharide;
(21) a twenty-first immunogenic complex comprising a biotinylated *S. pneumoniae* serotype 20B capsular polysaccharide, and one or more CP1 fusion proteins non-covalently complexed to the biotinylated polysaccharide;
(22) a twenty-second immunogenic complex comprising a biotinylated *S. pneumoniae* serotype 22F capsular polysaccharide, and one or more CP1 fusion proteins non-covalently complexed to the biotinylated polysaccharide;
(23) a twenty-third immunogenic complex comprising a biotinylated *S. pneumoniae* serotype 23F capsular polysaccharide, and one or more CP1 fusion proteins non-covalently complexed to the biotinylated polysaccharide; and
(24) a twenty-fourth immunogenic complex comprising a biotinylated *S. pneumoniae* serotype 33F capsular polysaccharide, and one or more CP1 fusion proteins non-covalently complexed to the biotinylated polysaccharide.

In some embodiments, a vaccine composition comprises:
(1) a first immunogenic complex comprising a biotinylated *S. pneumoniae* serotype 1 capsular polysaccharide, and one or more CP1 fusion proteins non-covalently complexed to the biotinylated polysaccharide;

(2) a second immunogenic complex comprising a biotinylated *S. pneumoniae* serotype 3 capsular polysaccharide, and one or more CP1 fusion proteins non-covalently complexed to the biotinylated polysaccharide;

(3) a third immunogenic complex comprising a biotinylated *S. pneumoniae* serotype 4 capsular polysaccharide, and one or more CP1 fusion proteins non-covalently complexed to the biotinylated polysaccharide;

(4) a fourth immunogenic complex comprising a biotinylated *S. pneumoniae* serotype 5 capsular polysaccharide, and one or more CP1 fusion proteins non-covalently complexed to the biotinylated polysaccharide;

(5) a fifth immunogenic complex comprising a biotinylated *S. pneumoniae* serotype 6A capsular polysaccharide, and one or more CP1 fusion proteins non-covalently complexed to the biotinylated polysaccharide;

(6) a sixth immunogenic complex comprising a biotinylated *S. pneumoniae* serotype 6B capsular polysaccharide, and one or more CP1 fusion proteins non-covalently complexed to the biotinylated polysaccharide;

(7) a seventh immunogenic complex comprising a biotinylated *S. pneumoniae* serotype 7F capsular polysaccharide, and one or more CP1 fusion proteins non-covalently complexed to the biotinylated polysaccharide;

(8) an eighth immunogenic complex comprising a biotinylated *S. pneumoniae* serotype 8 capsular polysaccharide, and one or more CP1 fusion proteins non-covalently complexed to the biotinylated polysaccharide;

(9) a ninth immunogenic complex comprising a biotinylated *S. pneumoniae* serotype 14 capsular polysaccharide, and one or more CP1 fusion proteins non-covalently complexed to the biotinylated polysaccharide;

(10) a tenth immunogenic complex comprising a biotinylated *S. pneumoniae* serotype 18C capsular polysaccharide, and one or more CP1 fusion proteins non-covalently complexed to the biotinylated polysaccharide;

(11) an eleventh immunogenic complex comprising a biotinylated *S. pneumoniae* serotype 19A capsular polysaccharide, and one or more CP1 fusion proteins non-covalently complexed to the biotinylated polysaccharide;

(12) a twelfth immunogenic complex comprising a biotinylated *S. pneumoniae* serotype 19F capsular polysaccharide, and one or more CP1 fusion proteins non-covalently complexed to the biotinylated polysaccharide;

(13) a thirteenth immunogenic complex comprising a biotinylated *S. pneumoniae* serotype 22F capsular polysaccharide, and one or more CP1 fusion proteins non-covalently complexed to the biotinylated polysaccharide;

(14) a fourteenth immunogenic complex comprising a biotinylated *S. pneumoniae* serotype 23F capsular polysaccharide, and one or more CP1 fusion proteins non-covalently complexed to the biotinylated polysaccharide; and

(15) a fifteenth immunogenic complex comprising a biotinylated *S. pneumoniae* serotype 33F capsular polysaccharide, and one or more CP1 fusion proteins non-covalently complexed to the biotinylated polysaccharide.

In some embodiments, a vaccine composition comprises:

(1) a first immunogenic complex comprising a biotinylated *S. pneumoniae* serotype 2 capsular polysaccharide, and one or more CP1 fusion proteins non-covalently complexed to the biotinylated polysaccharide;

(2) a second immunogenic complex comprising a biotinylated *S. pneumoniae* serotype 8 capsular polysaccharide, and one or more CP1 fusion proteins non-covalently complexed to the biotinylated polysaccharide;

(3) a third immunogenic complex comprising a biotinylated *S. pneumoniae* serotype 9N capsular polysaccharide, and one or more CP1 fusion proteins non-covalently complexed to the biotinylated polysaccharide;

(4) a fourth immunogenic complex comprising a biotinylated *S. pneumoniae* serotype 10A capsular polysaccharide, and one or more CP1 fusion proteins non-covalently complexed to the biotinylated polysaccharide;

(5) a fifth immunogenic complex comprising a biotinylated *S. pneumoniae* serotype 11A capsular polysaccharide, and one or more CP1 fusion proteins non-covalently complexed to the biotinylated polysaccharide;

(6) a sixth immunogenic complex comprising a biotinylated *S. pneumoniae* serotype 12F capsular polysaccharide, and one or more CP1 fusion proteins non-covalently complexed to the biotinylated polysaccharide;

(7) a seventh immunogenic complex comprising a biotinylated *S. pneumoniae* serotype 15B capsular polysaccharide, and one or more CP1 fusion proteins non-covalently complexed to the biotinylated polysaccharide;

(8) an eighth immunogenic complex comprising a biotinylated *S. pneumoniae* serotype 17F capsular polysaccharide, and one or more CP1 fusion proteins non-covalently complexed to the biotinylated polysaccharide; and (9) a ninth immunogenic complex comprising a biotinylated *S. pneumoniae* serotype 20B capsular polysaccharide, and one or more CP1 fusion proteins non-covalently complexed to the biotinylated polysaccharide.

Conjugated Immunogenic Complexes; Immunogenic and Vaccine Compositions Comprising Same In some embodiments, one or more polypeptides (e.g., antigenic polypeptides) of immunogenic complexes are conjugated to one or more polysaccharides. In some embodiments, one or more conjugated polysaccharides comprise a capsular polysaccharide of *S. pneumoniae*. In some embodiments, one or more polypeptides of conjugated immunogenic complex comprise an antigenic polypeptide of *S. pneumoniae*. In some embodiments, an antigenic polypeptide of a conjugated immunogenic complex is or comprises a fusion protein. In some such embodiments, a fusion protein of a conjugated immunogenic complex is or comprises CP1 fusion protein.

In some embodiments, a conjugated immunogenic complex comprises one or more *S. pneumoniae* capsular polysaccharides from, or derived from, one or more *S. pneumoniae* serotypes selected from 1, 2, 3, 4, 5, 6A, 6B, 6C, 6D, 6E, 6F, 6G, 6H, 7A, 7B, 7C, 7F, 8, 9A, 9L, 9N, 9V, 10A, 10B, 10C, 10F, 11A, 11B, 11C, 11D, 11E, 11F, 12A, 12B, 12F, 13, 14, 15A, 15B, 15C, 15F, 16A, 16F, 17A, 17F, 18A, 18B, 18C, 18F, 19A, 19B, 19C, 19F, 20A, 20B, 21, 22A, 22F, 23A, 23B, 23F, 24A, 24B, 24F, 25A, 25F, 27, 28A, 28F, 29, 31, 32A, 32F, 33A, 33B, 33C, 33D, 33E, 33F, 34, 35A, 35B, 35C, 35F, 36, 37, 38, 39, 40, 41A, 41F, 42, 43, 44, 45, 46, 47A, 47F, and 48. In some embodiments, a conjugated immunogenic complex comprises one or more S. pneumoniae capsular polysaccharides from, or derived from, one or more S. pneumoniae serotypes selected from 1, 2, 3, 4, 5, 6A, 6B, 7F, 8, 9N, 9V, 10A, 11A, 12F, 14, 15B, 17F, 18C, 19A, 19F, 20B, 22F, 23F, and 33F. In some embodiments, an immunogenic complex comprises one or more S. pneumoniae capsular polysaccharides from, or derived from, one or more S. pneumoniae serotypes selected from 1, 3, 4, 5, 6A, 6B, 7F, 9V, 14, 18C, 19A, 19F, 22F, 23F, and 33F. In some embodiments, an immunogenic complex comprises one or more S. pneumoniae capsular polysaccharides from, or derived from, one or more S. pneumoniae serotypes selected from 2, 8, 9N, 10A, 11A, 12F, 15B, 17F, and 20B.

In some embodiments, a conjugated immunogenic complex comprises:
(a) one or more CP1 proteins; and
(b) one or more S. pneumoniae capsular polysaccharides from, or derived from, one or more S. pneumoniae serotypes selected from 1, 2, 3, 4, 5, 6A, 6B, 6C, 6D, 6E, 6F, 6G, 6H, 7A, 7B, 7C, 7F, 8, 9A, 9L, 9N, 9V, 10A, 10B, 10C, 10F, 11A, 11B, 11C, 11D, 11E, 11F, 12A, 12B, 12F, 13, 14, 15A, 15B, 15C, 15F, 16A, 16F, 17A, 17F, 18A, 18B, 18C, 18F, 19A, 19B, 19C, 19F, 20A, 20B, 21, 22A, 22F, 23A, 23B, 23F, 24A, 24B, 24F, 25A, 25F, 27, 28A, 28F, 29, 31, 32A, 32F, 33A, 33B, 33C, 33D, 33E, 33F, 34, 35A, 35B, 35C, 35F, 36, 37, 38, 39, 40, 41A, 41F, 42, 43, 44, 45, 46, 47A, 47F, and 48, wherein the one or more CP1 proteins are covalently attached to the one or more polysaccharides.

In some embodiments, a conjugated immunogenic complex comprises:
(a) one or more CP1 proteins; and
(b) one or more S. pneumoniae capsular polysaccharides from, or are derived, one or more S. pneumoniae serotypes selected from 1, 2, 3, 4, 5, 6A, 6B, 7F, 8, 9N, 9V, 10A, 11A, 12F, 14, 15B, 17F, 18C, 19A, 19F, 20B, 22F, 23F, and 33F, wherein the one or more CP1 proteins are covalently attached to the one or more polysaccharides.

In some embodiments, a conjugated immunogenic complex comprises:
(a) one or more CP1 proteins; and
(b) one or more S. pneumoniae capsular polysaccharides from, or derived from, one or more S. pneumoniae serotypes selected from 1, 3, 4, 5, 6A, 6B, 7F, 9V, 14, 18C, 19A, 19F, 22F, 23F, and 33F, wherein the one or more CP1 proteins are covalently attached to the one or more polysaccharides.

In some embodiments, a conjugated immunogenic complex comprises:
(a) one or more CP1 proteins; and
(b) one or more S. pneumoniae capsular polysaccharides from, or derived from, one or more S. pneumoniae serotypes selected from 2, 8, 9N, 10A, 11A, 12F, 15B, 17F, and 20B, wherein the one or more CP1 proteins are covalently attached to the one or more polysaccharides.

In some embodiments, an immunogenic composition comprises one or more conjugated immunogenic complexes comprising:
(a) one or more CP1 proteins; and
(b) one or more S. pneumoniae capsular polysaccharides from, or derived from, one or more S. pneumoniae serotypes selected from 1, 2, 3, 4, 5, 6A, 6B, 6C, 6D, 6E, 6F, 6G, 6H, 7A, 7B, 7C, 7F, 8, 9A, 9L, 9N, 9V, 10A, 10B, 10C, 10F, 11A, 11B, 11C, 11D, 11E, 11F, 12A, 12B, 12F, 13, 14, 15A, 15B, 15C, 15F, 16A, 16F, 17A, 17F, 18A, 18B, 18C, 18F, 19A, 19B, 19C, 19F, 20A, 20B, 21, 22A, 22F, 23A, 23B, 23F, 24A, 24B, 24F, 25A, 25F, 27, 28A, 28F, 29, 31, 32A, 32F, 33A, 33B, 33C, 33D, 33E, 33F, 34, 35A, 35B, 35C, 35F, 36, 37, 38, 39, 40, 41A, 41F, 42, 43, 44, 45, 46, 47A, 47F, and 48, wherein the one or more CP1 proteins are covalently attached to the one or more polysaccharides.

In some embodiments, an immunogenic composition comprises one or more conjugated immunogenic complexes comprising:
(a) one or more CP1 proteins; and
(b) one or more S. pneumoniae capsular polysaccharides from, or derived from, one or more S. pneumoniae serotypes selected from 1, 2, 3, 4, 5, 6A, 6B, 7F, 8, 9N, 9V, 10A, 11A, 12F, 14, 15B, 17F, 18C, 19A, 19F, 20B, 22F, 23F, and 33F, wherein the one or more CP1 proteins are covalently attached to the one or more polysaccharides.

In some embodiments, an immunogenic composition comprises one or more conjugated immunogenic complexes comprising:
(a) one or more CP1 proteins; and
(b) one or more S. pneumoniae capsular polysaccharides from, or derived from, one or more S. pneumoniae serotypes selected from 1, 3, 4, 5, 6A, 6B, 7F, 9V, 14, 18C, 19A, 19F, 22F, 23F, and 33F, wherein the one or more CP1 proteins are covalently attached to the one or more polysaccharides.

In some embodiments, an immunogenic composition comprises one or more conjugated immunogenic complexes comprising:
(a) one or more CP1 proteins; and
(b) one or more S. pneumoniae capsular polysaccharides from, or derived from, one or more S. pneumoniae serotypes selected from 2, 8, 9N, 10A, 11A, 12F, 15B, 17F, and 20B, wherein the one or more CP1 proteins are covalently attached to the one or more polysaccharides.

In some embodiments, a vaccine composition comprises one or more conjugated immunogenic complexes comprising:
(a) one or more CP1 protein; and
(b) one or more S. pneumoniae capsular polysaccharides from, or derived from, one or more S. pneumoniae serotypes selected from 1, 2, 3, 4, 5, 6A, 6B, 6C, 6D, 6E, 6F, 6G, 6H, 7A, 7B, 7C, 7F, 8, 9A, 9L, 9N, 9V, 10A, 10B, 10C, 10F, 11A, 11B, 11C, 11D, 11E, 11F, 12A, 12B, 12F, 13, 14, 15A, 15B, 15C, 15F, 16A, 16F, 17A, 17F, 18A, 18B, 18C, 18F, 19A, 19B, 19C, 19F, 20A, 20B, 21, 22A, 22F, 23A, 23B, 23F, 24A, 24B, 24F, 25A, 25F, 27, 28A, 28F, 29, 31, 32A, 32F, 33A, 33B, 33C, 33D, 33E, 33F, 34, 35A, 35B, 35C, 35F, 36, 37, 38, 39, 40, 41A, 41F, 42, 43, 44, 45, 46, 47A, 47F, and 48, wherein the one or more CP1 proteins are covalently attached to the one or more polysaccharides.

In some embodiments, a vaccine composition comprises one or more conjugated immunogenic complexes comprising:
(a) one or more CP1 proteins; and
(b) one or more *S. pneumoniae* capsular polysaccharides from, or derived from, one or more *S. pneumoniae* serotypes selected from 1, 2, 3, 4, 5, 6A, 6B, 7F, 8, 9N, 9V, 10A, 11A, 12F, 14, 15B, 17F, 18C, 19A, 19F, 20B, 22F, 23F, and 33F, wherein the one or more CP1 proteins are covalently attached to the one or more polysaccharides.

In some embodiments, a vaccine composition comprises one or more conjugated immunogenic complexes comprising:
(a) one or more CP1 proteins; and
(b) one or more *S. pneumoniae* capsular polysaccharides from, or derived from, one or more *S. pneumoniae* serotypes selected from 1, 3, 4, 5, 6A, 6B, 7F, 9V, 14, 18C, 19A, 19F, 22F, 23F, and 33F, wherein the one or more CP1 proteins are covalently attached to the one or more polysaccharides.

In some embodiments, a vaccine composition comprises one or more conjugated immunogenic complexes comprising:

(a) one or more CP1 proteins; and
(b) one or more *S. pneumoniae* capsular polysaccharides from, or derived from, one or more *S. pneumoniae* serotypes selected from 2, 8, 9N, 10A, 11A, 12F, 15B, 17F, and 20B, wherein the one or more CP1 proteins are covalently attached to the one or more polysaccharides.

Uses of Immunogenic and Vaccine Compositions

In some embodiments, an immunogenic complex described herein that includes one or more antigenic polysaccharides is characterized in that one or more of the opsonization potential, or immune response to one or more antigenic polysaccharides is increased relative to a predetermined level, as measured by ELISA and or by a functional antibody assay. In some embodiments, one or more of the opsonization potential, immune response to the one or more antigenic polysaccharides is increased at least 1-fold, 2-fold, 3-fold, 4-fold, or 5-fold relative to a predetermined level, as measured by ELISA and or by a functional antibody assay. In some embodiments, the predetermined level is a pre-immune level. In some embodiments, the predetermined level is a pre-immune level. In some embodiments, one or more polypeptide antigens are carrier proteins for one or more antigenic polysaccharides.

In some embodiments, an immunogenic complex described herein, upon administration to a subject, induces an immune response against one or more pathogens in the subject at a level greater than a composition comprising an antigenic polysaccharide alone. In some embodiments, an immunogenic complex described herein, upon administration to a subject, induces an immune response against one or more pathogens in the subject at a level greater than a composition comprising a polypeptide antigen alone. In some embodiments, an immunogenic complex described herein, upon administration to a subject, induces a protective immune response.

In some embodiments, an immunogenic complex described herein, upon administration to a subject, induces an immune response against *S. pneumoniae*. In some embodiments, an immunogenic complex described herein, upon administration to a subject, induces an immune response against one or more serotypes of *S. pneumoniae*. In some embodiments, such an immune response may be directed against one or more (e.g., 1, 2, 3, 4, 5, 6, 7, 8, 9, 10 or more) serotypes of *Streptococcus pneumoniae*, wherein an immunogenic complex described herein includes polysaccharide(s) present in at least one or more (e.g., 1, 2, 3, 4, 5, 6, 7, 8, 9, 10 or more) of such serotype(s). In some embodiments, such an immune response may be directed against one or more (e.g., 1, 2, 3, 4, 5, 6, 7, 8, 9, 10 or more) serotypes of *Streptococcus pneumoniae*, wherein an immunogenic complex described herein does not include polysaccharide(s) present in at least one or more (e.g., 1, 2, 3, 4, 5, 6, 7, 8, 9, 10 or more) of such serotype(s). In some embodiments, such an immune response may be directed against two or more (e.g., 2, 3, 4, 5, 6, 7, 8, 9, 10 or more) serotypes of *Streptococcus pneumoniae*, wherein an immunogenic complex described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s). In some embodiments, an immunogenic complex described herein, upon administration to a subject, induces a protective immune response against one or more serotypes of *S. pneumoniae*. In some embodiments, such a protective response may be directed against one or more (e.g., 1, 2, 3, 4, 5, 6, 7, 8, 9, 10 or more) serotypes of *Streptococcus pneumoniae*, wherein an immunogenic complex described herein includes polysaccharide(s) present in at least one or more (e.g., 1, 2, 3, 4, 5, 6, 7, 8, 9, 10 or more) of such serotype(s). In some embodiments, such a protective response may be directed against one or more (e.g., 1, 2, 3, 4, 5, 6, 7, 8, 9, 10 or more) serotypes of *Streptococcus pneumoniae*, wherein an immunogenic complex described herein does not include polysaccharide(s) present in at least one or more (e.g., 1, 2, 3, 4, 5, 6, 7, 8, 9, 10 or more) of such serotype(s). In some embodiments, such a protective response may be directed against two or more (e.g., 2, 3, 4, 5, 6, 7, 8, 9, 10 or more) serotypes of *Streptococcus pneumoniae*, wherein an immunogenic complex described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s).

In some embodiments, the immune response is an antibody or B cell response. In some embodiments, the immune response is a T cell response. In some embodiments, the immune response is an innate immune response. In some embodiments, the immune response is a CD4+ T cell response, including $T_H1$, $T_H2$, or $T_H17$ response, or a CD8+ T cell response, or a CD4+ and CD8+ T cell response, or a CD4−/CD8− T cell response. In some embodiments, the immune response is an antibody or B cell response, and a T cell response. In some embodiments, the immune response is an antibody or B cell response, a T cell response, and an innate immune response. In some embodiments, the immune response is a protective immune response.

In some embodiments, an immunogenic complex described herein, upon administration to a subject, induces antibody production against one or more pathogens in the subject at a level greater than a composition comprising an antigenic polysaccharide alone. In some embodiments, an immunogenic complex described herein, upon administration to a subject, induces antibody production against one or more pathogens in the subject at level greater than a composition comprising a polypeptide antigen alone.

In some embodiments, an immunogenic composition or vaccine described herein, upon administration to a subject, induces an immune response against one or more pathogens in the subject at a level greater than a composition comprising an antigenic polysaccharide alone. In some embodiments, an immunogenic composition or vaccine described herein, upon administration to a subject, induces an immune response against one or more pathogens in the subject at a level greater than a composition comprising a polypeptide antigen alone. In some embodiments, an immunogenic complex described herein, upon administration to a subject, induces a protective immune response.

The S. pneumoniae immunogenic compositions and vaccines described herein may be used for prophylactic and/or therapeutic treatment of S. pneumoniae. Accordingly, this application provides a method for immunizing a subject suffering from or susceptible to S. pneumoniae infection, comprising administering an immunologically effective amount of any of the immunogenic compositions or vaccine formulations described herein. The subject receiving the vaccination may be a male or a female, and may be an infant, child, adolescent, or adult. In some embodiments, the subject being treated is a human. In other embodiments, the subject is a non-human animal. In some embodiments, an immunogenic complex described herein, upon administration to a subject, induces a protective immune response against one or more serotypes of S. pneumoniae.

In prophylactic embodiments, a vaccine composition (e.g., ones as described and/or utilized herein) is administered to a subject to induce an immune response that can help protect against the establishment of S. pneumoniae, for example by protecting against colonization, the first and necessary step in disease. In some embodiments, such an immune response may be directed against one or more (e.g., 1, 2, 3, 4, 5, 6, 7, 8, 9, 10 or more) serotypes of Streptococcus pneumoniae, wherein a vaccine composition described herein includes polysaccharide(s) present in at least one or more (e.g., 1, 2, 3, 4, 5, 6, 7, 8, 9, 10 or more) of such serotype(s). In some embodiments, such an immune response may be directed against one or more (e.g., 1, 2, 3, 4, 5, 6, 7, 8, 9, 10 or more) serotypes of Streptococcus pneumoniae, wherein a vaccine composition described herein does not include polysaccharide(s) present in at least one or more (e.g., 1, 2, 3, 4, 5, 6, 7, 8, 9, 10 or more) of such serotype(s) (non-vaccine types, NVTs). In some embodiments, such an immune response may be directed against two or more (e.g., 2, 3, 4, 5, 6, 7, 8, 9, 10 or more) serotypes of Streptococcus pneumoniae, wherein a vaccine composition described herein (i) includes polysaccharide(s) present in at least one or more (e.g., 1, 2, 3, 4, 5, 6, 7, 8, 9, 10 or more) of such serotype(s); and (ii) does not include polysaccharide(s) present in at least one or more (e.g., 1, 2, 3, 4, 5, 6, 7, 8, 9, 10 or more) of such serotype(s). Thus, in some aspects, the method inhibits infection by S. pneumoniae in a non-colonized or uninfected subject. In another aspect, the method may reduce the duration of colonization in a subject who is already colonized.

In therapeutic embodiments, the vaccine may be administered to a subject suffering from S. pneumoniae infection, in an amount sufficient to treat the subject. Treating the subject, in this case, refers to reducing S. pneumoniae symptoms and/or bacterial load and/or sequelae in an infected subject. In some embodiments, treating the subject refers to reducing the duration of symptoms or sequelae, or reducing the intensity of symptoms or sequelae. In some embodiments, the vaccine reduces transmissibility of S. pneumoniae from the vaccinated subject. In certain embodiments, the reductions described above are at least 25%, 30%, 40%, 50%, 60%, 70%, 80%, or 90%.

In therapeutic embodiments, the vaccine is administered to a subject post-infection. The vaccine may be administered shortly after infection, e.g. before symptoms or sequelae manifest, or may be administered during or after manifestation of symptoms or sequelae.

In some embodiments, the vaccine compositions of the invention confer protective immunity, allowing a vaccinated subject to exhibit delayed onset of symptoms or sequelae, or reduced severity of symptoms or sequelae, as the result of his or her exposure to the vaccine. In certain embodiments, the reduction in severity of symptoms or sequelae is at least 25%, 40%, 50%, 60%, 70%, 80%, or 90%. In particular embodiments, vaccinated subjects may display no symptoms or sequelae upon contact with S. pneumoniae, do not become colonized by S. pneumoniae, or both. Protective immunity is typically achieved by one or more of the following mechanisms: mucosal, humoral, or cellular immunity. Mucosal immunity is primarily the result of secretory IgA (sIGA) antibodies on mucosal surfaces of the respiratory, gastrointestinal, and genitourinary tracts. The sIGA antibodies are generated after a series of events mediated by antigen-processing cells, B and T lymphocytes, that result in sIGA production by B lymphocytes on mucosa-lined tissues of the body. Humoral immunity is typically the result of IgG antibodies and IgM antibodies in serum. Cellular immunity can be achieved through cytotoxic T lymphocytes or through delayed-type hypersensitivity that involves macrophages and T lymphocytes, as well as other mechanisms involving T cells without a requirement for antibodies. In particular, cellular immunity may be mediated by $T_H1$ or $T_H17$ cells.

In some embodiments, an immunogenic composition or vaccine described herein, upon administration to a subject, induces an immune response against S. pneumoniae. In some embodiments, an immunogenic composition or vaccine described herein, upon administration to a subject, induces an immune response against one or more (e.g., 1, 2, 3, 4, 5, 6, 7, 8, 9, 10, 11, 12, 13, 14, 15, 16, 17, 18, 19, 20, 21, 22, 23, 24, or more) serotypes of S. pneumoniae. In some embodiments, an immunogenic composition or vaccine described herein, upon administration to a subject, induces an immune response against all serotypes of S. pneumoniae comprised in such immunogenic composition or vaccine. In some embodiments, an immunogenic complex described herein, upon administration to a subject, induces a protective immune response against one or more (e.g., 1, 2, 3, 4, 5, 6, 7, 8, 9, 10, 11, 12, 13, 14, 15, 16, 17, 18, 19, 20, 21, 22, 23, 24, or more) serotypes of S. pneumoniae. In some embodiments, an immunogenic complex described herein, upon administration to a subject, induces a protective immune response against all serotypes of S. pneumoniae comprised in such immunogenic composition or vaccine.

In some embodiments, the immune response is an antibody or B cell response. In some embodiments, the immune response is a T cell response. In some embodiments, the immune response is an innate immune response. In some embodiments, the immune response is a CD4+ T cell response, including $T_H1$, $T_H2$, or $T_H17$ response, or a CD8+ T cell response, or a CD4+ and CD8+ T cell response, or CD4−/CD8− T cell response. In some embodiments, the immune response is an antibody or B cell response, and a T cell response. In some embodiments, the immune response is an antibody or B cell response, a T cell response, and an innate immune response. In some embodiments, the immune response is a protective immune response.

In some embodiments, an immunogenic composition or vaccine described herein, upon administration to a subject, induces an antibody or B cell response against one or more pathogens in the subject at a level greater than a composition comprising an antigenic polysaccharide alone. In some embodiments, an immunogenic composition or vaccine described herein, upon administration to a subject, induces an antibody or B cell response against one or more pathogens in the subject at level greater than a composition comprising a polypeptide antigen alone. In some embodiments, the immune response is a protective immune response.

In some embodiments, an immunogenic composition or vaccine described herein, upon administration to a subject, induces a T cell response against one or more pathogens in the subject at a level greater than a composition comprising an antigenic polysaccharide alone. In some embodiments, an immunogenic composition or vaccine described herein, upon administration to a subject, induces a T cell response against one or more pathogens in the subject at level greater than a composition comprising a polypeptide antigen alone. In some embodiments, the immune response is a protective immune response.

In some embodiments, upon administration to a subject, an immunogenic composition or vaccine described herein treats or prevents infection by *S. pneumoniae*. In some embodiments, upon administration to a subject, an immunogenic composition or vaccine described herein treats or prevents Invasive Pneumococcal Disease (IPD) due to infection by *S. pneumoniae*. In some embodiments, upon administration to a subject, an immunogenic composition or vaccine described herein treats or prevents bacteremia due to infection by *S. pneumoniae*. In some embodiments, upon administration to a subject, an immunogenic composition or vaccine described herein treats or prevents sepsis due to infection by *S. pneumoniae*. In some embodiments, upon administration to a subject, an immunogenic composition or vaccine described herein treats or prevents organ damage due to infection by *S. pneumoniae*. In some embodiments, upon administration to a subject, an immunogenic composition or vaccine described herein treats or prevents meningitis due to infection by *S. pneumoniae*. In some embodiments, upon administration to a subject, an immunogenic composition or vaccine described herein treats or prevents pneumonia due to infection by *S. pneumoniae*. In some embodiments, upon administration to a subject, an immunogenic composition or vaccine described herein treats or prevents otitis media due to infection by *S. pneumoniae*. In some embodiments, upon administration to a subject, an immunogenic composition or vaccine described herein treats or prevents sinusitis due to infection by *S. pneumoniae*.

In some embodiments, upon administration to a subject, an immunogenic composition or vaccine described herein inhibits or reduces the rate of occurrence of infection by *S. pneumoniae*. In some embodiments, upon administration to a subject, an immunogenic composition or vaccine described herein inhibits or reduces the rate of occurrence of Invasive Pneumococcal Disease (IPD) due to infection by *S. pneumoniae*. In some embodiments, upon administration to a subject, an immunogenic composition or vaccine described herein inhibits or reduces the rate of occurrence of bacteremia due to infection by *S. pneumoniae*. In some embodiments, upon administration to a subject, an immunogenic composition or vaccine described herein inhibits or reduces the rate of occurrence of sepsis due to infection by *S. pneumoniae*. In some embodiments, upon administration to a subject, an immunogenic composition or vaccine described herein inhibits or reduces the rate of occurrence of organ damage due to infection by *S. pneumoniae*. In some embodiments, upon administration to a subject, an immunogenic composition or vaccine described herein inhibits or reduces the rate of occurrence of meningitis due to infection by *S. pneumoniae*. In some embodiments, upon administration to a subject, an immunogenic composition or vaccine described herein inhibits or reduces the rate of occurrence of pneumonia due to infection by *S. pneumoniae*. In some embodiments, upon administration to a subject, an immunogenic composition or vaccine described herein inhibits or reduces the rate of occurrence of otitis media due to infection by *S. pneumoniae*. In some embodiments, upon administration to a subject, an immunogenic composition or vaccine described herein inhibits or reduces the rate of occurrence of sinusitis due to infection by *S. pneumoniae*.

In some embodiments, upon administration to a subject, an immunogenic composition or vaccine described herein reduces the severity of infection by *S. pneumoniae*. In some embodiments, upon administration to a subject, an immunogenic composition or vaccine described herein reduces the severity of Invasive Pneumococcal Disease (IPD) due to infection by *S. pneumoniae*. In some embodiments, upon administration to a subject, an immunogenic composition or vaccine described herein reduces the severity of bacteremia due to infection by *S. pneumoniae*. In some embodiments, upon administration to a subject, an immunogenic composition or vaccine described herein reduces the severity of sepsis due to infection by *S. pneumoniae*. In some embodiments, upon administration to a subject, an immunogenic composition or vaccine described herein reduces the severity of organ damage due to infection by *S. pneumoniae*. In some embodiments, upon administration to a subject, an immunogenic composition or vaccine described herein reduces the severity of meningitis due to infection by *S. pneumoniae*. In some embodiments, upon administration to a subject, an immunogenic composition or vaccine described herein reduces the severity of pneumonia due to infection by *S. pneumoniae*. In some embodiments, upon administration to a subject, an immunogenic composition or vaccine described herein reduces the severity of otitis media due to infection by *S. pneumoniae*. In some embodiments, upon administration to a subject, an immunogenic composition or vaccine described herein reduces the severity of sinusitis due to infection by *S. pneumoniae*.

In some embodiments, upon administration to a subject, an immunogenic composition or vaccine described herein inhibits transmission of *S. pneumoniae* from the subject to another subject. In some embodiments, upon administration to a subject, an immunogenic composition or vaccine described herein inhibits colonization by *S. pneumoniae* in the subject. In some embodiments, upon administration to a subject, an immunogenic composition or vaccine described herein inhibits colonization by *S. pneumoniae* in the nasopharynx of the subject.

In some embodiments, an immunogenic composition or vaccine described herein, upon administration to a subject, induces an immune response against one or more pathogens in the subject at a level greater than a control composition. In some embodiments, an immunogenic composition or vaccine described herein, upon administration to a subject, induces a protective immune response against one or more pathogens in the subject at a level greater than a control composition. In some embodiments, the level greater is about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 30%, about 35%, about 40%, about 45%, about 50%, about 55%, about 60%, about 65%, about 70%, about 75%, about 80%, about 85%, about 90%, or about 95% of the control composition. In some embodiments, the control composition may be PCV13 or PPSV23.

In some embodiments an immunogenic composition or vaccine described herein, upon administration to a subject, elicits immunogenicity non-inferior to (e.g., immunogenicity at least as effective as) that elicited by administration of PCV13. In some embodiments an immunogenic composition or vaccine described herein, upon administration to a subject, elicits immunogenicity non-inferior to (e.g., immunogenicity at least as effective as) that elicited by administration of PCV13 against one or more of S. pneumoniae serotypes 1, 3, 4, 5, 6A, 6B, 7F, 9V, 14, 18C, 19A, 19F and 23F. In some embodiments an immunogenic composition or vaccine described herein, upon administration to a subject, elicits immunogenicity non-inferior to (e.g., immunogenicity at least as effective as) that elicited by administration of PCV13 against each of S. pneumoniae serotypes 1, 3, 4, 5, 6A, 6B, 7F, 9V, 14, 18C, 19A, 19F and 23F. In some embodiments, the immunogenicity is determined by measuring the amount of anti-capsular polysaccharide antibody of one or more S. pneumoniae serotypes. In some embodiments the subject is a human. In some embodiments the human is between about 2 weeks of age and about 6 weeks of age. In some embodiments the human is between about 6 weeks of age and about 6 years of age. In some embodiments the human is between about 6 years of age and about 18 years of age. In some embodiments the human is between about 18 years of age and about 50 years of age. In some embodiments the human is about 50 years of age or older.

In some embodiments an immunogenic composition or vaccine described herein, upon administration to a subject, elicits immunogenicity superior to that elicited by administration of PCV13. In some embodiments an immunogenic composition or vaccine described herein, upon administration to a subject, elicits immunogenicity superior to that elicited by administration of PCV13 against one or more of S. pneumoniae serotypes 1, 3, 4, 5, 6A, 6B, 7F 9V, 14, 18C, 19A, 19F and 23F. In some embodiments an immunogenic composition or vaccine described herein, upon administration to a subject, elicits immunogenicity superior to that elicited by administration of PCV13 against each of S. pneumoniae serotypes 1, 3, 4, 5, 6A, 6B, 7F 9V, 14, 18C, 19A, 19F and 23F. In some embodiments, the immunogenicity is determined by measuring the amount of anti-capsular polysaccharide antibody of one or more S. pneumoniae serotypes. In some embodiments the subject is a human. In some embodiments the human is between about 2 weeks of age and about 6 weeks of age. In some embodiments the human is between about 6 weeks of age and about 6 years of age. In some embodiments the human is between about 6 years of age and about 18 years of age. In some embodiments the human is between about 18 years of age and about 50 years of age. In some embodiments the human is about 50 years of age or older.

In some embodiments an immunogenic composition or vaccine described herein, upon administration to a subject, elicits immunogenicity non-inferior to (e.g., immunogenicity at least as effective as) that elicited by administration of PPSV23. In some embodiments an immunogenic composition or vaccine described herein, upon administration to a subject, elicits immunogenicity non-inferior to (e.g., immunogenicity at least as effective as) that elicited by administration of PPSV23 against one or more of S. pneumoniae serotypes 1, 2, 3, 4, 5, 6B, 7F, 8, 9N, 9V, 10A, 11A, 12F, 14, 15B, 17F, 18C, 19F, 19A, 20A, 22F, 23F, and 33F. In some embodiments an immunogenic composition or vaccine described herein, upon administration to a subject, elicits immunogenicity non-inferior to (e.g., immunogenicity at least as effective as) that elicited by administration of PPSV23 against each of S. pneumoniae serotypes 1, 2, 3, 4, 5, 6B, 7F, 8, 9N, 9V, 10A, 11A, 12F, 14, 15B, 17F, 18C, 19F, 19A, 20A, 22F, 23F, and 33F. In some embodiments, the immunogenicity is determined by measuring the amount of anti-capsular polysaccharide antibody of one or more S. pneumoniae serotypes. In some embodiments the subject is a human. In some embodiments the human is between about 2 weeks of age and about 6 weeks of age. In some embodiments the human is between about 6 weeks of age and about 6 years of age. In some embodiments the human is between about 6 years of age and about 18 years of age. In some embodiments the human is between about 18 years of age and about 50 years of age. In some embodiments the human is about 50 years of age or older.

In some embodiments an immunogenic composition or vaccine described herein, upon administration to a subject, elicits immunogenicity superior to that elicited by administration of PPSV23. In some embodiments an immunogenic composition or vaccine described herein, upon administration to a subject, elicits immunogenicity superior to that elicited by administration of PPSV23 against one or more of S. pneumoniae serotypes 1, 2, 3, 4, 5, 6B, 7F, 8, 9N, 9V, 10A, 11A, 12F, 14, 15B, 17F, 18C, 19F, 19A, 20A, 22F, 23F, and 33F. In some embodiments an immunogenic composition or vaccine described herein, upon administration to a subject, elicits immunogenicity superior to that elicited by administration of PPSV23 against each of S. pneumoniae serotypes 1, 2, 3, 4, 5, 6B, 7F, 8, 9N, 9V, 10A, 11A, 12F, 14, 15B, 17F, 18C, 19F, 19A, 20A, 22F, 23F, and 33F. In some embodiments, the immunogenicity is determined by measuring the amount of anti-capsular polysaccharide antibody of one or more S. pneumoniae serotypes. In some embodiments the subject is a human. In some embodiments the human is between about 2 weeks of age and about 6 weeks of age. In some embodiments the human is between about 6 weeks of age and about 6 years of age. In some embodiments the human is between about 6 years of age and about 18 years of age. In some embodiments the human is between about 18 years of age and about 50 years of age. In some embodiments the human is about 50 years of age or older.

In some embodiments an immunogenic composition or vaccine described herein, upon administration to a subject, elicits immunogenicity non-inferior to (e.g., immunogenicity at least as effective as) that elicited by administration of PCV13 in combination with PPSV23 against one or more of S. pneumoniae serotypes 1, 3, 4, 5, 6A, 6B, 7F, 9V, 14, 18C, 19A, 19F and 23F. In some embodiments an immunogenic composition or vaccine described herein, upon administration to a subject, elicits immunogenicity non-inferior to (e.g., immunogenicity at least as effective as) that elicited by administration of PCV13 in combination with PPSV23 against each of S. pneumoniae serotypes 1, 3, 4, 5, 6A, 6B, 7F 9V, 14, 18C, 19A, 19F and 23F. In some embodiments an immunogenic composition or vaccine described herein, upon administration to a subject, elicits immunogenicity non-inferior to (e.g., immunogenicity at least as effective as) that elicited by administration of PCV13 in combination with PPSV23 against one or more of S. pneumoniae serotypes 1, 2, 3, 4, 5, 6B, 7F, 8, 9N, 9V, 10A, 11A, 12F, 14, 15B, 17F, 18C, 19F, 19A, 20A, 22F, 23F, and 33F. In some embodiments an immunogenic composition or vaccine described herein, upon administration to a subject, elicits immunogenicity non-inferior to (e.g., immunogenicity at least as effective as) that elicited by administration of PCV13 in combination with PPSV23 against each of *S. pneumoniae* serotypes 1, 2, 3, 4, 5, 6B, 7F, 8, 9N, 9V, 10A, 11A, 12F, 14, 15B, 17F, 18C, 19F, 19A, 20A, 22F, 23F, and 33F. In some embodiments, the immunogenicity is determined by measuring the amount of anti-capsular polysaccharide antibody of one or more *S. pneumoniae* serotypes. In some embodiments the subject is a human. In some embodiments the human is between about 2 weeks of age and about 6 weeks of age. In some embodiments the human is between about 6 weeks of age and about 6 years of age. In some embodiments the human is between about 6 years of age and about 18 years of age. In some embodiments the human is between about 18 years of age and about 50 years of age. In some embodiments the human is about 50 years of age or older. In some embodiments, the PCV13 is administered before the PPSV23. In some embodiments, the PCV13 is administered after the PPSV23. In some embodiments, the PCV13 is administered at approximately the same time as the PPSV23.

In some embodiments an immunogenic composition or vaccine described herein, upon administration to a subject, elicits immunogenicity superior to that elicited by administration of PCV13 in combination with PPSV23 against one or more of *S. pneumoniae* serotypes 1, 3, 4, 5, 6A, 6B, 7F, 9V, 14, 18C, 19A, 19F and 23F. In some embodiments an immunogenic composition or vaccine described herein, upon administration to a subject, elicits immunogenicity superior to that elicited by administration of PCV13 in combination with PPSV23 against each of *S. pneumoniae* serotypes 1, 3, 4, 5, 6A, 6B, 7F, 9V, 14, 18C, 19A, 19F and 23F. In some embodiments an immunogenic composition or vaccine described herein, upon administration to a subject, elicits immunogenicity superior to that elicited by administration of PCV13 in combination with PPSV23 against one or more of *S. pneumoniae* serotypes 1, 2, 3, 4, 5, 6B, 7F, 8, 9N, 9V, 10A, 11A, 12F, 14, 15B, 17F, 18C, 19F, 19A, 20A, 22F, 23F, and 33F. In some embodiments an immunogenic composition or vaccine described herein, upon administration to a subject, elicits immunogenicity superior to that elicited by administration of PCV13 in combination with PPSV23 against each of *S. pneumoniae* serotypes 1, 2, 3, 4, 5, 6B, 7F, 8, 9N, 9V, 10A, 11A, 12F, 14, 15B, 17F, 18C, 19F, 19A, 20A, 22F, 23F, and 33F. In some embodiments, the immunogenicity is determined by measuring the amount of anti-capsular polysaccharide antibody of one or more *S. pneumoniae* serotypes. In some embodiments the subject is a human. In some embodiments the human is between about 2 weeks of age and about 6 weeks of age. In some embodiments the human is between about 6 weeks of age and about 6 years of age. In some embodiments the human is between about 6 years of age and about 18 years of age. In some embodiments the human is between about 18 years of age and about 50 years of age. In some embodiments the human is about 50 years of age or older. In some embodiments, the PCV13 is administered before the PPSV23. In some embodiments, the PCV13 is administered after the PPSV23. In some embodiments, the PCV13 is administered at approximately the same time as the PPSV23.

In some embodiments an immunogenic composition or vaccine described herein, upon administration to a subject, elicits a functional antibody titer non-inferior to (e.g., a functional antibody titer at least as effective as) that elicited by administration of PCV13 against one or more of *S. pneumoniae* serotypes 1, 3, 4, 5, 6A, 6B, 7F, 9V, 14, 18C, 19A, 19F and 23F. In some embodiments an immunogenic composition or vaccine described herein, upon administration to a subject, elicits a functional antibody titer non-inferior to (e.g., a functional antibody titer at least as effective as) that elicited by administration of PCV13 against each of *S. pneumoniae* serotypes 1, 3, 4, 5, 6A, 6B, 7F, 9V, 14, 18C, 19A, 19F and 23F. In some embodiments, an immunogenic composition or vaccine described herein, upon administration to a subject, elicits a functional antibody titer non-inferior to (e.g., a functional antibody titer at least as effective as) that elicited by administration of PCV13 against one or more *S. pneumoniae* serotypes, wherein such an immunogenic composition or vaccine does not include polysaccharide(s) present in at least one or more of such *S. pneumoniae* serotypes (non-vaccine types, NVTs). In some embodiments, an immunogenic composition or vaccine described herein, upon administration to a subject, elicits a functional antibody titer non-inferior to (e.g., a functional antibody titer at least as effective as) that elicited by administration of PCV13 against (i) one or more of *S. pneumoniae* serotypes 1, 3, 4, 5, 6A, 6B, 7F, 9V, 14, 18C, 19A, 19F and 23F, and (ii) one or more additional *S. pneumoniae* serotypes, wherein such an immunogenic composition or vaccine does not include polysaccharide(s) present in at least one or more of such additional *S. pneumoniae* serotypes (non-vaccine types, NVTs). In some embodiments, the functional antibody titer is measured by an opsonophagocytic assay (e.g., ones as described herein). In some embodiments the subject is a human. In some embodiments the human is between about 2 weeks of age and about 6 weeks of age. In some embodiments the human is between about 6 weeks of age and about 6 years of age. In some embodiments the human is between about 6 years of age and about 18 years of age. In some embodiments the human is between about 18 years of age and about 50 years of age. In some embodiments the human is about 50 years of age or older.

In some embodiments an immunogenic composition or vaccine described herein, upon administration to a subject, elicits a functional antibody titer non-inferior to (e.g., a functional antibody titer at least as effective as) that elicited by administration of PCV13 against one or more of *S. pneumoniae* serotypes 2, 8, 9N, 10A, 11A, 12F, 15B, 17F, 20B, 22F and 33F. In some embodiments an immunogenic composition or vaccine described herein, upon administration to a subject, elicits a functional antibody titer non-inferior to (e.g., a functional antibody titer at least as effective as) that elicited by administration of PCV13 against each of *S. pneumoniae* serotypes 2, 8, 9N, 10A, 11A, 12F, 15B, 17F, 20B, 22F and 33F. In some embodiments, an immunogenic composition or vaccine described herein, upon administration to a subject, elicits a functional antibody titer non-inferior to (e.g., a functional antibody titer at least as effective as) that elicited by administration of PCV13 against one or more *S. pneumoniae* serotypes, wherein such an immunogenic composition or vaccine does not include polysaccharide(s) present in at least one or more of such *S. pneumoniae* serotypes (non-vaccine types, NVTs). In some embodiments an immunogenic composition or vaccine described herein, upon administration to a subject, elicits a functional antibody titer non-inferior to (e.g., a functional antibody titer at least as effective as) that elicited by administration of PCV13 against (i) one or more of *S. pneumoniae* serotypes 2, 8, 9N, 10A, 11A, 12F, 15B, 17F, 20B, 22F and 33F, and (ii) one or more additional *S. pneumoniae* serotypes, wherein such an immunogenic composition or vaccine does not include polysaccharide(s) present in at least one or more of such additional *S. pneumoniae* serotypes (non-vaccine types, NVTs). In some embodiments, the functional antibody titer is measured by an opsonophagocytic assay (e.g., ones as described herein). In some embodiments the subject is a human. In some embodiments the human is between about 2 weeks of age and about 6 weeks of age. In some embodiments the human is between about 6 weeks of age and about 6 years of age. In some embodiments the human is between about 6 years of age and about 18 years of age. In some embodiments the human is between about 18 years of age and about 50 years of age. In some embodiments the human is about 50 years of age or older.

In some embodiments an immunogenic composition or vaccine described herein, upon administration to a subject, elicits a functional antibody titer non-inferior to (e.g., a functional antibody titer at least as effective as) that elicited by administration of PPSV23 against one or more of S. pneumoniae serotypes 1, 2, 3, 4, 5, 6B, 7F, 8, 9N, 9V, 10A, 11A, 12F, 14, 15B, 17F, 18C, 19F, 19A, 20A, 22F, 23F, and 33F. In some embodiments an immunogenic composition or vaccine described herein, upon administration to a subject, elicits a functional antibody titer non-inferior to (e.g., a functional antibody titer at least as effective as) that elicited by administration of PPSV23 against each of S. pneumoniae serotypes 1, 2, 3, 4, 5, 6B, 7F, 8, 9N, 9V, 10A, 11A, 12F, 14, 15B, 17F, 18C, 19F, 19A, 20A, 22F, 23F, and 33F. In some embodiments, an immunogenic composition or vaccine described herein, upon administration to a subject, elicits a functional antibody titer non-inferior to (e.g., a functional antibody titer at least as effective as) that elicited by administration of PPSV23 against one or more S. pneumoniae serotypes, wherein such an immunogenic composition or vaccine does not include polysaccharide(s) present in at least one or more of such S. pneumoniae serotypes (non-vaccine types, NVTs). In some embodiments, an immunogenic composition or vaccine described herein, upon administration to a subject, elicits a functional antibody titer non-inferior to (e.g., a functional antibody titer at least as effective as) that elicited by administration of PPSV23 against (i) one or more of S. pneumoniae serotypes 1, 2, 3, 4, 5, 6B, 7F, 8, 9N, 9V, 10A, 11A, 12F, 14, 15B, 17F, 18C, 19F, 19A, 20A, 22F, 23F, and 33F, and (ii) one or more additional S. pneumoniae serotypes, wherein such an immunogenic composition or vaccine does not include polysaccharide(s) present in at least one or more of such additional S. pneumoniae serotypes (non-vaccine types, NVTs). In some embodiments, the functional antibody titer is measured by an opsonophagocytic assay (e.g., ones as described herein). In some embodiments the subject is a human. In some embodiments the human is between about 2 weeks of age and about 6 weeks of age. In some embodiments the human is between about 6 weeks of age and about 6 years of age. In some embodiments the human is between about 6 years of age and about 18 years of age. In some embodiments the human is between about 18 years of age and about 50 years of age. In some embodiments the human is about 50 years of age or older.

In some embodiments an immunogenic composition or vaccine described herein, upon administration to a subject, elicits a functional antibody titer non-inferior to (e.g., a functional antibody titer at least as effective as) that elicited by administration of PPSV23 against one or more of S. pneumoniae serotypes 6A and 20B. In some embodiments an immunogenic composition or vaccine described herein, upon administration to a subject, elicits a functional antibody titer non-inferior to (e.g., a functional antibody titer at least as effective as) that elicited by administration of PPSV23 against each of S. pneumoniae serotypes 6A and 20B. In some embodiments, an immunogenic composition or vaccine described herein, upon administration to a subject, elicits a functional antibody titer non-inferior to (e.g., a functional antibody titer at least as effective as) that elicited by administration of PPSV23 against one or more S. pneumoniae serotypes, wherein such an immunogenic composition or vaccine does not include polysaccharide(s) present in at least one or more of such S. pneumoniae serotypes (non-vaccine types, NVTs). In some embodiments, an immunogenic composition or vaccine described herein, upon administration to a subject, elicits a functional antibody titer non-inferior to (e.g., a functional antibody titer at least as effective as) that elicited by administration of PPSV23 against (i) one or more of S. pneumoniae serotypes 6A and 20B, and (ii) one or more additional S. pneumoniae serotypes, wherein such an immunogenic composition or vaccine does not include polysaccharide(s) present in at least one or more of such additional S. pneumoniae serotypes (non-vaccine types, NVTs). In some embodiments, the functional antibody titer is measured by an opsonophagocytic assay (e.g., ones as described herein). In some embodiments the subject is a human. In some embodiments the human is between about 2 weeks of age and about 6 weeks of age. In some embodiments the human is between about 6 weeks of age and about 6 years of age. In some embodiments the human is between about 6 years of age and about 18 years of age. In some embodiments the human is between about 18 years of age and about 50 years of age. In some embodiments the human is about 50 years of age or older.

In some embodiments an immunogenic composition or vaccine described herein, upon administration to a subject, elicits a functional antibody titer superior to that elicited by administration of PCV13 against one or more of S. pneumoniae serotypes 1, 3, 4, 5, 6A, 6B, 7F 9V, 14, 18C, 19A, 19F and 23F. In some embodiments an immunogenic composition or vaccine described herein, upon administration to a subject, elicits a functional antibody titer superior to that elicited by administration of PCV13 against each of S. pneumoniae serotypes 1, 3, 4, 5, 6A, 6B, 7F 9V, 14, 18C, 19A, 19F and 23F. In some embodiments, an immunogenic composition or vaccine described herein, upon administration to a subject, elicits a functional antibody titer superior to that elicited by administration of PCV13 against one or more S. pneumoniae serotypes, wherein such an immunogenic composition or vaccine does not include polysaccharide(s) present in at least one or more of such S. pneumoniae serotypes (non-vaccine types, NVTs). In some embodiments an immunogenic composition or vaccine described herein, upon administration to a subject, elicits a functional antibody titer superior to that elicited by administration of PCV13 against (i) one or more of S. pneumoniae serotypes 1, 3, 4, 5, 6A, 6B, 7F, 9V, 14, 18C, 19A, 19F and 23F, and (ii) one or more additional S. pneumoniae serotypes, wherein such an immunogenic composition or vaccine does not include polysaccharide(s) present in at least one or more of such additional S. pneumoniae serotypes (non-vaccine types, NVTs). In some embodiments, the functional antibody titer is measured by an opsonophagocytic assay (e.g., ones as described herein). In some embodiments the subject is a human. In some embodiments the human is between about 2 weeks of age and about 6 weeks of age. In some embodiments the human is between about 6 weeks of age and about 6 years of age. In some embodiments the human is between about 6 years of age and about 18 years of age. In some embodiments the human is between about 18 years of age and about 50 years of age. In some embodiments the human is about 50 years of age or older.

In some embodiments an immunogenic composition or vaccine described herein, upon administration to a subject, elicits a functional antibody titer superior to that elicited by administration of PCV13 against one or more of S. pneumoniae serotypes 2, 8, 9N, 10A, 11A, 12F, 15B, 17F, 20B, 22F and 33F. In some embodiments an immunogenic composition or vaccine described herein, upon administration to a subject, elicits a functional antibody titer superior to that elicited by administration of PCV13 against each of S. pneumoniae serotypes 2, 8, 9N, 10A, 11A, 12F, 15B, 17F, 20B, 22F and 33F. In some embodiments, an immunogenic composition or vaccine described herein, upon administration to a subject, elicits a functional antibody titer superior to that elicited by administration of PCV13 against one or more S. pneumoniae serotypes, wherein such an immunogenic composition or vaccine does not include polysaccharide(s) present in at least one or more of such S. pneumoniae serotypes (non-vaccine types, NVTs). In some embodiments, an immunogenic composition or vaccine described herein, upon administration to a subject, elicits a functional antibody titer superior to that elicited by administration of PCV13 against (i) one or more of S. pneumoniae serotypes 2, 8, 9N, 10A, 11A, 12F, 15B, 17F, 20B, 22F and 33F, and (ii) one or more additional S. pneumoniae serotypes, wherein such an immunogenic composition or vaccine does not include polysaccharide(s) present in at least one or more of such additional S. pneumoniae serotypes (non-vaccine types, NVTs). In some embodiments, the functional antibody titer is measured by an opsonophagocytic assay (e.g., ones described herein). In some embodiments the subject is a human. In some embodiments the human is between about 2 weeks of age and about 6 weeks of age. In some embodiments the human is between about 6 weeks of age and about 6 years of age. In some embodiments the human is between about 6 years of age and about 18 years of age. In some embodiments the human is between about 18 years of age and about 50 years of age. In some embodiments the human is about 50 years of age or older.

In some embodiments an immunogenic composition or vaccine described herein, upon administration to a subject, elicits a functional antibody titer superior to that elicited by administration of PPSV23 against one or more of S. pneumoniae serotypes 1, 2, 3, 4, 5, 6B, 7F, 8, 9N, 9V, 10A, 11A, 12F, 14, 15B, 17F, 18C, 19F, 19A, 20A, 22F, 23F, and 33F. In some embodiments an immunogenic composition or vaccine described herein, upon administration to a subject, elicits a functional antibody titer superior to that elicited by administration of PPSV23 against each of S. pneumoniae serotypes 1, 2, 3, 4, 5, 6B, 7F, 8, 9N, 9V, 10A, 11A, 12F, 14, 15B, 17F, 18C, 19F, 19A, 20A, 22F, 23F, and 33F. In some embodiments, an immunogenic composition or vaccine described herein, upon administration to a subject, elicits a functional antibody titer superior to that elicited by administration of PPSV23 against one or more S. pneumoniae serotypes, wherein such an immunogenic composition or vaccine does not include polysaccharide(s) present in at least one or more of such S. pneumoniae serotypes (non-vaccine types, NVTs). In some embodiments, an immunogenic composition or vaccine described herein, upon administration to a subject, elicits a functional antibody titer superior to that elicited by administration of PPSV23 against (i) one or more of S. pneumoniae serotypes 1, 2, 3, 4, 5, 6B, 7F, 8, 9N, 9V, 10A, 11A, 12F, 14, 15B, 17F, 18C, 19F, 19A, 20A, 22F, 23F, and 33F, and (ii) one or more additional S. pneumoniae serotypes, wherein such an immunogenic composition or vaccine does not include polysaccharide(s) present in at least one or more of such additional S. pneumoniae serotypes (non-vaccine types, NVTs). In some embodiments, the functional antibody titer is measured by an opsonophagocytic assay (e.g., ones as described herein). In some embodiments the subject is a human. In some embodiments the human is between about 2 weeks of age and about 6 weeks of age. In some embodiments the human is between about 6 weeks of age and about 6 years of age. In some embodiments the human is between about 6 years of age and about 18 years of age. In some embodiments the human is between about 18 years of age and about 50 years of age. In some embodiments the human is about 50 years of age or older.

In some embodiments an immunogenic composition or vaccine described herein, upon administration to a subject, elicits a functional antibody titer superior to that elicited by administration of PPSV23 against one or more of S. pneumoniae serotypes 6A and 20B. In some embodiments an immunogenic composition or vaccine described herein, upon administration to a subject, elicits a functional antibody titer superior to that elicited by administration of PPSV23 against each of S. pneumoniae serotypes 6A and 20B. In some embodiments, an immunogenic composition or vaccine described herein, upon administration to a subject, elicits a functional antibody titer superior to that elicited by administration of PPSV23 against one or more S. pneumoniae serotypes, wherein such an immunogenic composition or vaccine does not include polysaccharide(s) present in at least one or more of such S. pneumoniae serotypes (non-vaccine types, NVTs). In some embodiments, an immunogenic composition or vaccine described herein, upon administration to a subject, elicits a functional antibody titer superior to that elicited by administration of PPSV23 against (i) one or more of S. pneumoniae serotypes 6A and 20B, and (ii) one or more additional S. pneumoniae serotypes, wherein such an immunogenic composition or vaccine does not include polysaccharide(s) present in at least one or more of such additional S. pneumoniae serotypes (non-vaccine types, NVTs). In some embodiments, the functional antibody titer is measured by an opsonophagocytic assay (e.g., ones as described herein). In some embodiments the subject is a human. In some embodiments the human is between about 2 weeks of age and about 6 weeks of age. In some embodiments the human is between about 6 weeks of age and about 6 years of age. In some embodiments the human is between about 6 years of age and about 18 years of age. In some embodiments the human is between about 18 years of age and about 50 years of age. In some embodiments the human is about 50 years of age or older.

In some embodiments an immunogenic composition or vaccine described herein, upon administration to a subject, elicits a functional antibody titer non-inferior to (e.g., a functional antibody titer at least as effective as) that elicited by administration of PCV13 in combination with PPSV23 against one or more of S. pneumoniae serotypes 1, 3, 4, 5, 6A, 6B, 7F, 9V, 14, 18C, 19A, 19F and 23F. In some embodiments an immunogenic composition or vaccine described herein, upon administration to a subject, elicits a functional antibody titer non-inferior to (e.g., a functional antibody titer at least as effective as) that elicited by administration of PCV13 in combination with PPSV23 against each of S. pneumoniae serotypes 1, 3, 4, 5, 6A, 6B, 7F, 9V, 14, 18C, 19A, 19F and 23F. In some embodiments an immunogenic composition or vaccine described herein, upon administration to a subject, elicits a functional antibody titer non-inferior to (e.g., a functional antibody titer at least as effective as) that elicited by administration of PCV13 in combination with PPSV23 against one or more of S. pneumoniae serotypes 1, 2, 3, 4, 5, 6B, 7F, 8, 9N, 9V, 10A, 11A, 12F, 14, 15B, 17F, 18C, 19F, 19A, 20A, 22F, 23F, and 33F. In some embodiments an immunogenic composition or vaccine described herein, upon administration to a subject, elicits a functional antibody titer non-inferior to (e.g., a functional antibody titer at least as effective as) that elicited by administration of PCV13 in combination with PPSV23 against each of S. pneumoniae serotypes 1, 2, 3, 4, 5, 6B, 7F, 8, 9N, 9V, 10A, 11A, 12F, 14, 15B, 17F, 18C, 19F, 19A, 20A, 22F, 23F, and 33F. In some embodiments, an immunogenic composition or vaccine described herein, upon administration to a subject, elicits a functional antibody titer non-inferior to (e.g., a functional antibody titer at least as effective as) that elicited by administration of PCV13 in combination with PPSV23 against one or more S. pneumoniae serotypes, wherein such an immunogenic composition or vaccine does not include polysaccharide(s) present in at least one or more of such S. pneumoniae serotypes (non-vaccine types, NVTs). In some embodiments, an immunogenic composition or vaccine described herein, upon administration to a subject, elicits a functional antibody titer non-inferior to (e.g., a functional antibody titer at least as effective as) that elicited by administration of PCV13 in combination with PPSV23 against (i) one or more of S. pneumoniae serotypes 1, 3, 4, 5, 6A, 6B, 7F, 9V, 14, 18C, 19A, 19F and 23F, and (ii) one or more additional S. pneumoniae serotypes, wherein such an immunogenic composition or vaccine does not include polysaccharide(s) present in at least one or more of such additional S. pneumoniae serotypes (non-vaccine types, NVTs). In some embodiments, an immunogenic composition or vaccine described herein, upon administration to a subject, elicits a functional antibody titer non-inferior to (e.g., a functional antibody titer at least as effective as) that elicited by administration of PCV13 in combination with PPSV23 against (i) one or more of S. pneumoniae serotypes 1, 2, 3, 4, 5, 6B, 7F, 8, 9N, 9V, 10A, 11A, 12F, 14, 15B, 17F, 18C, 19F, 19A, 20A, 22F, 23F, and 33F, and (ii) one or more additional S. pneumoniae serotypes, wherein such an immunogenic composition or vaccine does not include polysaccharide(s) present in at least one or more of such additional S. pneumoniae serotypes (non-vaccine types, NVTs). In some embodiments, the functional antibody titer is measured by an opsonophagocytic assay (e.g., ones as described herein). In some embodiments the subject is a human. In some embodiments the human is between about 2 weeks of age and about 6 weeks of age. In some embodiments the human is between about 6 weeks of age and about 6 years of age. In some embodiments the human is between about 6 years of age and about 18 years of age. In some embodiments the human is between about 18 years of age and about 50 years of age. In some embodiments the human is about 50 years of age or older. In some embodiments, the PCV13 is administered before the PPSV23. In some embodiments, the PCV13 is administered after the PPSV23. In some embodiments, the PCV13 is administered at approximately the same time as the PPSV23.

In some embodiments an immunogenic composition or vaccine described herein, upon administration to a subject, elicits a functional antibody titer non-inferior to (e.g., a functional antibody titer at least as effective as) that elicited by administration of PCV13 in combination with PPSV23 against one or more of S. pneumoniae serotypes 2, 8, 9N, 10A, 11A, 12F, 15B, 17F, 20B, 22F and 33F. In some embodiments an immunogenic composition or vaccine described herein, upon administration to a subject, elicits a functional antibody titer non-inferior to (e.g., a functional antibody titer at least as effective as) that elicited by admin-istration of PCV13 in combination with PPSV23 against each of S. pneumoniae serotypes 2, 8, 9N, 10A, 11A, 12F, 15B, 17F, 20B, 22F and 33F. In some embodiments, an immunogenic composition or vaccine described herein, upon administration to a subject, elicits a functional antibody titer non-inferior to (e.g., a functional antibody titer at least as effective as) that elicited by administration of PCV13 in combination with PPSV23 against one or more S. pneumoniae serotypes, wherein such an immunogenic composition or vaccine does not include polysaccharide(s) present in at least one or more of such S. pneumoniae serotypes (non-vaccine types, NVTs). In some embodiments, an immunogenic composition or vaccine described herein, upon administration to a subject, elicits a functional antibody titer non-inferior to (e.g., a functional antibody titer at least as effective as) that elicited by administration of PCV13 in combination with PPSV23 against (i) one or more of S. pneumoniae serotypes 2, 8, 9N, 10A, 11A, 12F, 15B, 17F, 20B, 22F and 33F, and (ii) one or more additional S. pneumoniae serotypes, wherein such an immunogenic composition or vaccine does not include polysaccharide(s) present in at least one or more of such additional S. pneumoniae serotypes (non-vaccine types, NVTs). In some embodiments, the functional antibody titer is measured by an opsonophagocytic assay. In some embodiments the subject is a human. In some embodiments the human is between about 2 weeks of age and about 6 weeks of age. In some embodiments the human is between about 6 weeks of age and about 6 years of age. In some embodiments the human is between about 6 years of age and about 18 years of age. In some embodiments the human is between about 18 years of age and about 50 years of age. In some embodiments the human is about 50 years of age or older. In some embodiments, the PCV13 is administered before the PPSV23. In some embodiments, the PCV13 is administered after the PPSV23. In some embodiments, the PCV13 is administered at approximately the same time as the PPSV23.

In some embodiments an immunogenic composition or vaccine described herein, upon administration to a subject, elicits a functional antibody titer superior to that elicited by administration of PCV13 in combination with PPSV23 against one or more of S. pneumoniae serotypes 1, 3, 4, 5, 6A, 6B, 7F, 9V, 14, 18C, 19A, 19F and 23F. In some embodiments an immunogenic composition or vaccine described herein, upon administration to a subject, elicits a functional antibody titer superior to that elicited by administration of PCV13 in combination with PPSV23 against each of S. pneumoniae serotypes 1, 3, 4, 5, 6A, 6B, 7F, 9V, 14, 18C, 19A, 19F and 23F. In some embodiments an immunogenic composition or vaccine described herein, upon administration to a subject, elicits a functional antibody titer superior to that elicited by administration of PCV13 in combination with PPSV23 against one or more of S. pneumoniae serotypes 1, 2, 3, 4, 5, 6B, 7F, 8, 9N, 9V, 10A, 11A, 12F, 14, 15B, 17F, 18C, 19F, 19A, 20A, 22F, 23F, and 33F. In some embodiments an immunogenic composition or vaccine described herein, upon administration to a subject, elicits a functional antibody titer superior to that elicited by administration of PCV13 in combination with PPSV23 against each of S. pneumoniae serotypes 1, 2, 3, 4, 5, 6B, 7F, 8, 9N, 9V, 10A, 11A, 12F, 14, 15B, 17F, 18C, 19F, 19A, 20A, 22F, 23F, and 33F. In some embodiments, an immunogenic composition or vaccine described herein, upon administration to a subject, elicits a functional antibody titer superior to that elicited by administration of PCV13 in combination with PPSV23 against one or more S. pneumoniae serotypes, wherein such an immunogenic composition or vaccine does not include polysaccharide(s) present in at least one or more of such *S. pneumoniae* serotypes (non-vaccine types, NVTs). In some embodiments, an immunogenic composition or vaccine described herein, upon administration to a subject, elicits a functional antibody titer superior to that elicited by administration of PCV13 in combination with PPSV23 against (i) one or more of *S. pneumoniae* serotypes 1, 3, 4, 5, 6A, 6B, 7F, 9V, 14, 18C, 19A, 19F and 23F, and (ii) one or more additional *S. pneumoniae* serotypes, wherein such an immunogenic composition or vaccine does not include polysaccharide(s) present in at least one or more of such additional *S. pneumoniae* serotypes (non-vaccine types, NVTs). In some embodiments, an immunogenic composition or vaccine described herein, upon administration to a subject, elicits a functional antibody titer superior to that elicited by administration of PCV13 in combination with PPSV23 against (i) one or more of *S. pneumoniae* serotypes 1, 2, 3, 4, 5, 6B, 7F, 8, 9N, 9V, 10A, 11A, 12F, 14, 15B, 17F, 18C, 19F, 19A, 20A, 22F, 23F, and 33F, and (ii) one or more additional *S. pneumoniae* serotypes, wherein such an immunogenic composition or vaccine does not include polysaccharide(s) present in at least one or more of such additional *S. pneumoniae* serotypes (non-vaccine types, NVTs). In some embodiments, the functional antibody titer is measured by an opsonophagocytic assay (e.g., ones as described herein). In some embodiments the subject is a human. In some embodiments the human is between about 2 weeks of age and about 6 weeks of age. In some embodiments the human is between about 6 weeks of age and about 6 years of age. In some embodiments the human is between about 6 years of age and about 18 years of age. In some embodiments the human is between about 18 years of age and about 50 years of age. In some embodiments the human is about 50 years of age or older. In some embodiments, the PCV13 is administered before the PPSV23. In some embodiments, the PCV13 is administered after the PPSV23. In some embodiments, the PCV13 is administered at approximately the same time as the PPSV23.

In some embodiments an immunogenic composition or vaccine described herein, upon administration to a subject, elicits a functional antibody titer superior to that elicited by administration of PCV13 in combination with PPSV23 against one or more of *S. pneumoniae* serotypes 2, 8, 9N, 10A, 11A, 12F, 15B, 17F, 20B, 22F and 33F. In some embodiments an immunogenic composition or vaccine described herein, upon administration to a subject, elicits a functional antibody titer superior to that elicited by administration of PCV13 in combination with PPSV23 against each of *S. pneumoniae* serotypes 2, 8, 9N, 10A, 11A, 12F, 15B, 17F, 20B, 22F and 33F. In some embodiments, an immunogenic composition or vaccine described herein, upon administration to a subject, elicits a functional antibody titer superior to that elicited by administration of PCV13 in combination with PPSV23 against one or more *S. pneumoniae* serotypes, wherein such an immunogenic composition or vaccine does not include polysaccharide(s) present in at least one or more of such *S. pneumoniae* serotypes (non-vaccine types, NVTs). In some embodiments, an immunogenic composition or vaccine described herein, upon administration to a subject, elicits a functional antibody titer superior to that elicited by administration of PCV13 in combination with PPSV23 against (i) one or more of *S. pneumoniae* serotypes 2, 8, 9N, 10A, 11A, 12F, 15B, 17F, 20B, 22F and 33F, and (ii) one or more additional *S. pneumoniae* serotypes, wherein such an immunogenic composition or vaccine does not include polysaccharide(s) present in at least one or more of such additional *S. pneumoniae* serotypes (non-vaccine types, NVTs). In some embodiments, the functional antibody titer is measured by an opsonophagocytic assay (e.g., ones as described herein). In some embodiments the subject is a human. In some embodiments the human is between about 2 weeks of age and about 6 weeks of age. In some embodiments the human is between about 6 weeks of age and about 6 years of age. In some embodiments the human is between about 6 years of age and about 18 years of age. In some embodiments the human is between about 18 years of age and about 50 years of age. In some embodiments the human is about 50 years of age or older. In some embodiments, the PCV13 is administered before the PPSV23. In some embodiments, the PCV13 is administered after the PPSV23. In some embodiments, the PCV13 is administered at approximately the same time as the PPSV23.

In some embodiments, an immunogenic composition or vaccine described herein, upon administration to a subject, elicits immunogenicity against one or more of *S. pneumoniae* serotypes 1, 2, 3, 4, 5, 6A, 6B, 7F, 8, 9N, 9V, 10A, 11A, 12F, 14, 15B, 17F, 18C, 19A, 19F, 20B, 22F, 23F, and 33F. In some embodiments, an immunogenic composition or vaccine described herein, upon administration to a subject, elicits immunogenicity against each of *S. pneumoniae* serotypes 1, 2, 3, 4, 5, 6A, 6B, 7F, 8, 9N, 9V, 10A, 11A, 12F, 14, 15B, 17F, 18C, 19A, 19F, 20B, 22F, 23F, and 33F. In some embodiments, an immunogenic composition or vaccine described herein, upon administration to a subject, elicits immunogenicity against one or more *S. pneumoniae* serotypes, wherein such an immunogenic composition or vaccine does not include polysaccharide(s) present in at least one or more of such *S. pneumoniae* serotypes (non-vaccine types, NVTs). In some embodiments, an immunogenic composition or vaccine described herein, upon administration to a subject, elicits immunogenicity against (i) one or more of *S. pneumoniae* serotypes 1, 2, 3, 4, 5, 6A, 6B, 7F, 8, 9N, 9V, 10A, 11A, 12F, 14, 15B, 17F, 18C, 19A, 19F, 20B, 22F, 23F, and 33F, and (ii) one or more additional *S. pneumoniae* serotypes, wherein such an immunogenic composition or vaccine does not include polysaccharide(s) present in at least one or more of such additional *S. pneumoniae* serotypes (non-vaccine types, NVTs). In some embodiments, the immunogenicity is determined by measuring the amount of anti-capsular polysaccharide antibody against one or more *S. pneumoniae* serotypes 1, 2, 3, 4, 5, 6A, 6B, 7F, 8, 9N, 9V, 10A, 11A, 12F, 14, 15B, 17F, 18C, 19A, 19F, 20B, 22F, 23F, and 33F. In some embodiments, the immunogenicity is determined by measuring the amount of anti-capsular polysaccharide antibody against each of *S. pneumoniae* serotypes 1, 2, 3, 4, 5, 6A, 6B, 7F, 8, 9N, 9V, 10A, 11A, 12F, 14, 15B, 17F, 18C, 19A, 19F, 20B, 22F, 23F, and 33F. In some embodiments the amount of anti-capsular polysaccharide antibody measured is an amount that meets a pre-determined threshold. In some embodiments the total amount of anti-capsular polysaccharide antibody measured is an amount that meets a pre-determined threshold. In some embodiments the pre-determined threshold is a blood serum or plasma concentration between about 0.20 µg/mL to about 0.35 µg/mL. In some embodiments the pre-determined threshold is at least about 0.35 µg/mL. In some embodiments, the functional antibody titer is measured by an opsonophagocytic assay. In some embodiments the subject is a human. In some embodiments the human is between about 2 weeks of age and about 6 weeks of age. In some embodiments the human is between about 6 weeks of age and about 6 years of age. In some embodiments the human is between about 6 years of age and about 18 years of age. In some embodiments the human is between about 18 years of age and about 50 years of age. In some embodiments the human is about 50 years of age or older.

In some embodiments, an immunogenic composition or vaccine described herein, upon administration to a subject, elicits immunogenicity against one or more of S. pneumoniae serotypes 1, 3, 4, 5, 6A, 6B, 7F, 9V, 14, 18C, 19A, 19F and 23F. In some embodiments, an immunogenic composition or vaccine described herein, upon administration to a subject, elicits immunogenicity against each of S. pneumoniae serotypes 1, 3, 4, 5, 6A, 6B, 7F, 9V, 14, 18C, 19A, 19F and 23F. In some embodiments, an immunogenic composition or vaccine described herein, upon administration to a subject, elicits immunogenicity against one or more S. pneumoniae serotypes, wherein such an immunogenic composition or vaccine does not include polysaccharide(s) present in at least one or more of such S. pneumoniae serotypes (non-vaccine types, NVTs). In some embodiments, an immunogenic composition or vaccine described herein, upon administration to a subject, elicits immunogenicity against (i) one or more of S. pneumoniae serotypes 1, 3, 4, 5, 6A, 6B, 7F, 9V, 14, 18C, 19A, 19F and 23F, and (ii) one or more additional S. pneumoniae serotypes, wherein such an immunogenic composition or vaccine does not include polysaccharide(s) present in at least one or more of such additional S. pneumoniae serotypes (non-vaccine types, NVTs). In some embodiments, the immunogenicity is determined by measuring the amount of anti-capsular polysaccharide antibody against one or more S. pneumoniae serotypes 1, 3, 4, 5, 6A, 6B, 7F, 9V, 14, 18C, 19A, 19F and 23F. In some embodiments, the immunogenicity is determined by measuring the amount of anti-capsular polysaccharide antibody against each of S. pneumoniae serotypes 1, 3, 4, 5, 6A, 6B, 7F, 9V, 14, 18C, 19A, 19F and 23F. In some embodiments the amount of anti-capsular polysaccharide antibody measured is an amount that meets a pre-determined threshold. In some embodiments the total amount of anti-capsular polysaccharide antibody measured is an amount that meets a pre-determined threshold. In some embodiments the pre-determined threshold is a blood serum or plasma concentration between about 0.20 µg/mL to about 0.35 µg/mL. In some embodiments the pre-determined threshold is at least about 0.35 µg/mL. In some embodiments, the functional antibody titer is measured by an opsonophagocytic assay. In some embodiments the subject is a human. In some embodiments the human is between about 2 weeks of age and about 6 weeks of age. In some embodiments the human is between about 6 weeks of age and about 6 years of age. In some embodiments the human is between about 6 years of age and about 18 years of age. In some embodiments the human is between about 18 years of age and about 50 years of age. In some embodiments the human is about 50 years of age or older.

In some embodiments, an immunogenic composition or vaccine described herein, upon administration to a subject, elicits immunogenicity against one or more of S. pneumoniae serotypes 1, 2, 3, 4, 5, 6B, 7F, 8, 9N, 9V, 10A, 11A, 12F, 14, 15B, 17F, 18C, 19F, 19A, 20A, 22F, 23F, and 33F. In some embodiments, an immunogenic composition or vaccine described herein, upon administration to a subject, elicits immunogenicity against each of S. pneumoniae serotypes 1, 2, 3, 4, 5, 6B, 7F, 8, 9N, 9V, 10A, 11A, 12F, 14, 15B, 17F, 18C, 19F, 19A, 20A, 22F, 23F, and 33F. In some embodiments, an immunogenic composition or vaccine described herein, upon administration to a subject, elicits immunogenicity against one or more S. pneumoniae serotypes, wherein such an immunogenic composition or vaccine does not include polysaccharide(s) present in at least one or more of such S. pneumoniae serotypes (non-vaccine types, NVTs). In some embodiments, an immunogenic composition or vaccine described herein, upon administration to a subject, elicits immunogenicity against (i) one or more of S. pneumoniae serotypes 1, 2, 3, 4, 5, 6B, 7F, 8, 9N, 9V, 10A, 11A, 12F, 14, 15B, 17F, 18C, 19F, 19A, 20A, 22F, 23F, and 33F, and (ii) one or more additional S. pneumoniae serotypes, wherein such an immunogenic composition or vaccine does not include polysaccharide(s) present in at least one or more of such additional S. pneumoniae serotypes (non-vaccine types, NVTs). In some embodiments, the immunogenicity is determined by measuring the amount of anti-capsular polysaccharide antibody against one or more S. pneumoniae serotypes 1, 2, 3, 4, 5, 6B, 7F, 8, 9N, 9V, 10A, 11A, 12F, 14, 15B, 17F, 18C, 19F, 19A, 20A, 22F, 23F, and 33F. In some embodiments, the immunogenicity is determined by measuring the amount of anti-capsular polysaccharide antibody against each of S. pneumoniae serotypes 1, 2, 3, 4, 5, 6B, 7F, 8, 9N, 9V, 10A, 11A, 12F, 14, 15B, 17F, 18C, 19F, 19A, 20A, 22F, 23F, and 33F. In some embodiments the amount of anti-capsular polysaccharide antibody measured is an amount that meets a pre-determined threshold. In some embodiments the total amount of anti-capsular polysaccharide antibody measured is an amount that meets a pre-determined threshold. In some embodiments the pre-determined threshold is a blood serum or plasma concentration between about 0.20 µg/mL to about 0.35 µg/mL. In some embodiments the pre-determined threshold is at least about 0.35 µg/mL. In some embodiments, the functional antibody titer is measured by an opsonophagocytic assay. In some embodiments the subject is a human. In some embodiments the human is between about 2 weeks of age and about 6 weeks of age. In some embodiments the human is between about 6 weeks of age and about 6 years of age. In some embodiments the human is between about 6 years of age and about 18 years of age. In some embodiments the human is between about 18 years of age and about 50 years of age. In some embodiments the human is about 50 years of age or older.

In some embodiments an immunogenic composition or vaccine described herein, upon administration to a subject, (i) elicits a functional antibody titer superior to that elicited by administration of PCV13 against one or more of S. pneumoniae serotypes 1, 3, 4, 5, 6A, 6B, 7F, 9V, 14, 18C, 19A, 19F and 23F; and (ii) elicits immunogenicity against one or more of S. pneumoniae serotypes 1, 2, 3, 4, 5, 6A, 6B, 7F, 8, 9N, 9V, 10A, 11A, 12F, 14, 15B, 17F, 18C, 19A, 19F, 20B, 22F, 23F, and 33F. In some embodiments an immunogenic composition or vaccine described herein, upon administration to a subject, (i) elicits a functional antibody titer superior to that elicited by administration of PCV13 against each of S. pneumoniae serotypes 1, 3, 4, 5, 6A, 6B, 7F, 9V, 14, 18C, 19A, 19F and 23F; and (ii) elicits immunogenicity against each of S. pneumoniae serotypes 1, 2, 3, 4, 5, 6A, 6B, 7F, 8, 9N, 9V, 10A, 11A, 12F, 14, 15B, 17F, 18C, 19A, 19F, 20B, 22F, 23F, and 33F. In some embodiments, an immunogenic composition or vaccine described herein, upon administration to a subject, elicits (i) a functional antibody titer superior to that elicited by administration of PCV13 and (ii) immunogenicity (e.g., an innate immune response, an antibody or B cell response, and/or a T cell response), against one or more S. pneumoniae serotypes, wherein such an immunogenic composition or vaccine does not include polysaccharide(s) present in at least one or more of such S. pneumoniae serotypes (non-vaccine types, NVTs). In some embodiments, an immunogenic composition or vaccine described herein, upon administration to a subject, elicits (i) a functional antibody titer superior to that elicited by administration of PCV13 and (ii) immunogenicity (e.g., an innate immune response, an antibody or B cell response, and/or a T cell response), against one or more of S. pneumoniae serotypes 1, 2, 3, 4, 5, 6A, 6B, 7F, 8, 9N, 9V, 10A, 11A, 12F, 14, 15B, 17F, 18C, 19A, 19F, 20B, 22F, 23F, and 33F, and also against one or more additional S. pneumoniae serotypes, wherein such an immunogenic composition or vaccine does not include polysaccharide(s) present in at least one or more of such additional S. pneumoniae serotypes (non-vaccine types, NVTs). In some embodiments, the immunogenicity is determined by measuring the amount of anti-capsular polysaccharide antibody against each of S. pneumoniae serotypes 1, 2, 3, 4, 5, 6A, 6B, 7F, 8, 9N, 9V, 10A, 11A, 12F, 14, 15B, 17F, 18C, 19A, 19F, 20B, 22F, 23F, and 33F. In some embodiments, the functional antibody titer is measured by an opsonophagocytic assay (e.g., ones as described herein). In some embodiments the amount of anti-capsular polysaccharide antibody measured is an amount that meets a pre-determined threshold. In some embodiments the total amount of anti-capsular polysaccharide antibody measured is an amount that meets a pre-determined threshold. In some embodiments the pre-determined threshold is a blood serum or plasma concentration between about 0.20 µg/mL to about 0.35 µg/mL. In some embodiments the pre-determined threshold is at least about 0.35 µg/mL. In some embodiments the subject is a human. In some embodiments the human is between about 2 weeks of age and about 6 weeks of age. In some embodiments the human is between about 6 weeks of age and about 6 years of age. In some embodiments the human is between about 6 years of age and about 18 years of age. In some embodiments the human is between about 18 years of age and about 50 years of age. In some embodiments the human is about 50 years of age or older.

In some embodiments an immunogenic composition or vaccine described herein, upon administration to a subject, (i) elicits a functional antibody titer superior to that elicited by administration of PPSV23 against one or more of S. pneumoniae serotypes 1, 2, 3, 4, 5, 6B, 7F, 8, 9N, 9V, 10A, 11A, 12F, 14, 15B, 17F, 18C, 19F, 19A, 20A, 22F, 23F, and 33F; and (ii) elicits immunogenicity against one or more of S. pneumoniae serotypes 1, 2, 3, 4, 5, 6A, 6B, 7F, 8, 9N, 9V, 10A, 11A, 12F, 14, 15B, 17F, 18C, 19A, 19F, 20B, 22F, 23F, and 33F. In some embodiments an immunogenic composition or vaccine described herein, upon administration to a subject, (i) elicits a functional antibody titer superior to that elicited by administration of PPSV23 against each of S. pneumoniae serotypes 1, 2, 3, 4, 5, 6B, 7F, 8, 9N, 9V, 10A, 11A, 12F, 14, 15B, 17F, 18C, 19F, 19A, 20A, 22F, 23F, and 33F; and (ii) elicits immunogenicity against each of S. pneumoniae serotypes 1, 2, 3, 4, 5, 6A, 6B, 7F, 8, 9N, 9V, 10A, 11A, 12F, 14, 15B, 17F, 18C, 19A, 19F, 20B, 22F, 23F, and 33F. In some embodiments an immunogenic composition or vaccine described herein, upon administration to a subject, elicits (i) a functional antibody titer superior to that elicited by administration of PPSV23 and (ii) immunogenicity (e.g., an innate immune response, an antibody or B cell response, and/or a T cell response), against one or more S. pneumoniae serotypes, wherein such an immunogenic composition or vaccine does not include polysaccharide(s) present in at least one or more of such S. pneumoniae serotypes (non-vaccine types, NVTs). In some embodiments an immunogenic composition or vaccine described herein, upon administration to a subject, elicits (i) a functional antibody titer superior to that elicited by administration of PPSV23 and (ii) immunogenicity (e.g., an innate immune response, an antibody or B cell response, and/or a T cell response), against one or more of S. pneumoniae serotypes 1, 2, 3, 4, 5, 6A, 6B, 7F, 8, 9N, 9V, 10A, 11A, 12F, 14, 15B, 17F, 18C, 19A, 19F, 20B, 22F, 23F, and 33F, and also against one or more additional S. pneumoniae serotypes, wherein such an immunogenic composition or vaccine does not include polysaccharide(s) present in at least one or more of such additional S. pneumoniae serotypes (non-vaccine types, NVTs). In some embodiments, the immunogenicity is determined by measuring the amount of anti-capsular polysaccharide antibody against each of S. pneumoniae serotypes 1, 2, 3, 4, 5, 6A, 6B, 7F, 8, 9N, 9V, 10A, 11A, 12F, 14, 15B, 17F, 18C, 19A, 19F, 20B, 22F, 23F, and 33F. In some embodiments, the functional antibody titer is measured by an opsonophagocytic assay (e.g., ones as described herein). In some embodiments the amount of anti-capsular polysaccharide antibody measured is an amount that meets a pre-determined threshold. In some embodiments the total amount of anti-capsular polysaccharide antibody measured is an amount that meets a pre-determined threshold. In some embodiments the pre-determined threshold is a blood serum or plasma concentration between about 0.20 µg/mL to about 0.35 µg/mL. In some embodiments the pre-determined threshold is at least about 0.35 µg/mL. In some embodiments the subject is a human. In some embodiments the human is between about 2 weeks of age and about 6 weeks of age. In some embodiments the human is between about 6 weeks of age and about 6 years of age. In some embodiments the human is between about 6 years of age and about 18 years of age. In some embodiments the human is between about 18 years of age and about 50 years of age. In some embodiments the human is about 50 years of age or older.

In some embodiments an immunogenic composition or vaccine described herein, upon administration to a subject, (i) elicits a functional antibody titer superior to that elicited by administration of PCV13 in combination with PPSV23 against one or more of S. pneumoniae serotypes 2, 8, 9N, 10A, 11A, 12F, 15B, 17F, 20B, 22F and 33F; and (ii) elicits immunogenicity against one or more of S. pneumoniae serotypes 1, 2, 3, 4, 5, 6A, 6B, 7F, 8, 9N, 9V, 10A, 11A, 12F, 14, 15B, 17F, 18C, 19A, 19F, 20B, 22F, 23F, and 33F. In some embodiments an immunogenic composition or vaccine described herein, upon administration to a subject, (i) elicits a functional antibody titer superior to that elicited by administration of PCV13 in combination with PPSV23 against each of S. pneumoniae serotypes 2, 8, 9N, 10A, 11A, 12F, 15B, 17F, 20B, 22F and 33F; and (ii) elicits immunogenicity against each of S. pneumoniae serotypes 1, 2, 3, 4, 5, 6A, 6B, 7F, 8, 9N, 9V, 10A, 11A, 12F, 14, 15B, 17F, 18C, 19A, 19F, 20B, 22F, 23F, and 33F. In some embodiments an immunogenic composition or vaccine described herein, upon administration to a subject, elicits (i) a functional antibody titer superior to that elicited by administration of PCV13 in combination with PPSV23 and (ii) immunogenicity (e.g., an innate immune response, an antibody or B cell response, and/or a T cell response), against one or more S. pneumoniae serotypes, wherein such an immunogenic composition or vaccine does not include polysaccharide(s) present in at least one or more of such S. pneumoniae serotypes (non-vaccine types, NVTs). In some embodiments an immunogenic composition or vaccine described herein, upon administration to a subject, elicits (i) a functional antibody titer superior to that elicited by administration of PCV13 in combination with PPSV23 and (ii) immunogenicity (e.g., an innate immune response, an antibody or B cell response, and/or a T cell response), against one or more of *S. pneumoniae* serotypes 1, 2, 3, 4, 5, 6A, 6B, 7F, 8, 9N, 9V, 10A, 11A, 12F, 14, 15B, 17F, 18C, 19A, 19F, 20B, 22F, 23F, and 33F, and also against one or more additional *S. pneumoniae* serotypes, wherein such an immunogenic composition or vaccine does not include polysaccharide(s) present in at least one or more of such additional *S. pneumoniae* serotypes (non-vaccine types, NVTs). In some embodiments, the immunogenicity is determined by measuring the amount of anti-capsular polysaccharide antibody against each of *S. pneumoniae* serotypes 1, 2, 3, 4, 5, 6A, 6B, 7F, 8, 9N, 9V, 10A, 11A, 12F, 14, 15B, 17F, 18C, 19A, 19F, 20B, 22F, 23F, and 33F. In some embodiments, the functional antibody titer is measured by an opsonophagocytic assay (e.g., ones as described herein). In some embodiments the amount of anti-capsular polysaccharide antibody measured is an amount that meets a pre-determined threshold. In some embodiments the total amount of anti-capsular polysaccharide antibody measured is an amount that meets a pre-determined threshold. In some embodiments the pre-determined threshold is a blood serum or plasma concentration between about 0.20 µg/mL to about 0.35 µg/mL. In some embodiments the pre-determined threshold is at least about 0.35 µg/mL. In some embodiments the subject is a human. In some embodiments the human is between about 2 weeks of age and about 6 weeks of age. In some embodiments the human is between about 6 weeks of age and about 6 years of age. In some embodiments the human is between about 6 years of age and about 18 years of age. In some embodiments the human is between about 18 years of age and about 50 years of age. In some embodiments the human is about 50 years of age or older. In some embodiments, the PCV13 is administered before the PPSV23. In some embodiments, the PCV13 is administered after the PPSV23. In some embodiments, the PCV13 is administered at approximately the same time as the PPSV23.

In some embodiments, an immunogenic composition or vaccine described herein, upon administration to a subject, elicits an immunoprotective response against one or more of *S. pneumoniae* serotypes 1, 2, 3, 4, 5, 6A, 6B, 7F, 8, 9N, 9V, 10A, 11A, 12F, 14, 15B, 17F, 18C, 19A, 19F, 20B, 22F, 23F, and 33F. In some embodiments, an immunogenic composition or vaccine described herein, upon administration to a subject, elicits an immunoprotective response against each of *S. pneumoniae* serotypes 1, 2, 3, 4, 5, 6A, 6B, 7F, 8, 9N, 9V, 10A, 11A, 12F, 14, 15B, 17F, 18C, 19A, 19F, 20B, 22F, 23F, and 33F. In some embodiments, an immunogenic composition or vaccine described herein, upon administration to a subject, elicits an immunoprotective response against (i) at least one or more of *S. pneumoniae* serotypes 1, 2, 3, 4, 5, 6A, 6B, 7F, 8, 9N, 9V, 10A, 11A, 12F, 14, 15B, 17F, 18C, 19A, 19F, 20B, 22F, 23F, and 33F and (ii) one or more additional *S. pneumoniae* serotypes, wherein such an immunogenic composition or vaccine does not include polysaccharide(s) present in at least one or more of such additional *S. pneumoniae* serotypes (non-vaccine types, NVTs).

In some embodiments an immunogenic composition or vaccine described herein, upon administration to a subject, reduces *S. pneumoniae* colonization to a greater degree than administration of PCV13. In some embodiments an immunogenic composition or vaccine described herein, upon administration to a subject, reduces *S. pneumoniae* colonization by one or more of *S. pneumoniae* serotypes 1, 3, 4, 5, 6A, 6B, 7F, 9V, 14, 18C, 19A, 19F and 23F to a greater degree than administration of PCV13. In some embodiments an immunogenic composition or vaccine described herein, upon administration to a subject, reduces *S. pneumoniae* colonization by each of *S. pneumoniae* serotypes 1, 3, 4, 5, 6A, 6B, 7F, 9V, 14, 18C, 19A, 19F and 23F to a greater degree than administration of PCV13. In some embodiments an immunogenic composition or vaccine described herein, upon administration to a subject, reduces *S. pneumoniae* colonization to a greater degree than administration of PCV13 by (i) at least one or more of *S. pneumoniae* serotypes 1, 3, 4, 5, 6A, 6B, 7F, 9V, 14, 18C, 19A, 19F and 23F, and (ii) one or more additional *S. pneumoniae* serotypes, wherein such an immunogenic composition or vaccine does not include polysaccharide(s) present in at least one or more of such additional *S. pneumoniae* serotypes (non-vaccine types, NVTs). In some embodiments the subject is a human. In some embodiments the human is between about 2 weeks of age and about 6 weeks of age. In some embodiments the human is between about 6 weeks of age and about 6 years of age. In some embodiments the human is between about 6 years of age and about 18 years of age. In some embodiments the human is between about 18 years of age and about 50 years of age. In some embodiments the human is about 50 years of age or older.

In some embodiments an immunogenic composition or vaccine described herein, upon administration to a subject, reduces *S. pneumoniae* colonization to a greater degree than administration of PCV13. In some embodiments an immunogenic composition or vaccine described herein, upon administration to a subject, reduces *S. pneumoniae* colonization by one or more of *S. pneumoniae* serotypes 2, 8, 9N, 10A, 11A, 12F, 15B, 17F, 20B, 22F and 33F to a greater degree than administration of PCV13. In some embodiments an immunogenic composition or vaccine described herein, upon administration to a subject, reduces *S. pneumoniae* colonization by each of *S. pneumoniae* serotypes 2, 8, 9N, 10A, 11A, 12F, 15B, 17F, 20B, 22F and 33F to a greater degree than administration of PCV13. In some embodiments an immunogenic composition or vaccine described herein, upon administration to a subject, reduces *S. pneumoniae* colonization to a greater degree than administration of PCV13 by (i) at least one or more of *S. pneumoniae* serotypes 2, 8, 9N, 10A, 11A, 12F, 15B, 17F, 20B, 22F and 33F, and (ii) one or more additional *S. pneumoniae* serotypes, wherein such an immunogenic composition or vaccine does not include polysaccharide(s) present in at least one or more of such additional *S. pneumoniae* serotypes (non-vaccine types, NVTs). In some embodiments the subject is a human. In some embodiments the human is between about 2 weeks of age and about 6 weeks of age. In some embodiments the human is between about 6 weeks of age and about 6 years of age. In some embodiments the human is between about 6 years of age and about 18 years of age. In some embodiments the human is between about 18 years of age and about 50 years of age. In some embodiments the human is about 50 years of age or older.

In some embodiments an immunogenic composition or vaccine described herein, upon administration to a subject, reduces *S. pneumoniae* colonization to a greater degree than administration of PCV13. In some embodiments an immunogenic composition or vaccine described herein, upon administration to a subject, reduces *S. pneumoniae* colonization by one or more of *S. pneumoniae* serotypes 1, 2, 3, 4, 5, 6A, 6B, 7F, 8, 9N, 9V, 10A, 11A, 12F, 14, 15B, 17F, 18C, 19A, 19F, 20B, 22F, 23F, and 33F to a greater degree than administration of PCV13. In some embodiments an immunogenic composition or vaccine described herein, upon administration to a subject, reduces *S. pneumoniae* colonization by each of *S. pneumoniae* serotypes 1, 2, 3, 4, 5, 6A, 6B, 7F, 8, 9N, 9V, 10A, 11A, 12F, 14, 15B, 17F, 18C, 19A, 19F, 20B, 22F, 23F, and 33F to a greater degree than administration of PCV13. In some embodiments an immunogenic composition or vaccine described herein, upon administration to a subject, reduces *S. pneumoniae* colonization to a greater degree than administration of PCV13 by (i) at least one or more of *S. pneumoniae* serotypes 1, 2, 3, 4, 5, 6A, 6B, 7F, 8, 9N, 9V, 10A, 11A, 12F, 14, 15B, 17F, 18C, 19A, 19F, 20B, 22F, 23F, and 33F, and (ii) one or more additional *S. pneumoniae* serotypes, wherein such an immunogenic composition or vaccine does not include polysaccharide(s) present in at least one or more of such additional *S. pneumoniae* serotypes (non-vaccine types, NVTs). In some embodiments the subject is a human. In some embodiments the human is between about 2 weeks of age and about 6 weeks of age. In some embodiments the human is between about 6 weeks of age and about 6 years of age. In some embodiments the human is between about 6 years of age and about 18 years of age. In some embodiments the human is between about 18 years of age and about 50 years of age. In some embodiments the human is about 50 years of age or older.

In some embodiments an immunogenic composition or vaccine described herein, upon administration to a subject, reduces *S. pneumoniae* colonization to a greater degree than administration of PPSV23. In some embodiments an immunogenic composition or vaccine described herein, upon administration to a subject, reduces *S. pneumoniae* colonization by one or more of *S. pneumoniae* serotypes 1, 2, 3, 4, 5, 6B, 7F, 8, 9N, 9V, 10A, 11A, 12F, 14, 15B, 17F, 18C, 19F, 19A, 20A, 22F, 23F, and 33F to a greater degree than administration of PPSV23. In some embodiments an immunogenic composition or vaccine described herein, upon administration to a subject, reduces *S. pneumoniae* colonization by each of *S. pneumoniae* serotypes 1, 2, 3, 4, 5, 6B, 7F, 8, 9N, 9V, 10A, 11A, 12F, 14, 15B, 17F, 18C, 19F, 19A, 20A, 22F, 23F, and 33F to a greater degree than administration of PPSV23. In some embodiments an immunogenic composition or vaccine described herein, upon administration to a subject, reduces *S. pneumoniae* colonization to a greater degree than administration of PPSV23 by (i) at least one or more of *S. pneumoniae* serotypes 1, 2, 3, 4, 5, 6B, 7F, 8, 9N, 9V, 10A, 11A, 12F, 14, 15B, 17F, 18C, 19F, 19A, 20A, 22F, 23F, and 33F, and (ii) one or more additional *S. pneumoniae* serotypes, wherein such an immunogenic composition or vaccine does not include polysaccharide(s) present in at least one or more of such additional *S. pneumoniae* serotypes (non-vaccine types, NVTs). In some embodiments the subject is a human. In some embodiments the human is between about 2 weeks of age and about 6 weeks of age. In some embodiments the human is between about 6 weeks of age and about 6 years of age. In some embodiments the human is between about 6 years of age and about 18 years of age. In some embodiments the human is between about 18 years of age and about 50 years of age. In some embodiments the human is about 50 years of age or older.

In some embodiments an immunogenic composition or vaccine described herein, upon administration to a subject, reduces *S. pneumoniae* colonization to a greater degree than administration of PPSV23. In some embodiments an immunogenic composition or vaccine described herein, upon administration to a subject, reduces *S. pneumoniae* colonization by one or more of *S. pneumoniae* serotypes 6A and 20B to a greater degree than administration of PPSV23. In some embodiments an immunogenic composition or vaccine described herein, upon administration to a subject, reduces *S. pneumoniae* colonization by each of *S. pneumoniae* serotypes 6A and 20B to a greater degree than administration of PPSV23. In some embodiments an immunogenic composition or vaccine described herein, upon administration to a subject, reduces *S. pneumoniae* colonization to a greater degree than administration of PPSV23 by (i) at least one or more of *S. pneumoniae* serotypes 6A and 20B, and (ii) one or more additional *S. pneumoniae* serotypes, wherein such an immunogenic composition or vaccine does not include polysaccharide(s) present in at least one or more of such additional *S. pneumoniae* serotypes (non-vaccine types, NVTs). In some embodiments the subject is a human. In some embodiments the human is between about 2 weeks of age and about 6 weeks of age. In some embodiments the human is between about 6 weeks of age and about 6 years of age. In some embodiments the human is between about 6 years of age and about 18 years of age. In some embodiments the human is between about 18 years of age and about 50 years of age. In some embodiments the human is about 50 years of age or older.

In some embodiments an immunogenic composition or vaccine described herein, upon administration to a subject, reduces *S. pneumoniae* colonization to a greater degree than administration of PPSV23. In some embodiments an immunogenic composition or vaccine described herein, upon administration to a subject, reduces *S. pneumoniae* colonization by one or more of *S. pneumoniae* serotypes 1, 2, 3, 4, 5, 6A, 6B, 7F, 8, 9N, 9V, 10A, 11A, 12F, 14, 15B, 17F, 18C, 19A, 19F, 20B, 22F, 23F, and 33F to a greater degree than administration of PPSV23. In some embodiments an immunogenic composition or vaccine described herein, upon administration to a subject, reduces *S. pneumoniae* colonization by each of *S. pneumoniae* serotypes 1, 2, 3, 4, 5, 6A, 6B, 7F, 8, 9N, 9V, 10A, 11A, 12F, 14, 15B, 17F, 18C, 19A, 19F, 20B, 22F, 23F, and 33F to a greater degree than administration of PPSV23. In some embodiments an immunogenic composition or vaccine described herein, upon administration to a subject, reduces *S. pneumoniae* colonization to a greater degree than administration of PPSV23 by (i) at least one or more of *S. pneumoniae* serotypes 1, 2, 3, 4, 5, 6A, 6B, 7F, 8, 9N, 9V, 10A, 11A, 12F, 14, 15B, 17F, 18C, 19A, 19F, 20B, 22F, 23F, and 33F, and (ii) one or more additional *S. pneumoniae* serotypes, wherein such an immunogenic composition or vaccine does not include polysaccharide(s) present in at least one or more of such additional *S. pneumoniae* serotypes (non-vaccine types, NVTs). In some embodiments the subject is a human. In some embodiments the human is between about 2 weeks of age and about 6 weeks of age. In some embodiments the human is between about 6 weeks of age and about 6 years of age. In some embodiments the human is between about 6 years of age and about 18 years of age. In some embodiments the human is between about 18 years of age and about 50 years of age. In some embodiments the human is about 50 years of age or older.

In some embodiments an immunogenic composition or vaccine described herein, upon administration to a subject, reduces *S. pneumoniae* colonization to a greater degree than administration of PCV13 in combination with PPSV23. In some embodiments an immunogenic composition or vaccine described herein, upon administration to a subject, reduces *S. pneumoniae* colonization by one or more of *S. pneumoniae* serotypes 1, 2, 3, 4, 5, 6B, 7F, 8, 9N, 9V, 10A, 11A, 12F, 14, 15B, 17F, 18C, 19F, 19A, 20A, 22F, 23F, and 33F to a greater degree than administration of PCV13 in combination with PPSV23. In some embodiments an immunogenic composition or vaccine described herein, upon administration to a subject, reduces *S. pneumoniae* colonization by each of *S. pneumoniae* serotypes 1, 2, 3, 4, 5, 6B, 7F, 8, 9N, 9V, 10A, 11A, 12F, 14, 15B, 17F, 18C, 19F, 19A, 20A, 22F, 23F, and 33F to a greater degree than administration of PCV13 in combination with PPSV23. In some embodiments an immunogenic composition or vaccine described herein, upon administration to a subject, reduces S. pneumoniae colonization to a greater degree than administration of PCV13 in combination with PPSV23 by (i) at least one or more of S. pneumoniae serotypes 1, 2, 3, 4, 5, 6B, 7F, 8, 9N, 9V, 10A, 11A, 12F, 14, 15B, 17F, 18C, 19F, 19A, 20A, 22F, 23F, and 33F, and (ii) one or more additional S. pneumoniae serotypes, wherein such an immunogenic composition or vaccine does not include polysaccharide(s) present in at least one or more of such additional S. pneumoniae serotypes (non-vaccine types, NVTs). In some embodiments the subject is a human. In some embodiments the human is between about 2 weeks of age and about 6 weeks of age. In some embodiments the human is between about 6 weeks of age and about 6 years of age. In some embodiments the human is between about 6 years of age and about 18 years of age. In some embodiments the human is between about 18 years of age and about 50 years of age. In some embodiments the human is about 50 years of age or older. In some embodiments, the PCV13 is administered before the PPSV23. In some embodiments, the PCV13 is administered after the PPSV23. In some embodiments, the PCV13 is administered at approximately the same time as the PPSV23.

In some embodiments an immunogenic composition or vaccine described herein, upon administration to a subject, reduces S. pneumoniae colonization to a greater degree than administration of PCV13 in combination with PPSV23. In some embodiments an immunogenic composition or vaccine described herein, upon administration to a subject, reduces S. pneumoniae colonization by one or more of S. pneumoniae serotypes 2, 8, 9N, 10A, 11A, 12F, 15B, 17F, 20B, 22F and 33F to a greater degree than administration of PCV13 in combination with PPSV23. In some embodiments an immunogenic composition or vaccine described herein, upon administration to a subject, reduces S. pneumoniae colonization by each of S. pneumoniae serotypes 2, 8, 9N, 10A, 11A, 12F, 15B, 17F, 20B, 22F and 33F to a greater degree than administration of PCV13 in combination with PPSV23. In some embodiments an immunogenic composition or vaccine described herein, upon administration to a subject, reduces S. pneumoniae colonization to a greater degree than administration of PCV13 in combination with PPSV23 by (i) at least one or more of S. pneumoniae serotypes 2, 8, 9N, 10A, 11A, 12F, 15B, 17F, 20B, 22F and 33F, and (ii) one or more additional S. pneumoniae serotypes, wherein such an immunogenic composition or vaccine does not include polysaccharide(s) present in at least one or more of such additional S. pneumoniae serotypes (non-vaccine types, NVTs). In some embodiments the subject is a human. In some embodiments the human is between about 2 weeks of age and about 6 weeks of age. In some embodiments the human is between about 6 weeks of age and about 6 years of age. In some embodiments the human is between about 6 years of age and about 18 years of age. In some embodiments the human is between about 18 years of age and about 50 years of age. In some embodiments the human is about 50 years of age or older. In some embodiments, the PCV13 is administered before the PPSV23. In some embodiments, the PCV13 is administered after the PPSV23. In some embodiments, the PCV13 is administered at approximately the same time as the PPSV23.

In some embodiments an immunogenic composition or vaccine described herein, upon administration to a subject, reduces S. pneumoniae colonization to a greater degree than administration of PCV13 in combination with PPSV23. In some embodiments an immunogenic composition or vaccine described herein, upon administration to a subject, reduces S. pneumoniae colonization by one or more of S. pneumoniae serotypes 1, 2, 3, 4, 5, 6A, 6B, 7F, 8, 9N, 9V, 10A, 11A, 12F, 14, 15B, 17F, 18C, 19A, 19F, 20B, 22F, 23F, and 33F to a greater degree than administration of PCV13 in combination with PPSV23. In some embodiments an immunogenic composition or vaccine described herein, upon administration to a subject, reduces S. pneumoniae colonization by each of S. pneumoniae serotypes 1, 2, 3, 4, 5, 6A, 6B, 7F, 8, 9N, 9V, 10A, 11A, 12F, 14, 15B, 17F, 18C, 19A, 19F, 20B, 22F, 23F, and 33F to a greater degree than administration of PCV13 in combination with PPSV23. In some embodiments an immunogenic composition or vaccine described herein, upon administration to a subject, reduces S. pneumoniae colonization to a greater degree than administration of PCV13 in combination with PPSV23 by (i) at least one or more of S. pneumoniae serotypes 1, 2, 3, 4, 5, 6A, 6B, 7F, 8, 9N, 9V, 10A, 11A, 12F, 14, 15B, 17F, 18C, 19A, 19F, 20B, 22F, 23F, and 33F, and (ii) one or more additional S. pneumoniae serotypes, wherein such an immunogenic composition or vaccine does not include polysaccharide(s) present in at least one or more of such additional S. pneumoniae serotypes (non-vaccine types, NVTs). In some embodiments the subject is a human. In some embodiments the human is between about 2 weeks of age and about 6 weeks of age. In some embodiments the human is between about 6 weeks of age and about 6 years of age. In some embodiments the human is between about 6 years of age and about 18 years of age. In some embodiments the human is between about 18 years of age and about 50 years of age. In some embodiments the human is about 50 years of age or older. In some embodiments, the PCV13 is administered before the PPSV23. In some embodiments, the PCV13 is administered after the PPSV23. In some embodiments, the PCV13 is administered at approximately the same time as the PPSV23. In some embodiments, an immunogenic composition or vaccine described herein, upon administration to a subject, induces an immune response that can help protect against the establishment of S. pneumoniae, at a level greater than a control composition. In some embodiments, an immunogenic composition or vaccine described herein protects against colonization at a level greater than a control composition. In some embodiments, an immunogenic composition or vaccine described herein inhibits infection by S. pneumoniae in a non-colonized or uninfected subject at a level greater than a control composition. In some embodiments, an immunogenic composition or vaccine described herein reduces the duration of colonization by S. pneumoniae in a subject who is already colonized at a level greater than a control composition. In some embodiments, the level greater is about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 30%, about 35%, about 40%, about 45%, about 50%, about 55%, about 60%, about 65%, about 70%, about 75%, about 80%, about 85%, about 90%, or about 95% of the control composition. In some embodiments, the control composition may be PCV13 or PPSV23.

In some embodiments, an immunogenic composition or vaccine described herein, upon administration to a subject, induces an immune response against S. pneumoniae at a level greater than a control composition. In some embodiments, an immunogenic composition or vaccine described herein, upon administration to a subject, induces an immune response against one or more serotypes of *S. pneumoniae* at a level greater than a control composition. In some embodiments, the immune response is an antibody or B cell response. In some embodiments, the immune response is a T cell response. In some embodiments, the immune response is an innate immune response. In some embodiments, the immune response is a CD4+ T cell response, including $T_H1$, $T_H2$, or $T_H17$ response, or a CD8+ T cell response, or a CD4+ and CD8+ T cell response, or CD4−/CD8− T cell response. In some embodiments, the immune response is an antibody or B cell response, and a T cell response. In some embodiments, the immune response is an antibody or B cell response, a T cell response, and an innate immune response. In some embodiments, the immune response is a protective immune response. In some embodiments, the level greater is about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 30%, about 35%, about 40%, about 45%, about 50%, about 55%, about 60%, about 65%, about 70%, about 75%, about 80%, about 85%, about 90%, or about 95% of the control composition. In some embodiments, the control composition may be PCV13 or PPSV23.

In some embodiments, an immunogenic composition or vaccine described herein, upon administration to a subject, induces an antibody or B cell response against one or more pathogens in the subject at a level greater than a control composition. In some embodiments, the level greater is about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 30%, about 35%, about 40%, about 45%, about 50%, about 55%, about 60%, about 65%, about 70%, about 75%, about 80%, about 85%, about 90%, or about 95% of the control composition. In some embodiments, the control composition may be PCV13 or PPSV23.

In some embodiments, an immunogenic composition or vaccine described herein, upon administration to a subject, induces an antibody or B cell response against one or more pathogens in the subject at level greater than a control composition. In some embodiments, the level greater is about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 30%, about 35%, about 40%, about 45%, about 50%, about 55%, about 60%, about 65%, about 70%, about 75%, about 80%, about 85%, about 90%, or about 95% of the control composition. In some embodiments, the control composition may be PCV13 or PPSV23.

In some embodiments, an immunogenic composition or vaccine described herein, upon administration to a subject, induces a T cell response against one or more pathogens in the subject at a level greater than a control composition. In some embodiments, an immunogenic composition or vaccine described herein, upon administration to a subject, induces a T cell response against one or more pathogens in the subject at level greater than a control composition. In some embodiments, the level greater is about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 30%, about 35%, about 40%, about 45%, about 50%, about 55%, about 60%, about 65%, about 70%, about 75%, about 80%, about 85%, about 90%, or about 95% of the control composition. In some embodiments, the control composition may be PCV13 or PPSV23.

In some embodiments, upon administration to a subject, an immunogenic composition or vaccine described herein treats or prevents infection by *S. pneumoniae* in the subject at a level greater than a control composition. In some embodiments, upon administration to a subject, an immunogenic composition or vaccine described herein treats or prevents Invasive Pneumococcal Disease (IPD) due to infection by *S. pneumoniae* in the subject at a level greater than a control composition. In some embodiments, upon administration to a subject, an immunogenic composition or vaccine described herein treats or prevents bacteremia due to infection by *S. pneumoniae* in the subject at a level greater than a control composition. In some embodiments, upon administration to a subject, an immunogenic composition or vaccine described herein treats or prevents sepsis due to infection by *S. pneumoniae* in the subject at a level greater than a control composition. In some embodiments, upon administration to a subject, an immunogenic composition or vaccine described herein treats or prevents organ damage due to infection by *S. pneumoniae* in the subject at a level greater than a control composition. In some embodiments, upon administration to a subject, an immunogenic composition or vaccine described herein treats or prevents meningitis due to infection by *S. pneumoniae* in the subject at a level greater than a control composition. In some embodiments, upon administration to a subject, an immunogenic composition or vaccine described herein treats or prevents pneumonia due to infection by *S. pneumoniae* in the subject at a level greater than a control composition. In some embodiments, upon administration to a subject, an immunogenic composition or vaccine described herein treats or prevents otitis media due to infection by *S. pneumoniae* in the subject at a level greater than a control composition. In some embodiments, upon administration to a subject, an immunogenic composition or vaccine described herein treats or prevents sinusitis due to infection by *S. pneumoniae* in the subject at a level greater than a control composition. In some embodiments, the level greater is about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 30%, about 35%, about 40%, about 45%, about 50%, about 55%, about 60%, about 65%, about 70%, about 75%, about 80%, about 85%, about 90%, or about 95% of the control composition. In some embodiments, the control composition may be PCV13 or PPSV23.

In some embodiments, upon administration to a subject, an immunogenic composition or vaccine described herein inhibits or reduces the rate of occurrence of infection by *S. pneumoniae* in the subject at a level greater than a control composition. In some embodiments, upon administration to a subject, an immunogenic composition or vaccine described herein inhibits or reduces the rate of occurrence of Invasive Pneumococcal Disease (IPD) due to infection by *S. pneumoniae* in the subject at a level greater than a control composition. In some embodiments, upon administration to a subject, an immunogenic composition or vaccine described herein inhibits or reduces the rate of occurrence of bacteremia due to infection by *S. pneumoniae* in the subject at a level greater than a control composition. In some embodiments, upon administration to a subject, an immunogenic composition or vaccine described herein inhibits or reduces the rate of occurrence of sepsis due to infection by *S. pneumoniae* in the subject at a level greater than a control composition. In some embodiments, upon administration to a subject, an immunogenic composition or vaccine described herein inhibits or reduces the rate of occurrence of organ damage due to infection by *S. pneumoniae* in the subject at a level greater than a control composition. In some embodiments, upon administration to a subject, an immunogenic composition or vaccine described herein inhibits or reduces the rate of occurrence of meningitis due to infection by *S. pneumoniae* in the subject at a level greater than a control composition. In some embodiments, upon administration to a subject, an immunogenic composition or vaccine described herein inhibits or reduces the rate of occurrence of pneumonia due to infection by *S. pneumoniae* in the subject at a level greater than a control composition. In some embodiments, upon administration to a subject, an immunogenic composition or vaccine described herein inhibits or reduces the rate of occurrence of otitis media due to infection by *S. pneumoniae* in the subject at a level greater than a control composition. In some embodiments, upon administration to a subject, an immunogenic composition or vaccine described herein inhibits or reduces the rate of occurrence of sinusitis due to infection by *S. pneumoniae* in the subject at a level greater than a control composition. In some embodiments, the level greater is about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 30%, about 35%, about 40%, about 45%, about 50%, about 55%, about 60%, about 65%, about 70%, about 75%, about 80%, about 85%, about 90%, or about 95% of the control composition. In some embodiments, the control composition may be PCV13 or PPSV23.

In some embodiments, upon administration to a subject, an immunogenic composition or vaccine described herein reduces the severity of infection by *S. pneumoniae* in the subject at a level greater than a control composition. In some embodiments, upon administration to a subject, an immunogenic composition or vaccine described herein reduces the severity of Invasive Pneumococcal Disease (IPD) due to infection by *S. pneumoniae* in the subject at a level greater than a control composition. In some embodiments, upon administration to a subject, an immunogenic composition or vaccine described herein reduces the severity of bacteremia due to infection by *S. pneumoniae* in the subject at a level greater than a control composition. In some embodiments, upon administration to a subject, an immunogenic composition or vaccine described herein reduces the severity of sepsis due to infection by *S. pneumoniae* in the subject at a level greater than a control composition. In some embodiments, upon administration to a subject, an immunogenic composition or vaccine described herein reduces the severity of organ damage due to infection by *S. pneumoniae* in the subject at a level greater than a control composition. In some embodiments, the control composition may be PCV13 or PPSV23. In some embodiments, upon administration to a subject, an immunogenic composition or vaccine described herein reduces the severity of meningitis due to infection by *S. pneumoniae* in the subject at a level greater than a control composition. In some embodiments, upon administration to a subject, an immunogenic composition or vaccine described herein reduces the severity of pneumonia due to infection by *S. pneumoniae* in the subject at a level greater than a control composition. In some embodiments, upon administration to a subject, an immunogenic composition or vaccine described herein reduces the severity of otitis media due to infection by *S. pneumoniae* in the subject at a level greater than a control composition. In some embodiments, upon administration to a subject, an immunogenic composition or vaccine described herein reduces the severity of sinusitis due to infection by *S. pneumoniae* in the subject at a level greater than a control composition. In some embodiments, the level greater is about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 30%, about 35%, about 40%, about 45%, about 50%, about 55%, about 60%, about 65%, about 70%, about 75%, about 80%, about 85%, about 90%, or about 95% of the control composition. In some embodiments, the control composition may be PCV13 or PPSV23.

In some embodiments, upon administration to a subject, an immunogenic composition or vaccine described herein inhibits transmission of *S. pneumoniae* from the subject to another subject at a level greater than a control composition. In some embodiments, upon administration to a subject, an immunogenic composition or vaccine described herein inhibits colonization by *S. pneumoniae* in the subject at a level greater than a control composition. In some embodiments, upon administration to a subject, an immunogenic composition or vaccine described herein inhibits colonization by *S. pneumoniae* in the nasopharynx of the subject at a level greater than a control composition. In some embodiments, the level greater is about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 30%, about 35%, about 40%, about 45%, about 50%, about 55%, about 60%, about 65%, about 70%, about 75%, about 80%, about 85%, about 90%, or about 95% of the control composition. In some embodiments, the control composition may be PCV13 or PPSV23.

In some embodiments, an immunogenic composition or vaccine described herein is administered to a subject between about 6 weeks and about 5 years (e.g., prior to the 6$^{th}$ birthday) for active immunization for the prevention of invasive disease caused by *Streptococcus pneumoniae* serotypes 1, 2, 3, 4, 5, 6A, 6B, 7F, 8, 9N, 9V, 10A, 11A, 12F, 14, 15B, 17F, 18C, 19A, 19F, 20B, 22F, 23F and 33F.

In some embodiments, a MAPS24 vaccine is administered to a subject between about 6 weeks and about 5 years (e.g., prior to the 6$^{th}$ birthday) for active immunization for the prevention of invasive disease caused by *Streptococcus pneumoniae* serotypes 1, 2, 3, 4, 5, 6A, 6B, 7F, 8, 9N, 9V, 10A, 11A, 12F, 14, 15B, 17F, 18C, 19A, 19F, 20B, 22F, 23F and 33F.

In some embodiments an immunogenic composition or vaccine described herein is administered to a subject between about 6 years and about 17 years (e.g., prior to the 18$^{th}$ birthday) for active immunization for the prevention of invasive disease caused by *Streptococcus pneumoniae* serotypes 1, 2, 3, 4, 5, 6A, 6B, 7F, 8, 9N, 9V, 10A, 11A, 12F, 14, 15B, 17F, 18C, 19A, 19F, 20B, 22F, 23F and 33F.

In some embodiments, a MAPS24 vaccine is administered to a subject between about 6 years and about 17 years (e.g., prior to the 18$^{th}$ birthday) for active immunization for the prevention of invasive disease caused by *Streptococcus pneumoniae* serotypes 1, 2, 3, 4, 5, 6A, 6B, 7F, 8, 9N, 9V, 10A, 11A, 12F, 14, 15B, 17F, 18C, 19A, 19F, 20B, 22F, 23F and 33F.

In some embodiments an immunogenic composition or vaccine described herein is administered to a subject 18 years or older for active immunization for the prevention of invasive disease caused by *Streptococcus pneumoniae* serotypes 1, 2, 3, 4, 5, 6A, 6B, 7F, 8, 9N, 9V, 10A, 11A, 12F, 14, 15B, 17F, 18C, 19A, 19F, 20B, 22F, 23F and 33F.

In some embodiments, a MAPS24 vaccine is administered to a subject 18 years or older for active immunization for the prevention of invasive disease caused by *Streptococcus pneumoniae* serotypes 1, 2, 3, 4, 5, 6A, 6B, 7F, 8, 9N, 9V, 10A, 11A, 12F, 14, 15B, 17F, 18C, 19A, 19F, 20B, 22F, 23F and 33F.

In some embodiments an immunogenic composition or vaccine described herein is administered to a subject 18 years or older for active immunization for the prevention of pneumonia caused by *Streptococcus pneumoniae* serotypes 1, 2, 3, 4, 5, 6A, 6B, 7F, 8, 9N, 9V, 10A, 11A, 12F, 14, 15B, 17F, 18C, 19A, 19F, 20B, 22F, 23F and 33F.

In some embodiments, a MAPS24 vaccine is administered to a subject 18 years or older for active immunization for the prevention of pneumonia caused by *Streptococcus pneumoniae* serotypes 1, 2, 3, 4, 5, 6A, 6B, 7F, 8, 9N, 9V, 10A, 11A, 12F, 14, 15B, 17F, 18C, 19A, 19F, 20B, 22F, 23F and 33F.

In some embodiments an immunogenic composition or vaccine described herein is administered to a subject 18 years or older for active immunization for the prevention of invasive disease and pneumonia caused by *Streptococcus pneumoniae* serotypes 1, 2, 3, 4, 5, 6A, 6B, 7F, 8, 9N, 9V, 10A, 11A, 12F, 14, 15B, 17F, 18C, 19A, 19F, 20B, 22F, 23F and 33F.

In some embodiments, a MAPS24 vaccine is administered to a subject 18 years or older for active immunization for the prevention of invasive disease and pneumonia caused by *Streptococcus pneumoniae* serotypes 1, 2, 3, 4, 5, 6A, 6B, 7F, 8, 9N, 9V, 10A, 11A, 12F, 14, 15B, 17F, 18C, 19A, 19F, 20B, 22F, 23F and 33F.

Antibody Compositions

Some embodiments provide for an antibody composition comprising antibodies raised in a mammal immunized with an immunogenic complex of the invention. In some embodiments, an antibody comprises at least one antibody selected from the group consisting of mAbs and anti-idiotype antibodies. In some embodiments, an antibody composition comprises an isolated gamma globulin fraction. In some embodiments, an antibody composition comprises polyclonal antibodies. In some embodiments, the antibody composition is administered to a subject. In some embodiments, the antibody composition administered to a subject confers passive immunization.

Vaccine Formulations

Optimal amounts of components for a particular vaccine can be ascertained by standard studies involving observation of appropriate immune responses in subjects. Following an initial vaccination, subjects can receive one or several booster immunizations adequately spaced in time.

The immunogenic complexes described herein, and/or preparations thereof may be formulated in a unit dosage form for ease of administration and uniformity of dosage. The specific therapeutically effective dose level for any particular subject or organism may depend upon a variety of factors including the severity or degree of risk of infection; the activity of the specific vaccine or vaccine composition employed; other characteristics of the specific vaccine or vaccine composition employed; the age, body weight, general health, sex of the subject, diet of the subject, pharmacokinetic condition of the subject, the time of administration (e.g., with regard to other activities of the subject such as eating, sleeping, receiving other medicines including other vaccine doses, etc.), route of administration, rate of excretion of the specific vaccine or vaccine composition employed; vaccines used in combination or coincidental with the vaccine composition employed; and like factors well known in the medical arts.

Immunogenic complexes for use in accordance with the present disclosure may be formulated into compositions (e.g., pharmaceutical compositions) according to known techniques. Vaccine preparation is generally described in Vaccine Design (Powell and Newman, 1995). For example, an immunologically amount of a vaccine product can be formulated together with one or more organic or inorganic, liquid or solid, pharmaceutically suitable carrier materials. Preparation of pneumococcal polysaccharide and conjugate vaccines is described, for example, in U.S. Ser. No. 11/395,593, filed Mar. 31, 2006, the contents of which are incorporated herein by reference.

In general, pharmaceutically acceptable carrier(s) include solvents, dispersion media, and the like, which are compatible with pharmaceutical administration. For example, materials that can serve as pharmaceutically acceptable carriers include, but are not limited to sugars such as lactose, glucose, dextrose, and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; polyols such as glycerol, propylene glycol, and liquid polyethylene glycol; esters such as ethyl oleate and ethyl laurate; agar; buffering agents such as magnesium hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as preservatives, and antioxidants can also be present in the composition, according to the judgment of the formulator (Martin, 1975).

Vaccines may be formulated by combining one or more of the immunogenic complexes disclosed herein with carriers and/or other optional components by any available means including, for example, conventional mixing, granulating, dissolving, lyophilizing, or similar processes.

Vaccine compositions useful in the provided methods may be lyophilized up until they are about to be used, at which point they are extemporaneously reconstituted with diluent. In some embodiments, vaccine components or compositions are lyophilized in the presence of one or more other components (e.g., adjuvants), and are extemporaneously reconstituted with saline solution. Alternatively, individual components, or sets of components may be separately lyophilized and/or stored (e.g., in a vaccination kit), the components being reconstituted and either mixed prior to use or administered separately to the subject.

Lyophilization can produce a more stable composition (for instance by preventing or reducing breakdown of polysaccharide antigens). Lyophilizing of vaccines or vaccine components is well known in the art. Typically, a liquid vaccine or vaccine component is freeze dried, often in the presence of an anti-caking agent (such as, for example, sugars such as sucrose or lactose). In some embodiments, the anti-caking agent is present, for example, at an initial concentration of 10-200 mg/ml. Lyophilization typically occurs over a series of steps, for instance a cycle starting at −69° C., gradually adjusting to −24° C. over 3 h, then retaining this temperature for 18 h, then gradually adjusting to −16° C. over 1 h, then retaining this temperature for 6 h, then gradually adjusting to +34° C. over 3 h, and finally retaining this temperature over 9 h.

In some embodiments, a vaccine is a liquid. In some embodiments the liquid is a reconstituted lyophylate. In some embodiments a vaccine has a pH of about 5, about 6, about 7, or about 8. In some embodiments a vaccine has a pH between about 5 and about 7.5. In some embodiments a vaccine has a pH between 5 and 7.5. In some embodiments a vaccine has a pH between about 5.3 and about 6.3. In some embodiments a vaccine has a pH between 5.3 and 6.3. In some embodiments a vaccine has a pH of about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, or about 7.5.

Vaccines or vaccine components for use in accordance with the present invention may be incorporated into liposomes, cochleates, biodegradable polymers such as polylactide, poly-glycolide and poly-lactide-co-glycolides, or immune-stimulating complexes (ISCOMs).

In certain situations, it may be desirable to prolong the effect of a vaccine or for use in accordance with the present invention, for example by slowing the absorption of one or more vaccine components. Such delay of absorption may be accomplished, for example, by the use of a liquid suspension of crystalline or amorphous material with poor water solubility. The rate of absorption of the product then depends upon its rate of dissolution, which in turn, may depend upon size and form. Alternatively, or additionally, delayed absorption may be accomplished by dissolving or suspending one or more vaccine components in an oil vehicle. Injectable depot forms can also be employed to delay absorption. Such depot forms can be prepared by forming microcapsule matrices of one or more vaccine components a biodegradable polymers network. Depending upon the ratio of polymer to vaccine component, and the nature of the particular polymer(s) employed, the rate of release can be controlled.

Examples of biodegradable polymers that can be employed in accordance with the present invention include, for example, poly(orthoesters) and poly(anhydrides). One particular exemplary polymer is polylactide-polyglycolide.

Depot injectable formulations may also be prepared by entrapping the product in liposomes or microemulsions, which are compatible with body tissues.

Polymeric delivery systems can also be employed in non-depot formulations including, for example, oral formulations. For example, biodegradable, biocompatible polymers such as ethylene vinyl acetate, polyanhydrides, polyglycolic acid, collagen, polyorthoesters, and polylactic acid, etc., can be used in oral formulations. Polysaccharide antigens or conjugates may be formulated with such polymers, for example to prepare particles, microparticles, extrudates, solid dispersions, admixtures, or other combinations in order to facilitate preparation of useful formulations (e.g., oral).

Vaccines for use in accordance with the present invention include immunogenic compositions, and may additionally include one or more additional active agents (i.e., agents that exert a biological effect—not inert ingredients). For example, it is common in vaccine preparation to include one or more adjuvants. It will be appreciated that such additional agents may be formulated together with one or more other vaccine components, or may be maintained separately and combined at or near the time of administration. In some embodiments, such additional components may be administered separately from some or all of the other vaccine components, within an appropriate time window for the relevant effect to be achieved.

Adjuvants

The vaccine formulations and immunogenic compositions described herein may include an adjuvant. Adjuvants, generally, are agents that enhance the immune response to an antigen. Adjuvants can be broadly separated into two classes, based on their principal mechanisms of action: vaccine delivery systems and immunostimulatory adjuvants (see, e.g., Singh et al, 2003). In most vaccine formulations, the adjuvant provides a signal to the immune system so that it generates a response to the antigen, and the antigen is required for driving the specificity of the response to the pathogen. Vaccine delivery systems are often particulate formulations, e.g., emulsions, microparticles, immunestimulating complexes (ISCOMs), nanoparticles, which may be, for example, particles and/or matrices, and liposomes. In contrast, immunostimulatory adjuvants are sometimes from or derived from pathogens and can represent pathogen associated molecular patterns (PAMP), e.g., lipopolysaccharides (LPS), monophosphoryl lipid A (MPL), or CpG-containing DNA, which activate cells of the innate immune system.

Alternatively, adjuvants may be classified as organic and inorganic. Inorganic adjuvants include alum salts such as aluminum phosphate, amorphous aluminum hydroxyphosphate sulfate, and aluminum hydroxide, which are commonly used in human vaccines. Organic adjuvants comprise organic molecules including macromolecules. Non-limiting examples of organic adjuvants include cholera toxin/toxoids, other enterotoxins/toxoids or labile toxins/toxoids of Gram-negative bacteria, interleukins (e.g., IL-1, IL-2, IL-4, IL-5, IL-6, IL-7, IL-12, IL-15, IL-18, etc.), interferons (e.g., gamma interferon), granulocyte macrophage colony stimulating factor (GM-CSF), macrophage colony stimulating factor (M-CSF), and tumor necrosis factor (TNF).

Adjuvants may also be classified by the response they induce. In some embodiments, the adjuvant induces the generation, proliferation, or activation of $T_H1$ cells or $T_H2$ cells. In other embodiments, the adjuvant induces the generation, proliferation, or activation of B cells. In yet other embodiments, the adjuvant induces the activation of antigen-presenting cells. These categories are not mutually exclusive; in some cases, an adjuvant activates more than one type of cell.

In certain embodiments, the adjuvant induces the generation, proliferation, or activation of $T_H17$ cells. The adjuvant may promote the CD4+ or CD8+ T cells to secrete IL-17. In some embodiments, an adjuvant that induces the generation, proliferation, or activation of $T_H17$ cells is one that produces at least a 2-fold, and in some cases a 10-fold, experimental sample to control ratio in the following assay. In the assay, an experimenter compares the IL-17 levels secreted by two populations of cells: (1) cells from animals immunized with the adjuvant and a polypeptide known to induce $T_H17$ generation, proliferation, or activation, and (2) cells from animals treated with the adjuvant and an irrelevant (control) polypeptide. An adjuvant that induces the generation, proliferation, or activation of $T_H17$ cells may cause the cells of population (1) to produce more than 2-fold, or more than 10-fold more IL-17 than the cells of population (2). IL-17 may be measured, for example, by ELISA or ELISPOT. Certain toxins, such as cholera toxin and labile toxin (produced by enterotoxigenic E. coli, or ETEC), activate a $T_H17$ response. Thus, in some embodiments, the adjuvant is a toxin or toxoid. Cholera toxin was successfully used in the mouse model to induce protective immunity in conjunction with certain polypeptides from Table 1 (see Examples 5-8). One form of labile toxin is produced by Intercell. Mutant derivates of labile toxin (toxoids) that are active as adjuvants but significantly less toxic can be used as well. Exemplary detoxified mutant derivatives of labile toxin include mutants lacking ADP-ribosyltransferase activity. Particular detoxified mutant derivatives of labile toxin include LTK7 (Douce et al, 1995) and LTK63 (Williams et al, 2004), LT-G192 (Douce et al, 1999), and LTR72 (Giuliani et al, 1998).

In some embodiments, the adjuvant comprises a VLP (virus-like particle). One such adjuvant platform, Alphavirus replicons, induces the activation of $T_H17$ cells using alphavirus and is produced by Alphavax. In certain embodiments of the Alphavirus replicon system, alphavirus may be engineered to express an antigen of interest, a cytokine of interest (for example, IL-17 or a cytokine that stimulates IL-17 production), or both, and may be produced in a helper cell line. More detailed information may be found in U.S. Pat. Nos. 5,643,576 and 6,783,939. In some embodiments, a vaccine formulation is administered to a subject in combination with a nucleic acid encoding a cytokine.

Certain classes of adjuvants activate toll-like receptors (TLRs) in order to activate a $T_H17$ response. TLRs are well known proteins that may be found on leukocyte membranes, and recognize foreign antigens (including microbial antigens). Administering a known TLR ligand together with an antigen of interest (for instance, as a fusion protein) can promote the development of an immune response specific to the antigen of interest. One exemplary adjuvant that activates TLRs comprises Monophosphoryl Lipid A (MPL). Traditionally, MPL has been produced as a detoxified lipopolysaccharide (LPS) endotoxin obtained from Gram-negative bacteria, such as S. minnesota. In particular, sequential acid and base hydrolysis of LPS produces an immunoactive lipid A fraction (which is MPL), and lacks the saccharide groups and all but one of the phosphates present in LPS. A number of synthetic TLR agonists (in particular, TLR-4 agonists) are disclosed in Evans et al, 2003. Like MPL adjuvants, these synthetic compounds activate the innate immune system via TLR. Another type of TLR agonist is a synthetic phospholipid dimer, for example E6020 (Ishizaka et al, 2007). Various TLR agonists (including TLR-4 agonists) have been produced and/or sold by, for example, the Infectious Disease Research Institute (IRDI), Corixa, Esai, Avanti Polar Lipids, Inc., and Sigma Aldrich. Another exemplary adjuvant that activates TLRs comprises a mixture of MPL, Trehalose Dicoynomycolate (TDM), and dioctadecyldimethylammonium bromide (DDA). Another TLR-activating adjuvant is R848 (resiquimod).

In some embodiments, the adjuvant is or comprises a saponin. Typically, the saponin is a triterpene glycoside, such as those isolated from the bark of the *Quillaja saponaria* tree. A saponin extract from a biological source can be further fractionated (e.g., by chromatography) to isolate the portions of the extract with the best adjuvant activity and with acceptable toxicity. Typical fractions of extract from *Quillaja saponaria* tree used as adjuvants are known as fractions A and C.

In certain embodiments, combinations of adjuvants are used. Three exemplary combinations of adjuvants are MPL and alum, E6020 and alum, and MPL and an ISCOM.

Adjuvants may be covalently or non-covalently bound to antigens. In some embodiments, the adjuvant may comprise a protein which induces inflammatory responses through activation of antigen-presenting cells (APCs). In some embodiments, one or more of these proteins can be recombinantly fused with an antigen of choice, such that the resultant fusion molecule promotes dendritic cell maturation, activates dendritic cells to produce cytokines and chemokines, and ultimately, enhances presentation of the antigen to T cells and initiation of T cell responses (e.g., see Wu et al, 2005).

In some embodiments, immunogenic complexes described herein are formulated and/or administered in combination with an adjuvant. In some embodiments, the adjuvant is selected from the group consisting of aluminum phosphate, aluminum hydroxide, and phosphate aluminum hydroxide. In some embodiments, the adjuvant comprises aluminum phosphate. In some embodiments, the adjuvant is aluminum phosphate.

Typically, the same adjuvant or mixture of adjuvants is present in each dose of a vaccine. Optionally, however, an adjuvant may be administered with the first dose of vaccine and not with subsequent doses (i.e., booster shots). Alternatively, a strong adjuvant may be administered with the first dose of vaccine and a weaker adjuvant or lower dose of the strong adjuvant may be administered with subsequent doses. The adjuvant can be administered before the administration of the antigen, concurrent with the administration of the antigen or after the administration of the antigen to a subject (sometimes within 1, 2, 6, or 12 hours, and sometimes within 1, 2, or 5 days). Certain adjuvants are appropriate for human subjects, non-human animals, or both.

Vaccines for use in accordance with the present invention may include, or be administered concurrently with, other antimicrobial therapy. For example, such vaccines may include or be administered with one or more agents that kills or retards growth of a pathogen. Such agents include, for example, penicillin, vancomycin, erythromycin, azithromycin, and clarithromycin, cefotaxime, ceftriaxone, levoflaxin, gatifloxacin.

Alternatively or additionally, vaccines for use in accordance with the present invention may include, or be administered with, one or more other vaccines or therapies. For example, one or more non-pneumococcal antigens may be included in or administered with the vaccines.

Additional Components and Excipients

In addition to the antigens and the adjuvants described above, a vaccine formulation or immunogenic composition may include one or more additional components.

In certain embodiments, the vaccine formulation or immunogenic composition may include one or more stabilizers such as sugars (such as sucrose, glucose, or fructose), phosphate (such as sodium phosphate dibasic, potassium phosphate monobasic, dibasic potassium phosphate, or monosodium phosphate), glutamate (such as monosodium L-glutamate), gelatin (such as processed gelatin, hydrolyzed gelatin, or porcine gelatin), amino acids (such as arginine, asparagine, histidine, L-histidine, alanine, valine, leucine, isoleucine, serine, threonine, lysine, phenylalanine, tyrosine, and the alkyl esters thereof), inosine, or sodium borate.

In certain embodiments, the vaccine formulation or immunogenic composition includes one or more buffers such as a mixture of sodium bicarbonate and ascorbic acid.

In some embodiments, the vaccine formulation may be administered in saline, such as phosphate buffered saline (PBS), or distilled water.

In certain embodiments, the vaccine formulation or immunogenic composition includes one or more surfactants, for example, but not limited to, polysorbate 80 (TWEEN 80), polysorbate 20 (TWEEN 20), Polyethylene glycol p-(1, 1,3,3-tetramethylbutyl)-phenyl ether (TRITON X-100), and 4-(1,1,3,3-Tetramethylbutyl)phenol polymer with formaldehyde and oxirane (TYLOXAPOL). A surfactant can be ionic or non-ionic.

In certain embodiments, the vaccine formulation or immunogenic composition includes one or more salts such as sodium chloride, ammonium chloride, calcium chloride, or potassium chloride.

In certain embodiments, a preservative is included in the vaccine or immunogenic composition. In other embodiments, no preservative is used. A preservative is most often used in multi-dose vaccine vials, and is less often needed in single-dose vaccine vials. In certain embodiments, the preservative is 2-phenoxyethanol, methyl and propyl parabens, benzyl alcohol, and/or sorbic acid.

Methods of Administration

In some embodiments, immunogenic complexes are administered to a subject at risk of developing pneumococcal disease, e.g. an infant, a toddler, a juvenile, or an older adult. In some embodiments the subject is a human. In some embodiments the human is between about 2 weeks of age and about 6 weeks of age. In some embodiments the human is between about 6 weeks of age and about 6 years of age. In some embodiments the human is between about 6 years of age and about 18 years of age. In some embodiments the human is between about 18 years of age and about 50 years of age. In some embodiments the human is about 50 years of age or older. In some embodiments, immunogenic complexes are administered to a subject at elevated risk of developing pneumococcal disease, e.g., immunocompromised subjects, subjects having sickle cell disease or other hemoglobinopathies, congenital or acquired asplenia, splenic dysfunction, chronic renal failure or nephrotic syndrome, diseases associated with treatment with immunosuppressive drugs or radiation therapy (including malignant neoplasm, leukemia, lymphomas, Hodgkin's disease, or solid organ transplantation), congenital or acquired immunodeficiency, HIV infection, cerebrospinal fluid leaks, cochlear implant(s), chronic heart disease, chronic lung disease, diabetes mellitus, alcoholism, chronic liver disease, cigarette smoking, asthma, generalized malignancy, multiple myeloma, or solid organ transplantation. It will be appreciated that a subject can be considered at risk for developing a disease without having been diagnosed with any symptoms of the disease. For example, if the subject is known to have been, or to be intended to be, in situations with relatively high risk of infection, that subject will be considered at risk for developing the disease.

Any effective route of administration may be utilized such as, for example, oral, nasal, enteral, parenteral, intramuscular or intravenous, subcutaneous, transdermal, intradermal, rectal, vaginal, topical, ocular, pulmonary, or by contact application. In some embodiments, vaccine compositions may be injected (e.g., via intramuscular, intraperitoneal, intradermal and/or subcutaneous routes); or delivered via the mucosa (e.g., to the oral/alimentary, respiratory, and/or genitourinary tracts). Intranasal administration of vaccines may be particularly useful in some contexts, for example for treatment of pneumonia or otitis media (as nasopharyngeal carriage of pneumococci can be more effectively prevented, thus attenuating infection at its earliest stage). In some embodiments of the invention, it may be desirable to administer different doses of a vaccine by different routes; in some embodiments, it may be desirable to administer different components of one dose via different routes. In some embodiments, an immunogenic composition or vaccine disclosed herein is administered intramuscularly. In some embodiments, an immunogenic composition or vaccine disclosed herein is administered subcutaneously.

In some embodiments of the present invention, pharmaceutical compositions (e.g., vaccines) are administered intradermally. Conventional technique of intradermal injection, the "Mantoux procedure", comprises steps of cleaning the skin, and then stretching with one hand, and with the bevel of a narrow gauge needle (26-31 gauge) facing upwards the needle is inserted at an angle of between 10-15°. Once the bevel of the needle is inserted, the barrel of the needle is lowered and further advanced while providing a slight pressure to elevate it under the skin. The liquid is then injected very slowly thereby forming a bleb or bump on the skin surface, followed by slow withdrawal of the needle.

Devices that are specifically designed to administer liquid agents into or across the skin have been described, for example the devices described in WO 99/34850 and EP 1092444, also the jet injection devices described for example in WO 01/13977; U.S. Pat. Nos. 5,480,381, 5,599, 302, 5,334,144, 5,993,412, 5,649,912, 5,569,189, 5,704,911, 5,383,851, 5,893,397, 5,466,220, 5,339,163, 5,312,335, 5,503,627, 5,064,413, 5,520,639, 4,596,556, 4,790,824, 4,941,880, 4,940,460, WO 97/37705 and WO 97/13537. Other methods of intradermal administration of the vaccine preparations may include conventional syringes and needles, or devices designed for ballistic delivery of solid vaccines (WO 99/27961), or transdermal patches (WO 97/48440; WO 98/28037); or applied to the surface of the skin (transdermal or transcutaneous delivery WO 98/20734; WO 98/28037).

As described above, pharmaceutical compositions (e.g., vaccines) may be administered as a single dose or as multiple doses. It will be appreciated that an administration is a single "dose" so long as all relevant components are administered to a subject within a window of time; it is not necessary that every component be present in a single composition. For example, administration of two different immunogenic compositions, within a period of less than 24 h, is considered a single dose. To give but one example, immunogenic compositions having different antigenic components may be administered in separate compositions, but as part of a single dose. As noted above, such separate compositions may be administered via different routes or via the same route. Alternatively or additionally, in embodiments wherein a vaccine comprises a combination of immunogenic compositions and additional types of active agents, immunogenic compositions may be administered via one route, and a second active agent may be administered by the same route or by a different route.

Pharmaceutical compositions (e.g., vaccines) are administered in such amounts and for such time as is necessary to achieve a desired result. In certain embodiments of the present invention, a vaccine composition comprises an immunologically effective amount of at least immunogenic composition. The exact amount required to achieve an immunologically effective amount may vary, depending on the immunogenic composition, and from subject to subject, depending on the species, age, and general condition of the subject, the stage of the disease, the particular pharmaceutical mixture, its mode of administration, and the like.

The amount of polypeptide antigen(s), polysaccharide antigen(s) or conjugate(s) in each pharmaceutical composition (e.g., vaccine) dose is selected to allow the vaccine, when administered as described herein, to induce an appropriate immune-protective response without significant, adverse side effects.

In some embodiments, a pharmaceutical composition comprising an immunogenic complex disclosed herein induces a $T_H1$ and/or $T_H17$ cell response upon administration to a subject. In some embodiments, a pharmaceutical composition comprising an immunogenic complex disclosed herein induces an opsonic/bactericidal response against *S. pneumoniae* upon administration to a subject. In some embodiments, a pharmaceutical composition comprising an immunogenic complex disclosed herein reduces rate of transmission and/or colonization of the mucosal surfaces by *S. pneumoniae* upon administration to a subject.

In some embodiments, a pharmaceutical composition comprising an immunogenic complex disclosed herein reduces rate of transmission and/or colonization of the nasopharynx or the lungs by *S. pneumoniae* upon transmission.

Some embodiments provide for a method of immunizing a subject against *S. pneumoniae* infection comprising administering to the subject an immunologically effective amount of an immunogenic complex described herein. Some embodiments provide for a method of immunizing a subject against *S. pneumoniae* infection comprising administering to the subject an immunologically effective amount of an immunogenic composition described herein. Some embodiments provide for a method of immunizing a subject against *S. pneumoniae* infection comprising administering to the subject an immunologically effective amount of a vaccine composition described herein. Some embodiments provide for a method of immunizing a subject against *S. pneumoniae* infection comprising administering to the subject an immunologically effective amount of a pharmaceutical composition described herein.

Combination Prophylaxis or Combination Therapy

In some embodiments, an immunogenic complex, immunogenic composition, vaccine, or pharmaceutical composition disclosed herein may be administered in combination with another agent. In some embodiments, the agent is or comprises PCV13. In some embodiments, the agent is or comprises PPSV23. In some embodiments, the agent is or comprises an antibiotic.

Dosing

In some embodiments, administration of a vaccine (e.g., a vaccine composition) described herein may involve the delivery of a single dose. In some embodiments, administration may involve an initial dose followed by one or several additional immunization doses, adequately spaced. An immunization schedule is a program for the administration of one or more specified doses of one or more specified pneumococcal vaccines, by one or more specified routes of administration, at one or more specified ages of a subject.

The present disclosure provides immunization methods that involve administering at least one dose of a vaccine to an infant subject. In some embodiments, the infant subject is 18 months old or younger. In some embodiments, the infant subject is 12 months old or younger. In some embodiments, the infant subject has previously received one or more doses of a conjugated pneumococcal polysaccharide vaccine; in other embodiments, the infant subject is naïve to pneumococcal vaccines. In some embodiments, the infant subject has previously been infected with, or exposed to infection by *S. pneumoniae*.

The present disclosure provides immunization methods that involve administering at least one dose of a vaccine to a toddler subject. In some embodiments, the toddler subject is 5 years old or younger. In some embodiments, the toddler subject is 4 years old or younger. In some embodiments, the toddler subject has previously received one or more doses of a conjugated pneumococcal polysaccharide vaccine; in other embodiments, the toddler subject is naïve to pneumococcal vaccines. In some embodiments, the toddler subject has previously been infected with, or exposed to infection by *S. pneumoniae*.

The present disclosure provides immunization methods that involve administering at least one dose of a vaccine to a juvenile subject. In some embodiments, the juvenile subject is 18 years old or younger. In some embodiments, the juvenile subject is 15 years old or younger. In some embodiments, the juvenile subject has previously received one or more doses of a conjugated pneumococcal polysaccharide vaccine; in other embodiments, the juvenile subject is naïve to pneumococcal vaccines. In some embodiments, the juvenile subject has previously been infected with, or exposed to infection by *S. pneumoniae*.

The present disclosure provides immunization methods that involve administering at least one dose of a vaccine to an adult subject. In some embodiments, the adult subject is older than about 50 years of age. In some embodiments, the adult subject is older than about 65 years of age. In some embodiments, the adult subject has previously received one or more doses of a conjugated pneumococcal polysaccharide vaccine; in other embodiments, the adult subject is naïve to pneumococcal vaccines. In some embodiments, the adult subject has previously been infected with, or exposed to infection by *S. pneumoniae*.

Immunization schedules of the present disclosure are provided to induce an immune response (e.g., an immunoprotective response) in a subject sufficient to reduce at least one measure selected from the group consisting of incidence, prevalence, frequency, and/or severity of at least one infection, disease, or disorder, and/or at least one surrogate marker of the infection, disease, or disorder, in a population and/or subpopulation of the subject(s). A supplemental immunization schedule is one which has this effect relative to the standard schedule which it supplements. A supplemental schedule may call for additional administrations and/or supra-immunogenic doses of the immunogenic compositions disclosed herein, found in the standard schedule, or for the administration of vaccines not part of the standard schedule. A full immunization schedule of the present invention may comprise both a standard schedule and a supplemental schedule. Exemplary sample vaccination schedules are provided for illustrative purposes. Detailed descriptions of methods to assess immunogenic response discussed herein allow one to develop alterations to the sample immunization schedules without undue experimentation.

In some embodiments of the present disclosure, a first administration of a pneumococcal vaccine occurs when a subject is more than about 2 weeks old, more than about 5 weeks old, more than about 1 year old, more than about 2 years old, more than about 15 years old, or more than about 18 years old.

In some embodiments, a first administration of a pneumococcal vaccine occurs when a subject is about two months old. In some embodiments, a second administration of a pneumococcal vaccine occurs when a subject is about four months old. In some embodiments, a third administration of a pneumococcal vaccine occurs when a subject is about six months old. In some embodiments, a fourth administration of a pneumococcal vaccine occurs when a subject is between about twelve months old and about fifteen months old.

In some embodiments of the present disclosure, a first administration of a pneumococcal vaccine occurs when a subject is more than about 50 years old, more than about 55 years old, more than about 60 years old, more than about 65 years old, or more than about 70 years old.

In some embodiments of the disclosure, a single administration of vaccine is employed. It is possible that the purposes of the present invention can be served with a single administration, especially when one or more utilized vaccine polypeptide(s), polysaccharide(s) and/or immunogenic complex(es) or combinations thereof is/are strong, and in such a situation a single dose schedule is sufficient to induce a lasting immune-protective response.

In certain embodiments, it is desirable to administer two or more doses of vaccine, for greater immune-protective efficacy and coverage. Thus, in some embodiments, a number of doses is at least two, at least three or more doses. There is no set maximum number of doses, however it is good clinical practice not to immunize more often than necessary to achieve the desired effect.

Without being bound by theory, a first dose of vaccine administered according to the disclosure may be considered a "priming" dose. In certain embodiments, more than one dose is included in an immunization schedule. In such a scenario, a subsequent dose may be considered a "boosting" dose.

A priming dose may be administered to a naïve subject (a subject who has never previously received a conjugated polysaccharide vaccine). In some embodiments, a priming dose may be administered to a subject who has previously received conjugated polysaccharide vaccine at least five or more years previous to administration of an initial vaccine dose according to the invention. In other embodiments, a priming dose may be administered to a subject who has previously received a conjugated polysaccharide vaccine at least twenty or more years previous to administration of a priming vaccine according to the invention.

When an immunization schedule calls for two or more separate doses, the interval between doses is considered. The interval between two successive doses may be the same throughout an immunization schedule, or it may change as the subject ages. In immunization schedules of the present invention, once a first vaccine dose has been administered, there is a first interval before administration of a subsequent dose. A first interval is generally at least about 2 weeks, 1 month, 6 weeks, 2 months, 3 months, 6 months, 9 months, 12 months, or longer. Where more than one subsequent dose(s) are administered, second (or higher) intervals may be provided between such subsequent doses. In some embodiments, all intervals between subsequent doses are of the same length; in other embodiments, second intervals may vary in length. In some embodiments, the interval between subsequent doses may be at least about 12 months, at least about 15 months, at least about 18 months, at least about 21 months or at least about 2 years. In certain embodiments, the interval between doses may be up to 3 years, up to about 4 years, or up to about 5 years or 10 years or more. In certain embodiments, intervals between subsequent doses may decrease as the subject ages.

It will be appreciated by those skilled in the art that a variety of possible combinations and sub-combinations of the various conditions of timing of the first administration, shortest interval, largest interval and total number of administrations (in absolute terms, or within a stated period) exist, and all of these combinations and sub-combinations should be considered to be within the inventor's contemplation though not explicitly enumerated here.

Assays for Determining Immune Response

In some embodiments, a method of assessing the immunogenicity of an immunogenic composition described herein comprises evaluating, measuring, and/or comparing an immune response using one or more in vitro bioassays, including B cell and T cell responses such as antibody levels by ELISA, multiplex ELISA, MSD, Luminex, flow cytometry, $T_H1/T_H17$ cell response, cytokine level measurement and functional antibody levels as measured by opsonophagocytic killing (OPK), serum bactericidal killing (SBA), agglutination, motility, cytotoxicity, or adherence; and in vivo assays in animal models of pneumococcal disease (e.g. pneumonia, bacteremia, meningitis, sepsis, otitis media, nasopharyngeal colonization). Parameters of in vivo assays include bacterial clearance from mucosal surfaces or bloodstream, reduction or prevention of bacteremia, meningitis, sepsis, or otitis media, reduction or prevention of colonization of the nasopharynx, reduction of mortality, and passive and active protection following challenge with the pneumococcal pathogens that are the targets of the immunogenic composition. In some embodiments, the immune response is compared to a control composition. In some embodiments, a control composition may comprise an antigenic polysaccharide present in the immunogenic composition and not comprise an antigenic polypeptide present in the immunogenic composition. In some embodiments, a control composition may comprise an antigenic polypeptide present in the immunogenic composition and not comprise an antigenic polysaccharide present in the immunogenic composition. In some embodiments, a control composition may comprise an adjuvant present in the immunogenic composition, and not comprise an antigenic polysaccharide and/or an immunogenic polypeptide present in the immunogenic composition.

In some embodiments, a method of assessing the potency of an immunogenic composition described herein comprises evaluating, measuring, and/or comparing an immune response using one or more in vitro bioassays, including B cell and T cell responses such as antibody levels by ELISA, multiplex ELISA, MSD, Luminex, flow cytometry, $T_H1/T_H17$ cell response, cytokine level measurement and functional antibody levels as measured by OPK, serum bactericidal killing (SBA), internalization, activity neutralization, agglutination, motility, cytotoxicity, or adherence; and in vivo assays in animal models of pneumococcal disease (e.g. pneumonia, bacteremia, meningitis, sepsis, otitis media, nasopharyngeal colonization). Parameters of in vivo assays include bacterial clearance or reduction from mucosal surfaces or bloodstream, reduction or prevention of bacteremia, meningitis, sepsis, or otitis media, reduction or prevention of colonization of the nasopharynx, reduction of mortality, and passive and active protection following challenge with the pneumococcal pathogens that are the targets of the immunogenic composition. In some embodiments, the immune response is compared to a control composition. In some embodiments, a control composition may comprise an antigenic polysaccharide present in the immunogenic composition and not comprise an antigenic polypeptide present in the immunogenic composition. In some embodiments, a control composition may comprise an antigenic polypeptide present in the immunogenic composition and not comprise an antigenic polysaccharide present in the immunogenic composition. In some embodiments, a control composition may comprise an adjuvant present in the immunogenic composition, and not comprise an antigenic polysaccharide and/or an immunogenic polypeptide present in the immunogenic composition.

In some embodiments, a method of assessing the immunogenicity of a vaccine composition described herein comprises evaluating, measuring, and/or comparing an immune response using one or more in vitro bioassays, including B cell and T cell responses such as antibody levels by ELISA, multiplex ELISA, MSD, Luminex, flow cytometry, $T_H1/T_H17$ cell response, cytokine level measurement and functional antibody levels as measured by OPK, serum bactericidal killing (SBA), agglutination, motility, cytotoxicity, or adherence; and in vivo assays in animal models of pneumococcal disease (e.g. pneumonia, bacteremia, meningitis, sepsis, otitis media, nasopharyngeal colonization). Parameters of in vivo assays include bacterial clearance from mucosal surfaces or bloodstream, reduction or prevention of bacteremia, meningitis, sepsis, or otitis media, reduction or prevention of colonization of the nasopharynx, reduction of mortality, and passive and active protection following challenge with the pneumococcal pathogens that are the targets of the immunogenic composition. In some embodiments, the immune response is compared to a control composition. In some embodiments, a control composition may comprise an antigenic polysaccharide present in the vaccine composition and not comprise an antigenic polypeptide present in the vaccine composition. In some embodiments, a control composition may comprise an antigenic polypeptide present in the vaccine composition and not comprise an antigenic polysaccharide present in the vaccine composition. In some embodiments, a control composition may comprise an adjuvant present in the vaccine composition, and not comprise an antigenic polysaccharide and/or an immunogenic polypeptide present in the vaccine composition.

In some embodiments, a method of assessing the potency of a vaccine composition described herein comprises evaluating, measuring, and/or comparing an immune response using one or more in vitro bioassays, including B cell and T cell responses such as antibody levels by ELISA, multiplex ELISA, MSD, Luminex, flow cytometry, $T_H1/T_H17$ cell response, cytokine level measurement and functional antibody levels as measured by OPK, serum bactericidal killing (SBA), agglutination, motility, cytotoxicity, or adherence; and in vivo assays in animal models of pneumococcal disease (e.g. pneumonia, bacteremia, meningitis, sepsis, otitis media, nasopharyngeal colonization). Parameters of in vivo assays include bacterial clearance from mucosal surfaces or bloodstream, reduction or prevention of bacteremia, meningitis, sepsis, or otitis media, reduction or prevention of colonization of the nasopharynx, reduction of mortality, and passive and active protection following challenge with the pneumococcal pathogens that are the targets of the immunogenic composition. In some embodiments, the immune response is compared to a control composition. In some embodiments, a control composition may comprise an antigenic polysaccharide present in the vaccine composition and not comprise an antigenic polypeptide present in the vaccine composition. In some embodiments, a control composition may comprise an antigenic polypeptide present in the vaccine composition and not comprise an antigenic polysaccharide present in the vaccine composition. In some embodiments, a control composition may comprise an adjuvant present in the vaccine composition, and not comprise an antigenic polysaccharide and/or an immunogenic polypeptide present in the vaccine composition.

In some embodiments, a method of assessing the immunogenicity of a pharmaceutical composition described herein comprises evaluating, measuring, and/or comparing an immune response using one or more in vitro bioassays, including B cell and T cell responses such as antibody levels by ELISA, multiplex ELISA, MSD, Luminex, flow cytometry, $T_H1/T_H17$ cell response, cytokine level measurement and functional antibody levels as measured by OPK, serum bactericidal killing (SBA), agglutination, motility, cytotoxicity, or adherence; and in vivo assays in animal models of pneumococcal disease (e.g. pneumonia, bacteremia, meningitis, sepsis, otitis media, nasopharyngeal colonization). Parameters of in vivo assays include bacterial clearance from mucosal surfaces or bloodstream, reduction or prevention of bacteremia, meningitis, sepsis, or otitis media, reduction or prevention of colonization of the nasopharynx, reduction of mortality, and passive and active protection following challenge with the pneumococcal pathogens that are the targets of the immunogenic composition. In some embodiments, the immune response is compared to a control composition. In some embodiments, a control composition may comprise an antigenic polysaccharide present in the pharmaceutical composition and not comprise an antigenic polypeptide present in the pharmaceutical composition. In some embodiments, a control composition may comprise an antigenic polypeptide present in the pharmaceutical composition and not comprise an antigenic polysaccharide present in the pharmaceutical composition. In some embodiments, a control composition may comprise an adjuvant present in the pharmaceutical composition, and not comprise an antigenic polysaccharide and/or an immunogenic polypeptide present in the pharmaceutical composition.

In some embodiments, a method of assessing the potency of a pharmaceutical composition described herein comprises evaluating, measuring, and/or comparing an immune response using one or more in vitro bioassays, including B cell and T cell responses such as antibody levels by ELISA, multiplex ELISA, MSD, Luminex, flow cytometry, $T_H1/T_H17$ cell response, cytokine level measurement and functional antibody levels as measured by OPK, serum bactericidal killing (SBA), agglutination, motility, cytotoxicity, or adherence; and in vivo assays in animal models of pneumococcal disease (e.g. pneumonia, bacteremia, meningitis, sepsis, otitis media, nasopharyngeal colonization). Parameters of in vivo assays include bacterial clearance from mucosal surfaces or bloodstream, reduction or prevention of bacteremia, meningitis, sepsis, or otitis media, reduction or prevention of colonization of the nasopharynx, reduction of mortality, and passive and active protection following challenge with the pneumococcal pathogens that are the targets of the immunogenic composition. In some embodiments, the immune response is compared to a control composition. In some embodiments, a control composition may comprise an antigenic polysaccharide present in the pharmaceutical composition and not comprise an antigenic polypeptide present in the pharmaceutical composition. In some embodiments, a control composition may comprise an antigenic polypeptide present in the pharmaceutical composition and not comprise an antigenic polysaccharide present in the pharmaceutical composition. In some embodiments, a control composition may comprise an adjuvant present in the pharmaceutical composition, and not comprise an antigenic polysaccharide and/or an immunogenic polypeptide present in the pharmaceutical composition.

In some embodiments, a method of assessing the immunogenicity and/or potency of an immunogenic complex comprises evaluating an immune response to immunogenic or vaccine compositions comprising one or more immunogenic complexes. In some embodiments, the method of assessing the immunogenicity and/or potency of an immunogenic complex described herein comprises evaluating, measuring, and/or comparing an immune response using one or more in vitro bioassays, including B cell and T cell responses such as antibody levels by ELISA, multiplex ELISA, MSD, Luminex, flow cytometry, $T_H1/T_H17$ cell response, cytokine level measurement and functional antibody levels as measured by OPK, serum bactericidal killing (SBA), agglutination, motility, cytotoxicity, or adherence; and in vivo assays in animal models of pneumococcal disease (e.g. pneumonia, bacteremia, meningitis, sepsis, otitis media, nasopharyngeal colonization). Parameters of in vivo assays include bacterial clearance from mucosal surfaces or bloodstream, reduction or prevention of bacteremia, meningitis, sepsis, or otitis media, reduction or prevention of colonization of the nasopharynx, reduction in mortality, and passive and active protection following challenge with the pneumococcal pathogens that are the targets of the immunogenic composition.

Generally speaking, it may be desirable to assess humoral responses, cellular responses, and/or interactions between the two. Where humoral responses are being assessed, antibody titers and/or types (e.g., total IgG, IgG1, IgG2, IgM, IgA, etc.) to specific pathogen polysaccharides or polypeptides (either serotype-specific or conserved across two or more serotypes) may be determined, for example before and/or after administration of an initial or a boosting dose of vaccine (and/or as compared with antibody levels in the absence of antigenic stimulation). Cellular responses may be assessed by monitoring reactions such as delayed type hypersensitivity responses, etc. to the carrier protein. Cellular responses can also be measured directly by evaluating the response of peripheral blood mononuclear cells (PBMCs) monocytes to stimulation with the antigens of interest. Precursor and memory B cell populations may be assessed in enzyme linked immunospot (ELISpot) assays directed against specific pathogen polysaccharides or polypeptides.

Any of a variety of assays may be employed to detect levels and/or activity of antibodies in subject sera. Suitable assays include, for example, ligand binding assays, such as radioimmunoassay (RIAs), ELISAs, and multiplex assays (Luminex, Bioplex, MSD); functional assays, such as opsonophagocytic assays or internalization assays; and in vivo assays in animal models of pneumococcal disease (e.g. pneumonia, bacteremia, meningitis, sepsis, otitis media, nasopharyngeal colonization). Parameters of in vivo assays include bacterial clearance from mucosal surfaces or bloodstream, reduction or prevention of bacteremia, meningitis, sepsis, or otitis media, reduction or prevention of colonization of the nasopharynx, reduction in mortality, and passive and active protection following challenge with the pneumococcal pathogens that are the targets of the immunogenic composition.

The RIA method detects specific antibodies through incubation of sera with radiolabeled polysaccharides or polypeptides in suspension (e.g., Schiffman et al, 1980). The antigen-antibody complexes are then precipitated with ammonium sulfate and the radiolabeled pellets assayed for counts per minute (cpm).

In the ELISA detection method, specific antibodies from the sera of vaccinated subjects are quantitated by incubation with polysaccharides or polypeptides (either serotype-specific or conserved across two or more serotypes) which have been adsorbed to a solid support (e.g., Koskela and Leinonen (1981); Kojima et al, 1990; Concepcion and Frasch, 2001). The bound antibody is detected using enzyme-conjugated secondary detection antibodies. The ELISA also allows isotyping and subclassing of the immune response (i.e., IgM vs. IgG or IgG1 vs. IgG2) by using isotype- or subclass-specific secondary antibodies and can be adapted to evaluate the avidity of the antibodies (Anttila et al, 1998; Romero-Steiner et al, 2005). Multiplex assays (e.g., Luminex) facilitate simultaneous detection of antibodies to multiple antigens. Capsular polysaccharide(s) or polypeptides are conjugated to spectrally distinct microspheres that are mixed and incubated with serum. The antibodies bound to the polysaccharides or polypeptides on the coated microspheres are detected using a secondary antibody (e.g., R-Phycoerythrin-conjugated goat anti-human IgG).

An approach for assessing functional antibody in serum is an opsonophagocytic assay (OPA) or a concentrated opsonophagocytic assay (COPA), which quantitates only the antibodies that can opsonize the bacteria, leading to ingestion and killing of the bacteria. The standard assay utilizes a human phagocytic effector cell, a source of complement, bacteria, and diluted sera. The assay readout is the serum endpoint titer at which there is >50% killing compared to bacteria incubated with complement and human cells alone (Romero-Steiner et al, 1997). This killing OPA can also be multiplexed by utilizing target strains of pathogen that carry different antibiotic resistance markers (Kim et al, 2003). Another type of multiplex opsonic assay is a nonkilling assay in which the uptake by phagocytic effector cells of fluorescent stained encapsulated pathogen or fluorescent microspheres conjugated with antigenic polysaccharides or polypeptides from a target pathogen in the presence of diluted sera plus a complement source is evaluated by flow cytometry (Martinez et al, 1999). Opsonic activity of serum antibody plus complement can also be evaluated by measuring the oxidative response of phagocytic human effector cells to ingested pathogen (Munro et al. 1985; Ojo-Amaize et al. 1995).

Certain in vivo model systems can be used to evaluate the protection afforded by serum antibodies induced by vaccines of the present invention. In such passive protection systems, mice or rats are challenged with the pathogen plus diluted sera, and the endpoint titer of the sera which provides protection against pneumonia, bacteremia, colonization of organs or tissues, or mortality is determined (Stack et al. 1998; Saeland et al. 2000).

In some embodiments, efficacy of vaccination may be determined by assaying one or more cytokine levels by stimulating T cells from a subject after vaccination. The one or more cytokine levels may be compared to the one or more cytokine levels in the same subject before vaccination. Increased levels of the one or more cytokine, such as a 1.5 fold, 2-fold, 5-fold, 10-fold, 20-fold, 50-fold or 100-fold or more increase over pre-immunization cytokine levels, would indicate an increased response to the vaccine. In some embodiments, the one or more cytokines are selected from GM-CSP; IL-1α; IL-1β; IL-2; IL-3; IL-4; IL-5; IL-6; IL-7; IL-8; IL-10; IL-12; IL-17A, IL-17F or other members of the IL-17 family; IL-22; IL-23; IFN-α; IFN-β; IFN-γ; MIP-1α; MIP-1β; TGF-β; TNFα, or TNF-β. In a non-limiting example, efficacy of vaccination may be determined by assaying IL-17 levels (particularly IL-17A) by stimulating T cells from a subject after vaccination. The IL-17 levels may be compared to IL-17 levels in the same subject before vaccination. Increased IL-17 (e.g., IL-17A) levels, such as a 1.5 fold, 2-fold, 5-fold, 10-fold, 20-fold, 50-fold or 100-fold or more increase, would indicate an increased response to the vaccine.

In some embodiments, one may assay neutrophils in the presence of T cells or antibodies from the patient for pneumococcal killing. Increased pneumococcal killing, such as a 1.5 fold, 2-fold, 5-fold, 10-fold, 20-fold, 50-fold or 100-fold or more increase, would indicate an increased response to the vaccine. For example, one may measure $T_H17$ cell activation, where increased $T_H17$ cell activation, such as a 1.5 fold, 2-fold, 5-fold, 10-fold, 20-fold, 50-fold or 100-fold or more increase, correlates with an increased response to the vaccine. In another non-limiting example, one may measure $T_H1$ cell activation, where increased $T_H1$ cell activation, such as a 1.5 fold, 2-fold, 5-fold, 10-fold, 20-fold, 50-fold or 100-fold or more increase, correlates with an increased response to the vaccine. One may also measure levels of an antibody specific to the vaccine, where increased levels of the specific antibody, such as a 1.5 fold, 2-fold, 5-fold, 10-fold, 20-fold, 50-fold or 100-fold or more increase, are correlated with increased vaccine efficacy. In certain embodiments, two or more of these assays are used. For example, one may measure IL-17 levels and the levels of vaccine-specific antibody. Alternatively, one may follow epidemiological markers such as incidence of, severity of, or duration of pneumococcal infection in vaccinated individuals compared to unvaccinated individuals.

Vaccine efficacy may also be assayed in various model systems such as the mouse challenge model. For instance, BALB/c or C57BL/6 strains of mice may be used. After administering the test vaccine to a subject (as a single dose or multiple doses), the experimenter administers a challenge dose of S. pneumoniae. In some cases, a challenge dose administered intranasally is sufficient to cause S. pneumoniae colonization (especially nasal colonization) in an unvaccinated animal, and in some cases a challenge dose administered via aspiration is sufficient to cause sepsis and a high rate of lethality in unvaccinated animals. In some cases, a challenge dose administered via intraperitoneal injection is sufficient to cause sepsis and a high rate of lethality in unvaccinated animals. In some cases, a challenge dose administered via intravenous injection is sufficient to cause sepsis and a high rate of lethality in unvaccinated animals. One can then measure the reduction in colonization or the reduction in lethality in vaccinated animals.

Certain in vivo model systems can be used to evaluate the protection afforded by serum antibodies induced by vaccines of the present invention. In such passive protection systems, mice or rats are challenged with the pathogen plus diluted sera, and the endpoint titer of the sera which provides protection against bacteremia, colonization of organs or tissues, or mortality is determined (Stack et al. 1998; Saeland et al. 2000).

Kits

The present disclosure also provides for kits for producing an immunogenic complex as disclosed herein which is useful for an investigator to tailor an immunogenic complex with their preferred antigens, e.g., for research purposes to assess the effect of an antigen, or a combination of antigens on immune response. Such kits can be prepared from readily available materials and reagents. For example, such kits can comprise any one or more of the following materials: a container comprising a polysaccharide cross-linked with a plurality of first affinity molecules; a container comprising a complementary affinity molecule which associates with the first affinity molecule, wherein the complementary affinity molecule associates with an antigen or carrier protein; a container comprising an antigen; a container comprising a carrier protein; a container comprising an antigen associated with a complementary affinity molecule; a container comprising a carrier protein associated with a complementary affinity molecule.

In another embodiment, the kit comprises a container comprising a polysaccharide; a container comprising a plurality of first affinity molecules; and a container comprising a cross-linking reagent for cross-linking the first affinity molecules to the polysaccharide, for example, but not limited to, CDAP (1-cyano-4-dimethylaminopyridinium tetrafluoroborate), and EDC (1-Ethyl-3-[3-dimethylaminopropyl] carbodiimide hydrochloride).

In another embodiment, the kit comprises a container comprising an antigen or carrier protein, and a container comprising a complementary affinity molecule which associates with a first affinity molecule. In some embodiments, the kit further comprises a means to attach the complementary affinity molecule to the antigen or carrier protein, where the means can be by a cross-linking reagent or by some intermediary fusion protein.

In some embodiments, the kit can comprise at least one co-stimulation factor which can be added to the polymer. In some embodiments, the kit comprises a cross-linking reagent, for example, but not limited to, CDAP (1-cyano-4-dimethylaminopyridinium tetrafluoroborate); EDC (1-Ethyl-3-[3-dimethylaminopropyl] carbodiimide hydrochloride); sodium cyanoborohydride; cyanogen bromide; and ammonium bicarbonate/iodoacetic acid, for linking the co-factor to the polymer.

A variety of kits and components can be prepared for use in the methods described herein, depending upon the intended use of the kit, the particular target antigen and the needs of the user.

EXEMPLIFICATION

Example 1: S. pneumoniae Capsular Polysaccharides

Preparation and Purification

Methods of culturing pneumococci are well known in the art (e.g. Chase, 1967, Methods of Immunology and Immunochemistry 1:52). Methods of preparing pneumococcal capsular polysaccharides are also well known in the art (e.g., European Patent No. EP0497524). Isolates of pneumococcal serotypes are available from the ATCC or the National Collection of Type Cultures operated by Public Health England.

S. pneumoniae is identified as non-motile, Gram-positive, lancet-shaped diplococci that are alpha-hemolytic on blood agar. Most but not all strains are encapsulated. Serotypes are differentiated on the basis of Neufeld Test (Quelling reaction) using specific antisera (e.g., U.S. Pat. No. 5,847,112), latex agglutination, or multilocus sequence typing.

A frozen vial representing each of the S. pneumoniae serotypes present in the MAPS vaccine was thawed and used to generate a seed culture in appropriate pre-sterilized growth media. The seed culture was grown with temperature and pH control. The seed culture was transferred to a production fermenter that contained pre-sterilized growth media. The production culture was grown with temperature, pH and agitation rate control. The growth process was terminated with addition of an inactivating agent with a controlled temperature hold.

The purification process was initiated by removal of cell debris using a combination of centrifugation and filtration. The material was filtered followed by solvent-based fractionations to remove impurities and recover PS.

Specifications

All PS specifications in Table 1 were obtained from European Pharmacopoeia 9.0 Table 0966.-1, except for molecular size and serotype 6A, which are based on the manufacturer's certificate of analysis.

encoding fusion protein CP1 (Rhavi-GGGGSSS-SP1500-AAA-SP0785 ("GGGGSSS" disclosed as SEQ ID NO: 3)) was cloned into the pET-24a(+) vector using NdeI and XhoI restriction sites. Stop codons were inserted at the 3'-end of the CP1 DNA construct. After cloning was complete, DNA sequencing was performed to confirm the presence, orientation and sequence of the CP1 DNA construct inserted in the CP1/pET-24a(+) vector.

TABLE 1

Exemplary Polysaccharide (PS) Specifications

| Molecular type† | Protein | Nucleic acids | Total nitrogen | Phosphorus | Molecular size ($K_D$) ‡ | Molecular size ($K_D$) § | Uronic acids | Hexos-amines | Methyl-pentoses | O-acetyl Groups |
|---|---|---|---|---|---|---|---|---|---|---|
| 1 | ≤2 | ≤2 | 3.5-6 | 0-1.5 | ≤0.15 | | ≥45 | | | ≥1.8 |
| 2 | ≤2 | ≤2 | 0-1 | 0-1.0 | ≤0.15 | | ≥15 | | ≥38 | |
| 3 | ≤5 | ≤2 | 0-1 | 0-1.0 | ≤0.15 | | ≥40 | | | |
| 4 | ≤3 | ≤2 | 4-6 | 0-1.5 | ≤0.15 | | | ≥40 | | |
| 5 | ≤7.5 | ≤2 | 2.5-6.0 | ≤2 | | ≤0.60 | ≥12 | ≥20 | | |
| 6A | ≤1.5 | ≤1.5 | 0-2 | 2.5-5.0 | | ≤0.50 | | | ≥15 | |
| 6B | ≤2 | ≤2 | 0-2 | 2.5-5.0 | | ≤0.50 | | | ≥15 | |
| 7F | ≤5 | ≤2 | 1.5-4.0 | 0-1.0 | ≤0.20 | | | | ≥13 | |
| 8 | ≤2 | ≤2 | 0-1 | 0-1.0 | ≤0.15 | | ≥25 | | | |
| 9N | ≤2 | ≤1 | 2.2-4 | 0-1.0 | ≤0.20 | | ≥20 | ≥28 | | |
| 9V | ≤2 | ≤2 | 0.5-3 | 0-1.0 | | ≤0.45 | ≥15 | ≥13 | | |
| 10A | ≤7 | ≤2 | 0.5-3.5 | 1.5-3.5 | | ≤0.65 | | ≥12 | | |
| 11A | ≤3 | ≤2 | 0-2.5 | 2.0-5.0 | | ≤0.40 | | | | ≥9 |
| 12F | ≤3 | ≤2 | 3-5 | 0-1.0 | ≤0.25 | | | ≥25 | | |
| 14 | ≤5 | ≤2 | 1.5-4 | 0-1.0 | ≤0.30 | | | ≥20 | | |
| 15B | ≤3 | ≤2 | 1-3 | 2.0-4.5 | | ≤0.55 | | ≥15 | | |
| 17F | ≤2 | ≤2 | 0-1.5 | 0-3.5 | | ≤0.45 | | | ≥20 | |
| 18C | ≤3 | ≤2 | 0-1 | 2.4-4.9 | ≤0.15 | | | | ≥14 | |
| 19A | ≤2 | ≤2 | 0.6-3.5 | 3.0-7.0 | ≤0.45 | | | ≥12 | ≥20 | |
| 19F | ≤3 | ≤2 | 1.4-3.5 | 3.0-5.5 | ≤0.20 | | | ≥12.5 | ≥20 | |
| 20 | ≤2 | ≤2 | 0.5-2.5 | 1.5-4.0 | | ≤0.60 | | ≥12 | | |
| 22F | ≤2 | ≤2 | 0-2 | 0-1.0 | | ≤0.55 | ≥15 | | ≥25 | |
| 23F | ≤2 | ≤2 | 0-1 | 3.0-4.5 | ≤0.15 | | | | ≥37 | |
| 33F | ≤2.5 | ≤2 | 0-2 | 0-1.0 | | ≤0.50 | | | | |

Values shown are percentage contents of components of monovalent bulk PS.
†The different types are indicated using the Danish nomenclature.
‡ Cross-linked agarose for chromatography R.
§ Cross-linked agarose for chromatography R1.

Example 2: Preparation of Fusion Protein CP1

Vector Construction

Fusion protein CP1 comprises the biotin-binding portion of rhizavidin spanning amino acids 45 to 179 of the full-length protein encoded from the genome. The predicted signal sequences (amino acids 1-44) of rhizavidin were not incorporated. To optimize the expression level of CP1 in E. coli, the gene sequence that encodes rhizavidin polypeptide (amino acids 45-179; SEQ ID NO:2) was redesigned using E. coli-preferred expression codons, synthesized and cloned into plasmid pET24a(+). This synthetic rhizavidin gene was designated Rhavi.

To construct CP1, a DNA sequence encoding a flexible linker region consisting of seven amino acids (GGGGSSS; SEQ ID NO:3) was directly inserted into the 3' end of the synthetic Rhavi gene to provide separation from Rhavi and promote proper folding of the subsequent fusion protein. The genes encoding desired portions of SP1500 and SP0785 protein (not including predicted signal sequences; nucleic acid sequences SEQ ID NO:7 and SEQ ID NO:8, respectively) were synthesized and inserted into the Rhavi expression vector just beyond the linker region. Three residual amino acids (AAA) from a Not I restriction site of pET24a (+) separate SP1500 and SP0785, and may be referred to as the second linker of CP1.

Figure 2:
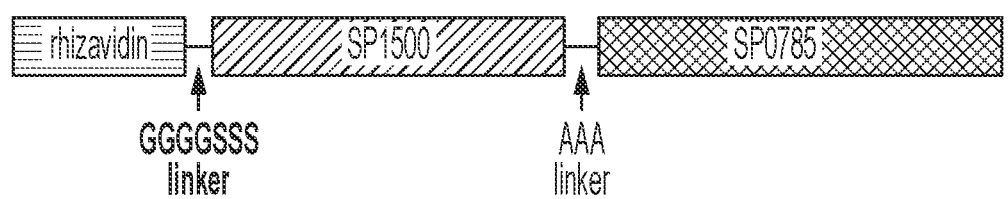
FIG. 2 is a schematic of an exemplary CP1 fusion protein. Such an exemplary CP1 fusion protein comprises a biotin-binding protein such as, e.g., a truncated rhizavidin protein (e.g., amino acids 45-179 of a wild-type rhizavidin protein), a first linker (e.g., a GGGGSSS linker (SEQ ID NO: 3)), a SP1500 polypeptide (e.g., amino acids 27-278 of a full-length *S. pneumoniae* SP1500 polypeptide), a second linker (e.g., the amino acid sequence AAA), and a SP0785 polypeptide (e.g., amino acids 33-399 of a full length *S. pneumoniae* SP0785 polypeptide). In some embodiments, a CP1 fusion protein may further comprise a detectable or purification tag (e.g., His tag). The amino acid sequence AAA can be from the Not I site on a PET21/24b plasmid, or synthesized. For a GGGGSSS linker (SEQ ID NO: 3), the SSS amino acid sequence can be from the Sac I site on a PET21/24b plasmid, with the GGGG (SEQ ID NO: 14) amino acid sequence added to create a flexible linker with minimal steric hindrance. Alternatively, the GGGGSSS linker (SEQ ID NO: 3) can be synthesized.
Figure 4:
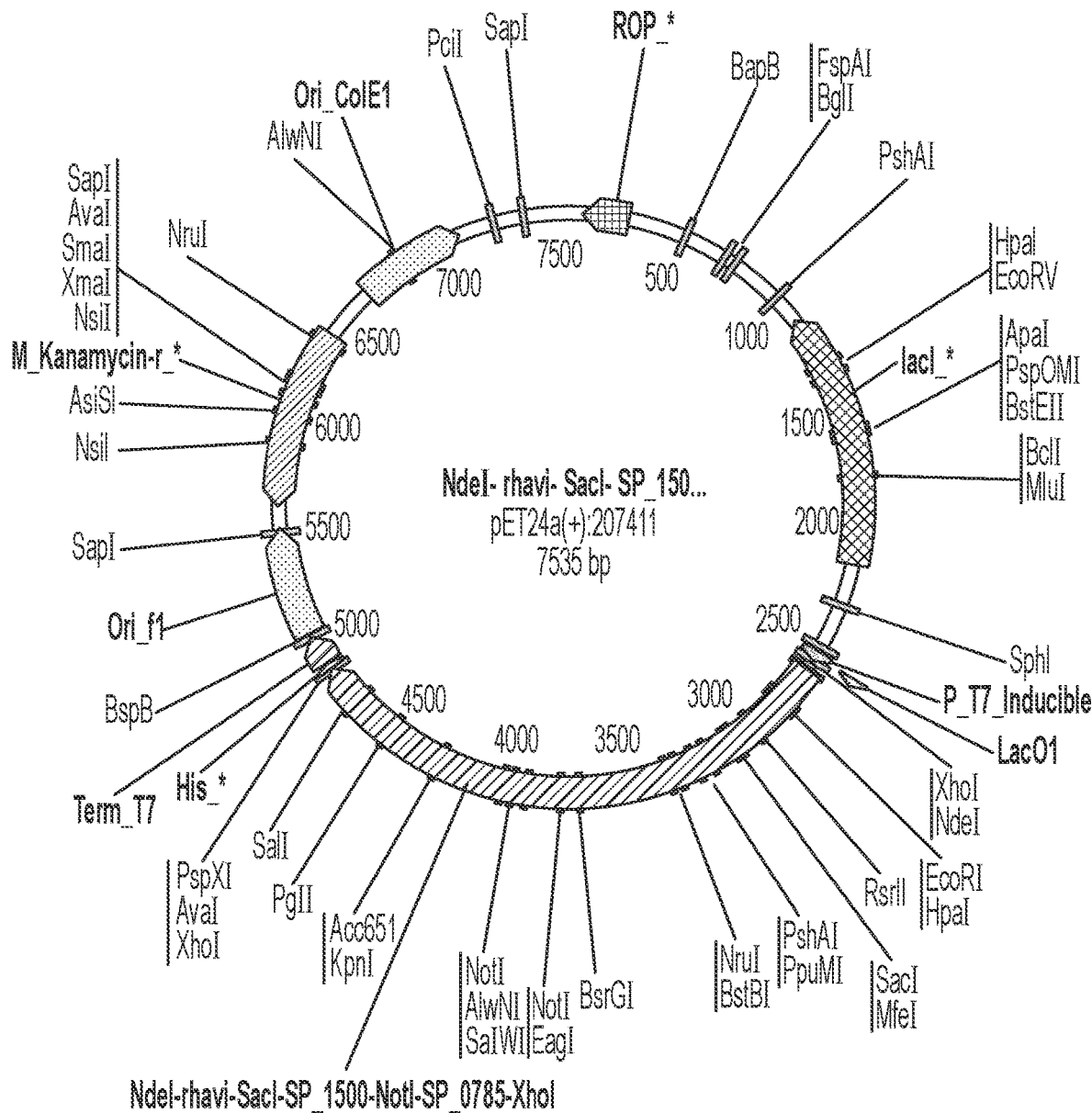
FIG. 4 is a schematic of an exemplary pET24a(+) CP1 construct.

A schematic of fusion protein CP1 is shown in FIG. 2. The construction of the plasmid pET24a(+)-CP1 is shown in FIG. 4 and the feature map in Table 2. The DNA sequence

TABLE 2

Feature Map

| Name | Start [bp] | End [bp] | Direction |
|---|---|---|---|
| Insert | 2613 | 4922 | Forward |
| ROP | 247 | 59 | Reverse |
| lacI | 2138 | 1059 | Reverse |
| P_T7_Inducible | 2528 | 2569 | Forward |
| LacO1 | 2549 | 2569 | Forward |
| His | 4923 | 4943 | Forward |
| Term_T7 | 4951 | 5079 | Forward |
| Ori_f1 | 5091 | 5546 | Forward |
| Kanamycin-r | 6400 | 5639 | Reverse |
| Ori_ColE1 | 6619 | 7069 | Forward | bp: base pair; His: Histidine tag; LacI: Lactose operon inhibitor r; LacO1: Lactose operator; Ori_ColE1: Colicin E1 origin of replication; Ori_f1: Origin of replication from F1 phage; Term_T7: T7 terminator; ROP: repressor of primer.

Establishment of Master Cell Bank (MCB)

To generate the Research Cell Bank (RCB), the CP1/pET-24a(+) vector was transformed into an E. coli expression strain.

Transformed E. coli cells were plated in culture plates containing Kanamycin. A single colony from the plate was selected and used to inoculate into liquid medium in a shaker flask. The flasks were placed in an incubator shaker for overnight culture and grown to the desired OD. The bacterial culture was then mixed with glycerol solution. The mixed solution was aliquoted into vials to make RCB.

To generate the MCB, RCB was inoculated into liquid medium in shaker flasks and grown to the desired OD. The bacterial culture was then brought to 15% glycerol, mixed and aliquoted into vials. The MCB vials were then placed at −80° C. (−70° C. to −90° C.) and selected vials were taken for quality assurance testing.

Manufacturing Process Overview

The CP1 fusion protein was expressed in E. coli. The expressed CP1 fusion protein was released from E. coli cells and purified in a series of chromatographic and filtration steps. The following section details the 300 L culture scale CP1 manufacturing process.

In summary, the process was initiated by thawing and inoculating cells from a MCB vial into cell medium. Initial cell expansion was performed in flask and then the bacterial culture was transferred to a 300 L fermenter.

Bacteria were harvested by centrifugation. The recovered cell paste was resuspended in a lysis buffer and fluidized by a microfluidizer. Bulk CP1 fusion protein in the fluidized cell lysate was purified by precipitation and chromatography steps. The final process stream was concentration and buffer exchange into 20 mM Tris, 150 mM NaCl at pH 8.0±0.1 via ultrafiltration membranes. Lastly, the CP1 fusion protein was 0.22 µm filtered immediately prior to bottling and stored at −80° C.

No raw materials contained animal- or human-derived components. For description of the cell, see above.

Upstream Process

Figure 5:
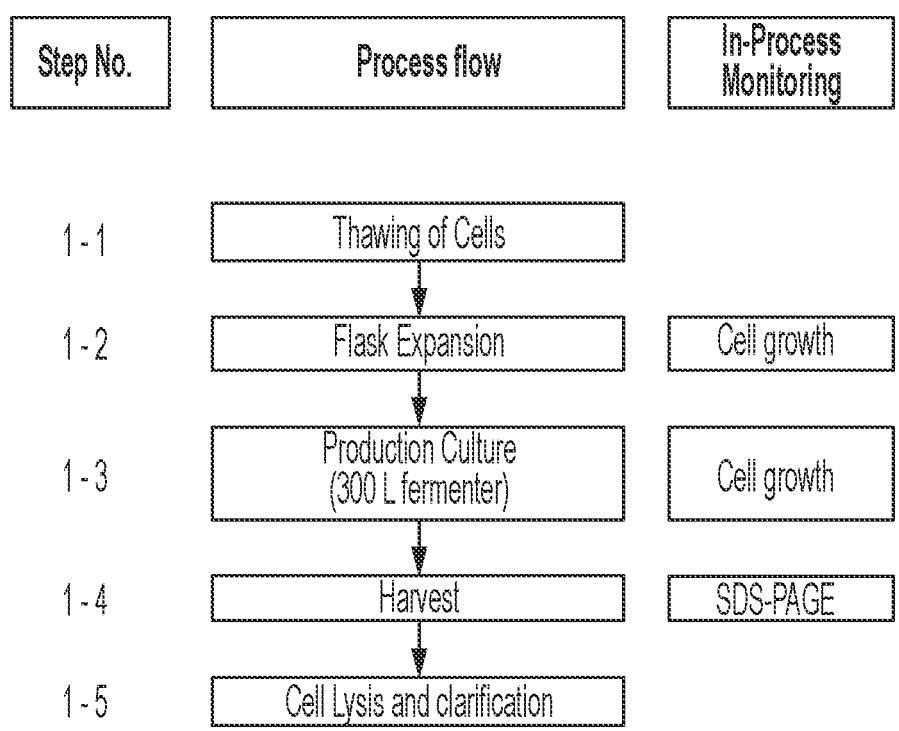
FIG. 5 is a flow-chart depicting an exemplary upstream manufacturing process for fusion protein CP1. An exemplary CP1 polypeptide is a fusion protein comprising a truncated rhizavidin [aa 45-179 of a full-length rhizavidin protein], a first linker (e.g., a GGGGSSS linker (SEQ ID NO: 3)), a SP1500 polypeptide, a second linker (e.g., the amino acid sequence AAA), and a SP0785 polypeptide. SDS-PAGE: Sodium dodecyl sulfate polyacrylamide gel electrophoresis.

A flow chart of the upstream process for CP1 is provided in FIG. 5 and details for the individual steps follow.

The cell culture utilized chemically defined media and components depending on the manufacturing step. The media used were cell media, production media, feed 1 media and feed 2 media. These media were used in inoculum expansion, production culture and feeding, respectively.

Step 1-1: Thawing of Cells

Sufficient cell medium was prepared and transferred into an appropriate culture flask and then frozen MCB is thawed.

Step 1-2: Flask Expansion Thawed MCB was inoculated and grown in a 2.5 L flask. Cell growth was monitored by a spectrophotometer at OD600.

Step 1-3: Production Culture

The production culture was run in fed-batch mode. To support product generation and to prolong the cell culture production period, feed 1 and feed 2 media were added after appropriate cell growth. Once the fermenter temperature reached the set point, isopropyl β-D-1-thiogalactopyranoside was added to induce CP1 fusion protein expression.

After approximately 18 hours from induction, harvest was begun by centrifugation.

Step 1-4: Harvest

Bacterial culture was harvested by continuous flow centrifugation.

Step 1-5: Cell Lysis and Clarification

The recovered cell paste was resuspended in lysis buffer and fluidized by a microfluidizer. The fluidized cell lysate, including bulk CP1 fusion protein, was centrifuged and the supernatant was recovered.

Downstream Process

Figure 6:
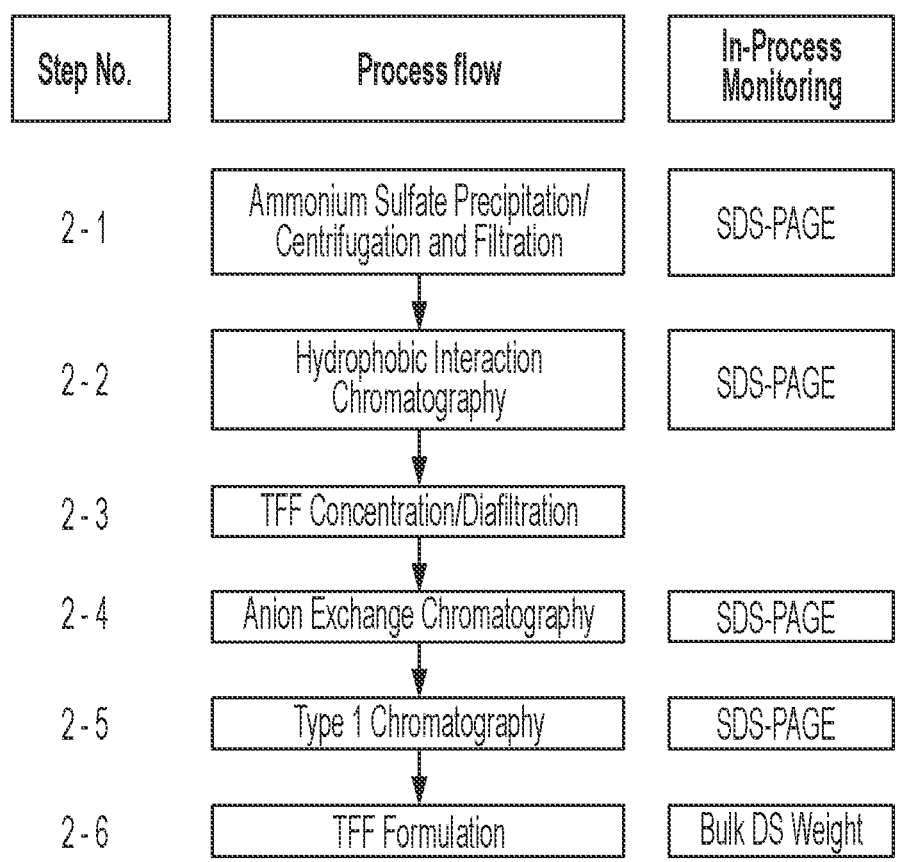
FIG. 6 is a flow-chart depicting an exemplary downstream manufacturing process for fusion protein CP1. An exemplary CP1 polypeptide is a fusion protein comprising a truncated rhizavidin [aa 45-179 of a full-length rhizavidin protein], a first linker (e.g., a GGGGSSS linker (SEQ ID NO: 3)), a SP1500 polypeptide, a second linker (e.g., the amino acid sequence AAA), and a SP0785 polypeptide. DS: drug substance; SDS-PAGE: sodium dodecyl sulfate polyacrylamide gel electrophoresis; TFF: tangential flow filtration.

After harvest and cell lysis, CP1 fusion protein was purified by several chromatography steps. A flow chart of CP1 purification process is provided in FIG. 6. The details for the individual steps follow.

Step 2-1: Ammonium Sulfate Precipitation/Centrifugation and Filtration

Ammonium sulfate solution was added to the clarified lysate and adjusted to a final concentration of 0.8 M. After mixing at room temperature, the clarified lysate with ammonium sulfate was centrifuged and the supernatant was recovered. The recovered supernatant was filtered through 0.22 µm filter and collected in an appropriate container.

Step 2-2: Hydrophobic Interaction Chromatography

The purpose of this step is to remove process-related contaminants. CP1 fusion protein bound to the resin was washed with high concentration ammonium sulfate buffer then eluted with elution buffer (the concentration of NaCl in the buffer was gradually reduced). A sodium dodecyl sulfate polyacrylamide gel electrophoresis (SDS-PAGE) analysis was performed with each fraction to confirm containing the CP1 fusion protein.

Step 2-3: Tangential Flow Filtration Concentration/Filtration

The elution pool was concentrated and then buffer exchanged with several-fold volumes of Tris-buffered saline using a 30 kDa filtration membrane. The filtrated tangential flow filtration (TFF) retentate was filtered by 0.22 µm filter.

Step 2-4: Anion Exchange Chromatography

The purpose of this step is to remove process-related contaminants. CP1 fusion protein bound to the resin was washed with NaCl wash buffer then eluted with NaCl elution buffer (the concentration of NaCl in the buffer was gradually increased). SDS-PAGE analysis was performed with each fraction to confirm containing the CP1 fusion protein.

Step 2-5: Type 1 Chromatography

The purpose of this step is to further remove process-related contaminants. CP1 fusion protein bound to the resin was washed with phosphate wash buffer then eluted with phosphate elution buffer (the concentration of phosphate in the buffer was gradually increased). SDS-PAGE analysis was performed with each fraction to confirm containing the CP1 fusion protein.

Step 2-6: TFF Formulation

The Type 1 chromatography fraction pool was concentrated and then buffer exchanged with several-fold volumes of formulation buffer (20 mM Tris, 150 mM sodium chloride, pH 8.0±0.1) using a 30 kDa filtration membrane. The formulated CP1 fusion protein was filtered through 0.22 µm filter.

Container Closure System

CP1 fusion protein was stored at −80° C. (−70° C. to −90° C.) in sterile polyethylene terephthalate bottles.

Example 3: Preparation of MAPS Immunogenic Complexes

Overview

The MAPS platform takes advantage of the high affinity (dissociation constant $[K_D] \approx 10^{15}M$), non-covalent binding between biotin and rhizavidin, a biotin-binding protein that has no significant predicted homology with human proteins. Rhizavidin, a naturally occurring dimeric protein in the avidin protein family, was first discovered in Rhizobium etli, a symbiotic bacterium of the common bean. Rhizavidin has only a 22% amino acid identity with chicken avidin, a protein commonly found in eggs, but with high conservation of amino acid residues involved in biotin binding. No cross-reactivity to rhizavidin was observed in human serum samples obtained from subjects exposed to avidin [Helppolainen et al, 2007], suggesting that rhizavidin antibodies may not cross-react with chicken avidin. Biotin conjugates have been used in several clinical applications without any reported adverse events [Buller et al, 2014; Paty et al, 2010;

Lazzeri et al, 2004]. The biotinylation of the PS and MAPS immunogenic complexing process in MAPS24 were optimized to consistently show no free biotin, thus reducing the potential for generating anti-biotin antibodies.

Figure 1:
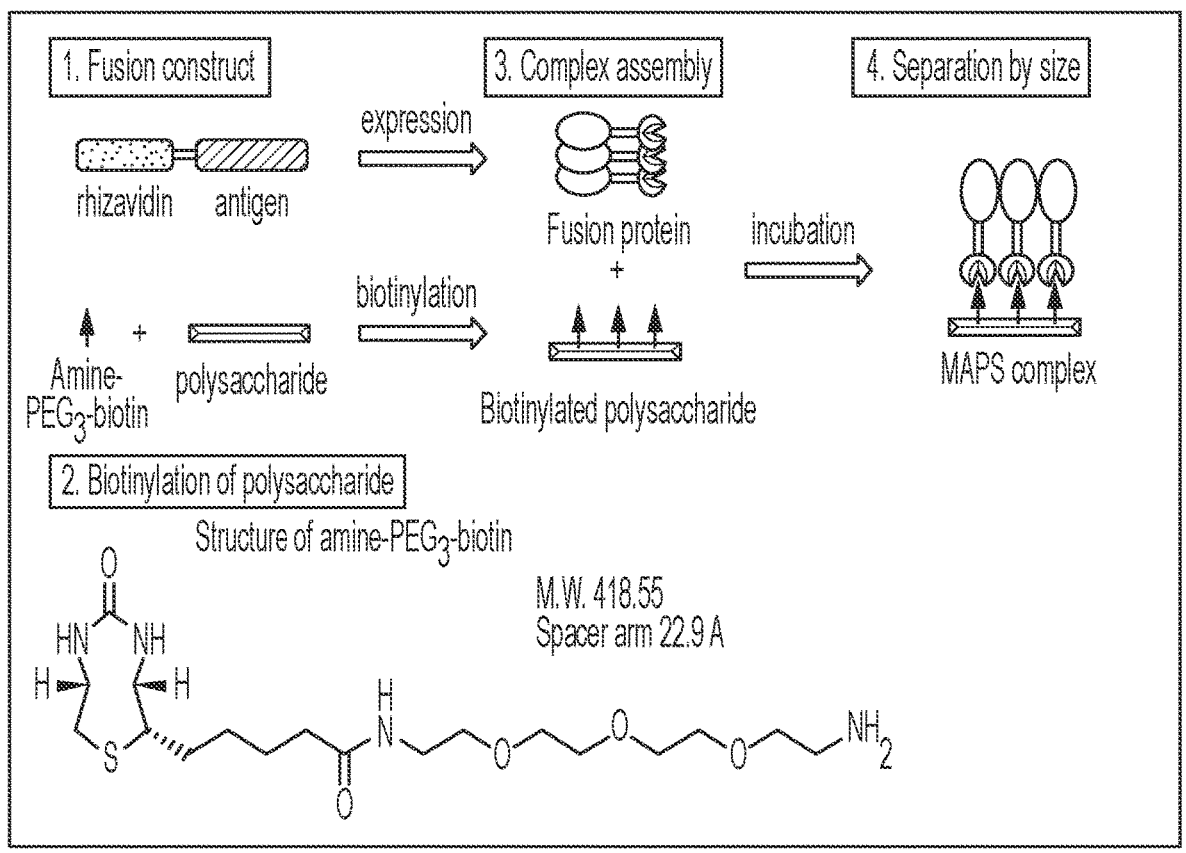
FIG. 1 is a schematic representation of an exemplary Multiple Antigen Presenting System (MAPS). In the exemplary embodiment shown, MAPS immunogenic complexes comprise one or more polypeptide antigens fused to the biotin-binding protein rhizavidin, or a biotin-binding domain or biotin-binding fragment thereof, and a biotinylated antigenic polysaccharide. In this figure, each MAPS complex is formed between one or more fusion proteins and a biotinylated polysaccharide by non-covalent binding of a truncated rhizavidin to biotin.

MAPS vaccine candidates comprise genetically constructed fusion proteins of rhizavidin, or a biotin-binding domain or biotin-binding fragment thereof, and the protein antigens of interest, which are then complexed with biotinylated PS of interest, leading to a specific assembly into integrated macromolecular immunogenic complexes that, when processed by the immune system, result in the activation of protective B- and T-cell immune responses, as shown schematically in FIG. 1.

MAPS24 is a novel pneumococcal vaccine candidate based on the proprietary MAPS platform. MAPS24 is a multi-valent MAPS vaccine containing 24 pneumococcal capsular polysaccharides of serotypes 1, 2, 3, 4, 5, 6A, 6B, 7F, 8, 9N, 9V, 10A, 11A, 12F, 14, 15B, 17F, 18C, 19A, 19F, 20B, 22F, 23F and 33F, individually biotinylated and complexed with CP1 fusion protein. MAPS15 is a multi-valent MAPS vaccine containing 15 pneumococcal capsular PS of serotypes 1, 3, 4, 5, 6A, 6B, 7F 9V, 14, 18C, 19A, 19F, 22F, 23F, and 33F), individually biotinylated and complexed with CP1 fusion protein. MAPS9 is a multi-valent MAPS vaccine containing 9 pneumococcal capsular PS of serotypes 2, 8, 9N, 10A, 11A, 12F, 15B, 17F, and 20B, individually biotinylated and complexed with CP1 fusion protein. CP1 comprises a genetic fusion construct of truncated rhizavidin and 2 pneumococcal proteins (SP1500 and SP0785) joined by linkers, as shown in FIG. 2. No available vaccine contains this unique combination of PS and polypeptide antigens which are capable of eliciting an immune response against such a broad range of pneumococcal serotypes.

Assembly of MAPS Immunogenic Complexes

Drug substance (MAPS immunogenic complex) comprises PS and CP1 fusion protein. Since PS is biotinylated and CP1 fusion protein has a rhizavidin biotin-binding domain, they are linked by the high affinity biotin-rhizavidin interaction. MAPS immunogenic complexation was conducted individually for each PS serotype.

The MAPS immunogenic complex was made from 2 key intermediates: PS of 24, 15, or 9 *S. pneumoniae* serotypes, and rhizavidin fusion protein CP1. The PS was activated by creation of a cyanate ester and then biotinylated. The biotinylated PS was mixed with the CP1 fusion protein to create a MAPS immunogenic complex, which is linked by the high affinity biotin-rhizavidin interaction.

The MAPS immunogenic complex was formulated with 150 mM sodium chloride and surfactant buffer, then 0.2 µm filtered immediately prior to bottling and storing at 2° C. to 8° C. This formulated MAPS immunogenic complex is referred to as MAPS drug substance.

No raw materials contained animal- or human-derived components.

Figure 7:
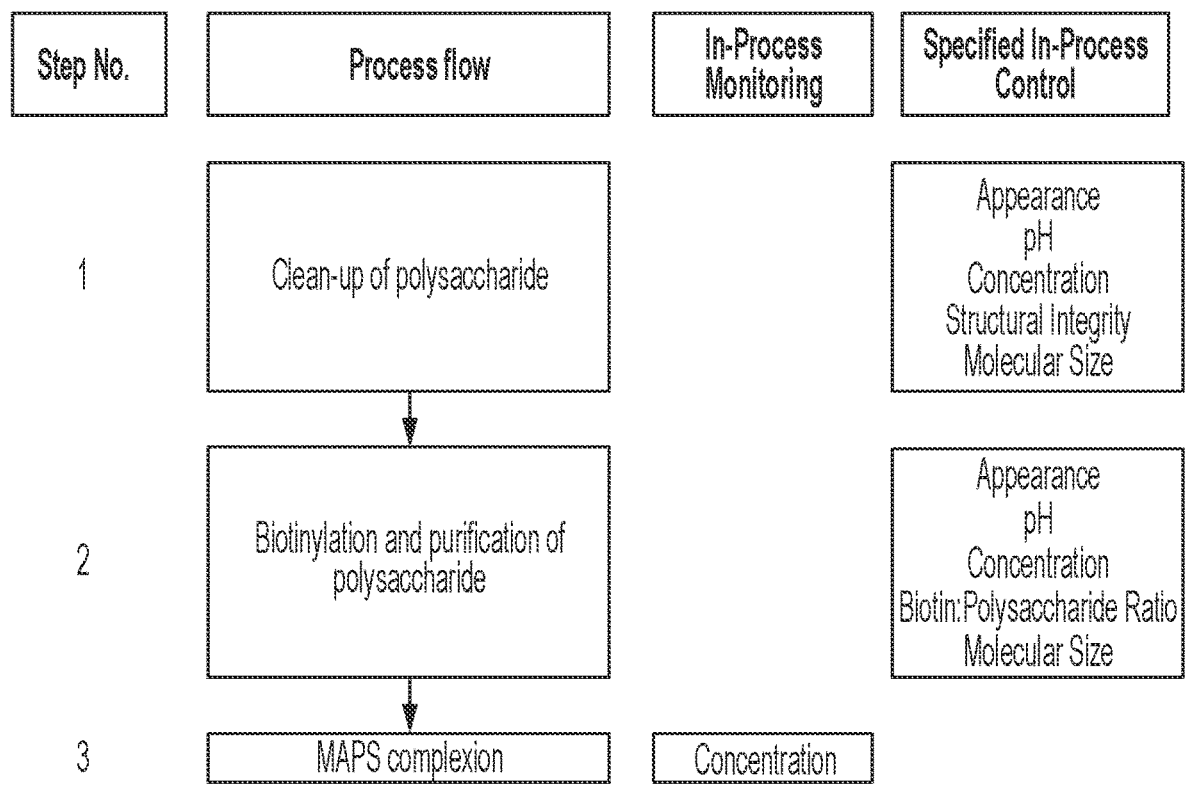
FIG. 7 is a flow-chart depicting an exemplary manufacturing process for MAPS immunogenic complexes, comprising biotinylation of antigenic polysaccharides and assembly with fusion protein CP1. MAPS: Multiple Antigen Presenting System.

A flow chart of MAPS Complexation Process is provided in FIG. 7 and details for the individual steps follows.

Step 1: Clean-Up of Polysaccharide

The purpose of this step is to remove process residuals. Dissolved PS was purified by filtration then exchanged with several-fold volumes of water for injection, followed by ultrafiltration to concentrate the PS. The cleaned-up PS was filtered by a 0.22 µm filter membrane.

Step 2: Biotinylation and Purification of Polysaccharide

The hydroxyl group on the PS was activated with a 1-cyano-4-dimethylamino-pyridinium tetrafluoroborate (CDAP) to create a highly active cyanoester. The cyanoesters were reacted with amine-PEG3-biotin and unreacted cyanoesters were capped with glycine. The biotinylated PS was buffer exchanged into 1 mM PBS in order to remove unreacted CDAP, amine-PEG3-biotin, glycine and residuals. After buffer exchange, the biotinylated PS was filtered with a 0.22 µm filter.

Step 3: MAPS Immunogenic Complexation

The biotinylated PS was mixed with the CP1 fusion protein in order to create a MAPS immunogenic complex, which is linked by a high affinity biotin-rhizavidin interaction. The MAPS immunogenic complex was purified to remove uncomplexed PS and protein by using a filtration membrane. After purification, the MAPS immunogenic complex was filtered with a 0.22 µm filter and stored at 2° C. to 8° C.

Specifications

Exemplary MAPS immunogenic complex/MAPS drug substance specifications are set forth in Table 3.

TABLE 3

Exemplary MAPS Drug Substance Specifications
Serotype
(1, 2, 3, 4, 5, 6A, 6B, 7F, 8, 9N, 9V, 10A, 11A, 12F,
14, 15B, 17F, 18C, 19A, 19F, 20B, 22F, 23F and 33F)

| Quality Attribute | Acceptance Criteria |
|---|---|
| Appearance | Clear, colorless, no particulate matter |
| pH | 5-7.5 |
| PS Identity | Positive |
| PS Concentration | >0.25 mg/mL |
| Protein Concentration | FIO |
| Free Protein | FIO |
| Free PS | <30% |
| Endotoxin | <1.25 × $10^{-2}$ EU/µg PS |
| Bioburden | ≤1 CFU/mL |

FIO: for information only; MAPS: multiple antigen-presenting system; PS: polysaccharide.

Example 4: MAPS24, MAPS15, and MAPS9 Vaccines

Drug Product

MAPS24 is a 24-valent MAPS vaccine comprising 24 types of MAPS immunogenic complexes. Each type of complex comprises polysaccharide from one of *S. pneumoniae* serotypes 1, 2, 3, 4, 5, 6A, 6B, 7F, 8, 9N, 9V, 10A, 11A, 12F, 14, 15B, 17F, 18C, 19A, 19F, 20B, 22F, 23F and 33F. In exemplary formulations, a MAPS24 vaccine is formulated so that each 0.5-mL dose of MAPS24 drug product comprises 1, 2 or 5 µg of each PS (from each of *S. pneumoniae* serotypes 1, 2, 3, 4, 5, 6A, 6B, 7F, 8, 9N, 9V, 10A, 11A, 12F, 14, 15B, 17F, 18C, 19A, 19F, 20B, 22F, 23F and 33F) contributed by each species of MAPS immunogenic complex. MAPS24 was formulated for IM administration with aluminum phosphate adjuvant. The total amount of aluminum per dose was 0.625 mg, which is below the FDA/WHO maximum recommended dose of 0.85 mg to 1.25 mg. This formulated solution exhibited a pH of about 5.8. A pH range of 5.3-6.3 is considered acceptable. MAPS15 and MAPS9 are 15-valent and 9-valent MAPS vaccines respectively. Exemplary MAPS15 and MAPS vaccines were formulated in the same manner as MAPS24 with the appropriate *S. pneumoniae* serotype PS as MAPS immunogenic complexes. The exemplary MAPS15 vaccines comprised 1, 2 or 5 µg of each *S. pneumoniae* serotype 1, 3, 4, 5, 6A, 6B, 7F, 9V, 14, 18C, 19A, 19F, 22F, 23F and 33F PS as MAPS immunogenic complexes. The exemplary MAPS9 comprised 1, 2 or 5 µg of each S. pneumoniae serotype 2, 8, 9N, 10A, 11A, 12F, 15B, 17F, and 20B as MAPS immunogenic complexes.

Vaccine Manufacturing Process

Figure 8A:
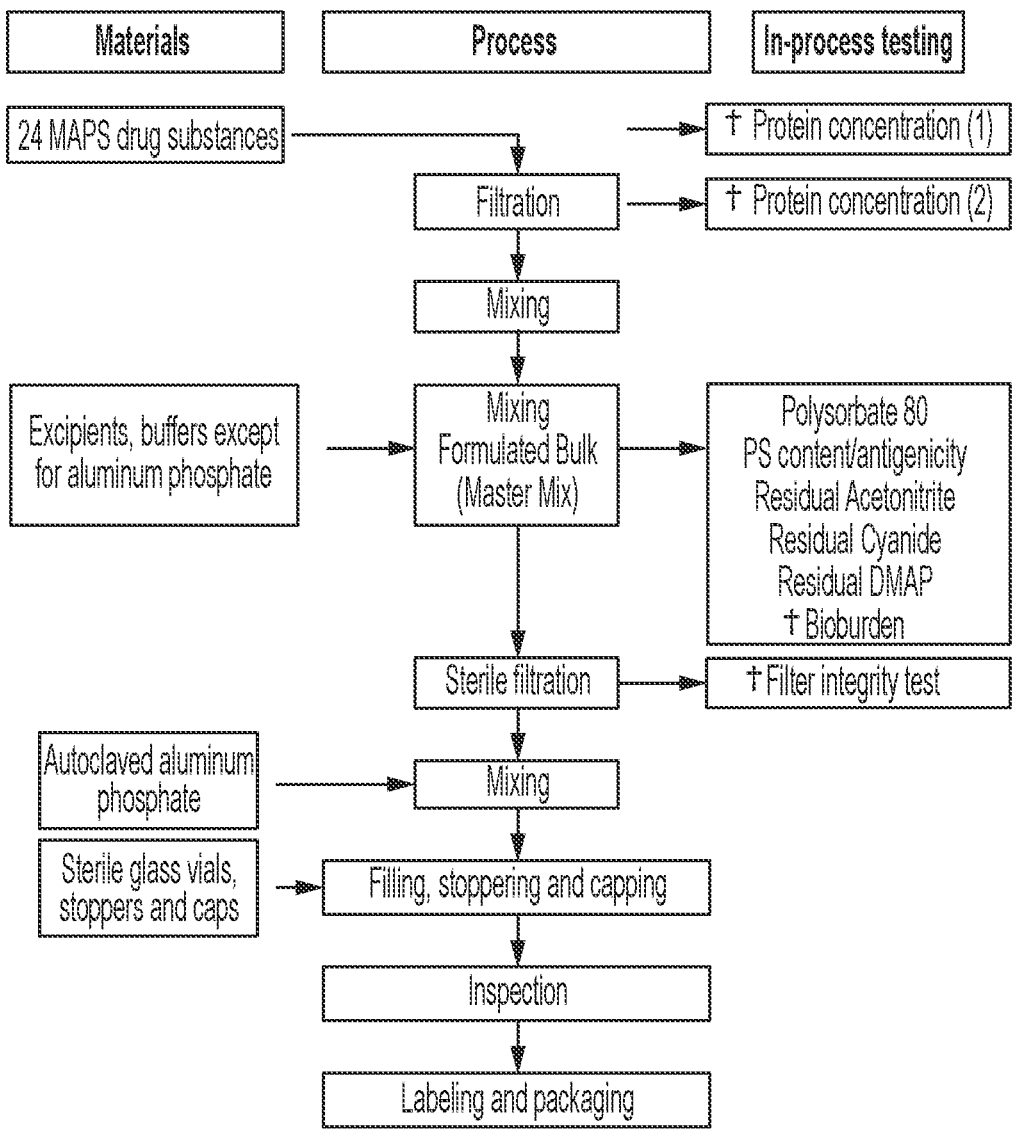
FIG. 8A and FIG. 8B are flow-charts depicting exemplary manufacturing processes for a MAPS vaccine. For example, such exemplary processes can be used to manufacture a MAPS24 vaccine, comprising MAPS immunogenic complexes that comprise capsular polysaccharides from 24 different *S. pneumoniae* serotypes. DMAP: 4-Dimethylaminopyridine; MAPS: Multiple Antigen Presenting System; PS: polysaccharide. † In-process tests
Figure 8B:
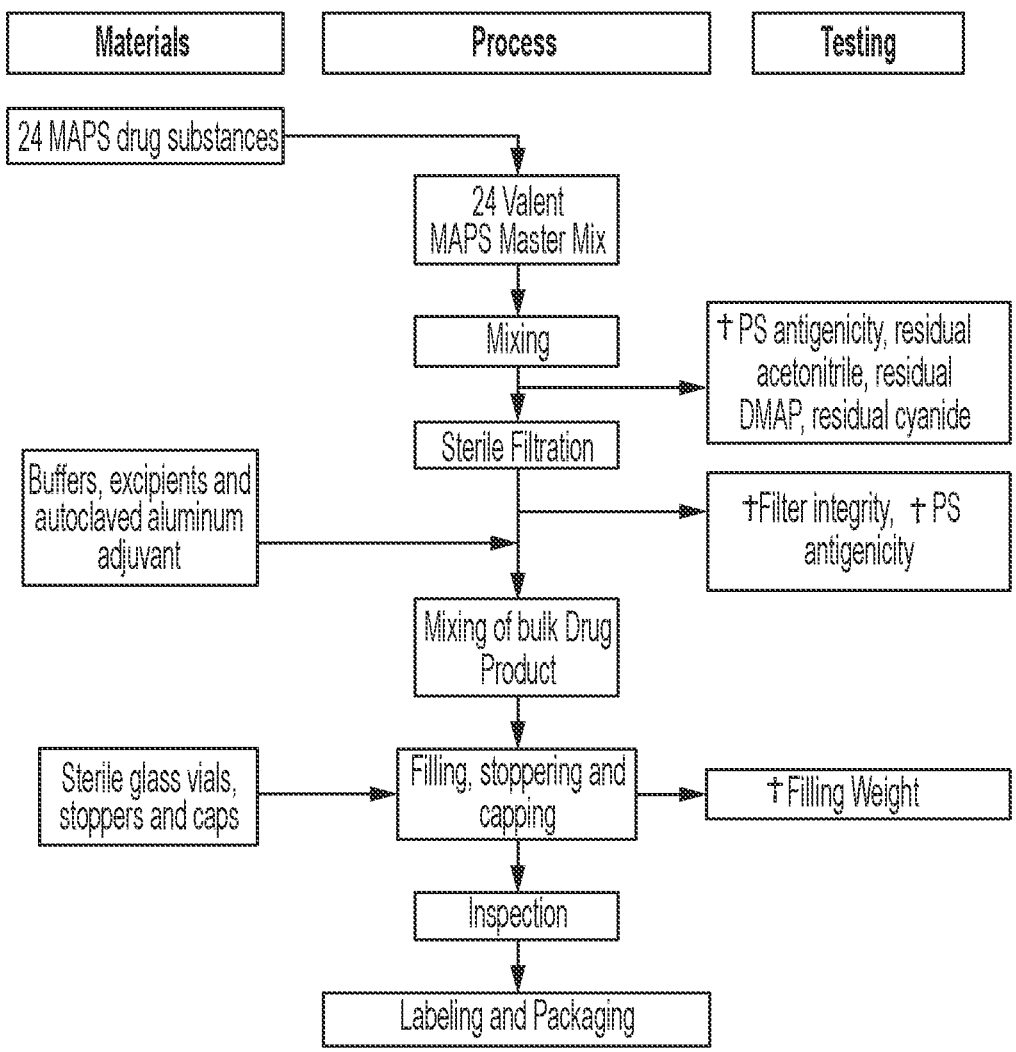
Figure 9:
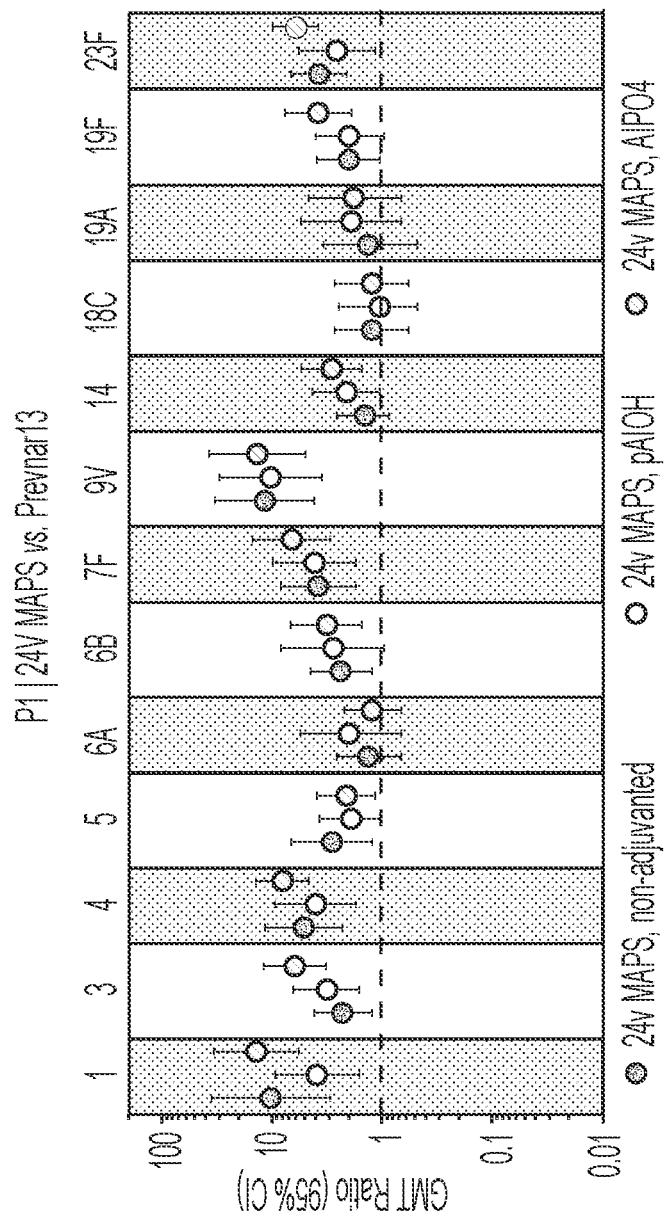
FIG. 9 illustrates immunogenicity of exemplary formulations of the 24-valent MAPS24 vaccine as compared to the 13-valent Prevnar 13 vaccine after a single dose. The graph depicts serotype-specific IgG antibody titers to polysaccharides of the indicated *S. pneumoniae* serotypes, obtained from sera collected two weeks after a first immunization (P1) with MAPS24 vaccine or Prevnar 13. MAPS24 vaccine used for immunization was non-adjuvanted, or adjuvanted with passivated aluminum hydroxide or aluminum phosphate, as indicated. Results are expressed as ratios of the geometric mean titer of IgG antibodies from MAPS24 sera relative to Prevnar 13 sera. Each circle on the graph shows the geometric mean titer ratio for the indicated MAPS24 sera, against polysaccharide(s) of the indicated *S. pneumoniae* serotype (top of graph). Dotted line shows a geometric mean titer ratio of 1. Error bars show the ±95% confidence interval. Abbreviations: 24v MAPS: 24-valent MAPS24 vaccine; AlPO$_4$: aluminum phosphate; pAlOH: passivated aluminum hydroxide; GMT Ratio: geometric mean titer ratio.
Figure 10:
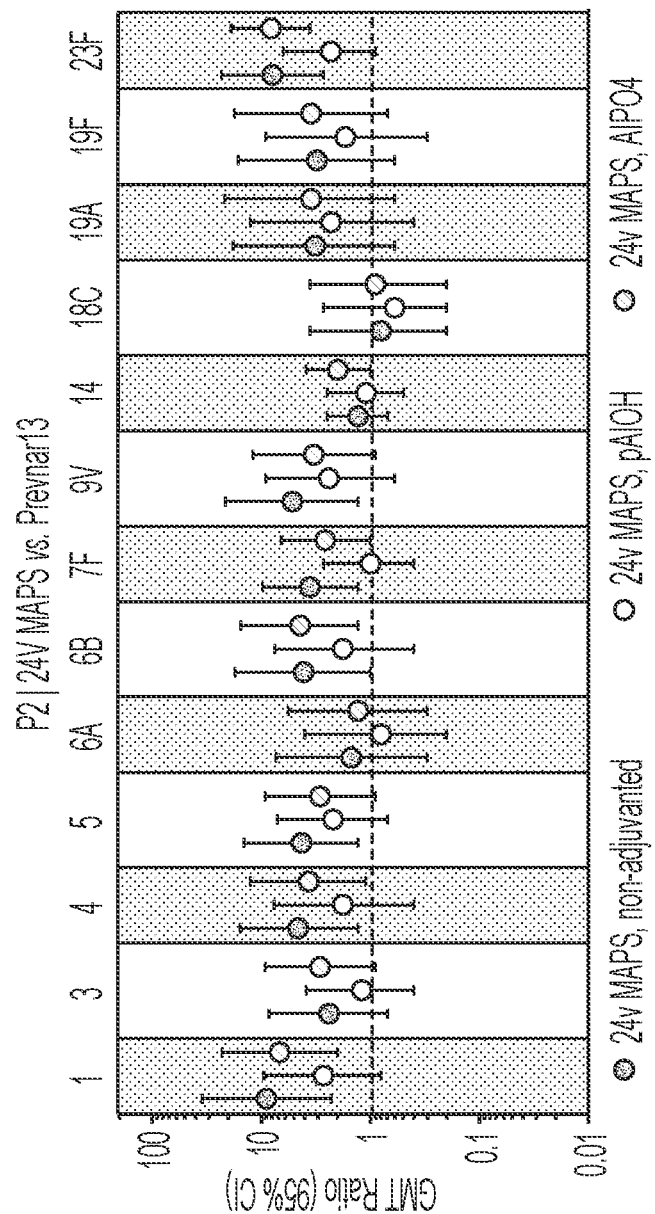
FIG. 10 illustrates immunogenicity of exemplary formulations of the 24-valent MAPS24 vaccine as compared to the 13-valent Prevnar 13 vaccine after a second dose. The graph depicts serotype-specific IgG antibody titers to polysaccharides of the indicated S. pneumoniae serotypes, obtained from sera collected two weeks after a second immunization (P2) with MAPS24 vaccine or Prevnar 13. MAPS24 vaccine used for immunization was non-adjuvanted, or adjuvanted with passivated aluminum hydroxide or aluminum phosphate, as indicated. Results are expressed as ratios of the geometric mean titer of IgG antibodies from MAPS24 sera relative to Prevnar 13 sera. Each circle on the graph shows the geometric mean titer ratio for the indicated MAPS24 sera, against polysaccharide(s) of the indicated S. pneumoniae serotype (top of graph). Dotted line shows a geometric mean titer ratio of 1. Error bars show the ±95% confidence interval. Abbreviations: 24v MAPS: 24-valent MAPS24 vaccine; AlPO$_4$: aluminum phosphate; pAlOH: passivated aluminum hydroxide; GMT Ratio: geometric mean titer ratio.
Figure 11:
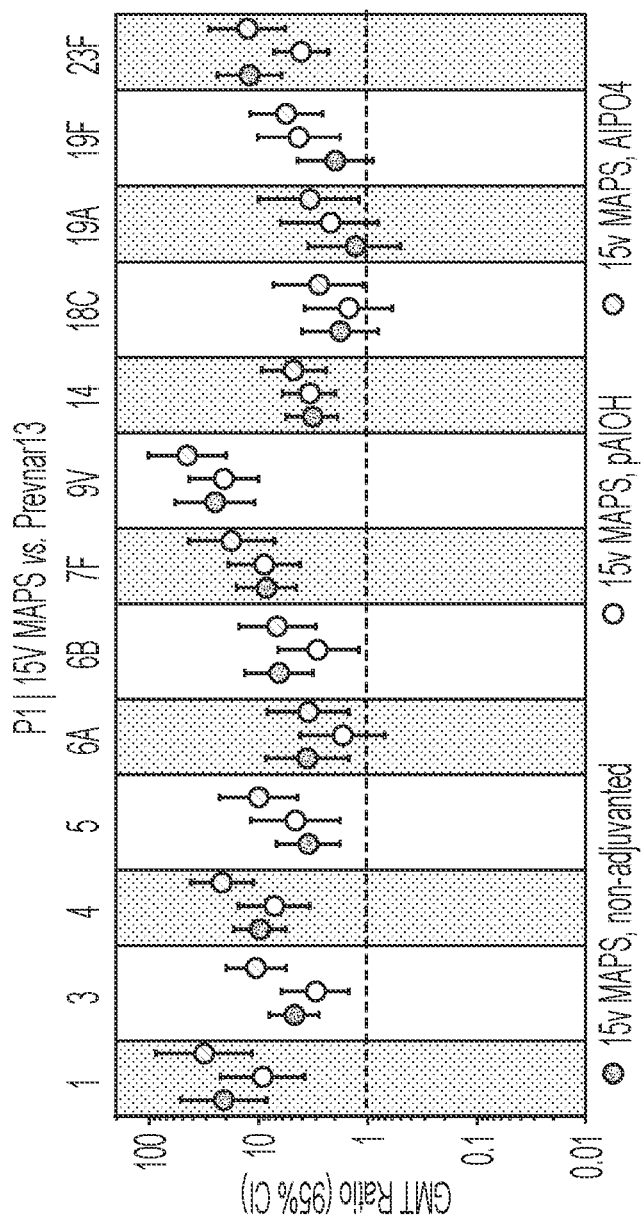
FIG. 11 illustrates immunogenicity of exemplary formulations of the 15-valent MAPS15 vaccine as compared to the 13-valent Prevnar 13 vaccine after a single dose. The graph depicts serotype-specific IgG antibody titers to polysaccharides of the indicated S. pneumoniae serotypes, obtained from sera collected two weeks after a first immunization (P1) with MAPS15 vaccine or Prevnar 13. MAPS15 vaccine used for immunization was non-adjuvanted, or adjuvanted with passivated aluminum hydroxide or aluminum phosphate, as indicated. Results are expressed as ratios of the geometric mean titer of IgG antibodies from MAPS24 sera relative to Prevnar 13 sera. Each circle on the graph shows the geometric mean titer ratio for the indicated MAPS24 sera, against polysaccharide(s) of the indicated S. pneumoniae serotype (top of graph). Dotted line shows a geometric mean titer ratio of 1. Error bars show the ±95% confidence interval. Abbreviations: 15v MAPS: 15-valent MAPS15 vaccine; AlPO$_4$: aluminum phosphate; pAlOH: passivated aluminum hydroxide; GMT Ratio: geometric mean titer ratio.
Figure 12:
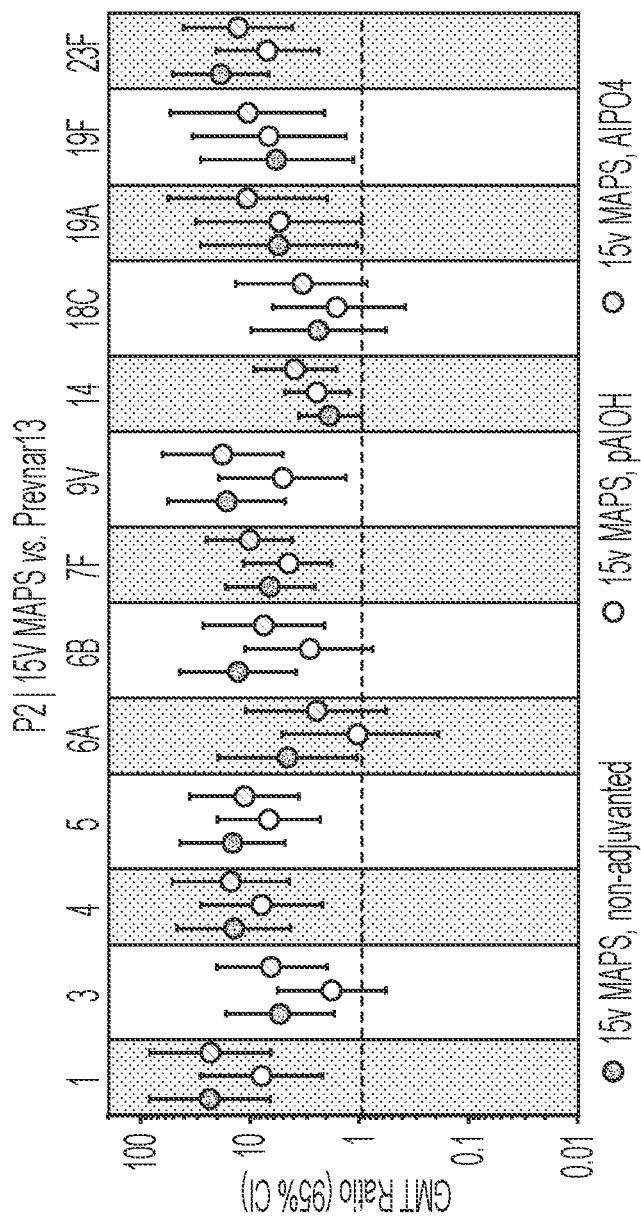
FIG. 12 illustrates immunogenicity of exemplary formulations of the 15-valent MAPS15 vaccine as compared to the 13-valent Prevnar 13 vaccine after a second dose. The graph depicts serotype-specific IgG antibody titers to polysaccharides of the indicated S. pneumoniae serotypes, obtained from sera collected two weeks after a second immunization (P2) with MAPS15 vaccine or Prevnar 13. MAPS15 vaccine used for immunization was non-adjuvanted, or adjuvanted with passivated aluminum hydroxide or aluminum phosphate, as indicated. Results are expressed as ratios of the geometric mean titer of IgG antibodies from MAPS24 sera relative to Prevnar 13 sera. Each circle on the graph shows the geometric mean titer ratio for the indicated MAPS24 sera, against polysaccharide(s) of the indicated S. pneumoniae serotype (top of graph). Dotted line shows a geometric mean titer ratio of 1. Error bars show the ±95% confidence interval. Abbreviations: 15v MAPS: 15-valent MAPS15 vaccine; AlPO$_4$: aluminum phosphate; pAlOH: passivated aluminum hydroxide; GMT Ratio: geometric mean titer ratio.

Drug products MAPS24, MAPS15 and MAPS9 were formulated by mixing the 24, 15, or 9 MAPS drug substances, compounding by mixing of excipients and buffers, filtering through a sterile filter, adding autoclaved aluminum phosphate and storing in glass vials at 2° C. to 8° C. Exemplary manufacturing processes are shown in FIG. 8A and FIG. 8B. Drug product specifications are provided in Table 4.

TABLE 4

Exemplary Drug Product Specifications (per PS)

| Quality Attribute | 1 µg Dose Specifications | 2 µg Dose Specifications | 5 µg Dose Specifications |
|---|---|---|---|
| Appearance | Grey/white homogeneous suspension | Grey/white homogeneous suspension | Grey/white homogeneous suspension |
| pH | 5.3-6.3 | 5.3-6.3 | 5.3-6.3 |
| PS Identity | Positive for each of the 24 serotypes | Positive for each of the 24 serotypes | Positive for each of the 24 serotypes |
| PS conc. | $2.0 \pm 0.6$ µg/mL | $4.0 \pm 1.2$ µg/mL | $10.0 \pm 3.0$ µg/mL |
| Total protein conc. | Report Result | Report Result | Report Result |
| Aluminum content | $1.25 \pm 0.25$ mg/mL | $1.25 \pm 0.25$ mg/mL | $1.25 \pm 0.25$ mg/mL |
| Osmolality | 200-400 mOsm/kg | 200-400 mOsm/kg | 200-400 mOsm/kg |
| Extractable volume | >0.5 mL | >0.5 mL | >0.5 mL |
| Endotoxin | <40 EU/dose | <40 EU/dose | <40 EU/dose |
| Sterility | Sterile | Sterile | Sterile |

Conc.: concentration; PS: polysaccharide.

Example 5: Immunogenicity of the Multivalent Pneumococcal Vaccines

Study 1: Evaluation of Serotype-Specific PS Antibody Titers Following Immunization with 24-Valent and 15-Valent MAPS Drug Product Methods MAPS immunogenic complexes were assembled by combining biotinylated polysaccharide with fusion protein CP1 in the presence of 20 mM Tris, pH 8.0, 150 mM sodium chloride and incubating under stirring conditions at room temperature for 16±4 hours. Aggregates formed during the reaction were removed by filtration through a 1.2 µm filter. The MAPS immunogenic complexes were then purified by diafiltration into 150 mM sodium chloride and sterile filtered using a 0.2 µm filter.

Individual MAPS immunogenic complexes were combined to create starting material at full human dose (2.2 µg of each PS per dose) for 24-valent (MAPS24) and 15-valent (MAPS15) drug product. 1.25 mg/ml (based on elemental aluminum content) of adjuvant, either p-Al(OH)$_3$ or AlPO$_4$ were added to these MAPS immunogenic complex mixtures (either 24v or 15v) in formulation buffer and incubated with end-over-end rotation for 18 hours at 4° C. to allow the MAPS immunogenic complexes to adsorb onto the adjuvants.

Six formulations were prepared at full human dose using 24-valent and 15-valent MAPS monovalents. These include: non-adjuvanted MAPS24 (Group A), p-Al(OH)$_3$ adjuvanted MAPS24 (Group B), AlPO$_4$ adjuvanted MAPS24 (Group C), non-adjuvanted MAPS15 (Group E), p-Al(OH)$_3$ adjuvanted MAPS15 (Group F) and AlPO$_4$ adjuvanted MAPS15 (Group G). Prevnar 13 (Group D), was used as control in this study. Prior to study start, Groups A-G above were diluted to 1/10 human dose (0.22 µg of each PS per dose except for PS 6B 0.44 µg PS per dose) with appropriate dilution buffers.

Six formulations were prepared at full human dose using 24-valent and 15-valent MAPS monovalents. These include: Non-adjuvanted MAPS24 (Group A), p-Al(OH)$_3$ adjuvanted MAPS24 (Group B), AlPO$_4$ adjuvanted MAPS24 (Group C), Non-adjuvanted MAPS15 (Group E), p-Al(OH)$_3$ adjuvanted MAPS15 (Group F) and AlPO$_4$ adjuvanted MAPS15 (Group G). Prevnar 13 (Group D), was used as control in this study. Prior to study start, Groups A-G above were diluted to 1/10 human dose (0.22 µg of each PS per dose except for PS 6B in Prevnar 13 with a 0.44 µg PS per dose) with appropriate dilution buffers (Table 5).

TABLE 5

Dilutions to Create Doses Used in Study

| Groups | Antigen | PS/Dose | Protein/Dose | Adjuvant |
|---|---|---|---|---|
| A | MAPS24, Non-adjuvanted | 0.22 µg each | 20.2 µg | NA |
| B | MAPS24, P-Al(OH)$_3$ | 0.22 µg each | 20.2 µg | P-Al(OH)$_3$ |
| C | MAPS24, AlPO$_4$ | 0.22 µg each | 20.2 µg | AlPO$_4$ |
| D | Prevnar 13 (Pfizer) | 0.22 µg each (0.44 µg 6B) | 3.4 µg | AlPO$_4$ |
| E | MAPS15, Non-adjuvanted | 0.22 µg each | 13.3 µg | NA |
| F | MAPS15, P-Al(OH)$_3$ | 0.22 µg each | 13.3 µg | P-Al(OH)$_3$ |
| G | MAPS15, AlPO$_4$ | 0.22 µg each | 13.3 µg | AlPO$_4$ |

NA, not applicable

Rabbit Immunization Protocol

As summarized in Table 6, New Zealand White (NZW) rabbits (AFV1110-1162) were immunized intramuscularly at a single site (in the thigh; 0.5 mL/site) on day 0 and at the alternate thigh on day 14 with one-tenth human dose (0.22 µg) of each PS for Group A-C, MAPS24; Group E-G, MAPS15, and Group D Prevnar 13 (except for PS 6B 0.44 µg PS per dose). Sera were collected before the first immunization (referred to as P0), second immunization (referred to as P1) and two weeks after the last immunization on day 28 (referred to as P2).

TABLE 6

Rabbit Immunization Study Groups

| Group | Antigen | Dose | Rabbit No | Rabbits | Vaccine Vol. | Admin Route | Immunization Schedule | Sera Collection |
|---|---|---|---|---|---|---|---|---|
| A | MAPS24, Non-adjuvanted | 1/10 (0.22 µg) | 1100-1108 | 9 | 0.5 mL | IM | 0, 14 | 0, 14, 28 |
| B | MAPS24, P-Al(OH)$_3$ | 1/10 (0.22 µg) | 1109-1117 | 9 | 0.5 mL | IM | 0, 14 | 0, 14, 28 |
| C | MAPS24, AlPO$_4$ | 1/10 (0.22 µg) | 1118-1126 | 9 | 0.5 mL | IM | 0, 14 | 0, 14, 28 |
| D | Prevnar 13 (Pfizer) | 1/10 *(0.22 µg) | 1127-1135 | 9 | 0.5 mL | IM | 0, 14 | 0, 14, 28 |
| E | MAPS15, Non-adjuvanted | 1/10 (0.22 µg) | 1136-1144 | 9 | 0.5 mL | IM | 0, 14 | 0, 14, 28 |
| F | MAPS15, P-Al(OH)$_3$ | 1/10 (0.22 µg) | 1145-1153 | 9 | 0.5 mL | IM | 0, 14 | 0, 14, 28 |
| G | MAPS15, AlPO$_4$ | 1/10 (0.22 µg) | 1154-1162 | 9 | 0.5 mL | IM | 0, 14 | 0, 14, 28 |

*6B dose was 0.44 µg for 1/10 human dose.

Immunogenicity: Evaluation of Serotype-Specific Polysaccharide Antibody Titers

To evaluate serotype-specific polysaccharide antibody titers in immunized rabbits, electrochemiluminescent based Meso Scale Discovery Immunoassay (MSD) was performed with U-plex plates coated with *Streptococcus pneumoniae* polysaccharides (PnPS) (serotypes 1, 2, 3, 4, 5, 6A, 6B, 7F, 8, 9V, 9N, 10A, 11A, 12F, 14, 15B, 17F, 18C, 19A, 19F, 22F, 23F, and 33F). The existing 13v serum standard (BCH14) and 13v internal control serum (BCH13), were spiked with 2, 8, 9N, 10A, 11A, 12F, 15B, 17F, 20A, 22F, and 33F specific antisera to generate Modified-BCH14 and Modified-BCH13 respectively (to facilitate the quantitation of the serotypes in the MAPS vaccine immunized rabbits). Briefly, 5-fold serial dilutions were created starting with a 1:200 dilution for the Modified-BCH14 using PBS-T, 1% BSA, and 5 µg/mL CWPS. The Modified-BCH13 (internal control serum) and the experimental test samples were diluted 1000-fold, 5000-fold, and 25000-fold with PBS-T, 1% BSA, and 5 µg/mL CWPS, respectively. Plates were washed with 1×PBS-T prior to adding the reference standard, control serum and the experimental test sera. After incubating at room temperature for one hour, plates were washed with PBS-T and secondary anti-rabbit SULFO-conjugated antibody was added. The plates were washed with PBS-T and 1× Read Buffer was added and the plates were read using an MSD Meso QuickPlex SQ 120 Model No. 1300.

Prevnar 13-Immunized Rabbit Sera Were Used as Control in this Study.

Results and Conclusion

Results are shown in FIGS. 9-13. Overall, equivalent or higher serotype-specific polysaccharide antibody responses were observed in groups that received 24-valent or 15-valent MAPS formulations at both P1 and P2 compared to Prevnar 13 group (represented as dotted line at GMT ratio of 1 in FIGS. 9-12). In general, higher titers were observed in the non-adjuvanted and the AlPO$_4$ adjuvanted groups, compared to p-Al(OH)$_3$ adjuvanted groups for all serotypes.

In FIGS. 9-12, the 24-valent or 15-valent MAPS formulation groups were compared to Prevnar 13 group (dotted line at GMT ratio of 1). If GMT ratio >1, then anti-PS titer for MAPS formulation groups is higher. If GMT ratio <1, then anti-PS titer for MAPS formulation groups is lower.

Figure 13:
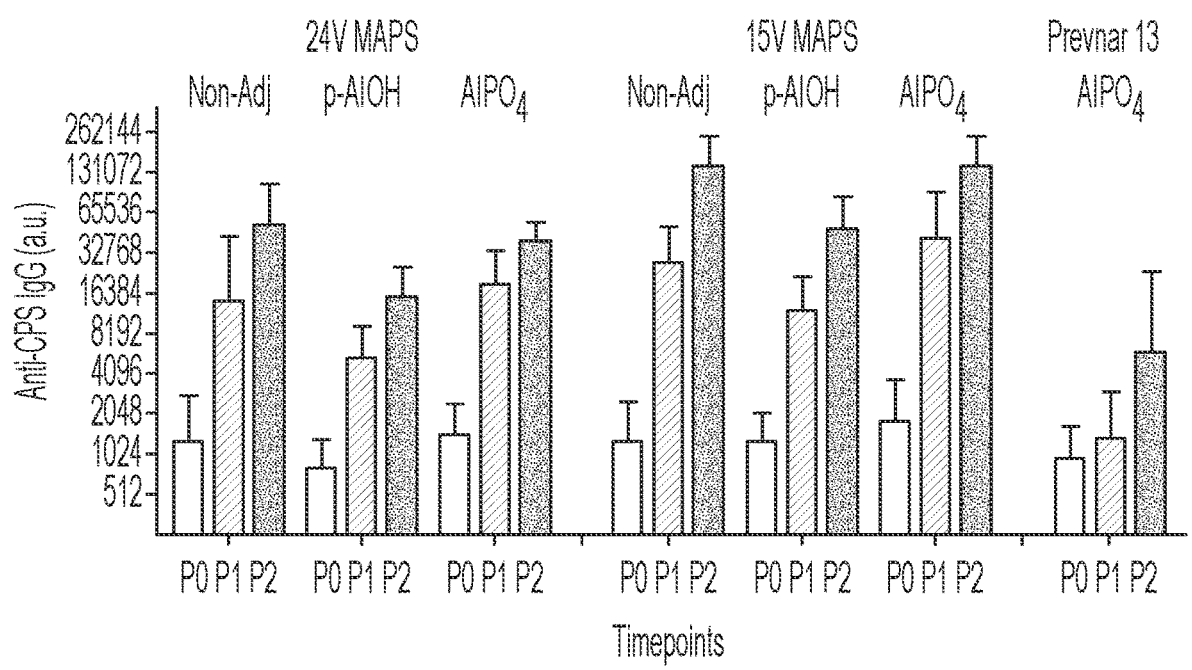
FIG. 13 illustrates immunogenicity of exemplary formulations of the 24-valent MAPS24 and 15-valent MAPS15 vaccines, as compared to the 13-valent Prevnar 13 vaccine. The graph depicts serotype-specific IgG antibody titers against capsular polysaccharide of representative S. pneumoniae serotype 1, obtained from sera collected prior to immunization (P0) and at two timepoints following immunization with MAPS24, MAPS15, or Prevnar 13 vaccines: P1=two weeks after first immunization, and P2=two weeks after second immunization. Vaccines used for immunization were non-adjuvanted, or adjuvanted with passivated aluminum hydroxide or aluminum phosphate, as indicated. Results are expressed in arbitrary units per ml. Each vertical bar on the graph shows geometric mean IgG antibody titer against capsular polysaccharide of S. pneumoniae serotype 1 for the indicated sera (top of graph) at the indicated timepoint (bottom of graph). Error bars show the 95% confidence interval. Abbreviations: CPS: capsular polysaccharide; Non-Adj: non-adjuvanted; 24V MAPS: 24-valent MAPS24 vaccine; 15V MAPS: 15-valent MAPS15 vaccine; AlPO$_4$: aluminum phosphate; p-AlOH: passivated aluminum hydroxide.

In FIG. 13, the antibody titer against PS of a representative individual serotype of *S. pneumoniae* (shown: serotype 1) in 24-valent or 15-valent MAPS formulation groups was compared to the titer against corresponding PS in the Prevnar 13 group.

Study 2: Evaluation of Serotype-Specific PS Antibody Titers Following Immunization with 24-Valent MAPS Drug Product in Comparison to PCV13

Figure 14:
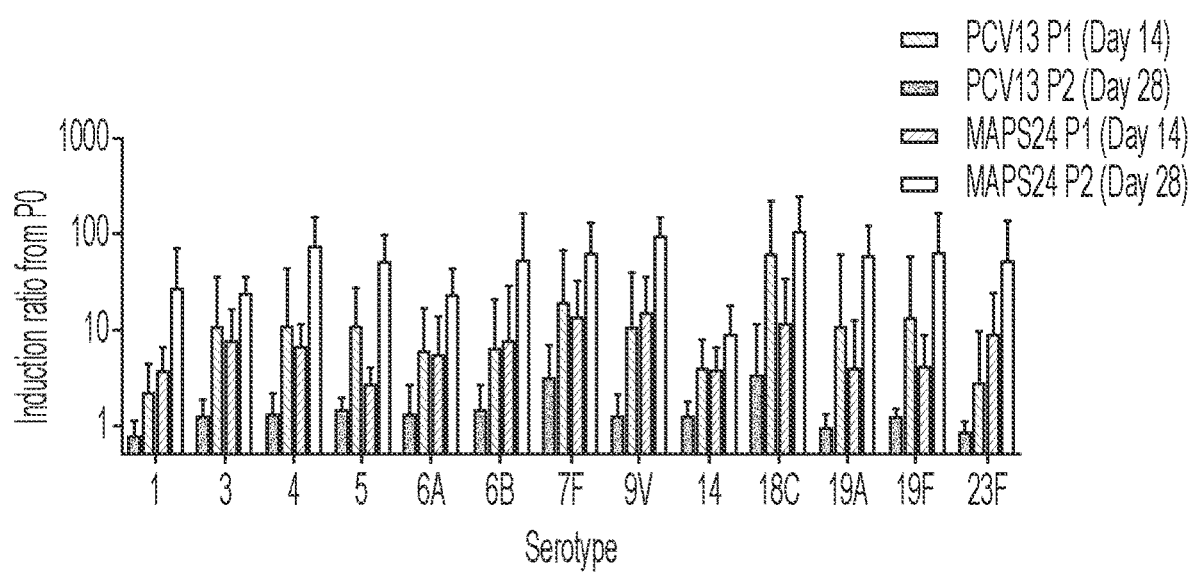
FIG. 14 illustrates immunogenicity of an exemplary formulation of the 24-valent MAPS24 vaccine as compared to the 13-valent Prevnar 13 vaccine after one and two doses. The graph depicts the induction ratio (fold change from baseline) for serotype-specific IgG antibodies against polysaccharides of S. pneumoniae serotypes 1, 3, 4, 5, 6A, 6B, 7F, 9V, 14, 18C, 19A, 19F, and 23F. Sera were collected prior to immunization (P0) and at two timepoints following immunization with MAPS24 or Prevnar 13 vaccines: P1 (day 14)=two weeks after first immunization, and P2 (day 28)=two weeks after second immunization. Each vertical bar on the graph represents the IgG antibody geometric mean titer induction ratio (P1/P0 or P2/P0) for the indicated sera, against polysaccharide(s) of the indicated S. pneumoniae serotype (bottom of graph). Error bars show the 95% confidence interval. Abbreviations: PCV13: 13-valent Prevnar 13 vaccine; MAPS24: 24-valent MAPS24 vaccine.
Figure 15:
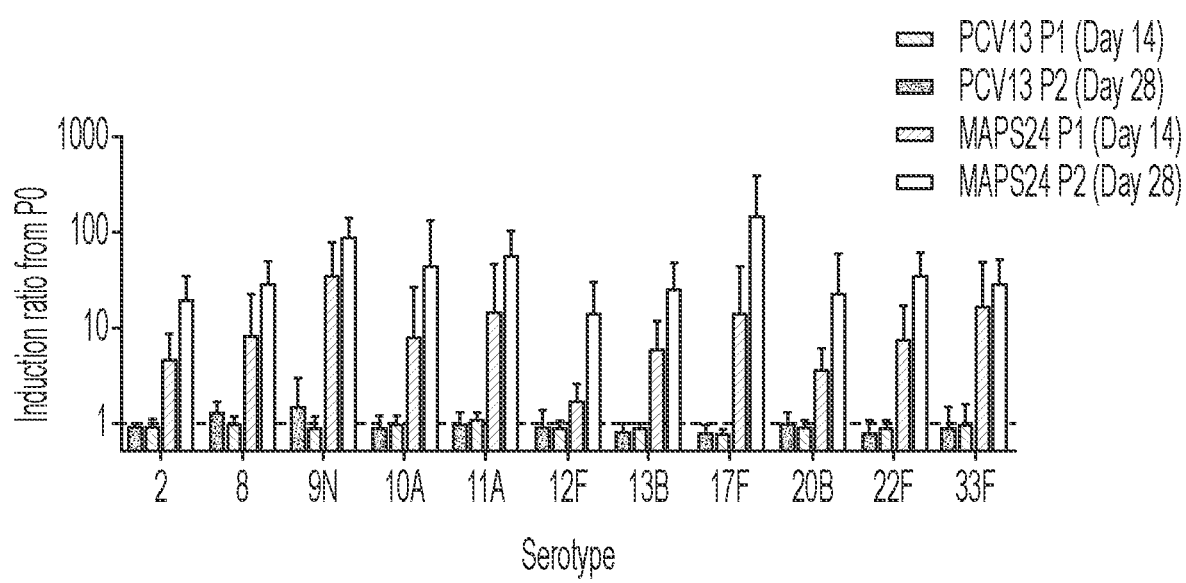
FIG. 15 illustrates immunogenicity of an exemplary formulation of the 24-valent MAPS24 vaccine as compared to the 13-valent Prevnar 13 vaccine after one and two doses. The graph depicts the induction ratio (fold change from baseline) for serotype-specific IgG antibodies against polysaccharides of S. pneumoniae serotypes 2, 8, 9N, 10A, 11A, 12F, 15B, 17F, 20B, 22F, and 33F. Sera were collected prior to immunization (P0) and at two timepoints following immunization with MAPS24 or Prevnar 13 vaccines: P1 (day 14)=two weeks after first immunization, and P2 (day 28)=two weeks after second immunization. Each vertical bar on the graph represents the IgG antibody geometric mean titer induction ratio (P1/P0 or P2/P0) for the indicated sera, against polysaccharide(s) of the indicated S. pneumoniae serotype (bottom of graph). Error bars show the 95% confidence interval. Abbreviations: PCV13: 13-valent Prevnar 13 vaccine; MAPS24: 24-valent MAPS24 vaccine.

One in vivo pharmacodynamics study was performed to evaluate the immunogenicity profile of MAPS24 in comparison to PCV13 at one-tenth of PCV13 human dose in rabbits. Test substance evaluated was MAPS24 formulated with AlPO$_4$ adjuvant. The MAPS24 test vaccine used in the nonclinical pharmacology study contained 2.2 µg of each PS per dose, corresponding to the amount of each PS found in a dose of PCV13 (except for 6B, 4.4 µg in PCV13). MAPS24 and PCV13 were diluted to one-tenth (0.22 µg of each PS, except for 6B, 0.44 µg in PCV13) in buffer, prior to administration (0.5 mL/dose) in rabbits. Overall, higher immune response was observed with the MAPS24 group in comparison to the PCV13 group for the majority of common serotypes (1, 3, 4, 5, 6A, 6B, 7F, 9V, 14, 18C, 19A, 19F and 23F), as shown in FIG. 14. Moreover, robust immune response was observed with MAPS24 group for additional serotypes (2, 8, 9N, 10A, 11A, 12F, 15B, 17F, 20B, 22F and 33F), as shown in FIG. 15.

Refer to Study 1 above for detailed methods.

Example 6: Immunogenicity and Protection Against Colonization

Study 1: Immunogenic Responses and Protective Effect of 12V and 6V MAPS with Immunogenic Complexes on CP1

One pharmacodynamic study was conducted to see if $T_H17$ responses and a protective effect against a pneumococci strain was induced by MAPS immunogenic complexes with CP1. In this study, 12-valent MAPS with CP1 (12V MAPS CP1; serotypes 1, 3, 4, 5, 6A, 7F, 9V, 14, 18C, 19A, 19F and 23F) and 6-valent MAPS with CP1 (6V MAPS CP1; serotypes 1, 3, 4, 5, 14 and 23F) were evaluated. A 6-valent MAPS with an alternate fusion protein (6V MAPS CP2a) and an inactivated whole-cell *S. pneumoniae* vaccine (WCB) were also evaluated. *S. pneumoniae* serotype 6B was used in the mouse challenge studies as the serotype was excluded from the MAPS immunogenic complexes.

$T_H17$ responses were evaluated after three immunizations. Peripheral blood samples were taken 2 weeks after the last immunization for ex vivo stimulation in the presence of the antigens as stimulant. The amount of interleukin 17A (IL-17A) secreted into media was then assessed after 6 days by ELISA. One to 2 weeks after bleed, mice were challenged with $10^7$ colony forming unit (CFU) of type 6B pneumococci (603 strain). Nasopharyngeal wash for each mouse was conducted 10 days post-infection and pneumococci CFU were calculated based on growth on blood agar.

Figure 16:
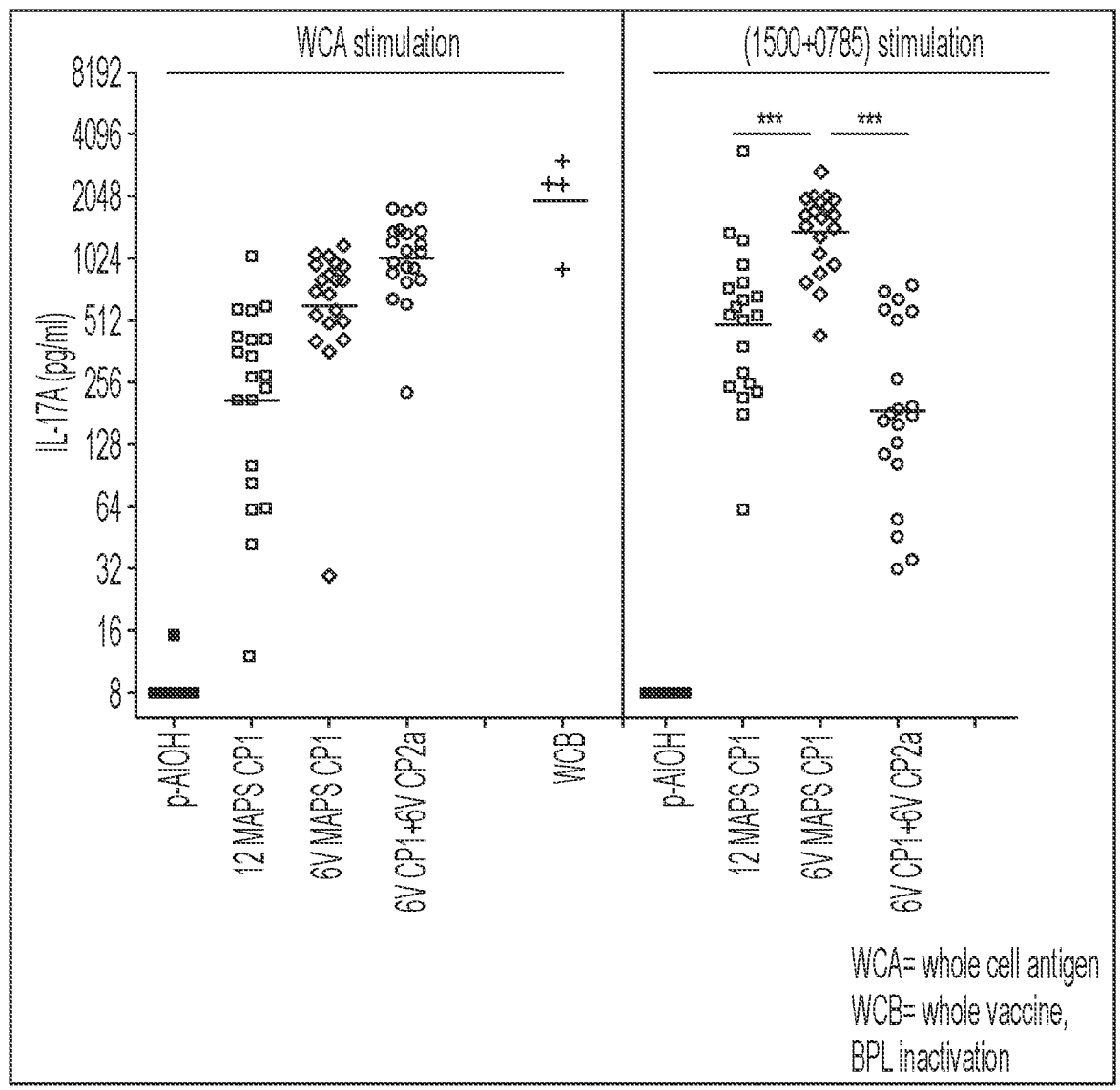
FIG. 16 illustrates $T_H17$ responses to exemplary vaccines comprising MAPS immunogenic complexes. Vaccines used for immunization were a 12-valent MAPS12 vaccine on CP1, a 6-valent MAPS6 vaccine on CP1, a 6-valent MAPS6 vaccine on an alternate fusion protein in combination with the preceding 6-valent MAPS6 vaccine on CP1, and an inactivated whole-cell S. pneumoniae vaccine (WCB). Peripheral blood samples of immunized mice were stimulated with whole-cell S. pneumoniae antigen (WCA; left panel), or a combination of SP1500 and SP0785 proteins (right panel). $T_H17$ responses of stimulated cells are shown by secretion of IL-17A in the media. Each point on the graph shows the concentration of secreted IL-17A for one mouse. Horizontal bars show the geometric mean concentration of secreted IL-17A for each group. Data were analyzed using Mann-Whitney U test (***: p<0.001). Abbreviations: BPL: betapropiolactone; CP1: rhizavidin [aa 45-179]-GGGGSSS-SP1500-AAA-SP0785 ("GGGGSSS" disclosed as SEQ ID NO: 3); CP2a: alternate fusion protein; MAPS: Multiple Antigen Presenting System; 12V CP1: 12-valent MAPS12 vaccine on CP1; 6V CP1: 6-valent MAPS6 vaccine on CP1; 6V CP2a: 6-valent MAPS6 vaccine on CP2a; p-AlOH: passivated aluminum hydroxide.
Figure 17:
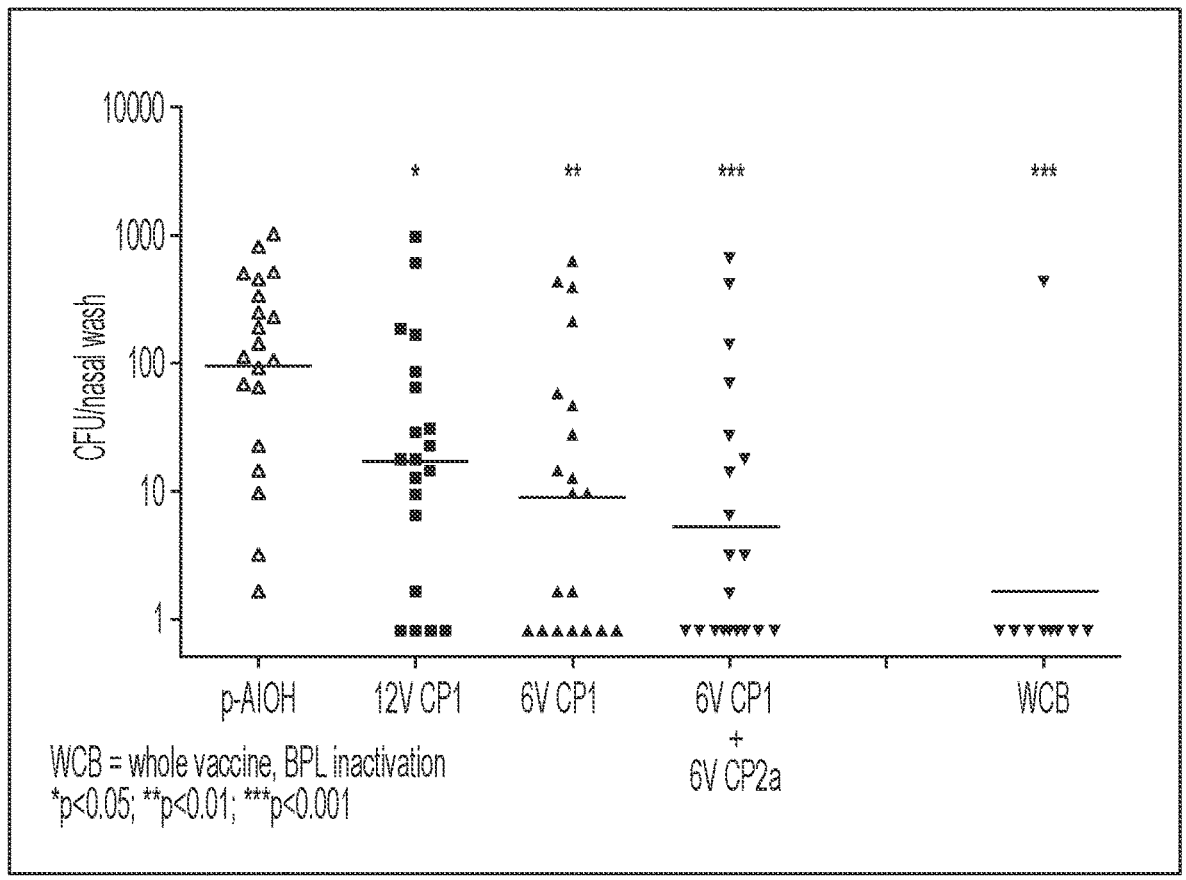
FIG. 17 illustrates protective effects of exemplary vaccines comprising immunogenic MAPS complexes. The graph depicts protection from colonization by S. pneumoniae following immunization with the indicated vaccines and intranasal challenge with S. pneumoniae serotype 6B (polysaccharide(s) of which is/are not included in the vaccines). Vaccines used for immunization were a 12-valent MAPS12 vaccine on CP1, a 6-valent MAPS6 vaccine on CP1, a 6-valent MAPS6 vaccine on an alternate fusion protein in combination with the preceding 6-valent MAPS6 vaccine on CP1, and an inactivated whole-cell S. pneumoniae vaccine (WCB). Each point on the graph represents S. pneumoniae CFU per nasal wash for one mouse. Horizontal bars represent the geometric mean S. pneumoniae CFU per nasal wash for each group. Data were analyzed using Mann-Whitney U test. Abbreviations: BPL: betapropiolactone; CFU: colony forming unit; CP1: rhizavidin [aa 45-179]-GGGGSSS-SP1500-AAA-SP0785 ("GGGGSSS" disclosed as SEQ ID NO: 3); CP2a: alternate fusion protein; MAPS: Multiple Antigen Presenting System; 12V CP1: 12-valent MAPS12 vaccine on CP1; 6V CP1: 6-valent MAPS6 vaccine on CP1; 6V CP2a: 6-valent MAPS6 vaccine on CP2a; p-AlOH: passivated aluminum hydroxide.

The immunization of 12V MAPS CP1 and 6V MAPS CP1 induced $T_H17$ response that was detected by stimulation with pneumococcal whole cell antigen (WCA), as well as SP1500 and SP0785 proteins, as shown in FIG. 16. Interestingly, as shown in FIG. 17, significant protection was demonstrated from nasopharyngeal colonization with a *S. pneumoniae* serotype 6B, a serotype that is not incorporated into the PS component of the multivalent MAPS with CP1, suggesting that protection is mediated through a CP1-directed immune response.

Study 2: Immunogenic Responses and Protective Effect of MAPS24 with Immunogenic Complexes on CP1

A pharmacodynamic study was conducted to see if a Th17 response to CP1 and a protective effect against a pneumococcal strain are induced by MAPS24. Mice were immunized with an exemplary formulation of a 24-valent MAPS vaccine (MAPS24) with adjuvant (MAPS24: serotypes 1, 2, 3, 4, 5, 6A, 6B, 7F, 8, 9N, 9V, 10A, 11A, 12F, 14, 15B, 17F, 18C, 19A, 19F, 20B, 22F, 23F and 33F), or with an exemplary formulation of a 23-valent MAPS vaccine (MAPS23) lacking the challenge serotype (*S. pneumoniae* serotype 6B) with adjuvant (MAPS23: serotypes 1, 2, 3, 4, 5, 6A, 7F, 8, 9N, 9V, 10A, 11A, 12F, 14, 15B, 17F, 18C, 19A, 19F, 20B, 22F, 23F and 33F). Mice were immunized with adjuvant only as a control.

Figure 18:
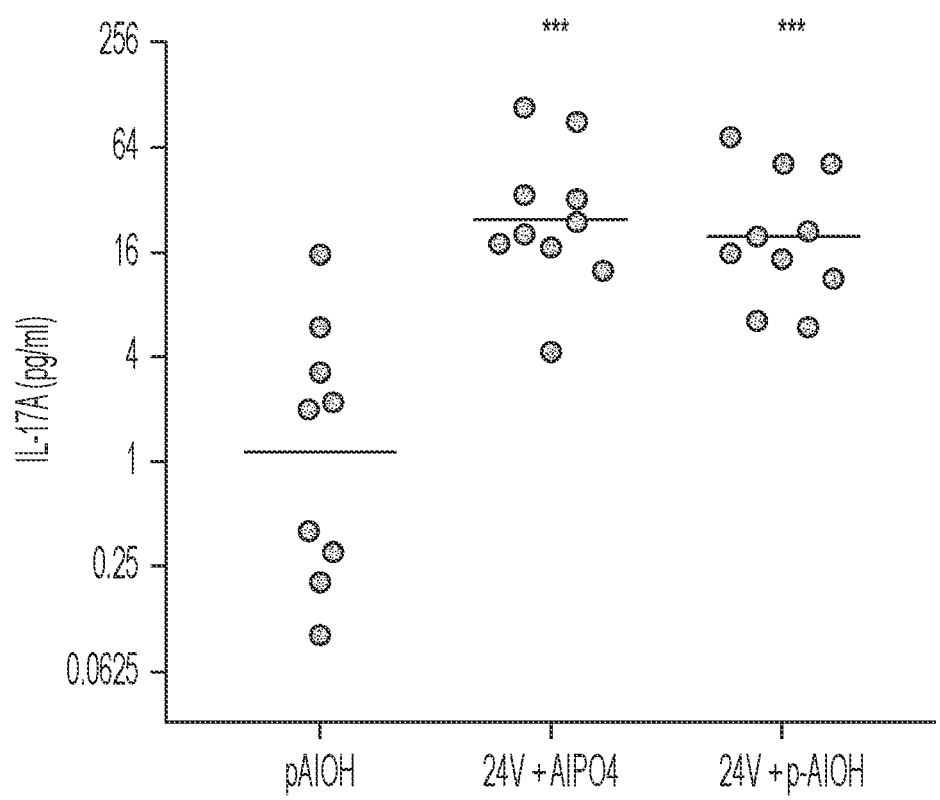
FIG. 18 illustrates $T_H17$ responses to exemplary vaccines comprising MAPS immunogenic complexes. Vaccines used for immunization were (i) a 24-valent MAPS24 vaccine on CP1 (24V) in combination with aluminum phosphate (AlPO$_4$) adjuvant, and (ii) a 24-valent MAPS vaccine on CP1 (24V) in combination with passivated aluminum hydroxide (p-AlOH) adjuvant. Splenocytes of immunized mice were stimulated with a fusion of SP1500 and SP0785 proteins. $T_H17$ responses of stimulated cells are shown by secretion of IL-17A in the media. Each point on the graph shows the concentration of secreted IL-17A for one mouse. Horizontal bars show the geometric mean concentration of secreted IL-17A for each group. Statistical analyses were performed in comparison with the p-AlOH control group using Mann-Whitney U test (***: p<0.001).

Th17 responses were evaluated after two immunizations. Splenocytes or peripheral blood collected 2 weeks after the last immunization were subjected to ex vivo stimulation in the presence of fused SP1500 and SP0785 proteins of CP1 as stimulant. The amount of interleukin 17A (IL-17A) secreted into the media was assessed 3 to 6 days after culture by electro-chemiluminescent based Meso Scale Immunoassay (MSD). Statistically significant increase in IL-17A was demonstrated for the 24-valent MAPS vaccine with adjuvant (e.g., passivated aluminum hydroxide (p-AlOH) or aluminum phosphate ($AlPO_4$)), compared to the control group immunized with adjuvant (e.g., passivated aluminum hydroxide) alone (FIG. 18).

Figure 19:
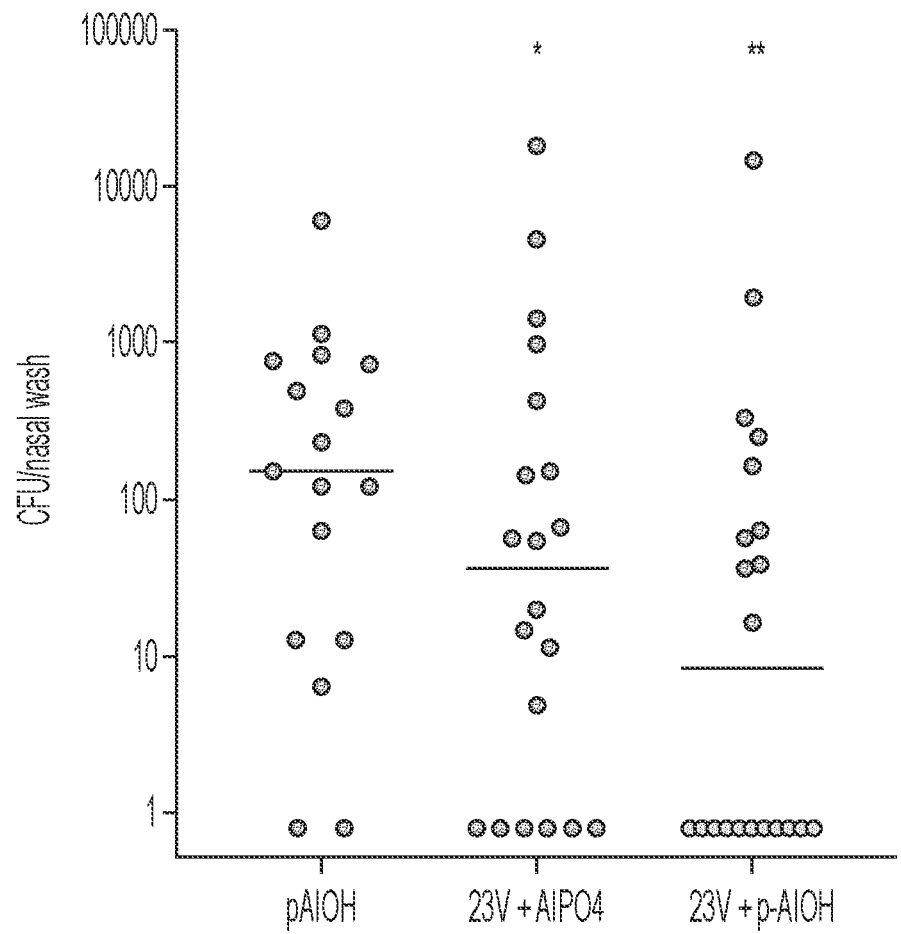
FIG. 19 illustrates protective effects of exemplary vaccines comprising MAPS immunogenic complexes. The graph depicts protection from colonization by S. pneumoniae following immunization with the indicated vaccines and intranasal challenge with S. pneumoniae serotype 6B (polysaccharide(s) of which is/are not included in the vaccines). Vaccines used for immunization were (i) a 23-valent MAPS23 vaccine (lacking serotype 6B) with CP1 (23V) in combination with aluminum phosphate (AlPO$_4$) adjuvant, and (ii) a 23-valent MAPS23 vaccine (lacking serotype 6B) with CP1 (23V) in combination with passivated aluminum hydroxide (p-AlOH) adjuvant. Each point on the graph represents S. pneumoniae colony forming unit (CFU) per nasal wash for one mouse. Horizontal bars represent the geometric mean S. pneumoniae CFU per nasal wash for each group. Statistical analyses were performed in comparison with the p-AlOH control group using Mann-Whitney U test (*: p=0.2, **: p=0.02).

Mice immunized with the 23-valent MAPS vaccine (lacking serotype 6B) and adjuvant control were challenged with $10^5$ to $10^7$ colony forming unit (CFU) of serotype 6B pneumococci (603 strain). Nasopharyngeal wash from each mouse was conducted 10 days after infection, and pneumococci CFU were calculated based on growth on blood agar. The group immunized with 23-valent MAPS vaccine and passivated aluminum hydroxide (p-AlOH)) had statistically significant reduction in the pneumococcal nasopharyngeal colonization, and the group immunized with 23-valent MAPS vaccine and aluminum phosphate ($AlPO_4$) demonstrated a trend of reduced pneumococcal nasal colonization (FIG. 19). Without wishing to be bound by theories, significant protection from nasopharyngeal colonization with *S. pneumoniae* serotype 6B, the polysaccharide component of which is not included in the tested 23-valent MAPS vaccine, indicates that protection may be mediated through immune response to the CP1 protein component of the vaccine, or to polysaccharide components of the vaccine with cross-reactivity to NVT *S. pneumoniae* strains, or to a combination of both.

Example 7. Antibodies from Sera Obtained from Animals Immunized with an Exemplary Formulation of MAPS24 Vaccine Bind to Non-Vaccine Type *S. pneumoniae*

Methods

Exemplary formulations comprising MAPS24 and rabbit immunization protocol used in this Example are described in Study 1 of Example 5. New Zealand White rabbits were immunized i.m. on days 0 and 14 with either an exemplary formulation of the 24-valent MAPS24 vaccine or with Prevnar 13, both adjuvanted with aluminum phosphate. Sera were collected prior to first immunization (P0) and two weeks after the second immunization (P2). To assess the binding capacity of antibodies from MAPS24-immunized rabbits for *S. pneumoniae* with capsular polysaccharide serotypes not included in MAPS24 or Prevnar13 (non-vaccine types, NVTs), an ELISA with whole-cell *S. pneumoniae* as the coating antigen was utilized. Such an exemplary assay detects rabbit IgG that bind to whole-cell *S. pneumoniae* coated on the ELISA plate through surface antigens such as protein or polysaccharide. To reduce binding and signal from non-immunized rabbit sera, the *S. pneumoniae*-coated plate was blocked with non-fat dry milk. In addition, rabbit sera were pre-incubated with both non-fat dry milk and *S. pneumoniae* cell-wall polysaccharide to adsorb any cell-wall polysaccharide-specific and any non-specific antibodies that could produce signal in the assay. Sera from rabbits immunized with MAPS24 (0.22 µg dose per polysaccharide) or Prevnar 13 (0.22 µg dose per polysaccharide, except 6B 0.44 µg dose) and corresponding pre-immunization sera were assayed for binding to six different serotypes of *S. pneumoniae* with capsular polysaccharide not incorporated into either vaccine. Whole-cell binding IgG titers were expressed as arbitrary units/ml.

Results and Conclusions

Figure 20:
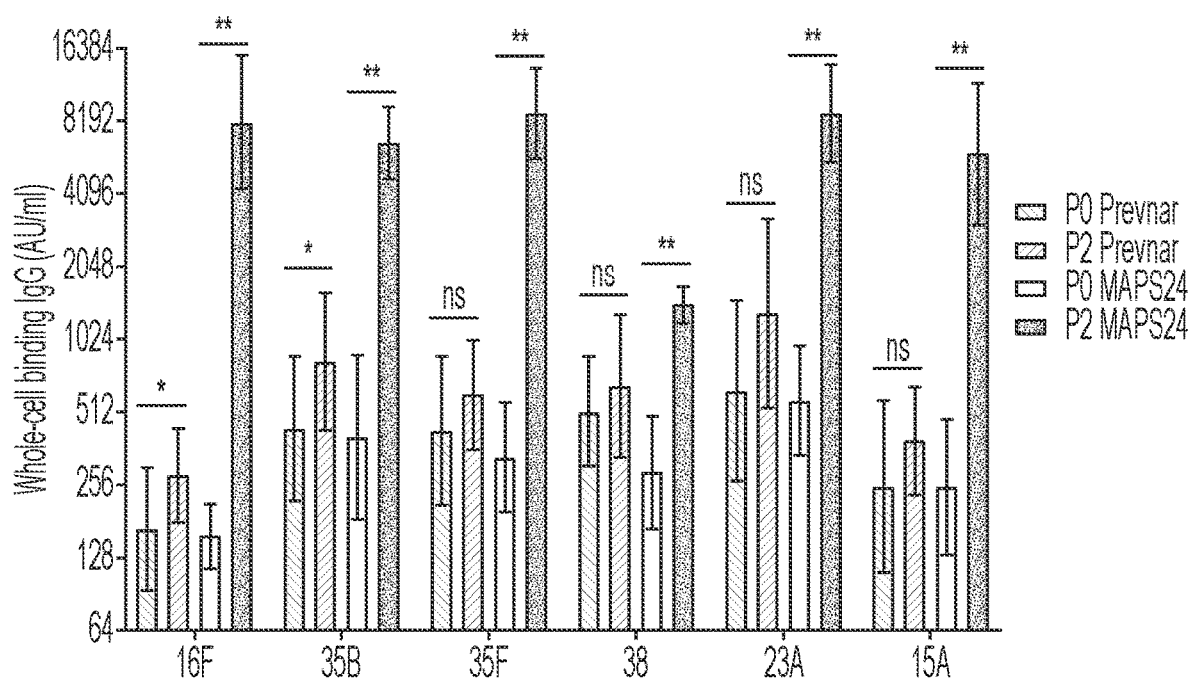
FIG. 20 illustrates immunogenicity of an exemplary formulation of the 24-valent MAPS24 vaccine as compared to the 13-valent Prevnar 13 vaccine. The graph depicts IgG antibody titers against whole-cell S. pneumoniae of the indicated serotypes, polysaccharides of which are not included in MAPS24 vaccine or Prevnar 13 (non-vaccine types, NVTs). Sera were collected prior to immunization (P0) and two weeks following second immunization (P2) with MAPS24 vaccine or Prevnar 13. Results are expressed in arbitrary units per ml. Each vertical bar on the graph denotes the geometric mean titer of whole-cell binding IgG antibodies for the indicated sera, against whole-cell S. pneumoniae of the indicated serotype (bottom of graph). Error bars show the ±95% confidence interval. Abbreviations: AU: arbitrary units; Prevnar: 13-valent Prevnar 13 vaccine; MAPS24: 24-valent MAPS24 vaccine; *p<0.05 and **p<0.01 for Wilcoxon matched pairs test; ns: not statistically significant.

As shown in FIG. 20, a statistically significant increase between pre-immunization (P0) and post-immunization (P2) IgG binding levels for MAPS24 sera was observed for all six serotypes ($p<0.01$ for all serotypes, two-tailed, Wilcoxon matched pairs test). There was no statistically significant difference between the binding IgG levels for P0 and P2 for Prevnar 13 sera for four of the six serotypes assayed and lower significance than MAPS24 for two serotypes.

Figure 21:
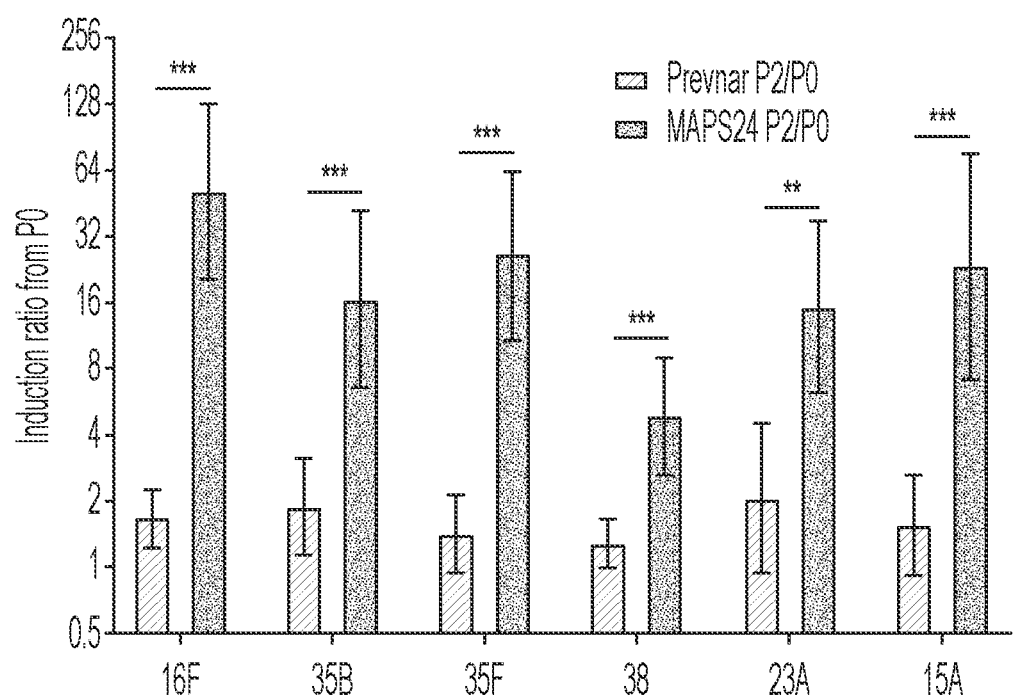
FIG. 21 illustrates immunogenicity of an exemplary formulation of the 24-valent MAPS24 vaccine as compared to the 13-valent Prevnar 13 vaccine after two doses. The graph depicts the induction ratio (fold-change from baseline) of IgG antibodies against whole-cell S. pneumoniae of the indicated serotypes, polysaccharides of which are not included in MAPS24 vaccine or Prevnar 13 (non-vaccine types, NVTs). Sera were collected prior to immunization (P0) and two weeks following second immunization (P2) with MAPS24 vaccine or Prevnar 13. Each vertical bar on the graph represents the IgG antibody geometric mean titer induction ratio (P2/P0) for the indicated sera, against whole-cell S. pneumoniae of the indicated serotype (bottom of graph). Error bars show the ±95% confidence interval. Abbreviations: Prevnar: 13-valent Prevnar 13 vaccine; MAPS24: 24-valent MAPS24 vaccine; P2/P0: post-2nd immunization (P2) IgG titer divided by pre-immune (P0) IgG titer; p<0.01 and * p<0.001 for Mann-Whitney test.

The induction ratios (fold-change) of the P2 IgG titers relative to the P0 IgG titers for each serum sample from both immunization groups were calculated, and the geometric mean induction ratio determined for antibody binding to each whole-cell NVT *S. pneumoniae* strain. As shown in FIG. 21, the induction ratio for all six serotypes was significantly higher for MAPS24-immunized rabbits than for Prevnar 13-immunized rabbits ($p<0.001$ for five serotypes and $p<0.01$ for one serotype, two tailed Mann-Whitney test).

Example 8: Opsonophagocytic Killing of Non-Vaccine Types of *S. pneumoniae*: MAPS 24

Methods

Exemplary formulations comprising MAPS24 and rabbit immunization protocol used in this Example are described in Study 1 of Example 5. New Zealand White rabbits were immunized i.m. on days 0 and 14 with an exemplary formulation of MAPS24 adjuvanted with aluminum phosphate. Sera were collected prior to first immunization (P0) and two weeks after the second immunization (P2).

To demonstrate presence of functional antibodies against non-vaccine types (NVTs) of *S. pneumoniae*, polysaccharides of which are not incorporated in the 24-valent MAPS vaccine, a modified concentrated opsonophagocytic assay (COPA) with sequential incubation steps was established. In such an exemplary assay, the presence of functional antibodies is shown by killing of NVT *S. pneumoniae* strains following incubation with immune sera. Briefly, frozen stocks of *S. pneumoniae* were thawed and resuspended at $2 \times 10^5$ CFU/ml in assay buffer (Hank's buffered saline with 10% heat-inactivated FBS). To each well of a 96-well plate, 20 µl of heat-inactivated rabbit serum diluted in assay buffer was added, followed by 10 µl of bacterial suspension in assay buffer. The bacteria and rabbit sera were incubated at room temperature for 30 minutes with shaking at 650 rpm. To each well, 10 µl of baby rabbit complement (Pel-Freeze Biologicals), neat or appropriately diluted in assay buffer, was added followed by incubation at room temperature for 30 min with shaking at 650 rpm. Differentiated HL60 cells (ATCC) were washed with assay buffer and resuspended to $1 \times 10^7$ cells/ml in assay buffer. To each well, 40 µl of this HL60 suspension was added (200 to 1, HL60 to bacteria ratio) followed by incubation at 37° C. with 5% $CO_2$ and shaking at 650 rpm for 1 hour. Each plate was transferred to ice and incubated for 20 minutes. Contents of each well were diluted in water $\frac{1}{5}$ and $\frac{1}{25}$, and each dilution was then plated on 5% blood agar plates. After overnight incubation at 37° C. with 5% $CO_2$, the CFU were counted for each sample and dilution, discarding data points with colony counts greater than 250 CFU.

Results and Conclusions

Figure 22:
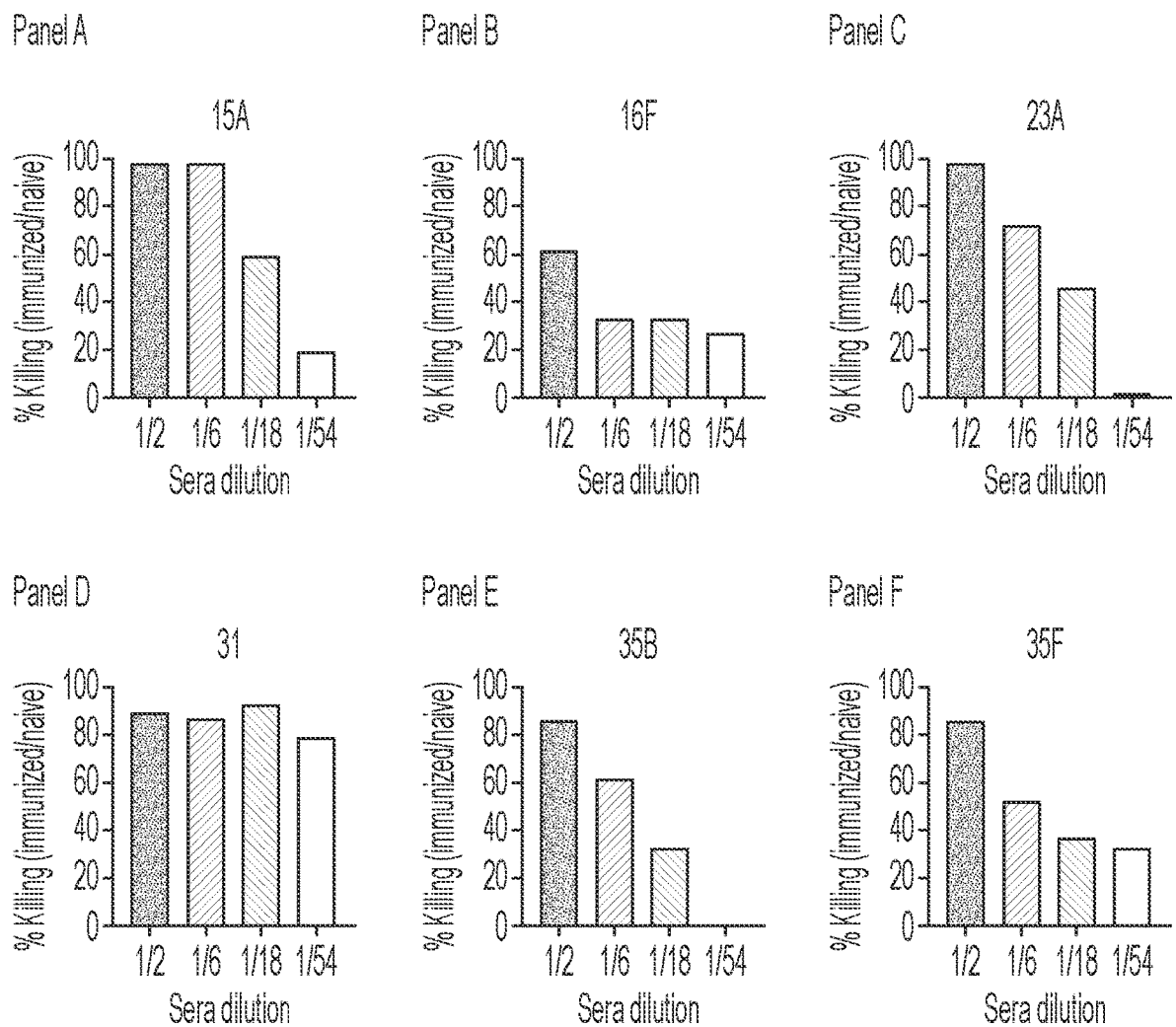
FIG. 22 illustrates the presence of functional antibodies against representative non-vaccine serotypes of S. pneumoniae in MAPS24 immune sera, using an opsonophagocytic killing assay. S. pneumoniae serotypes 15A, 16F, 23A, 31, 35B, and 35F, polysaccharides of which are not included in MAPS24 vaccine or Prevnar 13, were separately incubated in a modified concentrated opsonophagocytic assay (COPA) with heat-inactivated sera from rabbits immunized with an exemplary formulation of the 24-valent MAPS24 vaccine. The presence of functional antibodies is shown by killing of incubated S. pneumoniae. Sera were collected prior to immunization (P0) and two weeks following second immunization (P2). Results are expressed as percent killing activity, i.e., the percent reduction in S. pneumoniae colony forming units (CFU) following incubation with immune (P2) sera, relative to incubation with matched pre-immune (P0) sera. Each vertical bar of Panels A-F represents the percent killing activity observed with the indicated dilution of MAPS24 immune sera (bottom of each panel) against the indicated S. pneumoniae serotype (top of each panel).

Sera from rabbits immunized with MAPS24 were assayed at various dilutions, for example, ranging from 1:2 to 1:54, in comparison to matched naïve sera collected prior to immunization (pre-immune sera). Six different NVT *S. pneumoniae* strains were assayed separately (15A, 16F, 23A, 31, 35B and 35F). Colony forming units (CFU) were enumerated on blood agar plates. Killing activity was expressed as the percent reduction in CFU following incubation with immune sera compared to incubation with matched pre-immune sera, where the percent reduction is determined by [1−(CFU/ml for immune sera/CFU/ml for pre-immune sera)]*100. Without wishing to be bound by theory, in some embodiments, the killing activity of immune sera was dependent on both HL60 cells and active complement. As shown in FIG. 22, reduction of CFU for the immune sera at different dilutions over the matched pre-immune sera was observed for at least one or more (e.g., 1, 2, 3, 4, 5, or 6) non-vaccine serotypes. For example, reduction of CFU for the immune sera at $\frac{1}{18}$ dilution or lower over the matched pre-immune sera was observed for all six non-vaccine serotypes. Titration profiles for killing activity vary with the bacterial serotype. Without wishing to be bound by theories, in some embodiments, the functional antibodies against one or more non-vaccine serotypes (NVT) of *S. pneumoniae* generated by MAPS24 immunization may be directed to the CP1 protein component of the vaccine, or to the polysaccharide components of the vaccine with cross-reactivity to NVT *S. pneumoniae* strains, or to a combination of both.

Example 9: Opsonophagocytic Killing of Non-Vaccine Types of *S. pneumoniae*: MAPS24 and Prevnar 13

Methods

Exemplary formulations comprising MAPS24 and rabbit immunization protocol used in this Example are described in Study 1 of Example 5. New Zealand White rabbits were immunized i.m. on days 0 and 14 with either an exemplary formulation of MAPS24 or with Prevnar 13, both adjuvanted with aluminum phosphate. Sera were collected prior to first immunization (P0) and two weeks after the second immunization (P2). To demonstrate presence of functional antibodies against NVTs of *S. pneumoniae*, polysaccharides of which are not incorporated in the 24-valent MAPS vaccine or Prevnar13, a modified concentrated opsonophagocytic assay (COPA) with sequential incubation steps was performed as described in Example 8. In such an exemplary assay, the presence of functional antibodies is shown by killing of NVT *S. pneumoniae* strains following incubation with immune sera.

Results and Conclusions

Sera from rabbits immunized with either MAPS24 or Prevnar 13 were assayed at various dilutions, for example, ranging from 1:2 to 1:54, in comparison to matched naïve sera collected prior to immunization (pre-immune sera). Two different NVT *S. pneumoniae* strains (15A and 16F) were assayed separately. Colony forming units (CFU) were enumerated on blood agar plates. Results were expressed as the percent survival of bacteria incubated with immune sera compared to incubation with matched pre-immune sera.

Figure 23:
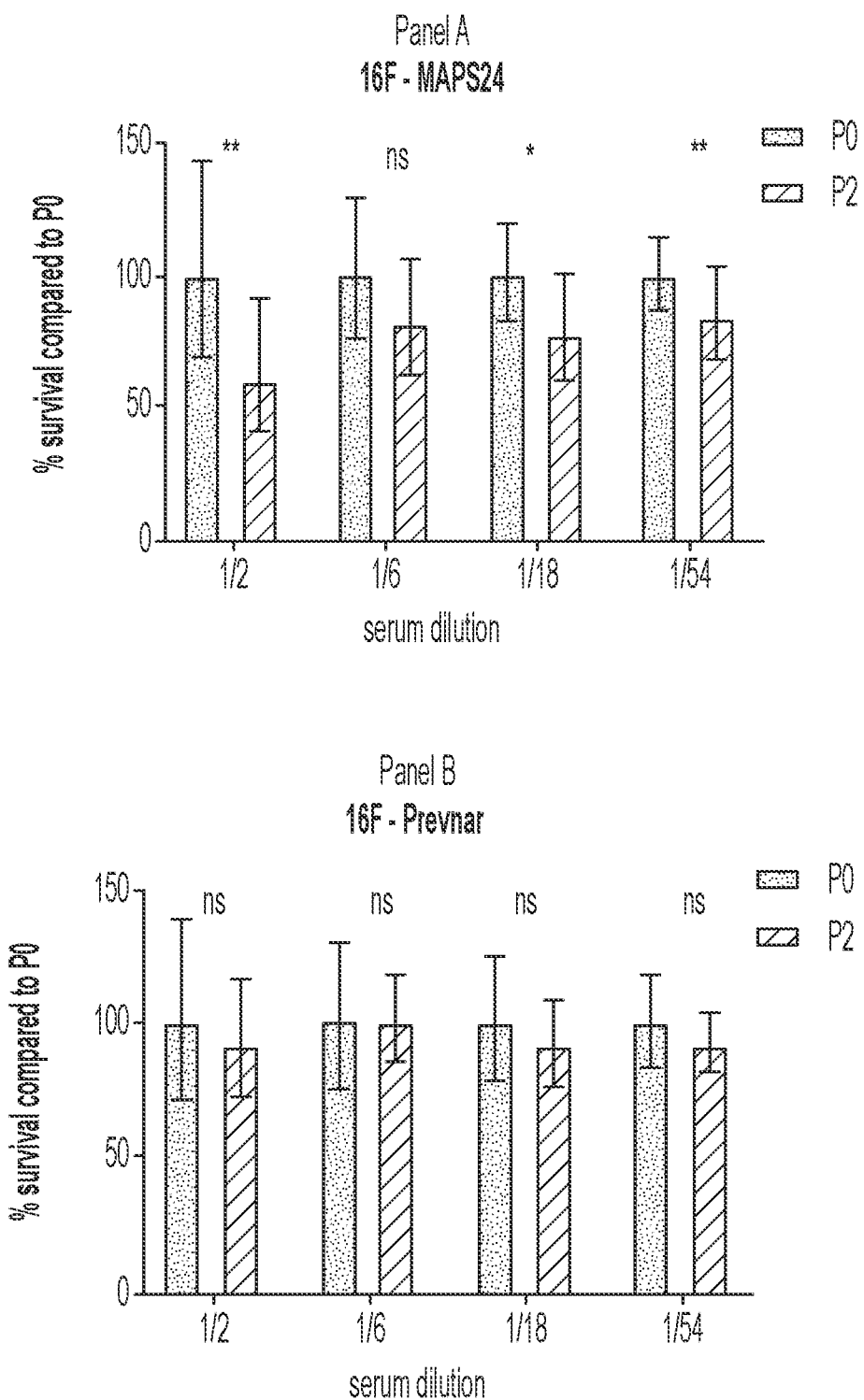
FIG. 23 illustrates the presence of functional antibodies against a representative non-vaccine serotype of S. pneumoniae (e.g., serotype16F) in MAPS24 immune sera, compared to Prevnar 13 immune sera, using an opsonophagocytic killing assay. S. pneumoniae serotype 16F, polysaccharide(s) of which is/are not included in MAPS24 vaccine or Prevnar 13, was incubated in a modified concentrated opsonophagocytic assay (COPA) with heat-inactivated sera from rabbits immunized with an exemplary formulation of the 24-valent MAPS24 vaccine or with Prevnar 13. The presence of functional antibodies was shown by killing of incubated S. pneumoniae. Sera were collected prior to immunization (P0)

FIG. 23 shows that NVT *S. pneumoniae* serotype 16F incubated with sera from MAPS24-immunized rabbits displayed reduced survival, as compared to bacteria incubated with sera from Prevnar13-immunized rabbits. Panel A of FIG. 23 shows a statistically significant reduction in survival of the NVT *S. pneumoniae* serotype 16F for three of the four tested dilutions of MAPS24-immunized rabbit sera when compared to pre-immune sera. In contrast, Panel B of FIG. 23 shows that the Prevnar 13-immunized rabbit sera did not result in significant decreases in bacterial survival at any dilution.

FIG. 24 shows that NVT *S. pneumoniae* serotype 15A incubated with sera from MAPS24-immunized rabbits displayed reduced survival, as compared to bacteria incubated with sera from Prevnar13-immunized rabbits. Panel A of FIG. 24 shows a statistically significant reduction in survival of the NVT *S. pneumoniae* serotype 15A for three of the four tested dilutions of MAPS24-immunized rabbit sera when compared to pre-immune sera. In contrast, Panel B of FIG. 24 shows that the Prevnar 13-immunized rabbit sera did not result in significant decreases in bacterial survival at any dilution.

Without wishing to be bound by theories, in some embodiments, the functional antibodies against one or more non-vaccine serotypes (NVT) of *S. pneumoniae* generated by MAPS24 immunization may be directed to the CP1 protein component of the vaccine, or to the polysaccharide components of the vaccine with cross-reactivity to NVT *S. pneumoniae* strains, or to a combination of both.

Example 10: Inhibition of Opsonophagocytic Killing of Non-Vaccine Type Serotype of *S. pneumoniae* with CP1

Examples 8 and 9 demonstrate the presence of functional antibodies by opsonophagocytic killing of non-vaccine type serotype(s) (NVTs) of *S. pneumoniae* using exemplary formulations of MAPS (e.g., MAPS24). To demonstrate specificity of functional antibodies against NVTs of *S. pneumoniae*, an inhibition variant of the modified concentrated opsonophagocytic assay (iCOPA) was established. In such an exemplary assay, the presence of functional antibodies is shown by killing of NVT *S. pneumoniae* serotypes following incubation with immune sera; the specificity of these functional antibodies is assayed by pre-incubation of the immune sera with a specific inhibitory reagent (e.g., a purified protein, e.g., fusion protein CP1) that inhibits or competes with binding of the functional antibodies to a target antigen and subsequent incubation with NVT S. pneumoniae serotypes, to determine if killing has been inhibited. Sera from rabbits immunized with MAPS24 were assayed at various dilutions, for example, ranging from 1:2 to 1:54, in comparison to matched naïve sera collected prior to immunization (pre-immune sera). Killing of the NVT S. pneumoniae 16F strain was assessed using immune sera with and without pre-incubation with the purified CP1 component of MAPS24. Colony forming units (CFU) were enumerated on blood agar plates. Killing activity was expressed as the percent reduction in CFU following incubation with immune sera compared to incubation with matched pre-immune sera, where the percent reduction is determined by [1−(CFU/ml for immune sera/CFU/ml for pre-immune sera)]*100. As shown in FIG. 25, the presence of functional antibodies to NVT S. pneumoniae 16F in immune sera, in the absence of a specific inhibitory reagent, is shown by percent killing activity for the immune sera over the pre-immune sera. Pre-incubation of the immune sera with purified CP1 protein, under conditions favoring competitive binding of functional antibodies to CP1 protein, resulted in lower percent killing activity. Without wishing to be bound by theory, this result indicates that functional antibodies against non-vaccine type serotype (e.g., serotype 16F) of S. pneumoniae generated by MAPS24 immunization may be directed to the CP1 protein component of the vaccine.

Example 11: Opsonophagocytic Killing of Non-Vaccine Type Serotype of S. pneumoniae: SP1500 and SP0785 Polypeptides This Example demonstrates the presence of functional antibodies against a representative NVT of S. pneumoniae in sera collected from animals immunized with SP1500 or SP0785 polypeptides (immune sera).

Methods

Exemplary rabbit immunization protocols used in this Example are described in Study 1 of Example 5. New Zealand White rabbits (n=3) were immunized i.m. separately on days 0, 14, and 28 with 100 µg of SP1500 or SP0785 polypeptides, adjuvanted with aluminum phosphate. Sera were collected prior to first immunization (P0) and two weeks after the third immunization (P3). Sera collected from the 3 rabbits at each timepoint were combined to form a pool and stored at −80° C. To demonstrate presence of functional antibodies against NVT S. pneumoniae 16F, polysaccharides of which are not incorporated in the SP1500- or SP0785-comprising formulations, a modified concentrated opsonophagocytic assay (COPA) with sequential incubation steps was performed as described in Example 8. In such an exemplary assay, the presence of functional antibodies is shown by killing of NVT S. pneumoniae 16F following incubation with immune sera.

Results. Sera from rabbits immunized with either SP1500 or SP0785 polypeptides were assayed at various dilutions, for example, ranging from 1:2 to 1:54, in comparison to matched naïve sera collected prior to immunization (pre-immune sera). Colony forming units (CFU) were enumerated on blood agar plates. Killing activity was expressed as the percent reduction in CFU following incubation with immune sera compared to incubation with matched pre-immune sera, where the percent reduction is determined by [1−(CFU/ml for immune sera/CFU/ml for pre-immune sera)]*100.

FIG. 26 shows that incubation with immune sera from rabbits separately immunized with SP1500 and SP0785 polypeptides resulted in killing activity against NVT S. pneumoniae serotype 16F for three of the four tested dilutions when compared to pre-immune sera. Without wishing to be bound by theory, this result indicates that functional antibodies against one or more non-vaccine serotypes (NVT) of S. pneumoniae may be generated by immunization with SP1500 or SP0785 polypeptides.

A pre-clinical study demonstrates that multivalent MAPS vaccines as described herein (e.g., MAPS24, MAPS15 and MAPS9 vaccines) are highly immunogenic in animal models and induce serotype-specific responses. MAPS24 confers clinically meaningful advantages over the current PCV13 vaccine at least by adding significant additional coverage to the target populations with an additional 11 serotypes. Further, MAPS24 generated functional antibodies against one or more non-vaccine serotypes. In addition, the MAPS24 vaccine simplifies the current complex pneumococcal immunization regimen in high-risk and older adults by providing protection against all included serotypes in a single dose instead of two doses of two different vaccines administered according to complex schedules.

```
Sequence Listing
rhizavidin protein, full-length [amino acids 1-179]:
                                                  SEQ ID NO: 1
MIITSLYATFGTIADGRRTSGGKTMIRTNAVAALVFAVATSALAFDASNFKDFSSIASASSSWQ

NQSGSTMIIQVDSFGNVSGQYVNRAQGTGCQNSPYPLTGRVNGTFIAFSVGWNNSTENCNSATG

WTGYAQVNGNNTEIVTSWNLAYEGGSGPAIEQGQDTFQYVPTTENKSLLKD, truncated rhizavidin protein, denoted Rhavi [amino acids
45-179]:
                                                  SEQ ID NO: 2
FDASNFKDFSSIASASSSWQNQSGSTMIIQVDSFGNVSGQYVNRAQGTGCQNSPYPLTGRVNGT

FIAFSVGWNNSTENCNSATGWTGYAQVNGNNTEIVTSWNLAYEGGSGPAIEQGQDTFQYVPTTE

NKSLLKD, linker sequence [7 amino acids]:
                                                  SEQ ID NO: 3
GGGGSSS, SP0785 protein lacking signal sequence and transmembrane
domain [amino acids 33-399]:
```

-continued

Note: One T394A mismatch with SP0785 NCBI Sequences ABJ54007.1 and YP816180

SEQ ID NO: 4
FRQPSQTALKDEPTHLVVAKEGSVASSVLLSGTVTAKNEQYVYFDASKGDLDEILVSVGDKVSE
GQALVKYSSSEAQAAYDSASRAVARADRHINELNQARNEAASAPAPQLPAPVGGEDATVQSPTP
VAGNSVASIDAQLGDARDARADAAAQLSKAQSQLDATTVLSTLEGTVVEVNSNVSKSPTGASQV
MVHIVSNENLQVKGELSEYNLANLSVGQEVSFTSKVYPDKKWTGKLSYISDYPKNNGEAASPAA
GNNTGSKYPYTIDVTGEVGDLKQGFSVNIEVKSKTKAILVPVSSLVMDDSKNYVWIVDEQQKAK
KVEVSLGNADAENQEITSGLTNGAKVISNPTSSLEEGKEVKADEATN,

SP1500 protein lacking signal sequence [amino acids 27-278]:
SEQ ID NO: 5
TSGDNWSKYQSNKSITIGFDSTFVPMGFAQKDGSYAGFDIDLATAVFEKYGITVNWQPIDWDLK
EAELTKGTIDLIWNGYSATDERREKVAFSNSYMKNEQVLVTKKSSGITTAKDMTGKTLGAQAGS
SGYADFEANPEILKNIVANKEANQYQTFNEALIDLKNDRIDGLLIDRVYANYYLEAEGVLNDYN
VFTVGLETEAFAVGARKEDTNLVKKINEAFSSLYKDGKFQEISQKWFGEDVATKEVKEGQ, fusion protein CP1:
SEQ ID NO: 6
MFDASNFKDFSSIASASSSWQNQSGSTMIIQVDSFGNVSGQYVNRAQGTGCQNSPYPLTGRVNG
TFIAFSVGWNNSTENCNSATGWTGYAQVNGNNTEIVTSWNLAYEGGSGPAIEQGQDTFQYVPTT
ENKSLLKDGGGGSSSTSGDNWSKYQSNKSITIGFDSTFVPMGFAQKDGSYAGFDIDLATAVFEK
YGITVNWQPIDWDLKEAELTKGTIDLIWNGYSATDERREKVAFSNSYMKNEQVLVTKKSSGITT
AKDMTGKTLGAQAGSSGYADFEANPEILKNIVANKEANQYQTFNEALIDLKNDRIDGLLIDRVY
ANYYLEAEGVLNDYNVFTVGLETEAFAVGARKEDTNLVKKINEAFSSLYKDGKFQEISQKWFGE
DVATKEVKEGQAAAFRQPSQTALKDEPTHLVVAKEGSVASSVLLSGTVTAKNEQYVYFDASKGD
LDEILVSVGDKVSEGQALVKYSSSEAQAAYDSASRAVARADRHINELNQARNEAASAPAPQLPA
PVGGEDATVQSPTPVAGNSVASIDAQLGDARDARADAAAQLSKAQSQLDATTVLSTLEGTVVEV
NSNVSKSPTGASQVMVHIVSNENLQVKGELSEYNLANLSVGQEVSFTSKVYPDKKWTGKLSYIS
DYPKNNGEAASPAAGNNTGSKYPYTIDVTGEVGDLKQGFSVNIEVKSKTKAILVPVSSLVMDDS
KNYVWIVDEQQKAKKVEVSLGNADAENQEITSGLTNGAKVISNPTSSLEEGKEVKADEATN, SP0785 gene encoding SP078S Protein lacking signal sequence
[amino acids 33-399]:
SEQ ID NO: 7
TTTAGACAACCTTCTCAGACTGCTCTAAAAGATGAGCCTACTCATCTTGTTGTTGCCAAGGAAG
GAAGCGTGGCCTCCTCTGTTTTATTGTCAGGGACAGTAACAGCAAAAAATGAACAATATGTTTA
TTTTGATGCTAGTAAGGGTGATTTAGATGAAATCCTTGTTTCTGTGGGCGATAAGGTCAGCGAA
GGGCAGGCTTTAGTCAAGTACAGTAGTTCAGAAGCGCAGGCGGCCTATGATTCAGCTAGTCGAG
CAGTAGCTAGGGCAGATCGTCATATCAATGAACTCAATCAAGCACGAAATGAAGCCGCTTCAGC
TCCGGCTCCACAGTTACCAGCGCCAGTAGGAGGAGAAGATGCAACGGTGCAAAGCCCAACTCCA
GTGGCTGGAAATTCTGTTGCTTCTATTGACGCTCAATTGGGTGATGCCCGTGATGCGCGTGCAG
ATGCTGCGGCGCAATTAAGCAAGGCTCAAAGTCAATTGGATGCAACAACTGTTCTCAGTACCCT
AGAGGGAACTGTGGTCGAAGTCAATAGCAATGTTTCTAAATCTCCAACAGGGGCGAGTCAAGTT
ATGGTTCATATTGTCAGCAATGAAAATTTACAAGTCAAGGGAGAATTGTCTGAGTACAATCTAG
CCAACCTTTCTGTAGGTCAAGAAGTAAGCTTTACTTCTAAAGTGTATCCTGATAAAAAATGGAC
TGGGAAATTAAGCTATATTTCTGACTATCCTAAAAACAATGGTGAAGCAGCTAGTCCAGCAGCC
GGGAATAATACAGGTTCTAAATACCCTTATACTATTGATGTGACAGGCGAGGTTGGTGATTTGA
AACAAGGTTTTTCTGTCAACATTGAGGTTAAAAGCAAAACTAAGGCTATTCTTGTTCCTGTTAG -continued

CAGTCTAGTAATGGATGATAGTAAAAATTATGTCTGGATTGTGGATGAACAACAAAAGGCTAAA

AAAGTTGAGGTTTCATTGGGAAATGCTGACGCAGAAAATCAAGAAATCACTTCTGGTTTAACGA

ACGGTGCTAAGGTCATCAGTAATCCAACATCTTCCTTGGAAGAAGGAAAAGAGGTGAAGGCTGA

TGAAGCAACTAAT,

SP1500 gene encoding SP1500 protein lacking signal sequence
[amino acids27-278]:
SEQ ID NO: 8
ACTAGTGGAGATAATTGGTCAAAGTACCAGTCTAACAAGTCTATTACTATTGGATTTGATAGTA

CTTTTGTTCCAATGGGATTTGCTCAGAAAGATGGTTCTTATGCAGGATTTGATATTGATTTAGC

TACAGCTGTTTTTGAAAAATACGGAATCACGGTAAATTGGCAACCGATTGATTGGGATTTGAAA

GAAGCTGAATTGACAAAAGGAACGATTGATCTGATTTGGAATGGCTATTCCGCTACAGACGAAC

GCCGTGAAAAGGTGGCTTTCAGTAACTCATATATGAAGAATGAGCAGGTATTGGTTACGAAGAA

ATCATCTGGTATCACGACTGCAAAGGATATGACTGGAAAGACATTAGGAGCTCAAGCTGGTTCA

TCTGGTTATGCGGACTTTGAAGCAAATCCAGAAATTTTGAAGAATATTGTCGCTAATAAGGAAG

CGAATCAATACCAAACCTTTAATGAAGCCTTGATTGATTTGAAAAACGATCGAATTGATGGTCT

ATTGATTGACCGTGTCTATGCAAACTATTATTTAGAAGCAGAAGGTGTTTTAAACGATTATAAT

GTCTTTACAGTTGGACTAGAAACAGAAGCTTTTGCGGTTGGAGCCCGTAAGGAAGATACAAACT

TGGTTAAGAAGATAAATGAAGCTTTTTCTAGTCTTTACAAGGACGGCAAGTTCCAAGAAATCAG

CCAAAAATGGTTTGGAGAAGATGTAGCAACCAAAGAAGTAAAAGAAGGACAG, codon-optimized sequence encoding fusion protein CP1
[nucleic acid]:
SEQ ID NO: 9
ATGTTCGACGCATCCAACTTTAAAGACTTTAGCAGCATCGCGTCCGCAAGCTCTAGCTGGCAGA

ATCAATCTGGTAGCACCATGATTATCCAAGTGGACAGCTTTGGTAACGTCAGCGGTCAATATGT

TAATCGTGCACAGGGTACGGGTTGTCAGAATTCTCCGTACCCGCTGACCGGTCGTGTTAACGGC

ACGTTCATCGCTTTCAGCGTCGGTTGGAACAATTCTACTGAAAATTGCAACAGCGCGACCGGTT

GGACGGGCTATGCACAAGTGAATGGCAATAACACCGAAATCGTCACGTCCTGGAATCTGGCGTA

TGAGGGTGGCAGCGGTCCGGCTATTGAACAGGGCCAGGATACCTTCCAATACGTCCCTACGACC

GAGAATAAGTCCCTTCTGAAAGACGGCGGTGGCGGTTCGAGCTCGACCAGCGGCGACAATTGGT

CCAAATACCAGAGCAACAAGAGCATCACGATCGGCTTCGACAGCACTTTTGTGCCGATGGGTTT

CGCGCAAAAAGACGGTAGCTACGCGGGTTTCGATATTGACCTGGCGACCGCTGTCTTTGAGAAA

TACGGCATTACGGTTAATTGGCAGCCGATTGATTGGGACCTGAAAGAGGCCGAACTCACCAAAG

GCACCATCGACCTGATCTGGAATGGTTACTCCGCAACCGATGAGCGTCGCGAAAAAGTTGCCTT

CAGCAACAGCTATATGAAGAATGAACAAGTGTTGGTAACCAAGAAATCTAGCGGCATTACGACC

GCGAAAGACATGACCGGTAAGACGCTGGGTGCGCAGGCCGGTAGCTCTGGCTATGCGGATTTCG

AGGCGAATCCTGAGATTCTGAAAAACATCGTTGCGAATAAAGAGGCGAACCAGTACCAGACCTT

TAACGAAGCACTGATCGACCTGAAAAACGATCGCATTGACGGTCTGCTGATCGATCGTGTGTAC

GCGAACTATTATCTGGAAGCCGAGGGCGTTCTGAACGATTATAATGTTTTTACCGTGGGTCTGG

AGACTGAGGCATTCGCGGTTGGTGCGCGCAAGGAAGATACCAACCTGGTTAAAAAGATTAATGA

GGCATTTAGCTCACTGTACAAGGACGGCAAGTTCCAAGAAATTAGCCAGAAGTGGTTCGGTGAA

GATGTTGCGACGAAAGAGGTTAAAGAGGGCCAAGCGGCCGCATTTCGCCAACCGAGCCAGACTG

CGTTGAAAGATGAGCCGACCCATCTGGTTGTTGCGAAAGAGGGCAGCGTGGCATCGAGCGTGCT

GCTGAGCGGTACGGTTACTGCCAAAAACGAACAATACGTGTACTTCGATGCTAGCAAGGGTGAT

-continued

CTGGATGAAATTCTGGTGAGCGTGGGTGACAAAGTTAGCGAAGGCCAGGCACTGGTGAAGTATT

CATCCTCCGAGGCACAGGCAGCGTACGACAGCGCAAGCCGCGCAGTGGCGCGTGCCGACCGTCA

CATTAACGAATTGAACCAAGCGCGTAACGAGGCCGCAAGCGCGCCAGCACCGCAGCTGCCGGCT

CCGGTGGGTGGCGAAGATGCGACGGTGCAGAGCCCGACCCCGGTTGCGGGTAATTCGGTCGCCA

GCATCGATGCGCAGCTGGGTGACGCGCGTGATGCCCGTGCGGATGCGGCTGCTCAACTGAGCAA

GGCTCAGAGCCAACTGGACGCGACGACGGTGCTGAGCACCTTGGAGGGTACCGTTGTCGAAGTC

AACAGCAATGTGAGCAAGAGCCCAACGGGTGCGAGCCAGGTTATGGTCCACATTGTGAGCAATG

AAAACTTACAGGTCAAGGGTGAGCTGAGCGAGTATAACCTGGCGAATCTGAGCGTTGGTCAAGA

GGTCAGCTTTACCAGCAAGGTCTACCCGGATAAGAAATGGACCGGCAAGTTGAGCTACATCAGC

GACTACCCGAAGAACAATGGCGAGGCAGCCTCCCCGGCAGCCGGCAACAATACCGGCTCTAAGT

ATCCGTACACCATCGACGTAACCGGTGAGGTCGGCGACCTGAAACAGGGTTTTAGCGTGAATAT

CGAAGTGAAGTCCAAGACCAAGGCAATTTTGGTTCCGGTTAGCTCCCTGGTGATGGACGATAGC

AAGAATTATGTGTGGATTGTCGACGAGCAACAGAAAGCGAAAAAAGTTGAAGTGAGCCTGGGCA

ATGCTGATGCCGAGAACCAAGAAATCACGTCTGGTCTGACCAACGGTGCGAAAGTTATTAGCAA

CCCGACCAGCAGCCTGGAAGAGGGTAAAGAGGTCAAAGCCGACGAAGCTACGAAC,

SP078S Protein, full-length [amino acids 1-399], TIGR4
strain:
SEQ ID NO: 10
MKKKNGKAKKWQLYAAIGAASVVVLGAGGILLFRQPSQTALKDEPTHLVVAKEGSVASSVLLSG

TVTAKNEQYVYFDASKGDLDEILVSVGDKVSEGQALVKYSSSEAQAAYDSASRAVARADRHINE

LNQARNEAASAPAPQLPAPVGGEDATVQSPTPVAGNSVASIDAQLGDARDARADAAAQLSKAQS

QLDATTVLSTLEGTVVEVNSNVSKSPTGASQVMVHIVSNENLQVKGELSEYNLANLSVGQEVSF

TSKVYPDKKWTGKLSYISDYPKNNGEAASPAAGNNTGSKYPYTIDVTGEVGDLKQGFSVNIEVK

SKTKAILVPVSSLVMDDSKNYVWIVDEQQKAKKVEVSLGNADAENQEITSGLTNGAKVISNPTS

SLEEGKEVKADEATN,

SP0785 gene encoding SP078S Protein, full-length [amino
acids 1-399], TIGR4 strain:
SEQ ID NO: 11
ATGAAGAAAAAGAATGGTAAAGCTAAAAAGTGGCAACTGTATGCAGCAATCGGTGCTGCGAGTG

TAGTTGTATTGGGTGCTGGGGGGATTTTACTCTTTAGACAACCTTCTCAGACTGCTCTAAAAGA

TGAGCCTACTCATCTTGTTGTTGCCAAGGAAGGAAGCGTGGCCTCCTCTGTTTTATTGTCAGGG

ACAGTAACAGCAAAAAATGAACAATATGTTTATTTTGATGCTAGTAAGGGTGATTTAGATGAAA

TCCTTGTTTCTGTGGGCGATAAGGTCAGCGAAGGGCAGGCTTTAGTCAAGTACAGTAGTTCAGA

AGCGCAGGCGGCCTATGATTCAGCTAGTCGAGCAGTAGCTAGGGCAGATCGTCATATCAATGAA

CTCAATCAAGCACGAAATGAAGCCGCTTCAGCTCCGGCTCCACAGTTACCAGCGCCAGTAGGAG

GAGAAGATGCAACGGTGCAAAGCCCAACTCCAGTGGCTGGAAATTCTGTTGCTTCTATTGACGC

TCAATTGGGTGATGCCCGTGATGCGCGTGCAGATGCTGCGGCGCAATTAAGCAAGGCTCAAAGT

CAATTGGATGCAACAACTGTTCTCAGTACCCTAGAGGGAACTGTGGTCGAAGTCAATAGCAATG

TTTCTAAATCTCCAACAGGGGCGAGTCAAGTTATGGTTCATATTGTCAGCAATGAAAATTTACA

AGTCAAGGGAGAATTGTCTGAGTACAATCTAGCCAACCTTTCTGTAGGTCAAGAAGTAAGCTTT

ACTTCTAAAGTGTATCCTGATAAAAAATGGACTGGGAAATTAAGCTATATTTCTGACTATCCTA

AAAACAATGGTGAAGCAGCTAGTCCAGCAGCCGGGAATAATACAGGTTCTAAATACCCTTATAC

TATTGATGTGACAGGCGAGGTTGGTGATTTGAAACAAGGTTTTTCTGTCAACATTGAGGTTAAA

AGCAAAACTAAGGCTATTCTTGTTCCTGTTAGCAGTCTAGTAATGGATGATAGTAAAAATTATG

-continued

```
TCTGGATTGTGGATGAACAACAAAAGGCTAAAAAAGTTGAGGTTTCATTGGGAAATGCTGACGC

AGAAAATCAAGAAATCACTTCTGGTTTAACGAACGGTGCTAAGGTCATCAGTAATCCAACATCT

TCCTTGGAAGAAGGAAAAGAGGTGAAGGCTGATGAAGCAACTAAT,
```

SP1500 protein, full-length [amino acids 1-278], TIGR4 strain:

SEQ ID NO: 12

```
MKKWMLVLVSLMTALFLVACGKNSSETSGDNWSKYQSNKSITIGFDSTFVPMGFAQKDGSYAGF

DIDLATAVFEKYGITVNWQPIDWDLKEAELTKGTIDLIWNGYSATDERREKVAFSNSYMKNEQV

LVTKKSSGITTAKDMTGKTLGAQAGSSGYADFEANPEILKNIVANKEANQYQTFNEALIDLKND

RIDGLLIDRVYANYYLEAEGVLNDYNVFTVGLETEAFAVGARKEDTNLVKKINEAFSSLYKDGK

FQEISQKWFGEDVATKEVKEGQ,
```

SP1500 gene encoding SP1500 protein, full-length [amino acids 1-278], TIGR4 strain:

SEQ ID NO: 13

```
ATGAAAAAATGGATGCTTGTATTAGTCAGTCTGATGACTGCTTTGTTCTTAGTAGCTTGTGGGA

AAAATTCTAGCGAAACTAGTGGAGATAATTGGTCAAAGTACCAGTCTAACAAGTCTATTACTAT

TGGATTTGATAGTACTTTTGTTCCAATGGGATTTGCTCAGAAAGATGGTTCTTATGCAGGATTT

GATATTGATTTAGCTACAGCTGTTTTTGAAAAATACGGAATCACGGTAAATTGGCAACCGATTG

ATTGGGATTTGAAAGAAGCTGAATTGACAAAAGGAACGATTGATCTGATTTGGAATGGCTATTC

CGCTACAGACGAACGCCGTGAAAAGGTGGCTTTCAGTAACTCATATATGAAGAATGAGCAGGTA

TTGGTTACGAAGAAATCATCTGGTATCACGACTGCAAAGGATATGACTGGAAAGACATTAGGAG

CTCAAGCTGGTTCATCTGGTTATGCGGACTTTGAAGCAAATCCAGAAATTTTGAAGAATATTGT

CGCTAATAAGGAAGCGAATCAATACCAAACCTTTAATGAAGCCTTGATTGATTTGAAAAACGAT

CGAATTGATGGTCTATTGATTGACCGTGTCTATGCAAACTATTATTTAGAAGCAGAAGGTGTTT

TAAACGATTATAATGTCTTTACAGTTGGACTAGAAACAGAAGCTTTTGCGGTTGGAGCCCGTAA

GGAAGATACAAACTTGGTTAAGAAGATAAATGAAGCTTTTTCTAGTCTTTACAAGGACGGCAAG

TTCCAAGAAATCAGCCAAAAATGGTTTGGAGAAGATGTAGCACCAAAGAAGTAAAAGAAGGACA

G,
```

REFERENCES

Anttila M, Eskola J, Ahman H, Käyhty H. Avidity of IgG for *Streptococcus pneumoniae* type 6B and 23F polysaccharides in infants primed with pneumococcal conjugates and boosted with polysaccharide or conjugate vaccines. J Infect Dis. 1998 June; 177(6):1614-21.

Buller H R, Halperin J, Hankey G J, Pillion G, Prins M H, Raskob G E. Comparison of idrabiotaparinux with vitamin K antagonists for prevention of thromboembolism in patients with atrial fibrillation: the Borsealis-Atrial Fibrillation study. J Throb Haemost. 2014; 12:824-30.

[CDC] Centers for Disease Control and Prevention. Preventing pneumococcal disease among infants and young children. Morbidity and Mortality Weekly Report. 2000; 49:1-55.

[CDC] Centers for Disease Control and Prevention. Prevention of pneumococcal disease among infants and children—use of 13-valent pneumococcal conjugate vaccine and 23-valent pneumococcal polysaccharide vaccine. Morbidity and Mortality Weekly Report. 2010; 59:1-24.

Chase (1967). Perinatal and infant mortality in the United States and six West European countries. Am J Public Health Nations Health. 1967 October; 57(10):1735-48.

Concepcion N F, Frasch C E. Pneumococcal type 22f polysaccharide absorption improves the specificity of a pneumococcal-polysaccharide enzyme-linked immunosorbent assay. Clin Diagn Lab Immunol. 2001 March; 8(2):266-72.

Douce et al. Mutants of *Escherichia coli* heat-labile toxin lacking ADP-ribosyltransferase activity act as non-toxic, mucosal adjuvants. PNAS Vol. 92, pp. 1644-1648, February 1995.

Douce et al. Genetically detoxified mutants of heat-labile toxin from *Escherichia coli* are able to act as oral adjuvants" Infect Immun. 1999 September; 67(9):4400-6)

Evans J T et al. Enhancement of antigen-specific immunity via the TLR-4 ligands MPL adjuvant and Ribi.529. Expert Rev Vaccines 2003 April; 2(2):219-29.

Geno K A, Gilbert G L, Song J Y, Skovsted I C, Klugman K P, Jones C et al. Pneumococcal Capsules and their types: past, present, and future. Clin Microbiol Rev 2015 July; 28(3):871-899.

Giuliani M M et al. Mucosal adjuvanticity and immunogenicity of LTR72, a novel mutant of *Escherichia coli* heat-labile enterotoxin with partial knockout of ADP-ribosyltransferase activity. J Exp Med. 1998 Apr. 6; 187(7):1123-32.

Gruber M F, Pratt D, Haase M. Licensing of pneumococcal conjugate vaccines for children and adults: Regulatory perspective from the European Medicines Agency and the U.S. Food and Drug Administration. In: Siber G R, Klugman K P, Mäkelä P H, eds. Pneumococcal Vaccines: The Impact of Conjugate Vaccine. Washington, D.C.: ASM Press; 2008; 183-96.

Helppolainen S H, Nurminen K P, Määttä J A, Halling K K, Slotte J P, Huhtala T, et al. Rhizavidin from *Rhizobium etli*: the first natural dimer in the avidin protein family. Biochem J. 2007; 405:397-405.

Holliger P, Prospero T, Winter G. "Diabodies": small bivalent and bispecific antibody fragments. Proc Natl Acad Sci USA. 1993 Jul. 15; 90(14):6444-8.

Ishizaka S T et al. "E6020: a synthetic Toll-like receptor 4 agonist as a vaccine adjuvant." Expert Rev. Vaccines. 2007 October; 6(5):773-84.

Kaufmann F, Lund E, Eddy B. Proposal for a change in the nomenclature of Diplococcus *pneumoniae* and a comparison of the Danish and American type designations. Intl Bulletin of Bacterial Nomenclature and Taxonomy 1960 January; 10(1):31-40.

Kim K H, Yu J, Nahm M H. Efficiency of a pneumococcal opsonophagocytic killing assay improved by multiplexing and by coloring colonies. Clin Diagn Lab Immunol. 2003 July; 10(4):616-21.

Lazzeri E, Pauwels E K, Erba P A, Volterrani D, Manca M, Bodei L, et al. Clinical feasibility of two-step streptavidin/111In-biotin scintigraphy in patients with suspected vertebral osteomyelitis. Eur J Nucl Med Mol Imaging. 2004; 31:1505-11.

Kojima K, Ishizaka A, Oshika E, Taguchi Y, Tomizawa K, et al. Quantitation of IgG subclass antibodies to pneumococcal capsular polysaccharides by ELISA, using Pneumovax-specific antibodies as a reference. Tohoku J Exp Med. 1990 July; 161(3):209-15.

Koskela M, Leinonen M. Comparison of ELISA and RIA for measurement of pneumococcal antibodies before and after vaccination with 14-valent pneumococcal capsular polysaccharide vaccine. J Clin Pathol. 1981 January; 34(1):93-8.

Martin, E W, Ed. Remington's Pharmaceutical Sciences. 15th ed. Easton, Pa.: Mack Publishing Company, 1975.

Martinez J E, Romero-Steiner S, Pilishvili T, Barnard S, Schinsky J, et al. A flow cytometric opsonophagocytic assay for measurement of functional antibodies elicited after vaccination with the 23-valent pneumococcal polysaccharide vaccine. Clin Diagn Lab Immunol. 1999 July; 6(4):581-6.

Meyers and Miller. CABIOS, 1989, 4:11-17.

Munro C S, Stanley P J, Cole P J. Assessment of biological activity of immunoglobulin preparations by using opsonized micro-organisms to stimulate neutrophil chemiluminescence. Clin Exp Immunol. 1985 July; 61(1):183-8.

Ojo-Amaize E A, Church J A, Barka N E, Agopian M S, Peter J B. A rapid and sensitive chemiluminescence assay for evaluation of functional opsonic activity of *Haemophilus influenzae* type b-specific antibodies. Clin Diagn Lab Immunol. 1995 May; 2(3):286-90

Paty I, Trellu M, Destors J M, Cortez P, Boelle E, Sanderink G. Reversibility of the anti-FXa activity of idrabiotaparinux (biotinylated idraparinux) by intravenous avidin infusion. J Thromb Haemost. 2010; 8:722-9.

PNEUMOVAX® 23 (prescribing information). Whitehouse Station, N.J.: Merck & Co.; May 2015.

PREVNAR 13® (prescribing information). New York, N.Y.: Pfizer; August 2017.

Poljak R J. Production and structure of diabodies. Structure. 1994 Dec. 15; 2(12):1121-3.

Powell M F and Newman M J, Eds. Vaccine Design: The Subunit and Adjuvant Approach. New York, N.Y.: Plenum Press, 1995.

Richter S S, Diekema D J, Heilmann K P, Dohrn C L, Riahi F, Doern G V. Changes in pneumococcal serotypes and antimicrobial resistance after introduction of the 13 valent conjugate vaccine in the United States. Antimicrob Agents Chemother. 2014; 58:6484-9.

Romero-Steiner S, Libutti D, Pais L B, Dykes J, Anderson P, et al. Standardization of an opsonophagocytic assay for the measurement of functional antibody activity against *Streptococcus pneumoniae* using differentiated HL-60 cells. Clin Diagn Lab Immunol. 1997 July; 4(4):415-22.

Romero-Steiner S, Holder P F, Gomez de Leon P, Spear W, Hennessy T W, et al. Avidity determinations for *Haemophilus influenzae* Type b anti-polyribosylribitol phosphate antibodies. Clin Diagn Lab Immunol. 2005 September; 12(9):1029-35.

Saeland E, Vidarsson G, Jonsdottir I. Pneumococcal pneumonia and bacteremia model in mice for the analysis of protective antibodies. Microb Pathog. 2000 August; 29(2):81-91.

Singh et al. Curr. HIV Res. 1:309-20, 2003.

Stack A M, Malley R, Thompson C M, Kobzik L, Siber G R, et al. Minimum protective serum concentrations of pneumococcal anti-capsular antibodies in infant rats. J Infect Dis. 1998 April; 177(4):986-90.

Williams et al., Innate imprinting by the modified heat-labile toxin of *Escherichia coli* (LTK63) provides generic protection against lung infectious disease. The Journal of Immunology, 2004 173:7435-7443.

Wu W, Huang J, Duan B, Traficante D C, Hong H, et al. $T_H17$-stimulating protein vaccines confer protection against *Pseudomonas aeruginosa* pneumonia. Am J Respir Crit Care Med. 2012 Sep. 1; 186(5):420-7.

Zhang F, Lu Y J, Malley R. Multiple antigen-presenting system (MAPS) to induce comprehensive B- and T-cell immunity. Proc Natl Acad Sci USA. 2013; 110:13564-9.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

We claim:

1. A method of immunizing a subject against *Streptococcus pneumoniae* infection and/or colonization comprising administering to the subject an immunologically effective amount of a multivalent vaccine comprising fifteen or more species of immunogenic complexes, wherein each species of the immunogenic complexes comprises:
(a) a biotinylated polysaccharide antigen comprising biotin and a polysaccharide antigen from a distinct *Streptococcus pneumoniae* serotype; and
(b) a fusion protein comprising:
(i) a biotin-binding moiety; and
(ii) at least one polypeptide antigen comprising;
a first polypeptide antigen comprising an SP1500 polypeptide or an antigenic fragment thereof; and
a second polypeptide antigen comprising an SP0785 polypeptide or an antigenic fragment thereof;
wherein the fusion protein comprises an amino acid sequence at least 90% identical to SEQ ID NO:6; and
wherein in each species of the immunogenic complexes, the biotinylated polysaccharide antigen is non-covalently associated with the biotin-binding moiety of the fusion protein.

2. The method of claim 1, wherein the *Streptococcus pneumoniae* serotype for each species of the immunogenic complexes is selected from 1, 2, 3, 4, 5, 6A, 6B, 6C, 6D, 6E, 6F, 6G, 6H, 7A, 7B, 7C, 7F, 8, 9A, 9L, 9N, 9V, 10A, 10B, 10C, 10F, 11A, 11B, 11C, 11D, 11E, 11F, 12A, 12B, 12F, 13, 14, 15A, 15B, 15C, 15F, 16A, 16F, 17A, 17F, 18A, 18B, 18C, 18F, 19A, 19B, 19C, 19F, 20A, 20B, 21, 22A, 22F, 23A, 23B, 23F, 24A, 24B, 24F, 25A, 25F, 27, 28A, 28F, 29, 31, 32A, 32F, 33A, 33B, 33C, 33D, 33E, 33F, 34, 35A, 35B, 35C, 35F, 36, 37, 38, 39, 40, 41A, 41F, 42, 43, 44, 45, 46, 47A, 47F, and 48.

3. The method of claim 1, wherein the *Streptococcus pneumoniae* serotype for each species of the immunogenic complexes is selected from 1, 2, 3, 4, 5, 6A, 6B, 7F, 8, 9N, 9V, 10A, 11A, 12F, 14, 15B, 17F, 18C, 19A, 19F, 20B, 22F, 23F, and 33F.

4. The method of claim 1, wherein the first polypeptide antigen comprises an amino acid sequence at least 90%, at least 91%, at least 92%, at least 93%, at least 94%, at least 95%, at least 96%, at least 97%, at least 98%, at least 99%, or at least 99.5% identical to SEQ ID NO:5 or an antigenic fragment thereof.

5. The method of claim 1, wherein the second polypeptide antigen comprises an amino acid sequence at least 90%, at least 91%, at least 92%, at least 93%, at least 94%, at least 95%, at least 96%, at least 97%, at least 98%, at least 99%, or at least 99.5% identical to SEQ ID NO:4 or an antigenic fragment thereof.

6. The method of claim 1, wherein the fusion protein comprises an amino acid sequence at least 90%, at least 91%, at least 92%, at least 93%, at least 94%, at least 95%, at least 96%, at least 97%, at least 98%, at least 99%, or at least 99.5% identical to SEQ ID NO:6.

7. The method of claim 1, wherein the biotin-binding moiety is a polypeptide comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:2 or a biotin-binding fragment thereof.

8. The method of claim 1, wherein the fusion protein comprises the amino acid sequence of SEQ ID NO: 6.

9. The method of claim 2, wherein the vaccine comprises twenty four or more species of the immunogenic complexes.

10. The method of claim 9, wherein the vaccine comprises:
a first immunogenic complex comprising (a) a biotinylated polysaccharide antigen comprising biotin and a polysaccharide antigen from *Streptococcus pneumoniae* serotype 1, and (b) a fusion protein;
a second immunogenic complex comprising (a) a biotinylated polysaccharide antigen comprising biotin and a polysaccharide antigen from *Streptococcus pneumoniae* serotype 2, and (b) a fusion protein;
a third immunogenic complex comprising (a) a biotinylated polysaccharide antigen comprising biotin and a polysaccharide antigen from *Streptococcus pneumoniae* serotype 3, and (b) a fusion protein;
a fourth immunogenic complex comprising (a) a biotinylated polysaccharide antigen comprising biotin and a polysaccharide antigen from *Streptococcus pneumoniae* serotype 4, and (b) a fusion protein;
a fifth immunogenic complex comprising (a) a biotinylated polysaccharide antigen comprising biotin and a polysaccharide antigen from *Streptococcus pneumoniae* serotype 5, and (b) a fusion protein;
a sixth immunogenic complex comprising (a) a biotinylated polysaccharide antigen comprising biotin and a polysaccharide antigen from *Streptococcus pneumoniae* serotype 6A, and (b) fusion protein;
a seventh immunogenic complex comprising (a) a biotinylated polysaccharide antigen comprising biotin and a polysaccharide antigen from *Streptococcus pneumoniae* serotype 6B, and (b) a fusion protein;
an eighth immunogenic complex comprising (a) a biotinylated polysaccharide antigen comprising biotin and a polysaccharide antigen from *Streptococcus pneumoniae* serotype 7F, and (b) a fusion protein;
a ninth immunogenic complex comprising (a) a biotinylated polysaccharide antigen comprising biotin and a polysaccharide antigen from *Streptococcus pneumoniae* serotype 8, and (b) a fusion protein;
a tenth immunogenic complex comprising (a) a biotinylated polysaccharide antigen comprising biotin and a polysaccharide antigen from *Streptococcus pneumoniae* serotype 9N, and (b) a fusion protein;
an eleventh immunogenic complex comprising (a) a biotinylated polysaccharide antigen comprising biotin and a polysaccharide antigen from *Streptococcus pneumoniae* serotype 9V, and (b) a fusion protein;
a twelfth immunogenic complex comprising (a) a biotinylated polysaccharide antigen comprising biotin and a polysaccharide antigen from *Streptococcus pneumoniae* serotype 10A, and (b) a fusion protein;
a thirteenth immunogenic complex comprising (a) a biotinylated polysaccharide antigen comprising biotin and a polysaccharide antigen from *Streptococcus pneumoniae* serotype 11A, and (b) a fusion protein;
a fourteenth immunogenic complex comprising (a) a biotinylated polysaccharide antigen comprising biotin and a polysaccharide antigen from *Streptococcus pneumoniae* serotype 12F, and (b) a fusion protein;
a fifteenth immunogenic complex comprising (a) a biotinylated polysaccharide antigen comprising biotin and a polysaccharide antigen from *Streptococcus pneumoniae* serotype 14, and (b) a fusion protein;
a sixteenth immunogenic complex comprising (a) a biotinylated polysaccharide antigen comprising biotin and a polysaccharide antigen from *Streptococcus pneumoniae* serotype 15B, and (b) a fusion protein;
a seventeenth immunogenic complex comprising (a) a biotinylated polysaccharide antigen comprising biotin and a polysaccharide antigen from *Streptococcus pneumoniae* serotype 17F, and (b) a fusion protein;
an eighteenth immunogenic complex comprising (a) a biotinylated polysaccharide antigen comprising biotin and a polysaccharide antigen from *Streptococcus pneumoniae* serotype 18C, and (b) a fusion protein;
a nineteenth immunogenic complex comprising (a) a biotinylated polysaccharide antigen comprising biotin and a polysaccharide antigen from *Streptococcus pneumoniae* serotype 19A, and (b) a fusion protein;
a twentieth immunogenic complex comprising (a) a biotinylated polysaccharide antigen comprising biotin and a polysaccharide antigen from *Streptococcus pneumoniae* serotype 19F, and (b) a fusion protein;
a twenty-first immunogenic complex comprising (a) a biotinylated polysaccharide antigen comprising biotin and a polysaccharide antigen from *Streptococcus pneumoniae* serotype 20B, and (b) a fusion protein;
a twenty-second immunogenic complex comprising (a) a biotinylated polysaccharide antigen comprising biotin and a polysaccharide antigen from *Streptococcus pneumoniae* serotype 22F, and (b) a fusion protein;
a twenty-third immunogenic complex comprising (a) a biotinylated polysaccharide antigen comprising biotin and a polysaccharide antigen from *Streptococcus pneumoniae* serotype 23F, and (b) a fusion protein; and
a twenty-fourth immunogenic complex comprising (a) a biotinylated polysaccharide antigen comprising biotin and a polysaccharide antigen from *Streptococcus pneumoniae* serotype 33F, and (b) a fusion protein;
wherein each fusion protein comprises;
  (i) a biotin-binding moiety;
  (ii) at least one polypeptide antigen comprising: a first polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:5 or an antigenic fragment thereof; and
  a second polypeptide antigen comprising an amino acid sequence at least 90%, at least 91%, at least 92%, at least 93%, at least 94%, at least 95%, at least 96%, at least 97%, at least 98%, at least 99%, or at least 99.5% identical to SEQ ID NO:4 or an antigenic fragment thereof;
and wherein in each of the immunogenic complexes, the biotinylated polysaccharide antigen is non-covalently associated with the biotin-binding moiety of the fusion protein.

11. The method of claim 1, wherein the vaccine induces an immune response.

12. The method of claim 11, wherein the immune response comprises an antibody or B cell response.

13. The method of claim 11, wherein the immune response comprises a CD4+ T cell response, a CD8+ T cell response, a CD4+ and CD8+ T cell response, or a CD4−/CD8− T cell response.

14. The method of claim 11, wherein the immune response comprises (i) an antibody or B cell response and (ii) a T cell response.

15. The method of claim 11, wherein the immune response is to at least one polysaccharide antigen or at least one polypeptide antigen of a fusion protein.

16. The method of claim 15, wherein the immune response comprises (i) an antibody or B cell response to at least one polysaccharide antigen, and (ii) a CD4+ T cell response, a CD8+ T cell response, a CD4+ and CD8+ T cell response, or a CD4−/CD8− T cell response to at least one polypeptide antigen of a fusion protein.

17. The method of claim 15, wherein the immune response comprises (i) an antibody or B cell response to at least one polysaccharide antigen, and (ii) an antibody or B cell response to at least one polypeptide antigen of a fusion protein.

18. The method of claim 15, wherein the immune response comprises (i) an antibody or B cell response to at least one polysaccharide antigen, and (ii) an antibody or B cell response and a CD4+ T cell response, a CD8+ T cell response, a CD4+ and CD8+ T cell response, or a CD4−/CD8− T cell response to at least one polypeptide antigen of a fusion protein.

19. The method of claim 1, wherein the vaccine induces an opsonic/bactericidal response against one or more serotypes of *Streptococcus pneumoniae*.

20. The method of claim 1, wherein the vaccine inhibits transmission of one or more serotypes of *Streptococcus pneumoniae* from the subject to another subject.

21. The method of claim 1, wherein the vaccine inhibits or reduces the rate of occurrence of Invasive Pneumococcal Disease (IPD) associated with or induced by one or more serotypes of *Streptococcus pneumoniae*.

22. The method of claim 1, wherein the vaccine reduces the severity of Invasive Pneumococcal Disease (IPD) associated with or induced by one or more serotypes of *Streptococcus pneumoniae*.

23. The method of claim 1, wherein the vaccine inhibits or reduces the rate of occurrence of bacteremia, sepsis, and/or meningitis associated with or induced by one or more serotypes of *Streptococcus pneumoniae*.

24. The method of claim 1, wherein the vaccine reduces the severity of bacteremia, sepsis, and/or meningitis associated with or induced by one or more serotypes of *Streptococcus pneumoniae*.

25. The method of claim 1, wherein the vaccine inhibits or reduces the rate of occurrence of organ damage associated with or induced by one or more serotypes of *Streptococcus pneumoniae*.

26. The method of claim 1, wherein the vaccine reduces the severity of organ damage associated with or induced by one or more serotypes of *Streptococcus pneumoniae*.

27. The method of claim 1, wherein the vaccine inhibits or reduces the rate of occurrence of pneumonia associated with or induced by one or more serotypes of *Streptococcus pneumoniae*.

28. The method of claim 1, wherein the vaccine reduces the severity of pneumonia associated with or induced by one or more serotypes of *Streptococcus pneumoniae*.

29. The method of claim 1, wherein the vaccine inhibits or reduces the rate of occurrence of otitis media associated with or induced by one or more serotypes of *Streptococcus pneumoniae*.

30. The method of claim 1, wherein the vaccine reduces the severity of otitis media associated with or induced by one or more serotypes of *Streptococcus pneumoniae*.

31. The method of claim 1, wherein the vaccine inhibits or reduces the rate of occurrence of sinusitis associated with or induced by one or more serotypes of *Streptococcus pneumoniae*.

32. The method of claim 1, wherein the vaccine reduces the severity of sinusitis associated with or induced by one or more serotypes of *Streptococcus pneumoniae*.

33. The method of claim 1, wherein the vaccine inhibits colonization of mucosal surfaces by one or more serotypes of *Streptococcus pneumoniae*.

34. The method of claim 1, wherein the vaccine inhibits colonization of the nasopharynx by one or more serotypes of *Streptococcus pneumoniae*.

35. The method of claim 1, wherein the subject is immunized against *Streptococcus pneumoniae* infection and/or colonization with at least one dose of the vaccine.

36. The method of claim 13, wherein the CD4+ T cell response is or comprises a $T_H1$, $T_H2$, and/or $T_H17$ response.

37. The method of claim 16, wherein the CD4+ T cell response is or comprises a $T_H1$, $T_H2$, and/or $T_H17$ response.

38. The method of claim 18, wherein the CD4+ T cell response is or comprises a $T_H1$, $T_H2$, and/or $T_H17$ response.

\* \* \* \* \*

UNITED STATES PATENT AND TRADEMARK OFFICE
CERTIFICATE OF CORRECTION

| | | |
|---|---|---|
| PATENT NO. | : 11,701,416 B2 | Page 1 of 1 |
| APPLICATION NO. | : 17/237168 | |
| DATED | : July 18, 2023 | |
| INVENTOR(S) | : Malley et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 15 days.

Signed and Sealed this
Nineteenth Day of August, 2025

Coke Morgan Stewart
*Acting Director of the United States Patent and Trademark Office*